United States Patent
De Haro Garcia et al.

(10) Patent No.: US 10,906,919 B2
(45) Date of Patent: Feb. 2, 2021

(54) FUSED PENTACYCLIC IMIDAZOLE DERIVATIVES

(71) Applicants: UCB Biopharma SRL, Brussels (BE); Sanofi, Paris (FR)

(72) Inventors: Teresa De Haro Garcia, Slough (GB); Michael Deligny, Brussels (BE); Jag Paul Heer, Slough (GB); Joanna Rachel Quincey, Slough (GB); Mengyang Xuan, Slough (GB); Zhaoning Zhu, Slough (GB); Daniel Christopher Brookings, Slough (GB); Mark Daniel Calmiano, Slough (GB); Yves Evrard, Brussels (BE); Martin Clive Hutchings, Slough (GB); James Andrew Johnson, Slough (GB); Sophie Jadot, Brussels (BE); Jean Keyaerts, Brussels (BE); Malcolm Mac Coss, Seabrook Island, SC (US); Matthew Duncan Selby, Slough (GB); Michael Alan Shaw, Slough (GB); Dominique Louis Leon Swinnen, Brussels (BE); Laurent Schio, Paris (FR); Yann Foricher, Paris (FR); Bruno Filoche-Romme, Paris (FR)

(73) Assignees: UCB Biopharma SRL, Brussels (BE); Sanofi, Paris (FR)

( * ) Notice: Subject to any disclaimer, the term of this patent is extended or adjusted under 35 U.S.C. 154(b) by 0 days.

(21) Appl. No.: 16/220,847

(22) Filed: Dec. 14, 2018

(65) Prior Publication Data

US 2019/0367535 A1 Dec. 5, 2019

Related U.S. Application Data

(62) Division of application No. 15/513,357, filed as application No. PCT/EP2015/072868 on Oct. 2, 2015, now Pat. No. 10,202,405.

(30) Foreign Application Priority Data

| Oct. 3, 2014 | (EP) | 14290299 |
| Apr. 7, 2015 | (EP) | 15162641 |
| Jun. 8, 2015 | (EP) | 15171036 |

(51) Int. Cl.

| C07D 519/00 | (2006.01) |
| C07F 7/18 | (2006.01) |
| C07D 491/08 | (2006.01) |
| A61K 31/4184 | (2006.01) |
| A61K 31/506 | (2006.01) |
| A61K 31/55 | (2006.01) |
| C07D 487/08 | (2006.01) |
| C07D 491/18 | (2006.01) |
| C07D 495/08 | (2006.01) |
| C07D 471/18 | (2006.01) |
| C07D 487/18 | (2006.01) |
| C07D 493/18 | (2006.01) |
| C07D 495/18 | (2006.01) |
| C07D 513/18 | (2006.01) |

(52) U.S. Cl.
CPC ........ C07D 519/00 (2013.01); A61K 31/4184 (2013.01); A61K 31/506 (2013.01); A61K 31/55 (2013.01); C07D 471/18 (2013.01); C07D 487/08 (2013.01); C07D 487/18 (2013.01); C07D 491/08 (2013.01); C07D 491/18 (2013.01); C07D 493/18 (2013.01); C07D 495/08 (2013.01); C07D 495/18 (2013.01); C07D 513/18 (2013.01); C07F 7/1804 (2013.01)

(58) Field of Classification Search
None
See application file for complete search history.

(56) References Cited

U.S. PATENT DOCUMENTS

2003/0187257 A1  10/2003  Gaudilliere

FOREIGN PATENT DOCUMENTS

| CL | 200202666 | 9/2003 |
| CL | 201001264 | 12/2011 |
| CL | 2016000922 | 1/2017 |
| CL | 2016002600 | 8/2017 |
| EP | 0449649 | 10/1991 |
| WO | 2004/087720 | 10/2004 |
| WO | 2009/156091 | 12/2009 |
| WO | 2012/135082 | 10/2012 |
| WO | 2012/177707 | 12/2012 |
| WO | 2013/186229 | 12/2013 |
| WO | 2014/009295 | 1/2014 |

(Continued)

OTHER PUBLICATIONS

Kumar et al., Molecular Diversity, 2013, 17(4), 753-766.

(Continued)

*Primary Examiner* — Heidi Reese
(74) *Attorney, Agent, or Firm* — McDonnell Boehnen Hulbert & Berghoff LLP

(57) ABSTRACT

A series of fused pentacyclic imidazole derivatives, being potent modulators of human TNFa activity, are accordingly of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders. In particular, the present invention is concerned with 6,7-dihydro-7,14-methanobenzimidazo[1,2-b][2,5]benzodiazocin-5(14H)-one derivatives and analogs thereof.

10 Claims, No Drawings

(56) References Cited

FOREIGN PATENT DOCUMENTS

| WO | 2014/009296 | 1/2014 |
|---|---|---|
| WO | 2015/086525 | 6/2015 |
| WO | 2015/086526 | 6/2015 |

OTHER PUBLICATIONS

Lynch et al., Chemistry—A European Journal, 2007, 13, 3218-3226.
Chimirri et al., Archly der Pharmazie, 2001, 334(6), 203-208.
Skibo, Expert Opinion on Therapeutic Patents, 1998.
Tansey & Szymkowski, Drug Discovery Today, 2009, 14, 1082-1088.
Van Hauwermeiren et al., J. Clin. Invest., 2013, 123, 2590-2603.
Bahrami et al., J. Org. Chem., 2009, 74, 9287-9291.
Lacko et al., Current Medicinal Chemistry, 2012, 19, 4699.
Carneiro et al., J. Sexual Medicine, 2010, 7, 3823-3834.
Wu et al., JAMA, 2013, 309, 2043-2044.
Wu et al., Arch Dermatol., 2012, 148(11):1244-1250.
Eichman and Stambuli, J. Org. Chem., 2009, 74, 4005-4008.
Hilpert et al., Journal of Medicinal Chemistry, 2013, 56(10), 3980-3995.
Armstrong et al., J. Org. Chem., 2013, 78, 10534.
Sakai et al., J. Org. Chem. 2007, 72, 5920-5922.
Okamura et al., Organic Letters, 2004, 6(8), 1305-1307.
Bentley et al., Organic Process Research & Development, 2002, 6, 109-112.
Nam et al., Bio-org, Med Chem., 2004, 12, 6255.
Washburn et al., J. Med. Chem. 2014, 57, 7509.

FUSED PENTACYCLIC IMIDAZOLE DERIVATIVES

This application is a divisional application of U.S. application Ser. No. 15/513,357 filed Mar. 22, 2017, which is a U.S. national phase application under 35 USC 371 of International Patent Application No. PCT/EP2015/072868, filed Oct. 2, 2015, which claims the benefit of European Application No. 15171036.5, filed Jun. 8, 2015; European Application No. 15162641.3, filed Apr. 7, 2015; and European Application No. 14290299.8, filed Oct. 3, 2014, the contents of each of which (including specification, claims, abstract, and drawings) are hereby incorporated into the present specification by reference.

The present invention relates to classes of fused pentacyclic imidazole derivatives, and to their use in therapy. More particularly, this invention is concerned with pharmacologically active substituted fused pentacyclic benzimidazole derivatives and analogs thereof. In particular, the present invention is concerned with 6,7-dihydro-7,14-methanobenzimidazo[1,2-b][2,5]benzodiazocin-5(14H)-one derivatives and analogs thereof.

These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

International patent applications WO2013/186229A1, WO2014/009295A1 and WO2014/009296A1 relate to fused imidazole derivatives which are modulators of the signalling of TNFα.

International patent applications WO2015/086525 and WO2015/086526 published Jun. 18, 2015 relate to fused tricyclic imidazole derivatives which are modulators of the signalling of TNFα.

None of the prior art available to date, however, discloses or suggests the precise structural class of fused pentacyclic imidazole derivatives as provided by the present invention.

The present invention provides a compound of formula (I) or an N-oxide thereof, or a pharmaceutically acceptable salt thereof:

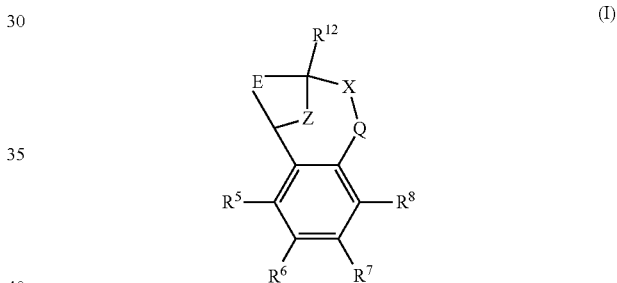

(I)

wherein
—X-Q- represents —O—, —O—C(O)—, —C(O)—O—, —O—C(CH—CN)—, —S—, —SO—, —SO$_2$—, —N(R$^g$)—, —N(R$^f$)—CO—, —CO—N(R$^f$)—, —N(R$^f$)—SO$_2$—, —SO$_2$—N(R$^f$)—, —S(O)(NR$^f$)—, —CH$_2$—CH$_2$—, —O—CH$_2$—, —CH$_2$—O—, —S—CH$_2$—, —SO—CH$_2$—, —SO$_2$—CH$_2$—, —CH$_2$—S—, —CH$_2$—SO—, —CH$_2$—SO$_2$—, —N(R$^g$)—CH$_2$—, —CH$_2$—N(R$^g$)—, —S(O)(NR$^f$)—CH$_2$—, —CH$_2$—S(O)(NR$^f$)—, —N(R$^f$)—C(S)—, —N=S(O)(CH$_3$)—O—C(=CH$_2$)— or —S(=N—CN)—, any of which groups may be optionally substituted by one or more substituents.

Z represents methylene;

E represents a fused heteroaromatic ring system selected from the groups of formula (Ea), (Eb) and (Ec),

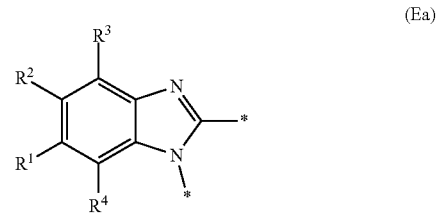

(Ea)

3

(Eb)

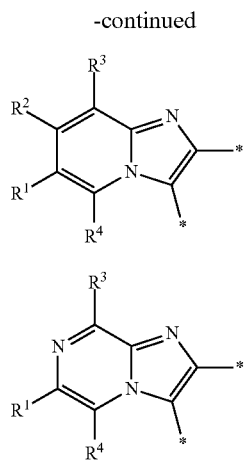

(Ec)

wherein the asterisk (*) represents the site of attachment of E to the remainder of the molecule;

$R^1$ represents hydrogen, halogen, cyano, trifluoromethyl, trifluoromethoxy, —$OR^a$, —$SR^a$, —$SOR^a$, —$SO_2R^a$, —$NR^bR^c$, —$NR^cCOR^d$, —$NR^cCO_2R^d$, —$NHCONR^bR^c$, —$NR^cSO_2R^e$, —$COR^d$, —$CO_2R^d$, —$CONR^bR^c$, —$SO_2NR^bR^c$, or —$S(O)(N—R^b)R^e$; or $C_{1-6}$ alkyl, $C_{3-7}$ cycloalkyl, $C_{4-7}$ cycloalkenyl, aryl, aryl($C_{1-6}$)alkyl, $C_{3-7}$ heterocycloalkyl, $C_{3-7}$ heterocycloalkenyl, heteroaryl, heteroaryl($C_{1-6}$)alkyl, ($C_{3-7}$)heterocycloalkyl($C_{1-6}$)alkyl-aryl-, ($C_{3-7}$)cycloalkyl-heteroaryl-, ($C_{3-7}$)cycloalkyl($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents; or $R^1$ represents ($C_{3-7}$)heterocycloalkenyl-aryl-, which group may be optionally substituted by one or more substituents;

$R^2$ represents hydrogen, halogen, cyano, nitro, hydroxy, trifluoromethyl, trifluoromethoxy or —$OR^a$; or $C_{1-6}$ alkyl optionally substituted by one or more substituents;

$R^3$ and $R^4$ independently represent hydrogen, halogen or trifluoromethyl; or $C_{1-6}$ alkyl, optionally substituted by one or more substituents;

$R^5$ and $R^8$ independently represent hydrogen, halogen, hydroxy, cyano, trifluoromethyl, difluoromethoxy, trifluoromethoxy, —$OR^a$, or $C_{1-6}$ alkylsulphonyl; or $C_{1-6}$ alkyl optionally substituted by one or more substituents;

$R^6$ and $R^7$ independently represent hydrogen, halogen, trifluoromethyl, $C_{1-6}$ alkyl or $C_{1-6}$ alkoxy;

$R^{12}$ represents hydrogen or $C_{1-6}$ alkyl;

$R^a$ represents $C_{1-6}$ alkyl, $C_{3-7}$ cycloalkyl, $C_{3-7}$ heterocycloalkyl, aryl, aryl($C_{1-6}$)alkyl, heteroaryl or heteroaryl($C_{1-6}$)alkyl, any of which groups may be optionally substituted by one or more substituents;

$R^b$ and $R^c$ independently represent hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents; or $R^b$ and $R^c$, when taken together with the nitrogen atom to which they are both attached, represent a heterocyclic moiety selected from azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piper-

4 azin-1-yl, homopiperidin-1-yl, homomorpholin-4-yl, homopiperazin-1-yl, (imino)(oxo)thiazinan-4-yl, (oxo)thiazinan-4-yl and (dioxo)thiazinan-4-yl, any of which groups may be optionally substituted by one or more substituents;

$R^d$ represents hydrogen; or $C_{1-6}$ alkyl, $C_{3-7}$ cycloalkyl, aryl, $C_{3-7}$ heterocycloalkyl or heteroaryl, any of which groups may be optionally substituted by one or more substituents;

$R^e$ represents $C_{1-6}$ alkyl, aryl or heteroaryl, any of which groups may be optionally substituted by one or more substituents;

$R^f$ represents hydrogen; or $C_{1-6}$ alkyl, $C_{3-7}$ cycloalkyl, or $C_{3-7}$ heterocycloalkyl, any of which groups may be optionally substituted by one or more substituents; and $R^g$ represents hydrogen; or $C_{1-6}$ alkyl, $C_{3-7}$ cycloalkyl, $C_{3-7}$ heterocycloalkyl, —CO—($C_{1-6}$)alkyl, or —$SO_2$—($C_{1-6}$)alkyl, any of which groups may be optionally substituted by one or more substituents; or $R^g$ represents —CO—($C_{3-7}$)heterocycloalkyl, —$SO_2$—($C_{3-7}$)cycloalkyl, —$SO_2$—($C_{3-7}$)heterocycloalkyl, —$SO_2$-aryl or —$SO_2$-heteroaryl, any of which groups may be optionally substituted by one or more substituents; or $R^g$ represents heteroaryl or ($C_{2-6}$) alkoxycarbonyl, either of which groups may be optionally substituted by one or more substituents.

The present invention also provides a compound of formula (I) as defined above or an N-oxide thereof, or a pharmaceutically acceptable salt thereof, for use in therapy.

In another aspect, the present invention also provides a compound of formula (I) as defined above or an N-oxide thereof, or a pharmaceutically acceptable salt thereof, for use in the treatment and/or prevention of disorders for which the administration of a modulator of TNFα function is indicated.

In another aspect, the present invention provides a compound of formula (I) as defined above or an N-oxide thereof, or a pharmaceutically acceptable salt thereof for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

In another aspect, the present invention provides for the use of a compound of formula (I) as defined above, or an N-oxide thereof, or a pharmaceutically acceptable salt thereof, for the manufacture of a medicament useful for the treatment and/or prevention of disorders for which the administration of a modulator of TNFα function is indicated.

In another aspect, the present invention provides for the use of a compound of formula (I) as defined above, or an N-oxide thereof, or a pharmaceutically acceptable salt thereof, for the manufacture of a medicament useful for the treatment of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above, or an N-oxide thereof, or a pharmaceutically acceptable salt thereof.

In another aspect, the present invention provides a method for the treatment and/or prevention of an inflammatory or autoimmune disorder, a neurological or neuro-degenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above or an N-oxide thereof, or a pharmaceutically acceptable salt thereof.

Where any of the groups in the compounds of formula (I) above is stated to be optionally substituted, this group may be unsubstituted, or substituted by one or more substituents. Typically, such groups will be unsubstituted, or substituted by one or two substituents. Suitable substitutents for each particular groups of compounds formula (I) are further described here after in the present specification.

The present invention includes within its scope salts of the compounds of formula (I) above. For use in medicine, the salts of the compounds of formula (I) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002.

The present invention includes within its scope solvates of the compounds of formula (I) above. Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

The present invention includes within its scope N-oxides of compounds of formula (I) above. Particular examples of N-oxides according to the present invention include pyrimidine N-oxide and pyridine N-oxide as illustrated in the Examples. The term "alkyl" as used herein refers to aliphatic hydrocarbon groups which may be straight or branched and may comprise 1 to 20 carbon atoms in the chain, suitably 1 to 15 carbon atoms in the chain, more suitably 1 to 10 carbon atoms in the chain. Suitable alkyl groups which may be present on the compounds of use in the invention include straight-chained and branched $C_{1-6}$ alkyl groups, for example $C_{1-4}$ alkyl groups. Illustrative alkyl groups include methyl and ethyl groups, and straight-chained or branched propyl, butyl and pentyl groups. Suitable alkyl groups include methyl, ethyl, n-propyl, and isopropyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The term "$C_{3-7}$ cycloalkyl" as used herein refers to monovalent groups of 3 to 7 carbon atoms derived from a saturated monocyclic hydrocarbon. Suitable $C_{3-7}$ cycloalkyl groups may comprise benzo-fused analogues thereof. Illustrative $C_{3-7}$ cycloalkyl groups include cyclopropyl, cyclobutyl, benzocyclobutenyl, cyclopentyl, indanyl, cyclohexyl and cycloheptyl.

The term "$C_{4-9}$ bicycloalkyl" as used herein refers to monovalent groups of 4 to 9 carbon atoms derived from a saturated bicyclic hydrocarbon. The term "$C_{4-7}$ cycloalkenyl" as used herein refers to monovalent groups of 4 to 7 carbon atoms derived from a partially unsaturated monocyclic hydrocarbon. Illustrative $C_{4-7}$ cycloalkenyl groups include cyclobutenyl, cyclopentenyl, cyclohexenyl and cycloheptenyl.

The term "aryl" as used herein, refers to an unsaturated aromatic carbocyclic group of from 6 to 14 carbon atoms having a single ring (e.g. phenyl) or multiple condensed rings (e.g. naphthyl). Illustrative aryl groups include phenyl.

Illustrative aryl($C_{1-6}$)alkyl groups include benzyl, phenylethyl and phenylpropyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Illustrative heterocycloalkyl groups include oxetanyl, azetidinyl, tetrahydrofuranyl, dihydrobenzo-furanyl, dihydrobenzothienyl, pyrrolidinyl, indolinyl, dihydroisoindolinyl, isoindolinyl, oxazolidinyl, thiazolidinyl, isothiazolidinyl, imidazolidinyl, tetrahydropyranyl, chromanyl, tetrahydro-thiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, hexahydro-[1,2,5]thiadiazolo[2,3-a]pyrazinyl, homopiperazinyl, morpholinyl, benzoxazinyl, thiomorpholinyl, azepanyl, oxazepanyl, diazepanyl, thiadiazepanyl, azocanyl, (imino) (oxo)thiazinanyl, (oxo)thiazinanyl, (dioxo)thiazinanyl, tetrahydrothiophenyl, (oxo)tetrahydrothiophenyl, (dioxo)tetrahydrothiophenyl and (oxo)thiomorpholinyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Illustrative heterocycloalkenyl groups include thiazolinyl, imidazolinyl, dihydropyranyl, dihydrothiopyranyl, 1,2,3,6-tetrahydropyridinyl, 1,2-dihydropyridinyl and 1,2-dihydropyrimidinyl. The term "$C_{4-9}$ heterobicycloalkyl" as used herein refers to a $C_{4-9}$ bicycloalkyl as defined herein, wherein one or more of the carbon atoms have been replaced by one or more heteroatoms selected from oxygen, sulphur and nitrogen. Illustrative heterobicycloalkyl groups include 3-azabicyclo[3.1.0]hexanyl, 2-oxa-5-azabicyclo[2.2.1]heptanyl, 6-azabicyclo[3.2.0]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo-[2.2.2]octanyl, 3-azabicyclo[3.2.1]octanyl, 8-azabicyclo[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl and 3,9-diazabicyclo[4.2.1]nonanyl. Illustrative heterobicycloalky groups additionally include 3,7-dioxa-9-azabicyclo[3.3.1]non-9-yl.

The term "$C_{4-9}$ spiroheterocycloalkyl" as used herein refers to saturated bicyclic ring systems containing 4 to 9 carbon atoms and at least one heteroatom selected from oxygen, sulphur and nitrogen, in which the two rings are linked by a common atom. Illustrative spiroheterocycloalkyl groups include 5-azaspiro[2.3]hexanyl, 5-azaspiro-[2.4]heptanyl, 2-azaspiro[3.3]heptanyl, 2-oxa-6-azaspiro[3.3]heptanyl, 2-oxa-6-azaspiro-[3.4]octanyl, 2-oxa-6-azaspiro[3.5]nonanyl, 7-oxa-2-azaspiro[3.5]nonanyl, 2-oxa-7-azaspiro [3.5]nonanyl and 2,4,8-triazaspiro[4.5]decanyl.

The term "heteroaryl" as used herein represents aromatic carbocyclic groups of from 5 to 14 carbon atoms having a single ring or multiple condensed rings, wherein one or more of the said carbon atoms have been replaced by one or more heteroatoms selected from oxygen, sulphur and nitrogen. Illustrative heteroaryl groups include furyl, benzofuryl, dibenzofuryl, thienyl, benzothienyl, thieno[2,3-c]pyrazolyl, thieno[3,4-b][1,4]dioxinyl, dibenzothienyl, pyrrolyl, indolyl, 2,3-dihydro-1H-isoindolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine atoms.

Where the compounds of formula (I) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto (CH$_2$C=O)↔enol (CH=CHOH) tautomers or amide (NHC=O)↔hydroxyimine (N=COH) tautomers. Formula (I) and the formulae depicted hereinafter are intended to represent all individual tautomers and all possible mixtures thereof, unless stated or shown otherwise.

An illustrative example of a tautomer in accordance with the present invention, is 2-oxo-(1H)-pyridinyl which is a tautomer of 2-hydroxy-pyridinyl.

Another illustrative example of a tautomer in accordance with the present invention, is 2-oxo-(1H)-pyrimidinyl which is a tautomer of 2-hydroxy-pyrimidinyl.

A particular sub-class of compounds in accordance with the present invention is the sub-class of compounds of formula (IA), or an N-oxide thereof, or a pharmaceutically acceptable salt thereof,

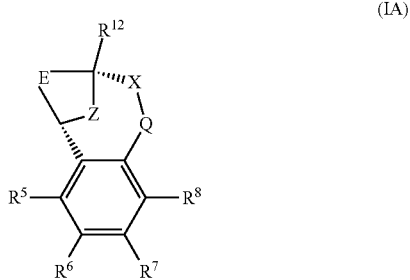

(IA)

wherein E, Z, —X-Q-, R$^5$, R$^6$, R$^7$ R$^8$ and R$^{12}$ are as defined above.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1$H, $^2$H (deuterium) or $^3$H (tritium) atom, preferably $^1$H. Similarly, by way of example, each individual carbon atom present in formula (I), or in the formulae depicted hereinafter, may be present as a $^{12}$C, $^{13}$C or $^{14}$C atom, preferably $^{12}$C.

Generally, —X-Q- represents —O—, —O—C(O)—, —C(O)—O—, —O—C(CH—CN)—, —S—, —SO—, —SO$_2$—, —N(R$^g$)—, —N(R$^f$)—CO—, —CO—N(R$^f$)—, —N(R$^f$)—SO$_2$—, —SO$_2$—N(R$^f$)—, —S(O)(NR$^f$)—, —CH$_2$—CH$_2$—, —O—CH$_2$—, —CH$_2$—O—, —S—CH$_2$—, —SO—CH$_2$—, —SO$_2$—CH$_2$—, CH$_2$—S—, —CH$_2$—SO—, —CH$_2$—SO$_2$—, —N(R$^g$)—CH$_2$—, —CH$_2$—N(R$^f$)—, —S(O)(NR$^f$)—CH$_2$—, —CH$_2$—S(O)(NR$^f$)—, —N(R$^f$)—C(S)—, —N=S(O)(CH$_3$), —O—C(=CH$_2$)— or —S(=N—CN)—, any of which groups may be substituted by one or more substituents.

More generally, —X-Q- represents —O—, —O—C(O)—, —C(O)—O—, —O—C(CH—CN)—, —S—, —SO—, —SO$_2$—, —N(R$^g$)—, —N(R$^f$)—CO—, —CO—N(R$^f$)—, —N(R$^f$)—SO$_2$—, —SO$_2$—N(R$^f$)—, —S(O)(NR$^f$)—, —CH$_2$—CH$_2$—, —O—CH$_2$—, —CH$_2$—O—, —S—CH$_2$—, —SO—CH$_2$—, —SO$_2$—CH$_2$—, CH$_2$—S—, —CH$_2$—SO—, —CH$_2$—SO$_2$—, —N(R$^g$)—CH$_2$—, —CH$_2$—N(R$^g$)—, —S(O)(NR$^f$)—CH$_2$—, —CH$_2$—S(O)(NR$^f$)— or —N(R$^f$)—C(S)—.

Typically, —X-Q- represents —O—, —O—C(O)—, —C(O)—O—, —O—C(CH—CN)—, —S—, —SO—, —SO$_2$—, —N(R$^g$)—, —N(R$^f$)—CO—, —CO—N(R$^f$)—, —N(R$^f$)—SO$_2$—, —SO$_2$—N(R$^f$)—, —S(O)(NR$^f$)—, —CH$_2$—CH$_2$—, —O—CH$_2$—, —CH$_2$—O—, —S—CH$_2$—, —SO—CH$_2$—, —SO$_2$—CH$_2$—, CH$_2$—S—, —CH$_2$—SO—, —CH$_2$—SO$_2$—, —N(R$^g$)—CH$_2$—, —CH$_2$—N(R$^g$)—, —S(O)(NR$^f$)—CH$_2$— or —CH$_2$—S(O)(NR$^f$)—.

In a first embodiment, —X-Q- represents —O—. In a second embodiment, —X-Q- represents —O—C(O)—. In a third embodiment according to the invention, —X-Q- represents —C(O)—O—. In a fourth embodiment, —X-Q- represents —O—C(CH—CN)—. In a fifth embodiment, —X-Q- represents —S—. In a sixth embodiment, —X-Q- represents —SO—. In a seventh embodiment, —X-Q- represents —SO$_2$—. In an eighth embodiment, —X-Q- represents —N(R$^g$)—. In a ninth embodiment, —X-Q- represents —N(R$^f$)—CO—. In a tenth embodiment, —X-Q- represents —CO—N(R$^f$)—. In an eleventh embodiment, —X-Q- represents —N(R$^f$)—SO$_2$—. In a twelfth embodiment, —X-Q- represents —SO$_2$—N(R$^f$)—. In a thirteenth embodiment, —X-Q- represents —S(O)(NR$^f$)—. In a fourteenth embodiment, —X-Q- represents optionally substituted —CH$_2$—CH$_2$—. In one aspect of that embodiment, —X-Q- represents —CH$_2$—CH$_2$—. In a fifteenth embodiment, —X-Q- represents—optionally substituted —O—CH$_2$—. In one aspect of that embodiment, —X-Q- represents —O—CH$_2$—. In a sixteenth embodiment, —X-Q- represents optionally substituted —CH$_2$—O—. In one aspect of that embodiment, —X-Q- represents —CH$_2$—O—. In a seventeenth embodiment, —X-Q- represents optionally substituted —S—CH$_2$—. In one aspect of that embodiment, X-Q- represents —S—CH$_2$—. In an eighteenth embodiment, —X-Q- represents optionally substituted —SO—CH$_2$—. In one aspect of that embodiment, —X-Q- represents —SO—CH$_2$—. In a nineteenth embodiment, —X-Q- represents optionally substituted —SO$_2$—CH$_2$—. In one aspect of that embodiment, —X-Q- represents —SO$_2$—CH$_2$—. In a twentieth embodiment, —X-Q- represents optionally substituted —CH$_2$—S—. In one aspect of that embodiment, —X-Q- represents optionally substituted —CH₂—S—. In a twenty-first embodiment, —X-Q- represents optionally substituted —CH₂—SO—. In one aspect of that embodiment, —X-Q- represents —CH₂—SO—. In a twenty-second embodiment, —X-Q- represents optionally substituted —CH₂—SO₂—. In one aspect of that embodiment, —X-Q- represents —CH₂—SO₂—. In a twenty-third embodiment, —X-Q- represents optionally substituted —N(R$^g$)—CH₂—. In one aspect of that embodiment, —X-Q- represents —N(R$^g$)—CH₂—. In a twenty-fourth embodiment, —X-Q- represents optionally substituted —CH₂—N(R$^g$)—. In one aspect of that embodiment, —X-Q- represents —CH₂—N(R$^g$)—. In a twenty-fifth embodiment, —X-Q- represents optionally substituted —S(O)(NR$^f$)—CH₂—. In one aspect of that embodiment, —X-Q- represents —S(O)(NR$^f$)—CH₂—. In a twenty-sixth embodiment, —X-Q- represents optionally substituted —CH₂—S(O)(NR$^f$)—. In one aspect of that embodiment, —X-Q- represents —CH₂—S(O)(NR$^f$)—. In a twenty-seventh embodiment, —X-Q- represents —N(R$^f$)—C(S)—. In a twenty-eighth embodiment, —X-Q- represents —N=S(O)(CH₃)—. In a twenty-ninth embodiment, —X-Q- represents —O—C(=CH₂)—. In a thirtieth embodiment —X-Q- represents —S(=N—CN)—. Typical substituents on —X-Q- include halogen, (C$_{1-6}$)alkyl and carboxy. Additional substituents on —X-Q- include trifluoromethyl. Further substituents on —X-Q-include (C$_{2-6}$)alkylcarbonyl, (C$_{2-6}$)alkoxycarbonyl, and hydroxy(C$_{1-6}$)alkyl.

Particular examples of substituents on —X-Q- include fluoro, methyl, carboxy, trifluoromethyl, methylcarbonyl, deuterated methyl, ethoxycarbonyl, hydroxyisopropyl, and hydroxymethyl.

Suitable substituents on —X-Q- include fluoro, methyl and carboxy.

Appropriately, —X-Q- represents —O—, —O—C(O)—, —O—C(CH—CN)—, —S—, —SO—, —SO₂—; or —N(R$^g$)—, —N(R$^f$)—CO—, —N(R$^f$)—SO₂—, O—CH₂—, —CH₂—S—, —CH₂—SO—, —CH₂—SO₂—, —N(R$^g$)—CH₂—, —N(R$^f$)—C(S)—, —N=S(O)(CH₃)—, —O—C(=CH₂)— or —S(=N—CN)—, any of which groups may be optionally substituted.

Particularly, —X-Q- represents —O—, —O—C(O)—, —O—C(CH—CN)—, —S—, —SO—, —SO₂—, —N(R$^g$)—, —N(R$^f$)—CO—, —N(R$^g$)—CH₂—, or —N(R$^f$)—C(S)—, any of which groups may be optionally substituted.

Suitably, —X-Q- represents —O—, —O—C(O)—, —O—C(CH—CN)—, —N(R$^g$)—, —N(R$^f$)—CO—, —N(R$^g$)—CH₂—, or —N(R$^f$)—C(S)—.

Typically, —X-Q- represents —N(R$^f$)—C(O)—, —O—C(O)— or —O—C(CH—CN)—.

Appositely, —X-Q- represents —N(R$^f$)—C(O)—.

Generally, Z represents methylene.

Generally, E represents a fused heteroaromatic ring system of formula (Ea) or a fused heteroaromatic ring system of formula (Eb).

In a first embodiment according to the present invention, E represents a fused heteroaromatic ring system of formula (Ea).

In a second embodiment according to the present invention, E represents a fused heteroaromatic ring system of formula (Eb).

In a third embodiment according to the present invention, E represents a fused heteroaromatic ring system of formula (Ec).

Particular sub-classes of compounds in accordance with the present invention include compounds of formula (IB), (IC), and (ID).

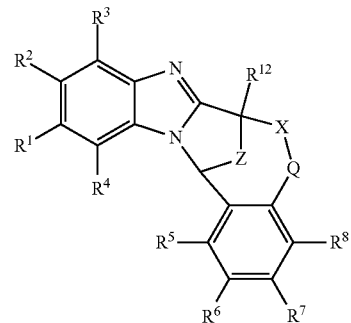

(IB)

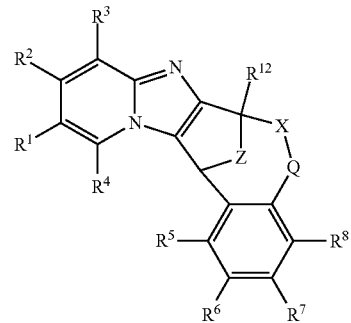

(IC)

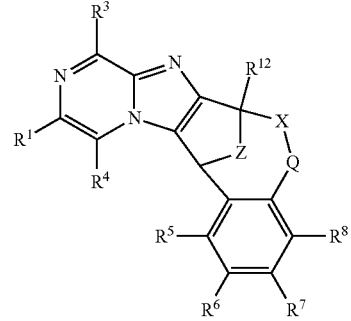

(ID)

wherein —X-Q-, Z, R$^1$, R$^2$, R$^3$, R$^4$, R$^5$, R$^6$, R$^7$, R$^8$ and R$^{12}$ are as defined above.

Particular sub-classes of compounds in accordance with the present invention include compounds of formula (IB) and (IC), wherein —X-Q-, Z, R$^1$, R$^2$, R$^3$, R$^4$, R$^5$, R$^6$, R$^7$, R$^8$ and R$^{12}$ are as defined above.

A particular sub-class of compounds in accordance with the present invention is the sub-class of compounds of formula (IB), wherein —X-Q-, Z, R$^1$, R$^2$, R$^3$, R$^4$, R$^5$, R$^6$, R$^7$, R$^8$ and R$^{12}$ are as defined above.

A further particular sub-class of compounds in accordance with the present invention is the sub-class of compounds of formula (IC), wherein —X-Q-, Z, R$^1$, R$^2$, R$^3$, R$^4$, R$^5$, R$^6$, R$^7$, R$^8$ and R$^{12}$ are as defined above.

Generally, R$^1$ represents hydrogen, halogen, or cyano; or aryl, C$_{3-7}$ heterocycloalkyl, heteroaryl, (C$_{3-7}$)cycloalkyl-heteroaryl, (C$_{3-7}$)heterocycloalkyl-heteroaryl, (C$_{4-9}$)bicycloalkyl-heteroaryl, (C$_{4-9}$)heterobicycloalkyl-heteroaryl-, (C$_{4-9}$)spiroheterocycloalkyl-heteroaryl-, (C$_{3-7}$)heterocycloalkenyl, or (C$_{3-7}$)heterocycloalkenyl-aryl-, any of which groups may be optionally substituted by one or more substituents.

Typically, R$^1$ represents hydrogen, halogen, or cyano; or aryl, C$_{3-7}$ heterocycloalkyl, heteroaryl, (C$_{3-7}$)cycloalkyl-heteroaryl, (C$_{3-7}$)heterocycloalkyl-heteroaryl, (C$_{4-9}$)bicycloalkyl-heteroaryl, $(C_{4-9})$heterobicycloalkyl-heteroaryl- or $(C_{4-9})$spiroheterocycloalkyl-heteroaryl-, any of which groups may be optionally substituted by one or more substituents.

More typically, $R^1$ represents halogen or cyano; or aryl, heteroaryl, $(C_{3-7})$cycloalkyl-heteroaryl, $(C_{3-7})$heterocycloalkyl-heteroaryl, $(C_{4-9})$heterobicycloalkyl-heteroaryl, $(C_{3-7})$heterocycloalkyl, $(C_{3-7})$heterocycloalkenyl, or $(C_{3-7})$heterocycloalkenyl-aryl, any of which groups may be optionally substituted by one or more substituents.

Even more typically, $R^1$ represents halogen or cyano; or aryl, heteroaryl, $(C_{3-7})$cycloalkyl-heteroaryl, $(C_{3-7})$heterocycloalkyl-heteroaryl, or $(C_{4-9})$heterobicycloalkyl-heteroaryl any of which groups may be optionally substituted by one or more substituents.

Particularly, $R^1$ represents hydrogen, halogen or cyano; or aryl, heteroaryl, $(C_{3-7})$heterocycloalkyl-heteroaryl, any of which groups may be optionally substituted by one or more substituents.

More particularly, $R^1$ represents halogen or cyano; or aryl, heteroaryl, or $(C_{3-7})$cycloalkyl-heteroaryl, any of which groups may be optionally substituted by one or more substituents.

Suitably, $R^1$ represents hydrogen; or $R^1$ represents aryl or heteroaryl, either of which groups may be optionally substituted by one or more substituents.

Appositely, $R^1$ represents aryl or heteroaryl, either of which groups may be optionally substituted by one or more substituents.

More suitably, $R^1$ represents heteroaryl, either of which groups may be optionally substituted by one or more substituents. In a first embodiment, $R^1$ represents hydrogen.

In a second embodiment, $R^1$ represents halogen. In one aspect of that embodiment, $R^1$ represents bromo. In another aspect of that embodiment, $R^1$ represents chloro.

In a third embodiment, $R^1$ represents cyano.

In a fourth embodiment, $R^1$ represents optionally substituted aryl. In one aspect of that embodiment, $R^1$ represents optionally substituted phenyl.

In fifth embodiment, $R^1$ represents optionally substituted $C_{3-7}$ heterocycloalkyl. In one aspect of that embodiment, $R^1$ represents azetidinyl.

In a sixth embodiment, $R^1$ represents optionally substituted heteroaryl. In one aspect of that embodiment, $R^1$ represents optionally substituted pyrimidinyl. In another aspect of that embodiment, $R^1$ represents optionally substituted pyridinyl.

In a seventh embodiment, $R^1$ represents optionally substituted $(C_{3-7})$cycloalkyl-heteroaryl-. In a first aspect of that embodiment, $R^1$ represents optionally substituted cyclohexylpyrazolyl-. In a second aspect of that embodiment, $R^1$ represents optionally substituted cyclohexylpyridinyl-. In a third aspect of that embodiment, $R^1$ represents optionally substituted cyclopropylpyrimidinyl-. In a fourth aspect of that embodiment, $R^1$ represents optionally substituted cyclobutylpyrimidinyl-. In a fifth aspect of that embodiment, $R^1$ represents optionally substituted cyclopentylpyrimidinyl-. In a sixth aspect of that embodiment, $R^1$ represents optionally substituted cyclohexylpyrimidinyl-.

In a seventh aspect of that embodiment, $R^1$ represents optionally substituted cyclohexyl-pyrazinyl-. In an eighth aspect of that embodiment, $R^1$ represents optionally substituted cyclopropylpyridinyl.

In an eighth embodiment, $R^1$ represents optionally substituted $(C_3-7)$-heterocycloalkyl-heteroaryl-. In a first aspect of that embodiment, $R^1$ represents optionally substituted pyrrolidinylpyridinyl-. In a second aspect of that embodiment, $R^1$ represents optionally substituted tetrahydropyranylpyridinyl-. In a third aspect of that embodiment, $R^1$ represents optionally substituted piperidinylpyridinyl-. In a fourth aspect of that embodiment, $R^1$ represents optionally substituted piperazinylpyridinyl-. In a fifth aspect of that embodiment, $R^1$ represents optionally substituted morpholinylpyridinyl-. In a sixth aspect of that embodiment, $R^1$ represents optionally substituted thiomorpholinyl-pyridinyl-. In a seventh aspect of that embodiment, $R^1$ represents optionally substituted diazepanylpyridinyl-. In an eighth aspect of that embodiment, $R^1$ represents optionally substituted oxetanylpyrimidinyl-. In a ninth aspect of that embodiment, $R^1$ represents optionally substituted azetidinylpyrimidinyl-. In a tenth aspect of that embodiment, $R^1$ represents optionally substituted tetrahydrofuranylpyrimidinyl-. In an eleventh aspect of that embodiment, $R^1$ represents optionally substituted pyrrolidinylpyrimidinyl-. In a twelfth aspect of that embodiment, $R^1$ represents optionally substituted tetrahydropyranyl-pyrimidinyl-. In a thirteenth aspect of that embodiment, $R^1$ represents optionally substituted piperidinylpyrimidinyl-. In a fourteenth aspect of that embodiment, $R^1$ represents optionally substituted piperazinylpyrimidinyl-. In a fifteenth aspect of that embodiment, $R^1$ represents optionally substituted morpholinylpyrimidinyl-. In a sixteenth aspect of that embodiment, $R^1$ represents optionally substituted thiomorpholinyl-pyrimidinyl-. In a seventeenth aspect of that embodiment, $R^1$ represents optionally substituted azepanylpyrimidinyl-. In an eighteenth aspect of that embodiment, $R^1$ represents optionally substituted oxazepanylpyrimidinyl-. In a nineteenth aspect of that embodiment, $R^1$ represents optionally substituted diazepanylpyrimidinyl-. In a twentieth aspect of that embodiment, $R^1$ represents optionally substituted thiadiazepanyl-pyrimidinyl-. In a twenty-first aspect of that embodiment, $R^1$ represents optionally substituted oxetanylpyrazinyl-. In a twenty-second aspect of that embodiment, $R^1$ represents optionally substituted piperidinylpyrazinyl-. In a twenty-third aspect of that embodiment, $R^1$ represents optionally substituted tetrahydropyranylpyridinyl-. In twenty-third aspect of that embodiment, $R^1$ represents (imino)(oxo)thiazinanyl-pyrimidinyl-. In twenty-fourth aspect of that embodiment, $R^1$ represents (oxo)thiazinanyl-pyrimidinyl-. In twenty-fifth aspect of that embodiment, $R^1$ represents (dioxo)thiazinanyl-pyrimidinyl-. In a twenty-sixth aspect of that embodiment, $R^1$ represents substituted (dioxo)tetrahydrothiophenyl-pyrimidinyl-. In a twenty-seventh aspect of that embodiment, $R^1$ represents substituted tetrahydrothiophenyl-pyrimidinyl-. In a twenty-eighth aspect of that embodiment, $R^1$ represents substituted (dioxo)thiomorpholinyl-pyrimidinyl-. In a twenty-ninth aspect of that embodiment, $R^1$ represents substituted azetidinyl-pyrazolyl. In a thirtieth aspect of that embodiment, $R^1$ represents substituted (oxo) tetrahydrothiophenyl-pyrimidinyl. In a thirty-first aspect, $R^1$ represents substituted (oxo)thiomorpholinyl.

In a ninth embodiment, $R^1$ represents optionally substituted $(C_{4-9})$bicycloalkyl-heteroaryl-.

In a tenth embodiment, $R^1$ represents optionally substituted $(C_{4-9})$-heterobicycloalkyl-heteroaryl-. In one aspect of that embodiment, $R^1$ represents optionally substituted (3,7-dioxa-9-azabicyclo[3.3.1]non-9-yl)-pyrimidinyl-. In a second aspect of this embodiment, $R^1$ represents optionally substituted (2-oxa-5-azabicyclo[2.2.1]heptanyl)-pyrimidinyl-. In a third aspect of that embodiment, $R^1$ represents optionally substituted (3-oxa-8-azabicyclo[3.2.1]oct-8-yl)-pyrimidinyl-. In a fourth aspect, $R^1$ represents optionally substituted (3,6-diazabicyclo[3.2.2]nonanyl)-pyrimidinyl-.

In an eleventh embodiment, $R^1$ represents optionally substituted $(C_{4-9})$-spiroheterocycloalkyl-heteroaryl-.

In a twelfth embodiment, $R^1$ represents optionally substituted $(C_{3-7})$heterocycloalkenyl. In one aspect of that embodiment, $R^1$ represents optionally substituted 1,2-dihydropyridinyl. In a second aspect of that embodiment, $R^1$ represents optionally substituted 1,2-dihydropyrimidinyl.

In a thirteenth embodiment, $R^1$ represents optionally substituted $(C_{3-7})$heterocycloalkenyl-aryl. In one aspect of that embodiment, $R^1$ represents optionally substituted imidazolyl-phenyl.

Typically, $R^1$ represents chloro or cyano; or phenyl, pyridinyl, pyrimidinyl, cyclopropyl-pyridinyl-, cyclobutyl-pyrimidinyl, cyclobutyl-pyridinyl-, cyclohexyl-pyrimidinyl-, (3,7-dioxa-9-azabicyclo[3.3.1]non-9-yl)-pyrimidinyl-, azetidinyl-pyrimidinyl-, azetidinyl-pyridinyl, pyrrolidinyl-pyridinyl-, pyrrolidinyl-phenyl-, piperazinyl-pyridinyl-, piperazinyl-pyrimidinyl-, pyrazolyl-, morpholinyl-pyrimidinyl-, thiomorpholinyl-pyrimidinyl-, (dioxo)thiomorpholinyl-pyrimidinyl-, (oxo)thiomorpholinyl-pyrimidinyl-, oxetanyl-pyridinyl-, oxetanyl-pyrimidinyl-, imidazolyl-phenyl, diazepanyl-pyrimidinyl-, (oxo)tetrahydrothiophenyl-pyrimidinyl-, (dioxo)tetrahydrothiophenyl-pyrimidinyl-, tetrahydrothiophenyl-pyrimidinyl azetidinyl-pyrazolyl-, (2-oxa-5-azabicyclo[2.2.1]heptanyl)-pyrimidinyl-, (3-oxa-8-azabicyclo[3.2.1]oct-8-yl)-pyrimidinyl-, (3,6-diazabicyclo[3.2.2]nonanyl)-pyrimidinyl-, tetrahydropyranyl-pyrimidinyl, azetidinyl, 1,2-dihydropyridinyl, or 1,2-dihydropyrimidinyl, any of which groups may be optionally substituted by one or more substituents.

Particularly, $R^1$ represents hydrogen, chloro or cyano; or phenyl, pyridinyl, or pyrimidinyl, any of which groups may be optionally substituted by one or more substituents.

Illustratively, $R^1$ represents pyrimidinyl, which may be optionally substituted by one or more substituents.

Typical examples of optional substituents on $R^1$ include one, two or three substituents independently selected from halogen, halo$(C_{1-6})$alkyl, cyano, cyano$(C_{1-6})$alkyl, nitro$(C_{1-6})$alkyl, $C_{1-6}$ alkyl, phosphate$(C_{1-6})$alkyl, $(C_{3-7})$cycloalkyl, trifluoromethyl, trifluoroethyl, $C_{2-6}$ alkenyl, hydroxy, hydroxy$(C_{1-6})$alkyl, $C_{1-6}$ alkoxy, $(C_{1-6})$alkoxy$(C_{1-6})$alkyl, trifluoroethoxy, carboxy$(C_{3-7})$cycloalkyloxy, $C_{1-6}$ alkylthio, $C_{1-6}$ alkylsulphonyl, $(C_{1-6})$alkylsulphonyl$(C_{1-6})$alkyl, oxo, amino, amino-$(C_{1-6})$alkyl, $C_{1-6}$ alkylamino, di$(C_{1-6})$alkylamino, $(C_{1-6})$alkoxy$(C_{1-6})$alkylamino, N-[$(C_{1-6})$alkyl]-N-[hydroxy$(C_{1-6})$alkyl]amino, $(C_{2-6})$alkylcarbonylamino$(C_{1-6})$alkyl, $C_{1-6}$ alkylsulphonylamino, N-[$(C_{1-6})$alkyl]-N-[$(C_{1-6})$alkylsulphonyl]amino, bis[$(C_{1-6})$alkyl-sulphonyl]amino, N-[$(C_{1-6})$alkyl]-N-[carboxy$(C_{1-6})$alkyl]amino, carboxy$(C_{3-7})$cycloalkyl-amino, carboxy$(C_{3-7})$cycloalkyl$(C_{1-6})$alkylamino, formyl, $C_{2-6}$ alkylcarbonyl, $(C_{2-6})$alkyl-carbonyloxy$(C_{1-6})$alkyl, carboxy, carboxy$(C_{1-6})$alkyl, $C_{2-6}$ alkoxycarbonyl, $C_{2-6}$ alkoxycarbonyl$(C_{1-6})$alkyl, morpholinyl$(C_{1-6})$alkoxycarbonyl, $C_{2-6}$ alkoxycarbonyl-methylidenyl, aminocarbonyl, aminosulphonyl, $(C_{1-6})$alkylsulphoximinyl and [$(C_{1-6})$alkyl][N-$(C_{1-6})$alkyl]sulphoximinyl. Additional examples of optional substituents on $R^1$ include $C_{1-6}$ alkyl phosphate-$C_{1-6}$ alkyl, sulphate-$C_{1-6}$ alkyl, carboxy$(C_{1-6})$alkyl-carbonyloxy-$C_{1-6}$ alkyl, and phosphate-methoxy-$C_{1-6}$ alkyl. A further additional example of optional substituent on $R^1$ include $(C_{2-6})$ alkoxycarbonyl-amino-$C_{1-6}$ alkyl. Additional optional substituents on $R^1$ include difluoromethyl, $(C_{1-6})$alkyl-sulphinyl-amino-, di$(C_{1-6})$alkylamino $(C_{1-6})$alkyl, di$(C_{1-6})$alkenylamino $(C_{1-6})$alkyl, $C_{1-6}$ alkylsulphonyl-amino-$C_{1-6}$ alkyl, and tetrahydrofuranyl.

Illustrative examples of optional substituents on $R^1$ include one, two or three substituents independently selected from halogen, cyano, cyano$(C_{1-6})$alkyl, $C_{1-6}$ alkyl, difluoromethyl, trifluoromethyl, hydroxy, (hydroxy)$(C_{1-6})$alkyl, amino, (amino)$(C_{1-6})$ alkyl, $C_{1-6}$ alkoxy, $(C_{1-6})$ alkoxy$(C_{1-6})$alkyl, $C_{2-6}$ alkylcarbonyl, $C_{2-6}$ alkoxycarbonyl, $(C_{2-6})$ alkoxycarbonyl-amino-$C_{1-6}$ alkyl, phosphate$(C_{1-6})$alkyl, $C_{1-6}$ alkylthio, $C_{1-6}$ alkylsulphonyl, oxo, $(C_{1-6})$alkylsulphoximinyl, $(C_{1-6})$alkylsulphinyl-amino-, di$(C_{1-6})$alkylamino $(C_{1-6})$alkyl, $(C_{2-6})$alkylcarbonylamino$(C_{1-6})$alkyl, di$(C_{1-6})$alkenylamino $(C_{1-6})$alkyl, $(C_{2-6})$alkylcarbonylamino $(C_{1-6})$alkyl, $C_{1-6}$ alkylsulphonyl-amino-$C_{1-6}$ alkyl, tetrahydrofuranyl, sulphate$(C_{1-6})$alkyl, and carboxy-$(C_{1-6})$alkylcarbonyloxy-$(C_{1-6})$alkyl.

Particular examples of optional substituents on $R^1$ include one, two or three substituents independently selected from $C_{1-6}$ alkyl, trifluoromethyl, hydroxy, (hydroxy)$(C_{1-6})$ alkyl, (amino)$(C_{1-6})$ alkyl, $C_{1-6}$ alkoxy, $(C_{1-6})$ alkoxy$(C_{1-6})$alkyl, $(C_{2-6})$ alkoxycarbonyl-amino-$C_{1-6}$ alkyl, phosphate$(C_{1-6})$alkyl, $C_{1-6}$ alkylsulphonyl, oxo and $(C_{1-6})$alkylsulphoximinyl.

Suitable examples of optional substituents on $R^1$ include one, two or three substituents independently selected from $C_{1-6}$ alkyl, hydroxy, (hydroxy)$(C_{1-6})$ alkyl, $C_{1-6}$ alkoxy, $(C_{1-6})$ alkoxy$(C_{1-6})$alkyl, phosphate$(C_{1-6})$alkyl, $C_{1-6}$ alkylsulphonyl, oxo and $(C_{1-6})$alkylsulphoximinyl.

Particular examples of optional substituents on $R^1$ include one, two or three substituents independently selected from (hydroxy)$(C_{1-6})$ alkyl and $(C_{1-6})$ alkoxy$(C_{1-6})$alkyl.

Typical examples of particular substituents on $R^1$ include one, two or three substituents independently selected from fluoro, chloro, fluoromethyl, fluoroisopropyl, cyano, cyanoethyl, nitromethyl, methyl, ethyl, isopropyl, phosphate-isopropyl, isopropylmethyl, cyclopropyl, cyclobutyl, trifluoromethyl, trifluoroethyl, ethenyl, hydroxy, hydroxymethyl, hydroxyisopropyl, methoxy, isopropoxy, methoxyisopropyl, trifluoro-ethoxy, carboxycyclobutyloxy, methylthio, methylsulphonyl, methylsulphonylmethyl, methylsulphonylethyl, oxo, amino, aminomethyl, aminoisopropyl, methylamino, dimethylamino, methoxyethylamino, N-(hydroxyethyl)-N-(methyl)amino, acetylaminomethyl, methylsulphonylamino, N-methyl-N-(methylsulphonyl)amino, bis(methylsulphonyl)amino, N-(carboxyethyl)-N-(methyl)amino, carboxycyclopentylamino, carboxycyclopropylmethylamino, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyaminocarbonyl, tetrazolyl, tetrazolylmethyl, hydroxyoxadiazolyl, aminocarbonyl, aminosulphonyl, methylsulphoximinyl and (methyl)(N-methyl)sulphoximinyl. Additional typical examples of optional substituents on $R^1$ include ethyl phosphate-isopropyl, sulphate-isopropyl, carboxy-ethyl-carbonyloxy-isopropyl, and phosphate-methoxy-isopropyl. A further additional typical example of substituents on $R^1$ include (tert-butoxycarbonyl)amino-isopropyl. Other additional typical examples of substituents on $R^1$ include (tert-butyl)carbonyl, methoxycarbonylamino-isopropyl, dimethylaminoisopropyl, (tert-butyl)sulphinyl-amino, (tert-butyl)sulphonylamino, methylsulphonylaminoisopropyl, methylcarbonylamino-isopropyl, cyanoisopropyl, difluoromethyl, tetrahydrofuranyl, di(propenyl)aminoisopropyl and hydroxyisobutyl.

Appropriate examples of optional substituents on $R^1$ include one, two or three substituents independently selected from methyl, difluoromethyl, trifluoromethyl, hydroxy, hydroxyisopropyl, methoxy, methoxyisopropyl, phosphate-isopropyl, (tert-butoxycarbonyl)amino-isopropyl, aminoisopropyl, dimethylaminoisopropyl, methyl-sulphonyl, methylsulphoximinyl, oxo, tert-butoxycarbonyl, (methoxycarbonyl)amino-isopropyl, methylthio, (tert-butyl)sulphinyl-amino, amino, (tert-butyl)sulphonyl-amino, methylsulphonylamino-isopropyl, methylcarbonylamino-isopropyl, fluoro, cyano, cyanoisopropyl, tetrahydrofuranyl, di(propenyl)aminoisopropyl, sulphate-isopropyl, carboxy-ethyl-carbonyloxy-isopropyl and (hydroxy)isobutyl.

Illustrative examples of optional substituents on $R^1$ include one, two or three substituents independently selected from methyl, trifluoromethyl, hydroxy, hydroxyisopropyl, methoxy, methoxyisopropyl, phosphate-isopropyl, (tert-butoxycarbonyl)amino-isopropyl, aminoisopropyl, methylsulphonyl and methylsulphoximinyl.

Suitable examples of optional substituents on $R^1$ include one, two or three substituents independently selected from methyl, hydroxy, hydroxyisopropyl, methoxy, methoxyisopropyl, phosphate-isopropyl, methyl-sulphonyl and methylsulphoximinyl.

Particular examples of substituents on $R^1$ include one, two or three substituents independently selected from hydroxyisopropyl and methoxyisopropyl.

In a particular embodiment, $R^1$ is substituted by hydroxy $(C_{1-6})$alkyl. In one aspect of that embodiment, $R^1$ is substituted by hydroxyisopropyl. In a particular aspect of that embodiment, $R^1$ is substituted by 2-hydroxyprop-2-yl.

In another particular embodiment, $R^1$ is substituted by $(C_{1-6})$ alkoxy$(C_{1-6})$alkyl. In one aspect of that embodiment, $R^1$ is substituted by methoxyisopropyl. In a particular aspect of this embodiment, $R^1$ is substituted by 2-methoxyprop-2-yl.

Illustrative values of $R^1$ include chloro, cyano, methylsulphonyl-phenyl, methylsulphoximinyl-phenyl, (dihydroxy)(methyl)cyclobutylpyrimidinyl, hydroxyisopropylpyridinyl, hydroxyisopropylpyrimidinyl, (methyl)(hydroxyisopropyl)pyrimidinyl, phosphate-isopropylpyrimidinyl, methoxypyridinyl, methoxyisopropylpyrimidinyl, 2-oxo-pyridin-(1H)-yl, (tert-butoxycarbonyl)aminoisopropyl-pyrimidinyl, aminoisopropylpyrimidinyl, (3,7-dioxa-9-azabicyclo[3.3.1]non-9-yl)-pyrimidinyl, (hydroxy)(trifluoromethyl)azetidinyl-pyrimidinyl, (methylsulphonyl)(methyl)phenyl, (methyl)(hydroxyisopropyl)pyridinyl, [(hydroxy)(trifluoromethyl)azetidinyl](methyl)pyrimidinyl methylsulphonylcyclopropylpyridinyl, (dimethyl)(hydroxyisopropyl)pyrimidinyl, (hydroxyisopropyl)(trifluoromethyl)pyrimidinyl, (tert-butoxycarbonyl)(hydroxy)pyrrolidine-pyridinyl, (hydroxy)pyrrolidine-pyridinyl, (methoxycarbonyl)aminoisopropyl-pyrimidinyl, piperazinylpyridinyl, (methylsulphonyl)piperazinyl-pyridinyl, (dimethylamino)isopropylpyrimidinyl, (oxo)piperazinylpyrimidinyl, (N-methyl)pyrazolyl, (methylthio)(methyl)phenyl, morpholinylpyrimidinyl, ((tert-butyl)sulphinylamino)cyclobutylpyridinyl, (amino)cyclobutylpyridinyl, ((tert-butyl)sulphinylamino)oxetanylpyridinyl, (amino)oxetanylpyridinyl, ((tert-butyl)sulphonylamino)oxetanylpyridinyl, pyrrolidinylpyridinyl, (dimethyl)imidazolylphenyl, (methylsulphonyl)aminoisopropylpyrimidinyl, methylcarbonylaminoisopropylpyrimidinyl, pyrrolidinyl-phenyl, (oxo) diazepanylpyrimidinyl, (hydroxy)(methyl)azetidinyl-pyrimidinyl, thiomorpholinylpyrimidinyl, (oxo) thiomorpholinylpyrimidinyl, (dioxo) thiomorpholinylpyrimidinyl, (difluoro)(hydroxy) cyclohexylpyrimidinyl, (hydroxy)(oxo) tetrahydrothiophenyl-pyrimidinyl, (hydroxy)(dioxo) tetrahydrothiophenyl-pyrimidinyl, (hydroxy) tetrahydrothiophenyl-pyrimidinyl, (hydroxy) oxetanylpyrimidinyl, (methylsulphonyl)azetidinyl-2,5-pyrazolyl, (oxo)(methyl)-1,2-dihydropyridinyl, (oxo)-1,2-dihydropyrimidinyl, (dihydroxy)(methyl)cyclohexylpyrimidinyl, cyanoisopropylpyrimidinyl, (cyano)(methyl)azetidinylpyrimidinyl, (2-oxa-5-azabicyclo[2.2.1]heptanyl)-pyrimidinyl-, (3-oxa-8-azabicyclo[3.2.1]oct-8-yl)-pyrimidinyl-, (oxo)(3,6-diazabicyclo[3.2.2]nonanyl)-pyrimidinyl-, (hydroxyisopropyl)azetidinyl, (difluoro) azetidinylpyrimidinyl, tetrahydropyranylpyrimidinyl, methylsulphoxyminylpyridinyl, (difluoromethyl)(hydroxyisopropyl)pyrimidinyl, (tetrahydrofuranyl)(hydroxyisopropyl)pyrimidinyl, di(propenyl)aminoisopropylpyrimidinyl, sulphate-isopropylpyrimidinyl, carboxy-ethyl-carbonyloxy-isopropyl-pyrimidinyl and (hydroxy)isobutylpyrimidinyl.

Specific values of $R^1$ include chloro, methylsulphonyl-phenyl, methylsulphoximinyl-phenyl, (dihydroxy)(methyl)cyclobutylpyrimidinyl, hydroxyisopropylpyridinyl, hydroxyisopropylpyrimidinyl, (methyl)(hydroxyisopropyl)pyrimidinyl, phosphate-isopropylpyrimidinyl, methoxypyridinyl, methoxyisopropylpyrimidinyl, 2-oxo-pyridin-(1H)-yl, (tert-butoxycarbonyl)aminoisopropyl-pyrimidinyl, aminoisopropylpyrimidinyl, (3,7-dioxa-9-azabicyclo[3.3.1]non-9-yl)-pyrimidinyl, (hydroxy)(trifluoromethyl)azetidinyl-pyrimidinyl, (methylsulphonyl)(methyl)phenyl and (methyl)(hydroxyisopropyl)pyridinyl.

Particular values of $R^1$ include methylsulphonyl-phenyl, methylsulphoximinyl-phenyl, (dihydroxy)(methyl)cyclobutylpyrimidinyl, hydroxyisopropylpyridinyl, hydroxyisopropylpyrimidinyl, (methyl)(hydroxyisopropyl)pyrimidinyl; phosphate-isopropylpyrimidinyl, methoxypyridinyl, methoxyisopropylpyrimidinyl and 2-oxo-pyridin-(1H)-yl.

Selected values of $R^1$ include hydroxyisopropylpyrimidinyl, particularly 2-(2-hydroxy-propan-2-yl)-pyrimidin-5-yl; methoxyisopropylpyrimidinyl, particularly 2-(2-methoxy-propan-2-yl)-pyrimidin-5-yl; aminoisopropylpyrimidinyl, particularly 2-(2-amino-propan-2-yl)-pyrimidin-5-yl; and phosphate-isopropylpyrimidinyl, particularly 2-(2-phosphate-propane-2-yl)-pyrimidin-5-yl.

In one embodiment, $R^1$ represents 2-(2-hydroxy-propan-2-yl)-pyrimidin-5-yl. In another embodiment, $R^1$ represents 2-(2-amino-propan-2-yl)-pyrimidin-5-yl. In a further embodiment, $R^1$ represents 2-(2-phosphate-propane-2-yl)-pyrimidin-5-yl.

Illustrative values of $R^1$ include hydroxyisopropylpyrimidinyl, particularly 2-(2-hydroxy-propan-2-yl)-pyrimidin-5-yl, and methoxyisopropylpyrimidinyl, particularly 2-(2-methoxy-propan-2-yl)-pyrimidin-5-yl.

Typically, $R^2$ represents hydrogen, halogen, trifluoromethyl, trifluoromethoxy or —$OR^a$; or $C_{1-6}$ alkyl optionally substituted by one or more substituents.

Suitably, $R^2$ represents hydrogen or halogen.

In a first embodiment, $R^2$ represents hydrogen. In a second embodiment, $R^2$ represents halogen. In one aspect of that embodiment, $R^2$ represents fluoro. In another aspect of that embodiment, $R^2$ represents chloro. In a third embodiment, $R^2$ represents cyano. In a fourth embodiment, $R^2$ represents nitro. In a fifth embodiment, $R^2$ represents hydroxy. In a sixth embodiment, $R^2$ represents trifluoromethyl. In a seventh embodiment, $R^2$ represents trifluoromethoxy. In an eighth embodiment, $R^2$ represents —$OR^a$. In a ninth embodiment, $R^2$ represents optionally substituted $C_{1-6}$ alkyl. In a first aspect of that embodiment, $R^2$ represents $C_{1-6}$ alkyl. In a particular aspect of this embodiment, $R^2$ represents methyl. In another particular aspect of this embodiment, $R^2$ represents ethyl. In a second aspect of that embodiment, $R^2$ represents monosubstituted methyl or monosubstituted ethyl.

Typical examples of optional substituents on $R^2$ include $C_{2-6}$ alkoxycarbonyl.

Typical examples of particular substituents on $R^2$ include ethoxycarbonyl.

Typical values of $R^2$ include hydrogen, fluoro, chloro, trifluoromethyl, trifluoromethoxy, —$OR^a$, methyl and ethoxycarbonylethyl.

Specific values of $R^2$ include hydrogen, bromo and fluoro.

Particular values of $R^2$ include hydrogen and fluoro.

Generally, $R^3$ represents hydrogen, halogen, trifluoromethyl, or $C_{1-6}$ alkyl.

Typically, $R^3$ represents hydrogen, halogen or $C_{1-6}$ alkyl.

In a first embodiment, $R^3$ represents hydrogen. In a second embodiment, $R^3$ represents halogen. In one aspect of that embodiment, $R^3$ represents fluoro. In a third embodiment, $R^3$ represents optionally substituted $C_{1-6}$ alkyl. In one aspect of that embodiment, $R^3$ represents $C_{1-6}$ alkyl. In a particular aspect of this embodiment, $R^3$ represents methyl. In another particular aspect of this embodiment, $R^3$ represents ethyl. In a fourth embodiment, $R^3$ represents trifluoromethyl.

Illustratively, $R^3$ represents hydrogen or trifluoromethyl.

In a particular embodiment, $R^3$ represents hydrogen.

Generally, $R^4$ represents hydrogen, halogen, trifluoromethyl, or $C_{1-6}$ alkyl.

Typically, $R^4$ represents hydrogen, halogen or $C_{1-6}$ alkyl.

In a first embodiment, $R^4$ represents hydrogen. In a second embodiment, $R^4$ represents halogen. In one aspect of that embodiment, $R^4$ represents fluoro. In a third embodiment, $R^4$ represents optionally substituted $C_{1-6}$ alkyl. In one aspect of that embodiment, $R^4$ represents $C_{1-6}$ alkyl. In a particular aspect of this embodiment, $R^4$ represents methyl. In another particular aspect of this embodiment, $R^4$ represents ethyl. In a fourth embodiment, $R^4$ represents trifluoromethyl.

Illustratively, $R^4$ represents hydrogen or trifluoromethyl.

In a particular embodiment, $R^4$ represents hydrogen.

Typically, $R^5$ represents halogen, cyano, difluoromethoxy, trifluoromethoxy, —$OR^a$, or $C_{1-6}$ alkylsulphonyl; or $C_{1-6}$ alkyl optionally substituted by one or more substituents.

Generally, $R^5$ represents halogen, —$OR^a$, difluoromethoxy or trifluoromethoxy.

In a first embodiment, $R^5$ represents hydrogen. In a second embodiment, $R^5$ represents halogen. In one aspect of that embodiment, $R^5$ represents chloro. In a second aspect of that embodiment, $R^5$ represents fluoro. In a third embodiment, $R^5$ represents cyano. In a fourth embodiment, $R^5$ represents hydroxy. In a fifth embodiment, $R^5$ represents trifluoromethyl. In a sixth embodiment, $R^5$ represents difluoromethoxy. In a seventh embodiment, $R^5$ represents trifluoromethoxy. In an eighth embodiment, $R^5$ represents —$OR^a$. In one aspect of that embodiment, $R^5$ represents methoxy. In a ninth embodiment, $R^5$ represents $C_{1-6}$ alkylsulphonyl. In one aspect of that embodiment, $R^5$ represents methylsulphonyl. In a tenth embodiment, $R^5$ represents optionally substituted $C_{1-6}$ alkyl. In one aspect of that embodiment, $R^5$ represents $C_{1-6}$ alkyl. In a particular aspect of this embodiment, $R^5$ represents methyl. In another particular aspect of this embodiment, $R^5$ represents ethyl.

Suitably, $R^5$ represents fluoro, methoxy, difluoromethoxy or trifluoromethoxy.

Appositely, $R^5$ represents fluoro, methoxy or difluoromethoxy.

Suitably, $R^5$ represents difluoromethoxy.

Generally, $R^6$ represents hydrogen, halogen or trifluoromethyl.

In a first embodiment, $R^6$ represents hydrogen. In a second embodiment, $R^6$ represents halogen. In one aspect of that embodiment, $R^6$ represents chloro. In a second aspect of that embodiment, $R^6$ represents fluoro. In a third aspect of that embodiment, $R^6$ represents bromo. In a third embodiment, $R^6$ represents trifluoromethyl. In a fourth embodiment, $R^6$ represents $C_{1-6}$ alkyl. In a first aspect of that embodiment, $R^6$ represents $C_{1-4}$ alkyl. In a second aspect of that embodiment $R^6$ represents $C_{1-3}$ alkyl. In a third aspect of that embodiment, $R^6$ represents $C_{1-2}$ alkyl. In a particular aspect of this embodiment, $R^6$ represents methyl. In another particular aspect of this embodiment, $R^6$ represents ethyl. In a fifth embodiment, $R^6$ represents $C_{1-6}$ alkoxy. In a particular aspect of that embodiment, $R^6$ represents methoxy.

Particularly, $R^6$ represents hydrogen, bromo or trifluoromethyl.

Illustratively, $R^6$ represents hydrogen or bromo.

Suitably, $R^6$ represents hydrogen.

In a first embodiment, $R^7$ represents hydrogen. In a second embodiment, $R^7$ represents halogen. In one aspect of that embodiment, $R^7$ represents chloro. In a second aspect of that embodiment, $R^7$ represents fluoro. In a third embodiment, $R^7$ represents trifluoromethyl. In a fourth embodiment, $R^7$ represents $C_{1-6}$ alkyl. In a first aspect of that embodiment, $R^7$ represents $C_{1-4}$ alkyl. In a second aspect of that embodiment $R^7$ represents $C_{1-3}$ alkyl. In a third aspect of that embodiment, $R^7$ represents $C_{1-2}$ alkyl. In a particular aspect of this embodiment, $R^7$ represents methyl. In another particular aspect of this embodiment, $R^7$ represents ethyl. In a fifth embodiment, $R^7$ represents $C_{1-6}$ alkoxy.

In a particular aspect of that embodiment, $R^7$ represents methoxy.

Illustratively, $R^7$ represents hydrogen or trifluoromethyl.

Suitably, $R^7$ represents hydrogen.

Generally, $R^8$ represents hydrogen, halogen or trifluoromethyl.

In a first embodiment, $R^8$ represents hydrogen. In a second embodiment, $R^8$ represents halogen. In one aspect of that embodiment, $R^8$ represents chloro. In a second aspect of that embodiment, $R^8$ represents fluoro. In a third embodiment, $R^8$ represents cyano. In a fourth embodiment, $R^8$ represents hydroxy. In a fifth embodiment, $R^8$ represents trifluoromethyl. In a sixth embodiment, $R^8$ represents difluoromethoxy. In a seventh embodiment, $R^8$ represents trifluoromethoxy. In an eighth embodiment, $R^8$ represents —$OR^a$. In one aspect of that embodiment, $R^8$ represents methoxy. In a ninth embodiment, $R^8$ represents $C_{1-6}$ alkylsulphonyl. In one aspect of that embodiment, $R^8$ represents methylsulphonyl. In a tenth embodiment, $R^8$ represents optionally substituted $C_{1-6}$ alkyl. In one aspect of that embodiment, $R^8$ represents $C_{1-6}$ alkyl. In a particular aspect of this embodiment, $R^8$ represents methyl. In another particular aspect of this embodiment, $R^8$ represents unsubstituted ethyl. In an eleventh embodiment, $R^8$ represents trifluoromethyl.

Particularly, $R^8$ represents hydrogen, chloro or trifluoromethyl

Illustratively, $R^8$ represents hydrogen or chloro.

Suitably, $R^8$ represents hydrogen.

Generally, $R^{12}$ represents hydrogen or $C_{1-6}$ alkyl.

Suitably, $R^{12}$ represents hydrogen or methyl.

Appositely, $R^{12}$ represents hydrogen.

Generally, $R^a$ represents $C_{1-6}$ alkyl, $C_{3-7}$ cycloalkyl, $C_{3-7}$ heterocycloalkyl, aryl, aryl($C_{1-6}$)alkyl, heteroaryl or heteroaryl($C_{1-6}$)alkyl, any of which groups may be optionally substituted by one or more substituents.

Generally, $R^b$ and $R^c$ independently represent hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^b$ and $R^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo)thiazinan-4-yl or (dioxo)thiazinan-4-yl any of which groups may be optionally substituted by one or more substituents.

Generally, $R^d$ represents hydrogen; or $C_{1-6}$ alkyl, $C_{3-7}$ cycloalkyl, aryl, $C_{3-7}$ heterocycloalkyl or heteroaryl, any of which groups may be optionally substituted by one or more substituents.

Generally, $R^e$ represents $C_{1-6}$ alkyl, aryl or heteroaryl, any of which groups may be optionally substituted by one or more substituents.

Typical examples of suitable substituents which may be present on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl.

Typical examples of specific substituents which may be present on $R^a$, $R^b$, $R^c$, $R^d$, or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

In a first embodiment, $R^a$ represents optionally substituted $C_{1-6}$ alkyl. In a first aspect of that embodiment, $R^a$ represents $C_{1-6}$ alkyl. In a particular aspect of this embodiment, $R^a$ represents methyl. In a second aspect of that embodiment, $R^a$ represents substituted $C_{1-6}$ alkyl. In a particular aspect of this embodiment, $R^a$ represents methoxyethyl. In a second embodiment, $R^a$ represents optionally substituted aryl. In a first aspect of this embodiment, $R^a$ represents aryl. In a particular aspect of this embodiment, $R^a$ represents phenyl. In a second aspect of that embodiment, $R^a$ represents monosubstituted aryl. In a particular aspect of this embodiment, $R^a$ represents methylphenyl. In a third embodiment, $R^a$ represents optionally substituted aryl($C_{1-6}$)alkyl.

In one aspect of that embodiment, $R^a$ represents aryl($C_{1-6}$)alkyl. In a particular aspect of this embodiment, $R^a$ represents benzyl. In a fourth embodiment, $R^a$ represents optionally substituted heteroaryl. In one aspect of this embodiment, $R^a$ represents heteroaryl. In a fifth embodiment, $R^a$ represents optionally substituted heteroaryl($C_{1-6}$)alkyl. In a particular aspect of this embodiment, $R^a$ represents dioxoisoindolylpropyl. In a sixth embodiment, $R^a$ represents $C_{3-7}$ cycloalkyl. In a seventh embodiment, $R^a$ represents $C_{3-7}$ heterocycloalkyl.

Appositely, $R^a$ represents $C_{1-6}$ alkyl. Illustratively, $R^a$ represents methyl.

Typically, $R^b$ represents hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Suitably, $R^b$ represents hydrogen or $C_{1-6}$ alkyl.

In a first embodiment, $R^b$ represents hydrogen. In a second embodiment, $R^b$ represents $C_{1-6}$ alkyl. In a particular aspect of that embodiment, $R^b$ represents methyl.

Typically, $R^c$ represents hydrogen; or $C_{1-6}$ alkyl, $C_{3-7}$ cycloalkyl or $C_{3-7}$ heterocycloalkyl, any of which groups may be optionally substituted by one or more substituents.

Suitably, $R^c$ represents hydrogen or $C_{1-6}$ alkyl.

In a first embodiment, $R^c$ is hydrogen. In a second embodiment, $R^c$ represents $C_{1-6}$ alkyl. In a one aspect of that embodiment, $R^c$ represents methyl. In a another aspect of that embodiment, $R^c$ represents ethyl.

Appositely, $R^c$ represents hydrogen or ethyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, (imino)(oxo)thiazinan-4-yl, (oxo)thiazinan-4-yl or (dioxo)thiazinan-4-yl, any of which groups may be optionally substituted by one or more substituents.

Specific values of the heterocyclic moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, amino carbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl, oxohomopiperazin-1-yl, (imino)(oxo)thiazinan-4-yl, (oxo)thiazinan-4-yl, and (dioxo)thiazinan-4-yl.

Typically, $R^d$ represents hydrogen; or $C_{1-6}$ alkyl, aryl or heteroaryl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

Suitably, $R^d$ represents hydrogen or $C_{1-6}$ alkyl.

In a first embodiment, $R^d$ represents hydrogen. In a second embodiment, $R^d$ represents optionally substituted $C_{1-6}$ alkyl. In one aspect of that embodiment, $R^d$ represents $C_{1-6}$ alkyl. In a third embodiment, $R^d$ represents optionally substituted aryl. In one aspect of that embodiment, $R^d$ represents phenyl. In a fourth embodiment, $R^d$ represents optionally substituted heteroaryl.

Appositely, $R^d$ represents hydrogen or methyl.

Typically, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In a first embodiment, $R^e$ represents optionally substituted $C_{1-6}$ alkyl. In a particular aspect of that embodiment, $R^e$ represents $C_{1-6}$ alkyl. In a particular aspect of this embodiment especially methyl. In a second embodiment, $R^e$ represents optionally substituted aryl. In one aspect of that embodiment, $R^e$ represents phenyl. In another aspect of that embodiment, $R^e$ represents monosubstituted aryl.

Suitably, $R^e$ represents methyl, propyl or methylphenyl.

Generally, $R^f$ represents hydrogen; or $C_{1-6}$ alkyl, $C_{3-6}$ cycloalkyl, or $C_{4-6}$ heterocycloalkyl, any of which groups may be optionally substituted by one or more substituents.

Suitably, $R^f$ represents hydrogen; or $C_{1-6}$ alkyl, which group may be optionally substituted by one or more substituents.

Generally, $R^g$ represents hydrogen; or $C_{1-6}$ alkyl, —CO—$(C_{1-6})$alkyl, —SO$_2$—$(C_{1-6})$alkyl. —CO—$(C_{3-7})$heterocycloalkyl, —SO$_2$—$(C_{3-7})$cycloalkyl, —SO$_2$—$(C_{3-7})$heterocycloalkyl, —SO$_2$-aryl, —SO$_2$-heteroaryl, heteroaryl or $(C_{2-6})$alkoxycarbonyl, any of which groups may be optionally substituted by one or more substituents.

More generally, $R^g$ represents hydrogen; or $C_{1-6}$ alkyl, —CO—$(C_{1-6})$alkyl, —SO$_2$—$(C_{1-6})$alkyl. —CO—$(C_{3-7})$heterocycloalkyl, —SO$_2$—$(C_{3-7})$cycloalkyl, —SO$_2$-aryl, —SO$_2$-heteroaryl, heteroaryl or $(C_{2-6})$alkoxycarbonyl, any of which groups may be optionally substituted by one or more substituents.

Typically, $R^g$ represents hydrogen; or $C_{1-6}$ alkyl, —CO—$(C_{1-6})$alkyl, —SO$_2$—$(C_{1-6})$alkyl. —CO—$(C_{3-7})$heterocycloalkyl, —SO$_2$—$(C_{3-7})$cycloalkyl, —SO$_2$—$(C_{3-7})$heterocycloalkyl, —SO$_2$-aryl or —SO$_2$-heteroaryl, any of which groups may be optionally substituted by one or more substituents.

Interestingly, $R^g$ represents hydrogen; or $C_{1-6}$ alkyl, $C_{3-6}$ cycloalkyl, $C_{4-6}$ heterocycloalkyl, —CO—$(C_{1-6})$alkyl, or —SO$_2$—$(C_{1-6})$alkyl, any of which groups may be optionally substituted by one or more substituents.

Suitably, $R^g$ represents hydrogen, optionally substituted $C_{1-6}$ alkyl, —CO—$(C_{1-6})$alkyl or —SO$_2$—$(C_{1-6})$alkyl.

Typically, substituents on $R^g$ include independently halogen, $C_{1-6}$ alkyl, carboxy and $C_{1-6}$ alkoxycarbonyl. Additional substituents on $R^g$ include trifluoromethyl, $C_{4-9}$ heterobicycloalkyl, $(C_{1-6}$ alkyl)sulphonyl, tri$(C_{1-6}$ alkyl)silyloxy, hydroxy and $(C_{1-6})$alkoxy.

Appositely, substituents on $R^f$ and $R^g$ include independently halogen and $C_{1-6}$ alkyl.

Particular examples of substituents on $R^g$ include independently methyl, trifluoromethyl, ethoxycarbonyl, 3,7-dioxa-9-azabicyclo[3.3.1]non-9-yl, methylsulphonyl, (tert-butyl)(di-methyl)silyloxyethyl, hydroxy and methoxy.

Particular examples of substituent on $R^f$ include trifluoromethyl, carboxy and hydroxy.

In a first embodiment, $R^f$ represents hydrogen. In a second embodiment, $R^f$ represents optionally substituted $C_{1-6}$ alkyl. In one aspect of that embodiment, $R^f$ represents $C_{1-6}$ alkyl. In a particular aspect of this embodiment, $R^f$ represents methyl. In another particular aspect of this embodiment, $R^f$ represents ethyl. In a further particular aspect of this embodiment, $R^f$ represents isopropyl. In another aspect of that embodiment, $R^f$ represents deuterated methyl. In a further aspect of that embodiment, $R^f$ represents substituted $C_{1-6}$ alkyl. In a third embodiment, $R^f$ represents optionally substituted $C_{3-6}$ cycloalkyl. In one aspect of that embodiment, $R^f$ represents $C_{3-6}$ cycloalkyl.

Particular values of $R^f$ include hydrogen, methyl, ethyl, isopropyl, (carboxy)methyl, (trifluoromethyl)methyl, (hydroxyisopropyl)methyl and deuterated methyl.

Illustrative values of $R^f$ include hydrogen, methyl, ethyl and isopropyl.

In a first embodiment, $R^g$ represents hydrogen. In a second embodiment, $R^g$ represents optionally substituted $C_{1-6}$ alkyl. In one aspect of that embodiment, $R^g$ represents $C_{1-6}$ alkyl. In a particular aspect of this embodiment, $R^g$ represents methyl. In another particular aspect of this embodiment, $R^g$ represents ethyl. In a further particular aspect of this embodiment, $R^g$ represents isopropyl. In a third embodiment, $R^g$ represents optionally substituted $C_{3-6}$ cycloalkyl. In one aspect of that embodiment, $R^g$ represents $C_{3-6}$ cycloalkyl. In a fourth embodiment, $R^g$ represents optionally substituted —CO—$(C_{1-6})$alkyl. In one aspect of that embodiment, $R^g$ represents —CO—$(C_{1-6})$alkyl. In a particular aspect of this embodiment, $R^g$ represents —CO—CH$_3$. In a fifth embodiment, $R^g$ represents optionally substituted —SO$_2$—$(C_{1-6})$alkyl. In one aspect of that embodiment, $R^g$ represents —SO$_2$—$(C_{1-6})$alkyl. In a particular aspect of this embodiment, $R^g$ represents —SO$_2$—CH$_3$. In a sixth embodiment, $R^g$ represents optionally substituted —CO—$(C_{3-7})$heterocycloalkyl. In a particular aspect of that embodiment, $R^g$ represents —CO-azetidinyl. In a seventh embodiment, $R^g$ represents optionally substituted —SO$_2$—$(C_{3-7})$cycloalkyl. In a particular aspect of that embodiment, $R^g$ represents —SO$_2$-cyclopropyl. In an eighth embodiment, $R^g$ represents optionally substituted —SO$_2$—$(C_{3-7})$heterocycloalkyl. In a ninth embodiment, $R^g$ represents optionally substituted —SO$_2$-aryl. In a particular aspect of that embodiment, $R^g$ represents optionally substituted —SO$_2$-phenyl. In a tenth embodiment, $R^g$ represents optionally substituted —SO$_2$-heteroaryl. In a particular aspect of that embodiment, $R^g$ represents optionally substituted —SO$_2$-pyridinyl. In an eleventh embodiment, $R^g$ represents optionally substituted heteroaryl. In a particular aspect of that embodiment, $R^g$ represents optionally substituted pyrimidinyl. In a twelfth embodiment, $R^g$ represents optionally substituted $(C_{2-6})$alkoxycarbonyl. In a particular aspect of that embodiment, $R^g$ represents ethoxycarbonyl.

Illustrative values of $R^g$ include hydrogen, methyl, carboxymethyl, ethoxycarbonylmethyl, methylcarbonyl, methylsulphonyl, (3,7-dioxa-9-azabicyclo[3.3.1]non-9-yl)methylcarbonyl, azetidinylcarbonyl, (methylsulphonyl)azetidinylcarbonyl, pyridinylsulphonyl, cyclopropylsulphonyl, (tert-butyl)(dimethyl)silyloxyethyl, hydroxyethyl, phenylsulphonyl, (methoxy)pyridinylsulphonyl, (pyridine-2(1H)-one)sulphonyl, pyrimidinyl and ethoxycarbonyl.

Selected values of $R^g$ include hydrogen, methyl, carboxymethyl, ethoxycarbonylmethyl, methylcarbonyl, methylsulphonyl, (3,7-dioxa-9-azabicyclo[3.3.1]non-9-yl)methylcarbonyl, azetidinylcarbonyl, (methylsulphonyl)azetidinylcarbonyl, pyridinylsulphonyl, cyclopropylsulphonyl, (tert-butyl)(dimethyl)silyloxyethyl, hydroxyethyl, phenylsulphonyl and (methoxy)pyridinylsulphonyl.

Particular values of $R^g$ include hydrogen, methyl, carboxymethyl, ethoxycarbonylmethyl, methylcarbonyl and methylsulphonyl.

Specific values of $R^g$ include hydrogen and methyl.

Illustrative values of —X-Q- include —O—, —O—CO—, —O—C(CH═CN)—, —S—, —SO—, —SO$_2$—, —NH—, —N(CO—CH$_3$)—, —N(SO$_2$—CH$_3$)—, —N(CH$_2$—CO—O—CH$_2$—CH$_3$)—, —N[(CO—CH$_2$-(3,7-dioxa-9-azabicyclo[3.3.1]non-9-yl)]-, —N[CO-(azetidin-3-yl)]-, —N[CO-(methylsulphonyl)azetidin-3-yl)]-, —N(CH$_2$—COOH), —N[(tert-butyl)(dimethyl)silyloxyethyl]-, —N(SO$_2$-pyridine-3-yl)-, —N—(SO$_2$-cyclopropyl)-, —N(CH$_3$)—CH$_2$—, —N(CH$_2$—CH$_2$—OH)—, —N(SO$_2$-phenyl)-, —N[SO$_2$-(6-methoxy-pyridin-3-yl)]-, —NH—CO—, —N(CH$_3$)—CO—, —N(CH$_2$CH$_3$)—CO—, —N(CH(CH$_3$)$_2$)—CO—, —N(CH$_2$—COOH)—CO—, —N(CH$_2$—CF$_3$)—CO—, —N(CH$_2$—CH$_2$—OH)—CO—, —N(CH$_2$—C(OH)(CH$_3$)$_2$)—CO—, —N(CD$_3$)-CO—, —NH—CH$_2$—, —N(CH$_2$—COOH)—CH$_2$—, —NH—CH(CF$_3$)—, —NH—CH(CH$_3$)—, —NH—C(S)—, —N(CO—CH$_3$)—CH(CH$_3$)—, —N(SO$_2$—CH$_3$)—CH$_2$—, —N(CO—CH$_3$)—CH(CH$_3$)—, —N═S(O)(CH$_3$)—, O—CH(CF$_3$)—, —CH(COOC$_2$H$_5$)—S—, —CH$_2$—S(O)—, —CH$_2$—S(O)$_2$—, —CH(CH(OH)(CH$_3$)$_2$)—S—, —CH(CH$_2$OH)—S—, —O—C(═CH$_2$)—, —N[S(O)$_2$-(pyridin-1H-2-one)], —NH—S(O)$_2$—, —N(pyrimidinyl)-, —N(COOC$_2$H$_5$)—, —S(═N—CN)—, —N(SO$_2$—CH$_3$)— and —N(C$_2$H$_5$)—CO—.

In a particular embodiment, the present invention provides a compound of formula (I) or an N-oxide thereof, or a pharmaceutically acceptable salt thereof:

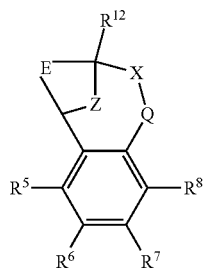

(I)

wherein

X-Q- represents —O—, —O—C(O)—, —O—C(CH═CN)—, —S—, —SO—, or —SO$_2$—; or —N(R$^g$)—, —N(R$^f$)—CO—, —N(R$^f$)—SO$_2$—, O—CH$_2$—, —CH$_2$—S—, —CH$_2$—SO—, —CH$_2$—SO$_2$—, —N(R$^g$)—CH$_2$—, —N(R$^f$)—C(S)—, —N═S(O)(CH$_3$)—, —O—C(═CH$_2$)— or —S(═N—CN)—, any of which groups may be optionally substituted;

Z represents methylene;

E represents a fused heteroaromatic ring system selected from the groups of formula (Ea) and (Eb);

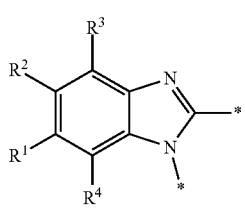

(Ea)

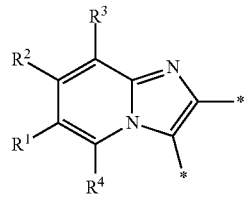

(Eb)

wherein the asterisk (*) represents the site of attachment of E to the remainder of the molecule;

R$^1$ represents halogen or cyano; or aryl, heteroaryl, (C$_{3-7}$)cycloalkyl-heteroaryl, (C$_{3-7}$)heterocycloalkyl-heteroaryl, (C$_{4-9}$)heterobicycloalkyl-heteroaryl, (C$_{3-7}$)heterocycloalkyl, (C$_{3-7}$)heterocycloalkenyl, or (C$_{3-7}$)heterocycloalkenyl-aryl, any of which groups may be optionally substituted by one or more substituents;

R$^2$ represents hydrogen or halogen;

R$^3$ represents hydrogen or trifluoromethyl;

R$^4$ represents hydrogen or trifluoromethyl;

R$^5$ represents halogen, —OR$^a$, difluoromethoxy or trifluoromethoxy;

R$^6$ represents hydrogen, halogen or trifluoromethyl;

R$^7$ represents hydrogen or trifluoromethyl;

R$^8$ represents hydrogen, halogen or trifluoromethyl;

R$^{12}$ represents hydrogen or C$_{1-6}$ alkyl;

R$^a$ represents C$_{1-6}$ alkyl;

R$^f$ represents hydrogen; or C$_{1-6}$ alkyl, which group may be optionally substituted by one or more substituents; and R$^g$ represents hydrogen; or C$_{1-6}$ alkyl, —CO—(C$_{1-6}$) alkyl, —SO$_2$—(C$_{1-6}$)alkyl. —CO—(C$_{3-7}$)heterocycloalkyl, —SO$_2$—(C$_{3-7}$)cycloalkyl, —SO$_2$-aryl, —SO$_2$-heteroaryl, heteroaryl or (C$_{2-6}$)alkoxycarbonyl, any of which groups may be optionally substituted by one or more substituents.

In a particular aspect of that embodiment, the present invention provides a compound of formula (I) or an N-oxide thereof, or a pharmaceutically acceptable salt thereof,

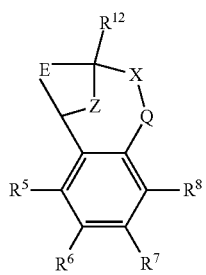

(I)

X-Q- include —O—, —O—CO—, —O—C(CH═CN)—, —S—, —SO—, SO$_2$—, —NH—, —N(CO—CH$_3$)—, —N(SO$_2$—CH$_3$)—, —N(CH$_2$—CO—O—CH$_2$—CH$_3$)—, —N[(CO—CH$_2$-(3,7-dioxa-9-azabicyclo[3.3.1]non-9-yl)]-, —N[CO-(azetidin-3-yl)]-, —N[CO-(methylsulphonyl)azetidin-3-yl)]-, —N(CH$_2$—COOH), —N[(tert-butyl)(dimethyl)silyloxyethyl]-, —N(SO$_2$-pyridine-3-yl)-, —N—(SO$_2$-cyclopropyl)-, —N(CH$_3$)—CH$_2$—, —N(CH$_2$—CH$_2$—OH)—, —N(SO$_2$-phenyl)-, —N[SO$_2$-(6-methoxy-pyridin-3-yl)]-, —NH—CO—, —N(CH$_3$)—CO—, —N(CH$_2$CH$_3$)—CO—, —N(CH(CH$_3$)$_2$)—CO—, —N(CH$_2$—COOH)—CO—, —N(CH$_2$—CF$_3$)—CO—, —N(CH$_2$—CH$_2$—OH)—CO—, —N(CH$_2$—C(OH)(CH$_3$)$_2$)—CO—, —N(CD$_3$)-CO—, —NH—CH$_2$—, —N(CH₂—COOH)—CH₂—, —NH—CH(CF₃)—, —NH—CH(CH₃)—, —NH—C(S)—, —N(CO—CH₃)—CH(CH₃)—, —N(SO₂—CH₃)—CH₂—, —N(CO—CH₃)—CH(CH₃)—, —N=S(O)(CH₃)—, O—CH(CF₃)—, —CH(COOC₂H₅)—S—, —CH₂—S(O)—, —CH₂—S(O)₂—, —CH(CH(OH)(CH₃)₂)—S—, —CH(CH₂OH)—S—, —O—C(=CH₂)—, —N[S(O)₂-(pyridin-1H-2-one)], —NH—S(O)₂—, —N(pyrimidinyl)-, —N(COOC₂H₅)—, —S(=N—CN)—, —N(SO₂—CH₃)— and —N(C₂H₅)—CO—;

R¹ represents chloro, cyano, methylsulphonyl-phenyl, methylsulphoximinyl-phenyl, (dihydroxy)(methyl)cyclobutylpyrimidinyl, hydroxyisopropylpyridinyl, hydroxyisopropylpyrimidinyl, (methyl)(hydroxyisopropyl)pyrimidinyl, phosphate-isopropylpyrimidinyl, methoxypyridinyl, methoxyisopropylpyrimidinyl, 2-oxo-pyridin-(1H)-yl, (tert-butoxycarbonyl)aminoisopropyl-pyrimidinyl, aminoisopropylpyrimidinyl, (3,7-dioxa-9-azabicyclo[3.3.1]non-9-yl)-pyrimidinyl, (hydroxy)(trifluoromethyl)azetidinyl-pyrimidinyl, (methylsulphonyl)(methyl)phenyl, (methyl)(hydroxyisopropyl)pyridinyl, [(hydroxy)(trifluoromethyl)azetidinyl](methyl)pyrimidinyl methylsulphonylcyclopropylpyridinyl, (dimethyl)(hydroxyisopropyl)pyrimidinyl, (hydroxyisopropyl)(trifluoromethyl)pyrimidinyl, (tert-butoxycarbonyl)(hydroxy)pyrrolidine-pyridinyl, (hydroxy)pyrrolidine-pyridinyl, (methoxycarbonyl)aminoisopropyl-pyrimidinyl, piperazinylpyridinyl, (methylsulphonyl)piperazinyl-pyridinyl, (dimethylamino)isopropylpyrimidinyl, (oxo)piperazinylpyrimidinyl, (N-methyl)pyrazolyl, (methylthio)(methyl)phenyl, morpholinylpyrimidinyl, ((tert-butyl)sulphinylamino)cyclobutylpyridinyl, (amino)cyclobutylpyridinyl, ((tert-butyl)sulphinylamino)oxetanylpyridinyl, (amino)oxetanylpyridinyl, ((tert-butyl)sulphonylamino)oxetanylpyridinyl, pyrrolidinylpyridinyl, (dimethyl)imidazolylphenyl, (methylsulphonyl)aminoisopropylpyrimidinyl, methylcarbonylaminoisopropylpyrimidinyl, pyrrolidinyl-phenyl, (oxo)diazepanylpyrimidinyl, (hydroxy)(methyl)azetidinyl-pyrimidinyl, thiomorpholinylpyrimidinyl, (oxo)thiomorpholinylpyrimidinyl, (dioxo)thiomorpholinylpyrimidinyl, (difluoro)(hydroxy)cyclohexylpyrimidinyl, (hydroxy)(oxo)tetrahydrothiophenyl-pyrimidinyl, (hydroxy)(dioxo)tetrahydrothiophenyl-pyrimidinyl, (hydroxy)tetrahydrothiophenyl-pyrimidinyl, (hydroxy)oxetanylpyrimidinyl, (methylsulphonyl)azetidinyl-2,5-pyrazolyl, (oxo)(methyl)-1,2-dihydropyridinyl, (oxo)-1,2-dihydropyrimidinyl, (dihydroxy)(methyl)cyclohexylpyrimidinyl, cyanoisopropylpyrimidinyl, (cyano)(methyl)azetidinylpyrimidinyl, (2-oxa-5-azabicyclo[2.2.1]heptanyl)-pyrimidinyl-, (3-oxa-8-azabicyclo[3.2.1]oct-8-yl)-pyrimidinyl-, (oxo)(3,6-diazabicyclo[3.2.2]nonanyl)-pyrimidinyl-, (hydroxyisopropyl)azetidinyl, (difluoro)azetidinylpyrimidinyl, tetrahydropyranylpyrimidinyl, methylsulphoxyminylpyridinyl, (difluoromethyl)(hydroxyisopropyl)pyrimidinyl, (tetrahydrofuranyl)(hydroxyisopropyl)pyrimidinyl, di(propenyl)aminoisopropylpyrimidinyl, sulphate-isopropylpyrimidinyl, carboxy-ethyl-carbonyloxy-isopropyl-pyrimidinyl and (hydroxy)isobutylpyrimidinyl;

R² represents hydrogen, bromo or fluoro;

R³ represents hydrogen or trifluoromethyl;

R⁴ represents hydrogen or trifluoromethyl;

R⁵ represents halogen, methoxy, difluoromethoxy or trifluoromethoxy;

R⁶ represents hydrogen, bromo, chloro, or trifluoromethyl;

R⁷ represents hydrogen or trifluoromethyl;

R⁸ represents hydrogen, chloro and trifluoromethyl;

R¹² represents hydrogen or methyl;

Rᶠ represents hydrogen, methyl, ethyl, isopropyl, (carboxy)methyl, (trifluoromethyl)methyl, (hydroxyisopropyl)methyl or deuterated methyl;

Rᵍ represents hydrogen, methyl, carboxymethyl, ethoxycarbonylmethyl, methylcarbonyl, methylsulphonyl, (3,7-dioxa-9-azabicyclo[3.3.1]non-9-yl)methylcarbonyl, azetidinylcarbonyl, (methylsulphonyl)azetidinylcarbonyl, pyridinylsulphonyl, cyclopropylsulphonyl, (tert-butyl)(dimethyl)silyloxyethyl, hydroxyethyl, phenylsulphonyl, (methoxy)pyridinylsulphonyl, (pyridine-2(1H)-one)sulphonyl, pyrimidinyl or ethoxycarbonyl; and Z and E are as defined in said particular embodiment.

A particular sub-group of the compounds of formula (IB) above is represented by the compounds of formula (IIB) and N-oxides thereof, and pharmaceutically acceptable salts thereof:

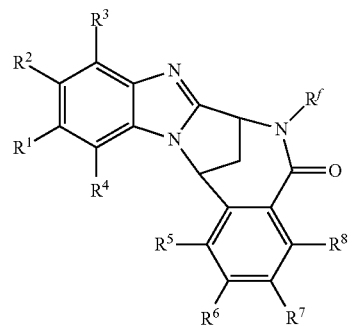

(IIB)

wherein R¹, R², R³, R⁴, R⁵, R⁶, R⁷, R⁸ and Rᶠ are as defined above.

A particular sub-group of compounds of formula (IIB) above is represented by the compounds of formula (IIB-A) and N-oxides thereof, and pharmaceutically acceptable salts thereof:

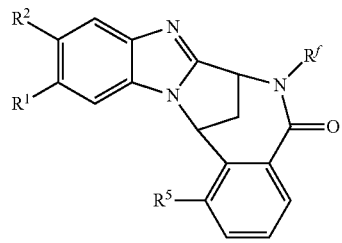

(IIB-A)

wherein R¹, R², R⁵ and Rᶠ are as defined above.

A particular sub-group of compounds of formula (IIB-A) above is represented by the compounds of formula (IIB-AB) and N-oxides thereof, and pharmaceutically acceptable salts thereof:

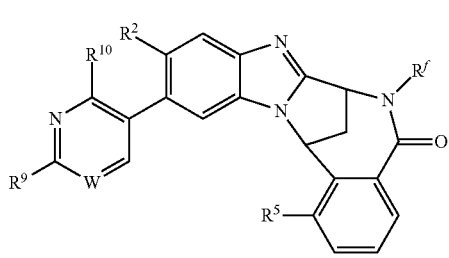

(IIB-AB)

wherein,
W represents N or C—H;
$R^9$ represents hydroxy($C_{1-6}$)alkyl, ($C_{1-6}$) alkoxy($C_{1-6}$)alkyl, amino($C_{1-6}$)alkyl or phosphate($C_{1-6}$)alkyl;
$R^{10}$ represents hydrogen or $C_{1-6}$ alkyl; and
$R^2$, $R^5$ and $R^f$ are as defined above.

In one embodiment, W represents N. In another embodiment, W represents C—H.

Suitably, $R^9$ represents hydroxy($C_{1-6}$)alkyl or ($C_{1-6}$) alkoxy($C_{1-6}$)alkyl.

Illustratively, $R^9$ represents hydroxyisopropyl or methoxyisopropyl.

Particular values of $R^9$ include 2-hydroxy-prop-2-yl and 2-methoxy-prop-2-yl.

In one embodiment, $R^9$ represents hydroxyisopropyl. In a particular aspect of that embodiment, $R^9$ represents 2-hydroxy-prop-2-yl.

In another embodiment, $R^9$ represents methoxyisopropyl. In a particular aspect of that embodiment, $R^9$ represents 2-methoxy-prop-2-yl.

In a further embodiment, $R^9$ represents aminoisopropyl. In a particular aspect of that embodiment, $R^9$ represents 2-amino-prop-2-yl.

In another embodiment, $R^9$ represents phosphate($C_{1-6}$) alkyl. In a particular aspect of that embodiment, $R^9$ represents 2-phosphate-prop-2-yl.

In one embodiment, $R^{10}$ represents hydrogen. In another embodiment, $R^{10}$ represents $C_{1-6}$ alkyl. In a particular aspect of this embodiment, $R^{10}$ represents methyl.

Illustratively, $R^{10}$ represents hydrogen or methyl.

Particularly, $R^{10}$ represents hydrogen.

A particular sub-group of compounds of formula (IIB-AB) above is represented by the compounds of formula (IIB-AB-A) and N-oxides thereof, and pharmaceutically acceptable salts thereof:

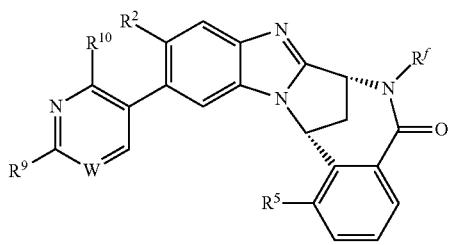

(IIB-AB-A)

wherein W, $R^f$, $R^2$, $R^5$, $R^9$ and $R^{10}$ are as defined above.

Another particular sub-group of the compounds of formula (IB) above is represented by the compounds of formula (IIC) and N-oxides thereof, and pharmaceutically acceptable salts thereof:

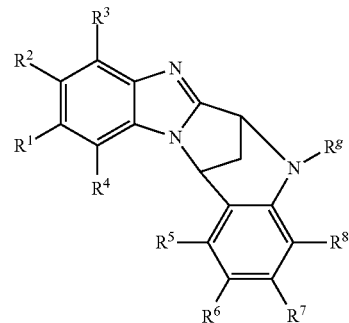

(IIC)

wherein $R^1$, $R^2$, $R^3$, $R^4$, $R^5$, $R^6$, $R^7$, $R^8$ and $R^g$ are as defined above.

Specific novel compounds in accordance with the present invention include each of the compounds whose preparation is described in the accompanying Examples, and pharmaceutically acceptable salts and solvates thereof, and co-crystals thereof.

Therefore, in a particular aspect, the present invention relates to compounds of formula (I) which are selected from the group consisting of (7R,14R)-1-(difluoromethoxy)-10-fluoro-11-[2-(2-hydroxypropan-2-yl)pyrimidin-5-yl]-6,7-dihydro-7,14-methanobenzimidazo[1,2-b][2,5]benzodiazocin-5(14H)-one; (7R,14R)-1-(difluoromethoxy)-10-fluoro-11-[2-(2-methoxypropan-2-yl)pyrimidin-5-yl]-6-methyl-6,7-dihydro-7,14-methanobenzimidazo[1,2-b][2,5] benzodiazocin-5(14H)-one; (7R,14R)-1-(difluoromethoxy)-11-[2-(2-hydroxypropan-2-yl)pyrimidin-5-yl]-6,7-dihydro-7,14-methanobenzimidazo[1,2-b][2,5]benzodiazocin-5 (14H)-one; (7R,14R)-1-(difluoromethoxy)-11-[2-(2-hydroxypropan-2-yl)pyrimidin-5-yl]-6-methyl-6,7-dihydro-7,14-methanobenzimidazo[1,2-b][2,5]benzodiazocin-5 (14H)-one; (7R,14R)-1-(difluoromethoxy)-6-ethyl-11-[2-(2-hydroxypropan-2-yl)pyrimidin-5-yl]-6,7-dihydro-7,14-methanobenzimidazo[1,2-b][2,5]benzodiazocin-5(14H)-one; (7R,14R)-1-(difluoromethoxy)-11-[2-(2-hydroxypropan-2-yl)pyrimidin-5-yl]-6-(propan-2-yl)-6,7-dihydro-7,14-methanobenzimidazo[1,2-b][2,5] benzodiazocin-5(14H)-one; (7R,14R)-1-(difluoromethoxy)-10-fluoro-11-[2-(2-hydroxypropan-2-yl)pyrimidin-5-yl]-7H-7,14-methanobenzimidazo[2,1-d][2,5]benzoxazocin-5 (14H)-one; (2Z)-[(7R,14R)-1-(difluoromethoxy)-10-fluoro-11-[2-(2-hydroxypropan-2-yl)pyrimidin-5-yl]-7H-7,14-methanobenzimidazo[2,1-d][2,5]benzoxazocin-5(14H)-ylidene]acetonitrile; (2E)-[(7R,14R)-1-(difluoromethoxy)-10-fluoro-11-[2-(2-hydroxypropan-2-yl)pyrimidin-5-yl]-7H-7,14-methanobenzimidazo[2,1-d][2,5]benzoxazocin-5(14H)-ylidene]acetonitrile; (7R,14R) and (7S,14S)-11-[2-(2-hydroxypropan-2-yl)pyrimidin-5-yl]-7,14-dihydro-7,14-methanopyrido[1',2': 1,2]imidazo[4,5-d][2]benzazocin-5 (6H)-one; (7R,14R)-11-chloro-1-(difluoromethoxy)-10-fluoro-6,7-dihydro-7,14-methanobenzimidazo[1,2-b][2,5] benzodiazocin-5(14H)-one; (7R,14R)-11-chloro-1-(difluoromethoxy)-6,7-dihydro-7,14-methanobenzimidazo [1,2-b][2,5]benzodiazocin-5(14H)-one; (7R,14R)-11-chloro-1-(difluoromethoxy)-5,6,7,14-tetrahydro-7,14-methanobenzimidazo[1,2-b][2,5]benzodiazocine; [(7R,14R)-1-(difluoromethoxy)-11-[2-(2-hydroxypropan-2-yl)pyrimidin-5-yl]-5,14-dihydro-7,14-methanobenzimidazo[1,2-b][2,5]benzodiazocin-6(7H)-yl]acetic acid; (7R,14R)-1-(difluoromethoxy)-11-[2-(2-hydroxypropan-2-yl)pyrimidin-5-yl]-6,7-dihydro-7,14-methanobenzimidazo[1, 2-b][2,5]benzodiazocine-5(14H)-thione; (7R,14R)-11-chloro-1-(difluoromethoxy)-10-fluoro-5,6,7,14-tetrahydro-7,14-methanobenzimidazo[1,2-b][2,5]benzodiazocine; 2-{5-[(7R,14R)-1-(difluoromethoxy)-10-fluoro-5,6,7,14-tetrahydro-7,14-methanobenzimidazo[1,2-b][2,5]benzodiazocin-11-yl]pyrimidin-2-yl}propan-2-ol; (7R,14R)-10-fluoro-11-[2-(2-hydroxypropan-2-yl)pyrimidin-5-yl]-1-methoxy-6,7-dihydro-7,14-methanobenzimidazo[1,2-b][2,5]benzodiazocin-5(14H)-one; (7R,14R)-1,10-difluoro-11-[2-(2-hydroxypropan-2-yl)pyrimidin-5-yl]-6,7-dihydro-7,14-methanobenzimidazo[1,2-b][2,5]benzodiazocin-5(14H)-one; (6R,12R)-2-chloro-11-(difluoromethoxy)-7,12-dihydro-6H-6,12-methanobenzimidazo[2,1-c][1,4]benzodiazepine; 2-{5-[(6R,12R)-11-(difluoromethoxy)-7,12-dihydro-6H-6,12-methanobenzimidazo[2,1-c][1,4]benzodiazepin-2-yl]pyrimidin-2-yl}propan-2-ol; 1-[(6R,12R)-2-chloro-11-(difluoromethoxy)-6H-6,12-methanobenzimidazo[2,1-c][1,4]benzodiazepin-7(12H)-yl]ethanone; 1-[(6R,12R)-11-(difluoromethoxy)-2-[2-(2-hydroxypropan-2-yl)pyrimidin-5-yl]-6H-6,12-methanobenzimidazo[2,1-c][1,4]benzodiazepin-7(12H)-yl]ethanone; (6R,12R)-2-chloro-11-(difluoromethoxy)-7-(methylsulfonyl)-7,12-dihydro-6H-6,12-methanobenzimidazo[2,1-c][1,4]benzodiazepine; 2-{5-[(6R,12R)-11-(difluoromethoxy)-7-(methylsulfonyl)-7,12-dihydro-6H-6,12-methanobenzimidazo[2,1-c][1,4]benzodiazepin-2-yl]pyrimidin-2-yl}propan-2-ol; (6R,12R)-2-chloro-11-(difluoromethoxy)-6H,12H-6,12-methanobenzimidazo[2,1-c][1,4]benzoxazepine; 2-{5-[(6R,12R)-11-(difluoromethoxy)-6H,12H-6,12-methanobenzimidazo[2,1-c][1,4]benzoxazepin-2-yl]pyrimidin-2-yl}propan-2-ol; (7R,14R)-1-(difluoromethoxy)-5-oxo-5,6,7,14-tetrahydro-7,14-methanobenzimidazo[1,2-b][2,5]benzodiazocine-11-carbonitrile; (7R,14R)-1-(difluoromethoxy)-11-[4-(methylsulfonyl)phenyl]-6,7-dihydro-7,14-methanobenzimidazo[1,2-b][2,5]benzodiazocin-5(14H)-one; (7R,14R)-1-(difluoromethoxy)-11-(6-methoxypyridin-3-yl)-6,7-dihydro-7,14-methanobenzimidazo[1,2-b][2,5]benzodiazocin-5(14H)-one; (7R,14R)-1-(difluoromethoxy)-11-(6-oxo-1,6-dihydropyridin-3-yl)-6,7-dihydro-7,14-methanobenzimidazo[1,2-b][2,5]benzodiazocin-5(14H)-one; (7R,14R)-1-(difluoromethoxy)-10-fluoro-11-[6-(2-hydroxypropan-2-yl)pyridin-3-yl]-6,7-dihydro-7,14-methanobenzimidazo[1,2-b][2,5]benzodiazocin-5(14H)-one; (7R,14R)-1-(difluoromethoxy)-11-[2-(2-hydroxypropan-2-yl)-6-methyl-pyrimidin-5-yl]-6,7-dihydro-7,14-methanobenzimidazo[1,2-b][2,5]benzodiazocin-5(14H)-one; (7R,14R)-1-(difluoromethoxy)-10-fluoro-11-[2-(2-hydroxypropan-2-yl)-6-methyl-pyrimidin-5-yl]-6,7-dihydro-7,14-methanobenzimidazo[1,2-b][2,5]benzodiazocin-5(14H)-one; (7R,14R)-1-(difluoromethoxy)-11-[6-(2-hydroxypropan-2-yl)pyridin-3-yl]-6,7-dihydro-7,14-methanobenzimidazo[1,2-b][2,5]benzodiazocin-5(14H)-one; (7R,14R)-1-(difluoromethoxy)-11-[4-(S-methylsulfonimidoyl)phenyl]-6,7-dihydro-7,14-methanobenzimidazo[1,2-b][2,5]benzodiazocin-5(14H)-one; (1R,11R)-18-(difluoromethoxy)-6-fluoro-5-[2-(2-hydroxypropan-2-yl)pyrimidin-5-yl]-3,9,12-triazapentacyclo[9.8.1.0$^{2,10}$.0$^{3,8}$.0$^{14,19}$]icosa-2(10),4,6,8,14(19),15,17-heptaen-13-one hydrochloride; (7R,14R)-1-(difluoromethoxy)-11-[2-(cis-1,3-dihydroxy-3-methylcyclobutyl)pyrimidin-5-yl]-6,7-dihydro-7,14-methanobenzimidazo[1,2-b][2,5]benzodiazocin-5(14H)-one; ethyl[(6R,12R)-11-(difluoromethoxy)-3-fluoro-2-[2-(2-hydroxypropan-2-yl)pyrimidin-5-yl]-6H-6,12-methanobenzimidazo[2,1-c][1,4]benzodiazepin-7(12H)-yl]acetate; (7R,14R)-1-(difluoromethoxy)-10-fluoro-11-[2-(2-hydroxypropan-2-yl)pyrimidin-5-yl]-6-methyl-6,7-dihydro-7,14-methanobenzimidazo[1,2-b][2,5]benzodiazocin-5(14H)-one; tert-butyl (2-{5-[(6R,12R)-11-(difluoromethoxy)-7-(methylsulfonyl)-7,12-dihydro-6H-6,12-methanobenzimidazo[2,1-c][1,4]benzodiazepin-2-yl]pyrimidin-2-yl}propan-2-yl)carbamate; 2-{5-[(6R,12R)-11-(difluoromethoxy)-7-(methylsulfonyl)-7,12-dihydro-6H-6,12-methanobenzimidazo[2,1-c][1,4]benzodiazepin-2-yl]pyrimidin-2-yl}propan-2-amine; azetidin-3-yl[(6R,12R)-2-chloro-11-(difluoromethoxy)-6H-6,12-methanobenzimidazo[2,1-c][1,4]benzodiazepin-7(12H)-yl]methanone; [(6R,12R)-11-(difluoromethoxy)-3-fluoro-2-[2-(2-hydroxypropan-2-yl)pyrimidin-5-yl]-6H-6,12-methanobenzimidazo[2,1-c][1,4]benzodiazepin-7(12H)-yl][1-(methylsulfonyl)azetidin-3-yl]methanone; 2-{5-[(6R,12R)-11-(difluoromethoxy)-3-fluoro-7,12-dihydro-6H-6,12-methanobenzimidazo[2,1-c][1,4]benzodiazepin-2-yl]pyrimidin-2-yl}propan-2-ol; azetidin-3-yl[(6R,12R)-2-chloro-11-(difluoromethoxy)-6H-6,12-methanobenzimidazo[2,1-c][1,4]benzodiazepin-7(12H)-yl]methanone; cis-1-{5-[(6R,12R)-11-(difluoromethoxy)-7-(methylsulfonyl)-7,12-dihydro-6H-6,12-methanobenzimidazo[2,1-c][1,4]benzodiazepin-2-yl]pyrimidin-2-yl}-3-methylcyclobutane-1,3-diol; (6R,12R)-11-(difluoromethoxy)-2-{2-[(1s,5s)-3,7-dioxa-9-azabicyclo[3.3.1]non-9-yl]pyrimidin-5-yl}-7-(methylsulfonyl)-7,12-dihydro-6H-6,12-methanobenzimidazo[2,1-c][1,4]benzodiazepine; [(6R,12R)-11-(difluoromethoxy)-3-fluoro-2-[2-(2-hydroxypropan-2-yl)pyrimidin-5-yl]-6H-6,12-methanobenzimidazo[2,1-c][1,4]benzodiazepin-7(12H)-yl]acetic acid; 2-{5-[(6R,12R)-11-(difluoromethoxy)-3-fluoro-7-(pyridin-3-ylsulfonyl)-7,12-dihydro-6H-6,12-methanobenzimidazo[2,1-c][1,4]benzodiazepin-2-yl]pyrimidin-2-yl}propan-2-ol; 1-{5-[(6R,12R)-11-(difluoromethoxy)-7-(methylsulfonyl)-7,12-dihydro-6H-6,12-methanobenzimidazo[2,1-c][1,4]benzodiazepin-2-yl]pyrimidin-2-yl}-3-(trifluoromethyl)azetidin-3-ol; 2-{5-[(6R,12R)-11-(difluoromethoxy)-3-fluoro-7-(methylsulfonyl)-7,12-dihydro-6H-6,12-methanobenzimidazo[2,1-c][1,4]benzodiazepin-2-yl]pyrimidin-2-yl}propan-2-ol; 2-{5-[(6R,12R)-7-(cyclopropylsulfonyl)-11-(difluoromethoxy)-3-fluoro-7,12-dihydro-6H-6,12-methanobenzimidazo[2,1-c][1,4]benzodiazepin-2-yl]pyrimidin-2-yl}propan-2-ol; 2-{5-[(6R,12R)-7-(2-{[tert-butyl(dimethyl)silyl]oxy}ethyl)-11-(difluoromethoxy)-3-fluoro-7,12-dihydro-6H-6,12-methanobenzimidazo[2,1-c][1,4]benzodiazepin-2-yl]pyrimidin-2-yl}propan-2-ol; 2-{5-[(6R,12R)-11-(difluoromethoxy)-3-fluoro-7-(2-hydroxyethyl)-7,12-dihydro-6H-6,12-methanobenzimidazo[2,1-c][1,4]benzodiazepin-2-yl]pyrimidin-2-yl}propan-2-ol; 2-{5-[(6R,12R)-11-(difluoromethoxy)-3-fluoro-7-(phenylsulfonyl)-7,12-dihydro-6H-6,12-methanobenzimidazo[2,1-c][1,4]benzodiazepin-2-yl]pyrimidin-2-yl}propan-2-ol; 2-(5-{(6R,12R)-11-(difluoromethoxy)-3-fluoro-7-[(6-methoxypyridin-3-yl)sulfonyl]-7,12-dihydro-6H-6,12-methanobenzimidazo[2,1-c][1,4]benzodiazepin-2-yl}pyrimidin-2-yl)propan-2-ol; 2-{5-[(6R,12R)-11-(difluoromethoxy)-3-fluoro-7-(phenylsulfonyl)-7,12-dihydro-6H-6,12-methanobenzimidazo[2,1-c][1,4]benzodiazepin-2-yl]pyrimidin-2-yl}propan-2-ol; 2-(5-{(6R,12R)-11-(difluoromethoxy)-3-fluoro-7-[(6-methoxypyridin-3-yl)sulfonyl]-7,12-dihydro-6H-6,12-methanobenzimidazo[2,1-c][1,4]benzodiazepin-2-yl}pyrimidin-2-yl)propan-2-ol; [(7R,14R)-1-(difluoromethoxy)-11-[2-(2-hydroxypropan-2-yl)

pyrimidin-5-yl]-5-oxo-5,14-dihydro-7,14-methanobenzimidazo[1,2-b][2,5]benzodiazocin-6(7H)-yl] acetic acid; (7R,14R)-1-(difluoromethoxy)-11-[2-(2-hydroxypropan-2-yl)pyrimidin-5-yl]-6-(2,2,2-trifluoroethyl)-6,7-dihydro-7,14-methanobenzimidazo[1,2-b][2,5]benzodiazocin-5(14H)-one; (7R,14R)-1-(difluoromethoxy)-6-(2-hydroxyethyl)-11-[2-(2-hydroxypropan-2-yl)pyrimidin-5-yl]-6,7-dihydro-7,14-methanobenzimidazo[1,2-b][2,5]benzodiazocin-5(14H)-one; (7R,14R)-1-(difluoromethoxy)-6-(2-hydroxy-2-methylpropyl)-11-[2-(2-hydroxypropan-2-yl)pyrimidin-5-yl]-6,7-dihydro-7,14-methanobenzimidazo[1,2-b][2,5]benzodiazocin-5(14H)-one; (7R,14R)-11-[2-(2-aminopropan-2-yl)pyrimidin-5-yl]-1-(difluoromethoxy)-6-(trideutero)methyl-6,7-dihydro-7,14-methanobenzimidazo[1,2-b][2,5]benzodiazocin-5(14H)-one; (7R,14R)-1-(difluoromethoxy)-11-{6-[3-hydroxy-3-(trifluoromethyl)azetidin-1-yl]-4-methylpyridin-3-yl}-6,7-dihydro-7,14-methanobenzimidazo[1,2-b][2,5]benzodiazocin-5(14H)-one; (6R,12R)-3,10-dibromo-2-chloro-11-(difluoromethoxy)-7-(methylsulfonyl)-7,12-dihydro-6H-6,12-methanobenzimidazo[2,1-c][1,4]benzodiazepine; (6R,12R)-2,8,10-trichloro-11-(difluoromethoxy)-7,12-dihydro-6H-6,12-methanobenzimidazo[2,1-c][1,4]benzodiazepine; (7R,14R)-1-(difluoromethoxy)-10-fluoro-11-[2-(2-hydroxypropan-2-yl)-4-methylpyrimidin-5-yl]-7,14-dihydro-7,14-methanopyrido[1',2':1,2]imidazo[4,5-d][2]benzazocin-5(6H)-one; (7R,14R)-1-(difluoromethoxy)-11-{2-[3-hydroxy-3-(trifluoromethyl)azetidin-1-yl]pyrimidin-5-yl}-6,7-dihydro-7,14-methanobenzimidazo[1,2-b][2,5]benzodiazocin-5(14H)-one; (7R,14R)-1-(difluoromethoxy)-10-fluoro-11-{2-[3-hydroxy-3-(trifluoromethyl)azetidin-1-yl]pyrimidin-5-yl}-6,7-dihydro-7,14-methanobenzimidazo[1,2-b][2,5]benzodiazocin-5(14H)-one; (7R,14R)-1-(difluoromethoxy)-11-{2-[(1s,5s)-3,7-dioxa-9-azabicyclo[3.3.1]non-9-yl]pyrimidin-5-yl}-10-fluoro-6,7-dihydro-7,14-methanobenzimidazo[1,2-b][2,5]benzodiazocin-5(14H)-one; (7R,14R)-1-(difluoromethoxy)-11-[2-methyl-4-(methylsulfonyl)phenyl]-6,7-dihydro-7,14-methanobenzimidazo[1,2-b][2,5]benzodiazocin-5(14H)-one; (7R,14R)-1-(difluoromethoxy)-11-[6-(2-hydroxypropan-2-yl)-4-methylpyridin-3-yl]-6,7-dihydro-7,14-methanobenzimidazo[1,2-b][2,5]benzodiazocin-5(14H)-one; (7R,14R)-11-[2-(2-aminopropan-2-yl)pyrimidin-5-yl]-1-(difluoromethoxy)-6,7-dihydro-7,14-methanobenzimidazo[1,2-b][2,5]benzodiazocin-5(14H)-one; (7R,14R)-11-[2-(2-aminopropan-2-yl)pyrimidin-5-yl]-1-(difluoromethoxy)-10-fluoro-6,7-dihydro-7,14-methanobenzimidazo[1,2-b][2,5]benzodiazocin-5(14H)-one; 2-{5-[(7R,14R)-1-(difluoromethoxy)-5-methyl-5,6,7,14-tetrahydro-7,14-methanobenzimidazo[1,2-b][2,5]benzodiazocin-11-yl]pyrimidin-2-yl}propan-2-ol; 2-{5-[(5R or 5S,7R,14R)-1-(difluoromethoxy)-5-methyl-5,6,7,14-tetrahydro-7,14-methanobenzimidazo[1,2-b][2,5]benzodiazocin-11-yl]pyrimidin-2-yl}propan-2-ol; 2-{5-[(5R or 5S,7R,14R)-1-(difluoromethoxy)-5-methyl-5,6,7,14-tetrahydro-7,14-methanobenzimidazo[1,2-b][2,5]benzodiazocin-11-yl]pyrimidin-2-yl}propan-2-ol; 1-[(7R,14R)-1-(difluoromethoxy)-11-[2-(2-hydroxypropan-2-yl)pyrimidin-5-yl]-5-methyl-5,14-dihydro-7,14-methanobenzimidazo[1,2-b][2,5]benzodiazocin-6(7H)-yl]ethanone; 1-[(7R,14R)-1-(difluoromethoxy)-11-[2-(2-hydroxypropan-2-yl)pyrimidin-5-yl]-5,14-dihydro-7,14-methanobenzimidazo[1,2-b][2,5]benzodiazocin-6(7H)-yl]ethanone; 2-{5-[(7R,14R)-1-(difluoromethoxy)-6-methyl-5,6,7,14-tetrahydro-7,14-methanobenzimidazo[1,2-b][2,5]benzodiazocin-11-yl]pyrimidin-2-yl}propan-2-ol; 2-{5-[(7R,14R)-1-(difluoromethoxy)-10-fluoro-6-(methylsulfonyl)-5,6,7,14-tetrahydro-7,14-methanobenzimidazo[1,2-b][2,5]benzodiazocin-11-yl]pyrimidin-2-yl}propan-2-ol; 2-{5-[(7R,14R)-1-(difluoromethoxy)-5-(trifluoromethyl)-5,6,7,14-tetrahydro-7,14-methanobenzimidazo[1,2-b][2,5]benzodiazocin-11-yl]pyrimidin-2-yl}propan-2-ol; 2-{5-[(5R,7R,14R)-1-(difluoromethoxy)-5-(trifluoromethyl)-5,6,7,14-tetrahydro-7,14-methanobenzimidazo[1,2-b][2,5]benzodiazocin-11-yl]pyrimidin-2-yl}propan-2-ol; 2-{5-[(5S,7R,14R)-1-(difluoromethoxy)-5-(trifluoromethyl)-5,6,7,14-tetrahydro-7,14-methanobenzimidazo[1,2-b][2,5]benzodiazocin-11-yl]pyrimidin-2-yl}propan-2-ol; 2-{5-[(5R,7R,14R)-1-(difluoromethoxy)-5-(trifluoromethyl)-5,6,7,14-tetrahydro-7,14-methanobenzimidazo[1,2-b][2,5]benzodiazocin-11-yl]pyrimidin-2-yl}propan-2-ol; 2-{5-[(5S,7R,14R)-1-(difluoromethoxy)-5-(trifluoromethyl)-5,6,7,14-tetrahydro-7,14-methanobenzimidazo[1,2-b][2,5]benzodiazocin-11-yl]pyrimidin-2-yl}propan-2-ol; (7R,14R)-1-(difluoromethoxy)-10-fluoro-11-[2-(2-hydroxypropan-2-yl)-1-oxidopyrimidin-5-yl]-6,7-dihydro-7,14-methanobenzimidazo[1,2-b][2,5]benzodiazocin-5(14H)-one; (7R,14R)-1-(difluoromethoxy)-11-{2-[3-hydroxy-3-(trifluoromethyl)azetidin-1-yl]-4-methylpyrimidin-5-yl}-6,7-dihydro-7,14-methanobenzimidazo[1,2-b][2,5]benzodiazocin-5(14H)-one; (7R,14R)-1-(difluoromethoxy)-10-fluoro-11-{2-[3-hydroxy-3-(trifluoromethyl)azetidin-1-yl]-4-methylpyrimidin-5-yl}-6,7-dihydro-7,14-methanobenzimidazo[1,2-b][2,5]benzodiazocin-5(14H)-one; (7R,14R)-1-(difluoromethoxy)-11-{6-[3-hydroxy-3-(trifluoromethyl)azetidin-1-yl]-2-methylpyridin-3-yl}-6,7-dihydro-7,14-methanobenzimidazo[1,2-b][2,5]benzodiazocin-5(14H)-one; (6R,12R)-2-chloro-11-(difluoromethoxy)-6H,12H-6,12-methanobenzimidazo[2,1-c][1,4]benzothiazepine; 2-{5-[(6R,12R)-11-(difluoromethoxy)-6H,12H-6,12-methanobenzimidazo[2,1-c][1,4]benzothiazepin-2-yl]pyrimidin-2-yl}propan-2-ol; (6R,7R,12S)-2-chloro-11-(difluoromethoxy)-6H,12H-6,12-methanobenzimidazo[2,1-c][1,4]benzothiazepine 7-oxide; (6R,7S,12S)-2-chloro-11-(difluoromethoxy)-6H,12H-6,12-methanobenzimidazo[2,1-c][1,4]benzothiazepine 7-oxide; 2-{5-[(6R,7R,12S)-11-(difluoromethoxy)-7-oxido-6H,12H-6,12-methanobenzimidazo[2,1-c][1,4]benzothiazepin-2-yl]pyrimidin-2-yl}propan-2-ol; 2-{5-[(6R,7S,12S)-11-(difluoromethoxy)-7-oxido-6H,12H-6,12-methanobenzimidazo[2,1-c][1,4]benzothiazepin-2-yl]pyrimidin-2-yl}propan-2-ol; (6R,12R)-2-chloro-11-(difluoromethoxy)-6H,12H-6,12-methanobenzimidazo[2,1-c][1,4]benzothiazepine 7,7-dioxide; 2-{5-[(6R,12R)-11-(difluoromethoxy)-7,7-dioxido-6H,12H-6,12-methanobenzimidazo[2,1-c][1,4]benzothiazepin-2-yl]pyrimidin-2-yl}propan-2-ol; 1-[(5R,7R,14R)-1-(difluoromethoxy)-11-[2-(2-hydroxypropan-2-yl)pyrimidin-5-yl]-5-methyl-5,14-dihydro-7,14-methanobenzimidazo[1,2-b][2,5]benzodiazocin-6(7H)-yl]ethanone; 1-[(5S,7R,14R)-1-(difluoromethoxy)-11-[2-(2-hydroxypropan-2-yl)pyrimidin-5-yl]-5-methyl-5,14-dihydro-7,14-methanobenzimidazo[1,2-b][2,5]benzodiazocin-6(7H)-yl]ethanone; 1-[(5R,7R,14R)-1-(difluoromethoxy)-11-[2-(2-hydroxypropan-2-yl)pyrimidin-5-yl]-5-methyl-5,14-dihydro-7,14-methanobenzimidazo[1,2-b][2,5]benzodiazocin-6(7H)-yl]ethanone; 1-[(5S,7R,14R)-1-(difluoromethoxy)-11-[2-(2-hydroxypropan-2-yl)pyrimidin-5-yl]-5-methyl-5,14-dihydro-7,14-methanobenzimidazo[1,2-b][2,5]benzodiazocin-6(7H)-yl]ethanone; (7R,14R)-10-fluoro-1-hydroxy-11-[2-(2-hydroxypropan-2-yl)pyrimidin-5-yl]-6,7-dihydro-7,14-methanobenzimidazo[1,2-b][2,5]

benzodiazocin-5(14H)-one; 2-{5-[(7R,14R)-1-(difluoromethoxy)-5-methyl-5-oxido-7,14-dihydro-7,14-methano-5λ-4-benzimidazo[2,1-d][1,2,5]benzothiadiazocin-11-yl]pyrimidin-2-yl}propan-2-ol; (7R,14R)-1-(difluoromethoxy)-11-{6-[1-(methylsulfonyl)cyclopropyl]pyridin-3-yl}-6,7-dihydro-7,14-methanobenzimidazo[1,2-b][2,5]benzodiazocin-5(14H)-one; (7R,14R)-1-(difluoromethoxy)-11-[2-(2-hydroxypropan-2-yl)pyrimidin-5-yl]-6,7-dimethyl-6,7-dihydro-7,14-methanobenzimidazo[1,2-b][2,5]benzodiazocin-5(14H)-one; (7R,14R)-1-(difluoromethoxy)-11-[2-(2-hydroxypropan-2-yl)pyrimidin-5-yl]-7-methyl-6,7-dihydro-7,14-methanobenzimidazo[1,2-b][2,5]benzodiazocin-5(14H)-one; (7R,14R)-11-[2-(2-aminopropan-2-yl)pyrimidin-5-yl]-1-(difluoromethoxy)-6,7-dimethyl-6,7-dihydro-7,14-methanobenzimidazo[1,2-b][2,5]benzodiazocin-5(14H)-one; (7R,14R)-1-(difluoromethoxy)-10-fluoro-11-[2-(2-hydroxypropan-2-yl)-4,6-dimethylpyrimidin-5-yl]-6,7-dihydro-7,14-methanobenzimidazo[1,2-b][2,5]benzodiazocin-5(14H)-one; 2-{5-[(5R,7R,14R)-1-(difluoromethoxy)-5-(trifluoromethyl)-5,14-dihydro-7H-7,14-methanobenzimidazo[2,1-d][2,5]benzoxazocin-11-yl]pyrimidin-2-yl}propan-2-ol; 2-{5-[(5S,7R,14R)-1-(difluoromethoxy)-5-(trifluoromethyl)-5,14-dihydro-7H-7,14-methanobenzimidazo[2,1-d][2,5]benzoxazocin-11-yl]pyrimidin-2-yl}propan-2-ol; (7R,14R)-1-(difluoromethoxy)-10-fluoro-11-[2-(2-hydroxypropan-2-yl)pyrimidin-5-yl]-12-(trifluoromethyl)-6,7-dihydro-7,14-methanobenzimidazo[1,2-b][2,5]benzodiazocin-5(14H)-one; (7R,14R)-1-(difluoromethoxy)-10-fluoro-11-[2-(2-hydroxypropan-2-yl)pyrimidin-5-yl]-4-(trifluoromethyl)-6,7-dihydro-7,14-methanobenzimidazo[1,2-b][2,5]benzodiazocin-5(14H)-one; (7R,14R)-1-(difluoromethoxy)-10-fluoro-11-[2-(2-hydroxypropan-2-yl)pyrimidin-5-yl]-9-(trifluoromethyl)-6,7-dihydro-7,14-methanobenzimidazo[1,2-b][2,5]benzodiazocin-5(14H)-one; (7R,14R)-1-(difluoromethoxy)-10-fluoro-11-[2-(2-hydroxypropan-2-yl)pyrimidin-5-yl]-2-(trifluoromethyl)-6,7-dihydro-7,14-methanobenzimidazo[1,2-b][2,5]benzodiazocin-5(14H)-one; (7R,14R)-1-(difluoromethoxy)-10-fluoro-11-[2-(2-hydroxypropan-2-yl)-4-(trifluoromethyl)pyrimidin-5-yl]-6,7-dihydro-7,14-methanobenzimidazo[1,2-b][2,5]benzodiazocin-5(14H)-one; (7R,14R)-1-(difluoromethoxy)-10-fluoro-11-[2-(2-hydroxypropan-2-yl)pyrimidin-5-yl]-3-(trifluoromethyl)-6,7-dihydro-7,14-methanobenzimidazo[1,2-b][2,5]benzodiazocin-5(14H)-one; 2-{5-[(6R,12R)-11-(difluoromethoxy)-3-fluoro-7,12-dihydro-6H-6,12-methanopyrido[1',2':1,2]imidazo[4,5-c][1]benzazepin-2-yl]pyrimidin-2-yl}propan-2-ol; (7R,14R)-1-(difluoromethoxy)-11-[2-(cis-1,3-dihydroxy-3-methylcyclobutyl)pyrimidin-5-yl]-6-trideutero-methyl-6,7-dihydro-7,14-methanobenzimidazo[1,2-b][2,5]benzodiazocin-5(14H)-one; Ethyl (7R,14S)-11-chloro-1-(difluoromethoxy)-6,7-dihydro-14H-7,14-methanobenzimidazo[2,1-d][1,5]benzothiazocine-6-carboxylate; ethyl (7R,14S)-1-(difluoromethoxy)-11-[2-(2-hydroxypropan-2-yl)pyrimidin-5-yl]-6,7-dihydro-14H-7,14-methanobenzimidazo[2,1-d][1,5]benzothiazocine-6-carboxylate; 2-{5-[(5R,7R,14R)-1-(difluoromethoxy)-5-oxido-6,7-dihydro-14H-7,14-methanobenzimidazo[2,1-d][1,5]benzothiazocin-11-yl]pyrimidin-2-yl}propan-2-ol; 2-{5-[(7R,14R)-1-(difluoromethoxy)-5,5-dioxido-6,7-dihydro-14H-7,14-methanobenzimidazo[2,1-d][1,5]benzothiazocin-11-yl]pyrimidin-2-yl}propan-2-ol
2-{5-[(6R,7R,14S)-1-(difluoromethoxy)-6-(2-hydroxypropan-2-yl)-6,7-dihydro-14H-7,14-methanobenzimidazo[2,1-d][1,5]benzothiazocin-11-yl]pyrimidin-2-yl}propan-2-ol; 2-{5-[(6S,7R,14S)-1-(difluoromethoxy)-6-(hydroxymethyl)-6,7-dihydro-14H-7,14-methanobenzimidazo[2,1-d][1,5]benzothiazocin-11-yl]pyrimidin-2-yl}propan-2-ol; 2-{5-[(6R,7R,14S)-1-(difluoromethoxy)-6-(hydroxymethyl)-6,7-dihydro-14H-7,14-methanobenzimidazo[2,1-d][1,5]benzothiazocin-11-yl]pyrimidin-2-yl}propan-2-ol; (7R,14R)-1-(difluoromethoxy)-11-[6-(2-hydroxypropan-2-yl)pyridin-3-yl]-6-trideuteromethyl-6,7-dihydro-7,14-methanobenzimidazo[1,2-b][2,5]benzodiazocin-5(14H)-one; (7R,14R)-1-(difluoromethoxy)-11-[6-(2-hydroxypropan-2-yl)-1-oxidopyridin-3-yl]-6,7-dihydro-7,14-methanobenzimidazo[1,2-b][2,5]benzodiazocin-5(14H)-one; (7R,14R)-1-(difluoromethoxy)-11-[6-(2-hydroxypropan-2-yl)-1-oxidopyridin-3-yl]-6-trideuteromethyl-6,7-dihydro-7,14-methanobenzimidazo[1,2-b][2,5]benzodiazocin-5(14H)-one; 2-{5-[(6R,12R)-11-(difluoromethoxy)-6H,12H-6,12-methanobenzimidazo[2,1-c][1,4]benzothiazepin-2-yl]pyrimidin-2-yl}propan-2-amine, dihydrochloride salt; tert-Butyl 3-{5-[(7R,14R)-1-(difluoromethoxy)-6-trideuteromethyl-5-oxo-5,6,7,14-tetrahydro-7,14-methanobenzimidazo[1,2-b][2,5]benzodiazocin-11-yl]pyridin-2-yl}-3-hydroxypyrrolidine-1-carboxylate; (7R,14R)-1-(difluoromethoxy)-11-[6-(3-hydroxypyrrolidin-3-yl)pyridin-3-yl]-6-trideuteromethyl-6,7-dihydro-7,14-methanobenzimidazo[1,2-b][2,5]benzodiazocin-5(14H)-one, dihydrochloride salt; methyl (2-{5-[(7R,14R)-1-(difluoromethoxy)-6-trideuteromethyl-5-oxo-5,6,7,14-tetrahydro-7,14-methanobenzimidazo[1,2-b][2,5]benzodiazocin-11-yl]pyrimidin-2-yl}propan-2-yl)carbamate; (7R,14R)-1-(difluoromethoxy)-11-[2-(2-hydroxypropan-2-yl)-4-methylpyrimidin-5-yl]-6-trideuteromethyl-6,7-dihydro-7,14-methanobenzimidazo[1,2-b][2,5]benzodiazocin-5(14H)-one; (7R,14R)-11-chloro-1-(difluoromethoxy)-5-methylidene-5,14-dihydro-7H-7,14-methanobenzimidazo[2,1-d][2,5]benzoxazocine; (7R,14R)-1-(difluoromethoxy)-11-{2-[3-hydroxy-3-(trifluoromethyl)azetidin-1-yl]-4-methyl pyrimidin-5-yl}-6-trideuteromethyl-6,7-dihydro-7,14-methanobenzimidazo[1,2-b][2,5]benzodiazocin-5(14H)-one; (7R,14R)-1-(difluoromethoxy)-11-[6-(piperazin-1-yl)pyridin-3-yl]-6,7-dihydro-7,14-methanobenzimidazo[1,2-b][2,5]benzodiazocin-5(14H)-one; (7R,14R)-1-(difluoromethoxy)-6-trideutero-methyl-11-[6-(piperazin-1-yl)pyridin-3-yl]-6,7-dihydro-7,14-methanobenzimidazo[1,2-b][2,5]benzodiazocin-5(14H)-one; (7R,14R)-1-(difluoromethoxy)-6-trideutero-methyl-11-{6-[4-(methylsulfonyl)piperazin-1 yl]pyridine-3-yl}-6,7-dihydro-7,14-methanobenzimidazo[1,2-b][2,5]benzodiazocin-5(14H)-one; (7R,14R)-1-(difluoromethoxy)-11-{2-[2-(dimethylamino)propan-2-yl]pyrimidin-5-yl}-6,7-dihydro-7,14-methanobenzimidazo[1,2-b][2,5]benzodiazocin-5(14H)-one; (7R,14R)-1-(difluoromethoxy)-11-[2-(3-oxopiperazin-1-yl)pyrimidin-5-yl]-6,7-dihydro-7,14-methanobenzimidazo[1,2-b][2,5]benzodiazocin-5(14H)-one; 1-[(6R,12R)-11-(difluoromethoxy)-2-(1-methyl-1H-pyrazol-4-yl)-6H-6,12-methanobenzimidazo[2,1-c][1,4]benzodiazepin-7(12H)-yl]-2-(3,7-dioxa-9-azabicyclo[3.3.1]non-9-yl)ethanone; (6R,12R)-2-chloro-11-(difluoromethoxy)-7-[(6-methoxypyridin-3-yl)sulfonyl]-7,12-dihydro-6H-6,12-methanobenzimidazo[2,1-c][1,4]benzodiazepine; 5-{[(6R,12R)-2-chloro-11-(difluoromethoxy)-6H-6,12-methanobenzimidazo[2,1-c][1,4]benzodiazepin-7(12H)-yl]sulfonyl}pyridin-2(1H)-one; 2-{5-[(7R,14R)-1-(difluoromethoxy)-5,5-dioxido-6,7-dihydro-14H-7,14-methanobenzimidazo[2,1-d][1,2,5]benzothiadiazocin-11-yl]pyrimidin-2-yl}propan-2-ol; (7R,14R)-

1-(difluoromethoxy)-11-[2-methyl-4-(methylsulfanyl)phenyl]-6,7-dihydro-7,14-methanobenzimidaz[1,2-b][2,5]benzodiazocin-5(14H)-one; (7R,14R)-1-(difluoromethoxy)-11-[2-(morpholin-4-yl)pyrimidin-5-yl]-6,7-dihydro-7,14-methanobenzimidazo[1,2-b][2,5]benzodiazocin-5(14H)-one; (6R,12R)-2-chloro-11-(difluoromethoxy)-7-(pyrimidin-2-yl)-7,12-dihydro-6H-6,12-methanobenzimidazo[2,1-c][1,4]benzodiazepine; ethyl-(6R,12R)-2-chloro-11-(difluoromethoxy)-6H-6,12-methanobenzimidazo[2,1-c][1,4]benzodiazepine-7(12H)-carboxylate; ethyl-(6R,12R)-11-(difluoromethoxy)-2-[2-(2-hydroxypropan-2-yl)pyrimidin-5-yl]-6H-6,12-methanobenzimidazo[2,1-c][1,4]benzodiazepine-7(12H)-carboxylate; N-(1-{5-[(7R,14R)-1-(difluoromethoxy)-6-trideuteromethyl-5-oxo-5,6,7,14-tetrahydro-7,14-methanobenzimidazo[1,2-b][2,5]benzodiazocin-11-yl]pyridin-2-yl}cyclobutyl)-2-methylpropane-2-sulfinamide; (7R,14R)-11-[6-(1-aminocyclobutyl)pyridin-3-yl]-1-(difluoromethoxy)-6-trideuteromethyl-6,7-dihydro-7,14-methanobenzimidazo[1,2-b][2,5]benzodiazocin-5(14H)-one; N-(3-{5-[(7R,14R)-1-(difluoromethoxy)-6-trideuteromethyl-5-oxo-5,6,7,14-tetrahydro-7,14-methanobenzimidazo[1,2-b][2,5]benzodiazocin-11-yl]pyridin-2-yl}oxetan-3-yl)-2-methylpropane-2-sulfinamide; (7R,14R)-11-[6-(3-aminooxetan-3-yl)pyridin-3-yl]-1-(difluoromethoxy)-6-trideuteromethyl-6,7-dihydro-7,14-methanobenzimidazo[1,2-b][2,5]benzodiazocin-5(14H)-one; N-(3-{5-[(7R,14R)-1-(difluoromethoxy)-6-methyl-5-oxo-5,6,7,14-tetrahydro-7,14-methanobenzimidazo[1,2-b][2,5]benzodiazocin-11-yl]pyridin-2-yl}oxetan-3-yl)-2-methylpropane-2-sulfinamide; N-(3-{5-[(7R,14R)-1-(difluoromethoxy)-5-oxo-5,6,7,14-tetrahydro-7,14-methanobenzimidazo[1,2-b][2,5]benzodiazocin-11-yl]-1-oxidopyridin-2-yl}oxetan-3-yl)-2-methylpropane-2-sulfonamide; (7R,14R)-1-(difluoromethoxy)-11-[4-(2,4-dimethyl-1H-imidazol-5-yl)phenyl]-6-trideuteromethyl-6,7-dihydro-7,14-methanobenzimidazo[1,2-b][2,5]benzodiazocin-5(14H)-one; (7R,14R)-1-(difluoromethoxy)-11-[4-(2,4-dimethyl-1H-imidazol-5-yl)phenyl]-6-trideuteromethyl-6,7-dihydro-7,14-methanobenzimidazo[1,2-b][2,5]benzodiazocin-5(14H)-one; (7R,14R)-1-(difluoromethoxy)-11-[4-(2,4-dimethyl-1H-imidazol-5-yl)phenyl]-6,7-dihydro-7,14-methanobenzimidazo[1,2-b][2,5]benzodiazocin-5(14H)-one; [(6R,7E,12R)-2-chloro-11-(difluoromethoxy)-6H-6,12-methano-7λ-4-benzimidazo[2,1-c][1,4]benzothiazepin-7(12H)-ylidene]cyanamide; N-(2-{5-[(7R,14R)-1-(difluoromethoxy)-6-methyl-5-oxo-5,6,7,14-tetrahydro-7,14-methanobenzimidazo[1,2-b][2,5]benzodiazocin-11-yl]pyrimidin-2-yl}propan-2-yl)methanesulfonamide; N-(2-{5-[(7R,14R)-1-(difluoromethoxy)-6-methyl-5-oxo-5,6,7,14-tetrahydro-7,14-methanobenzimidazo[1,2-b][2,5]benzodiazocin-11-yl]pyrimidin-2-yl}propan-2-yl)acetamide; (7R,14R)-1-(difluoromethoxy)-11-[4-(pyrrolidin-2-yl)phenyl]-6,7-dihydro-7,14-methanobenzimidazo[1,2-b][2,5]benzodiazocin-5(14H)-one; (7R,14R)-1-(difluoromethoxy)-6-trideutero-methyl-11-[2-(3-oxopiperazin-1-yl)pyrimidin-5-yl]-6,7-dihydro-7,14-methanobenzimidazo[1,2-b][2,5]benzodiazocin-5(14H)-one; (7R,14R)-1-(difluoromethoxy)-6-methyl-11-[2-(5-oxo-1,4-diazepan-1-yl)pyrimidin-5-yl]-6,7-dihydro-7,14-methanobenzimidazo[1,2-b][2,5]benzodiazocin-5(14H)-one; (7R,14R)-11-[4-(2-aminopropan-2-yl)phenyl]-1-(difluoromethoxy)-6,7-dihydro-7,14-methanobenzimidazo[1,2-b][2,5]benzodiazocin-5(14H)-one; (7R,14R)-1-(difluoromethoxy)-11-[2-(3-hydroxy-3-methylazetidin-1-yl)-4-methylpyrimidin-5-yl]-6,7-dihydro-7,14-methanobenzimidazo[1,2-b][2,5]benzodiazocin-5(14H)-one; (7R,14R)-1-(difluoromethoxy)-10-fluoro-6-trideuteromethyl-11-[2-(3-oxopiperazin-1-yl)pyrimidin-5-yl]-6,7-dihydro-7,14-methanobenzimidazo[1,2-b][2,5]benzodiazocin-5(14H)-one; (7R,14R)-1-(difluoromethoxy)-11-[2-(1-oxidothiomorpholin-4-yl)pyrimidin-5-yl]-6,7-dihydro-7,14-methanobenzimidazo[1,2-b][2,5]benzodiazocin-5(14H)-one; (7R,14R)-11-[2-(4,4-difluoro-1-hydroxycyclohexyl)pyrimidin-5-yl]-1-(difluoromethoxy)-6,7-dihydro-7,14-methanobenzimidazo[1,2-b][2,5]benzodiazocin-5(14H)-one; (7R,14R)-1-(difluoromethoxy)-11-[2-(3-hydroxy-1,1-dioxidotetrahydrothiophen-3-yl)pyrimidin-5-yl]-6,7-dihydro-7,14-methanobenzimidazo[1,2-b][2,5]benzodiazocin-5(14H)-one; (3R)-3-{5-[(7R,14R)-1-(difluoromethoxy)-5-oxo-5,6,7,14-tetrahydro-7,14-methanobenzimidazo[1,2-b][2,5]benzodiazocin-11-yl]pyrimidin-2-yl}-3-hydroxytetrahydrothiophenium-1-olate; (3S)-3-{5-[(7R,14R)-1-(difluoromethoxy)-5-oxo-5,6,7,14-tetrahydro-7,14-methanobenzimidazo[1,2-b][2,5]benzodiazocin-11-yl]pyrimidin-2-yl}-3-hydroxytetrahydrothiophenium-1-olate; (7R,14R)-1-(difluoromethoxy)-11-[2-(3-hydroxyoxetan-3-yl)pyrimidin-5-yl]-6,7-dihydro-7,14-methanobenzimidazo[1,2-b][2,5]benzodiazocin-5(14H)-one; (7R,14R)-1-(difluoromethoxy)-11-{1-[1-(methylsulfonyl)azetidin-3-yl]-1H-pyrazol-4-yl}-6,7-dihydro-7,14-methanobenzimidazo[1,2-b][2,5]benzodiazocin-5(14H)-one; (7R,14R)-1-(difluoromethoxy)-11-(2-hydroxypyrimidin-5-yl)-6,7-dihydro-7,14-methanobenzimidazo[1,2-b][2,5]benzodiazocin-5(14H)-one; (7R,14R)-1-(difluoromethoxy)-11-[2-(1,4-dihydroxy-4-methylcyclohexyl)pyrimidin-5-yl]-6,7-dihydro-7,14-methanobenzimidazo[1,2-b][2,5]benzodiazocin-5(14H)-one; 2-{5-[(7R,14R)-1-(difluoromethoxy)-5-oxo-5,6,7,14-tetrahydro-7,14-methanobenzimidazo[1,2-b][2,5]benzodiazocin-11-yl]pyrimidin-2-yl}-2-methylpropanenitrile; 1-{5-[(7R,14R)-1-(difluoromethoxy)-5-oxo-5,6,7,14-tetrahydro-7,14-methanobenzimidazo[1,2-b][2,5]benzodiazocin-11-yl]pyrimidin-2-yl}-3-methylazetidine-3-carbonitrile; (7R,14R)-1-(difluoromethoxy)-11-{2-[(1 S,4S)-2-oxa-5-azabicyclo[2.2.1]hept-5-yl]pyrimidin-5-yl}-6,7-dihydro-7,14-methanobenzimidazo[1,2-b][2,5]benzodiazocin-5(14H)-one; (7R,14R)-1-(difluoromethoxy)-11-[2-(thiomorpholin-4-yl)pyrimidin-5-yl]-6,7-dihydro-7,14-methanobenzimidazo[1,2-b][2,5]benzodiazocin-5(14H)-one; (7R,14R)-1-(difluoromethoxy)-11-{2-[3-(2-hydroxypropan-2-yl)azetidin-1-yl]pyrimidin-5-yl}-6,7-dihydro-7,14-methanobenzimidazo[1,2-b][2,5]benzodiazocin-5(14H)-one; (7R,14R)-11-[2-(3,3-difluoroazetidin-1-yl)pyrimidin-5-yl]-1-(difluoromethoxy)-6,7-dihydro-7,14-methanobenzimidazo[1,2-b][2,5]benzodiazocin-5(14H)-one; (7R,14R)-1-(difluoromethoxy)-11-[2-(3-oxa-8-azabicyclo[3.2.1]oct-8-yl)pyrimidin-5-yl]-6,7-dihydro-7,14-methanobenzimidazo[1,2-b][2,5]benzodiazocin-5(14H)-one; (7R,14R)-1-(difluoromethoxy)-11-[2-(7-oxo-3,6-diazabicyclo[3.2.2]non-3-yl)pyrimidin-5-yl]-6,7-dihydro-7,14-methanobenzimidazo[1,2-b][2,5]benzodiazocin-5(14H)-one; (7R,14R)-1-(difluoromethoxy)-11-[2-(1,1-dioxidothiomorpholin-4-yl)pyrimidin-5-yl]-6,7-dihydro-7,14-methanobenzimidazo[1,2-b][2,5]benzodiazocin-5(14H)-one; (7R,14R)-1-(difluoromethoxy)-11-(1-methyl-6-oxo-1,6-dihydropyridin-3-yl)-6,7-dihydro-7,14-methanobenzimidazo[1,2-b][2,5]benzodiazocin-5(14H)-one; (7R,14R)-1-(difluoromethoxy)-11-[2-(tetrahydro-2H-pyran-4-yl)pyrimidin-5-yl]-6,7-dihydro-7,14-methanobenzimidazo[1,2-b][2,5]benzodiazocin-5(14H)-one; (7R,14R)-11-[2-(2-aminopropan-2-yl)pyrimidin-5-yl]-1-(difluoromethoxy)-10-fluoro-6-trideutero methyl-6,7- dihydro-7,14-methanobenzimidazo[1,2-b][2,5]
benzodiazocin-5(14H)-one; (7R,14R) 10-fluoro-11-[2-(2-hydroxypropan-2-yl)pyrimidin-5-yl]-1-(trifluoromethoxy)-6,7-dihydro-7,14-methanobenzimidazo[1,2-b][2,5]
benzodiazocin-5(14H)-one; (7R,14R)-1-(difluoromethoxy)-10-fluoro-11-(3-(2-hydroxypropan-2-yl)azetidin-1-yl)-6,7-dihydro-7,14-methanobenzimidazo[1,2-b][2,5]
benzodiazocin-5(14H)-one; (7R,14R)-11-((2-aminopropan-2-yl)phenyl)-10-fluoro-1-(trifluoromethoxy)-6,7-dihydro-7,14-methanobenzimidazo[1,2-b][2,5]benzodiazocin-5(14H)-one; (7R,14R)-11-((2-aminopropan-2-yl)phenyl)-1-(difluoromethoxy)-1-fluoro-6,7-dihydro-7,14-methanobenzimidazo[1,2-b][2,5]benzodiazocin-5(14H)-one; (7R,14R)-1-(difluoromethoxy)-10-fluoro-11-[2-(2-hydroxypropan-2-yl)-4-(tetrahydrofuran-3-yl)pyrimidin-5-yl]-6,7-dihydro-7,14-methanobenzimidazo[1,2-b][2,5]
benzodiazocin-5(14H)-one; (7R,14R)-1-(difluoromethoxy)-11-[4-(difluoromethyl)-2-(2-hydroxypropan-2-yl)pyrimidin-5-yl]-10-fluoro-6,7-dihydro-7,14-methanobenzimidazo[1,2-b][2,5]benzodiazocin-5(14H)-one; (7R,14R)-1-(difluoromethoxy)-6-ethyl-11-[2-(2-hydroxypropan-2-yl)pyrimidin-5-yl]-7-methyl-6,7-dihydro-7,14-methanobenzimidazo[1,2-b][2,5]benzodiazocin-5
(14H)-one; (7R,14R)-11-[2-(2-aminopropan-2-yl)pyrimidin-5-yl]-1-(difluoromethoxy)-7-methyl-6,7-dihydro-7,14-methanobenzimidazo[1,2-b][2,5]
benzodiazocin-5(14H)-one; (7R,14R)-1-(difluoromethoxy)-6-ethyl-11-[2-(2-hydroxypropan-2-yl)pyrimidin-5-yl]-7-methyl-6,7-dihydro-7,14-methanobenzimidazo[1,2-b][2,5]
benzodiazocin-5(14H)-one; (7R,14R)-11-[2-(2-aminopropan-2-yl)pyrimidin-5-yl]-1-(difluoromethoxy)-7-methyl-6,7-dihydro-7,14-methanobenzimidazo[1,2-b][2,5]
benzodiazocin-5(14H)-one; (7R,14R)-1-(difluoromethoxy)-11-(2-{2-[di(prop-2-en-1-yl)amino]propan-2-yl}pyrimidin-5-yl)-6,7-dihydro-7,14-methanobenzimidazo[1,2-b][2,5]
benzodiazocin-5(14H)-one; (7R,14R)-1-(difluoromethoxy)-6-trideuteromethyl-11-[6-(S-methylsulfonimidoyl)pyridin-3-yl]-6,7-dihydro-7,14-methanobenzimidazo[1,2-b][2,5]
benzodiazocin-5(14H)-one; (7R,14R)-1-(difluoromethoxy)-1-[6-(S-methylsulfonimidoyl)pyridin-3-yl]-6,7-dihydro-7,14-methanobenzimidazo[1,2-b][2,5]benzodiazocin-5(14H)-one; (7R,14R)-1-(difluoromethoxy)-11-(2-{2-[di(prop-2-en-1-yl)amino]propan-2-yl}pyrimidin-5-yl)-6,7-dihydro-7,14-methanobenzimidazo[1,2-b][2,5]benzodiazocin-5(14H)-one; (7R,14R)-1-(difluoromethoxy)-10-fluoro-11-(2-((2R*)-hydroxybutan-2-yl)pyrimidin-5-yl)-6,7-dihydro-7,14-methanobenzo[f]benzo[4,5]imidazo[1,2-a][1,4]
diazocin-5(14H)-one; (7R,14R)-1-(difluoromethoxy)-10-fluoro-11-(2-((2S*)-hydroxybutan-2-yl)pyrimidin-5-yl)-6,7-dihydro-7,14-methanobenzo[f]benzo[4,5]imidazo[1,2-a][1,4]diazocin-5(14H)-one; 2-{5-[(7R,14R)-1-(difluoromethoxy)-10-fluoro-5-oxo-5,6,7,14-tetrahydro-7,14-methanobenzimidazo[1,2-b][2,5]benzodiazocin-11-yl]
pyrimidin-2-yl}propan-2-yl phosphate, disodium salt; 2-{5-[(7R,14R)-1-(difluoromethoxy)-10-fluoro-6-methyl-5-oxo-5,6,7,14-tetrahydro-7,14-methanobenzimidazo[1,2-b][2,5]
benzodiazocin-11-yl]pyrimidin-2-yl}propan-2-yl
phosphate, disodium salt; ammonium 2-(5-((7R,14R)-1-(difluoromethoxy)-10-fluoro-5-oxo-5,6,7,14-tetrahydro-7,14-methanobenzo[f]benzo[4,5]imidazo[1,2-a][1,4]diazocin-11-yl)pyrimidin-2-yl)propan-2-yl sulphate; and 4-((2-(5-((7R,14R)-1-(difluoromethoxy)-10-fluoro-5-oxo-5,6,7,14-tetrahydro-7,14-methanobenzo[f]benzo[4,5]imidazo[1,2-a][1,4]diazocin-11-yl)pyrimidin-2-yl)propan-2-yl)oxy)-4-oxobutanoic acid.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, inflammatory myopathy (including polymyositis, dermatomyositis, inclusion body myositis), scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behçet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy) and organ transplant rejection (including kidney allograft rejection).

Additional inflammatory and autoimmune disorders include scleritis, Takayasu arteritis, giant cell arteritis scleritis, hidradenitis suppurativa, pyoderma gangrenosum, sarcoidosis, polymyalgia rheumatica, axial spondylo arthritis. Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis (including iritis) and keratitis Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

Compounds according to the present invention can be particularly beneficial for the treatment of rheumatoid arthritis, psoriasis, psoriatic arthropathy, axial spondyloarthritis, juvenile idiopathic arthritis, Crohn's disease, ulcerative colitis, uveitis, Behçet's disease and Takayasu arteritis.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

It will be apparent to the person skilled in the art that there are various synthetic pathways that can lead to the compounds according to the invention. The following processes are aimed at illustrating some of these synthetic pathways but should not be construed in any way as a limitation on how the compounds according to the invention should be made.

It will also be apparent to the person skilled in the art that there may be variations in the synthetic pathways depending on the sub-classes of compounds of formula (I).

Compounds of formula (I) above, may be prepared by a process which comprises intramolecular cyclisation or includes reaction of an intermediate of formula (III),

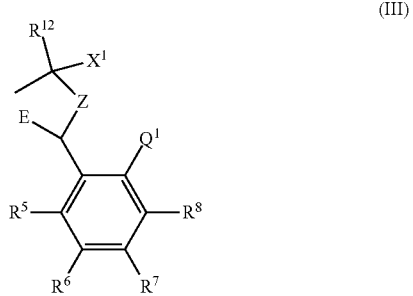

(III)

wherein E, Z, $R^5$, $R^6$, $R^7$, $R^8$ and $R^{12}$ are as defined above;
$X^1$ represents hydroxy, —SH, $CH_2$—OH, —$CO_2H$, —$NHR^f$, —$NHR^g$, —C(O)—$NHR^f$, Y, or —$CH_2$—Y;
$Q^1$ represents hydrogen, hydroxy, halogen, amino, —$SR^i$, —$CO_2H$, —$CH_2$—Y, —CO—R or —CH(OH)—$CF_3$
Y represents a suitable leaving group;
$R^f$ and $R^g$ are as defined above,
$R^i$ represents hydrogen, methyl, —CH—C(O)—O—$C_2H_5$, or —$(CH_2)_2$—C(O)—O—$CH_2$—CH($CH_2CH_3$) [$(CH_2)_3CH_3$]; and
$R^j$ represents hydrogen or methyl.

Suitably, Y represents halogen or $(C_{1-6})$alkylsulphonate.
Appositely, Y represents bromo or methylsulphonate.
Suitably, $R^f$ and $R^g$ represent hydrogen.
Compounds of formula (I) wherein $R^{12}$ represents hydrogen and —X-Q- represents —O— may be prepared by a process which comprises intramolecular cyclization of an intermediate of formula (III) wherein $R^{12}$ represents hydrogen, $X^1$ represents a leaving group Y, e.g. halogen, preferably bromo, and $Q^1$ represents hydroxy, in the presence of a base, for example sodium hydride or silver carbonate.

Alternatively, compounds of formula (I) wherein $R^{12}$ represents hydrogen and —X-Q- represents —O— may be prepared by a process which comprises intramolecular cyclization of an intermediate of formula (III) wherein $R^{12}$ represents hydrogen, $X^1$ represents hydroxy and $Q^1$ represents a leaving group Y, e.g. halogen, preferably bromo, in the presence of a base, e.g. an inorganic base such as cesium carbonate, and copper iodide, at elevated temperature.

Compounds of formula (I) wherein $R^{12}$ represents hydrogen and —X-Q- represents —O—C(CH═CN)— may be prepared by a process which comprises intramolecular cyclization of an intermediate of formula (III) wherein $R^{12}$ represents hydrogen, $X^1$ represents hydroxy and $Q^1$ represents —$CO_2H$, in the presence of cyanomethylenetributylphosphorane.

Such intramolecular cyclization is conveniently performed at elevated temperature in a suitable solvent, e.g., toluene.

Compounds of formula (I) wherein $R^{12}$ represents hydrogen and —X-Q- represents —O—C(O)— may be prepared by the same process as described above for compounds of formula (I) wherein $R^{12}$ represents hydrogen and —X-Q- represents —O—C(CH—CN)—, followed by treatment with a base, e.g., potassium hydroxide.

Alternatively, compounds of formula (I) wherein $R^{12}$ represents hydrogen and —X-Q- represents —O—C(O)— may be prepared by a process which comprises intramolecular cyclization of an intermediate of formula (III) wherein $R^{12}$ represents hydrogen, $X^1$ represents hydroxy and $Q^1$ represents —$CO_2H$, in the presence of an acid, e.g. a mineral acid, in a suitable solvent.

Compounds of formula (I) wherein $R^{12}$ represents hydrogen and —X-Q- represents —C(O)—O— may be prepared by a process which comprises intramolecular cyclization of an intermediate of formula (III) wherein $R^{12}$ represents hydrogen, $X^1$ represents —$CO_2H$ and $Q^1$ represents —OH, in the presence of thionyl chloride, or alternatively, by using a suitable coupling reagent, according to methods known to the person skilled in the art.

Compounds of formula (I) wherein $R^{12}$ represents hydrogen and —X-Q- represents —S—, may be prepared by a process which comprises intramolecular cyclization of an intermediate of formula (III) wherein $X^1$ represents —SH and $Q^1$ represents halogen, in the presence of a transition metal catalyst, according to a method analogous to that described in Stambuli J. et al, *J. Org. Chem.*, 2009, 74, 4005-4008.

Alternatively, compounds of formula (I) wherein $R^{12}$ represents hydrogen and —X-Q- represents —S—, may be prepared by a process which comprises reacting an intermediate of formula (III) wherein $R^{12}$ represents hydrogen, $X^1$ represents —OH and $Q^1$ represents —S—$(CH_2)_2$—C(O)—O—$CH_2$—CH($CH_2CH_3$) [$(CH_2)_3CH_3$], with methanesulphonylchloride in the presence of a base, e.g. N,N-diisopropylethylamine, in a suitable solvent, e.g. tetrahydrofuran, to afford the corresponding compound wherein $X^1$ represents a mesylate moiety, followed by reaction with a solution of sodium ethoxide.

Compounds of formula (I) wherein $R^{12}$ represents hydrogen and —X-Q- represents —N($R^g$)—, may be prepared by a process which comprises intramolecular cyclization of an intermediate of formula (III) wherein $R^{12}$ represents hydrogen, $X^1$ represents —$NHR^g$ and $Q^1$ represents halogen, in the presence of a suitable transition metal catalyst, according to methods known to the person skilled in the art.

The intramolecular cyclization may be conveniently effected in the presence of palladium(II)acetate and (+/−)-2,2'-bis(diphenylphosphino)1,1'-binaphthyl, in the presence of base, e.g., potassium carbonate or cesium carbonate, in a suitable solvent, e.g., toluene, at elevated temperature.

Alternatively, compounds of formula (I) wherein $R^{12}$ represents hydrogen and —X-Q- represents —N($R^g$)—, and $R^g$ represents hydrogen, may be prepared by a process which comprises intramolecular cyclization of an intermediate of formula (III) wherein $R^{12}$ represents hydrogen, $X^1$ is a leaving group Y, e.g. methylsulphonate, and $Q^1$ represents amino. The reaction is conveniently effected by first protecting the amino group of $Q^1$ with a suitable protecting group, e.g. tert-butoxy carbonyl, according to methods known to the person skilled in the art, followed by subsequent addition of a suitable base, e.g. sodium hydride in a suitable solvent, e.g. dimethyl formamide.

Alternatively, compounds of formula (I) wherein $R^{12}$ represents hydrogen, —X-Q- represents —N($R^g$)—, and $R^g$ represents —CO—($C_{3-7}$)heterocycloalkyl, may be prepared by a process which comprises intramolecular cyclization of an intermediate of formula (III) wherein $R^{12}$ represents hydrogen, $X^1$ represents —NH$R^g$, wherein $R^g$ is as defined above, and $Q^1$ represents halogen. The reaction is conveniently effected by addition of a suitable base, e.g. cesium acetate, and cuprous iodide in a suitable solvent, e.g. dimethylsulfoxide, at elevated temperature. Compounds of formula (I) wherein $R^{12}$ represents hydrogen, —X-Q- represents —N($R^g$)—, and $R^g$ represents respectively ($C_{2-6}$) alkoxycarbonyl, heteroaryl-$SO_2$-heteroaryl or —$SO_2$-aryl may be prepared via an analogous method to the one described here above for $R^g$ representing —CO—($C_{3-7}$) heterocycloalkyl.

Compounds of formula (I) wherein $R^{12}$ represents hydrogen or methyl, —X-Q- represents —N($R^f$)—C(O)—, may be prepared by a process which comprises intramolecular cyclization of an intermediate of formula (III) wherein $R^{12}$ represents hydrogen or methyl, $X^1$ represents —NH$R^f$ and $Q^1$ is halogen, preferably chloro, in the presence of carbon monoxide and a transition metal catalyst.

The reaction is conveniently carried out at elevated temperature, e.g. 100° C. or 150° C., and under an elevated pressure of carbon monoxide, in a suitable solvent, e.g., a cyclic ether such as 1,4-dioxane, or dimethylsulfoxide or dimethylacetamide The transition metal catalyst of use in the above reaction is suitably selected from dichloro[bis(dicyclohexylphosphino)propane] palladium(II), [bis(diphenylphosphino)xanthene] palladium(II) and 2,2-dichloro-1,1,3,3-tetracyclohexyl-1$\lambda^5$,3$\lambda^5$ palladacyclohexane.

Alternatively, a solution of palladium (II) acetate and 4,5-bis(diphenylphosphino)-9,9-dimethylxanthene in a suitable solvent may be used.

An analogous reaction may be performed using molybdenum hexacarbonyl as an alternative source of carbon monoxide.

Such intramolecular cyclization is conveniently performed in the presence of a base, e.g. an inorganic base such as sodium carbonate or by activation using molecular sieves.

Alternatively, compounds of formula (I) wherein, —X-Q- represents —N($R^f$)—C(O)—, may be prepared by a process which comprises intramolecular cyclization of an intermediate of formula (III) wherein, $X^1$ represents —NH$R^f$, $R^f$ represents hydrogen, and $Q^1$ is —COOH, in the presence of 4-methylmorpholine and (1-cyano-2-ethoxy-2-oxoethylidenaminooxy) dimethylamino-morpholinocarbenium hexafluorophosphate (COMU). The reaction is conveniently effected in acetonitrile.

Compounds of formula (I) wherein $R^{12}$ represents hydrogen and —X-Q- represents —C(O)—N($R^f$)— may be prepared by a process which comprises intramolecular cyclization of an intermediate of formula (III) wherein $R^{12}$ represents hydrogen, $X^1$ is —C(O)—NH($R^f$) and $Q^1$ is halogen, preferably bromine, in the presence of a suitable coupling reagent, according to methods known to the person skilled in the art.

Alternatively, compounds of formula (I) wherein $R^{12}$ represents hydrogen, —X-Q- represents —C(O)—N($R^f$)—, and $R^f$ represents hydrogen, may be prepared by a process which comprises intramolecular cyclization of an intermediate of formula (III) wherein $R^{12}$ represents hydrogen, $X^1$ represents —$CO_2$H and $Q^1$ represents amino. The reaction may be conveniently effected with a suitable coupling agent, e.g., 1-ethyl-3-(3-dimethylaminopropyl)carbodiimide (EDC), according to methods known to the person skilled in the art.

Compounds of formula (I) wherein $R^{12}$ represents hydrogen and —X-Q- represents —N($R^f$)—$SO_2$— may be prepared by a process which comprises intramolecular cyclization of an intermediate of formula (III) wherein $R^{12}$ represents hydrogen, $X^1$ represents —NH$R^f$ and $Q^1$ represents —SH, in the presence of hydrogen peroxide and thionyl chloride according to a method analogous to that described by K. Bahrami, M. M. Khodaei, M. Soheilizad, *J. Org. Chem.*, 2009, 74, 9287-9291.

The reaction is conveniently performed at room temperature in a suitable solvent, e.g. an apolar solvent such as acetonitrile and in the presence of an organic base, e.g. pyridine.

Compounds of formula (I) wherein $R^{12}$ represents hydrogen, —X-Q- represents —$SO_2$—N($R^f$)—, and $R^f$ represents hydrogen, may be prepared by a process analogous to the one described above for —X-Q- which represents —N($R^f$)—$SO_2$—, from an intermediate of formula (III) wherein $R^{12}$ represents hydrogen, $X^1$ represents —SH and $Q^1$ represents amino. The reaction is conveniently effected by first protecting the amino group of $Q^1$ with a suitable protecting group according to methods known to the person skilled in the art.

Compounds of formula (I) wherein $R^{12}$ represents hydrogen, —X-Q- represents —$CH_2$—$CH_2$— may be prepared by a process which comprises intramolecular cyclization of an intermediate of formula (III) wherein $R^{12}$ represents hydrogen, $X^1$ represents —$CH_2$—$CO_2$H and $Q^1$ represents hydrogen, for example applying Friedel Crafts reaction conditions, in the presence of polyphosphoric acid. The resulting intermediate, wherein —X-Q- represents —$CH_2$—C(O)— is subsequently reduced according to methods known to the person skilled in the art.

Compounds of formula (I) wherein —X-Q- represents $R^{12}$ represents hydrogen and —O—$CH_2$— may be prepared by a process which comprises intramolecular cyclization of an intermediate of formula (III) wherein $R^{12}$ represents hydrogen, $X^1$ represents hydroxy and $Q^1$ represents —$CH_2$—Y, wherein Y is a leaving group, e.g. halogen, preferably bromo, in the presence of a suitable base, according to methods known to the person skilled in the art.

Compounds of formula (I) wherein $R^{12}$ represents hydrogen and —X-Q- represents —$CH_2$—O— may be prepared by a process which comprises intramolecular cyclization of an intermediate of formula (III) wherein $R^{12}$ represents hydrogen, $X^1$ represents —$CH_2$—OH and $Q^1$ represents halogen, preferably bromo. This reaction is conveniently effected in the presence of a suitable transition metal catalyst, e.g. palladium (II) or copper (II) catalyst, according to methods known to the person skilled in the art.

Compounds of formula (I) wherein $R^{12}$ represents hydrogen and —X-Q- represents —S—$CH_2$ may be prepared by a process analogous to the process of preparation of compounds of formula (I) wherein —X-Q- represents —O—$CH_2$— starting from intermediates of formula (III) wherein $R^{12}$ represents hydrogen, $X^1$ represents —SH and $Q^1$ represents —$CH_2$—Y.

Compounds of formula (I) wherein $R^{12}$ represents hydrogen and —X-Q- represents —$CH_2$—S— may be prepared by a process which comprises intramolecular cyclization of an intermediate of formula (III) wherein $R^{12}$ represents hydrogen, $X^1$ is —$CH_2$—Y, Y is a suitable leaving group, e.g. halogen, and $Q^1$ represents —SH, in the presence of suitable base according to methods known to the person skilled in the art.

Compounds of formula (I) wherein $R^{12}$ represents hydrogen, —X-Q- represents —$CH_2$—N($R^g$)—, and $R^g$ represents hydrogen, may be prepared by a process which comprises intramolecular cyclization of an intermediate of formula (III) wherein $R^{12}$ represents hydrogen, $X^1$ is —$CH_2$—Y, wherein Y is a suitable leaving group, e.g. methylsulphonate, and $Q^1$ represents amino. The reaction is conveniently effected by first protecting the amino group of $Q^1$ with a suitable protecting group, e.g. tert-butoxy carbonyl, according to methods known to the person skilled in the art, followed by subsequent addition of a suitable base, e.g. sodium hydride in a suitable solvent, e.g. dimethyl formamide.

Compounds of formula (I) wherein $R^{12}$ represents hydrogen, —X-Q- represents —N($R^g$)—$CH_2$— and $R^g$ represents hydrogen may be prepared by a process involving intramolecular cyclization of the corresponding compound of formula (III) wherein $R^{12}$ represents hydrogen, $X^1$ represents —NH($R^g$) and wherein $Q^1$ represents formyl. The reaction is conveniently effected by (i) reaction with an acid, e.g. trifluoroacetic acid, in a suitable solvent, e.g. dichloromethane and (ii) reduction of the compound obtained as a result of step (i) with an appropriate reducing agent, e.g. polymer supported cyano borohydride or borane-dimethylsulphide complex, in a suitable solvent, e.g. tetrahydrofuran or a mixture of tetrahydrofuran and ethanol.

Compounds of formula (I) wherein $R^{12}$ represents hydrogen, —X-Q- represents —N($R^g$)—CH($CH_3$)— and $R^g$ represents hydrogen may be prepared according to a method analogous as the one described here above for compounds of formula (I) wherein —X-Q- represents —N($R^g$)—$CH_2$—, but from intermediate of formula (III) wherein $Q^1$ represents acetyl.

Compounds of formula (I) wherein $R^{12}$ represents hydrogen, —X-Q- represents —N($R^g$)—CH($CF_3$)— and $R^g$ represents hydrogen may be prepared according to a method analogous to the one described here above for compounds of formula (I) wherein $R^{12}$ represents hydrogen and —X-Q- represents —N($R^g$)—$CH_2$—, by reacting compound obtained as a result of step (i) with (trifluoromethyl)trimethyl silane, in the presence of trifluoroacetic acid and potassium hydrogen fluoride, in a suitable solvent, e.g. dimethylformamide.

Compounds of formula (I) wherein $R^{12}$ represents hydrogen, —X-Q- represents —N=S(O)($CH_3$)— may be prepared by a process involving intramolecular cyclization of the corresponding compound of formula (III) wherein, $X^1$ represents —NH($R^g$), $R^g$ represents hydrogen, and wherein $Q^1$ represents —$SCH_3$. The reaction is conveniently effected by (i) adding bromine in dichloromethane followed by (ii) oxidation e.g. with m-chloroperbenzoic acid.

Compounds of formula (I) wherein $R^{12}$ represents hydrogen, —X-Q- represents —O—CH($CF_3$)— may be prepared by a process involving intramolecular cyclization of the corresponding compound of formula (III) wherein, $X^1$ represents —hydroxy and wherein $Q^1$ represents —CH(OH)$CF_3$. The reaction is conveniently effected using cyanomethylenetributylphosphorane, in a suitable solvent, e.g. tetrahydrofuran, at elevated temperature, e.g. 100° C.

Compounds of formula (I) wherein $R^{12}$ represents hydrogen, —X-Q- represents —O—C(=$CH_2$)— may be prepared by a process involving intramolecular cyclization of the corresponding compound of formula (III) wherein, $X^1$ represents halogen, e.g. bromo, and wherein $Q^1$ represents —CO—$R^j$ and $R^j$ represents $CH_3$. The reaction is conveniently effected in the presence of sodium hydride in a suitable solvent, e.g. tetrahydrofuran, at low temperature.

Intermediates of formula (III) wherein E represents (Ea) as defined above, and $X^1$ represents hydroxy, may be prepared by a process which comprises the intramolecular cyclisation and desilylation of an intermediate of formula (IV),

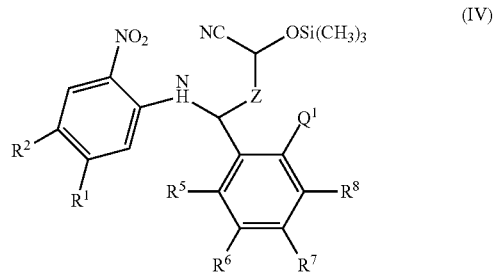

wherein Z, $R^1$, $R^2$, $R^5$, $R^6$, $R^7$, $R^8$ and $Q^1$ are as defined above.

The reaction is suitably performed in the presence of tin(II) chloride at elevated temperature in a polar solvent, e.g. ethanol.

Intermediate (IV) as defined above may be prepared by a process comprising reacting intermediate (V),

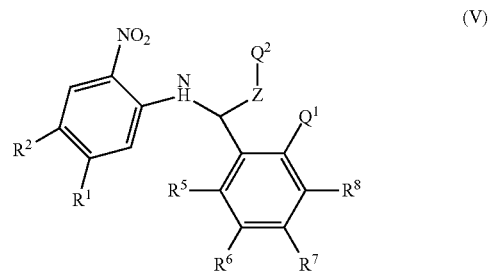

wherein $Q^2$ represents —C(O)—H, and $R^1$, $R^2$, $R^5$, $R^6$, $R^7$, $R^8$ and $Q^1$ are as defined above; with zinc iodide and triethylsilyl cyanide in the presence of a base, e.g. triethylamine.

Typically, the intermediate of formula (V) wherein $Q^2$ represents —C(O)—H may be prepared from the corresponding intermediate wherein $Q^2$ represents —$CO_2R^h$ and $R^h$ represents $C_{1-6}$ alkyl, by reduction with a conventional reducing agent, e.g. a metal hydride, such as diisobutylaluminium hydride (DIBAL-H).

The intermediate of formula (V) wherein $Q^2$ represents —$CO_2R^h$ may be obtained by a process which comprises reacting an intermediate of formula (VI) with an intermediate of formula (VII),

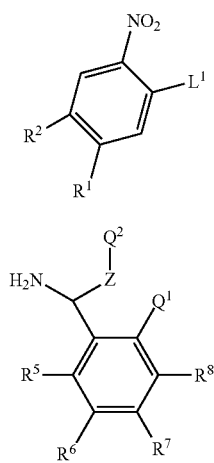

(VI)

(VII)

wherein $R^1$, $R^2$, $R^5$, $R^6$, $R^7$, $R^8$, Z, $Q^1$ and $Q^2$ are as defined above; and $L^1$ is a suitable leaving group, e.g. a halogen atom, for example bromine.

The reaction is conveniently performed in the presence of a base, e.g. an inorganic base, such as potassium carbonate, in a suitable solvent, e.g. an apolar solvent such as acetonitrile, at elevated temperature.

Intermediates of formula (VII) may be prepared by a multi-step process starting from an intermediate of formula (VIII),

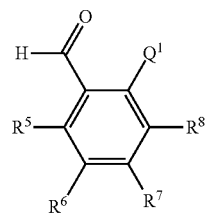

(VIII)

wherein $R^5$, $R^6$, $R^7$, $R^8$ and $Q^1$ are as defined above; which process comprises the following steps:
  (i) Reaction of intermediate (VIII) with (S)-t-butylsulfinamide in the presence of $K_3PO_4/KHPO_4$ in a suitable solvent, e.g. THF;
  (ii) Reacting the compound obtained from step (i) with a compound of formula $L^2$-Z-$Q^2$, wherein Z and $Q^2$ are as defined above and $L^2$ is a suitable leaving group, e.g. halogen, such as bromine, and activated zinc metal dust prepared according to conditions described in Hilpert, H. et al, *Journal of Medicinal Chemistry*, 2013, 56(10), 3980-3995, in the presence of transition metal salt, e.g. copper chloride at elevated temperature;
  (iii) Subsequent reaction with a strong mineral acid, e.g. hydrogen chloride.

Intermediates of formula (VIII) wherein $R^5$ represents halogen, e.g. chloro, may be transformed into the corresponding intermediate of formula (VIII) wherein $R^5$ represents difluoromethoxy by a process which comprises (i) reaction with potassium hydroxide, in water at low temperature and (ii) reaction with diethyl(bromodifluoromethyl) phosphonate, at low temperature.

Intermediates of formula (III) wherein E represents (Ea) as defined above, and —$X^1$ represents —NH($R^g$) and $R^g$ represents hydrogen, may be prepared by a process which comprises the reduction, intramolecular cyclization and desulfination of an intermediate of formula (IVa),

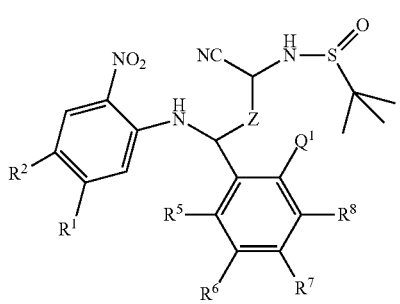

(IVa)

wherein Z, $R^1$, $R^2$, $R^5$, $R^6$, $R^7$, $R^8$ and $Q^1$ are as defined above.

The reaction is suitably performed in the presence of tin(II) chloride, followed by addition of a strong acid, e.g. hydrogen chloride, at elevated temperature in a polar solvent, e.g. ethanol.

Alternatively, the reduction and cyclization may be performed by a process involving (i) reduction using hydrogen under pressure, in the presence of zinc bromine and of platinum on charcoal and (ii) addition of a strong acid, e.g. hydrogen chloride, at elevated temperature in a polar solvent, e.g. ethanol.

Intermediates of formula (IVa), may be prepared by a multi-step process starting from corresponding intermediates (IVb),

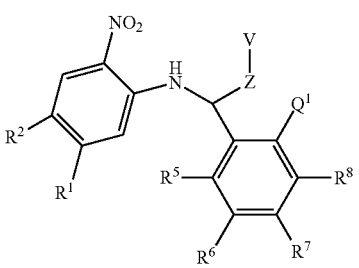

(IVb)

wherein Z, $R^1$, $R^2$, $R^5$, $R^6$, $R^7$, $R^8$ and $Q^1$ are as defined above, and V represents CH=$CH_2$, which process comprises:
  (i) Reacting intermediate (IVb) with sodium periodate, in the presence of potassium dioxide(dioxo)osmium hydrate and 2,6-dimethyl pyridine, followed by addition of sodium thiosulfate, to afford corresponding intermediates of formula (IVb) wherein V represents CH=O;
  (ii) Reacting intermediates of formula (IVb) wherein V represents CH=O with (R)-2-methylpropane-2-sulfinamide, in the presence of a transition metal catalyst, e.g. titanium (IV) isopropoxide, in a suitable solvent, e.g. dichloromethane, to afford corresponding intermediate of formula (IVb) wherein V represents CH=N—(SO)-tert-butyl;
  (iii) Further reaction with sodium cyanide, in the presence of scandium triflate, in a suitable solvent, e.g. tetrahydrofuran, to afford intermediates of formula (IVa).

Intermediates of formula (IVb) wherein Z, $R^1$, $R^2$, $R^5$, $R^6$, $R^7$, $R^8$ and $Q^1$ are as defined above, and V represents $CH=CH_2$, may be prepared by a process comprising reacting intermediates of formula (VIIa),

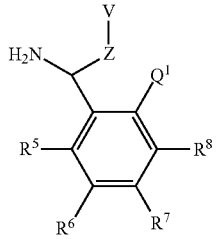

(VIIa)

wherein Z, V, $R^5$, $R^6$, $R^7$, $R^8$ and $Q^1$ are as defined above for intermediates of formula (IVb), with an intermediate of formula (VI) as defined above, wherein $L^1$ is a halogen, e.g. fluorine, under conditions analogous to those described for the preparation of intermediates of formula (V).

Intermediates of formula (VIIa) may be prepared by a process analogous to the one described for intermediates of formula (VII), but wherein $Q^2$ is replaced by V.

Intermediates of formula (III), wherein E represents (Eb) or (Ec), as defined above, and wherein $X^1$ represents hydroxy may be prepared from intermediates of formula (IIIA),

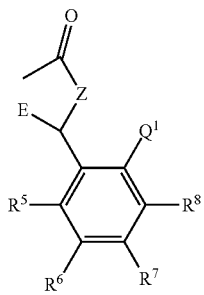

(IIIA)

wherein $R^5$, $R^6$, $R^7$, $R^8$, Z and $Q^1$ are as defined above; by reduction of the carbonyl moiety according to methods known to the person skilled in the art.

Intermediates of formula (III) wherein $X^1$ represents —NH($R^f$), $R^f$ represents hydrogen and $R^{12}$ represents methyl may be prepared from intermediate of formula (IIIA) using the following sequence of steps:

(i) Reacting intermediate of formula (IIIA) with 2-methyl-2-propanesulfinamide in the presence of Titanium (IV) isopropoxide, in a solvent, e.g. tetrahydrofuran, at a suitable temperature, e.g. 50° C.;

(ii) Adding a solution of methylmagnesium bromide, at low temperature, in a suitable solvent, e.g. dichloromethane;

(iii) Removing the tert-butyl sulphinyl moiety in the presence of a strong acid, e.g. HCl, in a suitable solvent, e.g. 1,4-dioxane.

Intermediates of formula (IIIA) may be prepared by a process which comprises intramolecular cyclization of an intermediate of formula (IX),

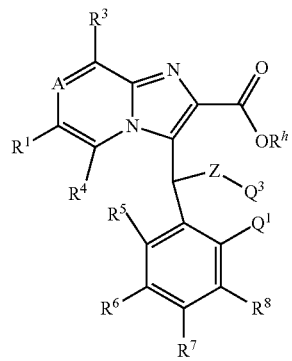

(IX)

wherein A is N or C—$R^2$, $Q^3$ is an electron withdrawing group, preferably an ester moiety, and $R^1$, $R^2$, $R^3$, $R^4$, $R^5$, $R^6$, $R^7$, $R^8$, $R^h$, Z and $Q^1$ are as defined above; in the presence of a base, in a suitable solvent at elevated temperature.

Intermediates of formula (IX) may be prepared by a process which includes reacting an intermediate of formula (X) with an intermediate of formula (XI),

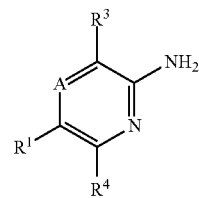

(X)

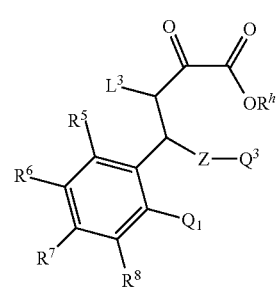

(XI)

wherein A, $R^1$, $R^3$, $R^4$, $R^5$, $R^6$, $R^7$, $R^8$, $R^h$, Z, $Q^1$ and $Q^3$ are as defined above; and $L^3$ is a suitable leaving group, typically a halogen atom, e.g. bromo.

The reaction is conveniently effected at an elevated temperature in a suitable solvent, e.g. a $(C_{1-4})$alkanol such as ethanol, or an ether such as 1,4-dioxane or dimethoxyethane, and in the presence of magnesium sulphate.

Alternatively, intermediates of formula (IX), wherein $Q^3$ is —$CO_2H$, may be prepared according to a process which comprises reacting an intermediate of formula (XII),

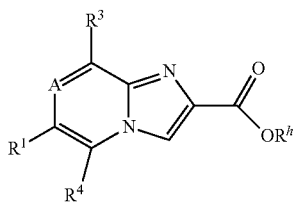

(XII)

wherein A, $R^1$, $R^3$, $R^4$, and $R^h$ are as defined above; with an intermediate of formula (VIII) as defined above, in the presence of Meldrum's acid, according to a method analogous to the one described in international patent application WO 2009/156091 or by M. Kerr et al. in J. Org. Chem 2013, 78, 10534.

The reaction is conveniently effected in a suitable solvent e.g. acetonitrile, in the the presence of proline and magnesium sulphate, at elevated temperature, e.g. 80° C.

Where they are not commercially available, the starting materials of formula (VI), (VIII), (X), (XI) and (XII) may be prepared by methods analogous to those described in the accompanying Examples, or by standard methods well known from the art.

Intermediates of formula (III) wherein $X^1$ represents amino, may be prepared from intermediates of formula (III) wherein $X^1$ is hydroxy, by a process which comprises (i) treatment with diphenylphosphorylazide and 1,8-diazabicyclo[5.4.0]undec-7-ene, in a suitable solvent, e.g. tetrahydrofuran, at low temperature, e.g. 0° C., and (ii) subsequent aza-wittig reaction using triphenylphosphine, in a suitable solvent, e.g. a mixture of water and toluene.

Intermediates of formula (III), wherein E represents (Eb) or (Ec), as defined above, and wherein $X^1$ represents amino may be prepared from intermediates of formula (IIIA), wherein $R^5$, $R^6$, $R^7$, $R^8$, Z and $Q^1$ are as defined above; by a process which comprises reacting intermediates of formula (IIIA) with a $C_{1-6}$ alkylsulfinamide, e.g. (R)-2-methylpropane-2-sulfinamide, in the presence of a transition metal catalyst, e.g. titanium tetrakis ethanolate, in a suitable solvent, e.g. dichloromethane, followed by reduction with a suitable reducing agent, e.g. sodium borohydride, in a suitable solvent, e.g. tetrahydrofuran.

Intermediates of formula (III) wherein $X^1$ represents a leaving group Y, e.g. halogen or $(C_{1-6})$alkylsulphonate, may be prepared from intermediates of formula (III) wherein $X^1$ is hydroxy, according to standard methods known to the person skilled in the art.

Intermediates of formula (III) wherein $X^1$ represents —SH, may be prepared from intermediates of formula (III) wherein $X^1$ is hydroxy or a leaving group Y, according to standard methods known to the person skilled in the art.

Intermediates of formula (III) wherein $X^1$ represents —$CO_2H$ may be prepared by hydrolysis of corresponding intermediates of formula (III) wherein $X^1$ represents cyano, according to standard methods known to the person skilled in the art.

Intermediates of formula (III) wherein $X^1$ represents cyano may be prepared by nucleophilic substitution of intermediates of formula (III) wherein $X^1$ represents a leaving group Y, and Y represents $(C_{1-6})$alkylsulphonate-, according to standard methods known to the person skilled in the art.

Intermediates of formula (III) wherein $X^1$ represents —$CH_2OH$ may be prepared by reduction of the corresponding intermediate of formula (III) wherein $X^1$ represents —$CO_2H$, in the presence of a suitable reducing reagent, e.g., $BH_3$.

Intermediates of formula (III) wherein $X^1$ represents —$CH_2$—Y may be prepared from Intermediates of formula (III) wherein $X^1$ represents —$CH_2OH$, according to methods analogous to those described here above for intermediates of formula (III) wherein $X^1$ represents a leaving group Y, e.g. halogen or $(C_{1-6})$alkylsulphonate.

Intermediates of formula (III) wherein $X^1$ represents —$NH(R^g)$ and $R^g$ represents —CO—$(C_{3-7})$heterocycloalkyl may be prepared by reacting compounds of formula (III) wherein $X^1$ represents —$NH_2$ with a $(C_{3-7})$heterocycloalkyl-COOH, in the presence of a base, e.g. N,N-diisopropylethylamine, and a coupling agent, e.g. HATU (N-[(dimethylamino)-1H-1,2,3-triazolo-[4,5-b]pyridin-1-ylmethylene]-N-ethylethanaminium hexafluorophosphate N-oxide), in a suitable solvent, e.g. dimethylformamide.

Intermediates of formula (III) wherein $Q^1$ represents formyl may be prepared from intermediates of formula (III) wherein $Q^1$ represents halogen, e.g. bromine, by a process involving (i) reaction with potassium vinylfluoroborate, in the presence of a base and a transition metal catalyst and (ii) reaction with sodium periodate and osmium tetraoxide, in the presence of a suitable solvent, e.g. a cyclic ether, such as 1,4-dioxane, at a suitable temperature, e.g. 0° C.

Suitable bases include inorganic bases, such as cesium carbonate and suitable transition metal catalysts include 1,1'-bis(diphenylphosphino)ferrocene-palladium(II)dichloride-dichloromethane complex.

Intermediates of formula (III) wherein $Q^1$ represents acetyl may be prepared from intermediates of formula (III) wherein $Q^1$ represents halogen, e.g. bromine, by a process involving (i) reaction with tributyl(1-ethoxyvinyl)tin, in the presence of bis(triphenylphosphine)palladium(II)-dichloride, in a suitable solvent, e.g. toluene, at elevated temperature, and (ii) reaction with an acid, e.g. para-toluenesulphonic acid.

Intermediates of formula (III) wherein $Q^1$ represents —S—$(CH_2)$—$(CH_2)$—C(O)—O—$CH_2$—$CH(CH_2CH_3)$ $[(CH_2)_3CH_3]$, may be prepared from intermediates of formula (III) wherein $Q^1$ represents halogen, e.g. bromine, by a process involving reaction with 3-mercaptopropionic acid-2-ethylester, in the presence of a suitable transition metal catalyst, e.g. tris(benzylideneacetone)dipalladium(0) and 4,5-bis(diphenylphosphino)-9,9-dimethylxanthene, in a suitable solvent, e.g. 1,4-dioxane, at elevated temperature.

Similarly, intermediates of formula (III) wherein $Q^1$ represents —S—$CH_2$—C(O)—O—$C_2H_5$$[(CH_2)_3CH_3]$, may be prepared from intermediates of formula (III) wherein $Q^1$ represents halogen, e.g. bromine, by a process involving reaction with ethylthioglycolate, in the presence of a suitable transition metal catalyst, e.g. tris(benzylideneacetone)dipalladium(0) and 4,5-bis(diphenylphosphino)-9,9-dimethylxanthene, in a suitable solvent, e.g. 1,4-dioxane, at elevated temperature.

Intermediates of formula (III) wherein $Q^1$ represents —S—$CH_3$ may be prepared from intermediates of formula (III) wherein $Q^1$ represents halogen, e.g. bromine, by a process which involves treatment with sodium thiomethoxide in a suitable solvent, e.g. dimethylsulphoxide, at elevated temperature.

Intermediates of formula (III) wherein $Q^1$ represents —CH(OH)—$CF_3$ may be prepared from intermediates of formula (III) wherein $Q^1$ represents —C(O)—H, by a process which involves reaction with tetrabutylammoniumfluoride, followed by (trifluoromethyl)trimethylsilane, in a suitable solvent, e.g. tetrahydrofuran, at low temperature.

It will be understood that any compound of formula (I) initially obtained from any of the above processes may, where appropriate, subsequently be elaborated into a further compound of formula (I) by techniques known from the art.

As an alternative to the methods described here above, compounds of formula (I) wherein —X-Q- represents —O—CH$_2$— may be prepared by a process involving reduction of compounds of formula (I) wherein —X-Q- represents —O—C(O)— carried out according to the method described in Sakai et al, *J. Org. Chem.* 2007, 72, 5920-5922.

Compounds of formula (I) wherein —X-Q- represents —N(R$^g$)—CH$_2$— may be prepared in a similar fashion from compounds of formula (I) wherein —X-Q- represents —N(R$^f$)—CO— or under any other conditions used for reduction of a lactam, known to the person skilled in the art.

Compounds of formula (I) wherein —X-Q- represents —S—, —CH$_2$—S— or —S—CH$_2$— may be transformed into compounds of formula (I) wherein —X-Q- represents respectively —SO— or —SO$_2$—; —CH$_2$—SO— or —CH$_2$—SO$_2$—; —SO—CH$_2$— or —SO$_2$—CH$_2$—, by performing oxidation according to methods known to the person skilled in the art.

Compounds of formula (I) wherein —X-Q- represents —SO—, —CH$_2$—SO— or —SO—CH$_2$— may be transformed into compounds of formula (I) wherein —X-Q- represents respectively —S(O)(NH)—, —CH$_2$—S(O)(NH)—, or —S(O)(NH)—CH$_2$—, by a method analogous to that described in Okamura, H. et al, *Organic Letters,* 2004, 6(8),1305-1307.

Compounds of formula (I) wherein —X-Q- represents —S— may be transformed into compounds of formula (I) wherein —X-Q- represents —S(=N—CN)— by a process involving reaction with iodobenzene diacetate, in the presence of cyanamide. The reaction is conveniently effected in acetonitrile at low temperature, e.g. 0° C.

Compounds of formula (I) wherein —X-Q- represents —N(R$^f$)—C(O)— may be converted into the corresponding compound of formula (I) wherein —X-Q- represents —N(R$^f$)—C(S)— by treatment with Lawesson's reagent according to methods known to the skilled person in the art.

Compounds of formula (I) wherein —X-Q- represents —NH— may be further transformed into compounds of formula (I) wherein —X-Q- represents —N(R$^g$)— wherein R$^g$ is an optionally substituted —CO—(C$_{1-6}$)alkyl, by reaction with chloracetyl chloride, in a suitable solvent, e.g. dichloromethane. Substituents may subsequently be introduced on the (C$_{1-6}$)alkyl moiety by treatment with a suitable base according to a method analogous to the ones described in the accompanying Examples.

Compounds of formula (I) or intermediates of formula (III) wherein R$^f$ or R$^g$ represent hydrogen, may further be transformed into the corresponding compounds of formula (I) or intermediates of formula (III) wherein R$^f$ or R$^g$ represent optionally substituted C$_{1-6}$ alkyl, or its deuterated equivalent, by reaction with the corresponding optionally substituted C$_{1-6}$ alkyl halide or deuterated equivalent, e.g. C$_{1-6}$ alkyl iodide or its deuterated equivalent, in the presence of a base, e.g. cesium carbonate or potassium bis(trimethylsilyl)amide (KHMDS), in a suitable solvent, e.g., dimethylformamide or THF Compounds of formula (I) or intermediates of formula (III) wherein R$^f$ or R$^g$ represent hydrogen, may further be transformed into the corresponding compounds of formula (I) or intermediates of formula (III) wherein R$^f$ or R$^g$ represent acetyl by reaction with acetic anhydride, in the presence of base, e.g. pyridine, in a suitable solvent, e.g. dichloromethane.

Compounds of formula (I) or intermediates of formula (III) wherein R$^f$ or R$^g$ represent hydrogen, may further be transformed into the corresponding compounds of formula (I) or intermediates of formula (III) wherein R$^f$ or R$^g$ represent methyl, by reaction with formaldehyde, in a suitable solvent, e.g. 2,2,2-trifluoroethanol, followed by reaction with a suitable reducing agent, e.g. sodium borohydride.

Compounds of formula (I) or intermediates of formula (III) wherein R$^f$ or R$^g$ represent hydrogen, may further be transformed into the corresponding compounds of formula (I) or intermediates of formula (III) wherein R$^f$ or R$^g$ represent (C$_{1-6}$)alkyl-sulphonyl by treatment with the appropriate (C$_{1-6}$) alkylsulphonyl halide, e.g. methane sulphonyl chloride, in the presence of a suitable base, e.g. N,N-diisopropylethylamine or triethylamine, in a suitable solvent e.g. dichloromethane.

A compound of formula (I) or an intermediate of formula (III) which contains a hydroxy group may be alkylated by treatment with the appropriate alkyl halide in the presence of a base, e.g. sodium hydride, or silver oxide.

A compound of formula (I) or an intermediate of formula (III) which contains hydroxy may be converted into the corresponding fluoro-substituted compound by treatment with diethylaminosulfur trifluoride (DAST) or bis(2-methoxyethyl)aminosulfur trifluoride (BAST). A compound of formula (I) which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound of formula (I) or an intermediate of formula (III) which contains an N—H moiety may be alkylated by treatment with the appropriate alkyl halide, typically at an elevated temperature in an organic solvent such as acetonitrile; or at ambient temperature in the presence of a base, e.g. potassium hydroxide, in a suitable solvent, e.g. THF, in the presence of tetra-butylammonium bromide; or at elevated temperature in the presence of a base, e.g. sodium hydride, with or without tetra-butylammonium iodate, in a suitable solvent, e.g. THF; or at elevated temperature in the presence of a an alkali metal carbonate such as potassium carbonate or cesium carbonate, in a suitable solvent, e.g. a dipolar aprotic solvent such as N,N-dimethylformamide. A compound of formula (I) which contains an N—H moiety may be methylated by treatment with formaldehyde in the presence of a reducing agent, e.g. sodium triacetoxyborohydride.

A compound of formula (I) or an intermediate of formula (III) which contains an N—H moiety may be acylated by treatment with the appropriate acid chloride, e.g. acetyl chloride, or with the appropriate carboxylic acid anhydride, e.g. acetic anhydride, typically at ambient temperature in the presence of a base, e.g. an organic base such as triethylamine.

A compound of formula (I) or an intermediate of formula (III) which contains an N—H moiety may be converted into the corresponding compound wherein the nitrogen atom is substituted by C$_{1-6}$ alkyl-sulphonyl, e.g. methylsulphonyl, by treatment with the appropriate C$_{1-6}$ alkylsulphonyl chloride, e.g. methanesulphonyl chloride, or with the appropriate C$_{1-6}$ alkylsulphonic acid anhydride, e.g. methanesulphonic anhydride, typically at ambient temperature in the presence of a base, e.g. an organic base such as triethylamine or N,N-diisopropylethyl-amine.

A compound of formula (I) or an intermediate of formula (III) which contains an N—H moiety may be converted into the corresponding compound wherein the nitrogen atom is substituted by $C_{1-6}$ alkoxy-carbonyl, e.g. methoxycarbonyl, by treatment with the corresponding $C_{1-6}$ alkoxy-carbonyl halide, in the presence of a base, e.g. potassium carbonate, in a suitable solvent, e.g., N,N'-dimethylformamide.

A compound of formula (I) or an intermediate of formula (III) substituted by amino (—$NH_2$) may be converted into the corresponding compound substituted by $C_{1-6}$ alkylsulphonylamino, e.g. methylsulphonyl-amino, or bis[($C_{1-6}$)alkylsulphonyl]amino, e.g. bis(methylsulphonyl)amino, by treatment with the appropriate $C_{1-6}$ alkylsulphonyl halide, e.g. a $C_{1-6}$ alkylsulphonyl chloride such as methanesulphonyl chloride, in the presence of a suitable base, e.g. N,N-diisopropylethylamine, in a suitable solvent e.g. dichloromethane Similarly a compound of formula (I) or an intermediate of formula (III) substituted by amino may be transformed into the corresponding compound of formula (I) or intermediate of formula (III) substituted by NH—$SO_2$—($C_{3-7}$)cycloalkyl, NH—$SO_2$—($C_{3-7}$)heterocycloalkyl, NH—$SO_2$-aryl or NH—$SO_2$-heteroaryl respectively from the corresponding ($C_{3-7}$)cycloalkyl-sulphonylhalide, ($C_{3-7}$)heterocycloalkyl-sulphonyl halide, aryl-sulphonyl-halide or heteroaryl-sulphonyl-halide.

Similarly, a compound of formula (I) substituted by hydroxy (—OH) may be converted into the corresponding compound substituted by $C_{1-6}$ alkyl-sulphonyloxy, e.g. methylsulphonyloxy, by treatment with the appropriate $C_{1-6}$ alkyl-sulphonyl halide, e.g. a $C_{1-6}$ alkylsulphonyl chloride such as methanesulphonyl chloride.

A compound of formula (I) or an intermediate of formula (III) substituted by amino (—$NH_2$) may be converted into the corresponding compound substituted by (tert-butyl)(dimethyl)silyloxyethyl-NH— by treatment with (bromoethoxy)-tert-butyldimethylsilane, in the presence of a suitable base, e.g. potassium carbonate, in a suitable solvent, e.g. dimethyl formamide, at elevated temperature.

A compound of formula (I) or an intermediate of formula (III) containing the moiety —S— may be converted into the corresponding compound containing the moiety —S(O)— by treatment with 3-chloroperoxy-benzoic acid. Likewise, a compound of formula (I) containing the moiety —S(O)— may be converted into the corresponding compound containing the moiety —S(O)$_2$— by treatment with 3-chloroperoxybenzoic acid.

Alternatively, a compound of formula (I) containing the moiety —S— may be converted into the corresponding compound containing the moiety —S(O)$_2$— by treatment with Oxone® (potassium peroxymonosulfate).

A compound of formula (I) or an intermediate of formula (III) containing an aromatic nitrogen atom may be converted into the corresponding N-oxide derivative by treatment with 3-chloroperoxy-benzoic acid.

A compound of formula (I) or an intermediate of formula (III) which contains a carbonyl may be converted into the corresponding alcohol by treatment with a suitable borohydride, e.g. lithium-tri-sec-butyl-borohydride or sodium borohydride, in a suitable solvent e.g. THF. A compound of formula (I) or an intermediate of formula (III) wherein $R^1$ represents halogen, e.g. bromo, may be converted into the corresponding compound wherein $R^1$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected at elevated temperature in the presence of a transition metal catalyst, e.g. [1,1'-bis(diphenylphosphino)ferrocene]dichloropalladium(II), tetrakis(triphenylphosphine)palladium(0), or bis[3-(diphenylphosphanyl)cyclopenta-2,4-dien-1-yl]iron-dichloropalladium-dichloromethane complex, and a base, e.g. an inorganic base such as sodium carbonate, potassium carbonate or cesium carbonate, or potassium phosphate, in a suitable solvent, e.g. 1,4-dioxane or a mixture of 1,4-dioxane and water.

Alternatively, a compound of formula (I) or an intermediate of formula (III) wherein $R^1$ represents halogen, e.g. bromo, may be converted into the corresponding compound wherein $R^1$ represents an optionally substituted aryl or heteroaryl moiety by treatment with the appropriately substituted aryl or heteroaryl boronic acid, in the presence of a transition metal catalyst, e.g. tris(dibenzylideneacetone)dipalladium(0), and tricyclohexylphosphoniumtetrafluoroborate, in the presence of a base, e.g. potassium phosphate, in a suitable solvent, e.g. cyclic ether, such as 1,4-dioxane. The reaction is conveniently effected at elevated temperature and microwave technology may be used. A compound of formula (I) wherein $R^1$ represents 2-oxo-(1H)-pyridinyl may be obtained by treatment of the corresponding compound of formula (I) wherein $R^1$ represents 2-methoxy-pyridinyl, with pyridine hydrochloride at elevated temperature, e.g. 160° C.

A compound of formula (I) or an intermediate of formula (III) wherein $R^1$ represents an ester moiety may be obtained by reacting the corresponding compound of formula (I) or the intermediate of formula (III) wherein $R^1$ is halogen, e.g. chloride, with a base, e.g. sodium carbonate, and the corresponding alcohol moiety in the presence of a transition metal catalyst, typically bis(dicyclohexylphosphino)propane] palladium(II).

A compound of formula (I) or an intermediate of formula (III) wherein $R^1$ represents cyano may be obtained by reacting the corresponding compound of formula (I) or the intermediate of formula (III) wherein $R^1$ is halogen, e.g. chloride, with zinc cyanide, in the presence of a transition metal catalyst, e.g. tetrakis(triphenylphosphine)palladium, in a suitable solvent, e.g., N,N-dimethylformamide. The reaction is conveniently effected at elevated temperature, e.g. 180° C., using microwave technology.

In general, a compound of formula (I) containing a —C≡C— functionality may be converted into the corresponding compound containing a —CH—CH— functionality by catalytic hydrogenation, typically by treatment with a hydrogenation catalyst, e.g. palladium on charcoal, under an atmosphere of hydrogen gas, optionally in the presence of a base, e.g. an alkali metal hydroxide such as sodium hydroxide.

A compound of formula (I) containing an ester moiety, e.g. a $C_{2-6}$ alkoxycarbonyl group such as methoxycarbonyl or ethoxycarbonyl, may be converted into the corresponding compound containing a carboxy (—$CO_2H$) moiety by treatment with an acid, e.g. a mineral acid such as hydrochloric acid.

A compound of formula (I) containing an ester moiety, e.g. a $C_{2-6}$ alkoxycarbonyl group such as methoxycarbonyl or ethoxycarbonyl, may alternatively be converted into the corresponding compound containing a carboxy (—$CO_2H$) moiety by treatment with a base, e.g. an alkali metal hydroxide selected from lithium hydroxide, sodium hydroxide and potassium hydroxide; or an organic base such as sodium methoxide or sodium ethoxide.

A compound of formula (I) containing a carboxy (—$CO_2H$) moiety may be converted into the corresponding compound containing an amide moiety by treatment with the appropriate amine in the presence of a condensing agent such as 1-ethyl-3-(3-dimethyl-aminopropyl)carbodiimide.

A compound of formula (I) containing a carbonyl (C=O) moiety may be converted into the corresponding compound containing a —C(CH$_3$)(OH)— moiety by treatment with methylmagnesium bromide. Similarly, a compound of formula (I) containing a carbonyl (C=O) moiety may be converted into the corresponding compound containing a —C(CF$_3$)(OH)— moiety by treatment with (trifluoromethyl)trimethylsilane and cesium fluoride. A compound of formula (I) containing a carbonyl (C=O) moiety may be converted into the corresponding compound containing a —C(CH$_2$NO$_2$)(OH)— moiety by treatment with nitromethane.

A compound of formula (I) containing a hydroxymethyl moiety may be converted into the corresponding compound containing a formyl (—CHO) moiety by treatment with an oxidising agent such as Dess-Martin periodinane. A compound of formula (I) containing a hydroxymethyl moiety may be converted into the corresponding compound containing a carboxy moiety by treatment with an oxidising agent such as tetrapropylammonium perruthenate.

A compound of formula (I) containing an aryl or an heteroaryl moiety may be transformed into the corresponding compound containing an aryl or heteroaryl moiety where a hydrogen atom has been substituted by a chloro or bromo substituent by reaction respectively with N-chlorosuccinimide or N-bromosuccinimide, in a suitable solvent, e.g. dimethylformamide, according to methods known to the person skilled in the art.

A compound of formula (I) containing an aryl moiety bearing a difluoromethoxy group may be transformed into the corresponding compound containing an aryl moiety where the difluoromethoxy group has been substituted by a hydroxy group, by reaction with sodiumbis(trimethylsilyl)amide, in a suitable solvent, e.g. THF, at low temperature.

A compound of formula (I) containing an aryl or an heteroaryl moiety may be transformed into the corresponding compound containing an aryl or heteroaryl moiety where a hydrogen atom has been substituted by a trifluoromethyl substituent by reaction respectively with (i) trifluoroacetic acid in a suitable solvent, e.g. acetonitrile, (ii) addition of trifluoromethanesulphonyl chloride, followed by [4,4'-Bis(tert-butyl)-2,2'-bipyridine]bis[3,5-difluoro-2-[5-(trifluoromethyl)-2-pyridinyl]phenyl]iridium(III) hexafluorophosphate, according to conditions analogous to those described by McMillan ate al. in Nature, 2011, 480, 224.

In one embodiment, the present invention provides compounds of formula (I), in particular compounds of formula (IB), (IC) or (ID) as defined above, wherein R$^1$ represents a substituted heteroaryl selected from the groups represented by formula (i), (ii), (iii), (iv) and (v), and their respective corresponding salts represented by formula (ia), (ib), (iia), (iiia), (iva), (va), and (vb):

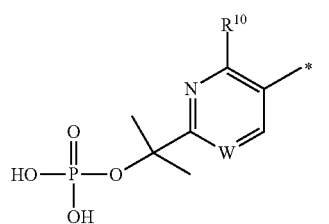

(i)

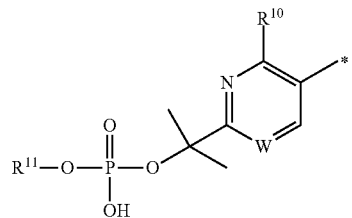

(ii)

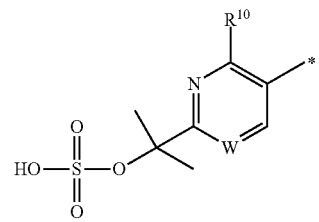

(iii)

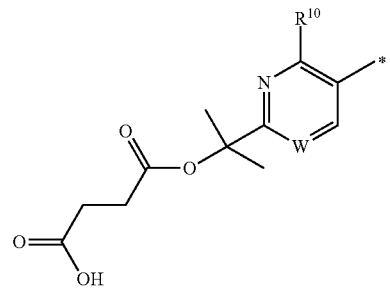

(iv)

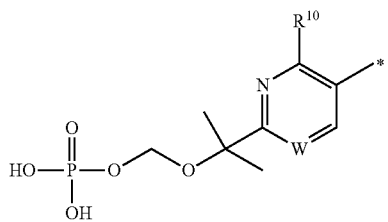

(v)

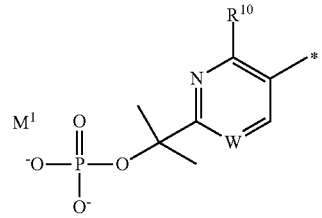

(ia)

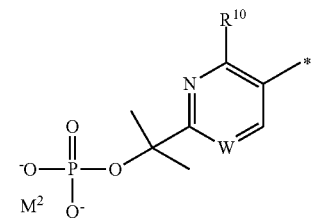

(ib)

-continued

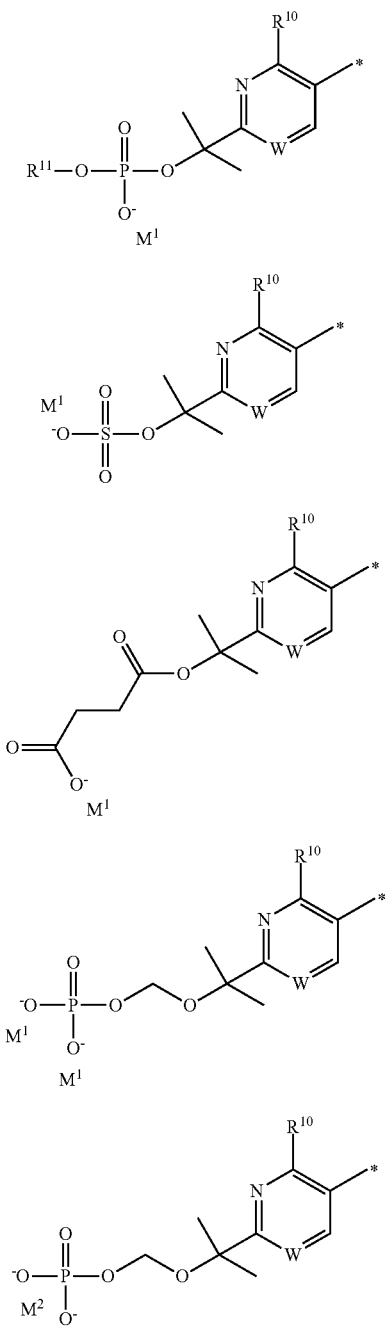

wherein
the asterisk (*) represents the site of attachment of $R^1$ to the remainder of the molecule;
W and $R^{10}$ are as defined above;
$R^{11}$ represents $C_{1-6}$ alkyl;
$M^1$ represents a monovalent cation; and
$M^2$ represents a divalent cation.

In a first aspect of this embodiment, the present invention relates to compounds of formula (I) wherein $R^1$ is heteroaryl substituted by phosphate-$C_{1-6}$ alkyl, e.g., represented by the group of formula (i), or salts thereof, represented respectively by groups of formula (ia) or (ib).

In a second aspect of this embodiment, the present invention relates to compounds of formula (I) wherein $R^1$ is heteroaryl substituted by $C_{1-6}$ alkyl phosphate-$C_{1-6}$ alkyl e.g., represented by the group of formula (ii), or salts thereof, represented by formula (iia).

In a third aspect of this embodiment, the present invention relates to compounds of formula (I) wherein $R^1$ is heteroaryl substituted by sulphate-$C_{1-6}$ alkyl, e.g. as represented by the group of formula (iii), or salts thereof represented by formula (iiia).

In a fourth aspect of this embodiment, the present invention relates to compounds of formula (I) wherein $R^1$ is heteroaryl substituted by carboxy-($C_{1-6}$)alkyl-carbonyloxy-$C_{1-6}$ alkyl, e.g. as represented by the group of formula (iv), or salts thereof represented by formula (iva).

In a fifth aspect of this embodiment, the present invention relates to compounds of formula (I) wherein $R^1$ is heteroaryl substituted by phosphate-methoxy-$C_{1-6}$ alkyl, e.g., as represented by the group of formula (v), or salts thereof represented respectively by the groups of formula (va) or (vb).

Typical examples of monovalent cation $M^1$ in accordance with the present invention include alkali metal cations or cations represented by formula $^+NH(R^k)_3$ wherein $R^k$ represents hydrogen or $C_{1-6}$ alkyl.

Suitably, $R^{11}$ represents ethyl.

In a first embodiment $M^1$ represents $Na^+$. In a second embodiment, $M^1$ represents $K^+$. In a third embodiment, $M^1$ represents $^+NH_4$. In a fourth embodiment $M^1$ represents $^+NH(C_{1-6}$ alkyl$)_3$. In a particular aspect of this embodiment, $M^1$ represents $^+NH(CH_2CH_3)_3$.

Suitably, $M^1$ represents $Na^+$.

Typical examples of divalent cations $M^2$ in accordance with the present invention include alkaline earth metal cations.

Suitably, $M^2$ represents $Ca^{2+}$.

In a particular aspect of this embodiment, the present invention relates to compounds of formula (I), in particular compounds of formula (IB), (IC) or (ID) as defined above, wherein $R^1$ represents a substituted heteroaryl selected from the groups represented by formula (i), (iii), (iv), and their respective salts of formula (iiia), (va) and (vb).

A compound of formula (I) wherein $R^1$ is heteroaryl substituted by phosphate-$C_{1-6}$ alkyl, e.g., as represented above by formula (i) may be prepared from the corresponding compound of formula (I) wherein $R^1$ is substituted by hydroxy-$C_{1-6}$ alkyl by i) treatment with di benzyl N,N-diisopropylphosphoramidite in a suitable solvent, e.g. dichloromethane, followed by treatment with hydrogen peroxide at low temperature and ii) subsequent hydrogenolysis, e.g. using hydrogen gas under pressure, in the presence of a suitable catalyst, e.g. palladium on charcoal, according to a method analogous to those described by S. P. Green et al. in Organic Process Research & Development, 2002, 6, 109-112. A compound of formula (I) wherein $R^1$ is heteroaryl substituted by a salt of phosphate-$C_{1-6}$ alkyl, e.g. as represented by formula (ia) or formula (ib) above, wherein $M^1$ and $M^2$ are independently alkali metal cation or alkaline earth metal cation, may be prepared by performing the above described hydrogenolysis step (ii) in the presence of a suitable alkali metal base or alkaline earth metal base. A compound of formula (I) wherein $R^1$ is heteroaryl substituted by $C_{1-6}$ alkyl phosphate-$C_{1-6}$ alkyl, e.g. as represented above by formula (ii), may be prepared from the corresponding compound of formula (I) wherein $R^1$ is substituted by hydroxy-$C_{1-6}$ alkyl by: i) first reacting cyanoethylphosphoramidite with a compound of formula $R^{11}$—OH, in the presence of diisopropylethylamine in a suitable solvent e.g. dichloromethane, ii) addition of compound of formula (I) wherein $R^1$ is substituted by hydroxy-$C_{1-6}$ alkyl in the presence of a suitable solvent, e.g. dichloromethane, (iii) followed by oxidation and subsequent treatment with a suitable base, according to a method analogous to those described by Nam, N—H. et al. in *Bio-org. Med Chem.*, 2004, 12, 6255 or Bennani, L. et al. in international patent application WO 2012/177707 A1.

A compound of formula (I) wherein $R^1$ is heteroaryl substituted by sulphate-$C_{1-6}$ alkyl, e.g. as represented above by formula (iii), may be prepared by treatment of the corresponding compound of formula (I) wherein $R^1$ is substituted by hydroxy-$C_{1-6}$ alkyl, with pyridine:sulphur trioxide complex, according to a method analogous to the one described by E. Lacko et al. in *Current Medicinal Chemistry*, 2012, 19, 4699, or alternatively, by treatment with chloro sulphonic acid in the presence of triethylamine, according to a method analogous to the one described in C. Guo et al. in international patent application WO 2004/087720 A1.

A compound of formula (I) wherein $R^1$ is heteroaryl substituted by carboxy($C_{1-6}$)alkyl-carbonyloxy-$C_{1-6}$ alkyl e.g. as represented by the group of formula (iv), may be prepared by reacting the corresponding compound of formula (I) wherein $R^1$ is substituted by hydroxy-$C_{1-6}$ alkyl, with an appropriate anhydride, e.g. succinic anhydride, in the presence of dimethylaminopyridine, in a suitable solvent, e.g. pyridine, at elevated temperature, according to a method analogous to the one described by C. Liu et al., in *Molecular Pharmaceutics*, 2014, 57, 7509 or W. N. Washburn et al. in *J. Med. Chem*, 2014, 57, 7509.

A compound of formula (I) wherein $R^1$ is heteroaryl substituted by phosphate-methoxy-$C_{1-6}$ alkyl e.g. as represented by the group of formula (v), may be prepared by reacting the corresponding compound of formula (I) wherein $R^1$ is substituted by hydroxy-$C_{1-6}$ alkyl, with a suitable base, e.g. sodium hydride, in a suitable solvent, e.g. dimethoxyethane, followed by addition of chloromethyldi-tert-butyl-phosphate, and subsequent dealkylation, at high temperature, according to a method analogous to the one described in international patent application WO 2012/135082 A1.

Compounds of formula (I) wherein $R^1$ is heteroaryl substituted by phosphate-$C_{1-6}$ alkyl, e.g. as represented by formula (i), which can be isolated as a result of the above hydrogenolysis step (ii), may be transformed into the corresponding compound of formula (I) wherein $R^1$ is heteroaryl substituted by a salt of phosphate-$C_{1-6}$ alkyl, e.g. as represented by formula (ia) wherein $M^1$ represents an alkali metal cation or a cation of formula $^+NH(R^k)_3$, or may be transformed into the corresponding compound of formula (I) wherein $R^1$ is heteroaryl substituted by a salt of phosphate-$C_{1-6}$ alkyl, e.g., as represented by formula (ib), wherein $M^2$ represents an alkaline earth metal cation, by treatment with the corresponding base, i.e. respectively an alkali metal base or the corresponding base of formula $N(R^k)_3$ or an alkaline earth metal base, in a suitable solvent according to methods known to the person skilled in the art. Suitable alkali metal bases include sodium hydroxide and potassium hydroxide.

Suitable alkaline earth metal bases include calcium hydroxide.

Suitable bases of formula $N(R^k)_3$ include ammonia ($NH_3$) and triethylamine.

Compounds of formula (I) wherein $R^1$ is heteroaryl substituted independently by $C_{1-6}$ alkyl phosphate-$C_{1-6}$ alkyl, e.g. as represented by the group of formula (ii), or by sulphate-$C_{1-6}$ alkyl, e.g. as represented by the group of formula (iii), or by carboxy($C_{1-6}$)alkyl-carbonyloxy-$C_{1-6}$ alkyl, e.g. as represented by the group of formula (iv), or by phosphate-methoxy-$C_{1-6}$ alkyl, e.g. as represented by the group of formula (v), may be transformed into their respective corresponding salts represented by formula (iia), (iiia), (iva), (va) and (vb), according to a method analogous to the one described above for compounds of formula (I) wherein $R^1$ is heteroaryl substituted by phosphate-$C_{1-6}$ alkyl.

Illustrative examples of compounds according to the present invention wherein $R^1$ is a substituted heteroaryl selected from the groups represented by formula (i), (ii), (iii), (iv) and (v), and their respective salts of formula (ia), (ib), (iia), (iiia), (iva), (va) as defined above, include the following compounds:

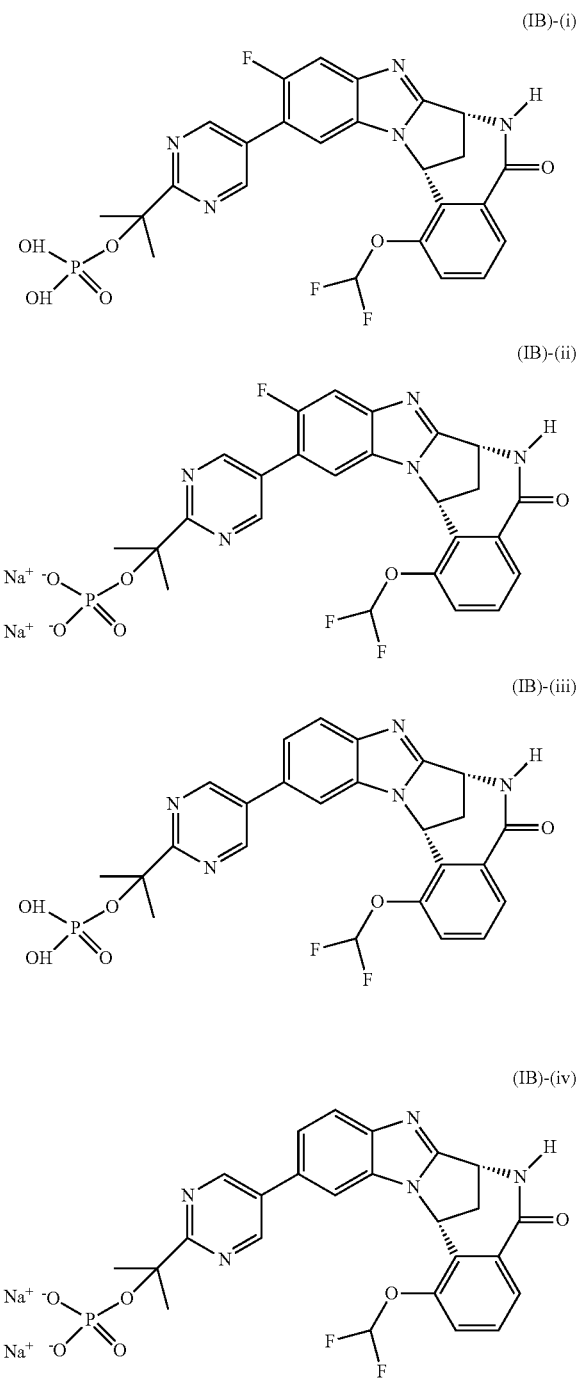

-continued
(IB)-(v)
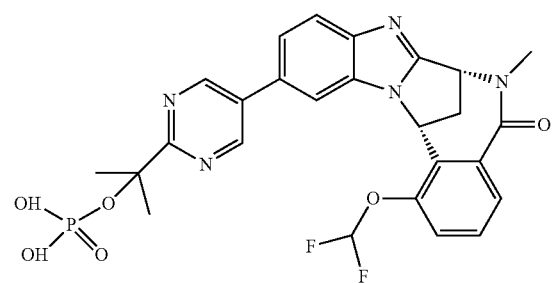
(IB)-(vi)
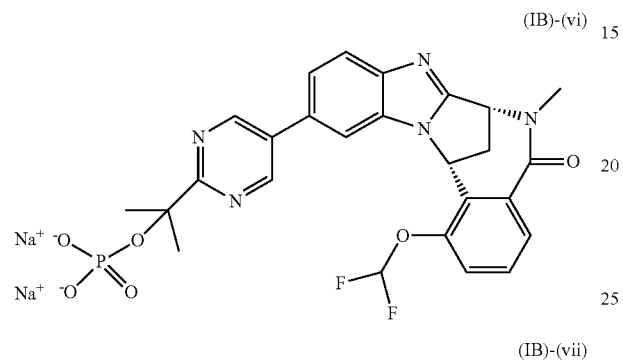
(IB)-(vii)
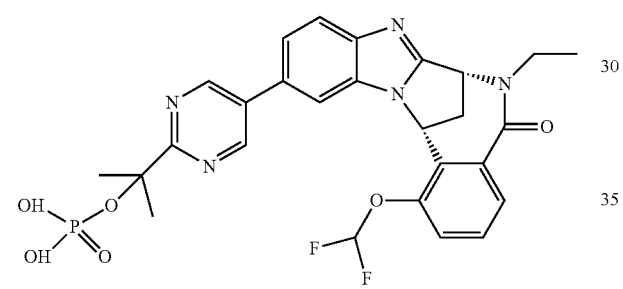
(IB)-(viii)
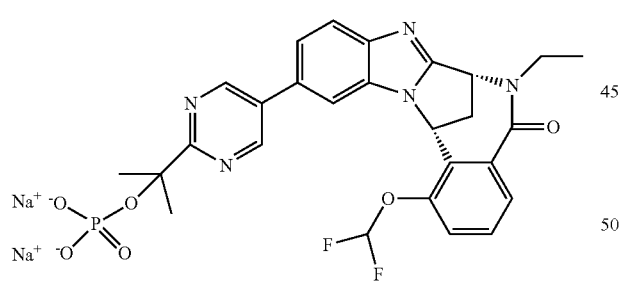
(IB)-(ix)
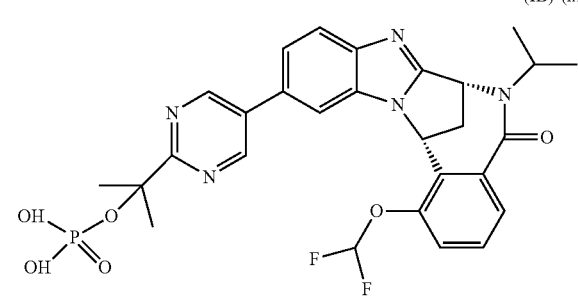
-continued
(IB)-(x)
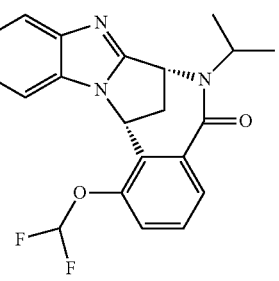
(IB)-(xi)
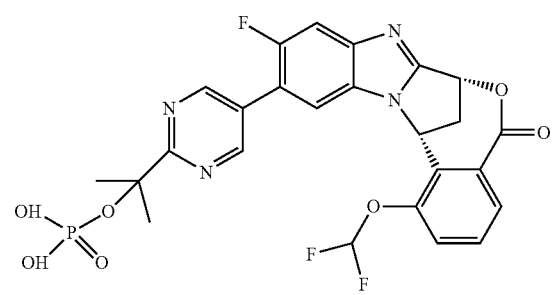
(IB)-(xii)
(IB)-(xiii)
(IB)-(xiv)
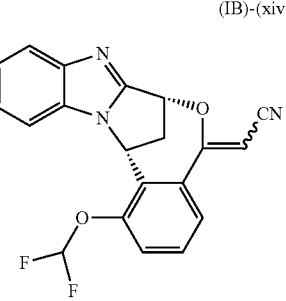

-continued
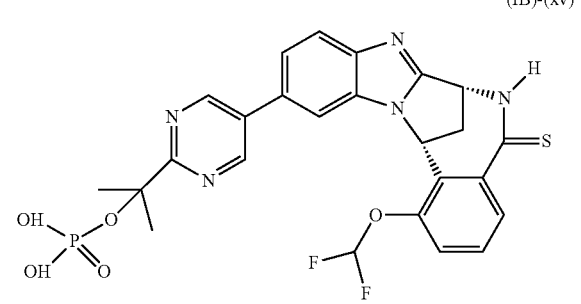
(IB)-(xv)
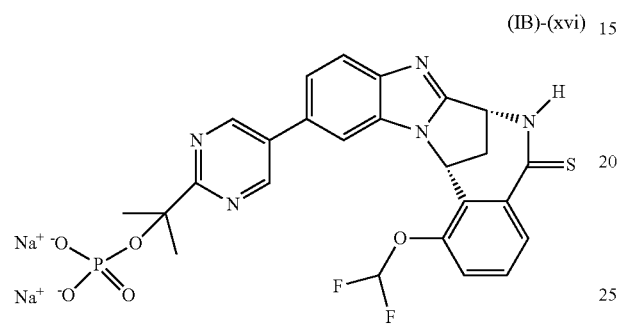
(IB)-(xvi)
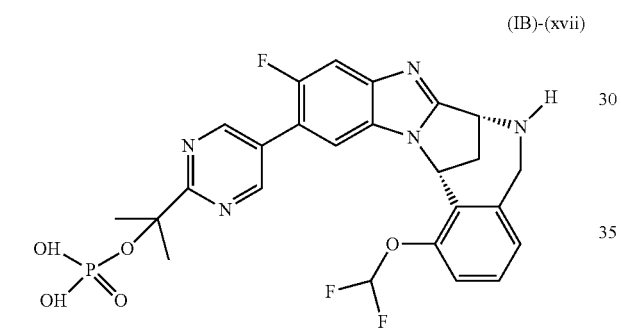
(IB)-(xvii)
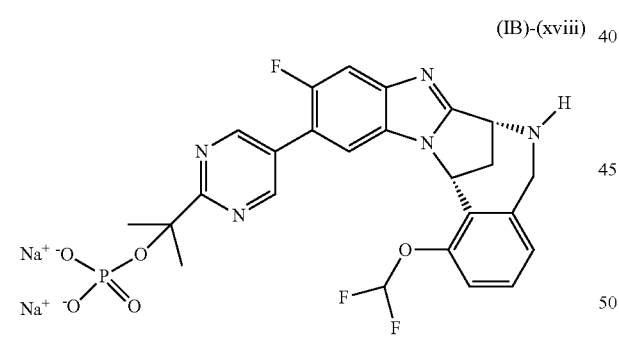
(IB)-(xviii)
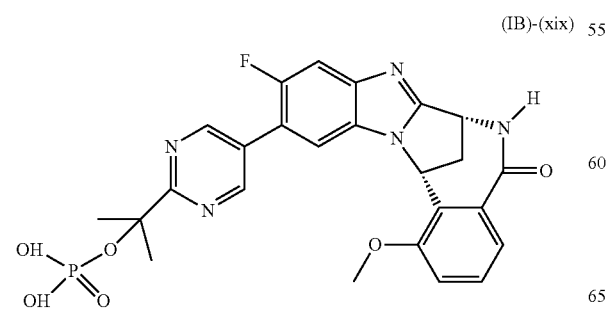
(IB)-(xix)
-continued
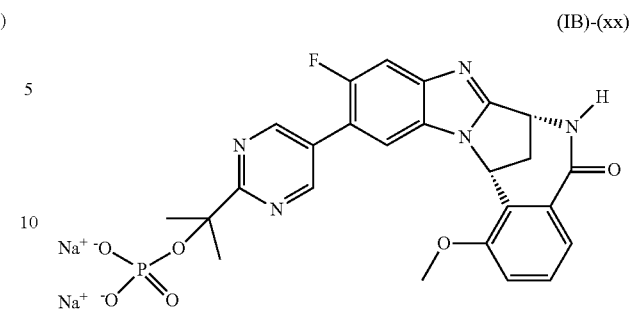
(IB)-(xx)
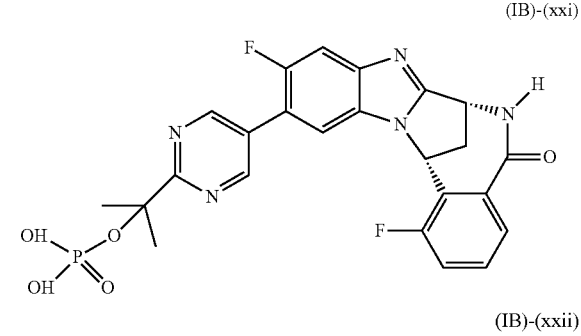
(IB)-(xxi)
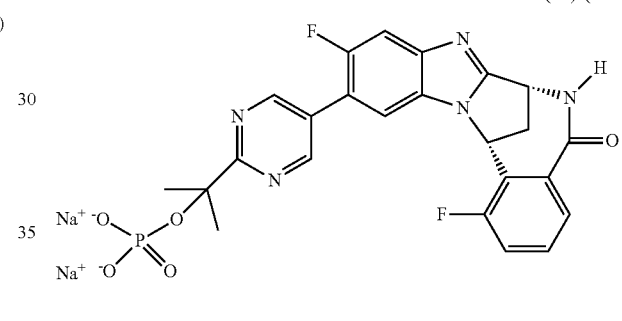
(IB)-(xxii)
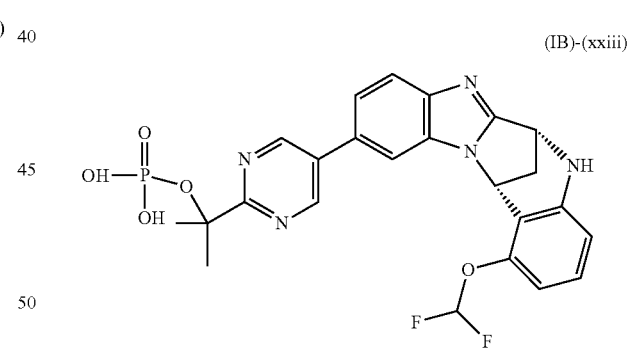
(IB)-(xxiii)
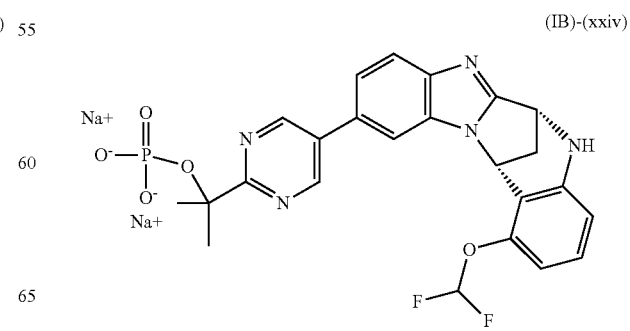
(IB)-(xxiv)

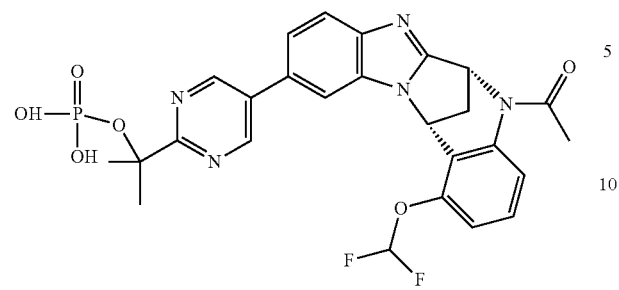
(IB)-(xxv)
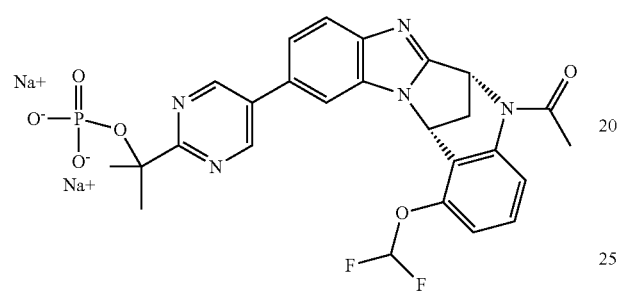
(IB)-(xxvi)
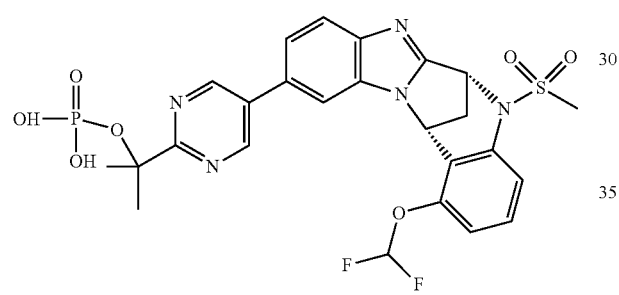
(IB)-(xxvii)
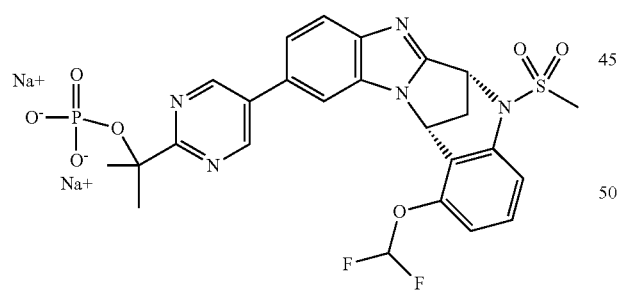
(IB)-(xxviii)
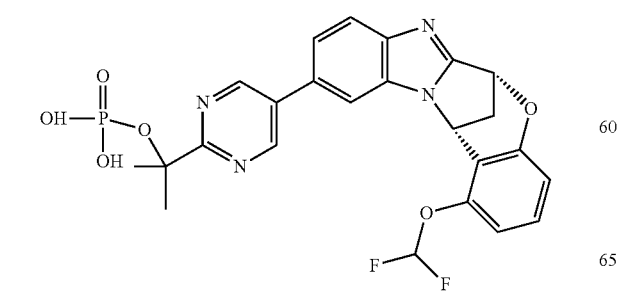
(IB)-(xxix)
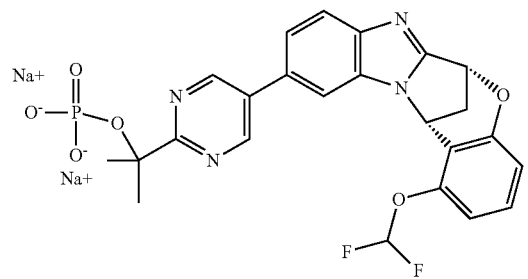
(IB)-(xxx)
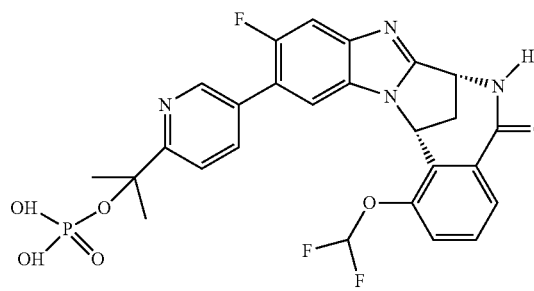
(IB)-(xxxi)
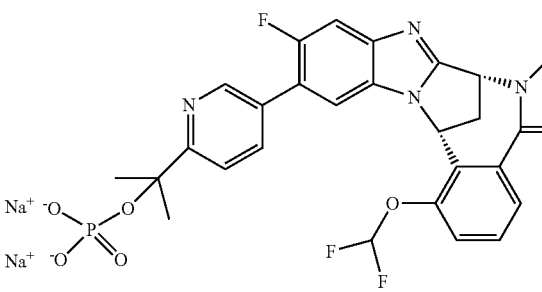
(IB)-(xxxi)
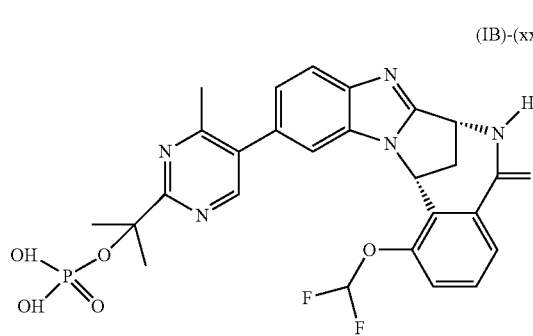
(IB)-(xxxiii)
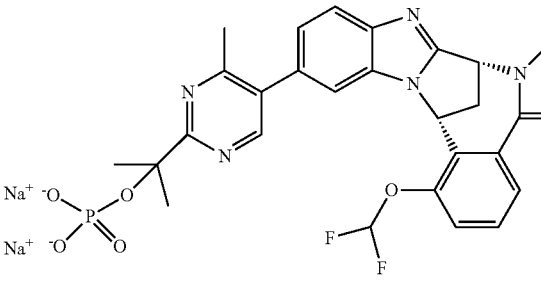
(IB)-(xxxiv)

(IB)-(xxxv)
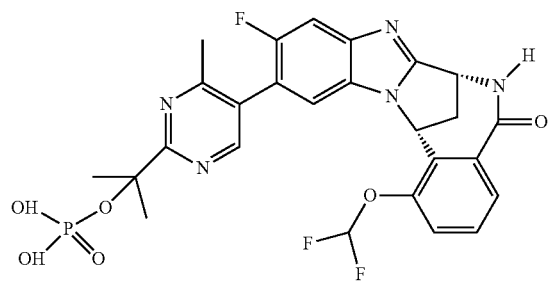
(IB)-(xxxvi)
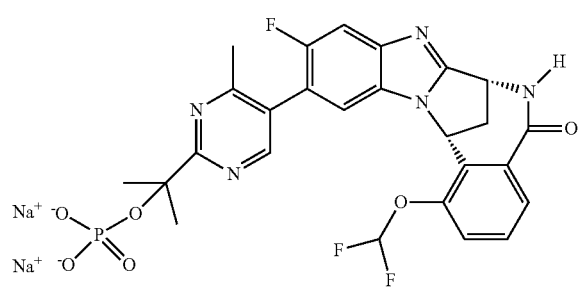
(IB)-(xxxvii)
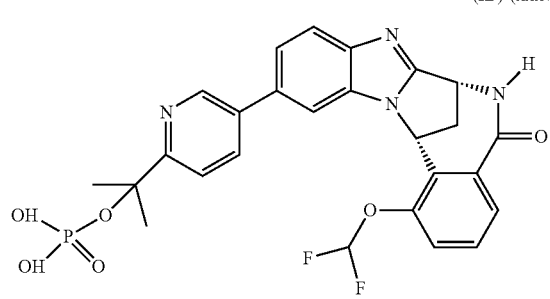
(IB)-(xxxviii)
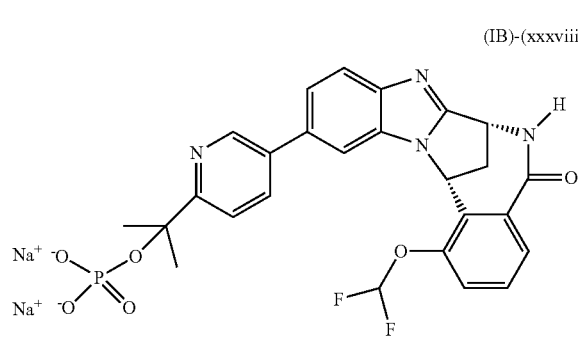
(IB)-(xxxix)
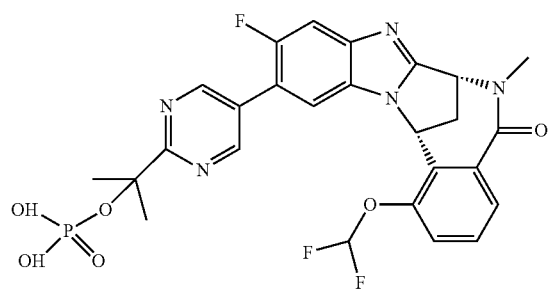
(IB)-(xl)
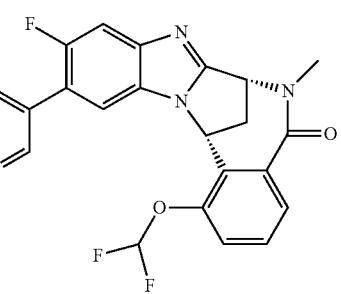
(IB)-(xli)
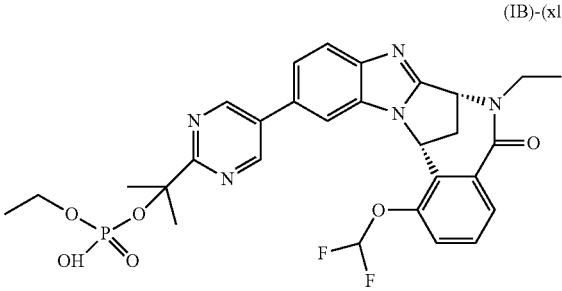
(IB)-(xlii)
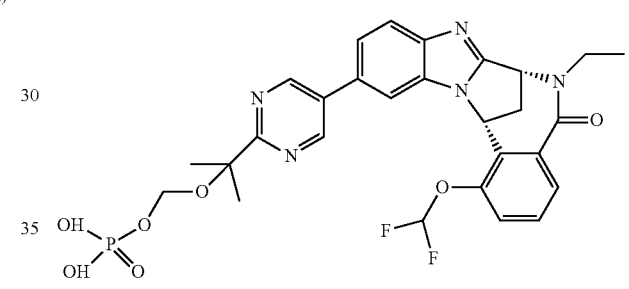
(IB)-(xliii)
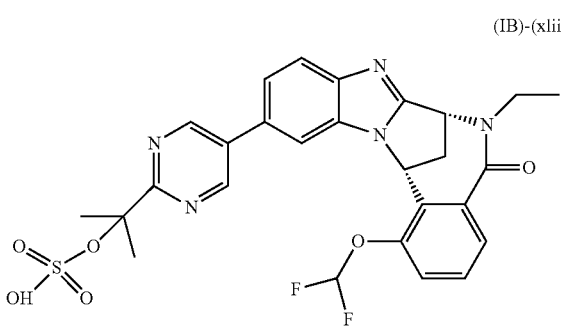
(IB)-(xliv)
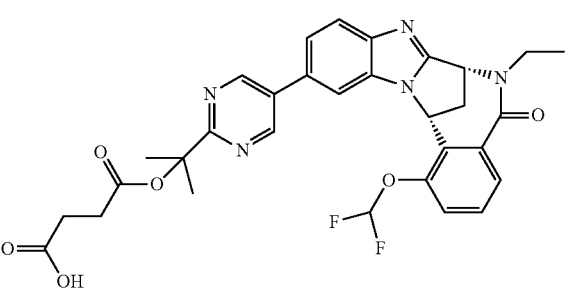

71
-continued
(IB)-(xlv)
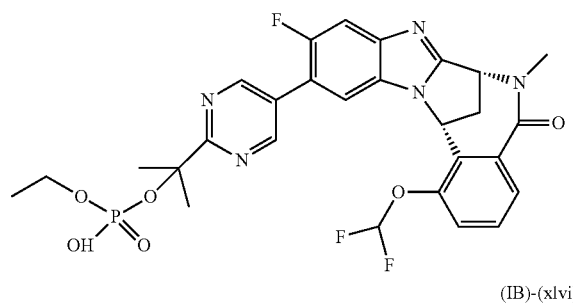
(IB)-(xlvi)
(IB)-(xlvii)
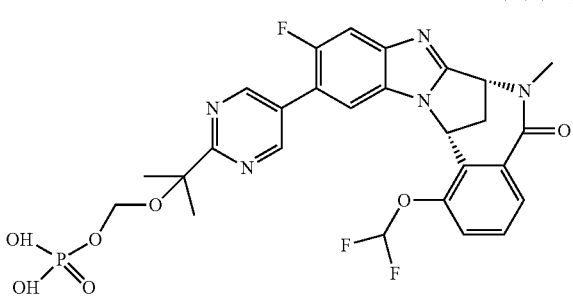
(IB)-(xlviii)
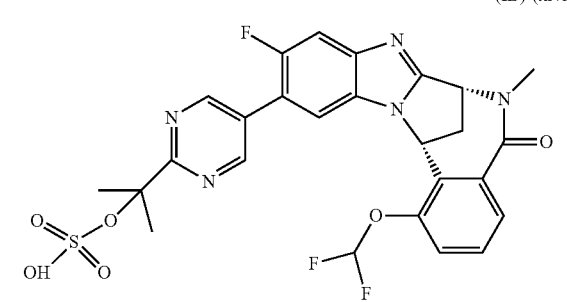
(IB)-(xlix)
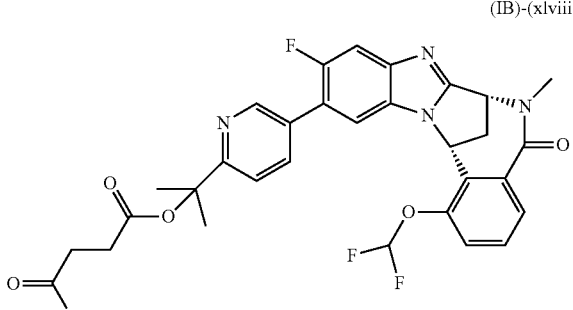
72
-continued
(IB)-(l)
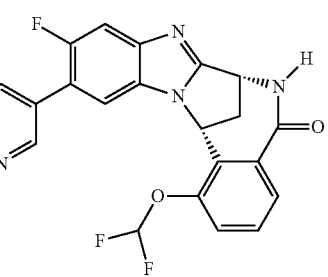
(IB)-(li)
(IB)-(lii)
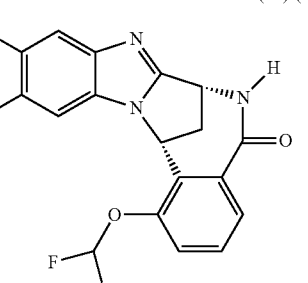
(IB)-(liii)
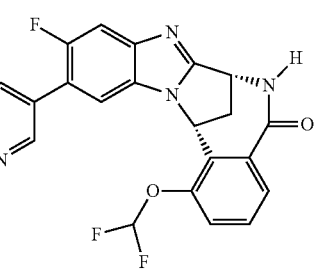
(IB)-(liv)
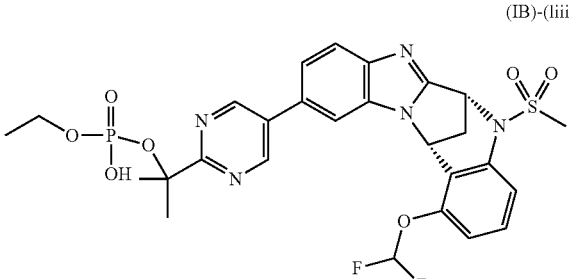

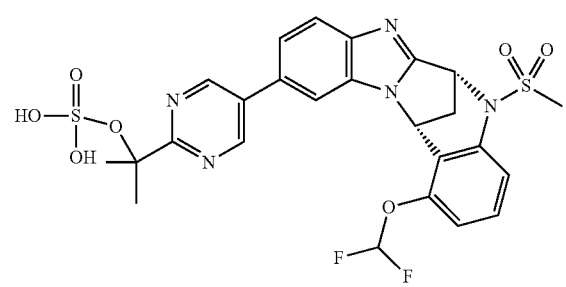
(IB)-(lv)
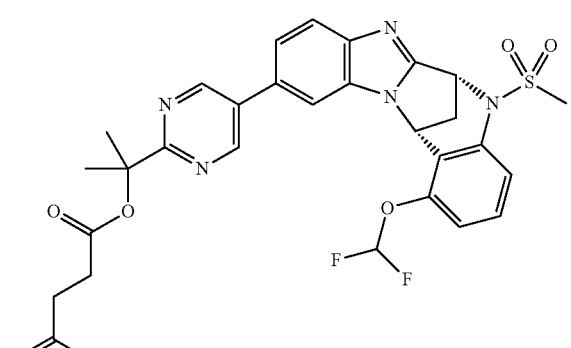
(IB)-(lvi)
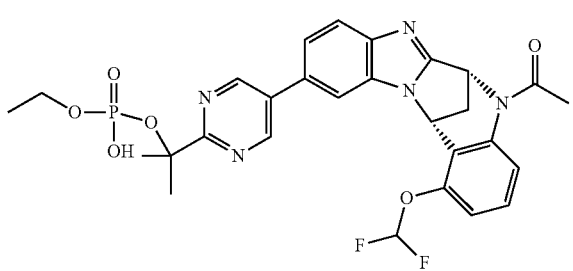
(IB)-(lvii)
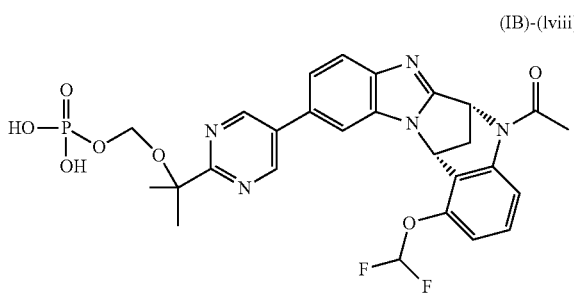
(IB)-(lviii)
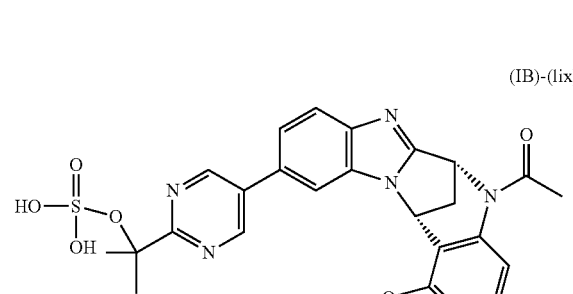
(IB)-(lix)
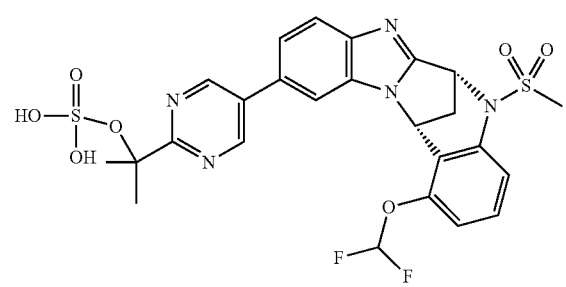
(IB)-(lx)
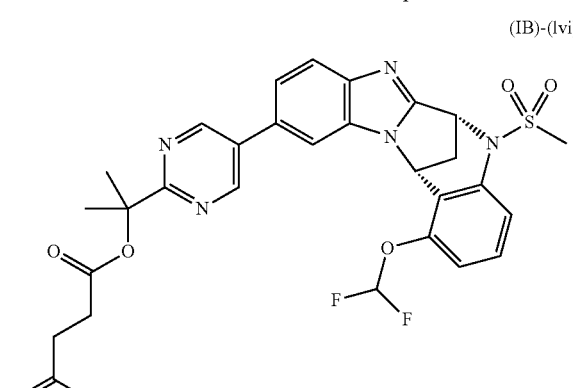
(IC)-(i)
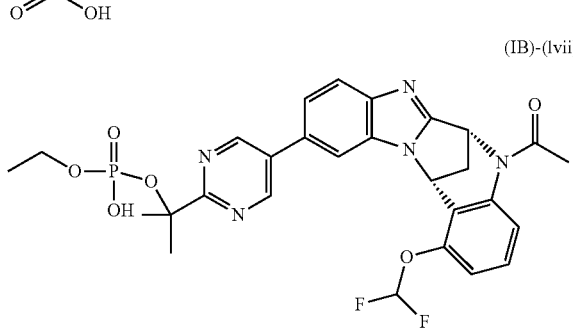
(IC)-(ii)
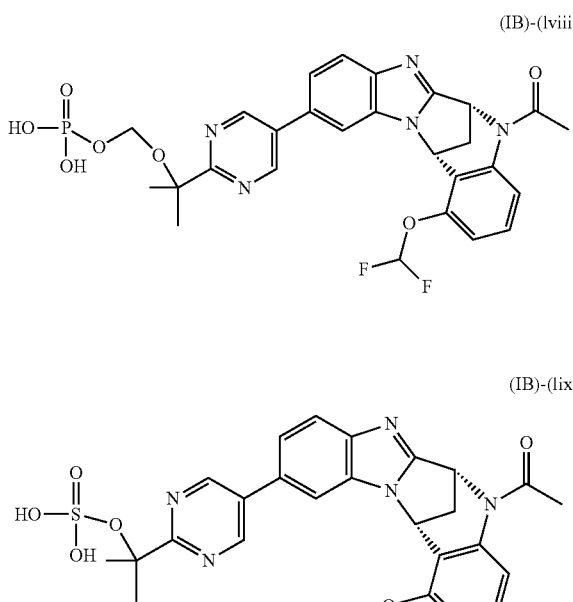
(IC)-(iii)
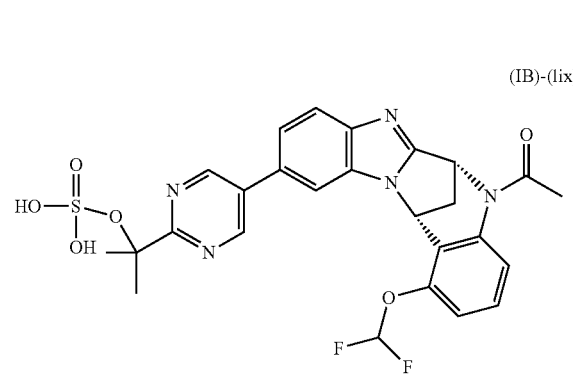
(IC)-(iv)

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention. Alternatively the non desired enantiomer may be racemized into the desired enantiomer, in the presence of an acid or a base, according to methods known to the person skilled in the art, or according to methods described in the accompanying Examples.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

Compounds in accordance with the present invention potently neutralise the activity of TNFα in a commercially available HEK-293 derived reporter cell line known as HEK-Blue™ CD40L. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, compounds of the present invention exhibit an IC$_{50}$ value of 50 μM or less, generally of 20 μM or less, usually of 5 μM or less. typically of 1 μM or less, suitably of 500 nM or less, ideally of 100 nM or less, and preferably of 25 nM or less (the skilled person will appreciate that a lower IC$_{50}$ FIGURE denotes a more active compound).

Certain compounds in accordance with the present invention potently inhibit the binding of a fluorescence conjugate to TNFα when tested in the fluorescence polarisation assay described herein. Indeed, when tested in that assay, compounds of the present invention exhibit an IC$_{50}$ value of 50 μM or less, generally of 20 μM or less, usually of 5 μM or less, typically of 1 μM or less, suitably of 500 nM or less, ideally of 100 nM or less, and preferably of 25 nM or less (as before, the skilled person will appreciate that a lower IC$_{50}$ FIGURE denotes a more active compound).

The compounds of the Examples have been tested in one or both of the assays described below.

Fluorescence Polarisation Assay

Preparation of Compound (A)

1-(2,5-Dimethylbenzyl)-6-[4-(piperazin-1-ylmethyl)phenyl]-2-(pyridin-4-yl-methyl)-1H-benzimidazole—hereinafter referred to as "Compound (A)"—can be prepared by the procedure described in Example 499 of WO 2013/186229; or by a procedure analogous thereto.

Preparation of Fluorescence Conjugate

Compound (A) (27.02 mg, 0.0538 mmol) was dissolved in DMSO (2 mL). 5 (−6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 μL aliquot was removed and diluted in a 80:20 mixture of AcOH:H$_2$O for LC-MS analysis on the 1200RR-6140 LC-MS system. The chromatogram showed two closely eluting peaks at retention times of 1.42 and 1.50 minutes, both with mass (M+H)$^+$=860.8 amu, corresponding to the two products formed with the 5- and 6-substituted carboxyfluorescein group. A further peak at retention time 2.21 minutes had a mass of (M+H)$^+$=502.8 amu, corresponding to Compound (A). No peak was observed for unreacted 5(−6) carboxyfluorescein succinimyl ester. The peak areas were 22.0%, 39.6% and 31.4% for the three signals, indicating a 61.6% conversion to the two isomers of the desired fluorescence conjugate at that time-point. Further 20 μL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of fluorescence conjugate, corresponding to an overall yield of 53% for the reaction and preparative HPLC purification.

Inhibition of Binding of Fluorescence Conjugate to TNFα

Compounds were tested at 10 concentrations starting from 25 μM in a final assay concentration of 5% DMSO, by pre-incubation with TNFα for 60 minutes at ambient temperature in 20 mM Tris, 150 mM NaCl, 0.05% Tween 20, before addition of the fluorescence conjugate and a further incubation for 20 hours at ambient temperature. The final concentrations of TNFα and the fluorescence conjugate were 10 nM and 10 nM respectively in a total assay volume of 25 μL. Plates were read on a plate reader capable of detecting fluorescence polarisation (e.g. an Analyst HT plate reader; or an Envision plate reader). An IC$_{50}$ value was calculated using XLfit™ (4 parameter logistic model) in ActivityBase.

When tested in the fluorescence polarisation assay, compounds of the accompanying Examples were found to exhibit IC$_{50}$ values of 50 μM or better.

When tested in the fluorescence polarisation assay, compounds of the accompanying Examples exhibit IC$_{50}$ values generally in the range of about 0.01 nM to about 50 µM, usually in the range of about 0.01 nM to about 20 µM, typically in the range of about 0.01 nM to about 5 µM, suitably in the range of about 0.01 nM to about 1 µM, ideally in the range of about 0.01 nM to about 500 nM, appositely in the range of about 0.01 nM to about 100 nM, and preferably in the range of about 0.01 nM to about 25 nM.

Reporter Gene Assay

Inhibition of TNFα-Induced NF-κB Activation

Stimulation of HEK-293 cells by TNFα leads to activation of the NF-κB pathway. The reporter cell line used to determine TNFα activity was purchased from InvivoGen. HEK-Blue™ CD40L is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a dose-dependent manner by TNFα, with an EC50 of 0.5 ng/mL for human TNFα. Compounds were diluted from 10 mM DMSO stocks (final assay concentration 0.3% DMSO) to generate a 10-point 3-fold serial dilution curve (30,000 nM to 2 nM final concentration, for example). Diluted compound was preincubated with TNFα for 60 minutes prior to addition to a 384-well microtitre plate and incubated for 18 h. The final TNFα concentration in the assay plate was 0.5 ng/mL. SEAP activity was determined in the supernatant using the colorimetric substrates QUANTI-Blue™ or HEK-Blue™ Detection media (InvivoGen). Percentage inhibitions for compound dilutions were calculated between a DMSO control and maximum inhibition (by excess control compound) and an $IC_{50}$ value calculated using XLfit™ (4 parameter logistic model) in ActivityBase.

When tested in the reporter gene assay, the compounds of the accompanying Examples were all found to exhibit $IC_{50}$ values of 50 µM or better.

When tested in the reporter gene assay, compounds of the accompanying Examples exhibit IC50 values generally in the range of about 0.01 nM to about 50 µM, usually in the range of about 0.01 nM to about 20 µM, typically in the range of about 0.01 nM to about 5 µM, usually in the range of about 0.01 nM to about 1 µM, suitably in the range of about 0.01 nM to about 500 nM, ideally in the range of about 0.01 nM to about 100 nM, and appositely in the range of about 0.01 nM to about 25 nM.

The following Examples illustrate the preparation of compounds according to the invention.

EXAMPLES

| Abbreviations | | | |
|---|---|---|---|
| DCM: | Dichloromethane | EtOAc: | Ethyl acetate |
| DMF: | N,N-Dimethylformamide | MeOH: | Methanol |
| DMSO: | Dimethylsulfoxide | SiO2: | Silica |
| Et2O: | Diethyl ether | h: | Hour |
| THF: | Tetrahydrofuran | AcOH: | Acetic acid |
| r.t.: | Room temperature | b s.: | Broad singlet |
| M: | Mass | | |
| Brine: | Saturated aqueous sodium chloride solution | | |
| HPLC: | High Performance Liquid Chromatography | | |
| LCMS: | Liquid Chromatography Mass Spectrometry | | |
| ES+: | Electrospray Positive Ionisation | | |
| TEA: | Triethylamine | | |
| DIPEA: | N,N-di-iso-propylethylamine | | |
| DIAD: | Diisopropyl (E)-1,2-diazenedicarboxylate | | |
| RT: | retention time | | |
| TBAF: | tetrabutyl ammonium fluoride | | |
| TLC: | Thin Layer Chromatography | | |
| MeCN: | Acetonitrile | | |
| DIBAL-H: | Diisobutylaluminium hydride | | |
| TMSCN: | Trimethylsilyl cyanide | | |
| DEA: | Diethanolamine | | |
| pTSA | para-toluene sulphonic acid monohydrate | | |
| TFA: | trifluoroacetic acid | | |
| DMA: | dimethyl acetamide | | |
| HATU: | N-[(Dimethylamino)-1H-1,2,3-triazolo-[4,5-b]pyridin-1-ylmethylene]-N-ethylmethanaminium hexafluorophosphate N-oxide | | |
| KHMDS: | Potassium bis(trimethylsilyl)amide | | |
| COMU: | (1-cyano-2-ethoxy-2-oxoethylidenaminooxy) dimethylamino-morpholino carbenium hexafluorophosphate | | |
| PdCl2(dcypp) | :dichloro-bis(dicyclohexylphosphino)propane] palladium(II) | | |
| [Ir{dF(CF3)ppy}2(dtbpy)]PF6 | [4,4'-Bis(tert-butyl)-2,2'-bipyridine]bis[3,5-difluoro-2-[5-(trifluoromethyl)-2-pyridinyl]phenyl]iridium(III) hexafluorophosphate | | |

Analytical Conditions

All NMRs were obtained either at 300 MHz or 400 MHz.

All reactions involving air- or moisture-sensitive reagents were performed under a nitrogen atmosphere using dried solvents and glassware.

All compound LCMS data was determined by using the method below:

Method 1: For Intermediates 1 to 7 and 15 to 17.

Shimadzu 2010—YMC Triart C18, 4.6×50 mm, 3 m column

Mobile phase A: 10 mM Ammonium Formate+0.1% Ammonia+water

Mobile phase B: 5% of mobile phase A+95% MeCN+0.1% Ammonia

Gradient program (Flow Rate 1.4 mL/min, Column Temperature 40° C.):

| Time | A % | B % |
|---|---|---|
| 0.1 | 70 | 30 |
| 2.5 | 5 | 95 |

| Time | A % | B % |
|---|---|---|
| 3.5 | 5 | 95 |
| 5.0 | 70 | 30 |
| 5.5 | 70 | 30 |

Method 2: For Intermediate 8 and 18

Shimadzu 2010—X-bridge C18 Waters 2.1×20 mm, 2.5 µm column

Mobile phase A: 10 mM Ammonium Formate+0.1% Ammonia+water

Mobile phase B: 5% of mobile phase A+95% MeCN+ 0.1% Ammonia

Gradient program (Flow Rate 1.0 mL/min, Column Temperature 40° C.):

| Time | A % | B % |
|---|---|---|
| 0.1 | 95 | 5 |
| 4.0 | 5 | 95 |
| 5.0 | 5 | 95 |
| 5.1 | 95 | 5 |
| 6.5 | 95 | 5 |

Method 3 for all Analytical LCMS Done in Basic Conditions. LCMS Basic:

A QDA Waters simple quadrupole mass spectrometer is used for LC-MS analysis.

This spectrometer is equipped with an ESI source and an UPLC Acquity Classic with diode array detector (210 to 400 nm.)

Data are acquired in a full MS scan from m/z 50 to 1000 in positive mode with an acidic elution The reverse phase separation is carried out at 45° C. on a Waters Acquity UPLC BEH C18 1.7 µm (2.1×50 mm) column for basic elution Gradient Elution is Done with:

H2O/ACN/Ammonium_formate (95/5/63 mg/1)+50 µl NH4OH (solvent A)

ACN/H2O/Ammonium_formate (95/5/63 mg/1)+50 µl NH4OH (solvent B).

Acidic Gradient Program:

HPLC flow rate: 0.6 ml/min to 0.7 ml/min, injection volume: 1 µl

Full flow in MS.

| Time (min) (ml/min) | A (%) | B (%) | Flow |
|---|---|---|---|
| 0 | 99 | 1 | 0.4 |
| 0.3 | 99 | 1 | 0.4 |
| 3.2 | 0 | 100 | 0.4 |
| 3.25 | 0 | 100 | 0.5 |
| 4 | 0 | 100 | 0.5 |
| 4.1 | 99 | 1 | 0.4 |
| 4.8 | 90 | 1 | 0.4 |

Method 4 for all Analytical LCMS in Acid Conditions: LCMS Acid:

A QDA Waters simple quadrupole mass spectrometer is used for LC-MS analysis.

This spectrometer is equipped with an ESI source and an UPLC Acquity Hclass with diode array detector (210 to 400 nm).

Data are acquired in a full MS scan from m/z 50 to 1000 in positive mode with an acidic elution. The reverse phase separation is carried out at 45° C. on a Waters Acquity UPLC HSS T3 1.8 µm (2.1×50 mm) column for acidic elution Gradient Elution is Done with:

Water (solvent A)

Acetonitrile (solvent B)

Water/Acetonitrile/Formic Acid 0.5% (solvent C)

Acidic Gradient Program:

HPLC flow rate: 0.6 ml/min to 0.7 ml/min, injection volume: 1 µl

Full flow in MS.

| Time (min) (ml/min) | A (%) | B (%) | C (%) | Flow |
|---|---|---|---|---|
| 0 | 90 | 0 | 10 | 0.6 |
| 0.3 | 90 | 0 | 10 | 0.6 |
| 3.2 | 0 | 90 | 10 | 0.6 |
| 3.25 | 0 | 90 | 10 | 0.7 |
| 4 | 0 | 90 | 10 | 0.7 |
| 4.1 | 90 | 0 | 10 | 0.6 |
| 5.4 | 90 | 0 | 10 | 0.6 |

Method 5 for all Examples:

Waters Acquity-SQD, Waters Acquity UPLC BEH C18, 2.1×50 mm, 1.7 µm column

Mobile phase A: 10 mM Ammonium Formate+0.1% Ammonia

Mobile phase B: 95% MeCN+5% H2O+0.1% Ammonia

Gradient Program (Flow Rate 1.0 mL/Min, Column Temperature 40° C.):

| Time | A % | B % |
|---|---|---|
| 0.00 | 95 | 5 |
| 0.50 | 95 | 5 |
| 1.75 | 5 | 95 |
| 2.00 | 5 | 95 |
| 2.25 | 95 | 5 |

It will be apparent to the person skilled in the art that different retention times (RT) may be obtained for LCMS if different analytical conditions are used.

Additional Analytical HPLC Methods

Method 6

Column: Waters Atlantis dC18 (2.1×100 mm, 3 µm column)

Flow rate: 0.6 mL/min

Solvent A: 0.1% Formic acid/water

Solvent B: 0.1% Formic acid/acetonitrile

Injection Volume: 3 µL

Column temperature: 40° C.

UV Detection wavelength: 215 nm

Eluent: 0 to 5 minutes, constant gradient from 95% solvent A+5% solvent B to 100% solvent B; 5 to 5.4 minutes, 100% solvent B; 5.4 to 5.42 minutes, constant gradient from 100% solvent B to 95% solvent A+5% solvent B; 5.42 to 7.00 minutes, 95% solvent A+5% solvent B.

Method 7

Column: Waters Atlantis dC18 (2.1×30 mm, 3 µm column)

Flow rate: 1 ml/min

Solvent A: 0.1% Formic acid/water

Solvent B: 0.1% Formic acid/acetonitrile

Injection volume: 3 μL
UV Detection wavelength: 215 nm
Eluent: 0 to 1.5 minutes, constant gradient from 95% solvent A+5% solvent B to 100% solvent B; 1.5 to 1.6 minutes, 100% solvent B; 1.60 to 1.61 minutes, constant gradient from 100% solvent B to 95% solvent A+5% solvent B; 1.61 to 2.00 minutes, 95% solvent A+5% solvent B.

Method 8
Column: Phenomenex Gemini $C_{18}$ (2.0 mm×100 mm, 3 μm column)
Flow rate: 0.5 mL/min
Solvent A: 2 mM Ammonium bicarbonate/water
Solvent B: Acetonitrile
Injection volume: 3 μL
Column temperature: 50° C.
UV Detection wavelength: 215 nM
Eluent: 0 to 5.5 minutes, constant gradient from 95% solvent A+5% solvent B to 100% solvent B; 5.5 to 5.9 minutes, 100% solvent B; 5.90 to 5.92 minutes, constant gradient from 100% solvent B to 95% solvent A+5% solvent B.

Method 9
Column: Phenomenex Gemini C18 (2.0 mm×50 mm, 3 μm column)
Flow rate: 1.0 mL/min
Solvent A: 2 mM Ammonium bicarbonate/water
Solvent B: Acetonitrile
Injection volume: 3 μL
Column temperature: 60° C.
UV Detection wavelength: 215 nM
Eluent: 0 to 1.8 minutes, constant gradient from 99% solvent A+1% solvent B to 100% solvent B; 1.8 to 2.1 minutes, 100% solvent B; 2.1 to 2.3 minutes, constant gradient from 100% solvent B to 99% solvent A+1% solvent B.

Method 10
Column: Waters XSelect (C18, 50×2.1 mm, 3.5μ)
Flow: 0.8 ml/min Column temp; 35° C.
Eluent A: 0.1% formic acid in acetonitrile
Eluent B: 0.1% formic acid in water
Lin. Gradient: t=0 min 5% A, t=3.5 min 98% A, t=6 min 98% A
Detection: DAD (220-320 nm)
Detection: MSD (ESI pos/neg) mass range: 100-800

Method 11
Column: Waters XSelect (C18, 30×2.1 mm, 3.5μ)
Flow: 1.0 ml/min Column temp; 35° C.
Eluent A: 0.1% formic acid in acetonitrile
Eluent B: 0.1% formic acid in water
Lin. Gradient: t=0 min 5% A, t=1.6 min 98% A, t=3 min 98% A
Detection: DAD (220-320 nm)
Detection: MSD (ESI pos/neg) mass range: 100-800

Method 12
Column: Waters XSelect (C18, 30×2.1 mm, 3.5μ)
Flow: 1.0 ml/min Column temp; 35° C.
Eluent A: 0.1% formic acid in acetonitrile
Eluent B: 0.1% formic acid in water
Lin. Gradient: t=0 min 5% A, t=1.6 min 98% A, t=4 min 98% A
Detection: DAD (220-320 nm)
Detection: MSD (ESI pos/neg) mass range: 100-800

Method 13
Column: Waters XSelect (C18, 30×2.1 mm, 3.5μ)
Flow: 1.0 ml/min Column temp; 35° C.
Eluent A: 0.1% formic acid in acetonitrile
Eluent B: 0.1% formic acid in water
Lin. Gradient: t=0 min 5% A, t=1.6 min 98% A, t=3 min 98% A
Detection: DAD (220-320 nm)
Detection: MSD (ESI pos/neg) mass range: 400-1600

Method 14 for the purification of Examples 107 to 112
Semi preparative HPLC column: Sunfire prep C18 5 μm 10×150 mm Isocratic elution: 25% of Solvent A (Water/Acetonitrile/formic acid (v/v/v; 95/5/0.05)) and 75% Solvent B (acetonitrile/formic acid (v/v; 100/0.075))
Flow rate: 7 mL/min Method 15 for the Analysis of Examples 107 to 112
The LCMS control was performed with a QM Waters triple quadrupole mass spectrometer coupled with an HPLC Alliance Waters 2795 quaternary pump. The reverse phase separation is carried out at 45° C. on a Waters Sunfire MS C18 column 5 μm (4.6×15 mm) for acidic elution.
Gradient elution is performed with water (Solvent A), acetonitrile (Solvent B) and water/acetonitrile/formic acid (Solvent C v/v/v 50/50/5).
Solution pH 3-4, gradient table as below:

| Time | A % | B % | C % | Flow |
|---|---|---|---|---|
| 0 | 90 | 0 | 10 | 1.9 |
| 1.5 | 90 | 0 | 10 | 1.9 |
| 7.15 | 2 | 88 | 10 | 2.4 |
| 10.5 | 2 | 88 | 10 | 2.4 |
| 10.6 | 90 | 0 | 10 | 1.9 |
| 13 | 90 | 0 | 10 | 1.9 |

Method 16:
Waters UPLC-SQD apparatus; ionization: electrospray in positive and/or negative mode (ES+/−); chromatographic conditions: column: Acquity CSH C18 1.7 μm-1×30 mm; solvents: A: $H_2O$ (0.1% formic acid) B: $CH_3CN$ (0.1% formic acid); column temperature: 45° C.; flow rate: 0.6 ml/min; gradient (2.0 min): from 5 to 50% of B in 1.0 min; 1.3 min: 100% of B; 1.45 min: 100% of B; 1.75 min: 5% of B; retention time=RT (min).

Method 17:
Waters HPLC-ZQ apparatus; ionization: electrospray in positive and/or negative mode (ES+/−); chromatographic conditions: column: XSelect CSH C18 3.5 μm-3.0×75 mm; solvents: A: $H_2O$ (0.1% formic acid) B: $CH_3CN$ (0.1% formic acid); column temperature: 60° C.; flow rate: 0.8 ml/min; gradient (6.0 min): 6% of B during 0.8 min; From 6% to 100% of B in 3.9 min; 4.8 min: 100% of B; 5.0 min: 6% of B; 6.0 min: 6% of B; retention time=RT (min).

Method 18:
Waters HPLC-ZQ apparatus; ionization: electrospray in positive and/or negative mode (ES+/−); chromatographic conditions: column: XSelect CSH C18 3.5 μm-3.0×75 mm; solvents: A: $H_2O$ (0.1% formic acid) B0$H_3CN$ (0.1% formic acid); column temperature: 60° C.; flow rate: 1.0 ml/min; gradient (7.0 min): 10% of B during 0.2 min; From 10 to 100% of B in 4.3 min; 4.85 min: 100% of B; 6.5 min: 10% of B; 7.0 min: 10% of B; retention time=RT (min).

Method 19:
Waters UPLC-SQD apparatus; ionization: electrospray in positive and/or negative mode (ES+/−); chromatographic conditions: column: Acquity CSH C18 1.7 μm-1×30 mm; solvents: A: $H_2O$ (0.1% formic acid) B: $CH_3CN$ (0.1% formic acid); column temperature: 45° C.; flow rate: 0.6 ml/min; gradient (4.0 min): 5% of B during 0.15 min; 1.3 min: From 5 to 100% of B in 3.15 min; 3.45 min: 100% of B; 3.85 min: 5% of B; 4.00 min: 5% of B; retention time=RT (min).

Method 20:

Waters UPLC-SQD apparatus; ionization: electrospray in positive and/or negative mode (ES+/−); chromatographic conditions: column: Acquity BEH C18 1.7 μm-2.1×50 mm; solvents: A: H₂O (0.1% formic acid) B: CH₃CN (0.1% formic acid); column temperature: 50° C.; flow rate: 0.8 ml/min; gradient (2.5 min): from 5 to 100% of B in 1.8 min; 2.4 min: 100% of B; 2.45 min: 100% to 5% of B in 0.05 min; retention time=RT (min).

Intermediate 1

2-chloro-6-(difluoromethoxy)benzaldehyde

To 2-chloro-6-hydroxy-benzaldehyde (20 g, 128.2 mmol) in MeCN (150 mL) was added an aqueous solution of potassium hydroxide (71.7 g, 1282 mmol) in water (50 mL) at 0° C. and the reaction mixture was stirred at 0° C. for 10 min. Diethyl (bromodifluoro methyl) phosphonate (36.4 mL, 205.1 mmol) was added at 0° C. The reaction mixture was stirred at 0° C. for 30 min. After completion of reaction (monitored by TLC), the reaction mixture was poured into water (500 mL). The aqueous layer was extracted with ethyl acetate (1 L×2). The organic layer was washed with water (500 mL), brine (500 mL) and dried over anhydrous sodium sulphate. The organic layer was evaporated under reduced pressure to yield the crude product which was purified by column chromatography (SiO2, 5% EtOAc in hexane) yielding the title compound (13.9 g, 53% yield) as a yellow oil.

$^1$H NMR (400 MHz, CDCl₃) δ 10.46 (s, 1H), 7.49 (t, J 8.2 Hz, 1H), 7.37 (dd, J 8.1, 1.1 Hz, 1H), 7.20 (m, 1H), 6.61 (t, 1H).

Intermediate 2

N-[[2-chloro-6-(difluoromethoxy)phenyl]methylene]-(S)-2-methyl-propane-2-sulfinamide To a solution of Intermediate 1 (20 g, 97.08 mmol) in dry THF (100 mL) at 0° C. was added (S)-(−)-t-butyl sulfinamide (12.92 g, 106.79 mmol), K₃PO₄ (61.73 g, 291.2 mmol) and K₂HPO₄ (50.6 g, 291.2 mmol). Then the reaction mixture was stirred at r.t. for 18 h. After completion of reaction (monitored by TLC), the reaction mixture was filtered through celite and washed with ethyl acetate (1 L). The organic layer was washed with water (500 mL), brine (500 mL) and dried over anhydrous sodium sulphate. The organic layer was evaporated under reduced pressure and the residue was purified chromatography (SiO2, 10% EtOAc in hexane) to afford the title compound (20 g, 87% yield) as a yellow oil.

$^1$H NMR (400 MHz, CDCl₃) δ 8.90 (s, 1H), 7.45-7.32 (m, 2H), 7.29-7.15 (m, 1H), 6.82-6.34 (m, 1H), 1.29 (s, 9H). LCMS (ES+) RT 2.73 min, 309.90 (M+H)⁺

Intermediate 3

Ethyl (3R)-3-[[(S)-tert-butylsulfinyl]amino]-3-[2-chloro-6-(difluoromethoxy)phenyl]propanoate This procedure used activated zinc and THF dried over sodium and benzophenone complex. Activated zinc was prepared using the following procedure: 150 g of zinc powder was taken in 1N HCl (500 mL), stirred for 10 min and decanted. The zinc dust powder was further washed with water (3×500 mL) and decanted. The powder was further washed with acetone (3×500 mL), decanted and dried under vacuum to afford 105 g of activated zinc.

To activated zinc dust (105 g, 1618 mmol) in dry THF (150 mL) was added CuCl (19.2 g, 194 mmol) and the reaction mixture was refluxed for 30 min. The reaction mixture was cooled to room temperature and ethyl bromoacetate (45 mL, 404 mmol in THF 100 mL) was added drop wise. The reaction mixture was stirred at 50° C. for 30 min. The reaction mixture was cooled to 0° C. and Intermediate 2 (50 g, 161 mmol in THF 100 mL) was added. The reaction mixture was warmed to r.t. and stirred for 3 h. After completion of reaction (monitored by TLC), the reaction mixture was filtered through celite and washed with ethyl acetate (700 mL). The organic layer was washed with 1N citric acid (500 mL), saturated solution of sodium bicarbonate (500 mL), water (500 mL) and brine (500 mL). The organic layer was separated, dried over anhydrous sodium sulphate and evaporated under reduced pressure. The residue was purified by chromatography (SiO₂, 40% EtOAc in hexane) to afford the title compound (59 g, 92% yield) as a yellow oil.

$^1$H NMR (400 MHz, CDCl₃) δ 7.29-7.21 (m, 2H), 7.05 (d, J 7.3 Hz, 1H), 6.82-6.34 (m, 1H), 5.59 (m, 1H), 4.36 (s, 1H), 4.18-4.02 (m, 2H), 3.25 (dd, J 15.6, 7.5 Hz, 1H), 3.01 (dd, J 15.3, 7.5 Hz, 1H), 1.31-1.11 (m, 12H).

Intermediate 4

Ethyl (3R)-3-amino-3-[2-chloro-6-(difluoromethoxy)phenyl]propanoate hydrochloride To a solution of Intermediate 3 (32 g, 80.6 mmol) in an Ether:EtOH (75 mL, 2:1) mixture was added 4M HCl in 1,4-dioxane (70 mL) and the reaction mixture was stirred at r.t. for 1 h. After completion of reaction (monitored by TLC), the reaction mixture was concentrated under reduced pressure and the residue was washed with diethyl ether (500 mL) to afford the title compound as a yellow solid (22 g, 93% yield).

$^1$H NMR (400 MHz, CDCl₃) δ 8.93 (d, J 6.2 Hz, 2H), 7.32-7.10 (m, 3H), 6.96 (s, 1H), 5.42 (m, 1H), 4.08 (q, J 7.0 Hz, 2H), 3.36 (dd, J 16.5, 7.0 Hz, 1H), 3.14 (dd, J 16.5, 7.8 Hz, 1H), 1.34 (t, J 7.1 Hz, 3H).

Intermediate 5

Ethyl (3R)-3-(5-bromo-4-fluoro-2-nitro-anilino)-3-[2-chloro-6-(difluoromethoxy)phenyl]propanoate To a solution of Intermediate 4 (5 g, 17.06 mmol) in MeCN (50 mL) was added potassium carbonate (7.06 g, 51.18 mmol) and 1-bromo-2,5-difluoro-4-nitrobenzene (4.86 g, 20.47 mmol). The reaction mixture was stirred at 80° C. for 16 h. After completion of reaction (monitored by TLC), the reaction mixture was diluted with ethyl acetate (100 mL) and washed with water (100 mL). The organic layer was separated, dried over anhydrous sodium sulphate and concentrated under reduced pressure. The residue was purified by chromatography (SiO₂, 20% EtOAc in hexane) to afford the title compound (6 g, 69% yield) as a yellow viscous liquid.

LCMS (ES+) RT 3.42 min, 510.90/512.90/514.90 (M+H)⁺

Intermediate 6

(3R)-3-(5-bromo-4-fluoro-2-nitro-anilino)-3-[2-chloro-6-(difluoromethoxy)phenyl]propanal To a solution of Intermediate 5 (6 g, 11.7 mmol) in THF (60 mL) at −78° C. was added DIBAL-H (23 mL, 23.5 mmol) drop wise. The reaction mixture was stirred for 2 h at −78° C. After completion of reaction (monitored by TLC), the reaction mixture was quenched with an aqueous solution of ammonium chloride (200 mL). The reaction mixture was diluted with ethyl acetate (200 mL) and filtered through celite. The filtrate was washed with water (200 mL) and the organic layer was separated, dried over sodium sulphate and evaporated under reduced pressure to afford the title compound (3 g, 57% yield) as a yellow oil, which was used in the next step without purification.

Intermediate 7

(4R)-4-(5-bromo-4-fluoro-2-nitro-anilino)-4-[2-chloro-6-(difluoromethoxy)phenyl]-2-trimethylsilyloxy-butanenitrile To a solution of Intermediate 6 (3 g, 6.42 mmol) in DCM (50 mL) was added $ZnI_2$ (0.2 g, 0.64 mmol), TEA (0.09 mL, 0.64 mmol) and TMSCN (1.6 mL, 12.84 mmol). The reaction mixture was stirred at r.t. for 3 h. After completion of reaction (monitored by TLC), the reaction mixture was diluted with water (100 mL) and the organic layer was separated. The organic layer was washed with water (100 mL), brine (100 mL), dried over anhydrous sodium sulphate and concentrated under reduced pressure to afford the title compound (3.25 g crude material) which was used for the next step without purification.

Intermediate 8

(1R)-7-bromo-1-[2-chloro-6-(difluoromethoxy)phenyl]-6-fluoro-2,3-dihydro-1H-pyrrolo[1,2-a]benzimidazol-3-ol

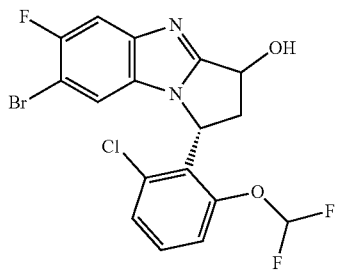 [SMILES: OC1C[C@H](c2c(Cl)cccc2OC(F)F)n2c1nc1cc(F)c(Br)cc12]

To a solution of Intermediate 7 (3 g, 5.3 mmol) in EtOH (50 mL) was added $SnCl_2$ (5 g, 26.46 mmol) and the reaction mixture was heated at 80° C. for 2 h. After completion of reaction (monitored by TLC), the reaction mixture was quenched with water (50 mL) and basified to pH-8 using 1N KOH (100 mL). The reaction mixture was diluted with ethyl acetate (100 mL) and filtered through celite. The organic layer was washed with water (100 mL), brine (100 mL), dried over anhydrous sodium sulphate and concentrated under reduced pressure. The residue was purified by chromatography ($SiO_2$, 0-70% EtOAc in hexane) to afford the title compound (1.1 g, 47% yield) as a pale brown solid.

$^1$H NMR (400 MHz, $CDCl_3$) δ 7.52 (m, 1H), 7.49-7.30 (m, 2H), 7.04-6.67 (m, 2H), 6.42 (m, 1H), 6.24-5.91 (m, 1H), 5.79-5.52 (m, 1H), 3.71-3.46 (m, 1H), 3.19 (m, 2H).

LCMS (ES+) RT 2.39 min, 447.0/449.0/451.0 $(M+H)^+$

Intermediates 9 and 10

(1R,3R)-7-bromo-1-[2-chloro-6-(difluoromethoxy)phenyl]-6-fluoro-2,3-dihydro-1H-pyrrolo[1,2-a]benzimidazol-3-ol and (1R,3S)-7-bromo-1-[2-chloro-6-(difluoromethoxy)phenyl]-6-fluoro-2,3-dihydro-1H-pyrrolo[1,2-a]benzimidazol-3-ol

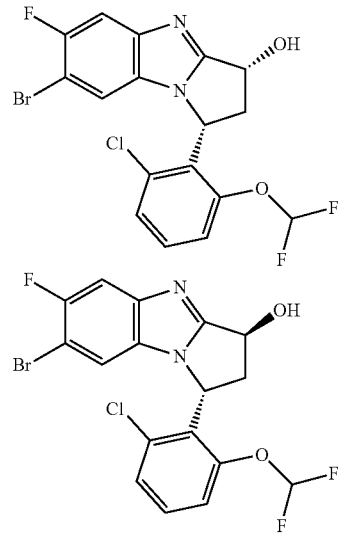

The title compounds were isolated by chiral purification of Intermediate 8 (15 g) under SFC conditions on Chirapak AD (column size: 50*216 mm*mm, flow 360 mL/min, 300 mg/injection/frequency: 8.5 minutes, 25° C., $CO_2$+20% MeOH). Chiral analysis was done on Chiralpak AD-H (column size: 250*4.6 mm, 5 μm, flow 1 mL/min at 30° C. using 80/20 heptane/ethyl acetate containing 0.1% DEA). Under analytical conditions the first eluting diastereoisomers (5.8 and 9.5 minutes) were a mixture of (R, 3S) and (1R,3R)-7-bromo-1-[2-chloro-6-(difluoromethoxy)phenyl]-6-fluoro-2,3-dihydro-1H-pyrrolo[1,2-a]benzimidazol-3-ol.

(1S,3R) and (1S,3S)-7-bromo-1-[2-chloro-6-(difluoromethoxy)phenyl]-6-fluoro-2,3-dihydro-1H-pyrrolo[1,2-a]benzimidazol-3-ol were isolated at 12.5 minutes and 21.5 minutes.

The mixture of a mixture of (1R,3S) and (1R,3R)-7-bromo-1-[2-chloro-6-(difluoromethoxy)phenyl]-6-fluoro-2,3-dihydro-1H-pyrrolo[1,2-a]benzimidazol-3-ol was separated by chiral separation under SFC conditions on Chiracel OD (column size: 50*266 mm*mm, flow 360 mL/min, 80 mg/injection/frequency: 4 minutes, 25° C., $CO_2$+20% MeOH). Chiral analysis was done on Chiralpak AD-H (column size: 250*4.6 mm, 5 μm, flow 1 mL/min at 30° C. using 70/30 heptane/ethyl acetate containing 0.1% DEA). Under analytical conditions the first eluting diastereoisomer (4.9 minutes) was the trans isomer, (1R,3S)-7-bromo-1-[2-chloro-6-(difluoromethoxy)phenyl]-6-fluoro-2,3-dihydro-1H-pyrrolo[1,2-a]benzimidazol-3-ol. Combined fractions were evaporated to yield Intermediate 10 (12.7 g, 50%). $^1$H NMR (400 MHz, CDCl3) δ 7.41 (m, 3H), 7.23 (d, J 8.0 Hz, 0.4H), 6.97 (m, 1.2H), 6.85 (d, J 5.8 Hz, 0.4H), 6.73 (t, J 72.3 Hz, 0.4H), 6.41 (m, 1H), 5.95 (dd, J 74.2, 70.8 Hz, 0.6H), 5.71 (m, 0.6H), 5.62 (d, J 7.4 Hz, 0.4H), 3.22 (m, 2H). as a mixture of rotamers 6/4. LCMS basic (ES$^+$) 2.50 min., 446.96/448.95/450.95 (M+H)$^+$.

Under analytical conditions the second eluting diastereoisomer (6.6 minutes) was the cis isomer, (1R,3R)-7-bromo-1-[2-chloro-6-(difluoromethoxy)phenyl]-6-fluoro-2,3-dihydro-1H-pyrrolo[1,2-a]benzimidazol-3-ol. Combined fractions were evaporated to yield Intermediate 9 (6.6 g, 26%). $^1$H NMR (400 MHz, CDCl$_3$) δ 7.45 (d, J 8.5 Hz, 1H), 7.31 (m, 1.8H), 7.20 (m, 0.6H), 7.08 (d, J 7.9 Hz, 0.6H), 6.88 (d, J 5.5 Hz, 0.6H), 6.74 (d, J 5.2 Hz, 0.4H), 6.61 (t, J 72.5 Hz, 0.4H), 6.15 (t, J 72.0 Hz, 0.6H), 6.08 (m, 1H), 5.63 (m, 1H), 3.56 (m, 0.6H), 3.43 (m, 0.4H), 2.98 (m, 0.4H), 2.80 (m, 0.6H), as a mixture of rotamers 6/4. LCMS acid (ES$^+$) 2.20 min, 446.96/448.95/450.91 (M+H)$^+$.

Under preparative conditions the order of elution was reversed.

Intermediate 10

(1R,3S)-7-bromo-1-[2-chloro-6-(difluoromethoxy) phenyl]-6-fluoro-2,3-dihydro-1H-pyrrolo[1,2-a]benzimidazol-3-ol

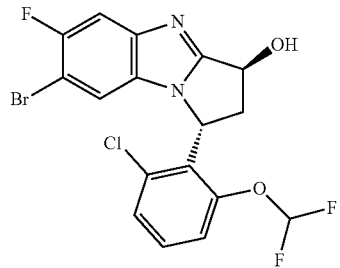 [SMILES: O[C@H]1C[C@H](c2c(Cl)cccc2OC(F)F)n2c1nc1cc(F)c(Br)cc12]

The title compound can also be prepared by the following procedure: Intermediate 9 (3.65 g, 8.146 mmol, 1 eq) and triphenylphosphine (2.62 g, 9.775 mmol, 1.2 eq) were solubilized in 8 mL of dry THF, under an inert atmosphere of nitrogen. Acetic acid (513 μL, 8.960 mmol, 1.1 eq) was added and the mixture cooled to 0° C. A solution of DIAD (2.42 mL, 12.220 mmol, 1.5 eq) in 8 mL of dry THF was added drop wise. The reaction was slowly warmed to r.t. and the reaction continued for 2 hours at this temperature. 20 mL of ethyl acetate were added to the reaction mixture before washing with 3×10 mL of a saturated solution of NaHCO$_3$. The organic layer was dried over anhydrous magnesium sulfate and concentrated under vacuum. The residue was purified by chromatography (SiO$_2$, 5% MeOH in DCM) giving 4.8 g (94% yield) of the inverted acetate intermediate which was used directly used in the next step. [(1R,3S)-7-bromo-1-[2-chloro-6-(difluoromethoxy)phenyl]-6-fluoro-2,3-dihydro-1H-pyrrolo[1,2-a]benzimidazol-3-yl]acetate (4.8 g, 9.800 mmol, 1 eq) was solubilized in 48 mL of methanol. Potassium carbonate (1.4 g, 9.800 mmol, 1 eq) was added and the reaction continued for 1 hour at r.t. The reaction was evaporated and the residue was taken up in ethyl acetate (50 mL) and water (20 mL). The organic layer was washed by water (2×20 mL), dried over sodium sulfate, filtered and concentrated under vacuum to give 4.7 g of the crude title compound as a slightly beige solid.

Intermediate 11 tert-butyl-dimethyl-[1-methyl-1-[5-(4,4,5,5-tetramethyl-1,3,2-dioxaborolan-2-yl)pyrimidin-2-yl] ethoxy]silane 2-(1-hydroxy-1-methylethyl)pyrimidine-5-boronic acid pinacol ester (10 g, 37.8601 mmol), tert-butyldimethylchlorosilane (11.76 g, 75.72 mmol) and imidazole (7.890 g, 115.89 mmol) were dissolved in anhydrous DMF (150 mL). The reaction was stirred at 85° C. for 4 days. EtOAc (100 mL) and water (250 mL) were added, the aqueous layer was extracted with 3×20 mL of EtOAc then the combined organic layers were washed with brine (3×20 mL). and dried over MgSO$_4$, filtered and concentrated in vacuo. The residue was purified by chromatography (SiO$_2$, 0-100% EtOAc in heptane) to afford the title compound as a transparent oil (12.0 g, 83.76%).

$^1$H NMR (400 MHz, CDCl$_3$) δ 9.04 (s, 2H), 1.70 (s, 6H), 1.40 (s, 12H), 0.94 (s, 9H), 0.01 (s, 6H). LCMS acid (ES$^+$) RT 3.04 min, 297.20 (M+H)$^+$.

Intermediate 12

(1R,3S)-7-[2-[1-[tert-butyl(dimethyl)silyl]oxy-1-methyl-ethyl]pyrimidin-5-yl]-1-[2-chloro-6-(difluoromethoxy)phenyl]-6-fluoro-2,3-dihydro-1H-pyrrolo [1,2-a]benzimidazol-3-ol

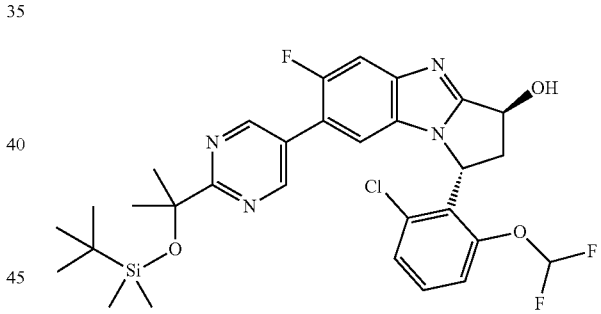

Intermediate 10 (5.12 g, 11.44 mmol), Intermediate 11 (5.19 g, 13.73 mmol) and cesium carbonate (5.59 g, 17.16 mmol, 1.5 eq) were placed in a tube, and filled with argon. Degassed 1,4-dioxane (41.2 mL, 3.6 mL/mmol) and degassed water (4.1 mL, 0.36 mL/mmol) were added and the resulting slurry was stirred at r.t. for 5 minutes before addition of [1,1'-bis(diphenylphosphino)ferrocene]dichloropalladium(II) (418.7 mg, 0.572 mmol, 0.05 eq). The reaction mixture was placed on a pre-heated stirring plate at 90° C. and stirred at this temperature for 2 h. Reaction mixture was cooled down to r.t. before addition of 50 mL of ethyl acetate and 50 mL of water. The aqueous layer extracted with 3×20 mL of ethyl acetate. Combined organic layers were dried over anhydrous magnesium sulfate, filtered and concentrated under reduced pressure.

The crude was purified by chromatography (SiO$_2$, 30-100% EtOAc in heptane) to afford the title compound (3.8 g, 53% yield).

LCMS basic (ES$^+$) RT 3.54 min., 619.20/621.16 (M+H)$^+$.

Intermediate 13

(1R,3R)-7-[2-[1-[tert-butyl(dimethyl)silyl]oxy-1-methyl-ethyl]pyrimidin-5-yl]-1-[2-chloro-6-(difluoromethoxy)phenyl]-6-fluoro-2,3-dihydro-1H-pyrrolo[1,2-a]benzimidazol-3-amine

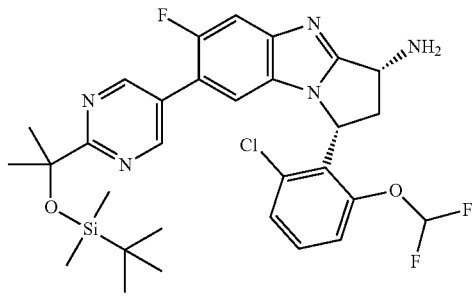 [SMILES: CC(C)(O[Si](C)(C)C(C)(C)C)c1ncc(-c2cc3c(cc2F)nc2n3[C@@H](c3c(Cl)cccc3OC(F)F)C[C@H]2N)cn1]

Intermediate 12 (3.369 g, 5.441 mmol) was suspended in 11 mL of dry toluene. At 0° C., diphenylphosphoryl azide (1.58 mL, 7.071 mmol) was added followed by addition of 1,8-diazabicyclo[5.4.0]undec-7-ene (1.139 mL, 7.616 mmol). The reaction was allowed to reach r.t. and stirred at this temperature for 2 h then heated at 50° C. for 18 h.

The reaction mixture was diluted by 100 mL of water and 100 mL of ethyl acetate. The aqueous layer was extracted by ethyl acetate (3×20 mL). Combined organic layers were washed with successively 20 mL of a saturated solution of NH$_4$Cl and 20 mL of a saturated solution of NaHCO$_3$, dried over anhydrous magnesium sulfate and concentrated in vacuum.

The crude azide intermediate was solubilized in a solution of tetrahydrofuran (50 mL, 10 mL/mmol) and water (5 mL, 1 mL/mmol) before addition of 1 M solution of trimethylphosphine in toluene (11 mL, 11 mmol). The reaction mixture was stirred at r.t. for 2 h. Solvents were evaporated and the residue was purified by chromatography (SiO$_2$, 5-8% MeOH in DCM) to afford the title compound (2.8 g, 83% yield).

LCMS basic (ES$^+$) RT=3.52 min., 618.20/620.20 (M+H)$^+$.

Intermediate 14

(7R,14R)-11-[2-(2-{[tert-butyl(dimethyl)silyl]oxy}propan-2-yl)pyrimidin-5-yl]-1-(difluoromethoxy)-10-fluoro-6,7-dihydro-7,14-methano-benzimidazo[1,2-b][2,5]benzodiazocin-5(14H)-one

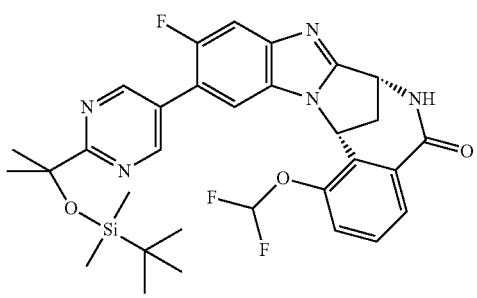 [SMILES: CC(C)(O[Si](C)(C)C(C)(C)C)c1ncc(-c2cc3c(cc2F)nc2n3[C@@H]3C[C@H]2NC(=O)c2cccc(OC(F)F)c23)cn1]

Intermediate 13 (2.78 g, 4.50 mmol, 1 eq), sodium carbonate (2.38 g, 22.5 mmol, 5 eq) and dichloro bis(dicyclohexylphosphino)propane] palladium(II) [Pd-133 from Johnson Matthey] (552 mg, 0.899 mmol, 0.2 eq) were solubilized/suspended in degassed (nitrogen) 1,4-dioxane (54 mL, 12 mL/mmol). The reaction mixture was heated overnight at 150° C. under 5 atmosphere of CO gas. The reaction mixture was filtered over celite, which was thoroughly washed with ethanol. Solvents were evaporated and the residue was purified by chromatography (SiO$_2$, 80-100% EtOAc in heptane), giving the title compound (1.39 g, 50% yield).

LCMS basic (ES$^+$) RT 3.47 min., 610.25/611.25 (M+H)$^+$

Intermediate 15 ethyl (3R)-3-(5-bromo-2-nitro-anilino)-3-[2-chloro-6-(difluoromethoxy)phenyl]propanoate Intermediate 15 was prepared, using the same procedure described for preparation of Intermediate 5, from Intermediate 4 (9.3 g, 28.3 mmol) and 4-bromo-2-fluoro-nitrobenzene (7.4 g, 34 mmol). The reaction was stirred overnight at 80° C. and purified by chromatography (SiO$_2$, 10% EtOAc in hexane). Intermediate 15 was obtained as a yellow oil (12.5 g, 90% yield).

LCMS (ES$^+$) 495 (M+H)$^+$

Intermediate 16

(3R)-3-(5-bromo-2-nitro-anilino)-3-[2-chloro-6-(difluoromethoxy)phenyl]propanal

Intermediate 16 was prepared from Intermediate 15 (12.5 g, 25.4 mmol) using the same procedure described for preparation of Intermediate 6. Following work-up the crude Intermediate 16 was purified by chromatography (SiO$_2$, 15% EtOAc in hexane) yielding Intermediate 16 (9 g, 80% yield) as a yellow oil.

$^1$H NMR (400 MHz, CDCl$_3$) δ 9.80 (d, J 1.3 Hz, 1H), 8.78 (d, J 9.0 Hz, 1H), 7.99 (d, J 9.0 Hz, 1H), 7.27 (d, J 3.2 Hz, 2H), 7.21-7.08 (m, 1H), 6.81-6.66 (m, 2H), 5.93 (m, 1H), 3.56-3.38 (m, 2H), 3.12 (dd, J 17.9, 5.2 Hz, 1H).

Intermediate 17

(4R)-4-(5-bromo-2-nitro-anilino)-4-[2-chloro-6-(difluoromethoxy)phenyl]-2-trimethylsilyloxy-butanenitrile Intermediate 17 was prepared from Intermediate 16 (9 g, 20 mmol) using the same procedure described for preparation of Intermediate 7. The reaction was stirred at r.t. for 2 h. After completion of reaction (monitored by TLC), water (200 mL) was added and extracted with DCM (500 mL). After evaporation of organic layer, the crude product, obtained as a yellow oil (9 g), was used directly for the next step without any purification.

Intermediate 18

(1R)-7-bromo-1-[2-chloro-6-(difluoromethoxy)phenyl]-2,3-dihydro-1H-pyrrolo[1,2-a]benzimidazol-3-ol

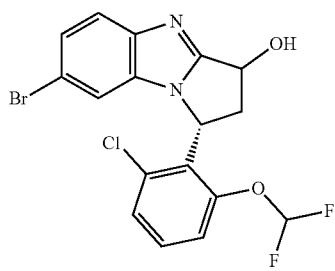 [SMILES: OC1C[C@H](c2c(Cl)cccc2OC(F)F)n2c1nc1ccc(Br)cc12]

Intermediate 18 was prepared from Intermediate 17 (9 g, 16.4 mmol) using the same procedure described for preparation of Intermediate 8. The crude product was purified by chromatography (SiO$_2$, 60% EtOAc in hexane) then triturated with hexane:ethyl acetate to yield the title compound (3 g, 43% yield) as a yellow solid.

LCMS (ES+) 431 (M+H)$^+$

Intermediate 19 and 20

(1R,3R)-7-bromo-1-[2-chloro-6-(difluoromethoxy)phenyl]-2,3-dihydro-1H-pyrrolo[1,2-a]benzimidazol-3-ol and (1R,3S)-7-bromo-1-[2-chloro-6-(difluoromethoxy)phenyl]-2,3-dihydro-1H-pyrrolo[1,2-a]benzimidazol-3-ol

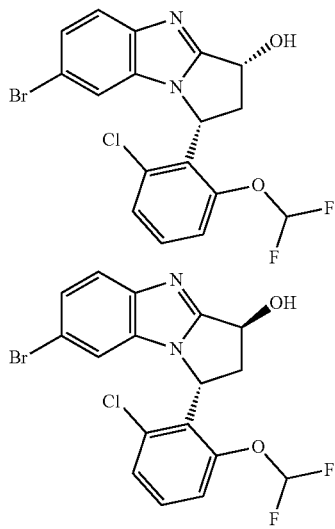

The title compounds were isolated by chiral purification of Intermediate 18 (12.5 g) by 2 successive chiral separation.

First Chiral Separation.

Under SFC conditions on Chiracel OD (column size: 50*266 mm*mm, flow 360 mL/min, 20 mg/injection/frequency: 4 minutes, 25° C., CO$_2$+20% MeOH). Chiral analysis was done on Chiralcel OD-H (column size: 250*4.6 mm, flow 1 mL/min at 30° C. using 100% methanol containing 0.1% DEA). Under analytical conditions the first eluting diastereoisomer (3.9 minutes) was either (1S,3R) or (1S,3S) 7-bromo-1-[2-chloro-6-(difluoromethoxy)phenyl]-2,3-dihydro-1H-pyrrolo[1,2-a]benzimidazol-3-ol. The second eluting diastereoisomers (4.7 minutes) were a mixture of (1R,3S) along with either (1S,3R) or (1S,3S)-7-bromo-1-[2-chloro-6-(difluoromethoxy)phenyl]-2,3-dihydro-1H-pyrrolo[1,2-a]benzimidazol-3-ol and the third eluting diastereoisomer (5.4 minutes) was (1R,3R)-7-bromo-1-[2-chloro-6-(difluoromethoxy)phenyl]-2,3-dihydro-1H-pyrrolo[1,2-a]benzimidazol-3-ol. Combined fractions of the third eluting diastereomer were evaporated to yield to Intermediate 19 (3.63 g, 29%). $^1$H NMR (400 MHz, DMSO) δ 7.57 (m, 2.3H), 7.45 (m, 0.8H), 7.35 (d, J 8.0 Hz, 0.6H), 7.26 (m, 1H), 7.17 (m, 0.3H), 6.83 (t, J 72.5 Hz, 1H), 6.69 (bs, 1H), 6.15 (m, 1H), 6.07 (m, 1H), 5.38 (m, 1H), 3.38 (m, 1H), 2.67 (m, 1H) as a mixture of rotamers 7/3. LCMS acid (ES$^+$) RT 4.31 min., 429.10/431.08/433.05 (M+H)$^+$.

Second Chiral Separation:

Under SFC conditions on Whelko 01 (R,R) (column size: 50*227 mm*mm, flow 360 mL/min, 690 mg/injection/frequency: 5.5 minutes, 25° C., CO$_2$+20% EtOH). Chiral analysis was done on Chiralcel OD-H (column size: 250*4.6 mm, flow 1 mL/min at 30° C. using 50/50 heptane/isopropyl alcohol containing 0.1% DEA).

Under analytical conditions, the first eluting diastereomer (4.1 minutes) was either (1S, 3R) or (1S,3S)-7-bromo-1-[2-chloro-6-(difluoromethoxy)phenyl]-2,3-dihydro-1H-pyrrolo[1,2-a]benzimidazol-3-ol.

Under analytical conditions, the second eluting diastereomer (5.9 minutes) was the trans isomer, (1R,3S)-7-bromo-1-[2-chloro-6-(difluoromethoxy)phenyl]-2,3-dihydro-1H-pyrrolo[1,2-a]benzimidazol-3-ol. Combined fractions were evaporated to yield Intermediate 20 (4.46 g, 36%). $^1$H NMR (400 MHz, DMSO) δ 7.55 (m, 3.4H), 7.31 (m, 1.4H), 7.12 (d, J 7.8 Hz, 0.6H), 7.03 (t, J 73.0 Hz, 0.6H), 6.89 (s, 0.6H), 6.81 (s, 0.4H), 6.32 (dd, J 8.4, 5.9 Hz, 1H), 6.10 (d, J 6.6 Hz, 1H), 5.32 (m, 0.6H), 5.26 (t, J 6.9 Hz, 0.4H), 3.13 (m, 1H), 2.93 (m, 1H). as a mixture of rotamers 6/4. LCMS acid (ES$^+$) RT 4.40 min., 429.05/431.08/433.05 (M+H)$^+$.

Under preparative conditions the order of elution was reversed.

Intermediate 20

(1R,3S)-7-bromo-1-[2-chloro-6-(difluoromethoxy)phenyl]-2,3-dihydro-1H-pyrrolo[1,2-a]benzimidazol-3-ol

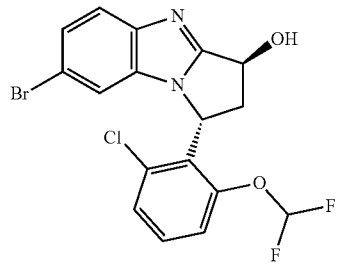 [SMILES: O[C@H]1C[C@H](c2c(Cl)cccc2OC(F)F)n2c1nc1ccc(Br)cc12]

The title compound was prepared from the same procedure as the preparation of Intermediate 10 starting from Intermediate 19 (3.63 g, 8.450 mmol), triphenylphosphine (2.66 g, 10.14 mmol), and acetic acid (0.5 mL, 9.295 mmol) THF (34 mL), DIAD (2.62 mL, 12.67 mmol) in 5 ml of dry THF giving 3.6 g (91%) of the inverted acetate intermediate which was used directly in the next step. Using the following conditions. [(1R,3S)-7-bromo-1-[2-chloro-6-(difluoromethoxy)phenyl]-2,3-dihydro-1H-pyrrolo[1,2a]benzimidazol-3-yl] acetate (4.0 g, 8.480 mmol) was solubilized in 40 mL of methanol. Potassium carbonate (1.1 g, 8.48 mmol, 1 eq) was added and the reaction continued for 1 hour at rt. The methanol was evaporated and the residue was taken up in ethyl acetate (50 mL) and water (20 mL). The organic layer was washed by water (2×20 mL), dried over anhydrous sodium sulfate, filtered and concentrated under vacuum to give 4.9 g of crude title compound as a brown oil use without further purification.

LCMS basic (ES$^+$) RT 2.46 min., 428.94/430.96/433.16 (M+H)$^+$.

Intermediate 21

(1R,3 S)-7-[2-[1-[tert-butyl(dimethyl)silyl]oxy-1-methyl-ethyl]pyrimidin-5-yl]-1-[2-chloro-6-(difluoromethoxy)phenyl]-2,3-dihydro-1H-pyrrolo[1,2-a]benzimidazol-3-ol

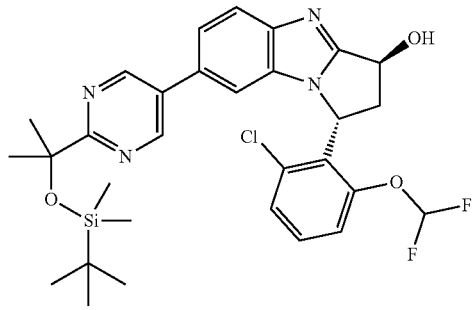 [SMILES: CC(C)(O[Si](C)(C)C(C)(C)C)c1ncc(-c2ccc3nc4n(c3c2)[C@@H](c2c(Cl)cccc2OC(F)F)C[C@@H]4O)cn1]

Intermediate 20 (4.46 g, 10.38 mmol), Intermediate 11 (3.92 g, 10.38 mmol) following the protocol described for intermediate 12 using cesium carbonate (5.07 g, 15.57 mmol), 1,4-dioxane (37.1 mL, 3.6 mL/mmol), water (3.7 mL, 0.36 mL/mmol), [1,1' bis(diphenylphosphino)ferrocene]dichloropalladium(II) (379.8 mg, 0.5191 mmol, 0.05 eq), The crude was purified by chromatography (SiO$_2$, 30-100% EtOAc in hexane) to yield the title compound (5.7 g, 92% yield).

LCMS acid (ES$^+$) RT 3.64 min., 601.29/603.21 (M+H)$^+$

Intermediate 22

(1R,3R)-7-[2-[1-[tert-butyl(dimethyl)silyl]oxy-1-methyl-ethyl]pyrimidin-5-yl]-1-[2-chloro-6-(difluoromethoxy)phenyl]-2,3-dihydro-1H-pyrrolo[1,2-a]benzimidazol-3-amine

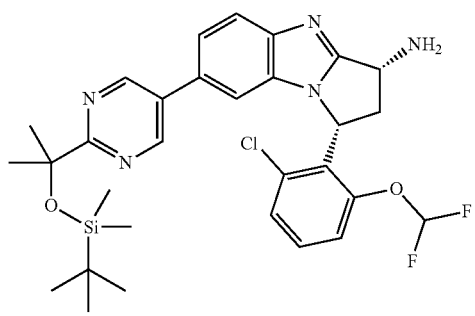 [SMILES: CC(C)(O[Si](C)(C)C(C)(C)C)c1ncc(-c2ccc3nc4n(c3c2)[C@@H](c2c(Cl)cccc2OC(F)F)C[C@H]4N)cn1]

Intermediate 22 was prepared from Intermediate 21 following the protocol described for intermediate 13, using toluene (34 mL), diphenylphosphoryl azide (5.0 mL, 24.22 mmol), 1,8-diazabicyclo[5.4.0]undec-7-ene (3.62 mL, 24.22 mmol) for the first step and tetrahydrofuran (172 mL), water (17 mL), 1 M solution of trimethylphosphine in toluene (34.6 mL, 20.8 mmol) for the second step.

The crude residue was purified by chromatography (SiO$_2$, 0-5% MeOH in DCM, 1% NH$_4$) to afford the title compound (7 g, 61% yield).

LCMS basic (ES$^+$) RT 3.49 min., 600.25/602.25 (M+H)$^+$

Intermediate 23

(7R,14R)-11-[2-(2-{[tert-butyl(dimethyl)silyl]oxy}propan-2-yl)pyrimidin-5-yl]-1-(difluoromethoxy)-6,7-dihydro-7,14-methanobenzimidazo[1,2-b][2,5]benzodiazocin-5(14H)-one

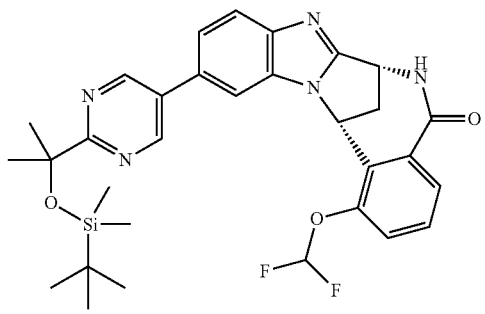 [SMILES: CC(C)(O[Si](C)(C)C(C)(C)C)c1ncc(-c2ccc3nc4n(c3c2)[C@@H]2C[C@H]4NC(=O)c3cccc(OC(F)F)c32)cn1]

Intermediate 23 was prepared from Intermediate 22 (7.00 g, 7.931 mmol) following the protocol described for Intermediate 14 using sodium carbonate (6.181 g, 58.31 mmol), dichloro bis(dicyclohexylphosphino)propane] palladium(II) [Pd-133 from Johnson Matthey] (1.43 g, 0.254 mmol), 1,4-dioxane (95 mL, 12 mL/mmol) and 5 atmosphere of CO gas.

The crude was purified by chromatography (SiO$_2$, 50-100% EtOAc in heptane) to afford the title compound (3.2 g, 62% yield) as a white solid.

$^1$H NMR (400 MHz, DMSO) δ 9.23 (d, J 6.8 Hz, 1H), 9.16 (s, 2H), 8.32 (dd, J 5.9, 3.5 Hz, 1H), 7.88 (dd, J 51.9, 43.2 Hz, 1H), 7.84 (s, 1H), 7.71 (dd, J 8.3, 1.8 Hz, 1H), 7.60 (m, 3H), 6.47 (d, J 7.1 Hz, 1H), 4.99 (t, J 6.8 Hz, 1H), 3.58 (m, 1H), 2.85 (d, J 13.4 Hz, 1H), 1.76 (s, 6H), 0.95 (s, 9H), 0.01 (s, 6H). LCMS basic (ES$^+$) RT 3.43 min., 592.27 (M+H)$^+$.

Intermediate 24

(7R,14R)-11-[2-(2-{[tert-butyl(dimethyl)silyl]oxy}propan-2-yl)pyrimidin-5-yl]-1-(difluoromethoxy)-6-methyl-6,7-dihydro-7,14-methanobenzimidazo[1,2-b][2,5]benzodiazocin-5(14H)-one

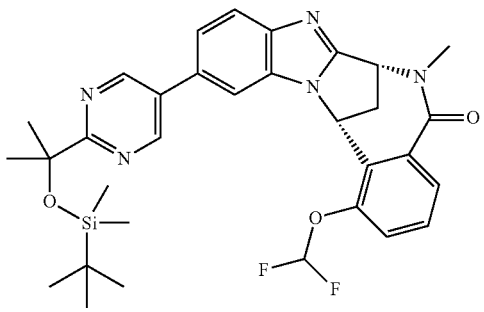 [SMILES: CN1C(=O)c2cccc(OC(F)F)c2[C@H]2C[C@@H]1c1nc3ccc(-c4cnc(C(C)(C)O[Si](C)(C)C(C)(C)C)nc4)cc3n12]

Intermediate 23 (1.0 g, 1.690 mmol) was dissolved in dry THF (10 mL/g) and tetrabutylammonium iodate (0.250 g, 0.676 mmol) was added. At 0° C., sodium hydride (60% in mineral oil) (0.081 g, 2.028 mmol) was added and the reaction mixture was stirred at r.t. for 35 minutes. Iodomethane (0.727 g, 5.070 mmol) was added and the reaction mixture was stirred at r.t. for 18 h. Distilled water (200 mL) was added, the mixture was extracted by of ethyl acetate (3×150 mL). Combined organic layers were dried over anhydrous magnesium sulfate and concentrated in vacuo. The residue was purified by chromatography (SiO$_2$, 50-100% EtOAc in heptane) to afford the title compound (0.868 g, 85% yield).

$^1$H NMR (400 MHz, CDCl$_3$) δ 8.95 (s, 2H), 8.54 (d, 8.2 Hz, 1H), 7.93 (d, J 8.5 Hz, 1H), 7.80 (s, 1H), 7.59 (d, J 8.5 Hz, 1H), 7.49 (t, J 8.2 Hz, 1H), 7.37 (d, J 8.2 Hz, 1H), 6.89 (t, J 72.5 Hz, 1H), 6.42 (d, J 6.9 Hz, 1H), 5.30 (d, J 6.7 Hz, 1H), 3.63 (m, 4H), 2.99 (d, J 13.6 Hz, 1H), 1.75 (s, 6H), 0.92 (s, 9H), 0.00 (s, 6H). LCMS basic (ES$^+$) RT 3.51 min., 606.25 (M+H)$^+$

Intermediate 25

(7R,14R)-11-[2-(2-{[tert-butyl(dimethyl)silyl]oxy}propan-2-yl)pyrimidin-5-yl]-1-(difluoromethoxy)-6-ethyl-6,7-dihydro-7,14-methanobenzimidazo[1,2-b][2,5]benzodiazocin-5(14H)-one

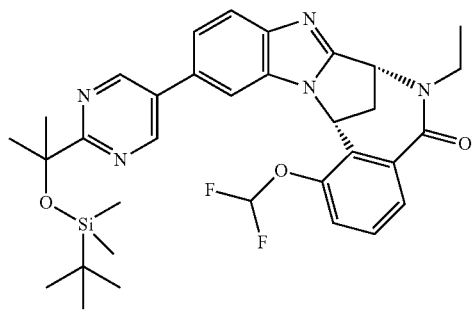 [SMILES: CCN1C(=O)c2cccc(OC(F)F)c2[C@H]2C[C@@H]1c1nc3ccc(-c4cnc(C(C)(C)O[Si](C)(C)C(C)(C)C)nc4)cc3n12]

Intermediate 23 (0.075 g, 0.127 mmol, 1 eq) was dissolved in dry THF (10 mL). At 0° C., sodium hydride (60% in mineral oil) (0.008 g, 0.190 mmol) was added and the reaction mixture was heated at 65° C. for 2.5 h, then was allowed to reach r.t. and iodoethane (0.059 g, 0.380 mmol) was added. The reaction mixture was then stirred at r.t. for 60 h. Additional Iodoethane (50 µL) was added and the reaction mixture was stirred at r.t. for 2 h. Distilled water (20 mL) was added, the mixture was extracted with 3×20 mL of ethyl acetate. Combined organic layers were dried over anhydrous magnesium sulfate and concentrated in vacuum. The residue was purified by chromatography (SiO$_2$, 50-100% EtOAc in heptane) to afford the title compound as a white solid (0.069 g, 88% yield).

LCMS basic (ES$^+$) RT 2.24 min. 506.23 (M+H)$^+$.

Intermediate 26

(7R,14R)-11-[2-(2-{[tert-butyl(dimethyl)silyl]oxy}propan-2-yl)pyrimidin-5-yl]-1-(difluoromethoxy)-6-(propan-2-yl)-6,7-dihydro-7,14-methanobenzimidazo[1,2-b][2,5]benzodiazocin-5(14H)-one

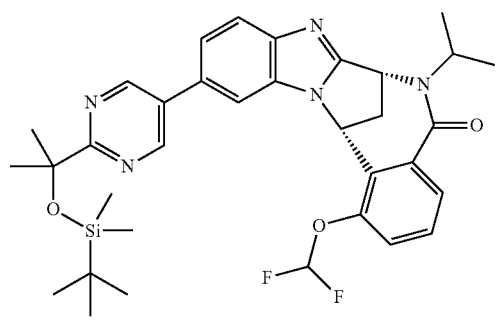 [SMILES: CC(C)N1C(=O)c2cccc(OC(F)F)c2[C@H]2C[C@@H]1c1nc3ccc(-c4cnc(C(C)(C)O[Si](C)(C)C(C)(C)C)nc4)cc3n12]

A solution of Intermediate 23 (25 mg, 0.0423 mmoL), potassium hydroxide (2.85 mg, 0.0507 mmoL), tetrabutylammonium bromide (12.26 mg, 0.0380 mmoL) and 2-iodopropane (14.36 mg, 0.0845 mmoL) in dry THF (0.8 mL) was stirred at r.t. for 24 h. The reaction mixture was quenched with water and extracted with ethyl acetate. The organic layer was washed with brine, dried over anhydrous magnesium sulphate and concentrated to dryness to afford the title compound (10 mg) which was used in the next step without further purification.

LCMS basic (ES$^+$) RT 3.60 min. 534.30 (M+H)$^+$.

Intermediate 27

(1R,3S)-1-[2-chloro-6-(difluoromethoxy)phenyl]-6-fluoro-7-[2-(1-hydroxy-1-methyl-ethyl)pyrimidin-5-yl]-2,3-dihydro-1H-pyrrolo[1,2-a]benzimidazol-3-ol

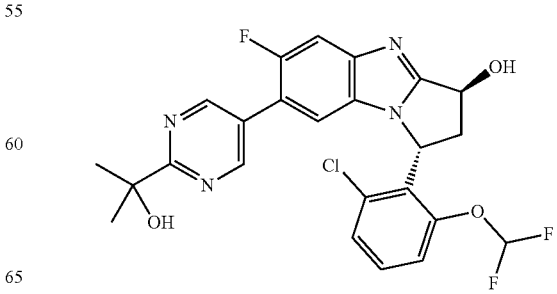

Intermediate 27 was prepared from Intermediate 20 (4.61 g, 10.30 mmol), following the protocol described for Intermediate 12, using 2-[5-(4,4,5,5-tetramethyl-1,3,2-dioxaborolan-2-yl)pyrimidin-2-yl]propan-2-ol (3.00 g, 11.330 mmol), cesium carbonate (5.03 g, 15.450 mmol), 1,4-dioxane (37.1 mL), water (3.7 mL), [1,1'-bis(diphenylphosphino)ferrocene]dichloropalladium(II) (376.8 mg, 0.5150 mmol). The crude was purified by chromatography (SiO$_2$, 30-100% EtOAc in heptane) to afford the title compound (3.6 g, 69%).

$^1$H NMR (400 MHz, CDCl$_3$) δ 8.77 (s, 1.2H), 8.73 (s, 0.8H), 7.59 (d, J=11.0 Hz, 1H), 7.37 (m, 2.8H), 7.23 (m, 0.6H), 6.99 (d, J=8.2 Hz, 0.6H), 6.84 (d, J=6.5 Hz, 0.6H), 6.74 (t, J=72.5 Hz, 0.6H), 6.70 (d, J=6.5 Hz, 0.4H), 6.51 (m, 1H), 6.02 (dd, J1=74.0 Hz, J2=71.0 Hz, 0.4H), 5.77 (dd, J1=7.8 Hz, J2=3.3 Hz, 0.6H), 5.68 (d, J=7.1 Hz, 0.4H), 4.60 (bs, 1H), 3.27 (m, 2H), 1.64 (s, 3.60H), 1.62 (s, 2.40). LCMS acid (ES$^+$)RT 1.91 min. 505.15/507.15 (M+H)$^+$.

Intermediate 28

Butyl 3-(difluoromethoxy)-2-[(1R,3 S)-6-fluoro-3-hydroxy-7-[2-(1-hydroxy-1-methyl-ethyl)pyrimidin-5-yl]-2,3-dihydro-1H-pyrrolo[1,2-a]benzimidazol-1-yl]benzoate

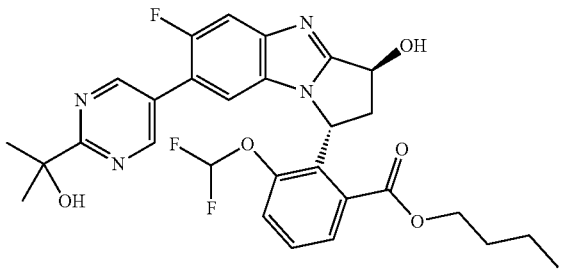 [SMILES: CCCCOC(=O)c1cccc(OC(F)F)c1[C@H]1C[C@H](O)c2nc3cc(F)c(-c4cnc(C(C)(C)O)nc4)cc3n21]

A solution of Intermediate 27 (900 mg, 1.783 mmoL), sodium carbonate (944 mg, 8.913 mmoL), dichloro [bis (dicyclohexylphosphino)propane] palladium(II) (54.7 mg, 0.08913 mmol) in 10 mL of 1-butanol was heated for 16 h at 150° C. under 4 atm of CO gas. The reaction mixture was concentrated in vacuo, the residue was taken up in 50 mL of ethyl acetate and washed with 3×20 mL of NaOH 0.1 M. The organic layer was dried over anhydrous sodium sulphate and concentrated in vacuo. The crude material was purified by chromatography (SiO$_2$, 80% EtOAc in hexane), to afford the title compound (490 mg, 48.2% yield).

LCMS acid (ES$^+$) RT 2.66 min. 571.25 (M+H)$^+$.

Intermediate 29

3-(difluoromethoxy)-2-[(1R,3S)-6-fluoro-3-hydroxy-7-[2-(1-hydroxy-1-methyl-ethyl)pyrimidin-5-yl]-2,3-dihydro-1H-pyrrolo[1,2-a]benzimidazol-1-yl]benzoic acid

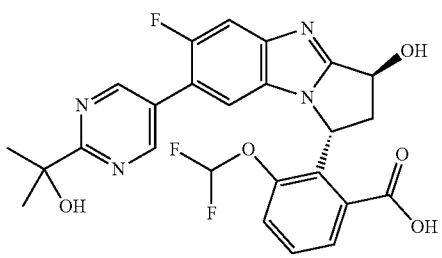 [SMILES: CC(C)(O)c1ncc(-c2cc3c(cc2F)nc2n3[C@@H](c3c(OC(F)F)cccc3C(=O)O)C[C@@H]2O)cn1]

Intermediate 28 (470 mg, 0.8237 mmoL) was dissolved in 4.7 mL of methanol. A 5 N solution of sodium hydroxide (0.3295 mL, 1.647 mmol) was added and the mixture was stirred at room temperature for 48 h. The reaction mixture was neutralized with HCl 1N and the solvent was evaporated. The aqueous phase was extracted with ethyl acetate (3×25 mL), the combined organic layers were dried over magnesium sulphate and concentrated in vacuo to afford crude 511 mg of the title compound used without further purification.

LCMS acid (ES$^+$) RT 2.05 min., 515.17 (M+H)$^+$.

Intermediate 30

Ethyl 6-bromoimidazo[1,2-a]pyridine-2-carboxylate

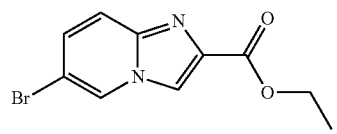

The title compound was prepared according to the procedure provided in international patent application WO 2014/009295.

Intermediate 31

3-(6-bromo-2-ethoxycarbonyl-imidazo[1,2-a]pyridin-3-yl)-3-(2-chlorophenyl)propanoic acid

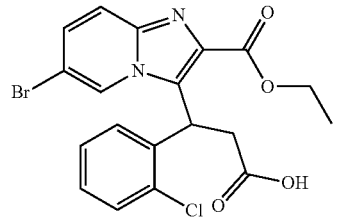 [SMILES: CCOC(=O)c1nc2ccc(Br)cn2c1C(CC(=O)O)c1ccccc1Cl]

Intermediate 30 (8 g, 29.73 mmol), 2-chlorobenzaldehyde (6.7 ml, 59.58 mmol), 2,2-dimethyl-1,3-dioxane-4,6-dione (8.6 g, 59.67 mmol), L-proline (170 mg, 1.48 mmol) and MgSO$_4$ (11 g, 91.39 mmol) in acetonitrile (80 mL) was heated at 90° C. for 33 h, followed by 100° C. 15 h. The reaction cooled to r.t., and the solid filtered off, and washed with methanol (2×50 mL). The filtrate was concentrated in vacuo and triturated with diethyl ether (50 mL) and sonicated for 10 min and resulting gum was filtered off and rinsed with diethyl ether (2×50 mL) yielding the title compound as beige solid (10.2 g, 76%). $^1$H NMR (500 MHz, Methanol-d$_4$) δ 8.79 (s, 1H), 7.74 (d, J 7.7 Hz, 1H), 7.67-7.55 (m, 2H), 7.43-7.34 (m, 2H), 7.34-7.20 (m, 1H), 5.56 (dd, J 9.5, 6.0 Hz, 1H), 4.35 (qt, J 7.4, 3.7 Hz, 2H), 3.70 (dd, J 16.7, 9.5 Hz, 1H), 3.40 (dd, J 16.7, 6.0 Hz, 1H), 1.34 (t, J 7.1 Hz, 3H). LCMS (ES$^+$) RT 1.24 min, 451.0/453.0 (M+H)$^+$.

Intermediate 32

Ethyl 6-bromo-3-[1-(2-chlorophenyl)-3-ethoxy-3-oxo-propyl]imidazo[1,2-a]pyridine-2-carboxylate

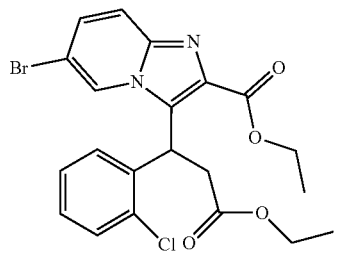 [SMILES: CCOC(=O)CC(c1ccccc1Cl)c1c(C(=O)OCC)nc2ccc(Br)cn12]

Thionyl chloride (4 ml, 55.14 mmol) was added to the stirred solution of Intermediate 31 (10.2 g, 20.1 mmol) in EtOH (100 mL) at 0° C. The reaction mixture warmed to r.t. and stirred for 20 h. The reaction mixture was concentrated in vacuo and resulting residue was triturated with EtOAc (100 mL) and washed with sat. NaHCO$_3$ (100 mL) and further extracted with EtOAc (2×50 mL). The combined organic layers were washed with water (50 mL), brine (50 mL), dried over sodium sulfate, filtered and concentrated in vacuo. The residue was purified by chromatography (SiO$_2$, 0-100% EtOAc in heptane) yielding the title compound as an orange gum (8.2 g, 85%). $^1$H NMR (500 MHz, CDCl$_3$) δ 8.40 (s, 1H), 7.65 (dd, J 7.8, 1.5 Hz, 1H), 7.55 (d, J 9.5 Hz, 1H), 7.34 (dd, J 7.9, 1.4 Hz, 1H), 7.28 (dd, J 9.5, 1.8 Hz, 1H), 7.27-7.23 (m, 1H), 7.20 (td, J 7.6, 1.6 Hz, 1H), 5.44 (dd, J 9.8, 5.6 Hz, 1H), 4.42 (q, J 7.1 Hz, 2H), 4.09-3.94 (m, 2H), 3.82 (dd, J 16.6, 9.9 Hz, 1H), 3.26 (dd, J 16.6, 5.5 Hz, 1H), 1.40 (t, J 7.1 Hz, 3H), 1.12 (t, J 7.1 Hz, 3H). LCMS (ES$^+$) RT 1.44 min, 479.0/481.0 (M+H)$^+$.

Intermediate 33

Ethyl 7-bromo-1-(2-chlorophenyl)-3-oxo-2,3-dihydro-1H-cyclopenta[4,5]imidazo[1,2-a]pyridine-2-carboxylate

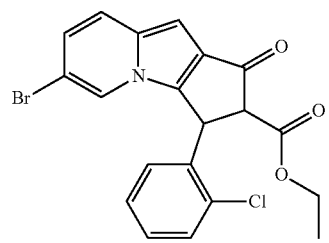 [SMILES: CCOC(=O)C1C(=O)c2cc3ccc(Br)cn3c2C1c1ccccc1Cl]

Intermediate 32 (4 g, 8.34 mmol) was co-evaporated twice with toluene (50 mL) and the residue dissolved in dry toluene (400 mL) and degassed with N$_2$(g) for 5 min. The mixture was cooled to −10° C. (external temp) and a 25% w/w solution of potassium 2-methylbutan-2-olate in toluene (7.5 mL, 13.37 mmol) was then added drop wise and stirred for 30 min at −10° C. The reaction mixture was quenched with acetic acid (2 mL) and diluted with water (200 mL), extracted with EtOAc (2×200 mL). The combined organic layer was washed with sat. aq. sodium bicarbonate (100 mL), brine (100 mL), dried over sodium sulfate, filtered and concentrated in vacuo yielding the title compound as a pale yellow solid (3.3 g, 82%). $^1$H NMR (500 MHz, CDCl$_3$) δ 7.77 (s, 1H), 7.65 (d, J 9.8 Hz, 1H), 7.52 (d, J 6.7 Hz, 1H), 7.40 (dd, J 9.8, 1.5 Hz, 1H), 7.32 (t, J 8.3 Hz, 1H), 7.25-7.15 (m, 1H), 6.67 (s, 1H), 5.59 (s, 1H), 4.30 (q, J 7.1 Hz, 2H), 3.89 (s, 1H), 1.33 (t, J 7.1 Hz, 3H). LCMS (ES$^+$) RT 1.35 min, 433.0/435.0 (M+H)$^+$.

Intermediate 34

7-bromo-1-(2-chlorophenyl)-1,2-dihydro-3H-cyclopenta[4,5]imidazo[1,2-a]pyridin-3-one

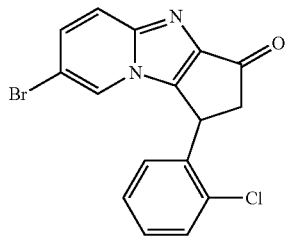 [SMILES: O=C1CC(c2ccccc2Cl)c2c1nc1ccc(Br)cn21]

Intermediate 33 (3.2 g, 6.64 mmol) was dissolved in DMSO (50 mL) and water (10 mL) then heated at 100° C. for 48 h. The reaction was cooled to r.t. and poured on to ice and left to stand for 1 h. The resulting residue was filtered off and washed with water yielding the title compound as a pale yellow solid (2.5 g, 99%). $^1$H NMR (500 MHz, CDCl$_3$) δ 7.81 (s, 1H), 7.65 (dd, J 9.8, 0.8 Hz, 1H), 7.52 (d, J 8.0 Hz, 1H), 7.38 (dd, J 9.8, 1.8 Hz, 1H), 7.29 (td, J 7.8, 1.6 Hz, 1H), 7.21 (t, J 7.4 Hz, 1H), 6.77 (s, 1H), 5.22 (s, 1H), 3.73 (dd, J 18.4, 7.1 Hz, 1H), 2.92 (d, J 19.0 Hz, 1H). LCMS (ES$^+$) RT 1.27 min, 361.0/363.0 (M+H)$^+$.

Intermediate 35

1-(2-chlorophenyl)-7-[2-(2-hydroxypropan-2-yl)pyrimidin-5-yl]-1,2-dihydro-3H-cyclopenta[4,5]imidazo[1,2-a]pyridin-3-one

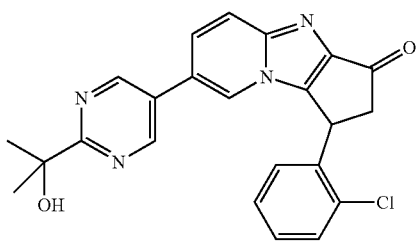 [SMILES: CC(C)(O)c1ncc(-c2ccc3nc4c(n3c2)C(c2ccccc2Cl)CC4=O)cn1]

Intermediate 34 (1 g, 2.65 mmol), 2-[5-(tetramethyl-1,3,2-dioxaborolan-2-yl)pyrimidin-2-yl]propan-2-ol (0.84 g, 3.19 mmol) were dissolved in dioxane (40 mL) then 2M disodium carbonate (4 mL) was added and the mixture was degassed with N$_2$ for 5 min. Bis[3-(diphenylphosphanyl)cyclopenta-2,4-dien-1-yl]iron; dichloromethane; dichloropalladium (108 mg, 0.13 mmol) was added and the reaction was heated to 80° C. for 1.5 hours. The reaction mixture was then cooled to r.t. and diluted with water (50 mL) and extracted with EtOAc (3×50 mL). The combined organic layers were washed with brine (50 mL), dried over sodium sulfate, filtered, concentrated in vacuo. The residue was purified by chromatography, (SiO$_2$, 10-100% EtOAc in heptane) yielding the title compound as a light brown solid (1.1 g, 96%). $^1$H NMR (500 MHz, CDCl$_3$) δ 8.81 (s, 2H), 7.91 (d, J 9.6 Hz, 1H), 7.87 (s, 1H), 7.53 (dd, J 9.5, 1.6 Hz, 2H), 7.29 (td, J 7.8, 1.5 Hz, 1H), 7.21 (t, J 7.4 Hz, 1H), 6.84 (s, 1H), 5.31 (s, 1H), 4.45 (s, 1H), 3.77 (dd, J 18.3, 7.0 Hz, 1H), 2.99 (d, J 18.9 Hz, 1H), 1.63 (s, 6H). LCMS (ES$^+$) RT 1.14 min, 419.0/421.0 (M+H)$^+$.

Intermediate 36

2-{5-[(1-(2-chlorophenyl)-3-(methoxyimino)-2,3-dihydro-1H-cyclopenta[4,5]imidazo[1,2-a]pyridin-7-yl]pyrimidin-2-yl}propan-2-ol

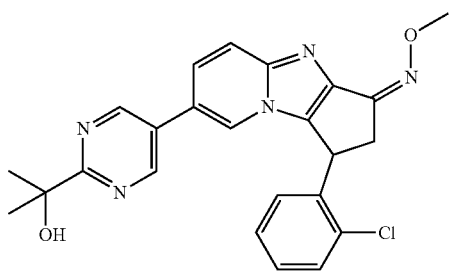 [SMILES: CO/N=C1/CC(c2ccccc2Cl)c2c1nc1ccc(-c3cnc(C(C)(C)O)nc3)cn21]

Intermediate 35 (500 mg, 1.11 mmol), O-methylhydroxylamine hydrochloride (185 mg, 2.22 mmol) and sodium acetate (182 mg, 2.22 mmol) in ethanol (20 mL) were heated at 85° C. for 6 h. The reaction mixture was cooled to r.t., concentrated in vacuo then diluted with sat. aq. sodium bicarbonate (50 mL) and extracted with EtOAc (3×50 mL). The combined organic layers were washed with brine (25 mL), dried over sodium sulfate, filtered, concentrated in vacuo yielding the title compound as beige solid (500 mg, 95%).

$^1$H NMR (500 MHz, CDCl$_3$) δ 8.80 (d, J 1.1 Hz, 2H), 7.98-7.73 (m, 2H), 7.54-7.36 (m, 2H), 7.26 (s, 2H), 6.94-6.64 (m, 1H), 5.31-5.09 (m, 1H), 4.48 (d, J 9.5 Hz, 1H), 4.07 (d, J 53.7 Hz, 3H), 3.97 (dd, J 18.2, 7.9 Hz, 1H), 3.23-3.10 (m, 1H), 1.56 (s, 6H).

LCMS (ES$^+$) RT 1.17 and 1.29 min, 448.0/450.0 (M+H)$^+$.

Intermediate 37

2-{5-[3-amino-1-(2-chlorophenyl)-2,3-dihydro-1H-cyclopenta[4,5]imidazo[1,2-a]pyridin-7-yl]pyrimidin-2-yl}propan-2-ol

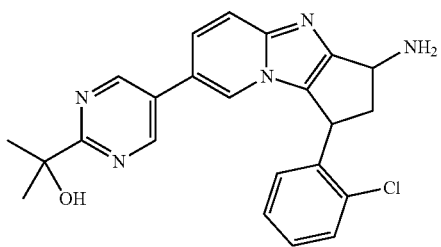 [SMILES: CC(C)(O)c1ncc(-c2ccc3nc4c(n3c2)C(c2ccccc2Cl)CC4N)cn1]

A solution of Intermediate 36 (500 mg, 1.12 mmol), 7M ammonia in MeOH (0.64 mL) in methanol (50 mL) was passed over a Raney Nickel cartridge at a flow-rate of 1 ml/min, 60 bar hydrogen pressure at 80° C. in a H-Cube® continuous-flow hydrogenation reactor. This process was repeated three times and mixture was concentrated in vacuo. The residue was purified by preparative HPLC yielding the title compound as an off white solid (300 mg, 64%). A 1.6:1 cis/trans mixture of distereosiomers was isolated. $^1$H NMR, cis diastereoisomer, (500 MHz, CDCl$_3$) δ 8.78 (s, 2H), 7.74 (d, J20.0 Hz, 2H), 7.51-7.44 (m, 1H), 7.40-7.33 (m, 1H), 7.24-7.17 (m, 2H), 7.14 (t, J 7.5 Hz, 1H), 7.00 (dd, J 7.6, 1.6 Hz, 1H), 4.96 (dd, J 8.1, 6.0 Hz, 1H), 4.59 (dd, J 7.4, 5.7 Hz, 3H), 3.69 (dt, J 13.5, 8.1 Hz, 1H), 2.11 (dt, J 13.4, 5.6 Hz, 1H), 1.61 (s, 6H). LCMS (ES$^+$) RT 1.60 min (cis) and 1.65 min (trans), 420.0/422.0 (M+H)$^+$.

Intermediate 38

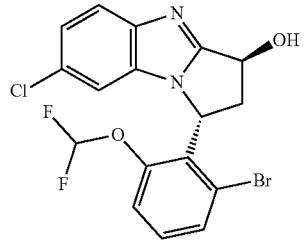 [SMILES: O[C@H]1C[C@H](c2c(Br)cccc2OC(F)F)n2c1nc1ccc(Cl)cc12]

(1R,3S)-7-chloro-1-[2-bromo-6-(difluoromethoxy)phenyl]-2,3-dihydro-1H-pyrrolo[1,2-a]benzimidazol-3-ol The title compound was prepared in a sequence of steps analogous to those described for Intermediate 10 starting from 2-bromo-6-hydroxy-benzaldehyde and utilising 4-chloro-2-fluoro-nitrobenzene instead of 1-bromo-2,5-difluoro-4-nitrobenzene in the fifth synthetic step.

Intermediate 39

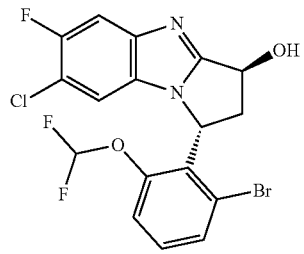 [SMILES: O[C@H]1C[C@H](c2c(Br)cccc2OC(F)F)n2c1nc1cc(F)c(Cl)cc12]

(1R,3S)-7-chloro-1-[2-bromo-6-(difluoromethoxy)phenyl]-6-fluoro-2,3-dihydro-1H-pyrrolo[1,2-a]benzimidazol-3-ol The title compound was prepared in a sequence of steps analogous to those described for Intermediate 10 starting from 2-bromo-6-hydroxy-benzaldehyde and utilising 1-chloro-2,5-difluoro-4-nitrobenzene, instead of 1-bromo-2,5-difluoro-4-nitrobenzene in the fifth synthetic step.

Intermediate 40

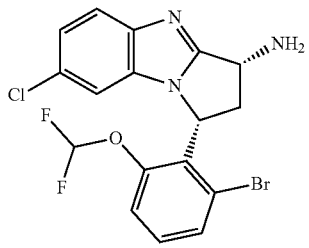 [SMILES: N[C@@H]1C[C@H](c2c(Br)cccc2OC(F)F)n2c1nc1ccc(Cl)cc12]

(1R,3R)-1-[2-bromo-6-(difluoromethoxy)phenyl]-7-chloro-2,3-dihydro-1H-pyrrolo[1,2-a]benzimidazol-3-amine Intermediate 38 (5 g, 11.64 mmol) was suspended in toluene (22 mL) and cooled to 0° C. before addition of diphenylphosphoryl azide (3.4 mL, 15 mmol) and 1,8-diazabicyclo[5.4.0]undec-7-ene (2.5 mL, 16 mmol). The mixture was allowed to warm up to r.t and stirred for 2 hours and subsequently at 45° C. overnight. The reaction mixture was diluted with EtOAc (150 mL) and the organic phase washed with a saturated aqueous solution of ammonium chloride (50 mL) then a saturated solution of aqueous sodium bicarbonate (50 mL), and concentrated in vacuo. The crude residue thus obtained was solubilized in THF (100 mL) and water (10 mL), trimethylphosphine (17.46 mL, 17.46 mmol) was added and the reaction mixture stirred overnight. The mixture was concentrated in vacuo, partitioned between EtOAc (200 mL) and water (150 mL). The organic layer was extracted with 0.2M HCl aq (3×200 mL). The combined acid layer was stirred in an ice bath, whilst 10% NaOH solution was added with stirring until pH increased to 10. The stirred was continued for further 15 minutes to complete precipitation. The precipitate was filtered, rinsed with water (20 mL), then dried under suction for 10 minutes before drying under high vacuum overnight to afford 3.92 g (78%) of the title compound as an off white solid. LCMS basic: RT 1.96 min. (ES+) 428/430 (M+H)+

Intermediate 41

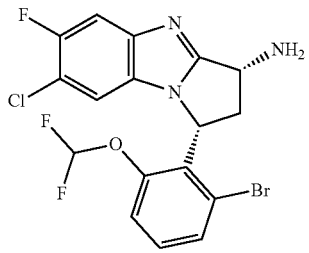 [SMILES: N[C@@H]1C[C@H](c2c(Br)cccc2OC(F)F)n2c1nc1cc(F)c(Cl)cc12]

(1R,3R)-1-[2-bromo-6-(difluoromethoxy)phenyl]-7-chloro-6-fluoro-2,3-dihydro-1H-pyrrolo[1,2-a]benzimidazol-3-amine The title compound was prepared from Intermediate 39 using the experimental protocol described for the preparation of Intermediate 40. The crude material was purified by column chromatography over silica gel using EtOAc/MeOH (100/0 to 70/30) as eluent, yielding 15 g (83%) of the title compound as an amorphous solid. LCMS basic: RT 2.04 min. (ES+) 446/448 (M+H)+.

Intermediate 42

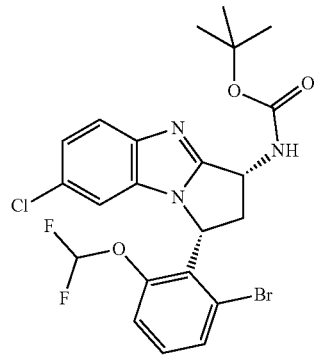 [SMILES: CC(C)(C)OC(=O)N[C@@H]1C[C@H](c2c(Br)cccc2OC(F)F)n2c1nc1ccc(Cl)cc12]

tert-butyl {(1R,3R)-1-[2-bromo-6-(difluoromethoxy)phenyl]-7-chloro-2,3-dihydro-1H-pyrrolo[1,2-a]benzimidazol-3-yl}carbamate To a solution of Intermediate 40 (700 mg, 2 mmol) in DCM (10 mL), at 0° C., was added dropwise triethylamine (500 µL, 4 mmol) and di-tert-butyl dicarbonate (400 mg, 2 mmol) portionwise. The reaction was stirred at 0° C. for 1 hour and at r.t overnight. The reaction mixture was poured into ice-water (20 mL) and the aqueous layer was extracted by DCM (3×10 mL). The combined organic layers were dried over $Na_2SO_4$, filtered and concentrated in vacuo. The residue was purified by column chromatography over silica gel (heptane/EtOAc 2/8), yielding 626 mg (70%) of the title compound. LCMS basic (ES+) RT 2.92 min., 528.0/530.0 (M+H)+

Intermediate 43

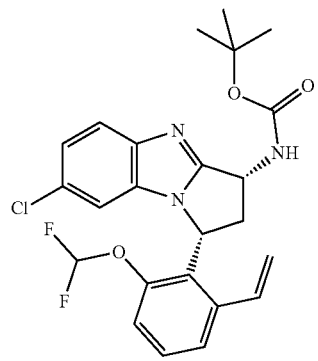 [SMILES: C=Cc1cccc(OC(F)F)c1[C@H]1C[C@@H](NC(=O)OC(C)(C)C)c2nc3ccc(Cl)cc3n21]

tert-butyl {(1R,3R)-7-chloro-1-[2-(difluoromethoxy)-6-ethenylphenyl]-2,3-dihydro-1H-pyrrolo[1,2-a]benzimidazol-3-yl}carbamate Intermediate 42 (250 mg, 0.473 mmol), potassium vinyltrifluoroborate (92.3 mg, 0.662 mmol), cesium carbonate (308 mg, 0.944 mmol), and 1,1'-bis(diphenylphosphino)ferrocene-palladium(II)dichloride dichloromethane complex (19.3 mg, 0.0236 mmol) were placed in a tube, and filled with argon. Degassed 1,4 dioxane (5 mL) and water (0.5 mL) were added and the resulting slurry was stirred at 110° C. overnight. The reaction mixture was cooled to ambient temperature, filtered and concentrated in vacuo. The crude material was purified by preparative reverse phase HPLC (basic conditions) to afford 175 mg (78%) of the title compound. LCMS basic (ES+) RT 2.91 min., 476/478(M+H)+.

Intermediate 44

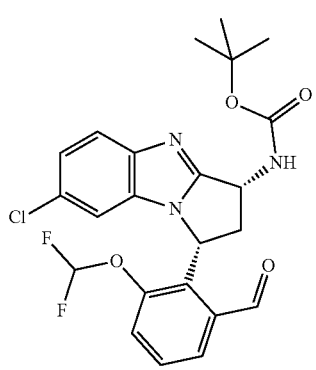 [SMILES: CC(C)(C)OC(=O)N[C@@H]1C[C@H](c2c(C=O)cccc2OC(F)F)n2c1nc1ccc(Cl)cc12]

tert-butyl {(1R,3R)-7-chloro-1-[2-(difluoromethoxy)-6-formylphenyl]-2,3-dihydro-1H-pyrrolo[1,2-a]benzimidazol-3-yl}carbamate Intermediate 43 (25 mg, 0.0526 mmol) was dissolved in 1,4 dioxane (0.4 mL) and water (0.1 mL). At 0° C., sodium periodate (34 mg, 0.158 mmol) followed by osmium tetroxide (26 µl, 0.0021 mmol) were added. The reaction mixture was allowed to warm to r.t and stirred overnight. The reaction was then diluted with EtOAc (2 mL) and water (2 mL). The aqueous layer was extracted with EtOAc (2×2 mL). The combined organic layers were washed with a saturated solution of sodium thiosulfate (2 mL), brine, dried over magnesium sulphate, filtered and concentrated under vacuum to afford the title compound which was used without further purification. LCMS basic (ES+) RT 2.65 min., 478/480(M+H)+

Intermediate 45

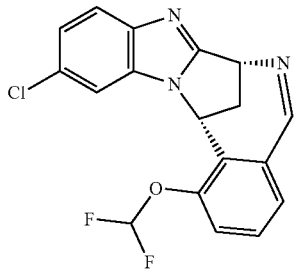 [SMILES: FC(F)Oc1cccc2c1[C@H]1C[C@@H](N=C2)c2nc3ccc(Cl)cc3n21]

(7R,14R)-11-chloro-1-(difluoromethoxy)-7,14-dihydro-7,14-methanobenzimidazo[1,2-b][2,5]benzodiazocine Intermediate 44 (0.0525 mmol) was dissolved in DCM/TFA (1/1). The reaction mixture was stirred at r.t for one hour. The reaction mixture was then concentrated under reduced pressure to afford the title compound as a TFA salt which was used without further purification. LCMS basic (ES+) RT 2.29 min., 360/362 (M+H)+

Intermediate 46

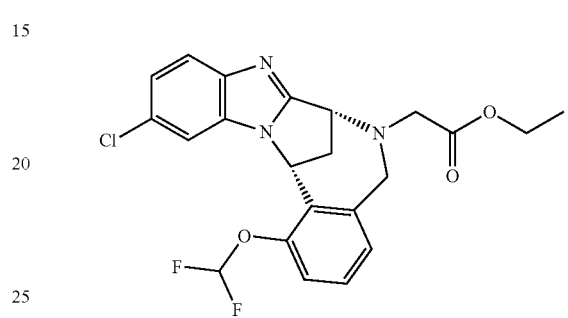

Ethyl [(7R,14R)-11-chloro-1-(difluoromethoxy)-5,14-dihydro-7,14-methanobenzimidazo[1,2-b][2,5]benzodiazocin-6(7H)-yl]acetate Example 12 (120 mg, 0.332 mmol) was dissolved in DMF (1 mL). Potassium carbonate (2 equiv., 0.663 mmol) and ethyl bromoacetate (1.2 equiv., 0.398 mmol) were added and the reaction mixture was stirred at r.t for 1 hour.

The mixture was filtered, rinsed with EtOAc and the volatiles removed in vacuo. The residue was taken up with EtOAc, washed with water, dried over magnesium sulphate, filtered and concentrated in vacuo. The crude compound was purified by reverse phase chromatography to afford 34 mg (23%) of the title compound. LCMS (ES+) 448/450 (M+H)+

Intermediate 47

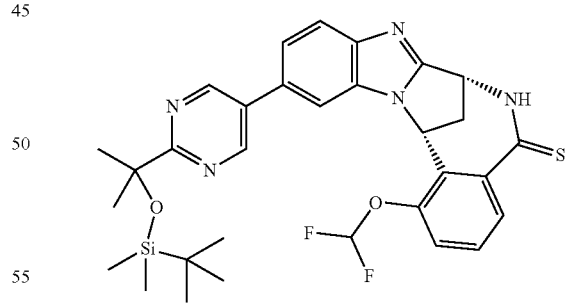

(7R,14R)-11-[2-(2-{[tert-butyl(dimethyl)silyl]oxy}propan-2-yl)pyrimidin-5-yl]-1-(difluoromethoxy)-6,7-dihydro-7,14-methanobenzimidazo[1,2-b][2,5]benzodiazocine-5(14H)-thione Intermediate 23 (150 mg, 0.254 mmol) was solubilized in toluene (6 mL) before addition of Lawessons reagent (114 mg, 0.28 mmol). The slurry was heated overnight at 120° C. The reaction mixture was concentrated in vacuo, and the residue taken up in DCM and filtered through a pad of silica gel eluting with DCM/MeOH (1/1) to afford 195 mg of the title compound as a brown solid used without further purification. LCMS acidic (ES+) RT 3.74 min. 608(M+H)+.

Intermediate 49

(S)—N-[(1Z)-(2-Chloro-6-methoxyphenyl)methylidene]-2-methylpropane-2-sulfinamide To a cooled (0° C.) solution of 2-chloro-6-methoxybenzaldehyde (15 g, 87.93 mmol) in tetrahydrofuran (180 mL) was added sequentially (S)-2-methylpropane-2-sulfinamide (11.7 g, 96.7 mmol), tripotassium phosphate (56 g, 264 mmol) and dipotassium hydrogen phosphate (46 g, 263.8 mmol). The cooling bath was removed and the resultant suspension was stirred at r.t. for 18 hours. The reaction mixture was filtered through a pad of celite. The filtrate was diluted with EtOAc (250 mL), washed with brine (200 mL), dried over sodium sulfate, filtered and concentrated in vacuo to a crude residue. The crude material was purified by flash column chromatography (0-50% EtOAc/heptanes) to afford 22.7 g (94%) of the title compound as a pale yellow solid. LCMS Method 6 (ES+) RT 1.61 min., 274.1 (M+H)+. $^1$H NMR (500 MHz, Chloroform-d) δ 8.95 (m, 1H), 7.33 (t, J=8.3 Hz, 1H), 7.07 (dd, J=8.1, 0.8 Hz, 1H), 6.95-6.84 (m, 1H), 3.88 (s, 3H), 1.29 (s, 9H).

Intermediate 50

(S)—N-[(1R)-1-(2-chloro-6-methoxyphenyl)but-3-en-1-yl]-2-methylpropane-2-sulfinamide To a suspension of zinc powder (27.9 g, 426.5 mmol) in anhydrous THF (100 mL) was added 1,2-dibromoethane (620 μL, 7.19 mmol) and the mixture heated to 70° C. After 10 minutes at this temperature, the heating was switched off and the reaction stirred for a further 30 minutes (internal temperature ca. 50° C.) and allowed to cool slowly to r.t. over 20 minutes. Chloro(trimethyl)silane (910 μL, 7.17 mmol) was then added dropwise. Effervescence and an exotherm to ~40° C. was observed, along with coagulation of the zinc. The reaction was heated to 50° C. for 10 min then allowed to cool to r.t. 3-Bromoprop-1-ene (18.5 mL, 213.8 mmol) was then added drop-wise at r.t. An exotherm to ~50° C. was observed during addition and the addition rate controlled to maintain the exotherm. After completion of addition, the resultant grey suspension was heated to 70° C. for 15 minutes, then cooled first to r.t. over 30 min, then to −40° C. Anhydrous THF (350 ml) was added, then a pre-cooled solution of Intermediate 49 (19.5 g, 71.1 mmol) in dry THF (100 mL) was added dropwise whilst maintaining an internal reaction temperature of between −35 and −40° C., then the resultant mixture stirred at −40° C. for 1 hour. The reaction was allowed to warm to r.t., decanted and filtered through a sinter funnel to remove excess zinc. The solids were washed with THF (2×80 mL). The filtrate was poured into saturated aqueous ammonium chloride solution (500 mL) and shaken well, then extracted with EtOAc (2×500 mL). The combined organic layers were washed with brine (500 mL), dried over sodium sulfate, filtered and concentrated in vacuo to afford ~56 g crude yellow oil. This material was purified by reverse-phase flash column chromatography (elution 0-100% MeCN (+0.1% NH$_4$OH)/H$_2$O (+0.1% NH$_4$OH)). The clean fractions were extracted with EtOAc (2×3 L). The combined organics were dried over sodium sulfate, filtered and concentrated to dryness under vacuum to yield 16.8 g (74%) of the title compound as colourless viscous oil. LCMS Method 6 (ES+) RT 1.63 min., 316.1 (M+H)+. $^1$H NMR (250 MHz, Chloroform-d) δ 7.14 (t, J=8.2 Hz, 1H), 6.97 (dd, J=8.1, 0.9 Hz, 1H), 6.87-6.72 (m, 1H), 5.70 (ddt, J=17.1, 10.1, 7.2 Hz, 1H), 5.26-4.91 (m, 2H), 4.53 (s, 1H), 3.86 (s, 3H), 2.81 (dtt, J=21.4, 13.8, 7.6 Hz, 2H), 1.10 (s, 9H).

Intermediate 51

(1R)-1-(2-chloro-6-methoxyphenyl)but-3-en-1-amine

Intermediate 50 (12.7 g, 40.21 mmol) was dissolved in diethyl ether (40 mL) and ethanol (20 mL) then 4M hydrogen chloride in 1,4-dioxane (31 mL) was added and the reaction mixture was stirred for 45 minutes. The reaction mixture was partitioned between water (150 mL) and diethyl ether (150 mL). The organic layer was re-extracted with 1M aq HCl solution (150 mL). The aqueous layers were combined, basified to pH 10 by addition of 6M aq NaOH solution and extracted with EtOAc (2×200 mL). The combined organic layers were dried over Na$_2$SO$_4$ and concentrated to dryness under vacuum to yield 9.19 g (97%) of the title compound as a pale yellow viscous oil. LCMS Method 6 (ES+) RT 1.49 min., 212.3 (M+H)+. $^1$H NMR (500 MHz, Chloroform-d) δ 7.10 (t, J=8.2 Hz, 1H), 6.96 (dd, J=8.1, 0.9 Hz, 1H), 6.79 (d, J=8.2 Hz, 1H), 5.77 (ddt, J=17.2, 10.2, 7.2 Hz, 1H), 5.11-4.92 (m, 2H), 4.56 (t, J=7.6 Hz, 1H), 3.86 (s, 3H), 2.61 (hept, J=7.3, 6.9 Hz, 2H).

Intermediate 52 tert-butyl-[1-[5-(2,5-difluoro-4-nitro-phenyl)pyrimidin-2-yl]-1-methyl-ethoxy]-dimethyl-silane The title compound can be prepared from Intermediate 11 and 1-bromo-2,5-difluoro-4-nitro-benzene by a palladium catalyzed Suzuki coupling following an analogous method to that described for Intermediate 12.

Intermediate 53

5-(2-{2-[(tert-butyldimethylsilyl)oxy]propan-2-yl}pyrimidin-5-yl)-N-[(1R)-1-(2-chloro-6-methoxyphenyl)but-3-en-1-yl]-4-fluoro-2-nitroaniline Intermediate 51 (2.51 g, 10.67 mmol) and Intermediate 52 7 (4.96 g, 10.9 mmol) were dissolved in acetonitrile (40 mL) and K$_2$CO$_3$ (4.4 g, 31.84 mmol) was added. The reaction mixture was stirred at 80° C. overnight. The reaction mixture was diluted with EtOAc (100 mL) and washed with water (2×75 mL), then brine (75 mL), dried (Na$_2$SO$_4$) and concentrated to dryness under vacuum to yield 7 g (98%) of the title compound as an orange gum. LCMS Method 6 (ES+) RT 2.64 min., 601.1 (M+H)+. $^1$H NMR (500 MHz, Chloroform-d) δ 8.94-8.74 (m, 3H), 7.99 (d, J=10.7 Hz, 1H), 7.18 (t, J=8.2 Hz, 1H), 7.00 (d, J=7.9 Hz, 2H), 6.83 (d, J=8.2 Hz, 1H), 5.80 (ddt, J=17.2, 10.1, 7.1 Hz, 1H), 5.48-5.25 (m, 1H), 5.16 (d, J=16.8 Hz, 1H), 5.07 (d, J=10.0 Hz, 1H), 3.88 (s, 3H), 3.04-2.86 (m, 1H), 2.79 (dt, J=13.3, 6.5 Hz, 1H), 1.70 (d, J=4.4 Hz, 6H), 0.90 (s, 9H), −0.02 (s, 6H).

Intermediate 54

(3R)-3-{[5-(2-{2-[(tert-butyldimethylsilyl)oxy]propan-2-yl}pyrimidin-5-yl)-4-fluoro-2-nitrophenyl]amino}-3-(2-chloro-6-methoxyphenyl)propanal Potassium dioxido(dioxo)osmium hydrate (2:1:2) (75 mg, 0.2 mmol) was added in one portion to a stirred solution of Intermediate 53 (6.85 g, 10.25 mmol), sodium periodate (13.1 g, 61.25 mmol) and 2,6-dimethylpyridine (2.4 mL, 20.67 mmol) in a 3:1 mixture of 1,4-dioxane and water (240 mL). The mixture was stirred overnight then sodium thiosulfate (11.3 g, 71.47 mmol) was added and the resulting mixture was stirred for 30 minutes before diluting with DCM (200 mL) and water (200 mL). The biphasic mixture was stirred for a further 15 minutes then the two layers were separated and the aqueous layer was re-extracted with DCM (2×100 mL). The combined organic extracts were dried over $Na_2SO_4$, filtered and concentrated in vacuo to yield 8.5 g of the title compound as an orange gum. LCMS Method 6 (ES+) RT 2.74 min., 603.1 (M+H)+. 1H NMR (250 MHz, Chloroform-d) δ 9.81 (s, 1H), 8.87 (d, J=1.6 Hz, 2H), 8.24-8.07 (m, 1H), 7.99 (d, J=10.7 Hz, 1H), 7.19 (d, J=8.2 Hz, 1H), 7.02 (dd, J=8.1, 1.0 Hz, 1H), 6.86 (d, J=8.2 Hz, 1H), 6.03 (td, J=9.3, 5.0 Hz, 1H), 5.62-5.45 (m, 1H), 3.94 (s, 3H), 3.53 (ddd, J=17.6, 8.9, 1.6 Hz, 1H), 3.01 (dd, J=17.8, 4.8 Hz, 1H), 1.71 (s, 6H), 0.91 (s, 9H), −0.01 (s, 6H).

Intermediate 55

(R)—N-[(1Z,3R)-3-{[5-(2-{2-[(tert-butyldimethylsilyl)oxy]propan-2-yl}pyrimidin-5-yl)-4-fluoro-2-nitrophenyl]amino}-3-(2-chloro-6-methoxyphenyl)propylidene]-2-methylpropane-2-sulfinamide To a solution of Intermediate 54 (8.5 g, 10.29 mmol) and (R)-2-methylpropane-2-sulfinamide (1.25 g, 10.3 mmol) in DCM (50 mL) was added dropwise titanium (4+) tetrapropan-2-olate (6.1 mL, 20.6 mmol) and the reaction mixture was stirred at 40° C. under nitrogen for 3 hours and 20 minutes. The reaction was diluted with DCM (100 mL) then quenched by the addition of brine (50 mL). The resultant sticky suspension was filtered through celite and the celite washed with further DCM (2×100 mL) and water (100 mL). The filtrate was separated and the aqueous layer was re-extracted with DCM (100 mL). The combined organics were dried ($Na_2SO_4$) and concentrated to dryness under vacuum to yield approximately 8 g of a crude orange gum. The crude product was purified on silica gel (DCM/EtOAc 100/0 to 95/5) to yield 3.61 g (50%) of the title compound as an orange gum. LCMS Method 6 (ES+) RT 2.56 min., 706.1 (M+H)+. 1H NMR (500 MHz, Chloroform-d) δ 8.96-8.79 (m, 3H), 8.10 (dd, J=5.7, 3.6 Hz, 1H), 7.99 (d, J=10.6 Hz, 1H), 7.21 (t, J=8.2 Hz, 1H), 7.11 (s, 1H), 7.02 (d, J=8.1 Hz, 1H), 6.85 (d, J=8.3 Hz, 1H), 5.88 (td, J=9.3, 4.9 Hz, 1H), 3.92 (s, 3H), 3.63-3.46 (m, 1H), 3.11 (d, J=16.3 Hz, 1H), 1.71 (d, J=3.8 Hz, 6H), 1.13 (s, 9H), 0.91 (s, 9H), −0.02 (s, 6H).

Intermediate 56

N-[(1R,3R)-3-{[5-(2-{2-[(tert-butyldimethylsilyl)oxy]propan-2-yl}pyrimidin-5-yl)-4-fluoro-2-nitrophenyl]amino}-3-(2-chloro-6-methoxyphenyl)-1-cyanopropyl]-2-methylpropane-2-sulfinamide Intermediate 55 (2.8 g, 3.96 mmol) was dissolved in anhydrous THF (50 mL) under nitrogen and scandium triflate (400 mg, 0.81 mmol) was added, followed by sodium cyanide (220 mg, 4.5 mmol). The reaction mixture was stirred under a flow of nitrogen overnight. The reaction mixture was diluted with EtOAc (100 mL) and washed with a saturated solution of $NaHCO_3$ (75 mL). The aqueous layer was re-extracted with EtOAc (75 mL) and the combined organics were washed with saturated brine (75 mL), dried over $Na_2SO_4$, filtered and concentrated to dryness under vacuum. The crude product was purified on silica gel (heptane/EtOAc 100/0 to 60/40) to yield to 1.52 g (44%) of the title compound as an orange gum. LCMS Method 6 (ES+) RT 2.41 min., 733.1 (M+H)+.
1H NMR (500 MHz, Chloroform-d) δ 8.94-8.62 (m, 3H), 8.02 (d, J=10.5 Hz, 1H), 7.26-7.14 (m, 2H), 7.03 (d, J=8.0 Hz, 1H), 6.85 (d, J=7.9 Hz, 1H), 5.81-5.61 (m, 1H), 4.49-4.26 (m, 1H), 3.92 (s, 3H), 3.86 (d, J=9.4 Hz, 1H), 2.93 (ddd, J=14.4, 9.7, 4.6 Hz, 1H), 2.48-2.23 (m, 1H), 1.71 (d, J=2.4 Hz, 6H), 1.19 (s, 9H), 0.90 (s, 9H), −0.03 (s, 6H).

Intermediate 57

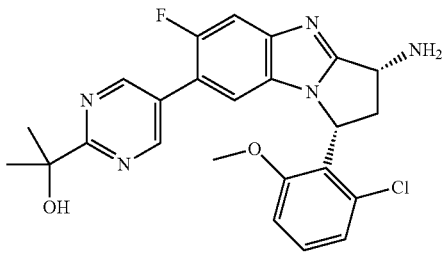 [SMILES: COc1cccc(Cl)c1[C@H]1C[C@@H](N)c2nc3cc(F)c(-c4cnc(C(C)(C)O)nc4)cc3n21]

2-{5-[(1R,3R)-3-amino-1-(2-chloro-6-methoxyphenyl)-6-fluoro-2,3-dihydro-1H-pyrrolo[1,2-a]benzimidazol-7-yl]pyrimidin-2-yl}propan-2-ol Intermediate 56 (1.52 g, 2.07 mmol) was dissolved in ethanol (16 mL) and tin (II) chloride (2.4 g, 12.66 mmol) was added, followed by 12M HCl (1.4 mL). The reaction mixture was stirred at 80° C. for 90 minutes. The reaction mixture was cooled to r.t., concentrated in vacuo to approximately 1 mL. The concentrated solution was dissolved in DCM (50 mL), basified with 2M aqueous NaOH solution until pH=10 and finally treated with 10% aqueous KF solution (25 mL). The mixture was filtered and the solids were washed with DCM (2×20 mL). The filtrate was separated and the aqueous layer was re-extracted with DCM (30 mL). The combined organic phases were dried over $Na_2SO_4$, filtered and concentrated to dryness under vacuum to yield the title compound (134 mg 14%) as an off-white solid.

The original solids can be washed with further EtOAc to yield a second crop of the title compound after removal of the volatiles in vacuo. If required additional purification can be performed by flash chromatography on silica gel (eluted with 0 to 100% EtOAc in heptane, followed by 0 to 20% MeOH in EtOAc). LCMS Method 6 (ES+) RT 3.76 min., 468.1 (M+H)+. 1H NMR (500 MHz, Chloroform-d) Major atropisomer—δ 8.71 (d, J=1.3 Hz, 2H), 7.56 (t, J=10.2 Hz, 1H), 7.33-7.27 (m, 1H), 7.16 (d, J=8.1 Hz, 1H), 6.75 (d, J=8.2 Hz, 1H), 6.66 (d, J=6.6 Hz, 1H), 6.19 (t, J=7.7 Hz, 1H), 4.74 (s, 1H), 4.60 (s, 2H), 3.61-3.52 (m, 1H), 3.38 (s, 3H), 2.67 (dt, J=14.4, 7.6 Hz, 1H), 1.62 (s, 6H).

Intermediate 58

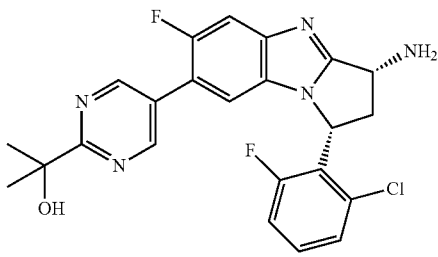 [SMILES: CC(C)(O)c1ncc(-c2cc3c(cc2F)nc2n3[C@@H](c3c(F)cccc3Cl)C[C@H]2N)cn1]

2-{5-[(1R,3R)-3-amino-1-(2-chloro-6-fluorophenyl)-6-fluoro-2,3-dihydro-1H-pyrrolo[1,2-a]benzimidazol-7-yl]pyrimidin-2-yl}propan-2-ol Intermediate 58 was prepared following an analogous 8 steps procedure to that described for Intermediate 41 through to Intermediate 57, starting from 2-chloro-6-fluorobenzaldehyde. to afford 1.1 g of the title compound as a beige solid. LCMS basic Method 3 (ES+) RT 2.02 min., 456.2/458.1 (M+H)⁺.

Intermediate 59

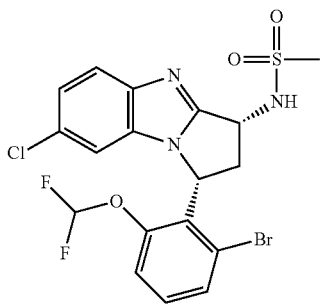 [SMILES: CS(=O)(=O)N[C@@H]1C[C@H](c2c(Br)cccc2OC(F)F)n2c1nc1ccc(Cl)cc12]

N-[(1R,3R)-1-[2-bromo-6-(difluoromethoxy)phenyl]-7-chloro-2,3-dihydro-1H-pyrrolo[1,2-a]benzimidazol-3-yl]methanesulfonamide To a mixture of Intermediate 40 (2.5 g, 5.8 mmol), N,N-diisopropylethylamine (1.22 mL, 6.97 mmol) in DCM (58.3 mL), methanesulfonyl chloride (0.6 mL, 8 mmol) was added at 0° C. and the mixture was stirred at r.t for 2 hours. Water (30 mL) was added to the reaction mixture and extracted with CH₂Cl₂ (2×30 mL). The organic phase was washed with saturated brine (20 mL) and the combined organic phases was dried with sodium sulphate, filtered and concentrated in vacuo to give a solid. The crude was triturated in diethylether, filtered, washed twice with diethylether then hexane and dried to give the title compound (2.8 g, 5.53 mmol, 95% yield) as a brown solid. LC/MS Method 3: RT 2.11 mins (pH 10), m/z 506 and 508.

Intermediate 60

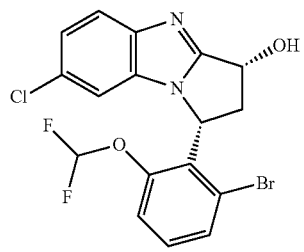 [SMILES: O[C@@H]1C[C@H](c2c(Br)cccc2OC(F)F)n2c1nc1ccc(Cl)cc12]

(1R,3R)-1-[2-bromo-6-(difluoromethoxy)phenyl]-7-chloro-2,3-dihydro-1H-pyrrolo[1,2-a]benzimidazol-3-ol Intermediate 38 (5 g, 11.64 mmol) and triphenylphosphine (3.7 g, 14 mmol) were added to a round bottom flask followed by acetic acid (0.7 mL, 10 mmol) and THF (12 mL). The reaction mixture was cooled down to 0° C. and DIAD (3.4 mL, 17 mmol) in THF (12 mL) was added dropwise. The mixture was stirred at 0° C. for 2 hours. The reaction mixture was warmed to ambient temperature and the crude mixture was extracted with EtOAc (3×20 mL). The organic phase was washed with saturated NaHCO₃ (20 mL) and saturated brine (20 mL), the combined organic phases was dried with sodium sulphate, filtered and concentrated in vacuo to give an oil which was purified by flash chromatography in silica gel (0 to 80% EtOAc in Hexane) to afford [(1R,3R)-1-[2-bromo-6-(difluoromethoxy)phenyl]-7-chloro-2,3-dihydro-1H-pyrrolo[1,2-a]benzimidazol-3-yl] acetate. The material was dissolved in MeOH (6.3 mL) and stirred with potassium carbonate (1.6 g, 12 mmol) for 45 minutes, the solid was filtered and washed with MeOH (30 mL) and water (10 mL) to give the title compound (4.3 g, 10 mmol, 86% yield) as a white solid. LC/MS Method 3: RT 2.07 mins (pH 10), m/z 429 and 431.

Intermediate 61

2-[4-methyl-5-(4,4,5,5-tetramethyl-1,3,2-dioxaborolan-2-yl)pyrimidin-2-yl]propan-2-ol 2-(5-bromo-4-methyl-pyrimidin-2-yl)propan-2-ol (1 g, 4.33 mmol), bis(pinacolato)diboron (2 equiv., 8.65 mmol), 1,1'-bis(diphenylphosphino)ferrocene-palladium(II)dichloride dichloromethane complex (0.05 equiv., 0.22 mmol), potassium acetate (4 equiv., 17.31 mmol) and 1,4-dioxane (5 mL) were placed in vial and then degassed. The mixture was then heated at 105° C. for 2 hours.

The reaction mixture was cooled and partitioned between EtOAc and water. The organic layer was dried over Na₂SO₄ and evaporated to give a dark brown solid, stored at 0° C. and used successfully in ensuing reactions after a period of several days.

Alternatively, Intermediate 61 May be Prepared by Applying the Following Procedure:

2-(5-bromo-4-methylpyrimidin-2-yl)propan-2-ol (8 g, 34.6 mmol), BISPIN (9.23 g, 36.3 mmol) and potassium acetate (10.2 g, 104 mmol) were combined in 1,4-dioxane (300 mL). Argon was bubbled through the mixture over 10 minutes. Then PdCl₂(dppf) (0.76 g, 1.04 mmol) was added and the mixture was stirred at 100° C. The reaction mixture was cooled to room temperature and filtered over a plug of celite and rinsed with EtOAc. The combined filtrate was concentrated under reduced pressure to give the title compound as dark brown oil (16.9 g) which was used as such.

$^1$H NMR (300 MHz, Chloroform-d) δ 8.90 (s, 1H), 5.04 (s, 1H), 2.71 (s, 3H), 1.57 (s, 6H), 1.36 (s, 12H). LC/MS Method 9: 2.15 minutes, [M+H]+: 278/279/280.

Intermediate 62

6-bromo-7-fluoroimidazo[1,2-a]pyridine-2-carboxylate 5-bromo-4-fluoropyridin-2-amine (100 g, 0.52 mol) was dissolved in dioxane (200 mL) and added slowly to a solution of ethyl 3-bromo-2-oxopropanoate (70 mL, 0.54 mol) in 1,4-dioxane (800 mL) and stirred at r.t for 1.5 hours. Further 1,4-dioxane (400 mL) was added and the mixture heated to 95° C. and stirred overnight. The mixture was cooled to r.t and concentrated in vacuo. The residue was dissolved in water (700 mL) and basified to pH ~9 with saturated aqueous sodium bicarbonate solution. The resulting solid was filtered and washed with water (2×200 mL) and diethyl ether (300 mL). The solid was dried in vacuo at 40° C. overnight to give the title compound (133 g, 86%) as a peach coloured solid. Method 7 HPLC-MS: MH+ m/z=288/290, RT=1.08 min (96%). $^1$H NMR (500 MHz, Chloroform-d) δ 8.35 (d, J=6.3 Hz, 1H), 8.11 (s, 1H), 7.39 (d, J=8.5 Hz, 1H), 4.45 (q, J=7.1 Hz, 2H), 1.43 (t, J=7.1 Hz, 3H).

Intermediate 63

{6-bromo-7-fluoroimidazo[1,2-a]pyridin-2-yl}methanol

Intermediate 62 (28.5 g, 95.3 mmol) was dissolved in anhydrous THF (500 mL) and cooled to −10° C. under nitrogen. 1M diisobutylaluminum hydride in heptane (200 mL) was added dropwise over ~30 minutes and the reaction mixture was stirred at −10° C. under nitrogen for 30 minutes then allowed to warm to 10° C. under nitrogen over 1 hour. The reaction mixture was cooled to −50° C. and quenched by dropwise addition of saturated aqueous solution of Rochelle's salt (150 mL), stirred at −50° C. for 30 minutes, then allowed to warm to ambient temperature. The mixture was diluted with water (250 mL) and extracted with EtOAc (3×1 L). The aqueous layer was filtered through celite and extracted with EtOAc (3×500 mL). The combined organics were dried (Na$_2$SO$_4$) and concentrated under vacuum to yield the title compound (22.5 g, 93%) as a yellow solid. Method 8 HPLC-MS: MH+ m/z=245/247, RT=2.93 min (94%). $^1$H NMR (500 MHz, DMSO-d$_6$) δ 9.03 (d, J=6.7 Hz, 1H), 7.74 (s, 1H), 7.54 (d, J=9.8 Hz, 1H), 5.23 (t, J=5.2 Hz, 1H), 4.56 (d, J=4.4 Hz, 2H).

Intermediate 64

3-[6-bromo-7-fluoro-2-(hydroxymethyl)imidazo[1,2-a]pyridin-3-yl]-3-[2-chloro-6-(difluoromethoxy)phenyl]propanoic acid Intermediate 63 (22.4 g, 84.02 mmol), 2-chloro-6-(difluoromethoxy)benzaldehyde (20.1 g, 92.4 mmol), 2,2-dimethyl-1,3-dioxane-4,6-dione (13.3 g, 92.4 mmol), L-proline (532 mg, 4.62 mmol) and MgSO$_4$ (15.2 g, 126 mmol) were suspended in anhydrous acetonitrile (110 mL), warmed to 100° C. and stirred under N$_2$(g) overnight. The mixture was cooled to RT, diluted with acetonitrile (100 mL) and filtered over a sintered glass funnel. The filter cake was further washed with acetonitrile (50 mL) and the combined filtrate treated with 6M sodium hydroxide in water (42 ml) and stirred at ambient temperature for 1 hour. The mixture was acidified (to pH 4) by treatment with 6M HCl (aq) then concentrated under vacuum to give a tan solid. The solid thus obtained was slurried in water (100 mL) for 2 hours then filtered to give the title compound (41.8 g, 83%) as a beige powder. Method 7 HPLC-MS: MH+ m/z 493/495, (M−H)$^-$ m/z 491/493 RT 0.91 min (84%), $^1$H NMR (500 MHz, DMSO-d$_6$) δ 8.44 (d, J=6.5 Hz, 1H), 7.65 (d, J=9.3 Hz, 1H), 7.41-7.37 (m, 2H), 7.19 (t, J=75.0 Hz, 1H), 7.17 (d, J=4.9 Hz, 1H), 5.37 (dd, J=8.7, 6.8 Hz, 1H), 4.64-4.51 (m, 2H), 3.47 (dd, J=16.5, 6.7 Hz, 1H), 3.29 (dd, J=16.5, 8.8 Hz, 1H).

Intermediate 65

6-bromo-3-{2-carboxy-1-[2-chloro-6-(difluoromethoxy)phenyl]ethyl}-7-fluoroimidazo[1,2-a]pyridine-2-carboxylic acid Chromium trioxide (167 mg, 1.66 mmol) and periodic acid (81.0 g, 355 mmol) were suspended in MeCN:H$_2$O (800 mL:8 mL). The resulting mixture was added to a stirred suspension of Intermediate 64 (41.8 g, 71.0 mmol) in MeCN:H$_2$O (312 mL:2.4 mL). The resulting mixture was stirred at r.t overnight then filtered through a sintered glass funnel. The resulting pale green filter cake was washed with acetonitrile (4×50 mL) and the filtrate concentrated under vacuum to give a gummy orange solid. This was partitioned between EtOAc (500 mL) and water (250 mL). The layers were separated and the aqueous phase further extracted with EtOAc (2×150 mL). The combined organic phase was washed with water (3×250 mL), dried (MgSO$_4$), filtered and concentrated under vacuum to leave an orange paste. This was slurried with water (200 mL) for 72 hours (weekend period) and filtered. The resulting yellow solid was washed with water (100 mL) and dried in vacuo at 40° C. to give the title compound (39.1 g, 96%) as a pale yellow powder. Method 7 HPLC-MS: MH+ m/z 507/509, RT 1.00 minutes. $^1$H NMR (500 MHz, DMSO-d$_6$) δ 12.39 (s, 2H), 8.73 (d, J=6.6 Hz, 1H), 7.74 (d, J=9.2 Hz, 1H), 7.39-7.30 (m, 2H), 7.16-7.11 (m, 1H), 7.10 (t, J=75.0 Hz, 1H), 5.79 (t, J=8.4 Hz, 1H), 3.46 (dd, J=17.3, 9.2 Hz, 1H), 3.20 (dd, J=17.3, 7.7 Hz, 1H).

Intermediate 66

Ethyl 6-bromo-3-{1-[2-chloro-6-(difluoromethoxy)phenyl]-3-ethoxy-3-oxopropyl}-7-fluoroimidazo[1,2-a]pyridine-2-carboxylate Potassium carbonate (25.0 g, 180 mmol) and iodoethane (14.6 ml, 181 mmol) were added to a stirred solution of Intermediate 65 (34 g, 60.3 mmol) in anhydrous DMF (350 mL) at r.t. The mixture was stirred under an atmosphere of nitrogen overnight then added slowly to vigorously stirred mixture of ice/water (1.2 L). After stirring at RT for a further 4 hours, the resulting light beige solid was filtered under vacuum and the filter cake slurried with water (50 mL). The solid was dried in vacuo at 40° C. to give the title compound (31.5 g, 88%) as a light beige powder. Method 7 HPLC-MS: MH+ m/z 564 RT 1.29 mins.

¹H NMR (500 MHz, DMSO-d₆) δ 8.74 (d, J=6.5 Hz, 1H), 7.77 (d, J=9.2 Hz, 1H), 7.40-7.33 (m, 2H), 7.30-6.96 (m, 2H), 5.82 (t, J=8.5 Hz, 1H), 4.23 (qq, J=7.0, 3.8 Hz, 2H), 3.98 (q, J=7.0 Hz, 2H), 3.49 (dd, J=17.1, 8.9 Hz, 1H), 3.27 (dd, J=14.8, 7.7 Hz, 1H), 1.24 (t, J=7.1 Hz, 3H), 1.03 (t, J=7.1 Hz, 3H).

Intermediate 67

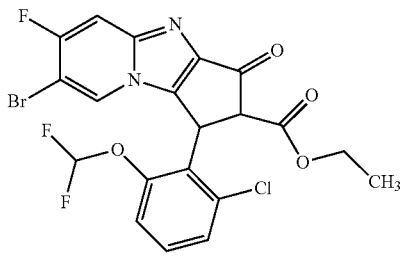 [SMILES: CCOC(=O)C1C(=O)c2nc3cc(F)c(Br)cn3c2C1c1c(Cl)cccc1OC(F)F]

Ethyl 11-bromo-3-[2-chloro-6-(difluoromethoxy)phenyl]-10-fluoro-5-oxo-1,7-diazatricyclo[6.4.0.0²,⁶]dodeca-2(6),7,9,11-tetraene-4-carboxylate Intermediate 67 was prepared from Intermediate 66 according to the method described for Intermediate 33. The crude material was purified by flash column chromatography (SiO₂, 800 g) eluting with a stepwise gradient in 500 mL vessels of 15-50% EtOAc in heptanes then 100% EtOAc to afford the title compound as a yellow/orange solid. (13.3 g, 50%). Method 7 HPLC-MS: MH+ m/z 517/519, RT 1.21 min (99%), ¹H NMR (500 MHz, DMSO-d₆) δ 8.51-8.34 (m, 1H), 7.94-7.83 (m, 1H), 7.56-7.42 (m, 2H), 7.39-6.68 (m, 2H), 5.77-5.63 (m, 1H), 4.28-4.13 (m, 2H), 4.07-4.00 (m, 1H), 1.27-1.19 (m, 3H).

Intermediate 68

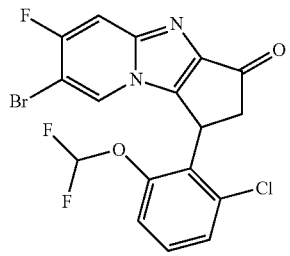 [SMILES: O=C1CC(c2c(Cl)cccc2OC(F)F)c2c1nc1cc(F)c(Br)cn21]

11-bromo-3-[2-chloro-6-(difluoromethoxy)phenyl]-10-fluoro-1,7-diazatricyclo[6.4.0.0²,⁶]dodeca-2(6),7,9,11-tetraen-5-one Intermediate 68 was prepared from Intermediate 67 (13.3 g, 25.7 mmol) according to the method described for Intermediate 34 to give the title compound (11.3 g, 89%) as an orange foam. Method 7 HPLC-MS: MH+ m/z 444/446, RT 1.19 minutes.

¹H NMR (500 MHz, Chloroform-d) δ 7.79-7.58 (m, 1H), 7.47-7.27 (m, 3H), 7.25-7.06 (m, 1H), 6.89-5.81 (m, 1H), 5.48-5.40 (m, 1H), 3.65-3.48 (m, 1H), 3.30-3.09 (m, 1H).

Intermediate 69

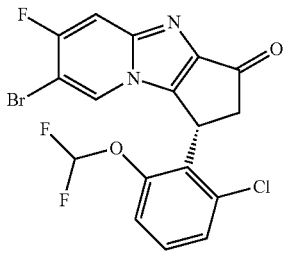

(3R)-11-bromo-3-[2-chloro-6-(difluoromethoxy)phenyl]-10-fluoro-1,7-diazatricyclo[6.4.0.0²,⁶]dodeca-2(6),7,9,11-tetraen-5-one The title compound was prepared by chiral separation of Intermediate 68 into the constituent enantiomers and the isolation of the second eluting peak according to the conditions outlined below:
Analytical Method: Liquid Chromatography
Column: Chiralcel OD 250×4.6 mm 5 µm
Temperature: 30° C.
Eluent: 100% MeOH+0.1% DEA
Flow rate: 1 ml/min
Enantiomer A: 4.943 min
Enantiomer B (Intermediate 69): 11.887 min
Preparative method, by SFC:
Column: Chiralcel OD 266×50 mm
Eluent: CO2+20% MeOH
Flow rate: 360 ml/min
Enantiomer A: depending on the amount injected (~5.2 min)
Enantiomer B (Intermediate 69): depending on the amount injected (~8.5 min)
Optical rotation of Enantiomer B Intermediate 69: α_D+117.6 (MeOH, cone 0.255 g/100 mL, T=25° C., wavelength 589 nM, cell path 10 cm).

Intermediate 70

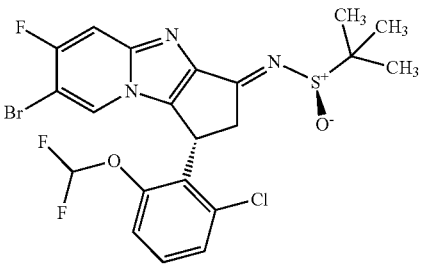 [SMILES: CC(C)(C)[S@@+]([O-])/N=C1\C[C@H](c2c(Cl)cccc2OC(F)F)c2c1nc1cc(F)c(Br)cn21]

(R)—N-[(3R,5E)-11-bromo-3-[2-chloro-6-(difluoromethoxy)phenyl]-10-fluoro-1,7-diazatricyclo[6.4.0.0²,⁶]dodeca-2(6),7,9,11-tetraen-5-ylidene]-2-methylpropane-2-sulfinamide Ti(OEt)₄ (1.59 mL, 2.48 mmol) was added a stirred solution of Intermediate 69 (0.57 g, 1.22 mmol) in anhydrous THF (12 mL) at r.t then (R)-2-methylpropane-2- sulfinamide (0.29 g, 2.43 mmol) was added and mixture was heated at 65° C. for 17 hours. The mixture was cooled to r.t, diluted with brine (10 mL), EtOAc (50 mL) and water (5 mL) and stirred for 15 min. The resulting solids were removed by filtration and the aqueous layer was further extracted with EtOAc (3×25 mL). The combined organic layers were washed with brine (25 mL), dried over sodium sulfate, filtered and concentrated in vacuo to afford the crude product as a beige solid. Purification by column chromatography (SiO$_2$ Biotage isolera), eluting with 0-100% EtOAc in heptanes afforded the title compound (600 mg, 90%) as a beige solid. Method 7 HPLC-MS: MH+ m/z 548, RT 1.20 min (99%), $^1$H NMR (500 MHz, Chloroform-d) δ 7.76-7.58 (m, 1H), 7.43-7.39 (m, 1H), 7.39-7.27 (m, 2H), 7.25-7.02 (m, 1H), 6.84-5.82 (m, 1H), 5.47-5.30 (m, 1H), 4.52-4.33 (m, 1H), 3.61-3.47 (m, 1H), 1.36 (s, 9H).

Intermediate 71

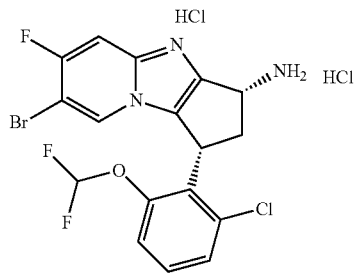 [SMILES: Cl ; N[C@@H]1C[C@H](c2c(Cl)cccc2OC(F)F)c2c1nc1cc(F)c(Br)cn21 ; Cl]

(3R,5R)-11-bromo-3-[2-chloro-6-(difluoromethoxy)phenyl]-10-fluoro-1,7-diazatricyclo[6.4.0.0$^{2,6}$]dodeca-2(6),7,9,11-tetraen-5-amine dihydrochloride Sodium borohydride (90 mg, 2.38 mmol) was added in one portion to a stirred solution of Intermediate 70 (600 mg, 1.09 mmol) in THF:water (14.7 mL:0.3 mL) under an atmosphere of nitrogen at −50° C. and the reaction maintained at this temperature for 30 minutes. The mixture was slowly warmed to 0° C. over 2 hours then stirred for a further 1 hour. The mixture was quenched with MeOH (1 mL) and diluted with water (25 mL). The intermediate was extracted with EtOAc (2×25 mL) and the combined organic phases dried (MgSO$_4$), filtered and concentrated in vacuo to leave an off-white foam (570 mg). This was dissolved in dioxane (10 mL) and treated with 4M HCl in dioxane (1.4 mL, 5.6 mmol). The mixture was stirred at RT for 30 minutes then concentrated to dryness to afford the title compound (480 mg, 67%) as an off-white solid. The title compound was used directly in the subsequent step without further purification. Method 9 HPLC-MS: MH+ m/z 446/448, RT 1.42 minutes.

Intermediate 72

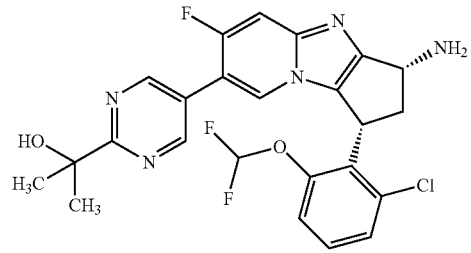 [SMILES: CC(C)(O)c1ncc(-c2cn3c4c(nc3cc2F)[C@H](N)C[C@@H]4c2c(Cl)cccc2OC(F)F)cn1]

2-{5-[(3R,5R)-5-amino-3-[2-chloro-6-(difluoromethoxy)phenyl]-10-fluoro-1,7-diazatricyclo[6.4.0.0$^{2,6}$]dodeca-2(6),7,9,11-tetraen-11-yl]pyrimidin-2-yl}propan-2-ol An aqueous solution of 2M K$_2$CO$_3$ (1.8 mL) was added to a stirred suspension of Intermediate 71 (480 mg, 0.73 mmol) and 2-[5-(tetramethyl-1,3,2-dioxaborolan-2-yl)pyrimidin-2-yl]propan-2-ol (232 mg, 0.88 mmol) in 1,4-dioxane (10 mL). The mixture was degassed under a flow of nitrogen for 10 minutes then treated with bis[3-(diphenylphosphanyl)cyclopenta-2,4-dien-1-yl]iron; DCM; dichloropalladium (60 mg, 0.07 mmol) and heated to 105° C. for 1.5 hours. The mixture was cooled to RT, diluted with EtOAc (30 mL) and filtered through a pad of Celite. The filter cake was further washed with EtOAc (2×20 mL). The filtrate was washed with water (25 mL) and the aqueous phase further extracted with EtOAc (2×25 mL). The combined organic phase was washed with brine (30 mL), dried (MgSO$_4$), filtered and concentrated in vacuo to give the crude product (750 mg) as a dark brown oil. Purification by column chromatography (KP-NH, SiO$_2$, Biotage isolera) eluting with 50-100% EtOAc in heptane followed by 0-50% MeOH in EtOAc to give the title compound (260 mg, 71%) as an off white solid. The material was azeotroped twice with toluene prior to use in the subsequent step. Method 8 HPLC-MS: MH+ m/z 504, RT 3.86 minutes, $^1$H NMR (500 MHz, DMSO-d$_6$) δ 8.90-8.78 (m, 2H), 8.18-7.90 (m, 1H), 7.68-7.54 (m, 1H), 7.45-7.36 (m, 1H), 7.37-6.66 (m, 3H), 5.14-4.92 (m, 2H), 4.48-4.32 (m, 1H), 3.57-3.34 (m, 1H), 2.95-2.54 (m, 2H), 2.23-1.93 (m, 1H), 1.51-1.47 (m, 6H).

Intermediate 73

2,2-Dichloro-3-oxocyclobutyl 2,2-dimethylpropanoate

To a stirred mixture of vinyl pivalate (30 g, 234 mmol) and zinc (31 g, 474 mmol) in ether (250 mL) was added a solution of 2,2,2-trichloroacetyl chloride (34 mL, 304 mmol) in ether (250 mL) dropwise over 2.5 hours in a water bath while maintaining the reaction temperature between 15-30° C. Reaction was filtered through Celite and washed through with EtOAc (200 mL). The filtrate was washed with water (200 mL), brine (200 mL), dried over sodium sulfate and concentrated under vacuum to afford the title compound (68 g, 97% at 80% purity) as an orange liquid.

δH (500 MHz, CDCl$_3$) ppm 5.40 (dd, J=8.4, 6.2 Hz, 1H), 3.70 (dd, J=18.9, 8.4 Hz, 1H), 3.39 (dd, J=18.9, 6.2 Hz, 1H), 1.28 (s, 9H).

Intermediate 74

3-Oxocyclobutyl 2,2-dimethylpropanoate

Zinc (74 g, 1.1 mol) was added to acetic acid (200 mL) with stirring and the suspension was cooled in an ice bath. Intermediate 73 (80%, 68 g, 228 mmol) in acetic acid (300 mL) was added dropwise over 2 hours. Upon completion of addition, the reaction was warmed to r.t and stirred for 1.5 hours. The reaction was filtered washed with DCM (100 mL). The filtrate was diluted with EtOAc (800 mL) and washed sequentially with water (3×250 mL), saturated aqueous NaHCO$_3$ solution (3×250 mL) and brine (50 mL). The organic phase was dried over sodium sulfate and concentrated under vacuum to give crude product as a brown oil (30 g) which was purified by dry flash chromatography on silica gel eluting with 0-10% EtOAc in heptanes to afford the title compound (11 g, 28%) as a clear colourless oil δH (500 MHz, CDCl$_3$) 5.26-5.19 (m, 1H), 3.51-3.40 (m, 2H), 3.19-3.07 (m, 2H), 1.22 (s, 9H).

Intermediate 75

3-(5-Bromopyrimidin-2-yl)-3-hydroxycyclobutyl 2,2-dimethylpropanoate 5-bromo-2-iodopyrimidine (16.7 g, 58.8 mmol) was dissolved in DCM (200 mL) with stirring and cooled to −78° C. under N$_2$. 2.5 M n-BuLi in hexane in hexane (23.5 mL) was added dropwise and stirred for 20 minutes at −78° C. Intermediate 74 (10 g, 58.8 mmol) in DCM (50 mL) was cooled in a dry ice bath and added in one portion. The reaction was stirred at −78° C. for 10 minutes. The reaction was quenched by addition of saturated aqueous NH$_4$Cl solution (20 mL) and allowed to warm to r.t, saturated aqueous NH$_4$Cl solution (50 mL) was added and the mixture was extracted with DCM (2×100 mL). The combined organic extracts were dried over sodium sulfate and concentrated under vacuum. The crude product was purified by column chromatography using 0-30% EtOAc in heptane to afford the title compound (7.6 g, 35%) as a yellow solid.

δH (500 MHz, CDCl$_3$) 8.78 (s, 2H), 5.22-5.14 (m, 1H), 3.03-2.93 (m, 2H), 2.67-2.58 (m, 2H), 1.22 (s, 9H).

Intermediate 76

1-(5-Bromopyrimidin-2-yl)cyclobutane-1,3-diol

Intermediate 75 (90%, 6 g, 16.4 mmol) was dissolved in MeOH (120 mL) and K$_2$CO$_3$ (11.3 g, 82 mmol) was added and the reaction stirred for 18 hours at r.t. The reaction was diluted with DCM (400 mL) and washed with water (150 mL). The aqueous phase was extracted with DCM (200 mL). The combined organic extracts were dried over sodium sulfate and concentrated under vacuum to afford the title compound (2.94 g, 73%) as an off-white solid.

δH (500 MHz, DMSO-d6) 8.98 (s, 2H), 5.63 (s, 1H), 5.08 (d, J=6.2 Hz, 1H), 4.09-3.92 (m, 1H), 2.87-2.79 (m, 2H), 2.28-2.14 (m, 2H).

Intermediate 77

3-(5-Bromopyrimidin-2-yl)-3-hydroxycyclobutan-1-one

To a stirred solution of Intermediate 76 (2 g, 8.1 mmol) in DCM (200 mL) was added Dess-Martin periodinane (4.1 g, 9.8 mmol). The reaction was stirred for 18 hours and the resulting suspension diluted with DCM (100 mL) and washed with saturated aqueous NaHCO$_3$ solution (100 mL). The aqueous layer was re-extracted with DCM (100 mL) and the combined organic extracts dried over sodium sulfate and concentrated. The crude product was purified by chromatography on silica gel eluting with 0-30% EtOAc in heptanes to afford the title compound (1.37 g, 69%) as an off white solid.

δH (500 MHz, DMSO-d6) 9.04 (s, 2H), 6.41 (s, 1H), 3.69-3.55 (m, 2H), 3.37-3.21 (m, 2H).

Intermediate 78

3-(5-Bromopyrimidin-2-yl)-3-[(tert-butyldimethylsilyl)oxy]cyclobutan-1-one

Intermediate 77 (1.37 g, 5.64 mmol) was dissolved in dry DMF (20 mL) with stirring under N$_2$ and cooled to 0° C. 1H-imidazole (1.9 g, 28.18 mmol) was added followed by tert-butyl(chloro)dimethylsilane (2.0 g, 13.5 mmol) and reaction was stirred at r.t for 20 hours. The reaction was diluted with DCM (150 mL) and washed with water (3×50 mL). The aqueous phase was re-extracted with DCM (50 mL). The combined organic extracts were dried over sodium sulfate and concentrated. The crude product was purified by chromatography on silica gel eluting with 0-20% EtOAc in heptanes to afford the title compound (1.6 g 79%) as a pale orange oil.

δH (500 MHz, DMSO-d6) 9.06 (s, 2H), 3.78-3.66 (m, 2H), 3.44-3.34 (m, 2H), 0.88 (s, 9H), 0.00 (s, 6H).

Intermediate 79

3-(5-Bromopyrimidin-2-yl)-3-[(tert-butyldimethylsilyl)oxy]-1-methylcyclobutan-1-ol Intermediate 78 (1.35 g, 3.78 mmol) was dissolved in dry ether (40 mL) under N$_2$ with stirring and cooled to 0° C. using an ice bath. 3M MeMgBr in diethylether (2.52 mL) was added dropwise and reaction stirred for 30 minutes at 0° C. The reaction was quenched with saturated aqueous NH$_4$Cl solution (20 mL) and then water (20 mL). The mixture was extracted with EtOAc (2×50 mL), dried over sodium sulfate and concentrated to give a yellow oil. This was purified by chromatography on silica gel eluting with 0-100% DCM in heptane followed by 0-20% EtOAc in DCM to afford the title compound as a mixture of separate cis and trans isomers (total yield, 1.19 g, 84%) as clear oils.

Major Isomer—Cis

δH (500 MHz, CDCl$_3$) 8.79 (s, 2H), 3.10-3.03 (m, 2H), 2.59-2.51 (m, 2H), 1.18 (s, 3H), 0.87 (s, 9H), −0.14 (s, 6H).

Minor Isomer—Trans

δH (500 MHz, CDCl$_3$) 8.79 (s, 2H), 2.78-2.63 (m, 4H), 1.49 (s, 3H), 0.95 (s, 9H), 0.04 (s, 6H).

Intermediate 80

1-Chloro-2,5-difluoro-4-nitrobenzene

A suspension of 2-chloro-1,4-difluorobenzene (98 g, 660 mmol) in concentrated sulphuric acid (250 ml, 4.69 mol) was cooled with an ice/salt mixture after which a solution of nitric acid (29.1 ml, 693 mmol) in sulphuric acid (100 ml, 1.88 mol) was added drop-wise over 1.5 hours whilst maintaining the temperature between −5 and +2° C. After 30 minutes, the reaction mixture was allowed to warm to ~17°

C. and slowly poured onto ice with stirring. The formed solid was isolated by filtration and the residue washed several times with water and air dried yielding the title compound (112 g, 88%) as a pale yellow powder.

$^1$H NMR (300 MHz, Chloroform-d) δ 7.94 (dd, J=7.9, 6.5 Hz, 1H), 7.45 (dd, J=9.8, 5.9 Hz, 1H).

Intermediate 81

2-(5-(2,5-difluoro-4-nitrophenyl)pyrimidin-2-yl)propan-2-ol

A mixture of Intermediate 80 (50 g, 258 mmol), 2-(5-(4,4,5,5-tetramethyl-1,3,2-dioxaborolan-2-yl)pyrimidin-2-yl)propan-2-ol (69.6 g, 264 mmol) and sodium carbonate (54.8 g, 517 mmol) in 1,4-dioxane (700 mL) and water (100 mL) was flushed with argon 3 times. Subsequently, tris(dibenzylideneacetone)dipalladium (5.91 g, 6.46 mmol) and tri-tert-butylphosphine tetrafluoroborate (7.50 g, 25.8 mmol) were added and the mixture was stirred at 80° C. overnight. The reaction mixture was cooled to r.t, filtered over celite and washed with EtOAc (1 L). The filtrate was washed with water (100 mL) and brine (2×200 mL) and the combined aqueous layers back-extracted with EtOAc (200 mL). The combined organic layers were dried over Na$_2$SO$_4$, filtered and concentrated in vacuo. The residue was purified by column chromatography (silica; 30% EtOAc in heptane). The product containing fractions were combined, concentrated in vacuo and crystallised from iPrOH to give the title compound as an orange solid (55 g) which can be further purified if required by trituration with di-isopropyl ether.

LCMS Method 11 RT=1.806 (99.5%); [M+H]$^+$=296.

$^1$H NMR (300 MHz, Chloroform-d) δ 8.95 (d, J=1.5 Hz, 2H), 8.02 (dd, J=9.2, 6.1 Hz, 1H), 7.46 (dd, J=10.4, 6.0 Hz, 1H), 4.47 (s, 1H), 1.66 (s, 6H).

Intermediate 82

(S)—N-(2-bromo-6-(difluoromethoxy)benzylidene)-2-methylpropane-2-sulfinamide (S)-2-methylpropane-2-sulfinamide (30 g, 248 mmol), potassium phosphate, dibasic (129 g, 743 mmol) and phosphoric acid, potassium salt (158 g, 743 mmol) were added to a cooled solution of 2-bromo-6-(difluoromethoxy)benzaldehyde (68.3 g, 272 mmol) in anhydrous THF (500 mL) at 0° C. The reaction mixture was allowed to warm to r.t and stirred overnight. The bulk of the THF was removed in vacuo and water and Et$_2$O were added to the residue. The layers were separated and the aqueous phase extracted with Et$_2$O. The combined organic layers were washed with brine, dried over Na$_2$SO$_4$, filtered and concentrated in vacuo yielding the title compound (90 g) as a dark oil which was used as such in the next reaction.

LCMS Method 11: RT=2.084 (97.6%); [M+H]$^+$=354/356 (Br pattern).

$^1$H NMR (300 MHz, Chloroform-d) δ 8.84 (s, 1H), 7.58 (dd, J=7.9, 1.2 Hz, 1H), 7.33 (t, J=8.1 Hz, 1H), 7.28-7.20 (m, 1H), 6.57 (t, J=73.8 Hz, 1H), 1.30 (s, 9H).

Intermediate 83

(S)—N—((R)-1-(2-bromo-6-(difluoromethoxy)phenyl)but-3-en-1-yl)-2-methylpropane-2-sulfinamide Under a nitrogen atmosphere, 1,2-dibromoethane (2.19 ml, 25.4 mmol) was added to a suspension of zinc (100 g, 1.52 mol) in anhydrous THF (250 mL). The suspension was warmed to mild reflux, allowed to cool down and heated to reflux again. This cycle was repeated twice more after which TMSCl (3.24 mL, 25.4 mmol) was added causing an exothermic reaction. After 15 minutes, 3-bromoprop-1-ene (55.2 mL, 635 mmol) was added dropwise at such a rate that the very light reflux was maintained without external heating. The suspension was stirred for an additional 30 minutes while allowing to cool to r.t. Stirring was stopped and excess zinc allowed to separate. The grey supernatant solution was transferred to a dropping funnel and the flask rinsed twice with anhydrous THF. This solution was added relatively fast to a solution of crude Intermediate 82 (89.9 g, 254 mmol) in anhydrous THF (1000 ml) which was pre-cooled to −60° C. (dry ice/acetone). After the addition was complete, the cooling bath was removed and the reaction mixture allowed to slowly warm to r.t overnight. The reaction mixture was quenched by adding saturated aqueous NH$_4$Cl solution (20 mL) and some ice. The bulk of the THF was removed in vacuo and saturated aqueous NH$_4$Cl solution was added to the residue until almost no solids remained. This mixture was extracted with Et$_2$O (3×200 mL). The combined organic layers were washed with saturated aqueous NH$_4$Cl solution, water and brine, dried over Na$_2$SO$_4$, filtered and concentrated in vacuo yielding the title compound (98.9 g) as a yellow-orange oil which was used as such in the next reaction.

LCMS Method 10: RT=3.183 (84.1%); [M+H]$^+$=396/398 (Br pattern); d.e.: 94.5% (the other diastereomer elutes at 3.43 minutes).

$^1$H NMR (300 MHz, Chloroform-d) δ 7.43 (d, J=7.9 Hz, 1H), 7.14 (t, J=8.1 Hz, 1H), 7.13-6.98 (m, 1H), 6.56 (t, J=73.8 Hz, 1H), 5.82-5.62 (m, 1H), 5.19 (q, J=8.0 Hz, 1H), 5.10-4.95 (m, 2H), 4.40-4.03 (m, 1H), 3.00-2.65 (m, 2H), 1.14 (s, 9H).

Intermediate 84

(R)-1-(2-bromo-6-(difluoromethoxy)phenyl)but-3-en-1-amine

At 0° C., HCl (1 M in Et$_2$O, 666 mL, 666 mmol) was added to a solution of crude Intermediate 83 (88.0 g, ~222 mmol) in ethanol (240 mL). After 3 hours, the reaction mixture was diluted with water and the layers were separated. The organic layer was extracted twice with aqueous HCl ((0.2 M). The combined aqueous layers were made alkaline (pH=~10) by slowly adding saturated aqueous Na$_2$CO$_3$ solution and the aqueous mixture thus obtained was extracted 3 times with Et$_2$O. The combined organic layers were washed with brine, dried over Na$_2$SO$_4$, filtered and concentrated in vacuo yielding the title compound (56.4 g) as a dark orange oil which was used as such in the next reaction.

LCMS Method 11: RT=1.360 (93.7%); [M+H]$^+$=292/294 (Br pattern).

$^1$H NMR (300 MHz, Chloroform-d) δ 7.41 (dd, J=7.6, 1.6 Hz, 1H), 7.14-6.98 (m, 2H), 6.56 (t, J=73.5 Hz, 1H), 5.86-5.68 (m, 1H), 5.13-4.97 (m, 2H), 4.59 (t, J=7.6 Hz, 1H), 2.61 (t, J=7.1 Hz, 2H), 1.85 (br s, 2H).

Intermediate 85

(R)-2-(5-(5-(((1-(2-bromo-6-(difluoromethoxy)phenyl)but-3-en-1-yl)amino)-2-fluoro-4-nitrophenyl)pyrimidin-2-yl)propan-2-ol Under a N$_2$ atmosphere, Intermediate 81 (54.2 g, 183 mmol), Intermediate 84 (56.4 g, ~183 mmol), and potassium carbonate (50.7 g, 367 mmol) were mixed in acetonitrile (anhydrous, 500 mL) and stirred at 80° C. for 2 days. After cooling to r.t, the reaction mixture was filtered through sand and rinsed with EtOAc. The filtrate was evaporated to give the title compound (106.1 g) as a dark red oil that was used as such in the next reaction.

$^1$H NMR (300 MHz, Chloroform-d) δ 8.83 (s, 2H), 8.70 (br d, J=7.0 Hz, 1H), 8.03 (d, J=10.7 Hz, 1H), 7.49 (dd, J=7.0, 2.2 Hz, 1H), 7.24-7.10 (m, 2H), 6.92 (br d, J=6.0 Hz, 1H), 6.58 (t, J=72.3 Hz, 1H), 5.91-5.73 (m, 1H), 5.36 (q, J=8.1 Hz, 1H), 5.22 (dd, J=17.0, 1.4 Hz, 1H), 5.13 (d, J=10.1 Hz, 1H), 4.67-4.50 (m, 1H), 3.09-2.70 (m, 2H), 1.65 (s, 6H).

Intermediate 86

(R)—N-(1-(2-bromo-6-(difluoromethoxy)phenyl) but-3-en-1-yl)-5-(2-(2-((tert-butyldimethylsilyl)oxy) propan-2-yl)pyrimidin-5-yl)-4-fluoro-2-nitroaniline Imidazole (60.1 g, 883 mmol) and tert-butyldimethylsilyl chloride (80 g, 531 mmol) were added to a solution of crude Intermediate 85 (99.8 g, ~176 mmol) in anhydrous N,N-dimethylformamide (250 mL). The mixture was warmed to 100° C. and stirred for 19 hours. After cooling to r.t, the reaction mixture was diluted with brine (1 L) and extracted with mixture of heptane and EtOAc (1:1, 500+200 mL). The combined organic layers were washed with water (2×100 mL) and brine (100 mL), dried over Na$_2$SO$_4$, filtered and concentrated in vacuo. The residue was purified by column chromatography (silica; 5-15% EtOAc in heptane) to give the title compound (107.1 g, 72% (over 5 steps)) as a red oil.

LCMS Method 12: RT=3.01 (94.9%); [M+H]$^+$=681/683 (Br pattern).

$^1$H NMR (300 MHz, Chloroform-d) δ 8.78 (s, 2H), 8.65 (br s, 1H), 8.00 (d, J=10.7 Hz, 1H), 7.44 (dd, J=6.8, 2.4 Hz, 1H), 7.19-7.08 (m, 2H), 6.92-6.81 (m, 1H), 6.54 (t, J=72.4 Hz, 1H), 5.88-5.74 (m, 1H), 5.33 (q, J=8.0 Hz, 1H), 5.20 (dd, J=17.0, 1.4 Hz, 1H), 5.11 (d, J=10.1 Hz, 1H), 3.01-2.71 (m, 2H), 1.69 (s, 3H), 1.68 (s, 3H), 0.89 (s, 9H), −0.05 (s, 6H).

Intermediate 87

(4R)-4-(2-bromo-6-(difluoromethoxy)phenyl)-4-((5-(2-(2-((tert-butyldimethylsilyl)oxy)propan-2-yl)pyrimidin-5-yl)-4-fluoro-2-nitrophenyl)amino)butane-1,2-diol Osmium tetroxide (4 wt % in water, 4.80 mL, 0.786 mmol) and 4-methylmorpholine-4-oxide (50 wt % in water, 94 mL, 393 mmol) were added to a solution of Intermediate 86 (107.1 g, 157 mmol) in a mixture of acetone (330 mL) and water (45 mL). The reaction mixture was stirred overnight at ambient temperature and concentrated in vacuo. The residue was mixed with aqueous Na$_2$S$_2$O$_3$ solution (10 wt %, 200 mL) and extracted twice with EtOAc. The combined organic layers were washed with brine, dried over Na$_2$SO$_4$, filtered and concentrated in vacuo yielding the title compound (120.1 g) as a dark red sticky oil that was used as such in the next reaction.

LCMS Method 12: RT=2.58 (95.3%); [M+H]$^+$=715/717 (Br pattern).

Intermediate 88

(R)-3-(2-bromo-6-(difluoromethoxy)phenyl)-3-((5-(2-(2-((tert-butyldimethylsilyl)oxy)propan-2-yl)pyrimidin-5-yl)-4-fluoro-2-nitrophenyl)amino)propanal A solution of crude Intermediate 87 (119 g, ~155 mmol) in THF (250 mL) was diluted with water (200 mL). To the resulting suspension, sodium periodate (68 g, 318 mmol) was added and another portion of sodium periodate (10.3 g, 48.2 mmol) after 3 hours. Stirring was continued for another hour after which the reaction mixture was quenched with aqueous Na$_2$S$_2$O$_3$ (10 wt %, 300 mL). The solids were filtered off and washed with EtOAc (500 mL). The organic layers were separated (some NaCl (s) added to enable layer separation) and the aqueous phase was extracted with EtOAc (200 mL). The combined organic layers were washed with a mixture of water (100 mL) and brine (50 mL) and brine (100 mL), dried over Na$_2$SO$_4$, filtered, and concentrated in vacuo to give the title compound (106.6 g) as a dark red thick syrup that was used as such in the next reaction.

LCMS Method 12: RT=2.73 (72.9%); [M+H]$^+$=683/685 (Br pattern) and RT=2.57 (19.5%); [M+H]$^+$=701/703 (Br pattern) product as hydrate.

$^1$H NMR (300 MHz, Chloroform-d) δ 9.81 (s, 1H), 8.86 (d, J=1.5 Hz, 2H), 8.68 (br d, J=8.6 Hz, 1H), 7.99 (d, J=10.6 Hz, 1H), 7.45 (dd, J=6.8, 2.4 Hz, 1H), 7.22-7.09 (m, 3H), 6.66 (t, J=72.2 Hz, 1H), 6.00 (td, J=9.0, 4.7 Hz, 1H), 3.55 (dd, J=17.9, 9.0 Hz, 1H), 3.08 (br d, J=16.9 Hz, 1H), 1.71 (s, 3H), 1.70 (s, 3H), 0.89 (s, 9H), −0.03 (s, 6H).

Intermediate 89

(R)—N—((R)-3-(2-bromo-6-(difluoromethoxy)phenyl)-3-((5-(2-(2-((tert-butyldimethylsilyl)oxy)propan-2-yl)pyrimidin-5-yl)-4-fluoro-2-nitrophenyl) amino)propylidene)-2-methylpropane-2-sulfinamide Titanium (IV) isopropoxide (87 g, 307 mmol, 91 mL) was added to a solution of crude Intermediate 88 (105 g, ~154 mmol) and (R)-(+)-2-methyl-2-propanesulfinamide (18.63 g, 154 mmol) in DCM (180 mL). After stirring overnight, the reaction mixture was poured out into a mixture of water (300 mL) and kieselguhr (30 g), stirred for 10 minutes, and filtered. The yellow solid was washed several times with DCM. The layers of the filtrate were separated and the organic layer was dried over Na$_2$SO$_4$, filtered and concentrated in vacuo yielding the title compound (114.5 g) as a yellow-orange glass that was used as such in the next reaction.

LCMS Method 12: RT=2.88 minutes; [M+H]$^+$=786/788 (Br pattern).

Intermediate 90

(R)—N—((R)-3-(2-bromo-6-(difluoromethoxy)phenyl)-3-((5-(2-(2-((tertbutyldimethylsilyl)oxy)propan-2-yl) pyrimidin-5-yl)-4-fluoro-2-nitrophenyl) amino) propylidene)-2-methylpropane-2-sulfinamide To a stirred solution of crude Intermediate 89 (103.6 g, ~139 mmol) in DCM (500 mL) was added yttrium(III) trifluoromethanesulfonate (3.53 g, 6.58 mmol). The flask was sealed with a suba seal and to the resulting mixture, trimethylsilyl cyanide (15.68 g, 158 mmol, 19.77 mL) was added by syringe in a steady stream. After stirring for 5 days, the reaction mixture was concentrated in vacuo and co-evaporated with EtOAc yielding the title compound (101 g) as a yellow-red foaming oil that was used as such in the next reaction.

LCMS Method 13: RT=2.70 minutes; [M+H]$^+$=813/815 (Br pattern).

Intermediate 91

(R)—N-((3R)-3-((2-amino-5-(2-(2-((tertbutyldimethylsilyl)oxy)propan-2-yl)pyrimidin-5-yl)-4-fluorophenyl)amino)-3-(2-bromo-6-(difluoromethoxy)phenyl)-1-cyanopropyl)-2-methylpropane-2-sulfinamide Under a N₂ atmosphere, platinum on charcoal (10 wt %, 13.88 g, 7.11 mmol) was added to a mixture of crude Intermediate 90 (106 g, ~147 mmol) and zinc(II) bromide (12.46 g, 55.3 mmol) in EtOAc (1000 mL). Subsequently, the reaction was purged with H₂ and stirred under atmospheric H₂ pressure for 3 days. The reaction mixture was flushed with N₂, filtered over kieselguhr and rinsed with EtOAc. The filtrate (~1.5 L) was washed with water (500 mL) and brine, dried over Na₂SO₄, filtered and concentrated in vacuo yielding the title compound (109 g) as a brown-yellow foaming oil that was used as such in the next reaction.

LCMS Method 11: RT=1.360 (76.5%); [M+H]⁺=783/785 (Br pattern).

Intermediate 92

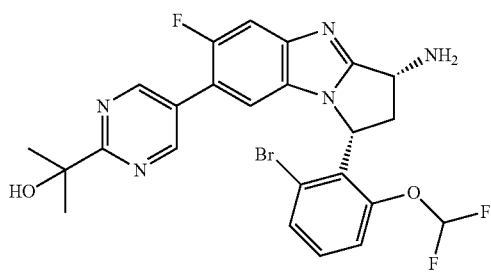 [SMILES: CC(C)(O)c1ncc(-c2cc3c(cc2F)nc2n3[C@@H](c3c(Br)cccc3OC(F)F)C[C@H]2N)cn1]

2-(5-((1R,3R)-3-amino-1-(2-bromo-6-(difluoromethoxy)phenyl)-6-fluoro-2,3-dihydro-1H benzo[d]pyrrolo[1,2-a]imidazol-7-yl)pyrimidin-2-yl)propan-2-ol To a stirred solution of crude Intermediate 91 (109 g, ~147 mmol) in ethanol (1000 mL) was added HCl (4 M in dioxane, 69.5 mL, 278 mmol). The resulting mixture was stirred at reflux for 8 hours and allowed to cool to r.t overnight. The reaction mixture was concentrated in vacuo and co-evaporated with ethanol. The residue was triturated in Et₂O (1.5 L) and the formed precipitate was isolated by filtration, washed with Et₂O, and dried on the filter. This material was taken up in iPrOH (250 mL) and stirred at reflux for 15 minutes. The resulting suspension was stirred under N₂ while allowing to cool to r.t. The resulting thick viscous suspension was diluted with iPrOH (250 mL) and filtered through a glass filter. The residue thus obtained was dissolved in water (1.5 L) and Et₂O (500 mL) while stirring. The layers were separated and the organic layer was extracted with aqueous HCl (0.1 M, 200 mL). The combined aqueous layers were washed with Et₂O (500 mL), made alkaline (pH=10) with NaOH (s, 40 g), and extracted with DCM (2×500 mL). The combined DCM layers were dried over Na₂SO₄, filtered and concentrated in vacuo. The residue thus obtained was co-evaporated with iPr₂O and Et₂O yielding the title compound (40.6 g, 48%) as a green foam.

LCMS Method 10: RT=2.37 minutes; [M+H]⁺=548/550 (Br pattern).

¹H NMR (300 MHz, Chloroform-d): 3:2 mixture of rotamers δ 8.74-8.70 (m, 2H), 7.61 (d, J=8.2 Hz, 0.6H), 7.57 (d, J=11.2 Hz, 1H), 7.45 (dd, J=6.6, 2.6 Hz, 0.4H), 7.37-7.28 (m, 1.4H), 7.04 (d, J=8.3 Hz, 0.6H), 6.71 (t, J=72.4 Hz, 0.4H), 6.59 (dd, J=12.0, 6.6 Hz, 1H), 6.23-6.13 (m, 1H), 5.92 (dd, J=74.5, 70.9 Hz, 0.6H), 4.72 (br s, 1H), 4.61 (br s, 1H), 3.70-3.41 (m, 1H), 2.77 (dt, J=13.5, 8.6 Hz, 0.4H), 2.63 (dt, J=13.7, 7.6 Hz, 0.6H), 2.03 (br s, 2H), 1.62 (s, 3.6H), 1.61 (s, 2.4H).

Intermediate 93

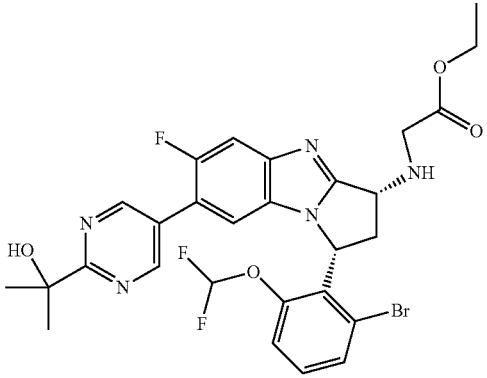 [SMILES: CCOC(=O)CN[C@@H]1C[C@H](c2c(Br)cccc2OC(F)F)n2c1nc1cc(F)c(-c3cnc(C(C)(C)O)nc3)cc12]

Ethyl 2-[[(1R,3R)-1-[2-bromo-6-(difluoromethoxy)phenyl]-6-fluoro-7-[2-(1-hydroxy-1-methyl-ethyl)pyrimidin-5-yl]-2,3-dihydro-1H-pyrrolo[1,2-a]benzimidazol-3-yl]amino]acetate Ethyl bromoacetate (91.3 mg, 0.54 mmol) was added to a solution of potassium carbonate (252 mg, 1.82 mmol), and Intermediate 92 (250 mg, 0.45 mmol) in DMF (1.5 mL). The reaction mixture was stirred at 70° C. for 2 hours. The reaction mixture was cooled to ambient temperature and the crude mixture was quenched with water and extracted with EtOAc (2×5 mL). The organic phase was washed with saturated brine (5 mL), the combined organic phases were dried with sodium sulphate, filtered and concentrated in vacuo to give an oil which was purified by flash chromatography in silica gel (0 to 100% EtOAc in hexanes) to afford the title compound (220 mg, 76% yield) as a brown solid.

LC/MS Method 3: RT 2.06 mins (pH 10), m/z 634/636.

Intermediate 94

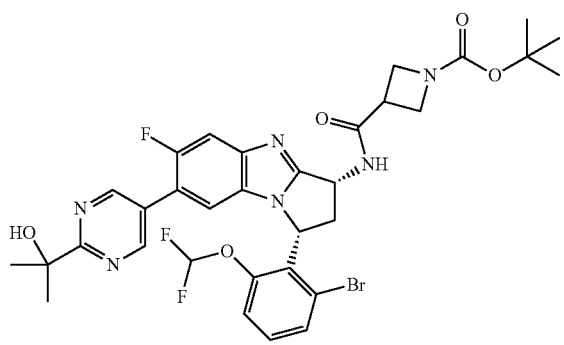 [SMILES: CC(C)(C)OC(=O)N1CC(C(=O)N[C@@H]2C[C@H](c3c(Br)cccc3OC(F)F)n3c2nc2cc(F)c(-c4cnc(C(C)(C)O)nc4)cc23)C1]

tert-butyl 3-[[(1R,3R)-1-[2-bromo-6-(difluoromethoxy)phenyl]-6-fluoro-7-[2-(1-hydroxy-1-methyl-ethyl)pyrimidin-5-yl]-2,3-dihydro-1H-pyrrolo[1,2-a]benzimidazol-3-yl]carbamoyl]azetidine-1-carboxylate Intermediate 92 (550 mg, 1.00 mmol) was added to a solution of 1-tert-butoxycarbonylazetidine-3-carboxylic acid (222 mg, 1.10 mmol), HATU (432 mg, 1.10 mmol) and N,N-di-isopropylethylamine (0.38 mL, 2.2 mmol) in DMF (20 mL). The reaction mixture was stirred at ambient temperature for 3 hours. Water was added and the reaction mixture extracted with EtOAc and the organic phases removed in vacuo to yield a crude product. The crude material was purified by column chromatography over silica gel using hexane/ethyl acetate (0 to 100%) as eluent, yielding 640 mg (87%) of the title compound as an amorphous solid. LCMS basic Method 3: RT 2.25 min, [M+H-BOC]$^+$=631.

Intermediate 95

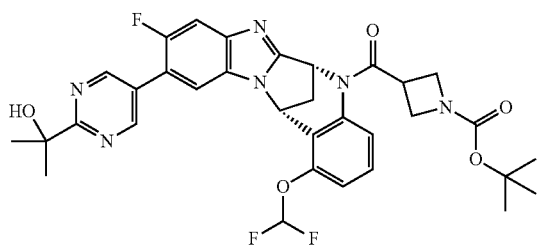 [SMILES: CC(C)(C)OC(=O)N1CC(C(=O)N2c3cccc(OC(F)F)c3[C@H]3C[C@@H]2c2nc4cc(F)c(-c5cnc(C(C)(C)O)nc5)cc4n23)C1]

tert-Butyl 3-{[(6R,12R)-11-(difluoromethoxy)-2-[2-(2-hydroxypropan-2-yl)pyrimidin-5-yl]-6H-6,12-methanobenzimidazo[2,1-c][1,4]benzodiazepin-7(12H)-yl]carbonyl}azetidine-1-carboxylate To Intermediate 94 was added cesium acetate anhydrous (420 mg, 2.18 mmol), cuprous iodide (170 mg, 0.87 mmol) and dimethyl sulfoxide (0.9 mL). The mixture was seal and purged 3 times with nitrogen. The reaction mixture was stirred for 18 hours at 100° C. Water and ethyl acetate were added to the reaction mixture and the two layers were separated. The aqueous layer was extracted with ethyl acetate and the combined organics were filtered through a phase separator and the solvent was evaporated. The crude material was purified by column chromatography over silica gel using hexane/ethyl acetate (0 to 100%) as eluent, yielding 158 mg (28%) of the title compound as a brown solid. LCMS Method 3: RT 2.72 min, [M+H]$^+$=651

Intermediate 96

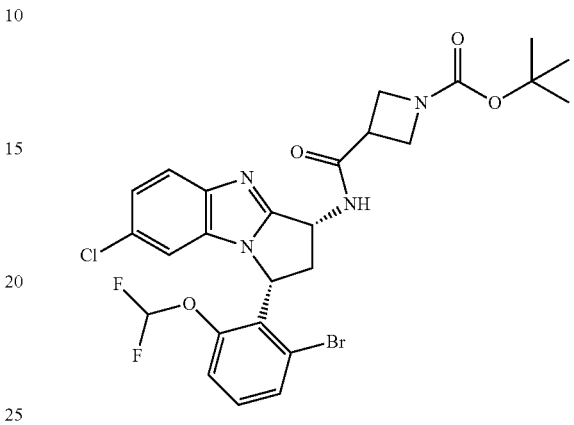

tert-butyl 3-[[(1R,3R)-1-[2-bromo-6-(difluoromethoxy)phenyl]-7-chloro-2,3-dihydro-1H-pyrrolo[1,2-a]benzimidazol-3-yl]carbamoyl]azetidine-1-carboxylate Intermediate 40 (250 mg, 0.58 mmol) was added to a solution of 1-tert-butoxycarbonylazetidine-3-carboxylic acid (130 mg, 0.65 mmol), HATU (252 mg, 0.643 mmol) and N,N-diisopropylethylamine (0.18 mL, 1.0 mmol) in DMF (11 mL). The reaction mixture was stirred at room temperature for 3 hours. Water was added to the reaction and the mixture extracted with EtOAc (×3), dried (sodium sulphate), filtered and concentrated in vacuo. The crude material was purified by column chromatography over silica gel using hexane/ethyl acetate (0 to 100%) as eluent, yielding 280 mg (78%) of the title compound as an amorphous solid.

LCMS Method 3: RT 2.48 minutes, [M+H]$^+$=611/613.

Intermediate 97

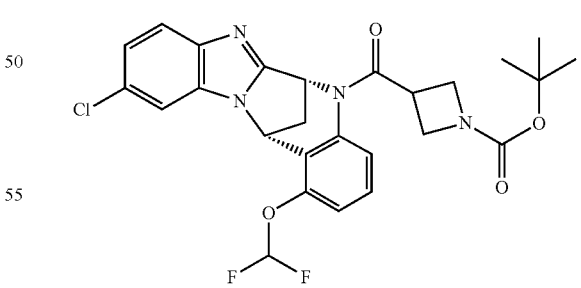

tert-butyl 3-{[(6R,12R)-2-chloro-11-(difluoromethoxy)-6H-6,12-methanobenzimidazo[2,1-c][1,4]benzodiazepin-7(12H)-yl]carbonyl}azetidine-1-carboxylate To Intermediate 96 (165 mg, 0.27 mmol) was added cesium acetate (130 mg, 0.67 mmol), cuprous iodide (52 mg, 0.27 mmol) and dimethyl sulfoxide (0.3 mL). The mixture was sealed in a pressure tube and purged 3 times with nitrogen. The reaction mixture was stirred at 100° C. overnight. Water and ethyl acetate were added to the reaction mixture and the two layers were separated. The aqueous layer was extracted with further ethyl acetate. The combined organic layer was filtered through a phase separator and the solvent was evaporated. The crude material was purified by column chromatography on silica gel using hexane/ethyl acetate (0 to 100%) as eluent, yielding 85 mg (59%) of the title compound as a brown solid. LCMS Method 3: RT 2.63 min., [M+H]$^+$=531/533.

Intermediate 98

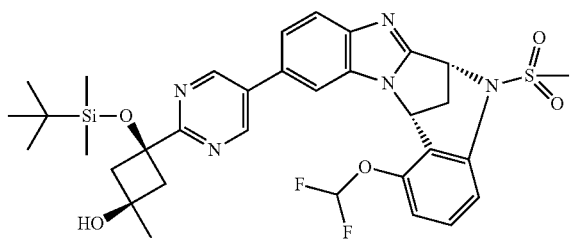 [SMILES: CC(C)(C)[Si](C)(C)O[C@]1(c2ncc(-c3ccc4nc5n(c4c3)[C@@H]3C[C@H]5N(S(C)(=O)=O)c4cccc(OC(F)F)c43)cn2)C[C@](C)(O)C1]

cis-3-{[tert-butyl(dimethyl)silyl]oxy}-3-{5-[(6R,12R)-11-(difluoromethoxy)-7-(methylsulfonyl)-7,12-dihydro-6H-6,12-methanobenzimidazo[2,1-c][1,4]benzodiazepin-2-yl]pyrimidin-2-yl}-1-methylcyclobutanol The title compound was prepared from 3-[tert-butyl(dimethyl)silyl]oxy-1-methyl-3-[5-(4,4,5,5-tetramethyl-1,3,2-dioxaborolan-2-yl)pyrimidin-2-yl], and Example 23 according to a method involving the same procedural steps as those described for Example 20, to give, following purification by column chromatography over silica gel using hexane/ethyl acetate (0 to 100%) as eluent the title compound as a white solid (83 mg, 37% yield).

LC/MS Method 3: RT 2.73 minutes, [M+H]$^+$=684.

Intermediate 99

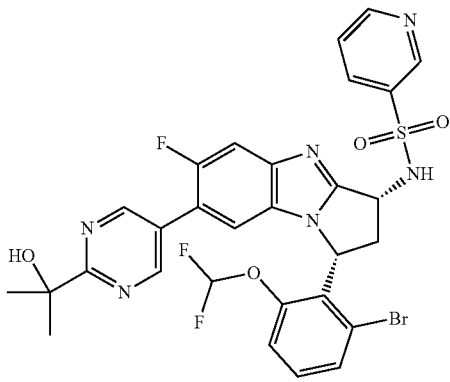 [SMILES: CC(C)(O)c1ncc(-c2cc3c(cc2F)nc2n3[C@@H](c3c(Br)cccc3OC(F)F)C[C@H]2NS(=O)(=O)c2cccnc2)cn1]

N-[(1R,3R)-1-[2-bromo-6-(difluoromethoxy)phenyl]-6-fluoro-7-[2-(1-hydroxy-1-methyl-ethyl)pyrimidin-5-yl]-2,3-dihydro-1H-pyrrolo[1,2-a]benzimidazol-3-yl]pyridine-3-sulfonamide Pyridine-3-sulfonyl chloride (1.1 eq, 0.6 mmol) was added to a solution of Intermediate 92 (300 mg, 0.55 mmol) and N,N-diisopropylethylamine (0.24 mL, 1.3 mmol) in dichloromethane (2.8 mL) at room temperature. The mixture was stirred for 1 hour before solvent was partially evaporated. The crude material was purified by column chromatography on silica gel using hexane/ethyl acetate (0 to 100%) as eluent, yielding 276 mg (73%) of the title compound. LCMS Method 3: RT 1.91 min. (pH 10), [M+H]+ =689.

Intermediate 100

1-[5-(4,4,5,5-tetramethyl-1,3,2-dioxaborolan-2-yl)pyrimidin-2-yl]-3-(trifluoromethyl)azetidin-3-ol To a solution of the trifluoroacetate salt of (trifluoromethyl)-3-aziditin-3-ol (5.8 g, 22.75 mmol) and 2-chloro-5-(4,4,5,5-tetramethyl-1,3,2-dioxaborolan-2-yl)pyrimidine (5 g, 20.75 mmol) in acetonitrile (80 mL) was added dropwise triethylamine (9.5 mL, 68.5 mmol) and the resultant mixture stirred overnight. LC/MS showed completion of reaction, concentrated to an off-white solid, ice-water was added, triturated, filtered, washed with cold water and dried by suction to give the title compound (6.1 g, 50%) as cream solid. $^1$H NMR (400 MHz, DMSO-d6): δ 8.53 (s, 2H), 7.46 (s, 1H), 4.32 (m, 2 H), 4.10 (d, J=10.3 Hz, 2H), 1.29 (s, 12H). LC/MS Method 3: m/z 346, RT 1.09 min (pH=10).

Intermediate 101

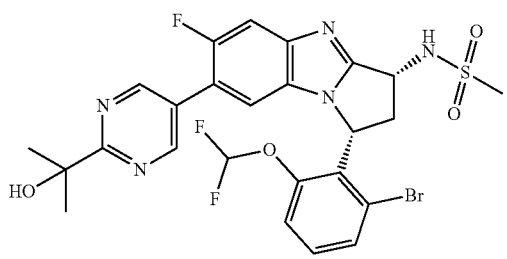 [SMILES: CC(C)(O)c1ncc(-c2cc3c(cc2F)nc2n3[C@@H](c3c(Br)cccc3OC(F)F)C[C@H]2NS(C)(=O)=O)cn1]

N-[(1R,3R)-1-[2-bromo-6-(difluoromethoxy)phenyl]-6-fluoro-7-[2-(1-hydroxy-1-methyl-ethyl)pyrimidin-5-yl]-2,3-dihydro-1H-pyrrolo[1,2-a]benzimidazol-3-yl]methanesulfonamide To a solution of Intermediate 92 (202 mg, 0.37 mmol) and 4-dimethylaminopyridine (6 mg, 0.05 mmol) in DCM (4 mL) at 0° C. was added N,N-diisopropylethylamine (76 μL, 0.43 mmol) followed by methanesulfonyl chloride (30 μL, 0.38 mmol). The reaction mixture was stirred at 0° C. for 10 minutes and then at room temperature for 45 minutes, after which time the reaction mixture was concentrated in vacuo. The residue was purified by column chromatography (SiO$_2$, 25-100% EtOAc in hexane) to give the title compound (193 mg, 83%) as a yellow solid.

LCMS Method 3: (ES+) 626/628 (M+H)$^+$, RT 1.90 minutes.

LCMS Method 4: (ES+) 626/628 (M+H)⁺, RT 1.86 minutes.

Intermediate 102

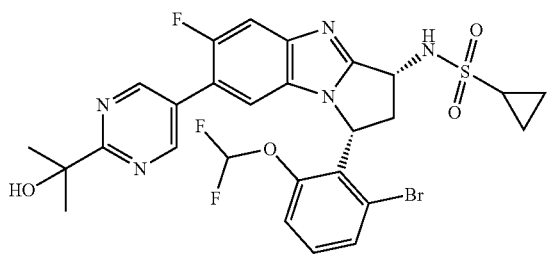 [SMILES: CC(C)(O)c1ncc(-c2cc3c(cc2F)nc2n3[C@@H](c3c(Br)cccc3OC(F)F)C[C@H]2NS(=O)(=O)C2CC2)cn1]

N-[(1R,3R)-1-[2-bromo-6-(difluoromethoxy)phenyl]-6-fluoro-7-[2-(1-hydroxy-1-methyl-ethyl)pyrimidin-5-yl]-2,3-dihydro-1H-pyrrolo[1,2-a]benzimidazol-3-yl]cyclopropanesulfonamide To a solution of Intermediate 92 (151 mg, 0.28 mmol) and 4-dimethylaminopyridine (5 mg, 0.04 mmol) in DCM (3 mL) at 0° C. was added N,N-diisopropylethylamine (58 µL, 0.33 mmol) followed by cyclopropanesulfonyl chloride (172 µL, 1.65 mmol). The reaction mixture was stirred at 0° C. for 10 minutes and then at room temperature for 18 hours, after which time the reaction mixture was partitioned between DCM (30 mL) and water (20 mL), the layers separated and the aqueous extracted with DCM (3×20 mL). The combined organics were dried (phase separator), and concentrated in vacuo. The residue was purified by column chromatography (SiO₂, 25-100% EtOAc in hexane) to give the title compound (110 mg, 61%) as a purple solid.

LCMS (ES+) Method 3: 652/654 (M+H)⁺, RT 2.20 minutes.
LCMS (ES+) Method 4: 652/654 (M+H)⁺, RT 2.01 minutes.

Intermediate 103

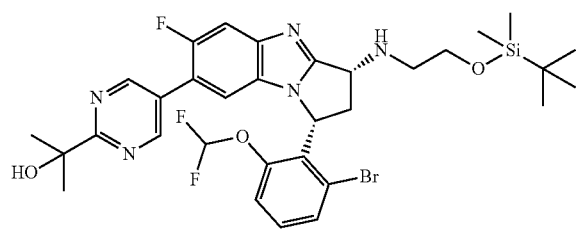 [SMILES: CC(C)(O)c1ncc(-c2cc3c(cc2F)nc2n3[C@@H](c3c(Br)cccc3OC(F)F)C[C@H]2NCCO[Si](C)(C)C(C)(C)C)cn1]

2-[5-[(1R,3R)-1-[2-bromo-6-(difluoromethoxy)phenyl]-3-[2-[tert-butyl(dimethyl)silyl]oxoethylamino]-6-fluoro-2,3-dihydro-1H-pyrrolo[1,2-a]benzimidazol-7-yl]pyrimidin-2-yl]propan-2-ol To a solution of Intermediate 92 (251 mg, 0.46 mmol) and potassium carbonate (252 mg, 1.82 mmol) in DMF (2 mL) was added (2-bromoethoxy)-tert-butyldimethylsilane (99 µL, 0.46 mmol) and reaction mixture stirred at 70° C. for 18 hours. The reaction mixture was partitioned between EtOAc (25 mL) and water (25 mL), layers separated and aqueous extracted with EtOAc (2×25 mL), the combined organics dried (phase separator) and concentrated in vacuo. The residue was purified by column chromatography (SiO₂, 0-100% EtOAc in hexane) to give the title compound (128 mg, 39%) as a brown oil.

LCMS (ES+) Method 3: 706/708 (M+H)⁺, RT 3.10 minutes.

Intermediate 104

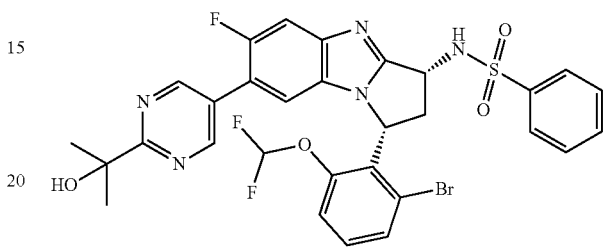

N-[(1R,3R)-1-[2-bromo-6-(difluoromethoxy)phenyl]-6-fluoro-7-[2-(1-hydroxy-1-methyl-ethyl)pyrimidin-5-yl]-2,3-dihydro-1H-pyrrolo[1,2-a]benzimidazol-3-yl]benzenesulfonamide To a solution of Intermediate 92 (202 mg, 0.37 mmol) and 4-dimethylaminopyridine (5 mg, 0.04 mmol) in DCM (4 mL) at 0° C. was added N,N-diisopropylethylamine (77 µL, 0.44 mmol) followed by benzenesulfonyl chloride (49 µL, 0.38 mmol). The reaction mixture was stirred at 0° C. for 5 minutes and then at room temperature for 1.5 hours. The reaction mixture was concentrated in vacuo and the residue purified by column chromatography (SiO₂, 0-60% EtOAc in hexane) to give the title compound (178 mg, 70%) as a yellow solid.

LCMS (ES+) Method 3: 688/690 (M+H)⁺, RT 2.20 minutes.
LCMS (ES+) Method 4: 688/690 (M+H)⁺, RT 2.01 minutes.

Intermediate 105

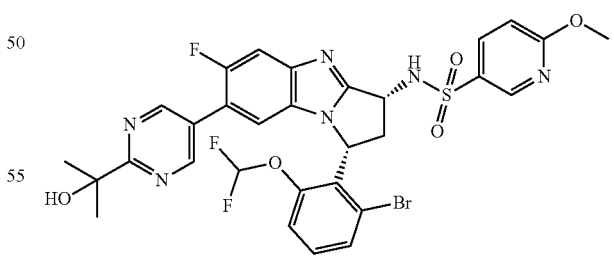

N-[(1R,3R)-1-[2-bromo-6-(difluoromethoxy)phenyl]-6-fluoro-7-[2-(1-hydroxy-1-methyl-ethyl)pyrimidin-5-yl]-2,3-dihydro-1H-pyrrolo[1,2-a]benzimidazol-3-yl]-6-methoxy-pyridine-3-sulfonamide To a solution of Intermediate 92 (150 mg, 0.27 mmol) and 4-dimethylaminopyridine (5 mg, 0.04 mmol) in DMF (3 mL) at 0° C. was added N,N-diisopropylethylamine (57 µL, 0.33 mmol) followed by 6-methoxypyridine-3-sulfonyl chloride (62 mg, 0.29 mmol). The reaction mixture was stirred at 0° C. for 5 minutes and then at room temperature 30 minutes. The reaction mixture was concentrated in vacuo. The residue was purified by column chromatography (SiO$_2$, 0-100% EtOAc in hexane) to give the title compound (148 mg, 75%) as a dark beige solid. LCMS (ES+) Method 3: 719/721 (M+H)$^+$, RT 2.30 minutes. LCMS (ES+) Method 4: 719/721 (M+H)$^+$, RT 2.42 minutes. δ$_H$ (300 MHz, DMSO-d$_6$) 8.77-8.97 (m, 1H), 8.71-8.77 (m, 3H), 8.19-8.26 (m, 1H), 7.59-7.68 (m, 1H), 7.39-7.50 (m, 2H), 7.38 (t, 1H, J 73.4 Hz), 7.07 (d, 1H, J 8.7 Hz), 6.65-6.71 (m, 1H), 6.04-6.21 (m, 1H), 5.22-5.44 (m, 1H), 5.05-5.07 (m, 1H), 3.96 (s, 3H), 3.05-3.24 (m, 1H), 2.59-2.79 (m, 1H), 1.47-1.52 (m, 6H).

Intermediate 106

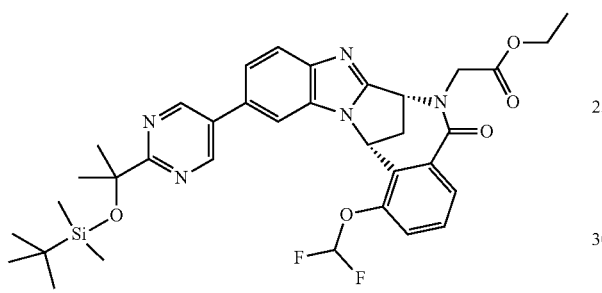

Ethyl [(7R,14R)-11-[2-(2-{[tert-butyl(dimethyl)silyl]oxy}propan-2-yl)pyrimidin-5-yl]-1-(difluoromethoxy)-5-oxo-5,14-dihydro-7,14-methanobenzimidazo[1,2-b][2,5]benzodiazocin-6(7H)-yl]acetate To a solution of Intermediate 23 (100 mg, 0.169 mmol) in THF (4 mL) was added potassium bis(trimethylsilyl)amide (0.2 mL, 0.2 mmol, 1M in THF) at −78° C. and stirred for 40 minutes before the addition of ethyl bromoacetate (25.0 µL, 0.225 mmol). The reaction mixture was stirred at −78° C. for 30 mins before being quenched with water. The mixture was extracted with DCM (2×20 mL), and the organics were combined, dried with Na$_2$SO$_4$, filtered and concentrated in vacuo. The crude product was columned on silica eluting with 0-5% MeOH/DCM to give the title compound (88 mg). LC/MS: Method 3: RT 3.53 minutes.

Intermediate 107

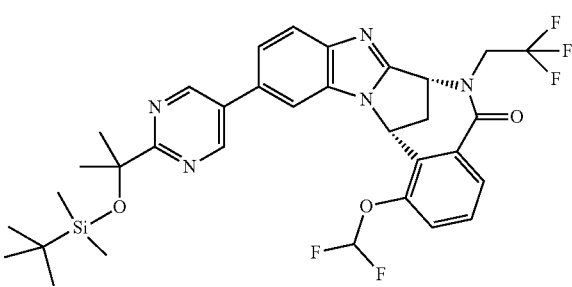 [SMILES: CC(C)(O[Si](C)(C)C(C)(C)C)c1ncc(-c2ccc3nc4n(c3c2)[C@@H]2C[C@H]4N(CC(F)(F)F)C(=O)c3cccc(OC(F)F)c32)cn1]

(7R,14R)-11-[2-(2-{[tert-butyl(dimethyl)silyl]oxy}propan-2-yl)pyrimidin-5-yl]-1-(difluoromethoxy)-6-(2,2,2-trifluoroethyl)-6,7-dihydro-7,14-methanobenzimidazo[1,2-b][2,5]benzodiazocin-5(14H)-one To a solution of Intermediate 23 (90.0 mg, 0.152 mmol) in DMF (3.5 mL) were added cesium carbonate (250 mg, 0.767 mmol) and 2-iodo-1,1,1-trifluoroethane (0.06 mL, 0.60 mmol) at ambient temperature. The reaction mixture was heated at 150° C. for 3 hours. The reaction mixture was partitioned between EtOAc (2×10 mL) and water (20 mL), and the organics were combined, dried with Na$_2$SO$_4$, filtered and concentrated in vacuo. The crude product was progressed to the next step without further purification.

LC/MS: Method 3 MH$^+$ 674, retention time 2.03 minutes.

Intermediate 108

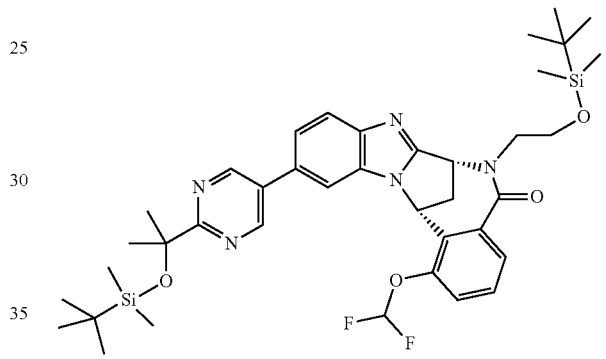

(7R,14R)-6-(2-{[tert-butyl(dimethyl)silyl]oxy}ethyl)-11-[2-(2-{[tert-butyl(dimethyl)silyl]oxy}propan-2-yl)pyrimidin-5-yl]-1-(difluoromethoxy)-6,7-dihydro-7,14-methanobenzimidazo[1,2-b][2,5]benzodiazocin-5(14H)-one To a solution of Intermediate 23 (100.0 mg, 0.169 mmol) in THF (4.0 mL) was added potassium bis(trimethylsilyl)amide (0.20 mL, 0.20 mmol, 1M in THF) at −78° C. followed by the addition of (2-bromoethoxy)-tert-butyldimethylsilane (50.0 µL, 0.231 mmol). The reaction mixture was heated in a microwave at 70° C. for 24 hours before being quenched with aqueous saturated NH$_4$Cl and extracted with EtOAc (2×10 mL). The organics were combined, dried with Na$_2$SO$_4$, filtered and concentrated in vacuo. The crude product was progressed to the next step without further purification. LC/MS Method 3: ESI MH+750, retention time 4.23 minutes.

Intermediate 109

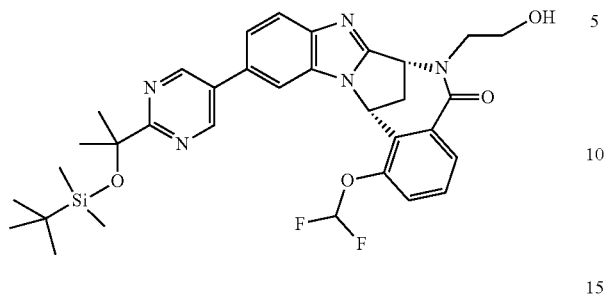

(7R,14R)-11-[2-(2-{[tert-butyl(dimethyl)silyl]oxy}propan-2-yl)pyrimidin-5-yl]-1-(difluoromethoxy)-6-(2-hydroxyethyl)-6,7-dihydro-7,14-methanobenzimidazo[1,2-b][2,5]benzodiazocin-5(14H)-one To a solution of Intermediate 108 (80.0 mg, 0.107 mmol) in THF (5.0 mL) was added a solution of tetrabutylammonium fluoride (0.20 mL, 0.20 mmol, 1M in THF) at ambient temperature and the mixture was stirred for 72 hours. The reaction mixture was partitioned between water (10 mL) and DCM (3×10 mL), and the organics were combined, dried with Na$_2$SO$_4$, filtered and concentrated in vacuo. The crude product was progressed to the next step.

LC/MS Method 3: ESI MH$^+$ 636, retention time 3.21 minutes.

Intermediate 110

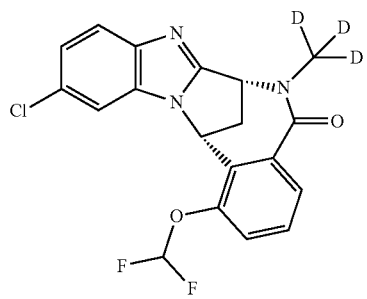 [SMILES: [2H]C([2H])([2H])N1C(=O)c2cccc(OC(F)F)c2[C@H]2C[C@@H]1c1nc3ccc(Cl)cc3n12]

(7R,14R)-11-chloro-1-(difluoromethoxy)-6-(trideutero)methyl-6,7-dihydro-7,14-methanobenzimidazo[1,2-b][2,5]benzodiazocin-5(14H)-one To a solution of Example 11 (90.0 mg, 0.24 mmol) in THF (4 mL) was added a solution of KHMDS in THF (1M, 0.25 mL, 0.25 mmol) dropwise at −78° C. and the mixture was stirred for 30 minutes before the addition of CD$_3$I (30.1 μL, 0.48 mmol). The reaction mixture was warmed to 0° C. and stirred for 3 hours. The reaction mixture was quenched with saturated aqueous NH$_4$Cl solution, extracted with EtOAc, dried with Na$_2$SO$_4$, filtered and concentrated in vacuo. The crude product was purified by column chromatography on silica eluting with 0-10% MeOH/EtOAc to give the title compound (95 mg, 99%). LC/MS Method 3: ESI MH$^+$ 393, retention time 1.93 minutes.

Intermediate 111

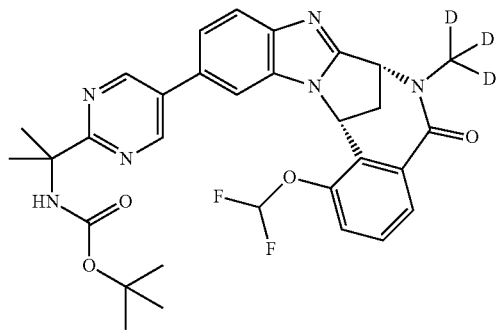 [SMILES: [2H]C([2H])([2H])N1C(=O)c2cccc(OC(F)F)c2[C@H]2C[C@@H]1c1nc3ccc(-c4cnc(C(C)(C)NC(=O)OC(C)(C)C)nc4)cc3n12]

tert-butyl (2-{5-[(7R,14R)-1-(difluoromethoxy)-6-(trideutero)methyl-5-oxo-5,6,7,14-tetrahydro-7,14-methanobenzimidazo[1,2-b][2,5]benzodiazocin-11-yl]pyrimidin-2-yl}propan-2-yl)carbamate To a solution of tert-butyl N-[1-methyl-1-[5-(4,4,5,5-tetramethyl-1,3,2-dioxaborolan-2-yl)pyrimidin-2-yl]ethyl]carbamate (260 mg, 0.72 mmol) and Intermediate 110 (94 mg, 0.24 mmol) in 1,4-dioxane (3 mL) were added K$_3$PO$_4$ (294 mg, 1.40 mmol), tricyclohexyl phosphonium tetrafluoroborate (15 mg, 0.04 mmol) and tris(dibenzylideneacetone)dipalladium(0) (28 mg, 0.03 mmol) were added. The mixture was degassed for 10 minutes with nitrogen before heating at 110° C. for 18 hours. The reaction mixture was quenched with water and extracted with EtOAc (2×10 mL), dried with Na$_2$SO$_4$, filtered and concentrated in vacuo. The crude product was purified by column chromatography on silica eluting with 0-10% MeOH/DCM to give the title compound (40 mg, 28%). LC/MS Method 3: ESI MH$^+$ 594, retention time 2.10 minutes.

Intermediate 112

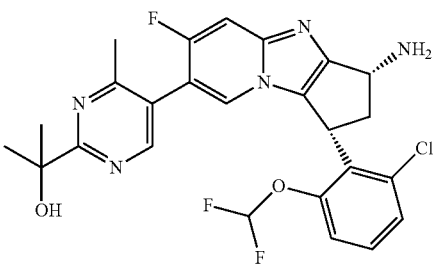 [SMILES: Cc1nc(C(C)(C)O)ncc1-c1cn2c3c(nc2cc1F)[C@H](N)C[C@@H]3c1c(Cl)cccc1OC(F)F]

rac 2-(5-{(1R,3R)-3-amino-1-[2-chloro-6-(difluoromethoxy)phenyl]-6-fluoro-2,3-dihydro-1H-cyclopenta[4,5]imidazo[1,2-a]pyridin-7-yl}-4-methylpyrimidin-2-yl)propan-2-ol Intermediate 61 (0.15 g, 0.6 mmol) and potassium acetate (0.15 g, 1.5 mmol) were suspended in anhydrous 1,4-dioxane (5 mL) in a sealable vessel. The mixture was stirred and degassed thoroughly under a stream of N$_2$(g) for 15 min then treated with bis[3-(diphenylphosphanyl)cyclopenta-2,4-dien-1-yl]iron; dichloromethane; dichloropalladium (0.02 g, 0.02 mmol), and a solution of Intermediate 71 (82%, 0.25 g, 0.4 mmol) in a mixture of dioxane (1 mL) and 2M K$_2$CO$_3$ in water (1.24 ml) was added and the mixture warmed to 100° C. overnight. After cooling to room temperature the mixture was diluted with EtOAc (25 mL) and filtered over a pad of celite. The filtrated was washed with water (10 mL), dried (MgSO$_4$), filtered and concentrated in vacuo to give the crude product (0.4 g) as a brown gum. Column chromatography (C18, biotgae isolera, 60 g) eluting with 0 to 50% acetonitrile in water spiked with 0.1% NH$_4$OH afforded the title compound (0.15 g, 58%) as an orange glass. The material was azeotroped twice with toluene prior to use in the subsequent step. Method 8 HPLC-MS: MH+ m/z 518, RT 1.43 minutes. $^1$H NMR (500 MHz, DMSO-d$_6$) δ 8.56-8.51 (m, 1H), 7.99-7.77 (m, 1H), 7.63-7.53 (m, 1H), 7.43-7.31 (m, 2H), 7.29-7.24 (m, 1H), 7.06-6.73 (m, 1H), 5.10-4.90 (m, 2H), 4.47-4.31 (m, 1H), 3.52-3.40 (m, 1H), 2.34-2.27 (m, 3H), 2.03-1.81 (m, 3H), 1.52-1.45 (m, 6H).

Intermediate 113

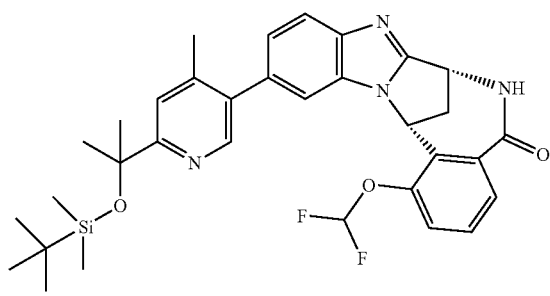 [SMILES: Cc1cc(C(C)(C)O[Si](C)(C)C(C)(C)C)ncc1-c1ccc2nc3n(c2c1)[C@@H]1C[C@H]3NC(=O)c2cccc(OC(F)F)c21]

(7R,14R)-11-[6-(2-{[tert-butyl(dimethyl)silyl]oxy}propan-2-yl)-4-methylpyridin-3-yl]-1-(difluoromethoxy)-6,7-dihydro-7,14-methanobenzimidazo[1,2-b][2,5]benzodiazocin-5(14H)-one The title compound was prepared from Example 11 (450 mg, 1.20 mmol) and tert-butyl-dimethyl-[1-methyl-1-[4-methyl-5-(4,4,5,5-tetramethyl-1,3,2-dioxaborolan-2-yl)-2-pyridyl]ethoxy]silane (483 mg, 1.86 mmol), by a palladium catalyzed Suzuki coupling according to a method involving the same procedural steps as those described for Example 20. The crude product was purified by flash chromatography (SiO$_2$, 0 to 100% EtOAc in DCM and then 1 to 10% MeOH in EtOAc) to obtain the title compound (650 mg, 81%) as a brown solid. LCMS Method 3 (ES+) RT 3.20 min, 605 (M+H)$^+$.

Intermediate 114 tert-butyl N-[1-(5-bromopyrimidin-2-yl)-1-methylethyl]carbamate 2-(5-bromopyrimidin-2-yl)propan-2-amine (200 mg, 0.92 mmol) was dissolved in THF (5 mL) and di-tert-butyl dicarbonate solution (1.0M) (1.3 mL, 1.3 mmol) in THF added. After 2 hours the solvents were removed in vacuo to afford the title compound as an orange gum (300 mg, 92%). LCMS Method 3 (ES+) RT 1.88 min, 338.0/340.0 (M+Na)$^+$.

Intermediate 115

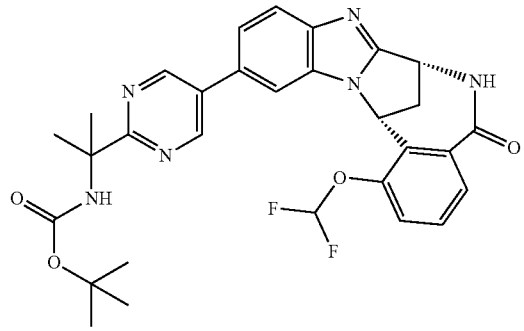 [SMILES: CC(C)(C)OC(=O)NC(C)(C)c1ncc(-c2ccc3nc4n(c3c2)[C@@H]2C[C@H]4NC(=O)c3cccc(OC(F)F)c32)cn1]

tert-butyl (2-{5-[(7R,14R)-1-(difluoromethoxy)-5-oxo-5,6,7,14-tetrahydro-7,14-methanobenzimidazo[1,2-b][2,5]benzodiazocin-11-yl]pyrimidin-2-yl}propan-2-yl)carbamate The title compound was prepared from Example 11 (300 mg, 0.80 mmol) and Intermediate 114 (252 mg, 0.80 mmol) in accordance with the Method described for Example 70. The crude product was purified by flash chromatography in (SiO$_2$, 0 to 100% EtOAc in DCM and then 1 to 10% MeOH in EtOAc) to obtain the title compound (154 mg, 33%).

LCMS Method 3 (ES+) RT 1.43 min, 577.2 (M+H)$^+$

Intermediate 116

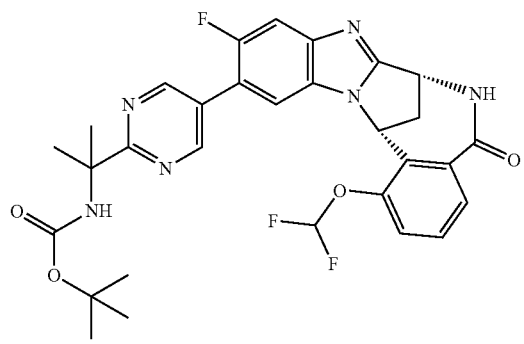 [SMILES: CC(C)(C)OC(=O)NC(C)(C)c1ncc(-c2cc3c(cc2F)nc2n3[C@@H]3C[C@H]2NC(=O)c2cccc(OC(F)F)c23)cn1]

tert-butyl (2-{5-[(7R,14R)-1-(difluoromethoxy)-10-fluoro-5-oxo-5,6,7,14-tetrahydro-7,14-methanobenzimidazo[1,2-b][2,5]benzodiazocin-11-yl]pyrimidin-2-yl}propan-2-yl)carbamate The title compound was prepared from Example 10 (50 mg, 0.13 mmol) and Intermediate 114 (100 mg, 0.32 mmol) in accordance with the Method described for Example 70. The product was purified by flash chromatography (SiO$_2$, 0 to 100% EtOAc in DCM and then 1 to 10% MeOH in EtOAc) to obtain the title compound (55 mg, 71%). LCMS Method 3 (ES+) RT 2.16 min, 595.2 (M+H)$^+$

Intermediate 117

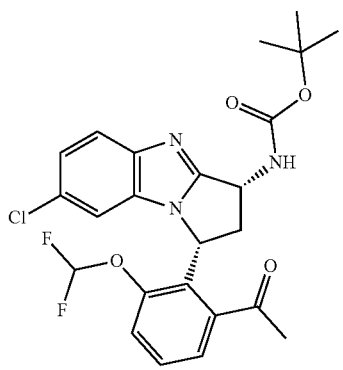 [SMILES: CC(=O)c1cccc(OC(F)F)c1[C@H]1C[C@@H](NC(=O)OC(C)(C)C)c2nc3ccc(Cl)cc3n21]

tert-butyl {(1R,3R)-1-[2-acetyl-6-(difluoromethoxy)phenyl]-7-chloro-2,3-dihydro-1H-pyrrolo[1,2-a]benzimidazol-3-yl}carbamate To a degassed solution of Intermediate 42 (1.4 g, 2.6 mmol) in dry toluene (30 mL) under argon were added tributyl(1-ethoxyvinyl)tin (1.1 mL g, 3.2 mmol) and bis(triphenylphosphine)-palladium(II)dichloride (100 mg, 0.141 mmol). The reaction mixture was heated at 105° C. for 48 hours. Further Tributyl(1-ethoxyvinyl)tin (0.7 g, 2.0 mmol) and bis(triphenylphosphine)palladium(II)-dichloride (64 mg, 0.0912 mmol) were added and the reaction mixture was heated for an additional 5 hours at 105° C. The reaction mixture was cooled to room temperature and poured onto a saturated aqueous solution of KF. The mixture was extracted with ethyl acetate, filtered over celite, dried over $MgSO_4$, filtered and concentrated in vacuo. The crude compound was re-dissolved in THF (50 mL), p-toluene sulfonic acid (200 mg) and water (5 mL) was added and the mixture was heated at 45° C. for 5 hours. The mixture was poured onto ice, neutralized with solid $NaHCO_3$ and extracted with ethyl acetate (×3). The combined organic layers were dried over $MgSO_4$, filtered and evaporated to dryness. The crude compound was purified by flash chromatography with ethyl acetate 50%-heptane 50% to afford 1.27 g of the title compound as a yellow solid. LCMS Method 3 basic (ES+) RT 2.75 min. 492.1 $(M+H)^+$.

Intermediate 118

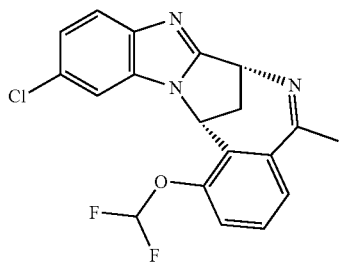 [SMILES: CC1=N[C@@H]2C[C@H](c3c(OC(F)F)cccc31)n1c2nc2ccc(Cl)cc21]

(7R,14R)-11-chloro-1-(difluoromethoxy)-5-methyl-7,14-dihydro-7,14-methanobenzimidazo[1,2-b][2,5]benzodiazocine A solution of Intermediate 117 (0.48 g, 0.976 mmol) in dichloromethane (10 mL) was cooled to 0° C. and trifluoroacetic acid (10 mL) was added dropwise. The reaction mixture was stirred overnight at room temperature. The mixture was poured on ice, brought to neutral pH with solid $NaHCO_3$ and extracted with dichloromethane (×3). The combined organic layers were dried over $MgSO_4$, filtered and concentrated in vacuo to afford 0.25 g (65%) of the title compound. LCMS basic Method 3 (ES+) RT 2.42 min., 374.1 $(M+H)^+$.

Intermediate 119

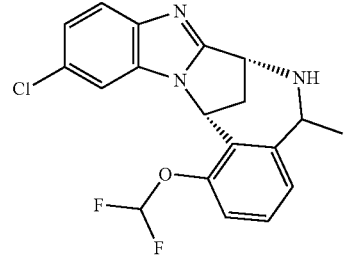 [SMILES: CC1N[C@@H]2C[C@H](c3c(OC(F)F)cccc31)n1c2nc2ccc(Cl)cc21]

(7R,14R)-11-chloro-1-(difluoromethoxy)-5-methyl-5,6,7,14-tetrahydro-7,14-methanobenzimidazo[1,2-b][2,5]benzodiazocine To a solution of Intermediate 118 (350 mg, 0.893 mmol) in a mixture of THF (8 mL) and EtOH (8 mL) were added macroporous polymer-supported cyanoborohydride (1.12 g, 4.4 mmol, 4.0 mmol/g loading) and acetic acid (50 µL). The reaction mixture was stirred overnight at room temperature. The reaction mixture was filtered over celite and concentrated in vacuo. The residue was poured onto ice/water and solid $NaHCO_3$ was added till pH=9. The aqueous phase was extracted with DCM (×3), the combined organic layers dried over $MgSO_4$, filtered and concentrated to dryness. The crude compound was purified by normal phase chromatography (DCM 95%-MeOH 5%) to afford 237 mg (71%) of the title compound as a mixture of diastereomers. LCMS Method 3 basic (ES+) RT 1.99 min., 376.1 $(M+H)^+$.

Intermediates 120 and 121

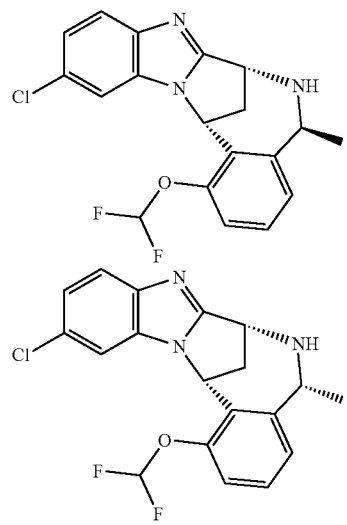

141

(5R,7R,14R)-11-chloro-1-(difluoromethoxy)-5-methyl-5,6,7,14-tetrahydro-7,14-methanobenzimidazo[1,2-b][2,5]benzodiazocine (5S,7R,14R)-11-chloro-1-(difluoromethoxy)-5-methyl-5,6,7,14-tetrahydro-7,14-methanobenzimidazo[1,2-b][2,5]benzodiazocine The title compounds were isolated from Intermediate 119 (0.118 g) by purification under SFC conditions on Chiralpak OD-A20 column (50*266, 360 mL/min, 25° C., CO$_2$+20% iPrOH, con: 24 g/l), yielding 37 mg (31%) of Intermediate 120 (RT 3.65 min) and 40.0 mg (34%) of Intermediate 121 (RT 7.57 min) respectively.

Intermediate 120: LCMS Method 4 (ES+) RT 2.18 min., 376.2 (M+H)$^+$.

Intermediate 121: LCMS Method 4 (ES+) RT 2.14 min., 376.2 (M+H)$^+$.

Intermediate 122

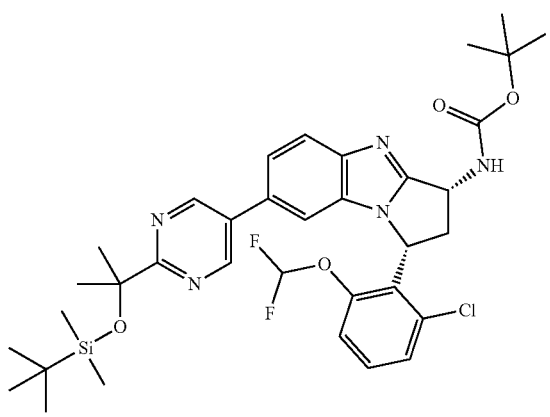 [SMILES: CC(C)(C)OC(=O)N[C@@H]1C[C@H](c2c(Cl)cccc2OC(F)F)n2c1nc1ccc(-c3cnc(C(C)(C)O[Si](C)(C)C(C)(C)C)nc3)cc12]

tert-butyl {(1R,3R)-7-[2-(2-{[tert-butyl(dimethyl)silyl]oxy}propan-2-yl)pyrimidin-5-yl]-1-[2-chloro-6-(difluoromethoxy)phenyl]-2,3-dihydro-1H-pyrrolo[1,2-a]benzimidazol-3-yl}carbamate Intermediate 22 (5 g, 8,331 mmol) was suspended in DCM (10 mL) and cooled on an ice bath. Triethylamine (2.6 mL, 18.33 mmol) and di-tert-butyl dicarbonate (2.2 g, 10.0 mmol) were added. The reaction was warmed to ambient temperature and stirred overnight. The reaction mixture was quenched by addition of water (10 mL). The aqueous layer was extracted by DCM (3×10 mL). The combined organic layers were dried over MgSO4, filtered and concentrated in vacuum. The residue was purified over silica gel (eluting with heptane/ethyl acetate 7/3) to afford 5.1 g (87%) of the title compound as a white solid.

LCMS Method 3 (ES+) RT 3.64 min., 700.3/702.3 (M+H)$^+$

142

Intermediate 123

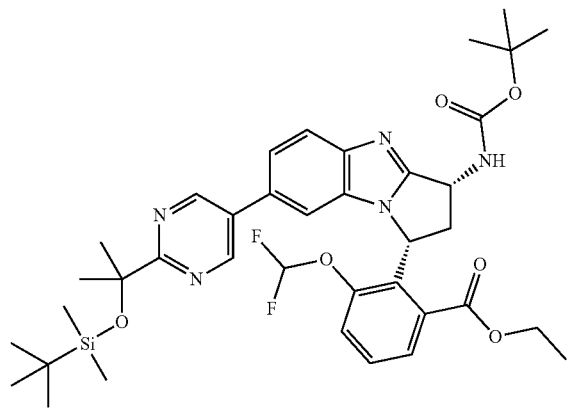 [SMILES: CCOC(=O)c1cccc(OC(F)F)c1[C@H]1C[C@@H](NC(=O)OC(C)(C)C)c2nc3ccc(-c4cnc(C(C)(C)O[Si](C)(C)C(C)(C)C)nc4)cc3n21]

Ethyl 2-{(1R,3R)-3-[(tert-butoxycarbonyl)amino]-7-[2-(2-{[tert-butyl(dimethyl)silyl]oxy}propan-2-yl)pyrimidin-5-yl]-2,3-dihydro-1H-pyrrolo[1,2-a]benzimidazol-1-yl}-3-(difluoromethoxy)benzoate Intermediate 122 (5 g, 7.14 mmol), potassium carbonate (1.50 g, 10.71 mmol), molecular sieve 4 A° powder (2 g) and dichloro[bis(dicyclohexylphosphino)propane]-palladium (II) (350 mg, 0.57 mmol) were suspended in dry dimethyl sulfoxide (50 mL) and ethanol (1.8 mL, 32 mmol). The slurry was stirred under 5 bars of CO gas at 100° C., overnight. The slurry was filtered through a pad of celite and rinsed with ethyl acetate (30 mL). The filtrate was washed successively by a saturated solution of aqueous NH$_4$Cl (20 mL), brine (20 mL), dried over MgSO$_4$, filtered and concentrated in vacuum affording 5.1 g of the crude title compound as a brown solid, used without further purification. LCMS Method 3 (ES+) RT 3.64 min., 738.1 (M+H)$^+$.

Intermediate 124

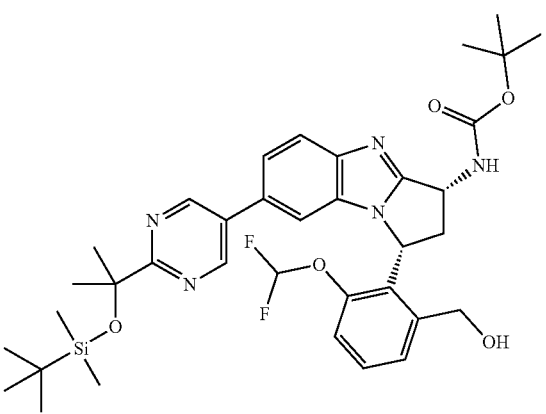 [SMILES: CC(C)(C)OC(=O)N[C@@H]1C[C@H](c2c(CO)cccc2OC(F)F)n2c1nc1ccc(-c3cnc(C(C)(C)O[Si](C)(C)C(C)(C)C)nc3)cc12]

tert-butyl {(1R,3R)-7-[2-(2-{[tert-butyl(dimethyl) silyl]oxy}propan-2-yl)pyrimidin-5-yl]-1-[2-(difluoromethoxy)-6-(hydroxymethyl)phenyl]-2,3-dihydro-1H-pyrrolo[1,2 a]benzimidazol-3-yl}carbamate Intermediate 123 6 (3 g) was dissolved in ethanol (30 mL). At 0° C., sodium borohydride (1.2 g) was added, followed by calcium chloride (1.805 g). The reaction mixture was warmed to room temperature and stirred for 4 hours. The reaction mixture was filtered through a pad of celite, and rinsed with ethyl acetate (2×20 mL). The filtrate was washed with water (2×20 mL) and brine (20 mL), and dried over MgSO$_4$. The residue was purified by basic reverse phase preparative HPLC yielding 948 mg (33%) of the title compound as a white solid. LCMS Method 3 (ES+) RT 3.45 minutes 696.3 (M+H)$^+$.

Intermediate 125

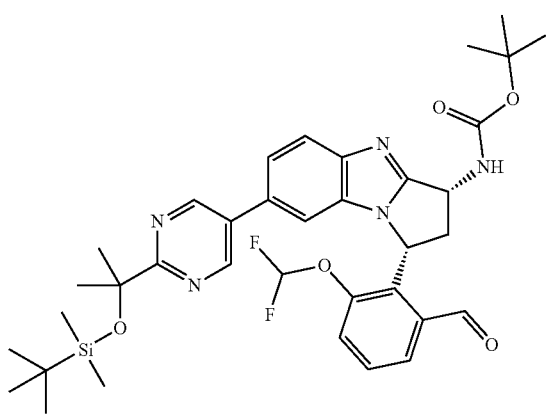 [SMILES: CC(C)(C)OC(=O)N[C@@H]1C[C@H](c2c(C=O)cccc2OC(F)F)n2c1nc1ccc(-c3cnc(C(C)(C)O[Si](C)(C)C(C)(C)C)nc3)cc12]

tert-butyl {(1R,3R)-7-[2-(2-{[tert-butyl(dimethyl) silyl]oxy}propan-2-yl)pyrimidin-5-yl]-1-[2-(difluoromethoxy)-6-formylphenyl]-2,3-dihydro-H-pyrrolo[1,2-a]benzimidazol-3-yl}carbamate Intermediate 124 (750 mg, 1.08 mmol) was dissolved in 1,4-dioxane (16 mL) before addition of manganese dioxide (2.3 g, 27 mmol) at room temperature. The reaction was stirred overnight. The crude reaction mixture was filtered through a pad of celite and rinsed with 20 mL of chloroform. The filtrate was concentrated to dryness in vacuum yielding to a crude 860 mg of title compound used without further purification. LCMS Method 3 basic (ES+) RT 5.85 minutes. 694.4 (M+H)$^+$.

Intermediate 126

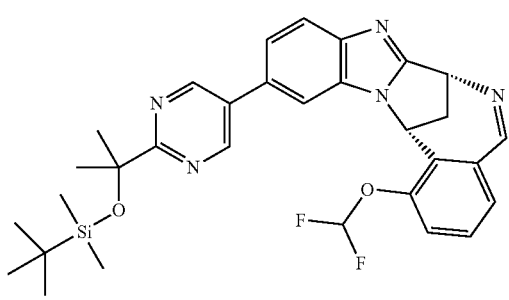 [SMILES: CC(C)(O[Si](C)(C)C(C)(C)C)c1ncc(-c2ccc3nc4n(c3c2)[C@@H]2C[C@H]4N=Cc3cccc(OC(F)F)c32)cn1]

(7R,14R)-11-[2-(2-{[tert-butyl(dimethyl)silyl] oxy}propan-2-yl)pyrimidin-5-yl]-1-(difluoromethoxy)-7,14-dihydro-7,14-methanobenzimidazo [1,2-b][2,5]benzodiazocine Intermediate 125 (860 mg, 1.24 mmol) was treated in accordance with the procedure described for the synthesis of Intermediate 118 to afford 710 mg (99%) of the title compound as a yellow glass.
LCMS Method 3 basic (ES+) RT 5.76 min., 576.2 (M+H)$^+$.

Intermediate 127

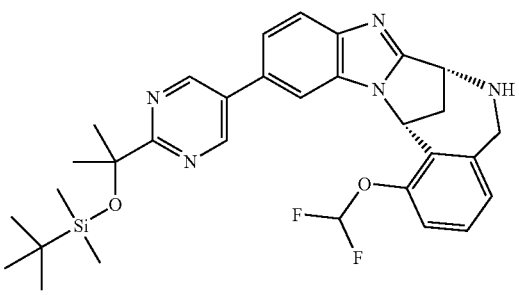 [SMILES: CC(C)(O[Si](C)(C)C(C)(C)C)c1ncc(-c2ccc3nc4n(c3c2)[C@@H]2C[C@H]4NCc3cccc(OC(F)F)c32)cn1]

(7R,14R)-11-[2-(2-{[tert-butyl(dimethyl)silyl] oxy}propan-2-yl)pyrimidin-5-yl]-1-(difluoromethoxy)-5,6,7,14-tetrahydro-7,14-methanobenzimidazo[1,2-b][2,5]benzodiazocine Intermediate 126 (710 mg, 1.23 mmol) was treated in accordance with the synthetic method described for Intermediate 119 to afford the title compound 655 mg (92%) as a yellow oil.
LCMS Method 3 basic (ES+) RT 5.84 min., 578.7 (M+H)$^+$.

Intermediate 128

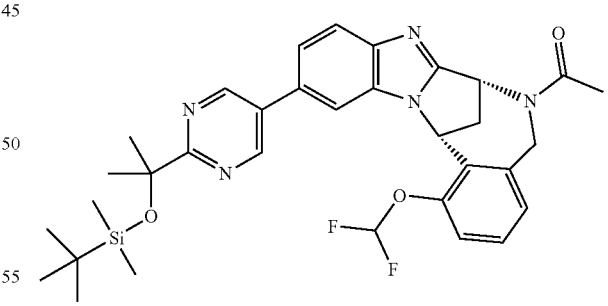

1-[(7R,14R)-11-[2-(2-{[tert-butyl(dimethyl)silyl] oxy}propan-2-yl)pyrimidin-5-yl]-1-(difluoromethoxy)-5,14-dihydro-7,14-methanobenzimidazo [1,2-b][2,5]benzodiazocin-6(7H)-yl]ethanone To a solution of Intermediate 127 (655 mg, 1.13 mmol) in dichloromethane (11 mL) was added successively pyridine (0.28 mL, 3.4 mmol) and acetic anhydride (0.22 mL, 2.27 mmol). The reaction mixture was stirred at room temperature for 90 minutes. The reaction mixture was washed by a saturated aqueous solution of NH₄Cl (2×20 mL) and a saturated aqueous solution of NaHCO₃ (2×10 mL). The aqueous phases were extracted by DCM (2×10 mL). The combined organic layers were dried over Na₂SO₄, filtered and concentrated under vacuum. The residue was purified by chromatography over silica gel (eluting with ethyl acetate 100% to ethyl acetate/ethanol 9/1), yielding to 300 mg (43%) of title compound as a yellow glass.

LCMS Method 3 basic (ES+) RT 5.84 min., 620.3 (M+H)⁺

Intermediate 129

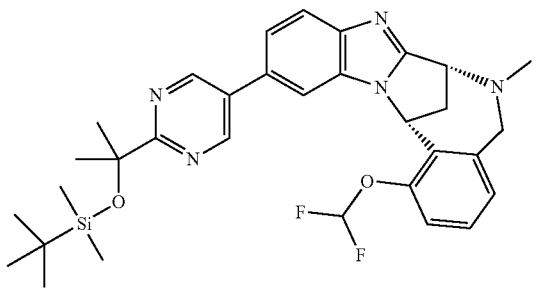 [SMILES: CN1Cc2cccc(OC(F)F)c2[C@H]2C[C@@H]1c1nc3ccc(-c4cnc(C(C)(C)O[Si](C)(C)C(C)(C)C)nc4)cc3n12]

(7R,14R)-11-[2-(2-{[tert-butyl(dimethyl)silyl]oxy}propan-2-yl)pyrimidin-5-yl]-1-(difluoromethoxy)-6-methyl-5,6,7,14-tetrahydro-7,14-methanobenzimidazo[1,2-b][2,5]benzodiazocine Intermediate 127 (30 mg, 0.051 mmol) in 2,2,2-trifluoroethanol (3 mL) and formaldehyde (1 mL, 25.97 mmol) was stirred at room temperature for 30 minutes before addition of sodium borohydride (20 mg, 0.52 mmol). The reaction mixture was heated at 70° C. for 2 hours. At room temperature, additional sodium borohydride (20 mg, 0.52 mmol) was added, and the reaction mixture heated at 70° C. for addition 1 hour. The reaction mixture was filtered through a pad of celite, and the residual solid washed by 2,2,2-trifluoroethanol (2×4 mL). The filtrate was concentrated in vacuum. The residue was used without further purification.

LCMS Method 3 basic (ES+) RT 5.97 min., 592.2 (M+H)⁺.

Intermediate 130

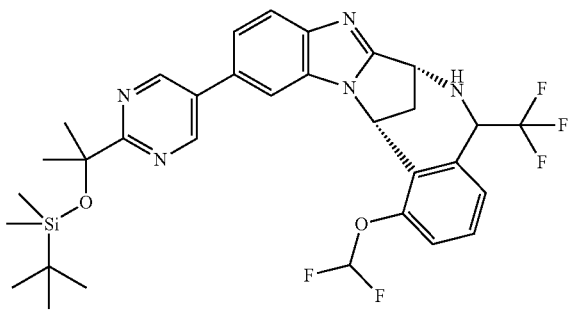 [SMILES: CC(C)(O[Si](C)(C)C(C)(C)C)c1ncc(-c2ccc3nc4n(c3c2)[C@@H]2C[C@H]4NC(C(F)(F)F)c3cccc(OC(F)F)c32)cn1]

(7R,14R)-11-[2-(2-{[tert-butyl(dimethyl) silyl]oxy}propan-2-yl)pyrimidin-5-yl]-1-(difluoromethoxy)-5-(trifluoromethyl)-5,6,7,14-tetrahydro-7,14-methanobenzimidazo[1,2-b][2,5]benzodiazocine To a solution of Intermediate 126 (0.074 mmol) in acetonitrile (1 mL) and N,N dimethylformamide (17 μl) was added successively at 0° C., trifluoroacetic acid (7 μL, 0.092 mmol), potassium hydrogen fluoride (4.4 mg, 0.055 mmol) and (trifluoromethyl)trimethylsilane (16 μL, 0.11 mmol). The resulting slurry was allowed to warm to ambient temperature overnight. The reaction mixture was then evaporated and purified by preparative basic reverse phase HPLC. This was followed by a second acidic preparative HPLC to afford the TFA salt of the title compound which was solubilized in EtOAc (2 mL) and washed with a saturated solution of NaHCO₃. The aqueous layer was extracted with EtOAc (2×2 mL). The combined organic layers were dried over magnesium sulphate, filtered and concentrated in vacuo to afford 7 mg (15%) of the title compound as a mixture of diastereoisomers.

LCMS Method 3 (ES+) RT 6.08 min., 646.2 (M+H)⁺.

Intermediate 131 and INTERMEDIATE 132

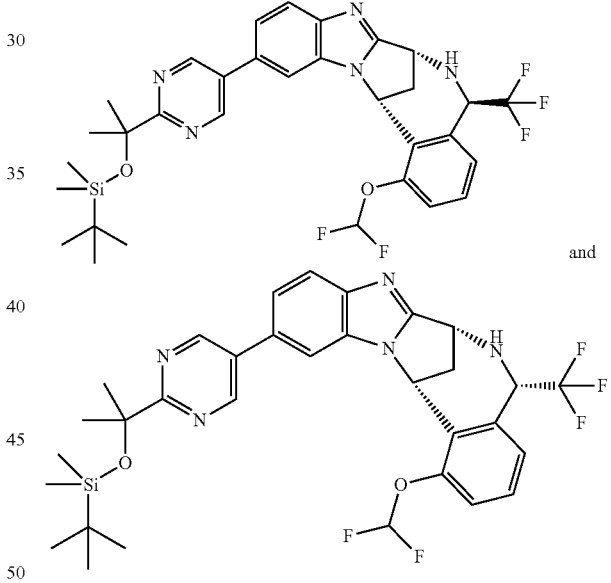

and (5R,7R,14R)-11-[2-(2-{[tert-butyl(dimethyl)silyl]oxy}propan-2-yl)pyrimidin-5-yl]-1-(difluoromethoxy)-5-(trifluoromethyl)-5,6,7,14-tetrahydro-7,14-methanobenzimidazo[1,2-b][2,5]benzodiazocine and (5S,7R,14R)-11-[2-(2-{[tert-butyl(dimethyl)silyl]oxy}propan-2-yl)pyrimidin-5-yl]-1-(difluoromethoxy)-5-(trifluoromethyl)-5,6,7,14-tetrahydro-7,14-methanobenzimidazo[1,2-b][2,5]benzodiazocine To a solution of Intermediate 126 (0.72 mmol) in acetonitrile (5 mL) and DMF (166 μL) was added successively at 0° C., trifluoroacetic acid (69 μL, 0.90 mmol), potassium hydrogen fluoride (43 mg, 0.54 mmol) and (trifluoromethyl) trimethylsilane (159 µL, 1.08 mmol). The resulting slurry was allowed to warm to room temperature for 3 hours. The reaction mixture was then diluted with EtOAc and a saturated aqueous solution of NaHCO₃. The two phases were separated and the aqueous layer further extracted with EtOAc (×2). The combined organic extracts were dried over magnesium sulphate, filtered and concentrated under reduced pressure.

The crude was purified over silica gel (eluting with dichloromethane-methanol- aqueous ammonia/97:2.7:0.3). This was followed by a second purification by reverse phase preparative HPLC to give the following diastereoisomers:

4.8 mg (1%) of Intermediate 131:
LCMS Method 3 (ES+) RT 3.65 min., 646.2 (M+H)⁺.
¹H NMR (400 MHz, CDCl₃) δ 8.72 (m, 2H), 7.19 (m, 1H), 7.05 (s, 2H), 7.00 (m, 1H), 6.85 (m, 2H), 6.35 (m, 1H), 5.33 (m, 1H), 4.52 (d, 1H, J=7.0 Hz), 3.48 (m, 1H), 2.83 (m, 1H), 2.42 (m, 1H), 1.67 (s, 6H), 0.87 (s, 9H), −0.07 (d, 6H, J=1.2 Hz).

2.8 mg (5%) of Intermediate 132:
LCMS Method 3 (ES+) RT 3.66 min., 646.2 (M+H)⁺.
¹H NMR (400 MHz, CDCl₃) δ 8.93 (m, 2H), 7.94 (m, 1H), 7.53 (m, 2H), 7.31 (m, 2H), 7.23 (m, 1H), 6.76 (m, 1H), 6.32 (m, 1H), 4.88 (m, 1H), 3.39 (m, 1H), 3.19 (m, 1H), 2.67 (m, 1H), 2.54 (m, 1H), 1.70 (s, 6H), 0.89 (s, 9H), −0.04 (s, 6H)

Intermediate 133

1-[4-methyl-5-(4,4,5,5-tetramethyl-1,3,2-dioxaborolan-2-yl)pyrimidin-2-yl]-3-(trifluoromethyl)azetidin-3-ol 1-(5-bromo-4-methyl-pyrimidin-2-yl)-3-(trifluoromethyl)azetidin-3-ol (700 mg, 2.24 mmol), bis(pinacolato)diboron (1.15 g, 4.49 mmol), 1,1'-bis(diphenylphosphino)ferrocene-palladium(II)dichloride dichloromethane complex (92 mg, 0.112 mmol), potassium acetate (890 mg, 8.97 mmol) and 1,4-dioxane (10 mL) were placed in a small RB flask, degassed and placed under nitrogen. The mixture was then heated at 105° C. for 2 hours. The mixture was cooled and partitioned between EtOAc and water. The organic layer was dried over Na₂SO₄, filtered and evaporated in vacuo to give the title compound as a dark brown solid 1.60 g. LC/MS Method 3: RT 1.93 minutes, m/z 360.

Intermediate 134

1-(5-bromo-6-methyl-2-pyridyl)-3-(trifluoromethyl)azetidin-3-ol 2,5-dibromo-6-methylpyridine (1.30 g, 5.18 mmol) and 3-(trifluoromethyl)azetidin-3-ol hydrochloride (1.00 g, 5.63 mmol) were added to a small RB flask with stirrer bar. N,N-diisopropylethylamine (0.90 mL, 5.2 mmol) was added and the mixture heated to 130° C. for 4 hours. The mixture was cooled, diluted with dichloromethane (50 mL) and washed with sodium bicarbonate solution (50 mL). The organic layer was dried (Na₂SO₄), filtered and concentrated in vacuo. Chromatography (silica, DCM gradient to 15% EtOAc in DCM) gave the title compound as a white solid (210 mg, 13.0% yield). ¹H NMR (400 MHz, DMSO-d₆) δ 7.70 (d, J=8.7 Hz, 1H), 7.32 (s, 1H), 6.32 (dd, J=8.7, 0.7 Hz, 1H), 4.19 (dd, J=9.6, 1.0 Hz, 2H), 3.93 (dt, J=9.4, 1.3 Hz, 2H), 2.42 (s, 3H).

LC/MS Method 3: RT 2.02 minutes, m/z 313/315.

Intermediate 135

1-[6-methyl-5-(4,4,5,5-tetramethyl-1,3,2-dioxaborolan-2-yl)-2-pyridyl]-3-(trifluoromethyl)azetidin-3-ol Intermediate 134 was treated in accordance with the synthetic procedure described for Intermediate 133 to afford the title compound as pale brown gum which was used without further purification. LC/MS Method 3: RT 2.29 minutes, m/z 359.

Intermediate 136

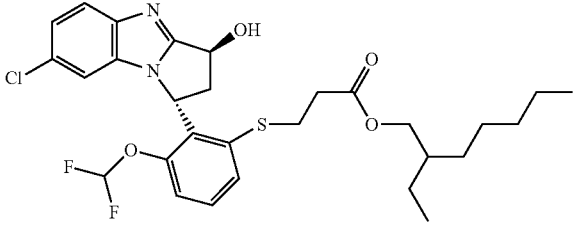 [SMILES: CCCCCC(CC)COC(=O)CCSc1cccc(OC(F)F)c1[C@H]1C[C@H](O)c2nc3ccc(Cl)cc3n21]

2-ethylhexyl 3-[2-[(1R,3S)-7-chloro-3-hydroxy-2,3-dihydro-1H-pyrrolo[1,2-a]benzimidazol-1-yl]-3-(difluoromethoxy)phenyl]sulfanylpropanoate N,N-di-iso-propylethylamine (1.63 mL, 9.31 mmol) was added to a solution of Intermediate 38 (2.00 g, 4.66 mmol) in 1,4-dioxane (10 mL). The mixture was evacuated and refilled with nitrogen. The catalyst, tris(dibenzylideneacetone)dipalladium(0) (213 mg, 0.233 mmol) and 4,5-bis(diphenylphosphino)-9,9-dimethylxanthene (275 mg, 0.466 mmol) and 3-mercaptopropionic acid 2-ethylhexyl ester (1.86 mL, 7.93 mmol) were added and the mixture was evacuated and filled with nitrogen and heated under nitrogen at 105° C. for 18 hours. The mixture was partitioned between EtOAc (250 mL) and saturated aqueous sodium bicarbonate solution (100 mL). The organic layer was dried (sodium sulfate), filtered and concentrated in vacuo to leave a yellow oil, 4.00 g. Purification by chromatography (silica, dichloromethane gradient up to 5% methanol in dichloromethane) afforded the title product as a pale yellow foam (2.10 g, 80% yield). ¹H NMR (300 MHz, DMSO-d₆) δ 7.62 (dd, J=8.6, 1.9 Hz, 1H), 7.54-7.41 (m, 1H), 7.36-7.21 (m, 1H), 7.21-7.09 (m, 1H), 7.06-6.86 (m, 1H), 6.74-6.52 (m, 1H), 6.46-6.21 (m, 1H), 6.03 (dd, J=6.7, 3.7 Hz, 1H), 5.36-5.07 (m, 1H), 4.05-3.80 (m, 2H), 3.35 (td, J=6.8, 2.6 Hz, 2H), 3.25-2.64 (m, 4H), 2.24 (ddt, J=24.0, 16.6, 8.4 Hz, 1H), 1.50 (dd, J=12.5, 6.4 Hz, 1H), 1.37-1.08 (m, 8H), 0.92-0.68 (m, 6H). LC/MS Method 3: RT 3.00 minutes, m/z 381/383.

Intermediate 137

1-(5-bromo-4-methyl-2-pyridyl)-3-(trifluoromethyl)azetidin-3-ol

The title compound was synthesised from 2,5-dibromo-4-methylpyridine and 3-(trifluoromethyl)azetidin-3-ol hydrochloride in accordance with the synthetic procedure described for Intermediate 134.

Intermediate 138

1-[4-methyl-5-(4,4,5,5-tetramethyl-1,3,2-dioxaborolan-2-yl)-2-pyridyl]-3-(trifluoromethyl)azetidin-3-ol Intermediate 137 was treated in accordance with the synthetic procedure described for Intermediate 135 to afford the title compound which was used without further purification.

Intermediate 139

Ethyl 5-bromo-4-methylpyrimidine-2-carboxylate 5-bromo-4-methylpyrimidine-2-carboxylic acid (17.8 g, 82 mmol) dissolved in ethanol (185 mL). Sulfuric acid (38.6 g, 394 mmol, 21 mL) was added and the resulting suspension was placed in a preheated oil bath of 80° C. Additional sulfuric acid (3.68 g, 37.5 mmol, 2 mL) added and heating continued for a further hour before cooling to room temperature. The solid was filtered and residue washed with EtOH. The filtrate was evaporated and the residue taken up in EtOAc (300 mL) and sat. aqueous NaHCO$_3$ solution (300 mL). The layers were separated and the aqueous phase extracted with EtOAc (300 mL). The combined organics were washed with brine (300 mL), dried (Na$_2$SO$_4$), filtered and evaporated to give a dark solid which was purified by column chromatography 300 g silica (20%→50% EtOAc in heptane) to give the title compound as a yellow solid (12.24 g, 44%). $^1$H NMR (300 MHz, Chloroform-d) δ 8.87 (s, 1H), 4.53 (q, J=7.1 Hz, 2H), 2.76 (s, 3H), 1.46 (t, J=7.1 Hz, 3H). LC/MS Method 11 RT 1.57 minutes, [M+H]+: 245/247 Br-isotope.

Intermediate 140

2-(5-bromo-4-methylpyrimidin-2-yl)propan-2-ol

Under a nitrogen atmosphere methyl magnesium bromide solution (3M in Et$_2$O 109 mmol, 36.4 ml) was added dropwise to a stirred mixture of Intermediate 139 (10.7 g, 43.7 mmol) in diethyl ether (300 mL) while cooled in an ice/water bath. During addition a suspension formed. When addition was completed the mixture was stirred at room temperature. The reaction mixture was carefully quenched with saturated aqueous NH$_4$Cl solution (300 mL). The resulting organic layer was separated and the aqueous phase was extracted with Et$_2$O (300 mL). The combined organics were washed with brine, dried (Na$_2$SO$_4$), filtered and evaporated to dryness to give an orange oil.

Purification by flash chromatography (300 g silica, 10%→50% EtOAc in heptane) gave the title compound as a light yellow oil (7.5 g, 74%). $^1$H NMR (300 MHz, Chloroform-d) δ 8.67 (s, 1H), 4.51 (s, 1H), 2.65 (s, 3H), 1.58 (s, 6H). LC/MS Method 9: [M+H]231/233 Br-isotope.

Intermediate 141

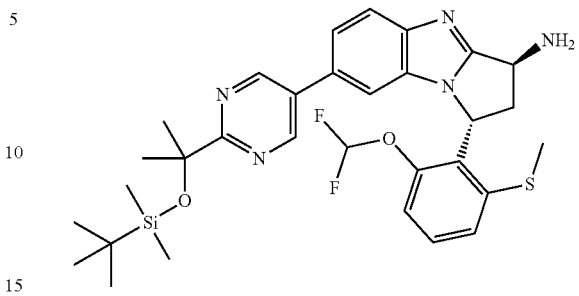

(1R,3R)-7-[2-(2-{[tert-butyl(dimethyl)silyl]oxy}propan-2-yl)pyrimidin-5-yl]-1-[2-(difluoromethoxy)-6-(methylsulfanyl)phenyl]-2,3-dihydro-1H-pyrrolo[1,2-a]benzimidazol-3-amine To a solution of Intermediate 22 (415 mg, 0.69 mmol) in DMSO (2 mL) was added sodium thiomethoxide (64 mg, 0.83 mmol). The reaction mixture was stirred for 25 minutes at 100° C. Water (20 mL) and ethyl acetate (40 mL) were added to the reaction mixture, and the two layers were separated. The aqueous layer was extracted with ethyl acetate (2×40 mL) and the combined organics layers were dried over MgSO$_4$, filtered and concentrated in vacuo. The crude material was purified over silica gel using DCM/MeOH/NH$_4$OH (100% DCM to 90/10/1) as eluent, yielding 310 mg (73%) of the title compound as a brown solid. LCMS Method 3 (ES+): RT 2.72 min, [M+H]+=612.2

Intermediate 142

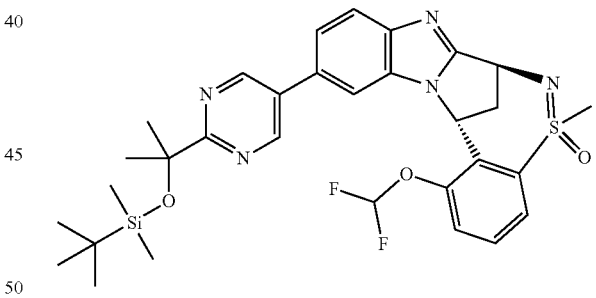

(7R,14R)-11-[2-(2-{[tert-butyl(dimethyl)silyl]oxy}propan-2-yl)pyrimidin-5-yl]-1-(difluoromethoxy)-5-methyl-7,14-dihydro-7,14-methano-5λ-4-benzimidazo[2,1-d][1,2,5]benzothiadiazocine 5-oxide To a degassed solution of Intermediate 141 (87 mg, 0.14 mmol) in MeOH (5 mL) was added a solution of bromine (19 mg, 0.12 mmol) in MeOH (0.5 mL). The reaction mixture was evaporated after 1 hour and the residue was solubilised in DCM (5 mL). The solution was degassed by bubbling of argon through the solution for 5 minutes. Potassium carbonate (63 mg, 0.45 mmol) and 3-chloroperbenzoic acid (74 mg, 0.43 mmol) were then added to the mixture. The mixture was stirred overnight at ambient

Intermediate 143

5-bromo-2-(1-methylsulfonylcyclopropyl)pyridine 5-bromo-2-[(methylsulfonyl)methyl]pyridine (300 mg, 1.20 mmol), 1,2-dibromoethane (0.12 mL, 1.40 mmol), benzyltributylammonium chloride (377 mg, 1.20 mmol) and sodium hydroxide 50% aqueous solution (7.5 mL, 94 mmol) were mixed in acetonitrile (8 mL). The reaction mixture was stirred at room temperature for 24 hours. Aqueous saturated NaCl solution and ethyl acetate were added to the reaction mixture and the two layers were separated. The organic layer was dried over MgSO$_4$, filtered and the solvent evaporated. The crude was purified by reverse phase basic preparative LCMS to yield 32 mg (10%) of the title compound as an off-white solid. LCMS Method 3 (ES+): RT 1.86 min, [M+H]+=276.

Intermediate 144

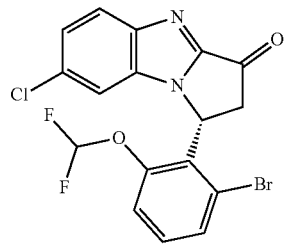 [SMILES: O=C1C[C@H](c2c(Br)cccc2OC(F)F)n2c1nc1ccc(Cl)cc12]

(1R)-1-[2-bromo-6-(difluoromethoxy)phenyl]-7-chloro-1,2-dihydro-3H-pyrrolo[1,2-a]benzimidazol-3-one To a solution of Intermediate 19 (3 g, 6.98 mmol) in chloroform (60 mL), was added manganese dioxide (3.64 g, 42 mmol) and the reaction mixture was stirred at room temperature for 3 hours, after which additional manganese dioxide (2 g, 23 mmol) was added and stirred overnight. The reaction mixture was filtered over celite, rinsed with chloroform (2×60 mL) and the filtrate concentrated in vacuo to yield 2.91 g (97%) of the title compound as a beige solid. LCMS Method 3 (ES+): RT 4.88 min, [M+H]+=427.

Intermediate 145

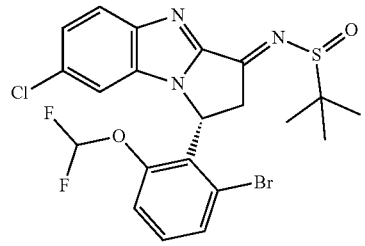 [SMILES: CC(C)(C)S(=O)/N=C1\C[C@H](c2c(Br)cccc2OC(F)F)n2c1nc1ccc(Cl)cc12]

N-{(1R,3E)-1-[2-bromo-6-(difluoromethoxy)phenyl]-7-chloro-1,2-dihydro-3H-pyrrolo[1,2-a]benzimidazol-3-ylidene}-2-methylpropane-2-sulfinamide Titanium(IV) isopropoxide (1.86 mL, 9.52 mmol) was added to a solution of Intermediate 144 (1.85 g, 4.33 mmol) in dry THF (43 mL). The mixture was stirred at room temperature for 10 minutes before addition of (R)-(+)-2-methyl-2-propanesulfinamide (642 mg, 5.2 mmol). The reaction mixture was stirred at 50° C. overnight. Further (R)-(+)-2-methyl-2-propanesulfinamide (320 mg, 2.58 mmol) was added and the reaction mixture stirred at 50° C. overnight. The reaction mixture was cooled to 0° C. and methanol was added followed by a saturated aqueous solution of NaHCO$_3$ until precipitation was observed. The slurry was diluted by EtOAc (50 mL) and filtered over celite. The filtrate was washed with brine, dried over Na$_2$SO$_4$, filtered and concentrated in vacuo. The residue was purified over silica gel (gradient EtOAc/heptane 20 to 50%) yielding 770 mg (34%) of the title compound as a brown solid. LCMS Method 3 (ES+): RT 2.82 min, [M+H]$^+$=530.

Intermediate 146

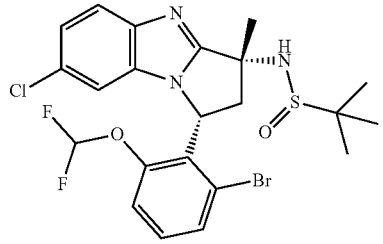 [SMILES: CC(C)(C)S(=O)N[C@]1(C)C[C@H](c2c(Br)cccc2OC(F)F)n2c1nc1ccc(Cl)cc12]

N-{(1R,3R)-1-[2-bromo-6-(difluoromethoxy)phenyl]-7-chloro-3-methyl-2,3-dihydro-1H-pyrrolo[1,2-a]benzimidazol-3-yl}-2-methylpropane-2-sulfinamide To a solution of Intermediate 145 (8 g, 15.1 mmol) in dry DCM (90 mL), cooled at −70° C., was added dropwise a solution of methyl magnesium bromide 3 M in diethyl ether (17.6 mL, 52.8 mmol). The reaction mixture was stirred at −70° C. for 10 minutes and at 0° C. for 2 hours before quenching by addition of a saturated solution of NH$_4$Cl (100 mL). The aqueous layer was extracted with DCM (2×100 mL). The combined organic layers were washed with saturated brine and dried over MgSO4, filtered and concentrated in vacuo. The residue was purified over silica gel (gradient ethyl heptane/acetate 50 to 100%), yielding to 2.91 g (35%) of the title compound as a beige solid. LCMS Method 3 (ES+): RT 2.68 min, [M+H]⁺=546.10

Intermediate 147

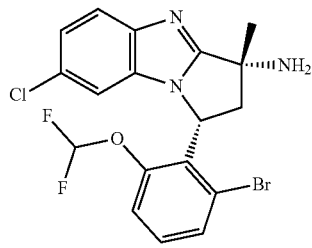 [SMILES: C[C@@]1(N)C[C@H](c2c(Br)cccc2OC(F)F)n2c1nc1ccc(Cl)cc12]

(1R,3R)-1-[2-bromo-6-(difluoromethoxy)phenyl]-7-chloro-3-methyl-2,3-dihydro-1H-pyrrolo[1,2-a]benzimidazol-3-amine Intermediate 146 (2.91 g, 5.32 mmol) was dissolved in dry 1,4-dioxane (150 mL). HCl/dioxane (4M) (6.65 mL, 27 mmol) was added and the reaction mixture was stirred at room temperature for 4 hours. The solvent was evaporated and the residue was taken up in EtOAc (50 mL) and a saturated aqueous solution of NaHCO₃ (20 mL) added. The organic layer was washed with saturated brine, dried over MgSO₄, filtered and concentrated in vacuo. The residue was dissolved in diethyl ether and evaporated yielding to 2.2 g (93%) of the title compound as a yellow solid. LCMS Method 3 (ES+): RT 2.43 min, [M+H]⁺=442.1.

Intermediate 148

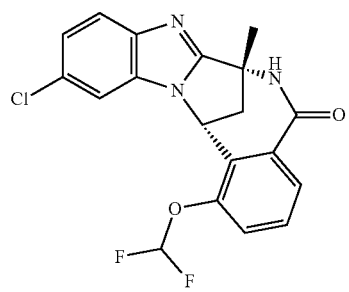 [SMILES: C[C@]12C[C@H](c3c(OC(F)F)cccc3C(=O)N1)n1c2nc2ccc(Cl)cc21]

(7R,14R)-11-chloro-1-(difluoromethoxy)-7-methyl-6,7-dihydro-7,14-methanobenzimidazo[1,2-b][2,5]benzodiazocin-5(14H)-one Intermediate 147 (50 mg, 0.11 mmol), potassium carbonate (23 mg, 0.170 mmol), dichloro[9,9-dimethyl-4,5-bis(diphenylphosphino)xanthene]palladium(II) (4 mg, 0.006 mmol) were mixed in degassed 1,4-dioxane (2 mL). The mixture was stirred under CO gas (3 bar) at 120° C. for 4 hours. Additional bis(diphenylphosphino)xanthene]palladium(II) (4 mg, 0.006 mmol) was introduced in the reactor at room temperature and the reaction continued under stirring under CO (3 bar) at 120° C. for 16 hours. The crude mixture was purified over silica gel (ethyl acetate as eluent), yielding 71 mg (37%) of the title compound as an off-white solid. LCMS Method 3 (ES+): RT 2.34 min, [M+H]+=390.

Intermediate 149

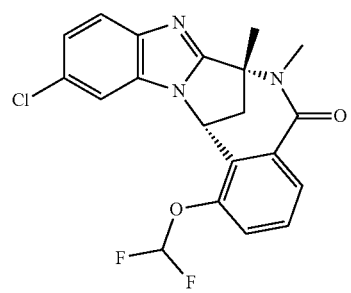 [SMILES: CN1C(=O)c2cccc(OC(F)F)c2[C@H]2C[C@]1(C)c1nc3ccc(Cl)cc3n12]

(7R,14R)-1-chloro-1-(difluoromethoxy)-6,7-dimethyl-6,7-dihydro-7,14-methanobenzimidazo[1,2-b][2,5]benzodiazocin-5(14H)-one Intermediate 148 (80 mg, 0.21 mmol) and tetrabutylammonium iodide (30 mg, 0.08 mmol) were mixed in dry THF (2 mL). At 0° C., sodium hydride (60% in mineral oil) (9 mg, 0.246 mmol) was added. The reaction mixture was stirred at room temperature for 35 minutes. Iodomethane (0.08 mL, 1.24 mmol) was added and the reaction mixture was stirred at ambient temperature overnight. The reaction mixture was quenched by addition of water (1 mL). The aqueous layer was extracted by EtOAc (3×2 mL). The combined organic layers were dried over MgSO₄, filtered and concentrated in vacuo. The residue was purified over silica gel (heptane/DCM 50% to 100%), yielding 60 mg (72%) of the title compound as a white solid. LCMS Method 4 (ES+): RT 2.63 min, [M+H]+ 404.

Intermediate 150

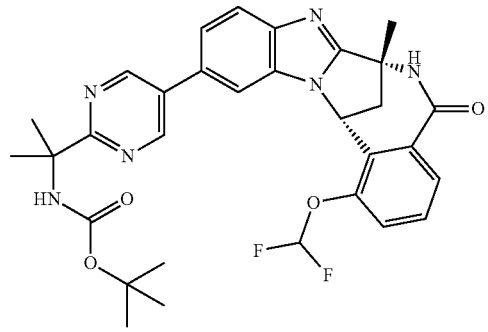 [SMILES: CC(C)(C)OC(=O)NC(C)(C)c1ncc(-c2ccc3nc4n(c3c2)[C@@H]2C[C@@]4(C)NC(=O)c3cccc(OC(F)F)c32)cn1]

tert-butyl (2-{5-[(7R,14R)-1-(difluoromethoxy)-7-methyl-5-oxo-5,6,7,14-tetrahydro-7,14-methanobenzimidazo[1,2-b][2,5]benzodiazocin-11-yl]pyrimidin-2-yl}propan-2-yl)carbamate tert-butyl N-[1-(5-bromopyrimidin-2-yl)-1-methyl-ethyl]carbamate (36 mg, 0.11 mmol), bis(pinacolato)diboron (36 mg, 0.14 mmol), potassium acetate (11 mg, 0.12 mmol), [1,1'-bis(diphenylphosphino)ferrocene]dichloropalladium (II) (6 mg, 0.008 mmol), were mixed in dioxane (3 mL). The reaction mixture was stirred at 100° C. for 2 hours. The reaction mixture was filtered through a 45 µM filter, and concentrated in vacuo. The residue was dissolved in n-butanol (5 mL) and Intermediate 148 (15 mg, 0.038 mmol), tricyclohexylphosphonium tetrafluoroborate (4 mg, 0.009 mmol), tris(dibenzenylideneacetone)dipaladium(0) (4 mg, 0.0038 mmol), potassium triphosphate (17 mg, 0.077 mmol) and water (50 μL) were added. The reaction mixture was stirred at 140° C. in a microwave for 25 minutes. The reaction mixture was filtered and purified by reverse phase basic preparative HPLC-MS to yield 13 mg (57%) of the title compound as a beige solid. LCMS Method 3 (ES+): RT 2.42 minutes, [M+H]+=591.

Intermediate 151

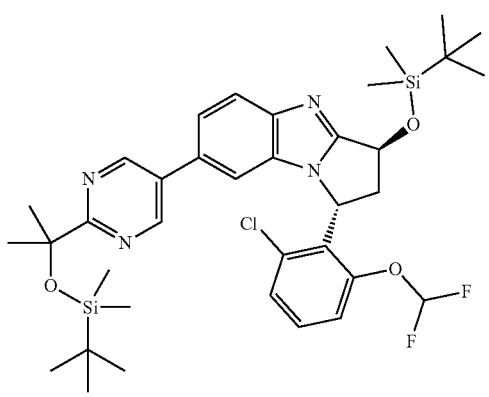 [SMILES: CC(C)(O[Si](C)(C)C(C)(C)C)c1ncc(-c2ccc3nc4n(c3c2)[C@@H](c2c(Cl)cccc2OC(F)F)C[C@@H]4O[Si](C)(C)C(C)(C)C)cn1]

(1R,3S)-3-{[tert-butyl(dimethyl)silyl]oxy}-7-[2-(2-{[tert-butyl(dimethyl)silyl]oxy}propan-2-yl)pyrimidin-5-yl]-1-[2-chloro-6-(difluoromethoxy)phenyl]-2,3-dihydro-1H-pyrrolo[1,2-a]benzimidazole To a solution of Intermediate 21 (2 g, 3.33 mmol) in DMF (12 mL) was added imidazole (283 mg, 4.16 mmol) and tert-butyldimethylchlorosilane (543 mg, 3.49 mmol) and the reaction mixture was stirred overnight at room temperature. The reaction was then diluted with diethyl ether (30 mL) and water (30 mL). The aqueous layer was extracted with diethyl ether (2×20 mL). The combined organic layers were washed with brine, dried over MgSO4, filtered and concentrated under reduced pressure to afford the title compound which was used in the next step without further purification. LCMS Method 3 (ES+): RT 7.09 min.

Intermediate 152

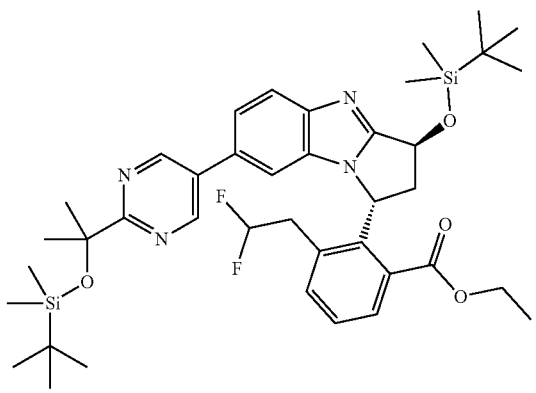 [SMILES: CCOC(=O)c1cccc(CC(F)F)c1[C@H]1C[C@H](O[Si](C)(C)C(C)(C)C)c2nc3ccc(-c4cnc(C(C)(C)O[Si](C)(C)C(C)(C)C)nc4)cc3n21]

Ethyl 2-{(1R,3R)-3-{[tert-butyl(dimethyl)silyl]oxy}-7-[2-(2-{[tert-butyl(dimethyl)silyl]oxy}propan-2-yl)pyrimidin-5-yl]-2,3-dihydro-1H-pyrrolo[1,2-a]benzimidazol-1-yl}-3-(difluoromethoxy)benzoate Intermediate 151 (2.05 g, 2.87 mmol), potassium carbonate (1.5 equiv., 4.30 mmol), molecular sieve 4 Å powder (860 mg) and dichloro[bis(dicyclohexylphosphino)propane]palladium(II) (0.08 equiv., 0.23 mmol) were suspended in dry dimethylsulfoxide (20 mL) and ethanol (0.75 mL). The reaction mixture was stirred at 100° C. under 5 bars of CO gas for 16 hours. After this time, another portion of dichloro[bis(dicyclohexylphosphino)propane]palladium(II) was added and the reaction stirred overnight at 100° C. under 5 bars of CO gas to complete the reaction. The reaction mixture was allowed to cool to ambient temperature, filtered over celite and partitioned between EtOAc (50 mL) and water (50 mL). The organic layer was washed with water (2×20 mL), dried over MgSO4, filtered and concentrated under reduced pressure. The residue was purified over silica gel (DCM:MeOH 99.5%:0.5%), yielding 824 mg (38%) of the title compound. LCMS Method 3 (ES+): RT 3.92 min, 753 (M+H)+.

Intermediate 153

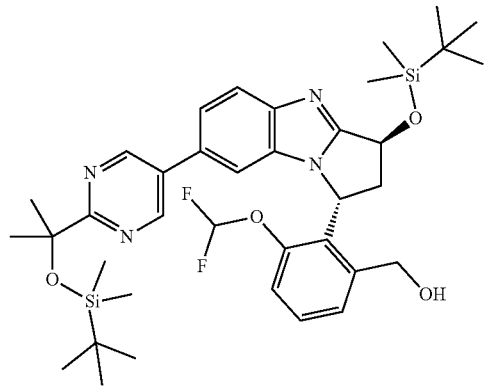 [SMILES: CC(C)(O[Si](C)(C)C(C)(C)C)c1ncc(-c2ccc3nc4n(c3c2)[C@@H](c2c(CO)cccc2OC(F)F)C[C@@H]4O[Si](C)(C)C(C)(C)C)cn1]

[2-{(1R,3S)-3-{[tert-butyl(dimethyl)silyl]oxy}-7-[2-(2-{[tert-butyl(dimethyl)silyl]oxy}propan-2-yl)pyrimidin-5-yl]-2,3-dihydro-1H-pyrrolo[1,2-a]benzimidazol-1-yl}-3-(difluoromethoxy)phenyl]methanol Intermediate 152 (780 mg, 1.04 mmol) was dissolved in dry ethanol (8 mL). At 0° C., sodium borohydride (317 mg, 8.30 mmol) followed by calcium chloride (460 mg, 4.15 mmol) were added. The reaction was allowed to warm to ambient temperature and stirred for 4 hours. The reaction was then diluted with EtOAc (20 mL) and water (10 mL). The organic layer was washed with brine, dried over MgSO4, filtered and concentrated under reduced pressure. The residue was purified over silica gel (hexane:ethyl acetate 80:20), yielding 233 mg (32%) of the title compound. LCMS Method 3 (ES+): RT 3.69 min, 711 (M+H)+.

Intermediate 154

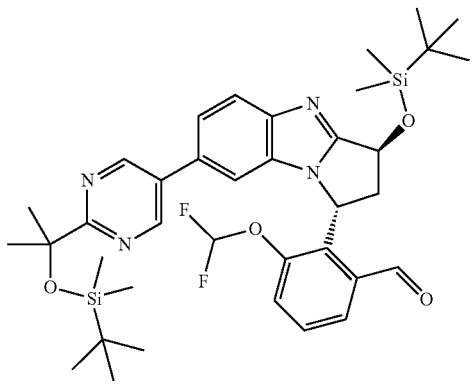 [SMILES: CC(C)(O[Si](C)(C)C(C)(C)C)c1ncc(-c2ccc3nc4n(c3c2)[C@@H](c2c(C=O)cccc2OC(F)F)C[C@@H]4O[Si](C)(C)C(C)(C)C)cn1]

2-{(1R,3S)-3-{[tert-butyl(dimethyl)silyl]oxy}-7-[2-(2-{[tert-butyl(dimethyl)silyl]oxy}propan-2-yl)pyrimidin-5-yl]-2,3-dihydro-1H-pyrrolo[1,2-a]benzimidazol-1-yl}-3-(difluoromethoxy)benzaldehyde Intermediate 153 (233 mg, 0.33 mmol) was dissolved in DCM (5 mL) before the addition of Dess-Martin periodinane (157 mg, 0.36 mmol). The slurry was stirred overnight at ambient temperature. Additional Dess-Martin periodinane (72 mg, 0.16 mmol) was added and the reaction mixture was stirred at room temperature for 3 hours to complete the reaction. The slurry was filtered and the filtrate was diluted with DCM (20 mL) and washed by a saturated aqueous solution of NaHCO$_3$ (10 mL). The aqueous layer was extracted with DCM (2×10 mL). The combined organic layers were dried over MgSO$_4$, filtered and concentrated under reduced pressure. The residue was purified over silica gel (hexane:ethyl acetate 80:20), yielding 190 mg (82%) of the title compound. LCMS Method 3 (ES+): RT 3.79 min, 709 (M+H)$^+$.

Intermediate 155

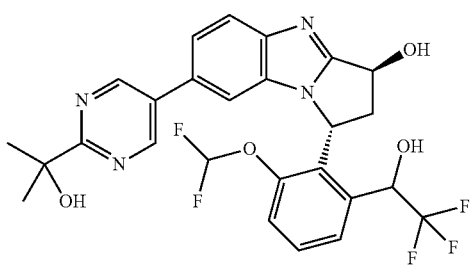 [SMILES: CC(C)(O)c1ncc(-c2ccc3nc4n(c3c2)[C@@H](c2c(OC(F)F)cccc2C(O)C(F)(F)F)C[C@@H]4O)cn1]

(1R,3S)-1-[2-(difluoromethoxy)-6-(2,2,2-trifluoro-1-hydroxyethyl)phenyl]-7-[2-(2-hydroxypropan-2-yl)pyrimidin-5-yl]-2,3-dihydro-1H-pyrrolo[1,2-a]benzimidazol-3-ol Intermediate 154 (190 mg, 0.27 mmol) was dissolved in tetrahydrofuran (3 mL). At 0° C., tetrabutylammonium fluoride (54 µL, 0.054 mmol) followed by (trifluoromethyl)trimethylsilane (79 µL, 0.54 mmol) were added. The reaction was allowed to warm to room temperature and stirred for 2 hours. The reaction was then diluted with EtOAc (10 mL) and water (5 mL). The aqueous layer was extracted with further EtOAc (2×5 mL). The combined organic layers were dried over MgSO$_4$, filtered and concentrated under reduced pressure. The residue was dissolved in methanol (1 ml) and p-toluenesulfonic acid monohydrate (255 mg, 1.34 mmol) was added. The reaction was stirred overnight at room temperature. Additional p-toluenesulfonic acid monohydrate (100 mg, 0.53 mmol) was added and the reaction mixture was stirred at ambient temperature overnight to complete the reaction. The reaction mixture was diluted with EtOAc (10 mL) and a saturated aqueous solution of NaHCO$_3$ (5 mL). The aqueous layer was extracted with EtOAc (2×5 mL). The combined organic layers were dried over MgSO$_4$, filtered and concentrated under reduced pressure. The residue was purified by reverse phase basic preparative HPLC-MS to afford 97 mg (66%) of the title compound as a white solid. LCMS Method 3 (ES+): RT 2.03 min, 551 (M+H)$^+$.

Intermediate 156

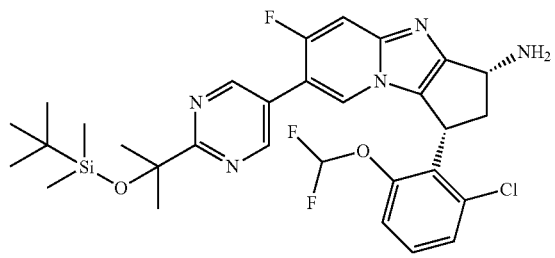 [SMILES: CC(C)(O[Si](C)(C)C(C)(C)C)c1ncc(-c2cn3c4c(nc3cc2F)[C@H](N)C[C@@H]4c2c(Cl)cccc2OC(F)F)cn1]

(1R,3R)-7-[2-(2-{[tert-butyl(dimethyl)silyl]oxy}propan-2-yl)pyrimidin-5-yl]-1-[2-chloro-6-(difluoromethoxy)phenyl]-6-fluoro-2,3-dihydro-H-cyclopenta[4,5]imidazo[1,2-a]pyridin-3-amine To a solution of Intermediate 72 (212 mg, 0.42 mmol) and 4-dimethylaminopyridine (4 mg, 0.033 mmol) in DCM (4 mL) at 0° C. was added N,N-di-isopropylethylamine (441 µL, 2.52 mmol), followed by tert-butyldimethylsilyl-trifluoromethanesulfonate (395 µL, 1.69 mmol). The reaction mixture was stirred at 0° C. for 20 minutes before the cooling bath was removed and the reaction mixture was allowed to warm up to room temperature. After 45 minutes the reaction mixture was diluted with DCM (100 mL) and washed with water (2×50 mL), brine (50 mL), dried (by passage through a phase separator cartridge) and concentrated in vacuo. The crude material was purified by column chromatography (SiO$_2$, 60-100% EtOAc in hexane, followed by 0-25% MeOH in EtOAc) and freeze dried from acetonitrile/water to give the title compound (190 mg, 73%) as an off-white solid.

LCMS Method 3 (ES+) 618 (M+H)$^+$, RT 3.44 minutes.

LCMS Method 4 (ES+) 618 (M+H)$^+$, RT 3.04 minutes.

Intermediate 157

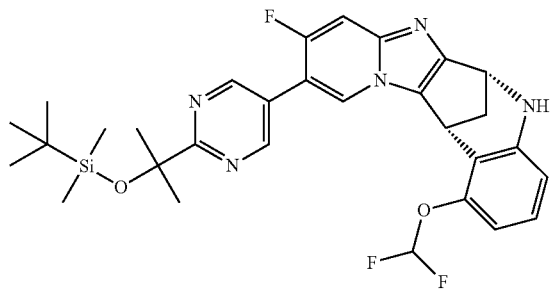 [SMILES: CC(C)(O[Si](C)(C)C(C)(C)C)c1ncc(-c2cn3c4c(nc3cc2F)[C@H]2C[C@@H]4c3c(cccc3OC(F)F)N2)cn1]

(6R,12R)-2-[2-(2-{[tert-butyl(dimethyl)silyl]oxy}propan-2-yl)pyrimidin-5-yl]-11-(difluoromethoxy)-3-fluoro-7,12-dihydro-6H-6,12-methanopyrido[1',2':1,2]imidazo[4,5-c][1]benzazepine To a microwave vial was added tris(dibenzylideneacetone)dipalladium(0) (9.5 mg, 0.01 mmol) and 2-(dicyclohexylphosphino)-2',4',6'-triisopropylbiphenyl (10.2 mg, 0.021 mmol), followed by degassed 1,4-dioxane (2 mL), and the microwave vial then sealed and degassed and stirred at room temperature for 30 minutes. After this time Intermediate 156 (125 mg, 0.20 mmol) and sodium tert-butoxide (41 mg, 0.40 mmol) then added and reaction mixture degassed and heated to 110° C. for 18 hours. The reaction mixture was partitioned between EtOAc (25 mL) and water (25 mL), the layers separated and aqueous extracted with EtOAc (25 mL). The combined organics were washed with brine (25 mL), dried (MgSO$_4$), filtered and concentrated in vacuo. The crude material was purified by column chromatography (SiO$_2$, 0-20% MeOH in DCM) to give the title compound (69 mg, 59%) as a dark brown glass.

$^1$H NMR (300 MHz, Methanol-d$_4$) δ 8.95 (d, J=1.6 Hz, 2H), 8.37 (d, J=7.3 Hz, 1H), 7.38 (d, J=11.2 Hz, 1H), 6.96 (t, J=75 Hz, 1H), 6.88 (t, J=8.1 Hz, 1H), 6.40-6.26 (m, 2H), 4.89-4.73 (m, 2H) 3.45-3.32 (m, 1H), 2.21 (d, J=10.5 Hz, 1H), 1.73 (s, 6H), 0.91 (s, 9H), −0.01 (s, 6H).

LCMS: Method 3 (ES+) 582 (M+H)$^+$, RT 3.39 minutes.
LCMS Method 4 (ES+) 582 (M+H)$^+$, RT 3.48 minutes.

Intermediate 159

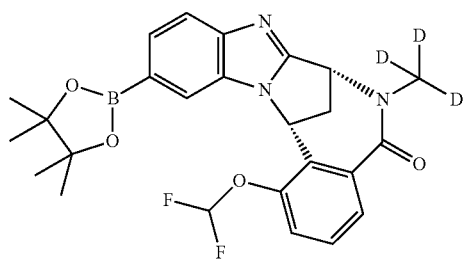 [SMILES: [2H]C([2H])([2H])N1C(=O)c2cccc(OC(F)F)c2[C@H]2C[C@@H]1c1nc3ccc(B4OC(C)(C)C(C)(C)O4)cc3n12]

(7R,14R)-1-(difluoromethoxy)-6-trideuteromethyl-11-(4,4,5,5-tetramethyl-1,3,2-dioxaborolan-2-yl)-6,7-dihydro-7,14-methanobenzimidazo[1,2-b][2,5]benzodiazocin-5(14H)-one To a solution of Intermediate 110 (2.01 g, 5.12 mmol) in 1,4-dioxane (18 mL) was added bis-(pinacolato)diboron (1.97 g, 7.8 mmol), potassium acetate, (1.5 g, 15.1 mmol), tricyclohexylphosphonium tetrafluoroborate (197 mg, 0.15 mmol) and tris(dibenzylideneacetone)dipalladium(0) (242 mg, 0.25 mmol). The reaction mixture was degassed for 10 minutes before heating to 140° C. in the microwave for 3 hours. Water and EtOAc was added to the reaction mixture and the aqueous phase extracted with further EtOAc. The combined organic layers were evaporated to give a crude residue which was purified by column chromatography on silica (eluent Hexane:EtOAc gradient from 0 to 100% followed by DCM:MeOH to 10% MeOH) to provide the title compound as a white solid (2.2 g, 89% yield). LC/MS: Method 3 RT 2.27 mins, [M+H]$^+$=485.

Intermediate 160

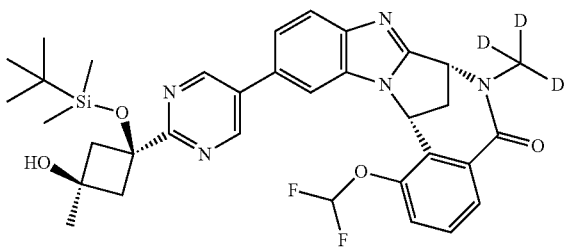 [SMILES: [2H]C([2H])([2H])N1C(=O)c2cccc(OC(F)F)c2[C@H]2C[C@@H]1c1nc3ccc(-c4cnc([C@]5(O[Si](C)(C)C(C)(C)C)C[C@@](C)(O)C5)nc4)cc3n12]

(7R,14R)-11-[2-(cis-1-{[tert-butyl(dimethyl)silyl]oxy}-3-hydroxy-3-methylcyclobutyl)pyrimidin-5-yl]-1-(difluoromethoxy)-6-trideuteromethyl-6,7-dihydro-7,14-methanobenzimidazo[1,2-b][2,5]benzodiazocin-5(14H)-one Intermediate 159 (401 mg, 0.83 mmol) and Intermediate 79 (403 mg, 1.08 mmol) in 1,4-dioxane (10 mL) were degassed, 1,1'-bis(diphenylphospino)ferrocene-palladium (II)dichloride dichloromethane complex (35 mg, 0.043 mmol) and K$_3$PO$_4$ (282 mg, 1.33 mmol) were added and reaction mixture degassed and then heated at 110° C. for 18 hours, or until LCMS analysis showed the reaction to be completed. The reaction mixture was allowed to cool to room temperature, partitioned between EtOAc (20 mL) and saturated aqueous sodium bicarbonate solution (20 mL), the layers were separated and the aqueous phase extracted with further EtOAc (3×25 mL). The combined organics were dried over sodium sulphate, filtered and concentrated in vacuo. The crude material was purified by column chromatography (SiO$_2$, 0-100% EtOAc in hexane, followed by 0-15% MeOH in DCM) to give the title compound (221 mg, 41%) as a yellow foam.

$^1$H NMR (300 MHz, DMSO-d$_6$) δ 9.12 (s, 2H), 8.27 (dd, J=5.9, 3.6 Hz, 1H), 7.78 (d, J=8.5 Hz, 2H), 7.69 (t, J=73.6 Hz, 1H), 7.65 (dd, J=8.3, 1.8 Hz, 1H), 7.52-7.44 (m, 2H), 6.31 (d, J=7.2 Hz, 1H), 5.25 (d, J=6.9 Hz, 1H), 5.03 (s, 1H), 3.58-3.45 (m, 1H), 3.10-3.02 (m, 1H), 2.84 (d, J=13.6 Hz, 1H), 2.56-2.45 (m, 2H), 2.48-2.40 (m, 1H), 0.93 (s, 3H), 0.80 (s, 6H), −0.19 (d, J=1.4 Hz, 9H).

LCMS: Method 3 (ES+) 651 (M+H)$^+$, RT 2.51 minutes.

161

Intermediate 161

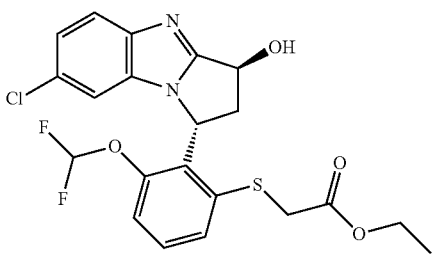 [SMILES: CCOC(=O)CSc1cccc(OC(F)F)c1[C@H]1C[C@H](O)c2nc3ccc(Cl)cc3n21]

Ethyl 2-[2-[(1R,3S)-7-chloro-3-hydroxy-2,3-di-hydro-1H-pyrrolo[1,2-a]benzimidazol-1-yl]-3-(difluoromethoxy)phenyl]sulfanylacetate The title compound was prepared from Intermediate 38 (2.02 g, 4.7 mmol), N,N-di-iso-propylethylamine (1.63 mL, 9.31 mmol), tris(dibenzylideneacetone)dipalladium(0) (213 mg, 0.23 mmol), 4,5-bis(diphenylphosphino)-9,9-dimethylxanthene (275 mg, 0.47 mmol) and ethyl thioglycolate (980 mg, 7.99 mmol) by the method of Intermediate 136. Crude material was purified by column chromatography (SiO$_2$, 20-100% EtOAc in hexane) to give the title compound (1.76 g, 80%) as a yellow solid.

LCMS: Method 3 (ES+) 469 (M+H)$^+$, RT 2.08 minutes.
LCMS: Method 4 (ES+) 469 (M+H)$^+$, RT 2.05 minutes.

Intermediate 162

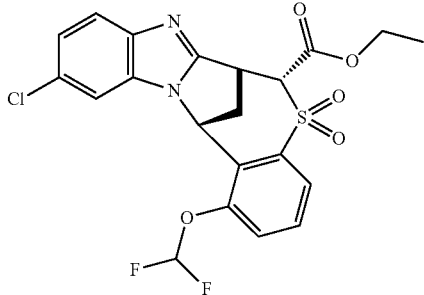

Ethyl (7S,14R)-11-chloro-1-(difluoromethoxy)-6,7-dihydro-14H-7,14-methanobenzimidazo[2,1-d][1,5]benzothiazocine-6-carboxylate 5,5-dioxide Intermediate 163

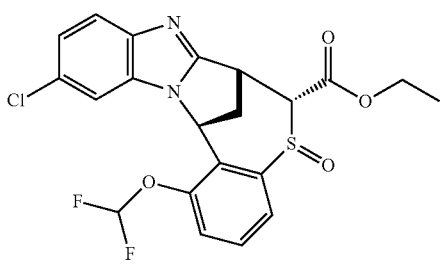

Ethyl (7R,14S)-11-chloro-1-(difluoromethoxy)-6,7-dihydro-14H-7,14-methanobenzimidazo[2,1-d][1,5]benzothiazocine-6-carboxylate 5-oxide To a solution of Example 115 (150 mg, 0.33 mmol) in DCM (5 mL) was added 3-chloroperoxybenzoic acid (149 mg, 0.66 mmol). The reaction mixture was stirred at room temperature for 18 hours, after which time the reaction mixture was partitioned between DCM (25 mL) and water (25 mL), layers separated and organics washed with saturated aqueous sodium bicarbonate solution. The aqueous phase was extracted with DCM (20 mL), the combined organics filtered through a phase separator and concentrated in vacuo. The residue was purified by column chromatography (SiO$_2$, 0-60% EtOAc in DCM) and freeze dried from acetonitrile/water to give Intermediate 162 (65 mg, 40%) as an off-white solid and Intermediate 163 (47 mg, 30%) as a white solid.

Intermediate 162

LCMS: Method 3 (ES+) 483 (M+H)$^+$, RT 2.12 minutes (minor diastereoisomer) and 2.26 minutes (major diastereoisomer)
LCMS: Method 4 (ES+) 483 (M+H)$^+$, RT 2.09 minutes (minor diastereoisomer) and 2.26 minutes (Major diastereoisomer).

Intermediate 163

LCMS: Method 3 (ES+) 467 (M+H)$^+$, RT 2.22 minutes (major diastereoisomer)
LCMS: Method 4 (ES+) 467 (M+H)$^+$, RT 2.20 minutes (Major diastereoisomer).

Intermediate 164

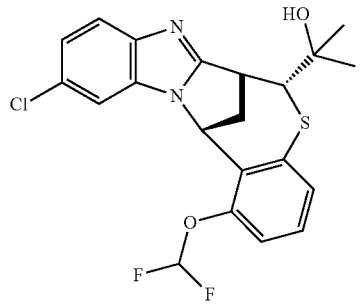

2-[(7S,14R)-11-chloro-1-(difluoromethoxy)-6,7-dihydro-14H-7,14-methanobenzimidazo[2,1-d][1,5]benzothiazocin-6-yl]propan-2-ol To a solution of Example 115 (98 mg, 0.22 mmol) in THF (5 mL) at 0° C. was added methylmagnesium bromide (3M in diethylether, 0.16 mL, 0.48 mmol). The reaction mixture was allowed to warm to room temperature and stirred for 18 hours. After this time the reaction was quenched with methanol, concentrated in vacuo and the residue partitioned between EtOAc (50 mL) and saturated aqueous sodium bicarbonate solution (50 mL), the layers separated and the aqueous phase extracted with EtOAc (3×30 mL), the combined organics were washed with brine (60 mL), dried (MgSO$_4$), filtered and concentrated in vacuo. Purification by column chromatography (SiO$_2$, 0-20% MeOH in DCM) and freeze drying from acetonitrile/water gave the title compound (28 mg, 29%).

LCMS: Method 3 (ES+) 437 (M+H)$^+$, RT 2.44 minutes.
LCMS: Method 4 (ES+) 437 (M+H)$^+$, RT 2.38 minutes.

Intermediate 165

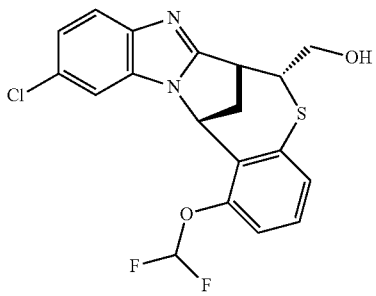

[(7S,14R)-11-chloro-1-(difluoromethoxy)-6,7-dihydro-14H-7,14-methanobenzimidazo[2,1-d][1,5]benzothiazocin-6-yl]methanol To a solution of Example 115 (88 mg, 0.15 mmol) in THF (1.5 mL) at -10° C. was added lithium aluminium hydride (2M solution in THF, 0.1 mL, 0.20 mmol). The reaction mixture was stirred below 0° C. for 1 hour after which time the reaction was quenched with a few drops of 2 M HCl, stirred and then basified with 10% NaOH (aq) (20 mL) and extracted with EtOAc (4×25 mL). The combined organic phases were dried (Na$_2$SO$_4$), filtered and concentrated in vacuo. Purification by column chromatography (SiO$_2$, 50-100% EtOAc in DCM, followed by 0-20% MeOH in EtOAc) and freeze drying from acetonitrile/water gave the title compound (35 mg, 57%) as a white solid.

LCMS: Method 3 (ES+) 409 (M+H)$^+$, RT 2.18 minutes (major diastereoisomer) and 2.22 minutes (minor diastereoisomer)
LCMS: Method 4 (ES+) 409 (M+H)$^+$, RT 2.14 minutes.

Intermediate 166

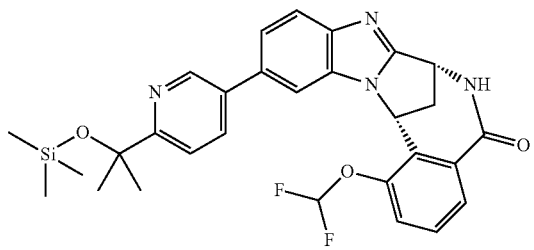 [SMILES: CC(C)(O[Si](C)(C)C)c1ccc(-c2ccc3nc4n(c3c2)[C@@H]2C[C@H]4NC(=O)c3cccc(OC(F)F)c32)cn1]

(7R,14R)-1-(difluoromethoxy)-11-[6-(2-trimethylsilyloxypropan-2-yl)pyridin-3-yl]-6,7-dihydro-7,14-methanobenzimidazo[1,2-b][2,5]benzodiazocin-5(14H)-one Example 11 (750 mg, 2.00 mmol), 6-(2-(trimethylsilyloxy)propan-2-yl)pyridine-3-boronic acid pinacol ester (1.41 g, 4.00 mmol), tris(dibenzylideneacetone)dipalladium (0) (94 mg, 0.1 mmol) and tricyclohexylphosphonium tetrafluoroborate (91 mg, 0.24 mmol, 97 mass %) were added to a round bottom flask, evacuated & refilled with nitrogen and 1,4-dioxane (10 mL) added followed by potassium phosphate (1.27 g, 6.00 mmol) in water (1 mL). The mixture was degassed, placed under nitrogen and heated to 105° C. overnight. The mixture was partitioned between EtOAc and water, the organic layer dried over sodium sulphate, filtered and concentrated in vacuo. The crude material was purified by chromatography, (EtOAc to 15% MeOH gradient). The product fractions were concentrated in vacuo to give the title compound as an off-white solid, (1.05 g, 96% yield). LC/MS Method 3: RT 1.61 minutes, m/z 549.

Intermediate 167 tert-Butyl 3-(5-bromo-2-pyridyl)-3-hydroxy-pyrrolidine-1-carboxylate 2,5-dibromopyridine (2.00 g, 8.27 mmol) was dissolved in toluene (40 mL), cooled to -78° C. and n-butyllithium (7.1 mL, 9.9 mmol, 1.40 M) solution in n-hexane added dropwise and stirred for 10 minutes before the addition of N-BOC-3-pyrrolidinone (1.61 g, 8.69 mmol) in toluene (3 mL). The mixture was stirred at -60° C. for 1 hour, quenched with methanol (2 mL) and partitioned between EtOAc and saturated aqueous ammonium chloride solution. The organic layer was concentrated in vacuo to yield a crude residue. Purification by chromatography (silica, 0 to 60% EtOAc gradient in iso-hexane) gave the title compound as an off-white solid (1.05 g, 3.06 mmol, 37% yield). $^1$H NMR (300 MHz, DMSO-d$_6$) δ 8.65 (dd, J=2.5, 0.7 Hz, 1H), 8.07 (dd, J=8.5, 2.4 Hz, 1H), 7.66 (d, J=8.5 Hz, 1H), 5.76 (s, 1H), 3.63 (t, J=11.3 Hz, 1H), 3.56-3.37 (m, 4H), 2.43-2.21 (m, 1H), 1.98-1.86 (m, 1H), 1.41 (s, 9H). LC/MS Method 3: RT 1.57 minutes, m/z 341/343 (-ve ion).

Intermediate 168

Methyl N-[1-(5-bromopyrimidin-2-yl)-1-methylethyl]carbamate

To a cooled (0° C.) solution of 2-(5-bromopyrimidin-2-yl)propan-2-amine (2 g, 9.25 mmol) in dichloromethane (50 mL) was added N,N-diisopropylethylamine (2.2 equiv., 20.3 mmol) followed by methyl chloroformate (1 equiv., 9.25 mmol) and the mixture stirred at room temperature for 4 hours. The dichloromethane solution was extracted with 2M HCl (×2) washed with saturated aqueous sodium bicarbonate solution, dried over sodium sulphate, filtered and the solvents removed in vacuo to give 2.6 g of a pale reddish solid which was used without further purification.

LCMS Method 3 RT=1.15 minutes

Intermediate 169

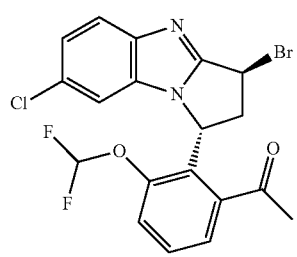 [SMILES: CC(=O)c1cccc(OC(F)F)c1[C@H]1C[C@H](Br)c2nc3ccc(Cl)cc3n21]

1-[2-[(1R,3S)-3-bromo-7-chloro-2,3-dihydro-1H-pyrrolo[1,2-a]benzimidazol-1-yl]-3-(difluoromethoxy)phenyl]ethanone Intermediate 181 (58.0 mg, 0.148 mmol) and triphenylphosphine (43.0 mg, 0.162 mmol) were dissolved in DCM (2 mL), and at 0° C. was added carbon tetrabromide (54.0 mg, 0.163 mmol). The reaction mixture was warmed up to ambient temperature and stirred for 3 hours, partitioned between water and DCM, and the organics, dried (MgSO$_4$), filtered and concentrated in vacuo. The crude material was purified by column chromatography (0%-5% MeOH in DCM) to afford the title compound (74 mg, 77%). LC/MS: Method 3 ESI MH$^+$ 455/457, retention time 2.18 minutes.

Intermediate 170

2-(5-bromopyrimidin-2-yl)-N,N-dimethyl-propan-2-amine

To a solution of 1-(5-bromopyrimidin-2-yl)-1-methylethylamine (500 mg, 2.20 mmol) in THF (15 mL) was added sodium hydride (97 mg, 2.43 mmol) at 0° C. The reaction mixture was stirred at 0° C. for 15 min before the addition of iodomethane (0.17 mL, 2.64 mmol) dropwise. The mixture was stirred at 0° C. for 30 mins before warming to room temperature and stirred for 16 hours. Iodomethane (0.165 mL, 2.64 mmol) was added and stirred for additional hour before being quenched with saturated aqueous NH$_4$Cl solution and extracted with DCM (3×10 mL). The organics were combined, dried with Na$_2$SO$_4$, filtered and concentrated in vacuo. The crude product was purified by column chromatography (0-5% MeOH in DCM) to give the title compound (120 mg, 22%).

LC/MS: Method 3 retention time 1.23 minutes.

Intermediate 171

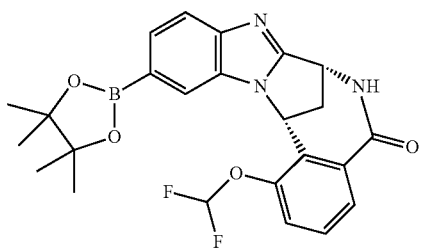 [SMILES: CC1(C)OB(c2ccc3nc4n(c3c2)[C@@H]2C[C@H]4NC(=O)c3cccc(OC(F)F)c32)OC1(C)C]

(7R,14R)-1-(difluoromethoxy)-11-(4,4,5,5-tetramethyl-1,3,2-dioxaborolan-2-yl)-6,7-dihydro-7,14-methanobenzimidazo[1,2-b][2,5]benzodiazocin-5(14H)-one Example 11 (150 mg, 0.40 mmol) in 1,4-dioxane (1.5 mL) was added to bis(pinacolato)diboron (150 mg, 0.59 mmol), potassium acetate, (117 mg, 1.19 mmol), tricyclohexylphosphonium tetrafluoroborate (15 mg, 0.040 mmol) and tris(dibenzylideneacetone)dipalladium(0) (19 mg, 0.02 mmol) were added. The reaction mixture was degassed for 10 minutes before heating to 140° C. in the microwave for 3 hours. The reaction mixture was partitioned between EtOAc and water and extracted with further EtOAC (×3). The combined organic phases were filtered through a phase separator and the solvents removed in vacuo to give the title compound which was used without further purification. LC/MS: Method 3 RT 2.09 mins, [M+H]$^+$=468.

Intermediate 172

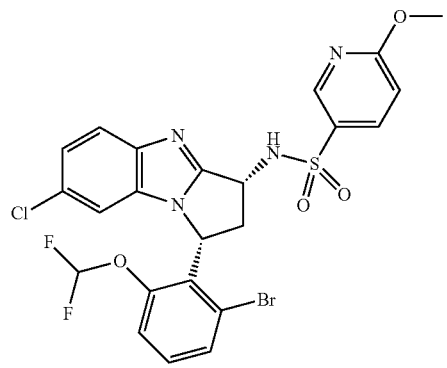 [SMILES: COc1ccc(S(=O)(=O)N[C@@H]2C[C@H](c3c(Br)cccc3OC(F)F)n3c2nc2ccc(Cl)cc23)cn1]

N-[(1R,3R)-1-[2-bromo-6-(difluoromethoxy)phenyl]-7-chloro-2,3-dihydro-1H-pyrrolo[1,2-a]benzimidazol-3-yl]-6-methoxy-pyridine-3-sulfonamide To a solution of Intermediate 40 (500 mg, 1.17 mmol) and N,N-di-isopropylethylamine (0.24 mL, 1.4 mmol, 180 mg) in dichloromethane (12 mL) was added 6-methoxypyridine-3-sulfonyl chloride (325 mg, 1.52 mmol). The reaction mixture was stirred at room temperature for 3 hours before the reaction mixture was concentrated in vacuo. The residue was purified by column chromatography (SiO$_2$, 0-100% EtOAc in hexane) to give the title compound (600 mg, 86%) as a dark beige solid. LCMS (ES+)

Method 3: 600/602 (M+H)$^+$, RT 2.4 minutes

Intermediate 173

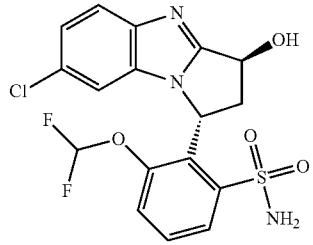 [SMILES: NS(=O)(=O)c1cccc(OC(F)F)c1[C@H]1C[C@H](O)c2nc3ccc(Cl)cc3n21]

2-[(1R,3S)-7-chloro-3-hydroxy-2,3-dihydro-1H-pyrrolo[1,2-a]benzimidazol-1-yl]-3-(difluoromethoxy)benzenesulfonamide To a solution of Intermediate 136 (1.0 g, 1.67 mmol) in dimethyl sulfoxide (2.8 mL), sodium ethoxide solution (3M in EtOH, 1.13 mL, 3.3 mmol) was added. The reaction mixture was stirred for 10 minutes before additional sodium ethoxide solution (3M in ethanol, 1.13 mL, 3.3 mmol) was added and the mixture stirred for 5 minutes. Hydroxylamine-O-sulfonic acid (1.0 g, 8.58 mmol) and sodium acetate (550 mg, 6.70 mmol) in 2 mL of water were added to the reaction mixture. The reaction mixture was stirred overnight at room temperature. EtOAc and water were added to the reaction mixture and the two phases were separated. The aqueous layer was extracted with EtOAc and the combined organic layers were filtered through a phase separator and the solvent was evaporated. The crude material was purified by column chromatography over silica gel using hexane/ethyl acetate (0 to 100%) then DCM:MeOH (0 to 20%) as eluent, yielding 300 mg (42%) of the title compound as a pale yellow solid. LCMS Method 3: RT 1.57 min, [M−H]+=430/432.

Intermediate 174

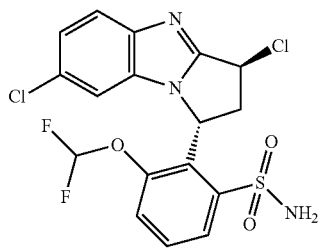 [SMILES: NS(=O)(=O)c1cccc(OC(F)F)c1[C@H]1C[C@H](Cl)c2nc3ccc(Cl)cc3n21]

2-[(1R,3S)-3,7-dichloro-2,3-dihydro-1H-pyrrolo[1,2-a]benzimidazol-1-yl]-3-(difluoromethoxy)benzenesulfonamide To a solution of Intermediate 173 (130 mg, 0.30 mmol) in THF (3 mL), DMAP (4 mg, 0.033 mmol) and N,N-di-isopropylethylamine (0.04 mL, 0.39 mmol) were added. The mixture was stirred at 0° C. before methanesulfonyl chloride (47 µL, 0.61 mmol) was added. The reaction mixture was stirred for 1 hour 30 minutes. Sodium hydride (18 mg, 0.45 mmol) was added at 0° C. and stirred for 1 hour before the mixture was heated to reflux overnight. The reaction was quenched by the addition of water and extracted with EtOAc (×3). The combined organic phases were dried over sodium sulphate, filtered and concentrated in vacuo. Purification by column chromatography over silica gel using hexane/ethyl acetate (0 to 100%) as eluent, the title compound was obtained as a mixture of diasteriomers which were separated by Achiral SFC purification, yielding 14 mg (11% yield) of the title compound as a white solid. LCMS Method 3: RT 1.63 min, [M−H]+=448/450.

Intermediate 175

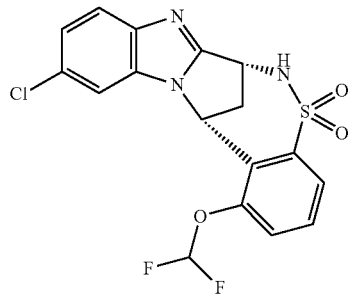 [SMILES: O=S1(=O)N[C@@H]2C[C@H](c3c(OC(F)F)cccc31)n1c2nc2ccc(Cl)cc21]

(7R,14R)-11-chloro-1-(difluoromethoxy)-6,7-dihydro-14H-7,14-methanobenzimidazo[2,1-d][1,2,5]benzothiadiazocine 5,5-dioxide To a solution of Intermediate 174 (14 mg, 0.031 mmol) in N,N-dimethylformamide (0.6 mL) was added sodium hydride (60 mass %, 1.87 mg, 0.047 mmol) and the reaction mixture was heated at 80° C. for 1 hour. Water and EtOAc were added and the two phase were separated. The aqueous layer was extracted with EtOAc and the combined organic layers were washed with brine and filtered through a phase separator. The solvent was evaporated, yielding 10 mg (78% yield) of the title compound as a green solid. LCMS Method 3: RT 1.70 min, [M−H]+=412/414

Intermediate 176

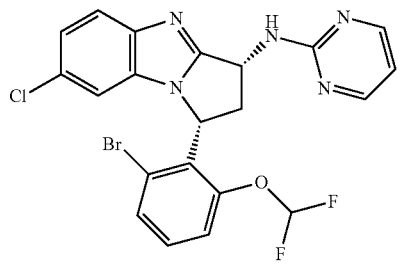 [SMILES: FC(F)Oc1cccc(Br)c1[C@H]1C[C@@H](Nc2ncccn2)c2nc3ccc(Cl)cc3n21]

(1R,3R)-1-[2-bromo-6-(difluoromethoxy)phenyl]-7-chloro-N-pyrimidin-2-yl-2,3-dihydro-1H-pyrrolo[1,2-a]benzimidazol-3-amine To a solution of Intermediate 40 (600 mg, 1.40 mmol) and 2-bromopyrimidine (334 mg, 2.10 mmol) in N,N-dimethylformamide (2.8 mL) was added N,N-di-isopropylethylamine. The reaction mixture was heated at 80° C. for 4 hours and then at 110° C. overnight. Water and EtOAc were added and the reaction mixture was extracted with further ethyl acetate. The combined organic layer was filtered through a phase separator and the solvent evaporated. The crude material was purified by column chromatography over silica gel using hexane/ethyl acetate (0 to 100%) then DCM:MeOH (0 to 20%) as eluent, yielding 205 mg (29% yield) of the title compound as a pale yellow solid. LCMS Method 3: RT 2.24 min, [M−H]+=506/508.

Intermediate 177

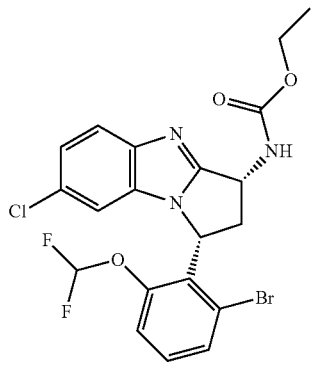 [SMILES: CCOC(=O)N[C@@H]1C[C@H](c2c(Br)cccc2OC(F)F)n2c1nc1ccc(Cl)cc12]

Ethyl-N-[(1R,3R)-1-[2-bromo-6-(difluoromethoxy)phenyl]-7-chloro-2,3-dihydro-1H-pyrrolo[1,2-a]benzimidazol-3-yl]carbamate To a solution of Intermediate 40 (400 mg, 0.93 mmol) in dichloromethane (4.6 mL). N,N-diisopropylethylamine (0.24 mL, 1.4 mmol) followed by ethyl chloroformate (116 μL, 1.21 mmol) were added and the reaction mixture was stirred for 1 hour. The solvent was evaporated and the residue was purified by column chromatography (SiO$_2$, 0-100% EtOAc in hexane) to give the title compound (350 mg, 75% yield) as a pale yellow solid.
LCMS (ES+) Method 3: 500/502 (M+H)$^+$, RT 2.23 minutes.

Intermediate 178

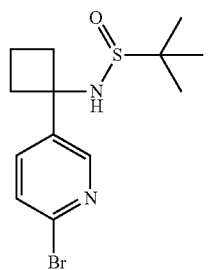 [SMILES: CC(C)(C)S(=O)NC1(c2ccc(Br)nc2)CCC1]

N-[1-(5-bromo-2-pyridyl)cyclobutyl]-2-methyl-propane-2-sulfinamide 2,5-dibromopyridine (1.4 g, 5.8 mmol) was dissolved in toluene (15 mL) and the reaction mixture was cooled to −60° C. after which time n-butyllithium (4 mL, 6.4 mmol) was added dropwise and the mixture was stirred at this temperature for 10 minutes. N-cyclobutylidene-2-methyl-propane-2-sulfinamide (1 g, 5.77 mmol) in 1 mL of toluene was added to the reaction mixture and stirred at −60° C. for 15 minutes. A saturated solution of NH$_4$Cl aq. was added and the reaction mixture was extracted with EtOAc and the combined organic layers was washed with brine and filtered through a phase separator and the solvent was evaporated under reduced pressure. The residue was purified by column chromatography (SiO$_2$, 0-100% EtOAc in hexane) to give the title compound (1.25 g, 65% yield) as a colourless oil. $^1$H NMR (300 MHz, Chloroform-d) δ 8.64 (dd, J=2.4, 0.7 Hz, 1H), 7.83 (dd, J=8.4, 2.4 Hz, 1H), 7.42 (dd, J=8.5, 0.7 Hz, 1H), 4.31 (s, 1H), 2.72-2.57 (m, 3H), 2.63-2.44 (m, 1H), 2.10 (ddt, J=18.7, 9.0, 7.0 Hz, 1H), 1.96-1.75 (m, 1H), 1.22 (s, 9H).

Intermediate 179

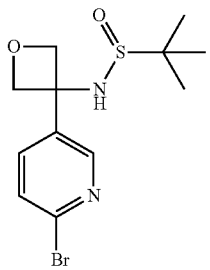 [SMILES: CC(C)(C)S(=O)NC1(c2ccc(Br)nc2)COC1]

N-[3-(5-bromo-2-pyridyl)oxetan-3-yl]-2-methyl-propane-2-sulfinamide 2,5-dibromopyridine (500 mg, 2.07 mmol) was dissolved in toluene (5 mL) and the reaction mixture was cooled to −60° C. before n-butyllithium (1.4 mL, 2.2 mmol) was added dropwise and the mixture stirred for 10 minutes. 2-methyl-N-(oxetan-3-ylidine)propane-2-sulfinamide (420 mg, 2.2 mmol) in 0.5 mL of toluene was added and the reaction mixture stirred at −60° C. for 15 minutes. A saturated solution of aqueous NH$_4$Cl was added and the reaction mixture extracted with EtOAc and the combined organic layers washed with brine, filtered through a phase separator and the solvent evaporated under reduced pressure. The residue was purified by column chromatography (SiO$_2$, 0-100% EtOAc in hexane) to give the title compound (550 mg, 80% yield) as a colourless oil. LC/MS: RT 1.35 mins (pH 10), [M+H]+=333/335. 1H NMR (400 MHz, Chloroform-d) δ 8.63 (dd, J=2.4, 0.7 Hz, 1H), 7.93 (dd, J=8.5, 2.3 Hz, 1H), 7.71 (dd, J=8.5, 0.8 Hz, 1H), 5.41 (s, 1H), 5.33 (d, J=7.0 Hz, 1H), 5.05 (d, J=6.6 Hz, 1H), 4.94 (d, J=6.6 Hz, 1H), 4.84 (dd, J=7.0, 0.8 Hz, 1H), 1.28 (s, 9H).

Intermediate 180

5-(4-bromophenyl)-2,4-dimethyl-1H-imidazole

To a solution of 1-(4-bromophenyl)-2-nitropropene (750 mg, 3.09 mmol), acetamidine hydrochloride (313 mg, 3.31 mmol) and potassium carbonate (421 mg, 3.015 mmol) in ethanol (12 mL) was added indium (III) chloride (33 mg, 0.149 mmol) and the reaction mixture was stirred at 70° C. overnight. Ethanol was evaporated and the crude reaction mixture was diluted with water (2 mL), and extracted with DCM. The organic layer was dried over anhydrous sodium sulphate, filtered and evaporated under vacuum to give a yellow solid. The residue was purified by column chromatography (hexane/ethyl acetate) to afford the title compound (270 mg, 35%) as a pale yellow solid. LC/MS Method 3: RT 1.62 minutes, [M+H]$^+$=251/253.

Intermediate 181

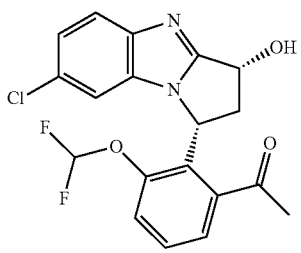 [SMILES: CC(=O)c1cccc(OC(F)F)c1[C@H]1C[C@@H](O)c2nc3ccc(Cl)cc3n21]

1-[2-[(1R,3R)-7-chloro-3-hydroxy-2,3-dihydro-1H-pyrrolo[1,2-a]benzimidazol-1-yl]-3-(difluoromethoxy)phenyl]ethanone Intermediate 60 (1.50 g, 3.49 mmol) was dissolved in toluene (20 mL), and tributyl(1-ethoxyvinyl)tin (2.53 mL, 7.67 mmol) and bis(triphenylphosphine)palladium(II) dichloride (250 mg, 0.36 mmol) were added. The reaction mixture was degassed and purged with N$_2$ 3 times before heating at 105° C. for 18 hours. The reaction mixture was diluted with saturated aqueous KF solution and extracted with EtOAc (×3). The combined organics were, dried (sodium sulphate) and concentrated in vacuo. The crude compound was purified by column chromatography eluting with 0-10% MeOH:DCM to give the enol ether intermediate. The intermediate was dissolved in THF/1N HCl (1:1, 40 mL) and stirred at room temperature for 1 hour before neutralisation with saturated sodium bicarbonate solution and extraction with EtOAc (2×50 mL). The organics were combined and concentrated in vacuo to give the desired methyl ketone (1.22 g, 3.10 mmol, 89%). LC/MS: ESI MH⁺ 393, retention time 1.31 minutes Method 3.

Intermediate 182

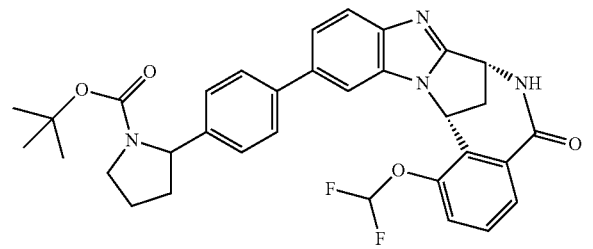 [SMILES: CC(C)(C)OC(=O)N1CCCC1c1ccc(-c2ccc3nc4n(c3c2)[C@@H]2C[C@H]4NC(=O)c3cccc(OC(F)F)c32)cc1]

tert-butyl 2-{4-[(7R,14R)-1-(difluoromethoxy)-5-oxo-5,6,7,14-tetrahydro-7,14-methanobenzimidazo[1,2-b][2,5]benzodiazocin- 11-yl] phenyl}pyrrolidine- 1-carboxylate To a solution of Example 11 (500 mg, 1.33 mmol) and tert-butyl 2-(4-(4,4,5,5-tetramethyl-1,3,2-dioxaborolan-2-yl)phenyl)pyrrolidine-1-carboxylate (768 mg, 2.00 mmol) in 1,4-dioxane (10 mL) was added K₃PO₄ (566 mg, 2.67 mmol), tricyclohexylphosphonium tetrafluoroborate (52 mg, 0.14 mmol) and tris(dibenzylideneacetone)dipalladium(0) (108 mg, 0.11 mmol) with several drops of water. The reaction mixture was degassed and flushed with nitrogen and then heated at 120 degrees in a microwave for 6 hours. The cooled reaction was diluted with H₂O (50 mL) and extracted with EtOAc×3. The combined organics were dried over Na₂SO₄, filtered and concentrated in vacuo. Purification by column chromatography, firstly with EtOAc in DCM (0 to 100%) and then with 0-10% MeOH/DCM gave the title compound (575 mg, 66%). LC/MS Method 3: RT 2.40 minutes, m/z 487.2 (-BOC).

Intermediate 182(a)

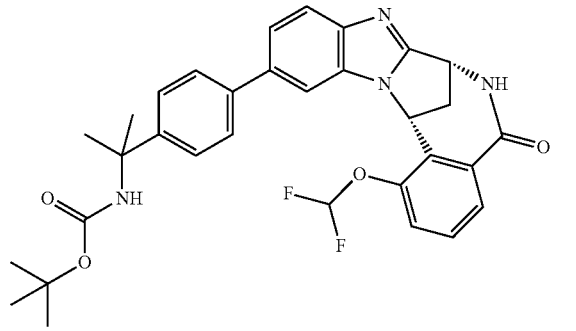 [SMILES: CC(C)(C)OC(=O)NC(C)(C)c1ccc(-c2ccc3nc4n(c3c2)[C@@H]2C[C@H]4NC(=O)c3cccc(OC(F)F)c32)cc1]

tert-Butyl (2-{4-[(7R,14R)-1-(difluoromethoxy)-5-oxo-5,6,7,14-tetrahydro-7,14-methanobenzimidazo[1,2-b][2,5]benzodiazocin- 11-yl]phenyl}propan-2-yl)carbamate The title compound can be prepared from Intermediate 171 (0.35 g, 0.93 mmol, 1 eq) and (tert-butyl 2-(4-bromophenyl)propan-2-ylcarbamate (1 eq) in accordance with the Method described for Example 137. Purification by flash chromatography on silica gel (0 to 100% EtOAc in DCM followed by 0 to 10% MeOH in DCM) afforded the title compound as a brown solid. LC/MS Method 3: RT 2.32 minutes, m/z 575.2

Intermediate 183

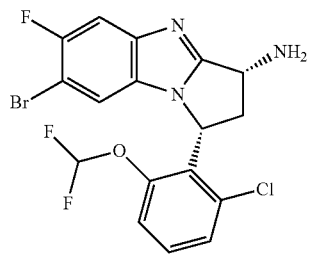 [SMILES: N[C@@H]1C[C@H](c2c(Cl)cccc2OC(F)F)n2c1nc1cc(F)c(Br)cc12]

(1R,3R)-1-[2-chloro-6-(difluoromethoxy)phenyl]-7-bromo-6-fluoro-2,3-dihydro-1H-pyrrolo[1,2-a]benzimidazol-3-amine The title compound may be prepared from Intermediate 10 in accordance with the Method described for Intermediate 40.

Intermediate 184

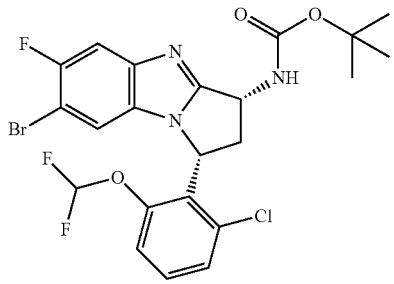 [SMILES: CC(C)(C)OC(=O)N[C@@H]1C[C@H](c2c(Cl)cccc2OC(F)F)n2c1nc1cc(F)c(Br)cc12]

tert-butyl {(1R,3R)-1-[2-chloro-6-(difluoromethoxy)phenyl]-7-bromo-6-fluoro-2,3-dihydro-1H-pyrrolo[1,2-a]benzimidazol-3-yl}carbamate The title compound may be prepared from Intermediate 183 in accordance with the Method described for Intermediate 42.

Intermediate 185

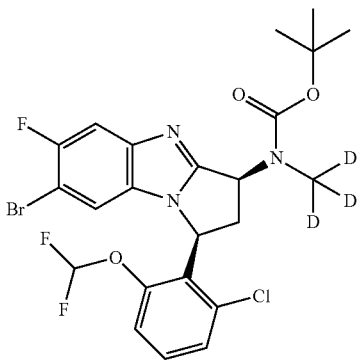 [SMILES: [2H]C([2H])([2H])N(C(=O)OC(C)(C)C)[C@H]1C[C@@H](c2c(Cl)cccc2OC(F)F)n2c1nc1cc(F)c(Br)cc12]

tert-butyl N-[(1R,3R)-7-bromo-1-[2-chloro-6-(difluoromethoxy)phenyl]-6-fluoro-2,3-dihydro-1H-pyrrolo[1,2-a]benzimidazol-3-yl]-N-(trideuteriomethyl)carbamate Intermediate 184 (300 mg, 0.549 mmol) was dissolved in tetrahydrofuran (10 mL). Potassium bis(trimethylsilyl)amide (0.6 mL, 0.6 mmol) was added dropwise at −78 degree and stirred for 30 minutes before the addition of iodomethane-d3 (0.06 mL, 1 mmol). The reaction mixture was stirred at −78° C. for 10 minutes before being left in an ice-water bath for 2 hours followed by 1 hour at room temperature. The reaction mixture was quenched with saturated ammonium chloride solution and extracted with EtOAc, the organics dried over Na₂SO₄ and concentrated in vacuo. Purification by column chromatography, eluting with 0%-10% MeOH in DCM, to afford the title compound as an off white solid (320 mg, 99%). LC/MS Method 3: RT 2.75 minutes, m/z 563.0/565.0

Intermediate 186

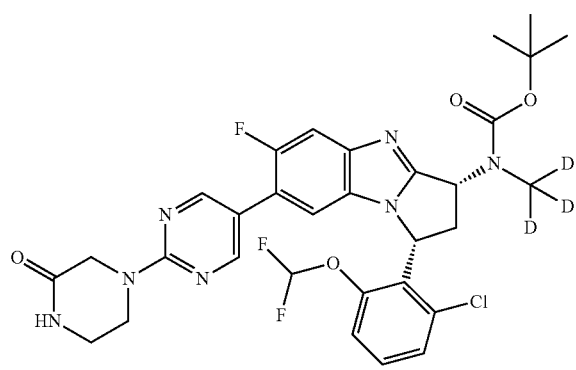 [SMILES: [2H]C([2H])([2H])N(C(=O)OC(C)(C)C)[C@@H]1C[C@H](c2c(Cl)cccc2OC(F)F)n2c1nc1cc(F)c(-c3cnc(N4CCNC(=O)C4)nc3)cc12]

tert-butyl-N-[(1R,3R)-1-[2-chloro-6-(difluoromethoxy)phenyl]-6-fluoro-7-[2-(3-oxopiperazin-1-yl)pyrimidin-5-yl]-2,3-dihydro-1H-pyrrolo[1,2-a]benzimidazol-3-yl]-N-trideuteriomethyl) carbamate Intermediate 185 (310 mg, 0.49 mmol), [2-(3-oxopiperazin-1-yl)pyrimidin-5-yl]boronic acid (0.55 mmol, 1.1 eq), potassium carbonate (115 mg, 0.83 mmol), palladium(II) acetate (7 mg, 0.03 mmol) and 4,5-bis(diphenylphosphino)-9,9-dimethylxanthene (19 mg, 0.033 mmol) were dissolved in DMSO (5 mL, 70 mmol) and a drop of water added. The mixture was degassed thoroughly and nitrogen flushed. The mixture was heated for 1 hour in a microwave at 110° C. The mixture was separated between EtOAc and brine (25 mL of each) and the aqueous extracted with EtOAc (25 mL) and the combined organics washed with 3×20 mL of brine, dried (phase separator)—and evaporated in vacuo. Purification by column chromatography on silica using a gradient EtOAc in DCM (0-100%) and then 1 to 15% MeOH in EtOAc to afford the title compound as an off white solid (210 mg, 64%). LC/MS Method 3: RT 2.28 minutes, m/z 661.2.

Intermediate 187

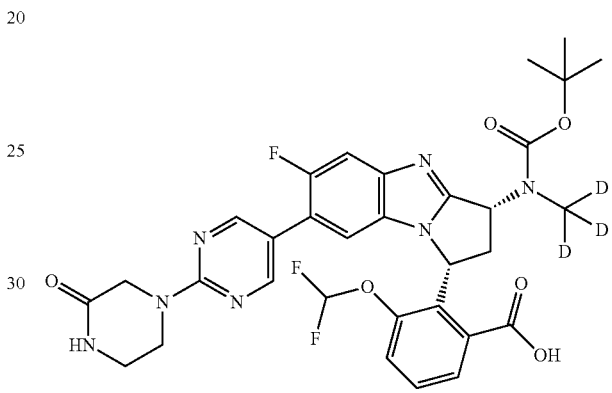

2-[(1R,3R)-3-[tert-butoxycarbonyl(trideuteriomethyl)amino]-6-fluoro-7-[2-(3-oxopiperazin-1-yl)pyrimidin-5-yl]-2,3-dihydro-1H-pyrrolo[1,2-a]benzimidazol-1-yl]-3-(difluoromethoxy) benzoic acid Into a 10 mL glass vial was placed Intermediate 186 (210 mg, 0.32 mmol), potassium carbonate (67 mg, 0.48 mmol), PdCl₂(dcypp) (15 mg, 0.025 mmol), dimethyl sulfoxide (5 mL), water (0.1 mL, 6 mmol) and the vial equipped with a stirring bar was placed into a high pressure reactor. The headspace of the reactor was vacuum purge cycled with CO at 14 psi (×3) and then left with a headspace pressure of 5 Bar. The vessel was heated to 105° C., (heating block temp) for a period of 24 hrs. The reaction mixture was separated between ethyl acetate and water (20 mL of each) and the organic layer was extracted with a further 2×20 mL of 10% sodium carbonate solution. The combined aqueous layers were then treated with citric acid until no longer basic. The solution was then extracted with ethyl acetate (3×20 mL) and these organics washed with 4×20 mL of water. The organics were dried (sodium sulfate), filtered and evaporated in vacuo to afford the title compound as a white solid ~90% pure. (120 mg, 56%). LC/MS Method 3: RT 1.51 minutes, m/z 671.2

Intermediate 188

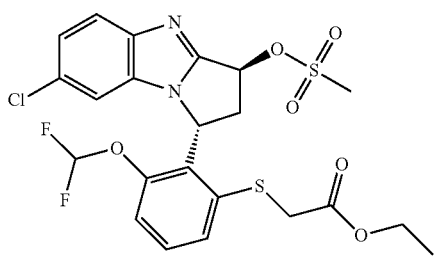 [SMILES: CCOC(=O)CSc1cccc(OC(F)F)c1[C@H]1C[C@H](OS(C)(=O)=O)c2nc3ccc(Cl)cc3n21]

Ethyl 2-[2-[(1R,3S)-7-chloro-3-methylsulfonyloxy-2,3-dihydro-1H-pyrrolo[1,2-a]benzimidazol-1-yl]-3-(difluoromethoxy)phenyl]sulfanylacetate To a solution of Intermediate 161 (1.35 g, 2.88 mmol) in DCM (30 mL) at 0° C. was added 4-dimethylaminopyridine (40 mg, 0.33 mmol), N,N-diisopropylethylamine (1.01 mL, 5.77 mmol) and methane sulfonyl chloride (335 µL, 4.32 mmol) and stirred for 45 minutes. After this time the reaction mixture was partitioned between DCM (40 mL) and water (50 mL), layers separated and the aqueous phase extracted with DCM (3×50 mL). Combined organics were washed with saturated aqueous sodium bicarbonate solution (100 mL), dried (phase separator) and concentrated in vacuo to give the title compound as orange brown solid (1.57 g, quantitative yield). The crude product was progressed to the next synthetic step without further purification.

Intermediate 189 tert-Butyl N-[1-methyl-1-[5-(4,4,5,5-tetramethyl-1,3,2-dioxaborolan-2-yl)pyrimidin-2-yl]ethyl]carbamate Bis(pinacolato)diboron (4.55 g, 17.6 mmol), Intermediate 114 (3.70 g, 11.7 mmol), potassium acetate (4.64 g, 46.8 mmol), 1,1'-bis(diphenylphosphino)ferrocene-palladium(II) dichloride dichloromethane complex (1000 mg, 1.22 mmol) and 1,4-dioxane (35 mL) were placed in a RBF and then degassed. The mixture was then heated at 105° C. for 1 hour, LCMS showed the completion of the reaction. The reaction mixture was diluted with H₂O and extracted with EtOAc (×3), and the organics combined, dried (MgSO₄), filtered and evaporated in vacuo. The crude material was used in the subsequent Suzuki coupling (3.6 g, 80%). LC/MS Method 3: RT 1.04 minutes, m/z 378.

Intermediate 190

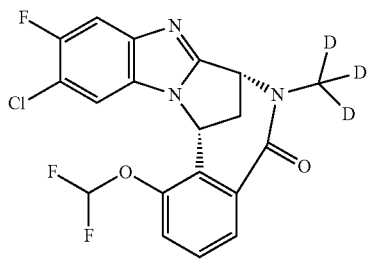 [SMILES: [2H]C([2H])([2H])N1C(=O)c2cccc(OC(F)F)c2[C@H]2C[C@@H]1c1nc3cc(F)c(Cl)cc3n12]

(7R,14R)-11-chloro-1-(difluoromethoxy)-10-fluoro-6-(trideutero)methyl-6,7-dihydro-7,14-methanobenzimidazo[1,2-b][2,5]benzodiazocin-5(14H)-one Example 10 (650 mg, 1.65 mmol) was dissolved in tetrahydrofuran (15 mL, 184 mmol) and potassium bis(trimethylsilyl)amide (1.8 mL, 1.8 mmol, 1 mol/L in TNF) was added dropwise at −78° C. and stirred for 30 minutes before the addition of iodomethane-d³ (0.16 mL, 2.5 mmol). The reaction mixture was stirred at −78° C. for 10 minutes before being left in an ice-water bath for 1 hour. The reaction mixture was quenched with aqueous saturated NH₄Cl solution and extracted with EtOAc (×3), the combined organics were dried over Na₂SO₄, filtered and concentrated in vacuo. The crude material was purified by column chromatography eluting with 0%-10% MeOH/DCM to afford the title compound (570 mg, 84%). ¹H NMR (300 MHz, DMSO-d6) δ 8.27 (dd, J=5.3, 4.1 Hz, 1H), 7.93-7.26 (m, 5H), 6.24 (d, J=7.1 Hz, 1H), 5.23 (d, J=7.1 Hz, 1H), 3.49 (dt, J=14.3, 7.3 Hz, 1H), 2.81 (d, J=13.8 Hz, 1H). LC/MS Method 3: RT 2.00 minutes, m/z 411.0

Intermediate 191

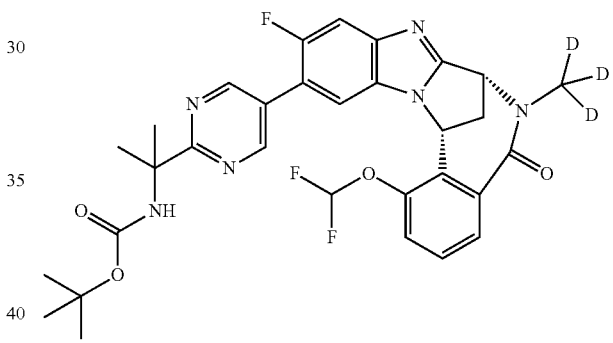

tert-Butyl (2-{5-[(7R,14R)-1-(difluoromethoxy)-10-fluoro-6-(trideutero)methyl-5-oxo-5,6,7,14-tetrahydro-7,14-methanobenzimidazo[1,2-b][2,5]benzodiazocin-11-yl]pyrimidin-2-yl}propan-2-yl)carbamate Intermediate 190 (570 mg, 1.38 mmol), Intermediate 189 (1.8 g, 4.0 mmol), potassium phosphate tribasic (1.05 g, 4.85 mmol) and tricyclohexylphosphonium tetrafluoroborate (65 mg, 0.17 mmol) were placed in a microwave vial and suspended in 1,4-dioxane (5 mL). The mixture was degassed and purged with N₂ 3 times, followed by the addition of tris(dibenzylideneacetone) dipalladium(0) (130 mg, 0.13 mmol) and three drops of water. The reaction mixture was heated at 140° C. for 2 hours in a microwave. The reaction cooled to room temperature and quenched with H₂O (20 mL) and extracted with EtOAc (3×25 mL). The combined organics were dried over (Na₂SO₄), filtered and the solvents removed in vacuo. The residue was purified by column chromatography on silica eluting with 0 to 20% MeOH in EtOAc to afford the title compound (420 mg, 50%). LC/MS Method 3: RT 2.19 minutes, m/z 612.2

Intermediate 192

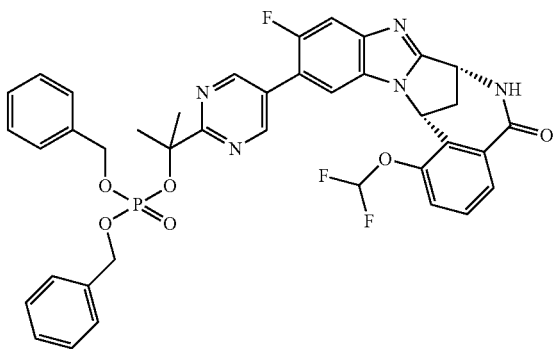 [SMILES: CC(C)(OP(=O)(OCc1ccccc1)OCc1ccccc1)c1ncc(-c2cc3c(cc2F)nc2n3[C@@H]3C[C@H]2NC(=O)c2cccc(OC(F)F)c23)cn1]

2-{5-[(7R,14R)-1-(difluoromethoxy)-10-fluoro-5-oxo-5,6,7,14-tetrahydro-7,14-methanobenzimidazo[1,2-b][2,5]benzodiazocin-11-yl]pyrimidin-2-yl}propan-2-yl, di-O-benzyl phosphate Example 1 (26.0 g, 52.5 mmol) was suspended in dichloromethane (450 mL), placed under nitrogen and 5-methyl-1H-tetrazole (8.38 g, 99.7 mmol) was added and the mixture cooled to 5° C. in an ice bath, evacuated and refilled with nitrogen twice then stirred for 5 minutes before adding dibenzyl N,N-di-isopropylphosphoramidite (28.2 mL, 83.9 mmol). The reaction was stirred for 5 minutes before warming to room temperature and stirred for one further hour. The mixture was cooled to 0° C. in an ice bath then hydrogen peroxide solution (5.96 mL, 105 mmol, 50.0% w/w in water) was added. The mixture was stirred for 1 hour and monitored by LCMS until oxidation was complete. The mixture was washed with 0.25M sodium metabisulphite solution (250 mL), then saturated aqueous sodium bicarbonate solution (150 mL) and saturated brine (200 mL). The organic phase was dried (sodium sulfate), filtered and concentrated in vacuo to a pale yellow gum. The crude product was purified by chromatography on silica (EtOAc to 15% MeOH in EtOAc) to give a crude residue which was azeotroped with toluene (×3) to give the title compound as a white solid, (31.0 g, 78%). $^1$H NMR (d$^6$-DMSO, 300 MHz) δ: 1.87 (s, 6H), 2.75 (d, 1H, J=13.4 Hz), 3.50 (m, 1H), 4.92 (t, 1H, J=6.8 Hz), 5.02-5.05 (m, 4H), 6.36 (d, 1H, J=7.1 Hz), 7.25 (m, 10H), 7.55 (m, 3H), 7.69 (d, 1H, J=11.5 Hz), 8.24 (dd, 1H, J=5.3, 4.2 Hz), 8.99 (s, 2H), 9.16 (d, 1H, J=6.8 Hz). LC/MS Method 3: RT 2.49 minutes, m/z 756.

Intermediate 193

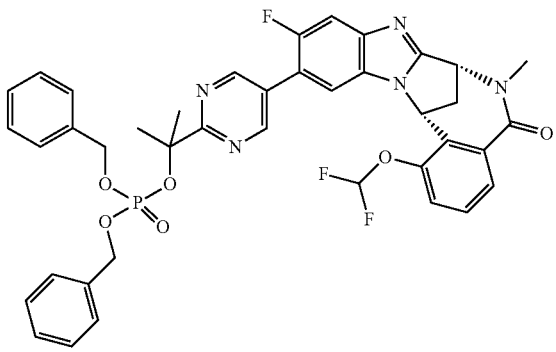 [SMILES: CN1C(=O)c2cccc(OC(F)F)c2[C@H]2C[C@@H]1c1nc3cc(F)c(-c4cnc(C(C)(C)OP(=O)(OCc5ccccc5)OCc5ccccc5)nc4)cc3n12]

2-{5-[(7R,14R)-1-(difluoromethoxy)-10-fluoro-6-methyl-5-oxo-5,6,7,14-tetrahydro-7,14-methanobenzimidazo[1,2-b][2,5]benzodiazocin-11-yl]pyrimidin-2-yl}propan-2-yl, di-O-benzyl phosphate To a solution of Intermediate 192 (4.00 g, 5.29 mmol) in THF (70 mL) was added a solution of KHMDS in THF (1M, 5.60 mL, 5.60 mmol) dropwise at −78° C. and the mixture was stirred for 45 minutes before the addition of iodomethane (0.37 mL, 5.90 mmol). The reaction mixture was warmed to 0° C. and stirred for 2.5 hours before the reaction completed. The reaction mixture was quenched with saturated aqueous NH$_4$Cl solution and extracted with EtOAc (×3), the combined organics were dried with Na$_2$SO$_4$, filtered and concentrated in vacuo. Purification by column chromatography eluting with 0-10% MeOH in EtOAc gave the title compound (3.20 g, 4.2 mmol, 79%). LC/MS Method 3: ES$^+$ (M+H)$^+$ 770, retention time 2.67 minutes.

Intermediate 194

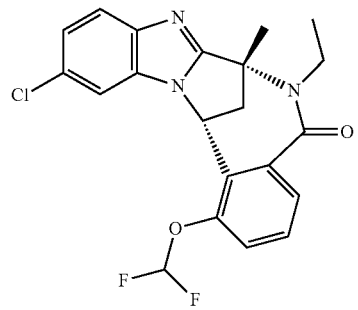 [SMILES: CCN1C(=O)c2cccc(OC(F)F)c2[C@H]2C[C@]1(C)c1nc3ccc(Cl)cc3n12]

(7R,14R)-11-chloro-1-(difluoromethoxy)-6-ethyl-7-methyl-6,7-dihydro-7,14-methanobenzimidazo[1,2-b][2,5]benzodiazocin-5(14H)-one Intermediate 148 (100 mg, 0.25 mmol) was dissolved in dry THF (2.5 mL). at the reaction was cooled to 0° C. and sodium hydride (60% in mineral oil) (12 mg, 0.30 mmol) was added. The reaction mixture was stirred at room temperature for 35 minutes. Iodomethane (0.27 mL, 3.34 mmol) was added and the reaction mixture was stirred at 50° C. overnight. The reaction mixture was quenched by addition of water (2 mL). The aqueous layer was extracted by EtOAc (3×150 mL). The combined organic layers were dried over MgSO$_4$, filtered and concentrated in vacuo. The residue was purified over silica gel (heptane/AcOEt 1/1), yielding to 35 mg (32%) of the title compound as a white solid. LCMS (Method 3 ES+): RT 2.60 min, [M+H]+ 418.

Intermediate 195

2-chloro-6-(trifluoromethoxy)benzaldehyde

N,N-Di-isopropylamine (38.4 ml, 271 mmol) was added dropwise to a solution of n-butyllithium (1.6 M, 169 ml, 271 mmol) in THF (180 ml) at 0° C. and the reaction mixture was stirred and allowed to warm to room temperature over 30 mins. The LDA solution was then added drop wise over 10 minutes to a solution of 1-chloro-3-(trifluoromethoxy)benzene (50 g, 246 mmol) in THF (500 ml) at −70° C. and the resulting mixture was stirred at −70° C. for 30 minutes.

Finally N,N-dimethylformamide (23 ml, 296 mmol) was added dropwise and the resultant mixture stirred at −70° C. for 30 minutes.

The reaction was quenched at −70° C. by addition of NH₄Cl (saturated aqueous solution) to pH 7-8 and the resulting mixture was extracted with EtOAc (3×75 ml). The combined organic phases were washed with water (100 ml), brine (100 ml), dried over magnesium sulfate, filtered and concentrated under reduced pressure to provide the title compound (55 g, 99% yield).

LCMS (Method 16, ES+) RT 1.32 min., 224 [M+H]⁺.

Intermediate 196

(S,E)-N-(2-chloro-6-(trifluoromethoxy)benzylidene)-2-methylpropane-2-sulfinamide (S)-2-Methylpropane-2-sulfinamide (49.9 g, 411 mmol), potassium hydrogen phosphate (196 g, 1.12 mol) and potassium phosphate (238.2 g, 1.12 mol) were added to a solution of Intermediate 195 (84 g, 374 mmol) in THF (2000 ml) at room temperature. The resulting reaction mixture was stirred at room temperature over 20 hours, filtered and the solid was washed with EtOAc (3×200 ml). The filtrate was concentrated under reduced pressure to isolate the title compound (123 g).

LCMS (Method 16, ES+) RT 1.45 min., 328 [M+H]⁺.

Intermediate 197

Ethyl (R)-3-(((S)-tert-butylsulfinyl)amino)-3-(2-chloro-6-(trifluoromethoxy)phenyl)-propanoate A solution of ethyl bromoacetate (106.1 ml, 938.2 mmol) in THF (100 ml) was added dropwise over 2 hours to a solution of zinc (245.5 g, 3.75 mol) and cuprous chloride (44.6 g, 450 mmol) in THF (800 ml) at 20-25° C. (NB: prior to this addition, the solution of Zn and CuCl was heated at 70° C. over 30 mins and cooled down to room temperature). Once the addition was complete the reaction mixture was warmed to 50° C. over 1 hour. The reaction mixture was cooled to 0° C. and a solution of Intermediate 196 (123 g, 375.29 mmol) in THF (500 ml) was added dropwise over 60 mins. The resulting reaction mixture was warmed to room temperature over 20 hours and filtered over charcoal. The cake was washed with EtOAc (3×250 ml) and the combined filtrates were washed with water (500 ml), with 10% citric acid solution (1000 ml) and brine (500 ml). The organic phase was dried over magnesium sulfate, filtered and concentrated under reduced pressure to give the title compound (155 g, 99% yield).

LCMS (Method 16, ES+) RT 1.36 min., 416 [M+H]⁺.

Intermediate 198

Ethyl (R)-3-amino-3-(2-chloro-6-(trifluoromethoxy)phenyl)propanoate hydrochloride 4M Hydrochloric acid solution in 1,4-dioxane (326.1 ml, 1.3 mol) was added dropwise over 30 mins to a solution of Intermediate 197 (155 g, 372.7 mmol) in a mixture of ethanol (107 ml) and diethyl ether (215 ml) at room temperature. The reaction mixture was then stirred for 2 hours and the resulting suspension was filtered. The cake was washed with Et₂O (3×250 ml), with pentane (250 ml) and dried under suction to yield 49 g of the title compound. The filtrate was concentrated under reduced pressure to provide a viscous residue. Et₂O was added to the residue, and the mixture was stirred over 20 hours. The resulting suspension was filtered and the isolated cake was washed with Et₂O (3×250 ml), with pentane (250 ml), and dried to yield 70 g of the title compound as the hydrochloride salt. LCMS (Method 16, ES+) RT 0.59 min., 311 [M+H]⁺.

Intermediate 199

Ethyl (R)-3-((5-bromo-4-fluoro-2-nitrophenyl)amino)-3-(2-chloro-6-(trifluoromethoxy)-phenyl)propanoate 1-Bromo-2,5-difluoro-4-nitrobenzene (30.2 g, 126.7 mmol) was added to a solution of ethyl Intermediate 198 (49 g, 140.8 mmol) in N,N-dimethylformamide (200 ml) and N,N-diisopropylamine (46.76 ml, 281.5 mmol) was added. The reaction mixture was heated at 85° C. over two hours and, once cooled to room temperature, was then concentrated under reduced pressure. The resulting residue was dissolved in EtOAc (500 ml), washed with water (500 ml), 10% citric acid solution (2×500 ml) and brine (500 ml). The organic phase was dried over magnesium sulfate, filtered and concentrated under reduced pressure. The resulting crude was purified by SiO₂ flash chromatography with EtOAc/n-Heptane (2/98) as eluent to provide the title compound (45 g, 60% yield).

LCMS (Method 16, ES+) RT 1.60 min., 531 [M+H]⁺.

Intermediate 200

(R)-3-((5-bromo-4-fluoro-2-nitrophenyl)amino)-3-(2-chloro-6-(trifluoromethoxy)phenyl)-propanal Diisobutylaluminium hydride was added dropwise over 2 hours to a solution of Intermediate 199 (10 g, 18.9 mmol) in THF (100 ml) at −70° C. under argon. The reaction mixture was stirred over 2 hours at −70° C. The reaction was quenched at −70° C. by addition of NH₄Cl (saturated aqueous solution) to pH=6 and the resulting suspension was filtered over a charcoal pad washing with EtOAc (75 mL). The filtrate was extracted with EtOAc (3×75 mL. The combined organic phases were washed with water (100 ml), brine (100 ml), dried over MgSO₄, filtered and concentrated under reduced pressure. The resulting residue was purified by SiO₂ flash chromatography with EtOAc/n-Heptane (1/4) as eluent to give the title compound (5.8 g, 63% yield).

LCMS (Method 17, ES+) RT 4.83 min., 487 [M+H]⁺.

Intermediate 201

(R)—N—((R,Z)-3-((5-bromo-4-fluoro-2-nitrophenyl)amino)-3-(2-chloro-6-(trifluoromethoxy)-phenyl)propylidene)-2-methylpropane-2-sulfinamide (R)-2-Methylpropane-2-sulfinamide (1.47 g, 11.9 mmol) was added to a solution of Intermediate 200 (5.8 g, 11.35 mmol) and titanium(IV) isopropoxide (3.36 ml, 11.35 mmol) in dichloromethane (100 ml) at room temperature. The reaction was heated at reflux for 20 hours.

After cooling to room temperature the reaction was quenched by addition of brine (50 ml) and the resulting mixture was stirred for 30 mins. The suspension was filtered over a charcoal pad, washed with dichloromethane until the filtrate is colourless. The filtrate was washed with brine (20 mL), dried over magnesium sulfate, filtered and concentrated under reduced pressure to afford the title compound (6.6 g, 99% yield).

LCMS (Method 18, ES+) RT 5.31 min., 588 [M+H]+.

Intermediate 202

(R)—N-((1R,3R)-3-((5-bromo-4-fluoro-2-nitrophenyl)amino)-3-(2-chloro-6-(trifluoromethoxy)phenyl)-1-cyanopropyl)-2-methylpropane-2-sulfinamide Scandium(III) trifluoromethanesulfonate (1.30 g, 2.62 mmol) was added to a solution of Intermediate 201 (7.7 g, 13.08 mmol) in dichloromethane (75 ml) at room temperature followed by trimethylsilyl cyanide (3.44 ml, 26.16 mmol). The reaction mixture was then stirred over 92 hours at room temperature. The reaction was quenched by addition of water (100 ml) and the resulting mixture was extracted with dichloromethane (2×50 ml). Combined organic phases were washed with brine (50 ml), dried over magnesium sulfate, filtered and concentrated under reduced pressure to provide the title compound (7.5 g, 93% yield).

LCMS (Method 18, ES+) RT 4.89 min., 615 [M+H]+.

Intermediate 203

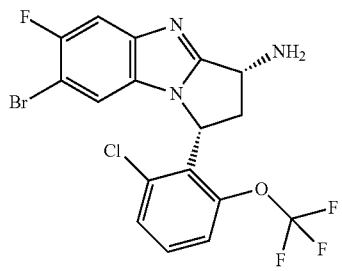 [SMILES: N[C@@H]1C[C@H](c2c(Cl)cccc2OC(F)(F)F)n2c1nc1cc(F)c(Br)cc12]

7-Bromo-1-(2-chloro-6-(trifluoromethoxy)phenyl)-6-fluoro-2,3-dihydro-1H-benzo[d]pyrrolo[1,2-a]imidazole-3-amine Stannous chloride (11.78 g, 60.9 mmol) was added to a solution of Intermediate 202 (7.5 g, 12.18 mmol) in ethanol (75 ml). The reaction mixture was heated at reflux over 2 hours and water (40 ml) was then added. The resulting solution was heated to reflux for 16 hours.

Once cooled to room temperature water (100 ml) and 2M Sodium hydroxide aqueous solution was added until pH=9.0 while keeping the solution temperature below 30° C. The resulting suspension was filtered over a charcoal pad and washed through with dichloromethane (5×50 ml). The filtrate was extracted with further dichloromethane (5×50 ml). The combined organic phases were washed with brine (20 ml), dried over magnesium sulfate, filtered and concentrated under reduced pressure to provide the title compound as cis/trans mixture of isomers (4/1, 3.00 g, 53% yield).

LCMS (Method 18, ES+) RT 2.83 min., 464 [M+H]+.

Intermediate 204

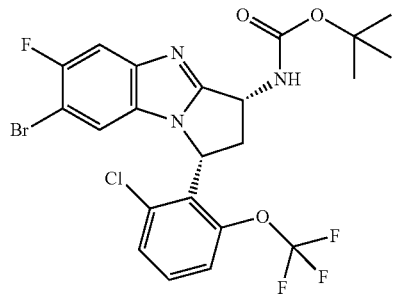 [SMILES: CC(C)(C)OC(=O)N[C@@H]1C[C@H](c2c(Cl)cccc2OC(F)(F)F)n2c1nc1cc(F)c(Br)cc12]

tert-butyl ((1R,3R)-7-bromo-1-(2-chloro-6-(trifluoromethoxy)phenyl)-6-fluoro-2,3-dihydro-1H-benzo[d]pyrrolo[1,2-a]imidazole-3-yl)carbamate Di-tert-butyl carbonate (1.99 ml, 9.04 mmol) was added to a solution of Intermediate 203 (3.00 g, 6.46 mmol) in dichloromethane (20 ml) at room temperature. The reaction mixture was then stirred for 20 hours and concentrated under reduced pressure. The resulting residue was purified by SiO2 flash chromatography with EtOAc/n-Heptane (1/4) as eluent to give the title compound (1.8 g, 49% yield).

LCMS (Method 19, ES+) RT 2.51 min., 464 [M-BOC+H]+.

Intermediate 205

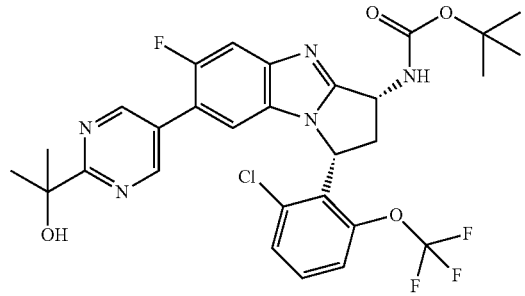 [SMILES: CC(C)(C)OC(=O)N[C@@H]1C[C@H](c2c(Cl)cccc2OC(F)(F)F)n2c1nc1cc(F)c(-c3cnc(C(C)(C)O)nc3)cc12]

tert-Butyl ((1R,3R)-1-(2-chloro-6-(trifluoromethoxy)phenyl)-6-fluoro-7-(2-(2-hydroxypropan-2-yl)pyrimidin-5-yl)-2,3-dihydro-1H-benzo[d]pyrrolo[1,2-a]imidazole-3-yl)carbamate 2-(5-(4,4,5,5-Tetramethyl-1,3,2-dioxaborolan-2-yl)pyrimidin-2-yl)propan-2-ol (0.26 g, 0.97 mmol) was added to a solution of Intermediate 204 (0.50 g, 0.89 mmol) in 1,4-dioxane (5 ml) under argon. Potassium carbonate (0.370 g, 2.66 mmol) was added to the solution and the reaction mixture was purged with argon prior. bis(diphenylphosphino)ferrocene palladium(II)dichloride dichloromethane complex (0.023 g, 0.026 mmol) was added and the reaction mixture was heated at 90° C. for 2 hours and then cooled to room temperature. The reaction was quenched by addition of iced water and the resulting mixture was extracted with EtOAc (2×30 ml). The combined organic phases were washed with brine (2×20 mL), dried over magnesium sulfate, filtered and concentrated under reduced pressure. The resulting residue was purified by SiO₂ flash chromatography with DCM/MeOH (100/0 to 98/2) followed by SiO2 flash chromatography with EtOAc/n-Heptane (3/7 to 1/1) as eluent to give the title compound (0.350 g, 64% yield).

LCMS (Method 20, ES+) RT 1.38 min., 622 [M+H]⁺.

Intermediate 206

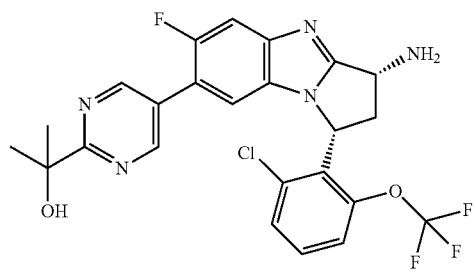 [SMILES: CC(C)(O)c1ncc(-c2cc3c(cc2F)nc2n3[C@@H](c3c(Cl)cccc3OC(F)(F)F)C[C@H]2N)cn1]

2-(5-((1R,3R)-3-amino-1-(2-chloro-6-(trifluoromethoxy)phenyl)-6-fluoro-2,3-dihydro-1H-benzo[d]pyrrolo[1,2-a]imidazole-7-yl)pyrimidin-2-yl)propan-2-ol 2N Hydrochloric acid solution in diethyl ether (2.8 ml, 5.63 mmol) was added to a solution of Intermediate 205 (0.35 g, 0.56 mmol) in dichloromethane (10 ml). The reaction mixture was stirred at room temperature over 72 hours.

Water was added and the aqueous phase was treated with 2N sodium hydroxide aqueous solution until pH=12. The resulting mixture was extracted with dichloromethane (2×50 ml) and then with EtOAc (2×50 ml). The combined organic phases were dried over magnesium sulfate, filtered and concentrated under reduced pressure to afford the title compound (300 mg).

LCMS (Method 20, ES+) RT 0.67 min., 522 [M+H]⁺.

Intermediate 207

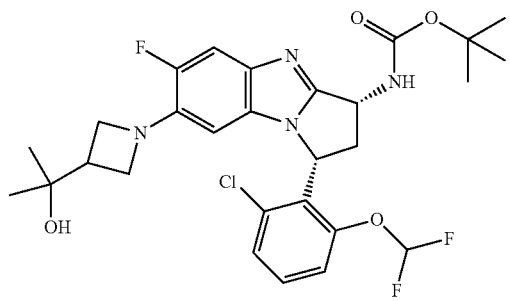 [SMILES: CC(C)(C)OC(=O)N[C@@H]1C[C@H](c2c(Cl)cccc2OC(F)F)n2c1nc1cc(F)c(N3CC(C(C)(C)O)C3)cc12]

tert-Butyl ((1R,3R)-1-(2-chloro-6-(difluoromethoxy)phenyl)-6-fluoro-7-(3-(2-hydroxypropan-2-yl)azetidin-1-yl)-2,3-dihydro-1H-benzo[d]pyrrolo[1,2-a]imidazol-3-yl)carbamate 2-(Azetidin-3-yl)propan-2-ol hydrochloride (0.208 g, 1.37 mmol) and cesium carbonate (0.890 g, 2.74 mmol) were added to a solution of Intermediate 184 (0.500 g, 0.91 mmol) in a mixture of toluene/DMF (99/1, 15 ml). The resulting mixture was purged with argon. (R/S)-(+/−)-2,2'-Bis(diphenylphosphino)-1,1'-binaphthyl (0.018 g, 0.027 mmol) and tris(benzylideneacetone)dipalladium(0) (0.009 g, 0.009 mmol) were added. The reaction mixture was then heated in a microwave at 100° C. over 2 hours. As traces of the expected azetidinyl derivative were detected by LCMS, a second addition of all reagents [2-(azetidin-3-yl)propan-2-ol hydrochloride (0.208 g, 1.37 mmol), cesium carbonate (0.890 g, 2.74 mmol), (R/S)-(+/−)-2,2'-Bis(diphenylphosphino)-1,1'-binaphthyl (0.018 g, 0.027 mmol) and tris(benzylideneacetone)-dipalladium(0) (0.009 g, 0.009 mmol)] was carried out. The reaction mixture was then heated in microwave at 100° C. for a further 2 hours.

Water (50 ml) was added and the resulting mixture was extracted with EtOAc (3×50 ml). The combined organic phases were dried over sodium sulfate, filtered and concentrated under reduced pressure. The resulting residue was purified by SiO₂ flash chromatography with DCM/MeOH (100/0 to 95/5) as eluent to give the title compound (0.249 g, 47% yield).

LCMS (Method 20, ES+) RT 1.09 min., 581 [M+H]⁺.

Intermediate 208

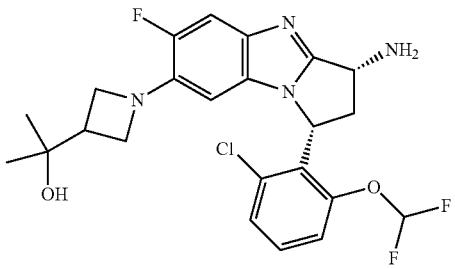 [SMILES: CC(C)(O)C1CN(c2cc3c(cc2F)nc2n3[C@@H](c3c(Cl)cccc3OC(F)F)C[C@H]2N)C1]

2-(1-((1R,3R)-3-amino-1-(2-chloro-6-(difluoromethoxy)phenyl)-6-fluoro-2,3-dihydro-1H-benzo[d]pyrrolo[1,2-a]imidazol-7-yl)azetidin-3-yl)propan-2-ol Trifluoroacetic acid (0.33 ml, 4.29 mmol) was added to a solution of Intermediate 207 (0.249 g, 0.428 mmol) in dichloromethane (5 ml). The reaction mixture was stirred at room temperature over 24 hours.

Water (30 ml) was added and the aqueous phase was treated with 2N sodium hydroxide aqueous solution until pH=12. The resulting mixture was extracted with dichloromethane (2×30 ml) and EtOAc (1x 30 ml). The combined organic phases were dried over sodium sulfate, filtered and concentrated under reduced pressure to provide the title compound (0.157 g, 76% yield).

LCMS (Method 20, ES+) RT 0.64 min., 481 [M+H]⁺.

Intermediate 209

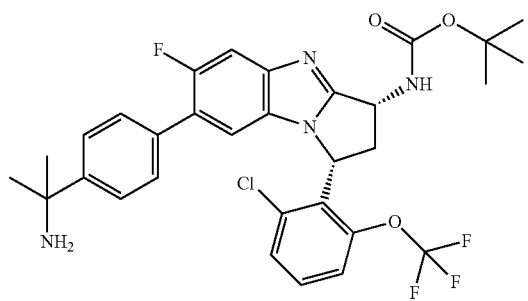 [SMILES: CC(C)(C)OC(=O)N[C@@H]1C[C@H](c2c(Cl)cccc2OC(F)(F)F)n2c1nc1cc(F)c(-c3ccc(C(C)(C)N)cc3)cc12]

tert-butyl ((1R,3R)-7-(4-(2-aminopropan-2-yl)phenyl)-1-(2-chloro-6-(trifluoromethoxy)-phenyl)-6-fluoro-2,3-dihydro-1H-benzo[d]pyrrolo[1,2-a]imidazole-3-yl)carbamate A solution of 2-(4-(4,4,5,5-tetramethyl-1,3,2-dioxaborolan-2-yl)phenyl)propan-2-amine in 1,4-dioxane (10 ml) was added to a solution of Intermediate 204 (0.500 g, 0.885 mmol) in 1,4-dioxane (40 ml) under argon. Sodium carbonate (0.188 g, 1.77 mmol) and water (1 ml) were added to the solution and purged with argon prior to addition of tris(dibenzylideneacetone)dipalladium(0) (0.021 g, 0.022 mmol) and tri-tert-butylphosphonium tretrafluoroborate (0.026 g, 0.088 mmol) were added and the reaction mixture was heated at 90° C. for 3 hours and then cooled to room temperature over 15 hours. Water (30 ml added and the resulting mixture extracted with EtOAc (2×30 ml). The combined organic phases were washed with brine (2×20 ml), dried over sodium sulfate, filtered and concentrated under reduced pressure. The resulting residue was purified by SiO$_2$ flash chromatography with DCM/MeOH (100/0 to 9/1) as eluent to give the title compound (0.250 g, 46% yield).

LCMS (Method 20, ES+) RT 0.91 min., 619 [M+H]$^+$.

Intermediate 210

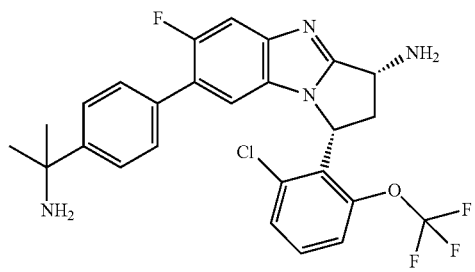 [SMILES: CC(C)(N)c1ccc(-c2cc3c(cc2F)nc2n3[C@@H](c3c(Cl)cccc3OC(F)(F)F)C[C@H]2N)cc1]

(1R,3R)-7-(4-(2-aminopropan-2-yl)phenyl)-1-(2-chloro-6-(trifluoromethoxy)phenyl)-6-fluoro-2,3-dihydro-1H-benzo[d]pyrrolo[1,2-a]imidazole-3-amine 2N Hydrochloric acid solution in diethyl ether (2.0 ml, 4.04 mmol) was added to a solution of Intermediate 209 (0.250 g, 0.404 mmol) in dichloromethane (10 ml). The reaction mixture was stirred at room temperature for 72 hours. Water (30 ml) was added and the aqueous phase was treated with 2N sodium hydroxide aqueous solution until to pH=12. The resulting mixture was extracted with dichloromethane (2×50 ml) and then with EtOAc (2×50 ml). The combined organic phases were dried over sodium sulfate, filtered and concentrated under reduced pressure to afford the title compound (0.195 g, 93% yield).

LCMS (Method 20, ES+) RT 0.45 min., 519 [M+H]$^+$.

Intermediate 211

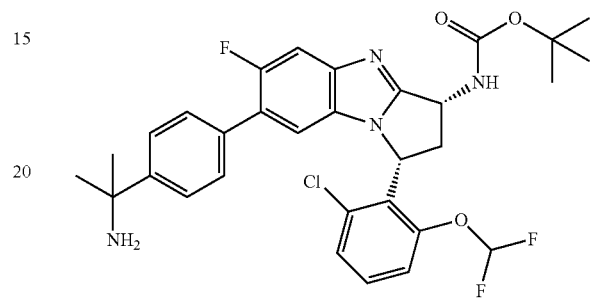

tert-butyl ((1R,3R)-7-(4-(2-aminopropan-2-yl)phenyl)-1-(2-chloro-6-(difluoromethoxy)phenyl)-6-fluoro-2,3-dihydro-1H-benzo[d]pyrrolo[1,2-a]imidazole-3-yl)carbamate The title compound was prepared from Intermediate 184 (0.500 g, 0.91 mmol) in accordance with the synthetic procedure described for Intermediate 209 after purification by SiO$_2$ flash chromatography with DCM/MeOH (100/0 to 95/5) as eluent to give (0.324 g, 59% yield).

LCMS (Method 20, ES+) RT 0.86 min., 601 [M+H]$^+$.

Intermediate 212

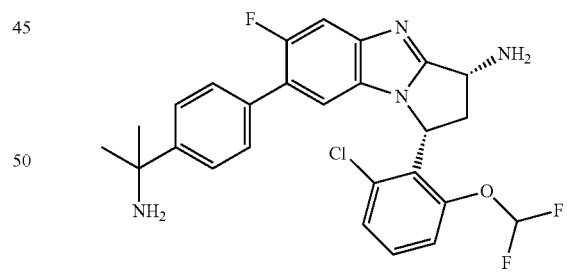

(1R,3R)-7-(4-(2-aminopropan-2-yl)phenyl)-1-(2-chloro-6-(difluoromethoxy)phenyl)-6-fluoro-2,3-dihydro-1H-benzo[d]pyrrolo[1,2-a]imidazole-3-amine The title compound was prepared from Intermediate (0.324 g, 0.54 mmol) in accordance with the synthetic procedure described for Intermediate 210 to afford the title compound (0.240 g, 89% yield).

LCMS (Method 20, ES+) RT 0.43 min., 501 [M+H]$^+$.

Intermediate 213

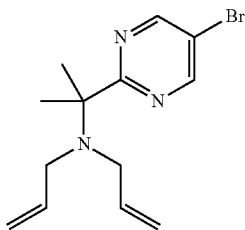 [SMILES: C=CCN(CC=C)C(C)(C)c1ncc(Br)cn1]

N,N-diallyl-2-(5-bromopyrimidin-2-yl)propan-2-amine

To a mixture of 2-(5-bromopyrimidin-2-yl)propan-2-amine (3.00 g, 13.9 mmol) and potassium carbonate (5.81 g, 41.6 mmol) in acetonitrile (50 mL) was added allyl bromide (3.56 g, 29.1 mmol) and the mixture heated to 50° C. for 4 hours. A further portion of allyl bromide (850 mg, 6.95 mmol) was added and the reaction allowed to stir at room temperature for 72 hours. The mixture was partitioned between diethyl ether (200 mL) and 2M HCl. The organic phase was further extracted with 2M HCl (×2) and the aqueous phase washed with diethylether (×2). The aqueous phase was cooled on ice and made basic with solid sodium hydroxide. The aqueous was then extracted with dichloromethane and the organic solvents dried over sodium sulphate, filtered and the volatiles removed in vacuo to give the title compound as a red oil, (3.40 g, 83% yield). LCMS Method 3 (ES+) RT 2.63 minutes, 296/298 (M+H)$^+$. $^1$H NMR (300 MHz, DMSO-d$^6$) 8.96 (s, 2H), 5.80-5.60 (m, 2H), 5.10-4.85 (m, 4H), 3.20-3.10 (m, 4H), 1.50 (s, 6H).

Intermediate 214

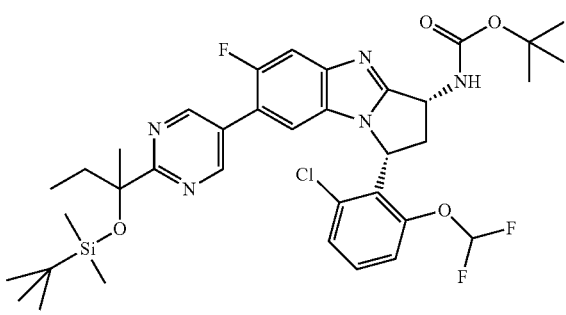 [SMILES: CCC(C)(O[Si](C)(C)C(C)(C)C)c1ncc(-c2cc3c(cc2F)nc2n3[C@@H](c3c(Cl)cccc3OC(F)F)C[C@H]2NC(=O)OC(C)(C)C)cn1]

tert-butyl ((1R,3R)-7-(2-(2-((tert-butyldimethylsilyl)oxy)butan-2-yl)pyrimidin-5-yl)-1-(2-chloro-6-(difluoromethoxy)phenyl)-6-fluoro-2,3-dihydro-1H-benzo[d]pyrrolo[1,2-a]imidazol-3-yl)carbamate A solution of 2-(2-((tert-butyldimethylsilyl)oxy)butan-2-yl)-5-(4,4,5,5-tetramethyl-1,3,2-dioxaborolan-2-yl)pyrimidine [prepared from 5-bromo-2-(2-((tert-butyldimethylsilyl)oxy)butan-2-yl)pyrimidine (0.500 g, 1.45 mmol), bis(pinacolato)diboron (0.450 g, 1.74 mmol) potassium acetate (0.426 g, 4.34 mmol), 1,1'-bis(diphenylphosphino)ferrocene palladium(II)dichloride dichloromethane complex (0.037 g, 0.043 mmol) in 1,4-dioxane (10 ml) at 95° C. during 2 hours] in 1,4-dioxane (10 ml) was added to a solution of Intermediate 184 (0.650 g, 1.19 mmol) in 1,4-dioxane (40 ml) under argon. Sodium carbonate (0.253 g, 2.38 mmol), water (1 ml) were added and the suspension purged with argon. tris(dibenzylideneacetone)dipalladium(0) (0.029 g, 0.030 mmol) and tri-tert-butylphosphonium tretrafluoroborate (0.035 g, 0.119 mmol) were added and the reaction mixture was heated at 95° C. for 3 hours before cooling to room temperature.

Water (30 ml) was added and the resulting mixture was extracted with EtOAc (2×30 ml). The combined organic phases were washed with brine (30 ml), dried over sodium sulfate, filtered and concentrated under reduced pressure. The resulting residue was purified by SiO$_2$ flash chromatography with DCM/MeOH (100/0 to 98/2) as eluent to give a brown viscous oil. Purification by preparative HPLC provided the title compound (0.310 g, 36% yield).

LCMS (Method 20, ES+) RT 1.98 min., 732 [M+H]$^+$.

Intermediate 215

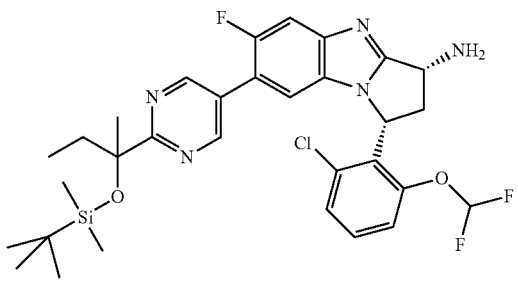 [SMILES: CCC(C)(O[Si](C)(C)C(C)(C)C)c1ncc(-c2cc3c(cc2F)nc2n3[C@@H](c3c(Cl)cccc3OC(F)F)C[C@H]2N)cn1]

(1R,3R)-7-(2-(2-((tert-butyldimethylsilyl)oxy)butan-2-yl)pyrimidin-5-yl)-1-(2-chloro-6-(difluoromethoxy)phenyl)-6-fluoro-2,3-dihydro-1H-benzo[d]pyrrolo[1,2-a]imidazol-3-amine 2N Hydrochloric acid solution in diethyl ether (1.9 ml, 3.82 mmol) was added to a solution of Intermediate 214 (0.280 g, 0.382 mmol) in dichloromethane (10 ml). The reaction mixture was stirred at room temperature for 3 hours.

Water (30 ml) was added and the aqueous phase was treated with 2N sodium hydroxide aqueous solution until pH=12. The resulting mixture was extracted with dichloromethane (2×30 ml) and with EtOAc (1× 30 ml). The combined organic phases were dried over sodium sulfate, filtered and concentrated under reduced pressure to provide the title compound (0.200 g, 78% yield).

LCMS (Method 16, ES+) RT 1.34 min., 632 [M+H]$^+$.

Intermediate 216

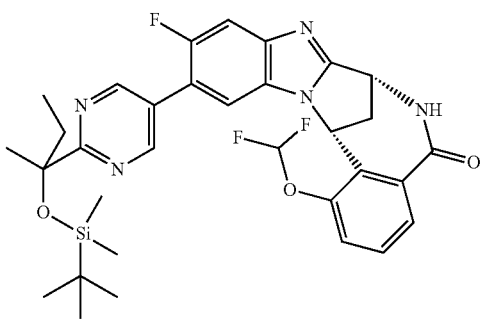 [SMILES: CCC(C)(O[Si](C)(C)C(C)(C)C)c1ncc(-c2cc3c(cc2F)nc2n3[C@@H]3C[C@H]2NC(=O)c2cccc(OC(F)F)c23)cn1]

(7R,14R)-11-(2-(2-((tert-butyldimethylsilyl)oxy)
butan-2-yl)pyrimidin-5-yl)-1-(difluoromethoxy)-10-
fluoro-6,7-dihydro-7,14-methanobenzo[f]benzo[4,5]
imidazo[1,2-a][1,4]diazocin-5(14H)-one A 0.6M solution of phenol in anhydrous DMSO (0.63 ml, 0.38 mmol) was added to a solution of Intermediate 215 (0.200 g, 0.32 mmol) in anhydrous DMSO (6 ml). Potassium carbonate (0.066 g, 0.47 mmol), dried 4 Å molecular sieves (0.240 g), dichloro-[bis(dicyclohexylphosphino)propane] palladium(II) (0.019 g, 0.032 mmol) were added.

The reaction mixture was heated at 100° C. under 3 bars of carbon monoxide over 24 hours.

EtOAc (100 ml) was added and the resulting mixture was washed with water (3×100 ml), brine (100 ml), dried over magnesium sulfate, filtered and concentrated under reduced pressure. The resulting crude residue was purified by $SiO_2$ flash chromatography with DCM/MeOH (98/2 to 95/5) as eluent to afford the title compound (0.176 g, 89% yield) LCMS (Method 20, ES+) RT 1.84 min., 624 [M+H]+.

Example 1

(7R,14R)-1-(difluoromethoxy)-10-fluoro-11-[2-(2-hydroxypropan-2-yl)pyrimidin-5-yl]-6,7-dihydro-7,14-methanobenzimidazo[1,2-b][2,5]benzodiazocin-5(14H)-one

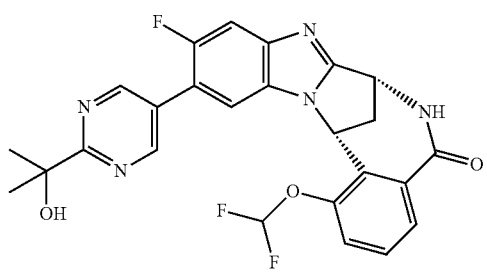 [SMILES: CC(C)(O)c1ncc(-c2cc3c(cc2F)nc2n3[C@@H]3C[C@H]2NC(=O)c2cccc(OC(F)F)c23)cn1]

Intermediate 14 was dissolved with pTSA (2.092, 11.00 mmol, 5 eq) in methanol (60 mL) and the mixture was stirred overnight at r.t. The reaction mixture was diluted with EtOAC (200 mL) and a saturated solution of $NaHCO_3$ (200 mL) was added. The aqueous layer was extracted by 3×50 mL of EtOAc and the combined organic layers were dried over magnesium sulfate, filtered and concentrated in vacuo. The obtained residue was taken up in a minimum of EtOAc, triturated, and filtered off. The obtained precipitate was washed with EtOAc and dried to afford the title compound (1.6 g, 76%).

$^1$H NMR (400 MHz, CDCl$_3$) δ 8.89 (s, 2H), 8.46 (d, J 8.0 Hz, 1H), 7.59 (m, 2H), 7.48 (m, 2H), 7.38 (m, 1H), 6.84 (t, J 72.5 Hz, 1H), 6.37 (d, J 7.0 Hz, 1H), 5.00 (t, J 6.4 Hz, 1H), 4.68 (s, 1H), 3.51 (dt, J 13.4, 7.0 Hz, 1H), 2.90 (d, J 13.3 Hz, 1H), 1.67 (s, 6H). LCMS Method 3 (ES+) RT 1.28 min, 496.0 (M+H)+.

Example 2

(7R,14R)-1-(difluoromethoxy)-10-fluoro-11-[2-(2-methoxypropan-2-yl)pyrimidin-5-yl]-6-methyl-6,7-dihydro-7,14-methanobenzimidazo[1,2-b][2,5]benzodiazocin-5(14H)-one

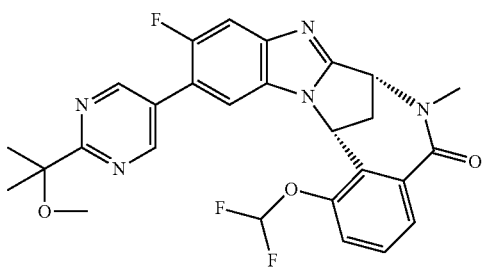 [SMILES: COC(C)(C)c1ncc(-c2cc3c(cc2F)nc2n3[C@@H]3C[C@H]2N(C)C(=O)c2cccc(OC(F)F)c23)cn1]

Example 1 (8 mg, 0.01615 mmol) was dissolved in 0.2 mL of dry THF. Sodium hydride (60% in mineral oil, 1.6 mg, 0.04037 mmoL) was added and the reaction mixture was heated at 65° C. for 1.5 h. Methyliodide (2.3 mg, 0.01615 mmoL) was added at r.t. and the mixture stirred at r.t for 16 h.

An excess of methyliodide was then added to the mixture and stirred for 1 h. Water was added, the mixture was extracted with ethyl acetate, the combined organic layers were dried over magnesium sulphate and concentrated in vacuo to the title compound as an off white solid (3 mg, 35.7%).

$^1$H NMR (400 MHz, DMSO) δ ppm 8.93 (s, 2H), 8.51 (d, J 8.2 Hz, 1H), 7.54 (m, 2H), 7.44 (t, J 8.2 Hz, 1H), 7.32 (d, J 8.1 Hz, 1H), 6.84 (t, J 72.8 Hz, 1H), 6.28 (d, J 7.2 Hz, 1H), 4.98 (d, J 7.1 Hz, 1H), 3.52 (s, 3H), 3.48 (m, 1H), 3.28 (s, 3H), 2.90 (d, J 13.6 Hz, 1H), 1.70 (s, 6H). LCMS Method 3 (ES+) RT 1.39 min, 524.0 (M+H)+.

Example 3

(7R,14R)-1-(difluoromethoxy)-11-[2-(2-hydroxypropan-2-yl)pyrimidin-5-yl]-6,7-dihydro-7,14-methanobenzimidazo[1,2-b][2,5]benzodiazocin-5(14H)-one

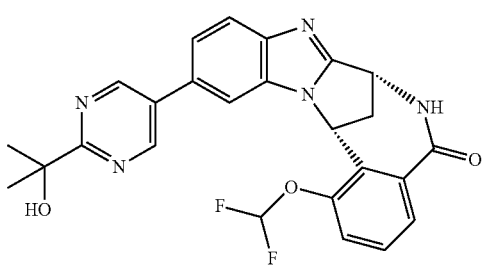 [SMILES: CC(C)(O)c1ncc(-c2ccc3nc4n(c3c2)[C@@H]2C[C@H]4NC(=O)c3cccc(OC(F)F)c32)cn1]

Intermediate 23 (525 mg, 0.8873 mmoL) was dissolved in 60 mL of methanol and cooled to 0° C. pTSA (1 g, 0.7031 mmoL) was added and the mixture stirred at room temperature for 16 h. The mixture was cooled down to 0° C., pTSA (1 g, 0.7031 mmoL) was added and the reaction mixture was heated at 60° C. for 2 h. The solvent was evaporated, the residue was taken up in dichloromethane and washed with saturated aqueous sodium hydrogen carbonate. The aqueous layer was extracted with DCM, the combined layers were dried over anhydrous MgSO$_4$, filtered and concentrated in vacuo. The crude compound was triturated with EtOAc filtered, washed with a minimum of cold ethyl acetate and dried in vacuo to afford the title compound as a white solid (318 mg, 75%).

$^1$H NMR (400 MHz, DMSO) δ ppm 9.14 (d, J 6.9 Hz, 1H), 9.04 (s, 2H), 8.25 (dd, J 4.6 Hz, J 4.1 Hz, 1H), 7.86-7.50 (m, 6H), 6.38 (d J 7.0 Hz, 1H), 5.12 (s, 1H), 4.92 (t, J 6.8 Hz, 1H), 3.49 (m, 1H), 2.77 (d, J 13.3 Hz, 1H), 1.54 (s, 6H). LCMS Method 3 (ES$^+$) RT 1.26 min, 478.0 (M+H)$^+$.

Example 4

(7R,14R)-1-(difluoromethoxy)-11-[2-(2-hydroxypropan-2-yl)pyrimidin-5-yl]-6-methyl-6,7-dihydro-7,14-methanobenzimidazo[1,2-b][2,5]benzodiazocin-5(14H)-one

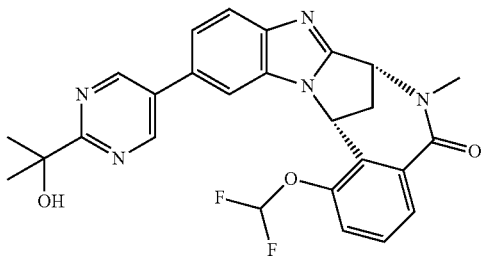 [SMILES: CN1C(=O)c2cccc(OC(F)F)c2[C@H]2C[C@@H]1c1nc3ccc(-c4cnc(C(C)(C)O)nc4)cc3n12]

Intermediate 24 was dissolved in methanol (20 mL/g), pTSA (0.600 g, 3.152 mmol, 2.2 eq) was added and the reaction mixture was stirred at r.t. overnight. APTS (0.300 g, 1.176 mmol, 1.1 eq) was added and the reaction mixture was heated at 40° C. for 2 h, then 45° C. for 1 h and following 50° C. for 15 minutes until disappearance of starting material in LCMS. EtOAc (600 mL) was added and the mixture was washed successively with a saturated solution of NaHCO$_3$ (200 mL) and a saturated solution of NaCl (200 mL), dried over anhydrous magnesium sulfate, filtered and concentrated in vacuo, diluted with diethylether (150 mL) and concentrated in vacuo to afford the title compound as an off-white solid (0.701 g, 99%).

$^1$H NMR (400 MHz, CDCl$_3$) δ 8.83 (s, 2H), 8.43 (d, J=8.2 Hz, 1H), 7.84 (d, J=8.5 Hz, 1H), 7.70 (s, 1H), 7.47 (d, J=8.6 Hz, 1H), 7.39 (t, J=8.2 Hz, 1H), 7.26 (d, J=8.1 Hz, 1H), 6.79 (t, J=72.5 Hz, 1H), 6.33 (d, J=7.2 Hz, 1H), 5.25 (d, J=7.1 Hz, 1H), 3.55 (d, J=7.1 Hz, 1H), 3.53 (s, 3H), 3.38 (d, J=6.7 Hz, 1H), 2.89 (d, J=13.7 Hz, 1H), 1.57 (s, 6H). LCMS Method 3 (ES$^+$) RT 1.30 min, 492.0 (M+H)$^+$.

Example 5

(7R,14R)-1-(difluoromethoxy)-6-ethyl-11-[2-(2-hydroxypropan-2-yl)pyrimidin-5-yl]-6,7-dihydro-7,14-methanobenzimidazo[1,2-b][2,5]benzodiazocin-5(14H)-one

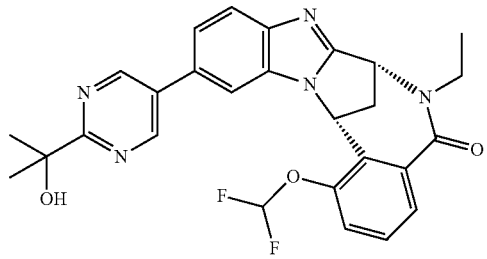 [SMILES: CCN1C(=O)c2cccc(OC(F)F)c2[C@H]2C[C@@H]1c1nc3ccc(-c4cnc(C(C)(C)O)nc4)cc3n12]

Intermediate 25 (69 mg, 0.1113 mmoL) was dissolved in 1 mL of methanol, pTSA (105.9 mg, 34.0908 mmoL) was added and the mixture was stirred at r.t. for 16 h. EtOAc was added, washed with saturated aqueous sodium hydrogen carbonate and brine. The organic layer was dried over magnesium sulphate and concentrated in vacuo. The residue was purified by chromatography (SiO2, 75% EtOAc in heptane) and triturated with diethyl ether to afford the title compound as an off white solid (23 mg, 40.9%).

$^1$H NMR (400 MHz, CDCl$_3$) δ ppm 8.95 (s, 2H), 8.56 (d, J=7.4 Hz, 1H), 7.93 (m, 1H), 7.81 (s, 1H), 7.54 (m, 1H), 7.48 (m, 1H), 7.35 (d, J=7.2 Hz, 1H), 6.89 (t, J=72.3 Hz, 1H), 6.41 (s, 1H), 5.25 (m, 1H), 4.17 (m, 1H), 3.95 (m, 1H), 3.59 (m, 1H), 2.93 (m, 1H), 1.68 (s, 6H), 1.49 (m, 3H). LCMS Method 3 (ES$^+$) RT 1.36 min, 506.0 (M+H)$^+$.

Example 6

(7R,14R)-1-(difluoromethoxy)-11-[2-(2-hydroxypropan-2-yl)pyrimidin-5-yl]-6-(propan-2-yl)-6,7-dihydro-7,14-methanobenzimidazo[1,2-b][2,5]benzodiazocin-5(14H)-one

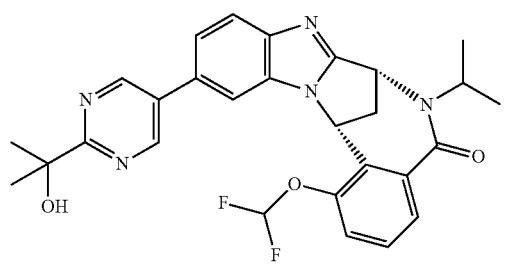 [SMILES: CC(C)N1C(=O)c2cccc(OC(F)F)c2[C@H]2C[C@@H]1c1nc3ccc(-c4cnc(C(C)(C)O)nc4)cc3n12]

Intermediate 26 (10 mg, 0.0158 mmoL) was dissolved in MeOH (0.2 mL) and pTSA (6.6 mg, 0.0347 mmoL) was added. The mixture was stirred at r.t. After 16 h, pTSA (6.6 mg, 0.0347 mmoL) was again added and the mixture heated at 50° C. for 1 h. The reaction mixture was concentrated, the residue dissolved in EtOAc washed with saturated aqueous sodium hydrogen carbonate and brine. The organic layer was dried over anhydrous magnesium sulphate, concentrated in vacuo and triturated with diethyl ether to afford the title compound as a white solid (7 mg, 85.4% yield).

LCMS (ES$^+$) Method 3 RT 1.42 min, 520.0 (M+H)$^+$.

Example 7

(7R,14R)-1-(difluoromethoxy)-10-fluoro-11-[2-(2-hydroxypropan-2-yl)pyrimidin-5-yl]-7H-7,14-methanobenzimidazo[2,1-d][2,5]benzoxazocin-5(14H)-one

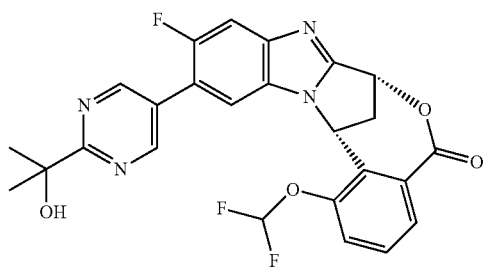 [SMILES: CC(C)(O)c1ncc(-c2cc3c(cc2F)nc2n3[C@@H]3C[C@H]2OC(=O)c2cccc(OC(F)F)c23)cn1]

To a suspension of Intermediate 29 (50 mg, 0.0972 mmoL) in 1 mL of toluene was added cyanomethylenetributylphosphorane (25.9 mg, 0.0282 mmoL) and the reaction mixture was heated at 100° C. for 16 h. The mixture was cooled to r.t., taken up with EtOAc and washed with 1N sodium hydroxide. The organic layer was dried over magnesium sulphate and concentrated in vacuo and triturated with diethyl ether to afford the title compound as an off-white solid (3 mg, 6.2% yield).

$^1$H NMR (400 MHz, DMSO) δ ppm 8.96 (s, 2H), 8.08 (d, J=7.9 Hz, 1H), 7.76 (d, J=11.3 Hz, 1H), 7.65 (t, J=73.8 Hz, 1H), 7.61 (m, 2H), 7.55 (m, 1H), 6.47 (d, J=6.8 Hz, 1H), 6.10 (d, J=5.3 Hz, 1H), 5.17 (bs, 1H), 3.61 (m, 1H), 3.18 (d, J=14.7 Hz, 1H), 1.49 (m, 6H). LCMS Method 3 (ES$^+$) RT 1.36 min, 497.0 (M+H)$^+$.

Example 8

(2Z)-[(7R,14R)-1-(difluoromethoxy)-10-fluoro-11-[2-(2-hydroxypropan-2-yl)pyrimidin-5-yl]-7H-7,14-methanobenzimidazo[2,1-d][2,5]benzoxazocin-5(14H)-ylidene]acetonitrile and (2E)-[(7R,14R)-1-(difluoromethoxy)-10-fluoro-11-[2-(2-hydroxypropan-2-yl)pyrimidin-5-yl]-7H-7,14-methanobenzimidazo[2,1-d][2,5]benzoxazocin-5(14H)-ylidene]acetonitrile

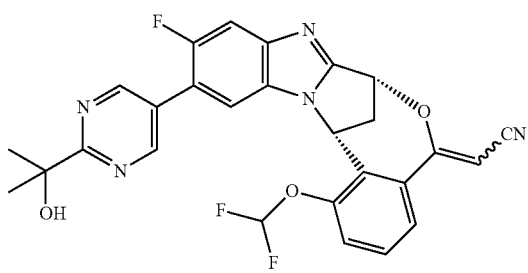 [SMILES: CC(C)(O)c1ncc(-c2cc3c(cc2F)nc2n3[C@@H]3C[C@H]2OC(=CC#N)c2cccc(OC(F)F)c23)cn1]

To a suspension of Intermediate 29 (50 mg, 0.0972 mmoL) in 1 mL of toluene was added cyanomethylenetributylphosphorane (25.9 mg, 0.0282 mmoL) and the reaction mixture was heated at 100° C. for 16 h. The reaction was concentrated in vacuo and the residue was purified by reverse phase preparative LCMS (basic conditions). The residue was dissolved in 2 mL of MeOH and passed through an acidic exchange-ion column (400 mg, conditioning: MeOH 10 mL), followed by washing of the column with 10 mL of methanol. The compound was discharged from the resin by elution of 10 mL of ammonia (1 M in methanol) and concentrated in vacuo. The residue was purified by preparative TLC with EtOAc-hexane (8/2), to afford the title compound as a colourless oil (2.5 mg, 4.95% yield) in a 6/4 mixture of Z/E isomers.

$^1$H NMR (400 MHz, CDCl3) δ ppm 8.93 (s, 1.2H), 8.90 (s, 0.8H), 7.69 (t, J=11.5 Hz, 1H), 7.60 (d, J=7.6 Hz, 0.6H), 7.40 (m, 3H), 7.25 (d, J=7.4 Hz, 0.4H), 6.84 (t, J=72.5 Hz, 0.4H), 6.83 (t, J=72.3 Hz, 0.6H), 6.28 (m, 1H), 6.01 (d, J=4.3 Hz, 0.4H), 5.87 (d, J=4.1 Hz, 0.6H), 5.34 (s, 0.6H), 5.07 (s, 0.4H), 3.32 (m, 1H), 3.07 (d, J=14.1 Hz, 0.4H), 3.02 (d, J=13.9 Hz, 0.6H, 1.67 (s, 6H).

LCMS Method 3 (ES$^+$) RT 1.39 min, 520.0 (M+H)$^+$.

Example 9

(7R,14R) and (7S,14S)-11-[2-(2-hydroxypropan-2-yl)pyrimidin-5-yl]-7,14-dihydro-7,14-methanopyrido[1',2':1,2]imidazo[4,5-d][2]benzazocin-5(6H)-one

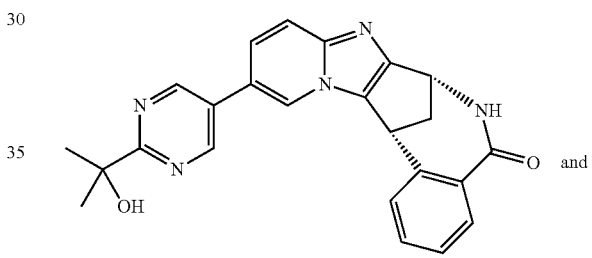

and

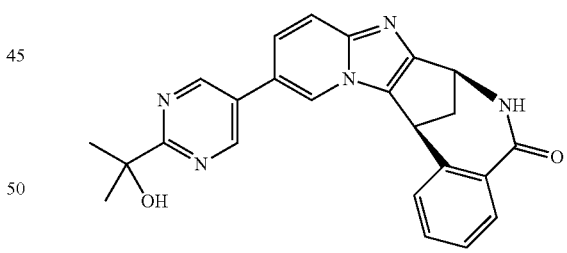

The title compound was prepared from Intermediate 37 (300 mg, 0.71 mmol), Na$_2$CO$_3$ (378 mg, 3.57 mmol) and dichloro [bis(dicyclohexylphosphino)propane]palladium(II) [Pd-133 from Johnson Matthey] (40 mg, 0.06 mmol), 1,4-dioxane (9 mL) under CO gas (5 bars) at 150° C. for 15 h, following the protocol described for Intermediate 14 (5.5 mg, 2%). $^1$H NMR (500 MHz, DMSO-d$_6$) δ 9.10 (s, 2H), 8.90 (s, 1H), 8.70 (d, J 6.3 Hz, 1H), 8.28 (d, J 8.0 Hz, 1H), 7.95 (d, J 7.5 Hz, 1H), 7.66 (d, J 9.4 Hz, 1H), 7.61 (d, J 9.4 Hz, 1H), 7.48 (t, J 7.4 Hz, 1H), 7.27 (t, J 7.7 Hz, 1H), 5.11 (s, 1H), 4.75 (d, J 6.1 Hz, 1H), 4.69 (t, J 6.3 Hz, 1H), 2.44 (d, J 12.6 Hz, 2H), 1.54 (s, 6H).

LCMS Method 3 (ES$^+$) RT 1.64 min, 412.0 (M+H)$^+$.

Example 10

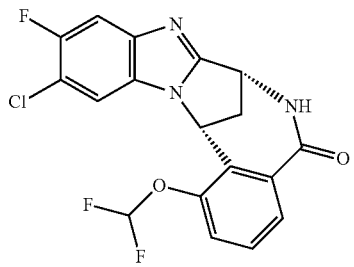 [SMILES: O=C1N[C@@H]2C[C@H](c3c(OC(F)F)cccc31)n1c2nc2cc(F)c(Cl)cc21]

(7R,14R)-11-chloro-1-(difluoromethoxy)-10-fluoro-6,7-dihydro-7,14-methanobenzimidazo[1,2-b][2,5]benzodiazocin-5(14H)-one In a high pressure reactor, Intermediate 41 (927 mg, 2.076 mmol) was solubilized in dry 1,4-dioxane (21 mL). Potassium carbonate (1.4 g, 10.4 mmol) was added. A solution of palladium(II) acetate (23.3 mg, 0.1038 mmol) and 4,5-bis(diphenylphosphino)-9,9-dimethylxanthene (61.9 mg, 0.1038 mmol) in 1 mL of dry dioxane was then added. The reactor was closed and degassed by 3 successive vacuum/nitrogen cycles and then with CO by 3 successive vacuum/CO cycles. The bomb was charged with CO to 8 psi and heated at 110° C. overnight. The reaction mixture was subsequently filtered through a pad of celite and the pad rinsed by 50 mL of EtOAc. The filtrate was concentrated in vacuo and the residue purified over silica gel using AcOEt/MeOH 10/0 to 9/1 to yield 534 mg (65%) of the title compound as a pale brown solid. LCMS basic: RT 1.97 min. (ES+) 394/396 (M+H)$^+$. 1H NMR (400 MHz, DMSO): 9.13 (d, J=6.8 Hz, 1H), 8.23 (dd, J1=6.9 Hz, J2=2.6 Hz, 1H), 7.70 (d, J=10.1 Hz, 1H), 7.60 (t, J=73.2 Hz, 1H), 7.51 (m, 3H), 6.30 (d, J=7.1 Hz, 1H), 4.88 (t, J=6.8 Hz, 1H), 3.45 (m, 1H), 2.73 (d, J=13.4 Hz, 1H).

Example 11

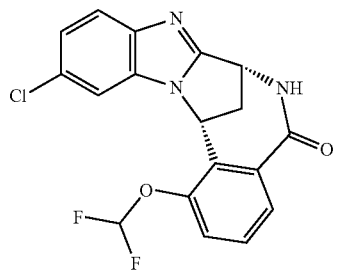 [SMILES: O=C1N[C@@H]2C[C@H](c3c(OC(F)F)cccc31)n1c2nc2ccc(Cl)cc21]

(7R,14R)-11-chloro-1-(difluoromethoxy)-6,7-dihydro-7,14-methanobenzimidazo[1,2-b][2,5]benzodiazocin-5(14H)-one Intermediate 40 (3.7 g, 8.6 mmol), activated molecular sieve 4A powder (1.2 g), potassium carbonate (1.5 equiv., 13 mmol) followed by dichloro[9,9-dimethyl-4,5-bis(diphenylphosphino)xanthene]palladium(II) (0.04 equiv., 0.35 mmol) were poured into the center of the 100 mL Glass Parr reaction vessel. 3 cycles of vacuum (~20 mmHg) followed by Argon were applied to the closed reactor.

Anhydrous dimethyl sulfoxide (35 mL) was added, followed by phenol 5M in DMSO (1.1 equiv., 9.5 mmol). The solution was degassed by 3 vacuum (~20 mmHg)/argon cycles followed by 3 cycles of vacuum/CO resulting in a final CO pressure of 1 bar.

The mixture was stirred and heated overnight at 100° C. under the CO atmosphere. The reaction was cooled to 30° C., the reactor vessel was opened and EtOAc (40 mL) was added. The resulting mixture was filtered on a pad of Celite, evaporated in vacuo to yield a green oil.

The residue thus obtained was taken up in EtOAc (100 mL) and the organic layer was washed with water, K$_2$CO$_3$ (saturated aqueous solution) and brine (saturated aqueous solution). The aqueous layer was then re-extracted with EtOAc (1×50 mL). The combined organic layers were dried over MgSO$_4$, filtered and evaporated to dryness. The obtained green solid (3.65 g), was taken up in EtOAc, the insoluble material was filtered and rinsed with Et$_2$O to afford 1.06 g (33.1%) of the title compound as a grey solid.

The filtrate can be purified by flash chromatography to provide additional product if required: LCMS basic: MH+ m/z=376, RT 1.90 minutes.

$^1$H NMR (300 MHz, DMSO) δ 9.12 (d, 1H, J=6.7 Hz), 8.23 (dd, 1H, J=7.0, 2.4 Hz), 7.60 (m, 5H), 7.20 (dd, 1H, J=8.7, 2.1 Hz), 6.29 (d, 1H, J=7.1 Hz), 4.87 (dd, 1H, J=6.7 Hz, 6.7 Hz), 3.46 (m, 1H), 2.72 (d, 1H, J=13.4 Hz).

Example 12

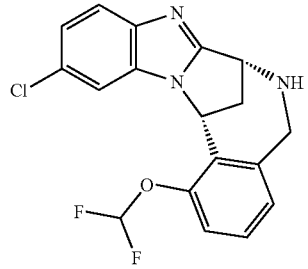 [SMILES: FC(F)Oc1cccc2c1[C@H]1C[C@@H](NC2)c2nc3ccc(Cl)cc3n21]

(7R,14R)-11-chloro-1-(difluoromethoxy)-5,6,7,14-tetrahydro-7,14-methanobenzimidazo[1,2-b][2,5]benzodiazocine Intermediate 45 (0.0525 mmol) was solubilized in THF (0.5 mL) and ethanol (0.5 mL). Polymer-supported cyanoborohydride (33 mg, 0.132 mmol, 4 mmol/g) was added. The reaction mixture was subjected to an orbital shaker for 2 hours. The reaction mixture was then filtered and evaporated under reduced pressure. The crude material was purified by preparative reverse phase HPLC (basic condition) to afford 7 mg (37%) of the title compound. LCMS basic (ES+) RT 3.5 min., 362/364(M+H)+. LCMS acidic (ES+) RT 2.12 min., 362/364(M+H)+.

$^1$H NMR (400 MHz, CDCl3) δ 7.69 (m, 1H), 7.20 (m, 3H), 7.13 (m, 1H), 6.99 (m, 1H), 6.73 (m, 1H), 6.10 (m, 1H), 4.77 (m, 1H), 3.66 (m, 1H), 3.21 (m, 1H), 3.01 (d, 1H, J=15.3 Hz), 2.94 (m, 1H), 2.50 (m, 1H).

Example 13

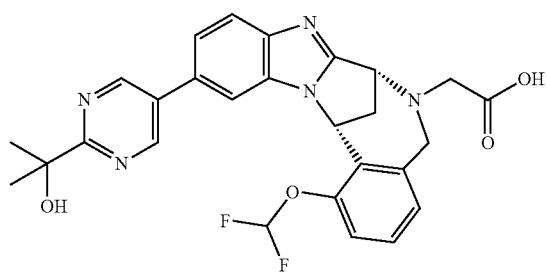 [SMILES: CC(C)(O)c1ncc(-c2ccc3nc4n(c3c2)[C@@H]2C[C@H]4N(CC(=O)O)Cc3cccc(OC(F)F)c32)cn1]

[(7R,14R)-1-(difluoromethoxy)-11-[2-(2-hydroxy-propan-2-yl)pyrimidin-5-yl]-5,14-dihydro-7,14-methanobenzimidazo[1,2-b][2,5]benzodiazocin-6(7H)-yl]acetic acid Intermediate 46 (34 mg, 0.076 mmol), 2-(1-hydroxy-1-methylethyl) pyrimidine-5-boronic acid pinacol ester (2.5 equiv., 0.190 mmol), K₃PO₄ (2 equiv., 0.152 mmol), tris (dibenzylideneacetone)dipalladium(0) (0.05 equiv., 0.0038 mmol), and tricyclohexylphosphonium tetrafluoroborate (0.12 equiv., 0.0091 mmol) were dissolved in a degassed mixture of 1,4 dioxane (0.9 mL) and water (0.1 mL). The reaction mixture was heated overnight at 105° C.

The mixture was cooled to r.t; water was added and the mixture extracted with EtOAc. The aqueous layer was brought to pH 2-3 with HCl 1N, extracted with EtOAc, dried over magnesium sulphate, filtered and concentrated in vacuo. The crude product was purified by reverse phase chromatography to afford 3 mg (7.5%) of the title compound as a white solid at 90% purity. LCMS (ES+) 522/523 (M+H)⁺

Example 14

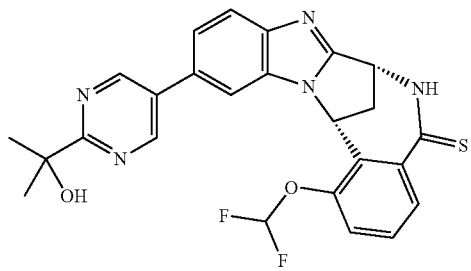 [SMILES: CC(C)(O)c1ncc(-c2ccc3nc4n(c3c2)[C@@H]2C[C@H]4NC(=S)c3cccc(OC(F)F)c32)cn1]

(7R,14R)-1-(difluoromethoxy)-11-[2-(2-hydroxypropan-2-yl)pyrimidin-5-yl]-6,7-dihydro-7,14-methanobenzimidazo[1,2-b][2,5]benzodiazocine-5(14H)-thione To a solution of Intermediate 47 5 (15 mg, 0.025 mmol) in MeOH (1 mL) was added p-toluenesulfonic acid monohydrate (23.5 mg, 0.124 mmol). The slurry was stirred overnight at r.t. The reaction mixture was quenched with NaHCO₃ (10% aqueous solution) and extracted with EtOAc (3×5 mL). The organic layer was dried over MgSO₄, filtered and concentrated in vacuo. The residue was purified by preparative TLC (DCM/MeOH 9/1) followed by a second purification by flash chromatography on silica gel (DCM/MeOH 100/0 to 95/5) to afford 9 mg (74%) of the title compound. LCMS acidic (ES+) RT 2.29 min., 494(M+H)⁺.

Example 15

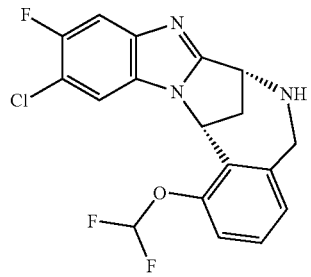 [SMILES: Fc1cc2nc3n(c2cc1Cl)[C@@H]1C[C@H]3NCc2cccc(OC(F)F)c21]

(7R,14R)-11-chloro-1-(difluoromethoxy)-10-fluoro-5,6,7,14-tetrahydro-7,14-methanobenzimidazo[1,2-b][2,5]benzodiazocine Example 10 (178 mg, 0.452 mmol) was solubilized in dry THF (5 mL). At 0° C., borane dimethyl sulfide complex (340 μL, 2M solution in THF, 0.68 mmol) was added. The reaction mixture was allowed to warm to r.t. and stirred overnight. The reaction mixture was concentrated in vacuo, the residue was taken up in MeOH, stirred and heated under reflux for 48 hours. The reaction mixture was concentrated in vacuo and the residue was purified by reverse phase preparative LCMS (basic condition) to afford 65 mg (38%) of the title compound. LCMS basic (ES+) RT 3.55 min., 380/382(M+H)+. LCMS acidic (ES+) RT 3.56 min., 380/382(M+H)+. ¹H NMR (400 MHz, CDCl3) δ ppm 7.52 (d, 1H, J=9.6 Hz), 7.23 (m, 2H), 7.12 (m, 1H), 6.97 (d, 1H, J=7.4 Hz), 6.71 (m, 1H), 6.09 (d, 1H, J=7.6 Hz), 4.70 (d, 2H, J=5.9 Hz), 3.64 (m, 1H), 3.21 (m, 1H), 2.98 (d, 1H, J=15.3 Hz), 2.48 (d, 1H, J=12.6 Hz).

Example 16

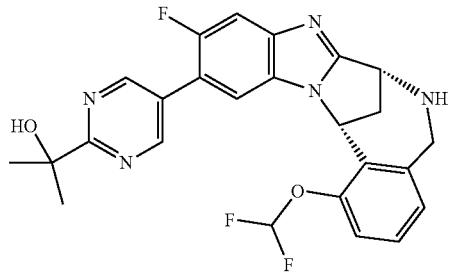 [SMILES: CC(C)(O)c1ncc(-c2cc3c(cc2F)nc2n3[C@@H]3C[C@H]2NCc2cccc(OC(F)F)c23)cn1]

2-{5-[(7R,14R)-1-(difluoromethoxy)-10-fluoro-5,6,7,14-tetrahydro-7,14-methanobenzimidazo[1,2-b][2,5]benzodiazocin-11-yl]pyrimidin-2-yl}propan-2-ol Example 15 (47 mg, 0.1237 mmol), 2-[5-(4,4,5,5-tetramethyl-1,3,2-dioxaborolan-2-yl)pyrimidin-2-yl]propan-2-ol (82 mg, 0.3105 mmol), tricyclohexylphosphonium tetrafluoroborate (5.524 mg, 0.01485 mmol), tris (dibenzylideneacetone)dipalladium(0) (5.6 mg, 0.0061 mmol), and K$_3$PO$_4$ (52.5 mg, 0.248 mmol) were placed in a tube, and filled with argon. Degassed 1,4 dioxane (1 mL) and water (100 μL) were added and the resulting slurry was stirred at 105° C. for 2 hours. The reaction mixture was cooled to r.t. before addition of EtOAc (2 mL) and water (2 mL). The aqueous layer extracted with EtOAc (2×2 mL). The combined organic layers were dried over magnesium sulphate, filtered and concentrated in vacuo. The crude was purified by reverse phase preparative LCMS (acidic condition) to afford the TFA salt of the title compound which was solubilized in EtOAc (2 mL) and washed with a saturated solution of NaHCO$_3$. The aqueous layer was extracted with EtOAc (2×2 mL). The combined organic layers were dried over magnesium sulphate, filtered and concentrated in vacuo to afford 33 mg (55%) of the title compound as a white solid. LCMS basic (ES+) RT 3.69 min., 482(M+H)+.

LCMS acidic (ES+) RT 1.91 min., 482(M+H)$^+$. $^1$H NMR (400 MHz, CDCl3) δ ppm 8.87 (m, 2H), 7.62 (m, 1H), 7.25 (s, 1H), 7.20 (m, 1H), 7.12 (m, 1H), 6.99 (m, 1H), 6.72 (m, 1H), 6.17 (m, 1H), 4.78 (m, 1H), 4.66 (m, 1H), 3.66 (m, 1H), 3.25 (m, 1H), 3.05 (m, 1H), 2.53 (m, 1H), 1.65 (s, 6H).

Example 17

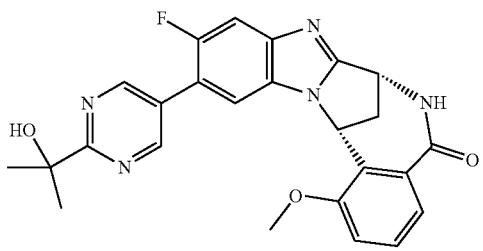 [SMILES: COc1cccc2c1[C@H]1C[C@@H](NC2=O)c2nc3cc(F)c(-c4cnc(C(C)(C)O)nc4)cc3n21]

(7R,14R)-10-fluoro-11-[2-(2-hydroxypropan-2-yl) pyrimidin-5-yl]-1-methoxy-6,7-dihydro-7,14-methanobenzimidazo[1,2-b][2,5]benzodiazocin-5(14H)-one Intermediate 57 (145 mg, 0.31 mmol) was dissolved in anhydrous DMA (3 mL) in a 25 mL pressure reactor and Na$_2$CO$_3$ (165 mg, 1.56 mmol) was added. The mixture was degassed with a stream of nitrogen for 10 minutes then the pressure vessel was sealed and subjected to three vacuum/nitrogen flush cycles, before repeating the process with carbon monoxide and charging the pressure to 3.0 bar. The mixture was stirred for 5 minutes then heated to 150° C. and stirred at this temperature overnight. The reactor was allowed to cool to r.t. The reaction mixture was diluted with EtOAc (20 mL) and filtered through a pad of celite, washing with excess EtOAc (20 mL). The filtrate was washed with water (15 mL), then brine (15 mL), dried (Na$_2$SO$_4$) and concentrated to dryness under vacuum to yield 160 mg of a crude residue. Purification by reverse phase chromatography (eluting with 0-100% MeCN (+0.1% NH$_4$OH)/H$_2$O (+0.1% NH$_4$OH)) to yield 2.1 mg (1.5%) of the title compound as a beige solid. LCMS Method 6 (ES+) RT 3.52 min., 460.2 (M+H)+. $^1$H NMR (500 MHz, MeOH-d4) δ 8.95 (d, J=1.5 Hz, 2H), 8.04 (dd, J=8.0, 1.1 Hz, 1H), 7.64 (d, J=6.8 Hz, 1H), 7.50 (d, J=11.2 Hz, 1H), 7.40 (t, J=8.1 Hz, 1H), 7.37-7.29 (m, 1H), 6.62 (d, J=7.1 Hz, 1H), 4.96 (d, J=6.7 Hz, 1H), 4.13 (s, 3H), 3.51 (dt, J=13.5, 6.9 Hz, 1H), 2.80 (d, J=13.4 Hz, 1H), 1.65 (s, 6H), 1.63-1.57 (m, 1H).

Example 18

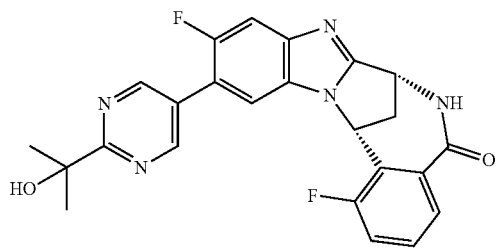 [SMILES: CC(C)(O)c1ncc(-c2cc3c(cc2F)nc2n3[C@@H]3C[C@H]2NC(=O)c2cccc(F)c23)cn1]

(7R,14R)-1,10-difluoro-11-[2-(2-hydroxypropan-2-yl)pyrimidin-5-yl]-6,7-dihydro-7,14-methanobenzimidazo[1,2-b][2,5]benzodiazocin-5(14H)-one To a solution of Intermediate 58 (200 mg, 0.44 mmol) in 1,4-dioxane (5 mL) was added sodium carbonate (232 mg, 2.19 mmol) dichloropalladium; dicyclohexyl(3-dicyclohexyl-phosphanylpropyl)-phosphane (53.8 mg, 0.0877 mmol). The reaction mixture was stirred at 160° C. under 5 bar of CO pressure overnight. The reaction mixture was filtered through a celite pad and rinsed with ethanol (10 mL). The filtrate was evaporated and the crude was dissolved in DCM (10 mL) and treated with a saturated aqueous solution of NH$_4$Cl (5 mL) The organic layer was concentrated in vacuo, and the residue purified on silica gel (DCM/iPrOH/aq NH$_3$ 90:9:1), yielding 32 mg (16%) of the title compound.

LCMS acidic Method 4 (ES+) RT 2.06 min., 448.2 (M+H)$^+$

Example 19

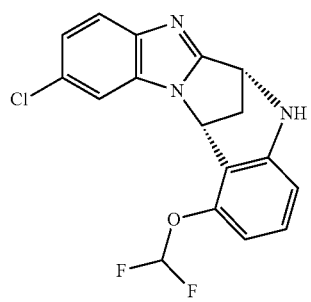 [SMILES: FC(F)Oc1cccc2c1[C@H]1C[C@@H](N2)c2nc3ccc(Cl)cc3n21]

(6R,12R)-2-chloro-11-(difluoromethoxy)-7,12-dihydro-6H-6,12-methanobenzimidazo[2,1-c][1,4]benzodiazepine A mixture of Intermediate 40 (500 mg, 1.17 mmol), potassium carbonate (322 mg, 2.33 mmol), 4,5-bis(diphenylphosphino)-9,9-dimethylxanthene (69 mg, 0.12 mmol) and palladium(II) acetate (26 mg, 0.12 mmol) in 1,4-dioxane (16 mL) was de-gassed and stirred at 110° C. under nitrogen for 15 hours. The reaction mixture was cooled to ambient temperature and 4,5-bis(diphenylphosphino)-9,9-dimethylxanthene (69 mg, 0.12 mmol) and palladium(II) acetate (26 mg, 0.12 mmol) were added to the reaction mixture. The solvent was de-gassed and the mixture was stirred at 110° C. for 18 hours. The reaction mixture was cooled to ambient temperature, filtered through celite and the latter was washed with EtOAc. The combined filtrate and washings were evaporated to dryness using an oil pump to give an oil which was purified by flash chromatography on silica gel (25 to 100% EtOAc in hexanes) to afford the title compound (249 mg, 0.71 mmol, 61% yield) as a brown solid. LC/MS Method 3: RT 2.29 mins (pH 10), m/z 348 and 350.

$^1$H NMR: (CD$_3$OD, 300 MHz) δ: 2.48 (d, J=11.2 Hz, 1H), 2.99 (dt, J=11.2, 4.5 Hz, 1H), 4.87 (m, 1H (overlap with the residual water), 5.93 (d, J=4.5 Hz, 1H), 6.40 (d, J=8.1 Hz, 2H), 6.96 (t, J=74 Hz, 1H), 7.00 (d, J=8.1 Hz, 1H), 7.17 (dd, J=8.6, 2.0 Hz, 1H), 7.46 (d, J=2.0 Hz, 1H), 7.53 (d, J=8.6 Hz, 1H).

Example 20

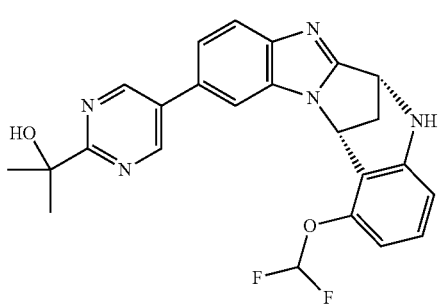 [SMILES: CC(C)(O)c1ncc(-c2ccc3nc4n(c3c2)[C@@H]2C[C@H]4Nc3cccc(OC(F)F)c32)cn1]

2-{5-[(6R,12R)-11-(difluoromethoxy)-7,12-dihydro-6H-6,12-methanobenzimidazo[2,1-c][1,4]benzodiazepin-2-yl]pyrimidin-2-yl}propan-2-ol A mixture of 2-[5-(4,4,5,5-tetramethyl-1,3,2-dioxaborolan-2-yl)pyrimidin-2-yl]propan-2-ol (purchased from commercial sources) (110.5 mg, 0.42 mmol), Example 19 (97 mg, 0.28 mmol), K$_3$PO$_4$ (118.3 mg, 0.56 mmol), and tricyclohexylphosphonium tetrafluoroborate (15.9 mg, 0.042 mmol) was solubilized in 1,4-dioxane (1.95 mL) and water (0.19 mL) and the mixture degassed with nitrogen before addition of tris(dibenzylideneacetone)dipalladium(0) (18.4 mg, 0.019 mmol). The reaction mixture was heated at 105° C. for 15 hours or until LCMS showed reaction to be complete. The reaction mixture was cooled to ambient temperature and the crude mixture was extracted with EtOAc (3×10 mL). The combined organic phases were washed with saturated brine (2×10 mL), dried over sodium sulphate, filtered and concentrated in vacuo to give an oil which was purified by preparative HPLC (pH=10) to afford the title compound (23 mg, 0.051 mmol, 18% yield) as a white solid. LC/MS Method 3: RT 2.09 mins (pH 10), m/z 450.

$^1$H NMR: (DMSO-d$_6$, 300 MHz) δ:1.54 (s, 6H), 2.38 (d, J=11.3 Hz, 1H), 2.94 (dt, J=11.3, 4.3 Hz, 1H), 4.91 (t, J=3.5 Hz, 1H), 5.11 (bs, 1H), 5.91 (d, J=4.3 Hz, 1H), 6.34 (d, J=8.3 Hz, 2H), 6.97 (t, J=8.3 Hz, 1H), 7.15 (d, J=3.7 Hz, 1H), 7.38 Hz (dd, J=73, 1.7 Hz, 1H), 7.54 (dd, J=8.4, 1.7 Hz, 1H), 7.68-7.72 (m, 2H), 9.06 (s, 2H).

Example 21

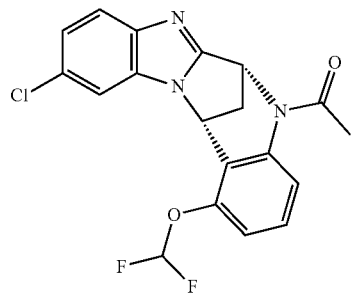 [SMILES: CC(=O)N1c2cccc(OC(F)F)c2[C@H]2C[C@@H]1c1nc3ccc(Cl)cc3n12]

1-[(6R,12R)-2-chloro-11-(difluoromethoxy)-6H-6,12-methanobenzimidazo[2,1-c][1,4]benzodiazepin-7(12H)-yl]ethanone Example 19 (245 mg, 0.7044 mmol) was dissolved in pyridine (2 mL) and acetic anhydride (2 mL). The mixture was stirred at 110° C. for 15 hours. The reaction mixture was cooled to ambient temperature and quenched with 2N NaOH aq. (2 mL). The crude mixture was extracted with EtOAc (2×10 mL). The organic phase was washed with saturated brine (10 mL), the combined organic phases was dried with sodium sulphate, filtered and concentrated in vacuo to give an oil which was purified by flash chromatography on silica gel (0 to 100% EtOAc in hexanes) to afford the title compound (177 mg, 65% yield) as a yellow solid. LC/MS Method 3: RT 2.08 mins (pH 10), m/z 390 and 392.

$^1$H NMR: (CD$_3$OD, 300 MHz) δ: 2.66 (d, J=11.9 Hz, 1H), 2.69 (s, 3H), 3.20 (dt, J=11.9, 4.5 Hz, 1H), 5.99 (d, J=3.9 Hz, 1H), 6.10 (d, J=4.5 Hz, 1H), 6.94 (d, J=8.3 Hz, 1H), 7.08 (t, J=73.4 Hz, 1H), 7.20-7.28 (m, 2H), 7.53 (d, J=8.7 Hz, 1H), 7.59 (d, J=2.0 Hz, 1H), 8.22 (d, J=8.7 Hz, 1H).

Example 22

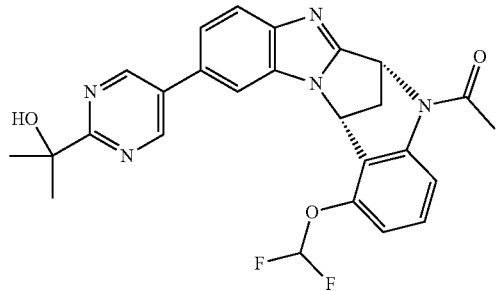 [SMILES: CC(=O)N1c2cccc(OC(F)F)c2[C@H]2C[C@@H]1c1nc3ccc(-c4cnc(C(C)(C)O)nc4)cc3n12]

1-[(6R,12R)-11-(difluoromethoxy)-2-[2-(2-hydroxypropan-2-yl)pyrimidin-5-yl]-6H-6,12-methanobenzimidazo[2,1-c][1,4]benzodiazepin-7(12H)-yl]ethanone The title compound was prepared from 2-[5-(4,4,5,5-tetramethyl-1,3,2-dioxaborolan-2-yl)pyrimidin-2-yl]propan-2-ol (179.9 mg, 0.68 mmol), and Example 21 according to a method involving the same procedural steps as those described for Example 20, to give, following purification by preparative HPLC (pH=10), a white solid (13 mg, 0.026 mmol, 5.8% yield): LC/MS Method 3: RT 1.93 mins (pH 10), m/z 492.

$^1$H NMR: (DMSO-d$_6$, 300 MHz) δ:1.54 (s, 6H), 2.61 (d, J=12.4 Hz, 1H), 2.69 (s, 3H), 3.20 (dt, J=12.1, 4.5 Hz, 1H), 5.75 (s, 1H), 6.00 (d, J=3.2 Hz, 1H), 6.08 (d, J=4.3 Hz, 1H), 6.93 (d, J=8.2 Hz, 1H), 7.29 (t, J=8.5 Hz, 1H), 7.46 Hz (dd, J=72.1, 1.7 Hz, 1H), 7.61 (dd, J=8.5, 1.8 Hz, 1H), 7.76-7.80 (m, 2H), 8.21 (d, J=8.5 Hz, 1H), 9.07 (s, 2H).

Example 23

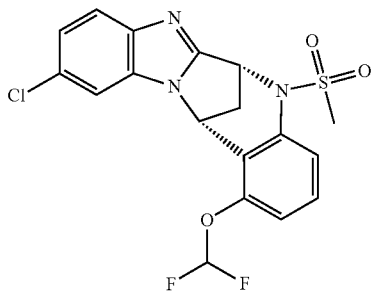 [SMILES: CS(=O)(=O)N1c2cccc(OC(F)F)c2[C@H]2C[C@@H]1c1nc3ccc(Cl)cc3n12]

(6R,12R)-2-chloro-11-(difluoromethoxy)-7-(methyl-sulfonyl)-7,12-dihydro-6H-6,12-methanobenzimidazo[2,1-c][1,4]benzodiazepine To a round bottom flask were added Intermediate 59 (2.80 g, 5.52 mmol), palladium(II) acetate (248 mg, 1.11 mmol), (+/−)-2,2'-bis(diphenylphosphino)-1,1'-binaphthyl (1.38 g, 2.21 mmol) and potassium carbonate (1.93 g, 13.8 mmol). The mixture was sealed and purged 3 times with nitrogen. Toluene (55 mL) was added to the reaction mixture and the vial was kept under nitrogen and stirred for 15 hours at 110° C. Then, the reaction mixture was cooled to ambient temperature, filtered through celite and the latter was washed with EtOAc. The combined filtrate and washings were evaporated to dryness using an oil pump to give an oil which was purified by flash chromatography in silica gel (0 to 100% EtOAc in Hexane) to afford the title compound (1.87 g, 4.39 mmol, 79.5% yield) as a brown solid. LC/MS Method 3: RT 2.15 mins (pH 10), m/z 426 and 428.

$^1$H NMR: (DMSO-d$_6$, 300 MHz) δ: 2.64 (d, J=12.0 Hz, 1H), 3.05 (s, 3H), 3.18 (dt, J=12.0, 4.2 Hz, 1H), 5.92 (d, J=3.6 Hz, 1H), 6.08 (d, J=4.2 Hz, 1H), 6.94 (dd, J=8.3, 0.7 Hz, 1H), 7.22 (dd, J=8.7, 2.1 Hz, 1H), 7.34 (t, J=8.5 Hz, 1H), 7.44 (t, J=73.2 Hz, 1H), 7.47 (d, J=1.8 Hz, 1H), 7.57 (d, J=8.6 Hz, 1H), 7.66 (d, J=8.6 Hz, 1H).

Example 24

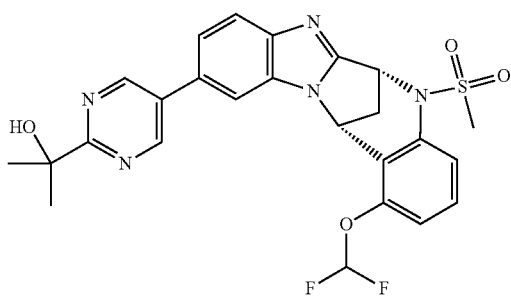 [SMILES: CC(C)(O)c1ncc(-c2ccc3nc4n(c3c2)[C@@H]2C[C@H]4N(S(C)(=O)=O)c3cccc(OC(F)F)c32)cn1]

2-{5-[(6R,12R)-11-(difluoromethoxy)-7-(methyl-sulfonyl)-7,12-dihydro-6H-6,12-methanobenzimidazo[2,1-c][1,4]benzodiazepin-2-yl]pyrimidin-2-yl}propan-2-ol The title compound was prepared from 2-[5-(4,4,5,5-tetramethyl-1,3,2-dioxaborolan-2-yl)pyrimidin-2-yl]propan-2-ol, and Example 23 according to a method involving the same procedural steps as those described for Example 20 to give, following purification by flash chromatography on silica gel (0 to 100% EtOAc in hexane), a white solid (542 mg, 84% yield). LC/MS Method 3: RT 2.04 mins (pH 10), m/z 528.

$^1$H NMR: (DMSO-d$_6$, 300 MHz) δ: 1.55 (s, 6H), 2.68 (d, J=12.1 Hz, 1H), 3.05 (s, 3H), 3.24 (dt, J=12.3, 4.5 Hz, 1H), 5.12 (s, 1H), 5.96 (d, J=3.6 Hz, 1H), 6.13 (d, J=4.3 Hz, 1H), 6.93 (d, J=8.3 Hz, 1H), 7.34 (t, J=8.5 Hz, 1H), 7.50 Hz (dd, J=72.4, 1.5 Hz, 1H), 7.62-7.56 (m, 2H), 7.67 (d, J=1.5 Hz, 1H), 7.81 (d, J=8.3 Hz, 1H), 9.07 (s, 2H).

Example 25

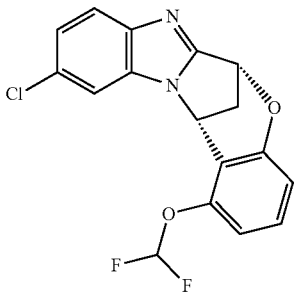 [SMILES: FC(F)Oc1cccc2c1[C@H]1C[C@@H](O2)c2nc3ccc(Cl)cc3n21]

(6R,12R)-2-chloro-11-(difluoromethoxy)-6H,12H-6,12-methanobenzimidazo[2,1-c][1,4]benzoxazepine A mixture of Intermediate 60 (287 mg, 0.668 mmol), cesium carbonate (440 mg, 1.33 mmol), 8-hydroxyquinoline (10 mg, 0.068 mmol), in toluene (0.7 mL) was degassed followed by the addition of copper (I) iodide (6.5 mg, 0.033 mmol). The reaction mixture was stirred at 100° C. for 15 hours. The reaction mixture was cooled to ambient temperature, filtered through celite and the latter was washed with CH$_2$Cl$_2$. The combined filtrate and washings were evaporated to dryness using an oil pump to give an oil which was purified by flash chromatography on silica gel (0 to 75% EtOAc in Hexane) to afford the title compound (40 mg, 0.1147 mmol, 17.17% yield) as a red solid. LC/MS Method 3: RT 2.5 mins (pH 10), m/z 349 and 351.

$^1$H NMR: (CD$_3$OD, 300 MHz) δ: 2.75 (d, J=12.4 Hz, 1H), 3.13 (ddd, J=12.4, 4.4, 1.4 Hz, 1H), 5.83 (d, J=1.4 Hz, 1H), 6.01 (d, J=4.4 Hz, 1H), 6.63 (dd, J=8.4 Hz, 1H), 6.70 (dd, J=8.3 Hz, 1H), 7.01 (t, J=73.4 Hz, 1H), 7.15 (t, J=8.4 Hz, 1H), 7.21 (dd, J=8.6, 1.9 Hz, 1H), 7.53 (d, J=1.6 Hz, 1H), 7.58 (d, J=8.6 Hz, 1H).

Example 26

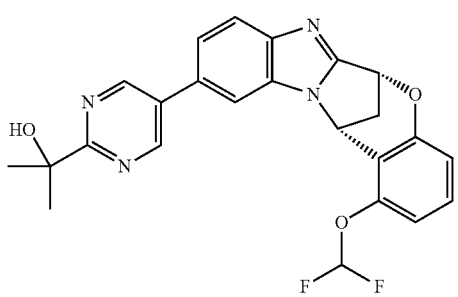 [SMILES: CC(C)(O)c1ncc(-c2ccc3nc4n(c3c2)[C@@H]2C[C@H]4Oc3cccc(OC(F)F)c32)cn1]

2-{5-[(6R,12R)-11-(difluoromethoxy)-6H,12H-6,12-methanobenzimidazo[2,1-c][1,4]benzoxazepin-2-yl]pyrimidin-2-yl}propan-2-ol The title compound was prepared from 2-[5-(4,4,5,5-tetramethyl-1,3,2-dioxaborolan-2-yl)pyrimidin-2-yl]propan-2-ol, and Example 25 according to a method involving the same procedural steps as those described for Example 20 to give, following purification by flash chromatography on silica gel (0 to 100% EtOAc in Hexane) a white solid (4.5 mg, 12% yield). LC/MS Method 3: RT 2.02 mins (pH 10), m/z 451.

$^1$H NMR: (DMSO-d$_6$, 300 MHz) δ:1.48 (s, 6H), 2.68 (d, J=12.9 Hz, 1H), 3.09 (ddd, J=12.9, 4.2, 1.5 Hz, 1H), 5.05 (s, 1H), 5.92 (d, J=1.5 Hz, 1H), 5.92 (d, J=4.2 Hz, 1H), 6.60 (d, J=8.3 Hz, 1H), 6.65 (d, J=8.5 Hz, 1H), 7.12 (t, J=8.3 Hz, 1H), 7.35 (dd, J=72.4, 1.5 Hz, 1H), 7.55 (dd, J=8.6, 1.7 Hz, 1H), 7.74 (m, 2H), 9.01 (s, 2H).

Example 27

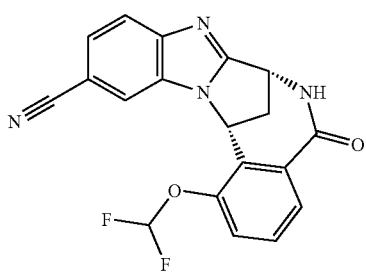 [SMILES: N#Cc1ccc2nc3n(c2c1)[C@@H]1C[C@H]3NC(=O)c2cccc(OC(F)F)c21]

(7R,14R)-1-(difluoromethoxy)-5-oxo-5,6,7,14-tetrahydro-7,14-methanobenzimidazo[1,2-b][2,5]benzodiazocine-11-carbonitrile To a mixture of Example 11 (100 mg, 0.266 mmol), zinc cyanide (35 mg, 0.298 mmol) and tetrakis (triphenylphosphine) palladium (31 mg, 0.0266 mmol) was added N,N-dimethyl-formamide (3 mL). The mixture was degassed for 3 minutes before being heated in microwave at 180° C. for 20 minutes. The reaction mixture was partitioned between EtOAc (30 mL) and water (40 mL), and the organics were washed with saturated brine (20 mL), dried over Na$_2$SO$_4$, filtered and concentrated in vacuo. The crude product was purified by preparative HPLC (reverse phase) to give the title compound (5.1 mg, 5.2% yield) as a white solid. LC/MS Method 3: ESI MH$^+$ 367, retention time 1.69 minutes (pH 10).

$^1$H NMR: (DMSO-d6, 400 MHz) δ 9.17 (d, J=6.8 Hz, 1H), 8.23 (dd, J=7.5, 1.8 Hz, 1H), 7.79 (m, 2H), 7.7-7.4 (m, 4H), 6.38 (d, J=7.1 Hz, 1H), 4.94 (t, J=6.8 Hz, 1H), 3.50 (m, 1H), 2.77 (d, J=13.5 Hz, 1H).

Example 28

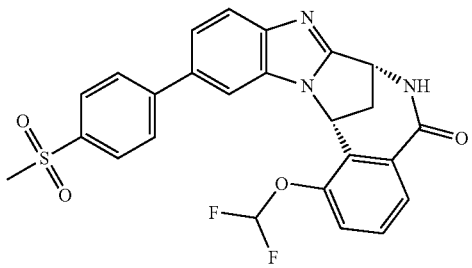 [SMILES: CS(=O)(=O)c1ccc(-c2ccc3nc4n(c3c2)[C@@H]2C[C@H]4NC(=O)c3cccc(OC(F)F)c32)cc1]

(7R,14R)-1-(difluoromethoxy)-11-[4-(methylsulfonyl)phenyl]-6,7-dihydro-7,14-methanobenzimidazo[1,2-b][2,5]benzodiazocin-5(14H)-one The title compound was prepared from 4-methylsulfonylphenyl-boronic acid, and Example 11 according to a method involving the same procedural steps as those described for Example 20, following purification by flash chromatography on a 100 g-SNAP Biotage silica cartridge eluting with 0%-10% MeOH/EtOAc followed by prep HPLC (reverse phase, 30%-50% MeCN/H$_2$O, pH 10) to give (8.83 mg, 0.178 mmol, 48%) as a white solid.

LC/MS Method 3: ESI MH$^+$ 496.0, retention time 1.82 minutes (pH 10).

$^1$H NMR: (DMSO-d6, 300 MHz) δ 9.14 (d, J=6.6 Hz, 1H), 8.23 (dd, J=5.7, 3.8 Hz, 1H), 8.00 (d, J=8.6 Hz, 1H), 7.9-7.4 (m, 9H), 6.37 (d, J=7.1 Hz, 1H), 4.89 (t, J=6.6 Hz, 1H), 3.49 (m, 1H), 3.27 (s, 3H), 2.75 (d, J=13.4 Hz, 1H).

Example 29

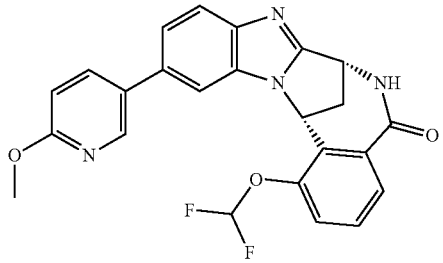 [SMILES: COc1ccc(-c2ccc3nc4n(c3c2)[C@@H]2C[C@H]4NC(=O)c3cccc(OC(F)F)c32)cn1]

(7R,14R)-1-(difluoromethoxy)-11-(6-methoxypyridin-3-yl)-6,7-dihydro-7,14-methanobenzimidazo[1,2-b][2,5]benzodiazocin-5(14H)-one The title compound was prepared from 2-methoxy-5-pyridineboronic acid and Example 11, according to a method involving the same procedural steps as those described for Example 20, following purification by flash chromatography to give (29 mg, 24%) as a white solid.

LC/MS Method 3: ESI MH⁺ 449.0, retention time 2.07 minutes (pH 10).

¹H NMR: (DMSO-d6, 400 MHz) δ 9.13 (d, J=6.8 Hz, 1H), 8.42 (d, J=2.32 Hz, 1H), 8.23 (dd, J=5.9, 3.4 Hz, 1H), 7.9-7.4 (m, 7H), 6.93 (d, J=8.6 Hz, 1H), 6.35 (d, J=7.1 Hz, 1H), 4.88 (t, J=6.8 Hz, 1H), 3.91 (s, 3H), 3.48 (m, 1H), 2.73 (d, J=13.3 Hz, 1H).

Example 30

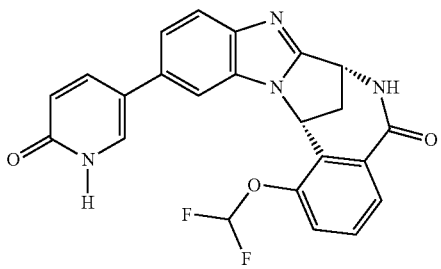 [SMILES: O=C1N[C@@H]2C[C@H](c3c(OC(F)F)cccc31)n1c2nc2ccc(-c3ccc(=O)[nH]c3)cc21]

(7R,14R)-1-(difluoromethoxy)-11-(6-oxo-1,6-dihydropyridin-3-yl)-6,7-dihydro-7,14-methanobenzimidazo[1,2-b][2,5]benzodiazocin-5(14H)-one A mixture of Example 29 (22.4 mg, 0.050 mmol) and pyridine hydrochloride (29.0 mg, 0.246 mmol) were heated at 160° C. for 5 minutes and allowed to cool to ambient temperature. The mixture was then diluted with DCM/MeOH, concentrated and purified by prep HPLC (reverse phase) to afford the desired product (22.0 mg, 0.051 mmol, 78%) as a white solid.

LC/MS Method 3: ESI MH⁺ 435.0, retention time 1.34 minutes (pH 10).

¹H NMR: (DMSO-d6, 300 MHz) δ 11.8 (br s, 1H), 9.11 (d, J=6.7 Hz, 1H), 8.22 (m, 1H), 7.9-7.3 (m, 8H), 6.44 (d, J=9.5 Hz, 1H), 6.31 (d, J=7.1 Hz, 1H), 4.86 (t, J=6.7 Hz, 1H), 3.46 (m, 1H), 2.72 (d, J=13.4 Hz, 1H).

Example 31

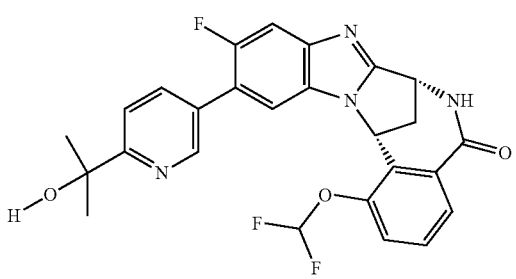 [SMILES: CC(C)(O)c1ccc(-c2cc3c(cc2F)nc2n3[C@@H]3C[C@H]2NC(=O)c2cccc(OC(F)F)c23)cn1]

(7R,14R)-1-(difluoromethoxy)-10-fluoro-11-[6-(2-hydroxypropan-2-yl)pyridin-3-yl]-6,7-dihydro-7,14-methanobenzimidazo[1,2-b][2,5]benzodiazocin-5(14H)-one A degassed mixture of Example 10 (299 mg, 0.56 mmol), 6-(2-(trimethylsilyloxy)propan-2-yl)pyridine-3-boronic acid pinacol ester (295 mg, 0.84 mmol), tris(dibenzylideneacetone)dipalladium(0) (26.0 mg, 0.03 mmol), potassium phosphate tribasic (296 mg, 1.40 mmol), and tricyclohexylphosphonium tetrafluoroborate (26.0 mg, 0.07 mmol) in 1,4-dioxane (4.5 mL) and water (0.5 mL) was heated to 105° C. overnight. The reaction mixture was cooled to r.t, diluted with EtOAc (50 mL) and washed with water (2×50 mL). The organic layer was dried (Na₂SO₄), filtered and concentrated in vacuo. The residues were dissolved in DCM (4 mL) and 4M HCl solution (1.5 mL) was added. The solution was stirred at r.t for 1 hour. Saturated aqueous sodium carbonate solution (50 mL) was added, and the aqueous layer separated. The organic layer was washed with brine (50 mL), dried (Na₂SO₄), filtered and concentrated in vacuo to give a crude oil. The crude material was purified by column chromatography, eluting with 0-100% EtOAc in DCM, followed by 0-10% MeOH in EtOAc to give the title compound as an off-white powder (105 mg, 38% yield).

¹H NMR (400 MHz, DMSO) δ 9.15 (d, 1H, J=6.8 Hz), 8.61 (s, 1H), 8.26-8.21 (m, 1H), 7.90 (dt, 1H, J=1.9, 8.2 Hz), 7.77 (d, 1H, J=8.2 Hz), 7.61 (t, 1H, J=75 Hz), 7.61 (d, 1H, J=11.5 Hz), 7.52-7.50 (m, 3H), 6.34 (d, 1H, J=7.1 Hz), 5.27 (s, 1H), 4.91 (t, 1H, J=6.8 Hz), 3.52-3.45 (m, 1H), 2.75 (d, 1H, J=13.4 Hz), 1.49 (s, 6H). LCMS Method 3 ESI MH+495.1

Example 32

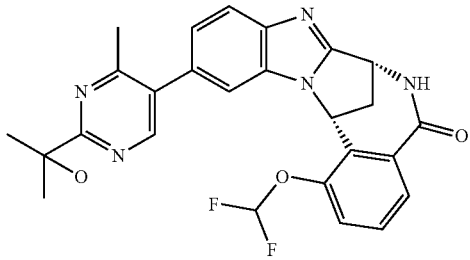 [SMILES: Cc1nc(C(C)(C)O)ncc1-c1ccc2nc3n(c2c1)[C@@H]1C[C@H]3NC(=O)c2cccc(OC(F)F)c21]

(7R,14R)-1-(difluoromethoxy)-11-[2-(2-hydroxypropan-2-yl)-6-methyl-pyrimidin-5-yl]-6,7-dihydro-7,14-methanobenzimidazo[1,2-b][2,5]benzodiazocin-5(14H)-one The title compound was synthesised from Example 11 (240 mg, 0.639 mmol), and Intermediate 61 (213.2 mg, 0.7664 mmol), according to a method involving the same procedural steps as those described for Example 20 to give, after purification by flash column chromatography, an oil, which was subsequently freeze dried to provide a white solid (115 mg, 0.234 mmol, 36%).

1H NMR (400 MHz, DMSO) δ 9.15 (d, 1H, 6.6 Hz), 8.61 (s, 1H), 8.23 (dd, 1H, 4.8 Hz), 7.73 (d, 1H, 8.3 Hz), 7.56, (m, 1H), 7.51 (m, 3H), 7.22 (dd, 1H, J=8.3, 1.7 Hz), 6.34 (d, 1H, J=7.1 Hz), 5.07 (s, 1H), 4.91 (t, 1H, J=6.6 Hz), 3.50 (m, 1H), 2.76 (d, 1H, J=13.3 Hz), 2.46 (s, 3H), 1.54 (s, 6H). HPLC-MS Method 3 (pH10): MH+ m/z=492.2, RT 1.81 minutes; Method 4 (pH3): MH+ m/z=492.2, RT 1.80 minutes.

Example 33

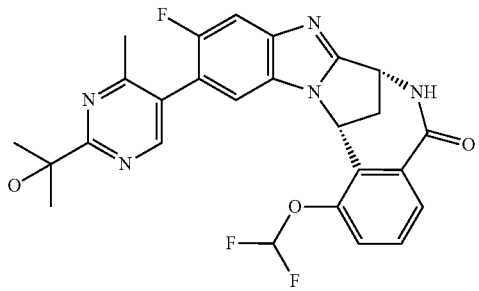 [SMILES: Cc1nc(C(C)(C)O)ncc1-c1cc2c(cc1F)nc1n2[C@@H]2C[C@H]1NC(=O)c1cccc(OC(F)F)c12]

(7R,14R)-1-(difluoromethoxy)-10-fluoro-11-[2-(2-hydroxypropan-2-yl)-6-methyl-pyrimidin-5-yl]-6,7-dihydro-7,14-methanobenzimidazo[1,2-b][2,5]benzodiazocin-5(14H)-one The title compound was synthesised from Example 10 (300 mg, 0.762 mmol), and Intermediate 61 (254.3 mg, 0.9142 mmol), according to a method involving the same procedural steps as those described for Example 20, to give, after purification by column chromatography, an oil, which was subsequently freeze dried to give a white solid (125 mg, 0.245 mmol, 32%).

1H NMR (400 MHz, DMSO) δ 9.15 (d, 1H, J=6.8 Hz), 8.62 (s, 1H), 8.22 (dd, 1H, J=6.2, 3.2 Hz), 7.65 (d, 1H, J=10.8 Hz), 7.53 (d, 1H, 7.8 Hz), 7.52 (d, 1H, 7.8 Hz), 7.51 (t, 1H, 72 Hz) 7.39 (d, 1H, J=6.6 Hz), 6.33 (d, 1H, 7.1 Hz), 5.08 (s, 1H), 4.87 (t, 1H, J=6.8 Hz), 3.50 (dt, 1H, 13.6, 6.8 Hz), 2.75 (d, 1H, J=13.4 Hz), 2.33 (d, 3H, 1 Hz), 1.54 (s, 6H). HPLC-MS Method 3 (pH10): MH+ m/z=510.2, RT 1.88 minutes; Method 4 (pH3): MH+ m/z=510.2, RT 1.91 minutes.

Example 34

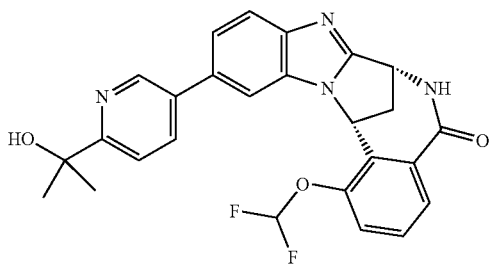 [SMILES: CC(C)(O)c1ccc(-c2ccc3nc4n(c3c2)[C@@H]2C[C@H]4NC(=O)c3cccc(OC(F)F)c32)cn1]

(7R,14R)-1-(difluoromethoxy)-11-[6-(2-hydroxypropan-2-yl)pyridin-3-yl]-6,7-dihydro-7,14-methanobenzimidazo[1,2-b][2,5]benzodiazocin-5(14H)-one Example 11 (140 mg, 0.373 mmol) and 6-(2-(trimethylsilyloxy)propan-2-yl)pyridine-3-boronic acid pinacol ester (171 mg, 0.484 mmol) were added to a small microwave tube and tris(dibenzylideneacetone)dipalladium(0) (17.6 mg, 0.0186 mmol) and tricyclohexylphosphonium tetrafluoroborate (17.0 mg, 0.0447 mmol) were added with dioxane (2 mL), followed by K₃PO₄ (158 mg, 0.745 mmol) in water (1 mL). The mixture was degassed and heated to 105° C. for 18 hours. The mixture was diluted with EtOAc (30 mL) and washed with water (10 mL). The organic was concentrated in vacuo, re-dissolved in DCM (10 mL) and 4.0M HCl in dioxane (5 mL) added and the mixture was stirred at r.t for 1 hour. The mixture was partitioned between DCM and sodium carbonate (20 mL). The organic phase was dried (Na₂SO₄), filtered and concentrated in vacuo. Purification by preparative HPLC gave the title compound (35 mg, 20%) as a white solid.

¹H NMR: (d6-DMSO, 300 MHz) δ:1.48 (s, 6H), 2.74 (d, 1H, J=13.3 Hz), 3.49 (m, 1H), 4.88 (t, 1H, J=6.7 Hz), 5.24 (s, 1H), 6.35 (d, 1H, J=7.0 Hz), 7.49-7.53 (m, 3H), 7.69-7.72 (m, 3H), 7.66 (t, 1H, J$_{H-F}$=73.2 Hz), 7.97 (dd, 1H, J=5.6, 8.2 Hz), 8.21-8.24 (m, 1H), 8.73 (d, 1H, J=1.8 Hz), 9.13 (d, 1H, 6.8 Hz). LC/MS Method 3: RT 1.76 mins (pH 10), m/z 477.

Example 35

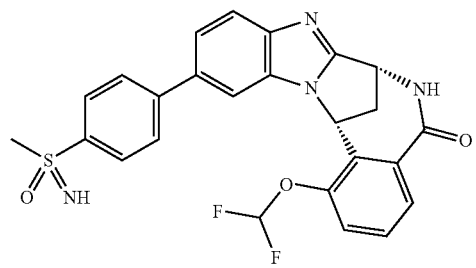 [SMILES: CS(=N)(=O)c1ccc(-c2ccc3nc4n(c3c2)[C@@H]2C[C@H]4NC(=O)c3cccc(OC(F)F)c32)cc1]

(7R,14R)-1-(difluoromethoxy)-11-[4-(S-methylsulfonimidoyl)phenyl]-6,7-dihydro-7,14-methanobenzimidazo[1,2-b][2,5]benzodiazocin-5(14H)-one Example 11 (200 mg, 0.532 mmol) and imino-methyl-oxo-[4-(4,4,5,5-tetramethyl-1,3,2-dioxaborolan-2-yl)phenyl]-sulfane (210 mg, 0.745 mmol), tris(dibenzylideneacetone)-dipalladium(0) (25.1 mg, 0.0266 mmol) and tricyclohexylphosphonium tetrafluoroborate (24.2 mg, 0.0639 mmol) were added to a small microwave tube. 1,4-Dioxane (2 mL) was added, followed by K₃PO₄ (226 mg, 1.06 mmol) in water (0.3 mL). The mixture was degassed, placed under nitrogen and heated to 105° C. for 18 hours. LCMS showed a poor conversion. Another identical portion of catalyst, ligand and the boronate as above were added along with more dioxane (0.5 mL) and water (0.2 mL) and the mixture heated to 110° C. for a further 18 hours. The mixture was partitioned between EtOAc and water (50 mL each) The organic layer was dried over sodium sulphate, filtered and concentrated in vacuo. The material was subjected to column chromatography (silica, 0 to 20% MeOH in DCM) and the product containing fractions were concentrated in vacuo to give a brown solid, which, after further purification by prep HPLC provided the title compound (9.1 mg, 3.5%) as a white solid. ¹H NMR: (d6-DMSO, 300 MHz) δ:2.74 (d, 1H, J=13.3 Hz), 3.11 (d, 3H, J=0.8 Hz), 3.49-3.54 (m, 1H), 4.24 (s, 1H), 4.89 (t, 1H, J=6.7 Hz), 6.36 (d, 1H, J=7.0 Hz), 7.49-7.56 (m, 3H), 7.67 (dt, 1H, J$_{H-F}$=73.3, 1.0 Hz), 7.71-7.74 (m, 2H), 7.80-7.83 (m, 2H), 7.98-8.01 (m, 2H), 8.21-8.24 (m, 1H), 9.14 (d, 1H, 6.7 Hz). LC/MS Method 3: RT 1.54 mins (pH 10), m/z 495.

Example 36

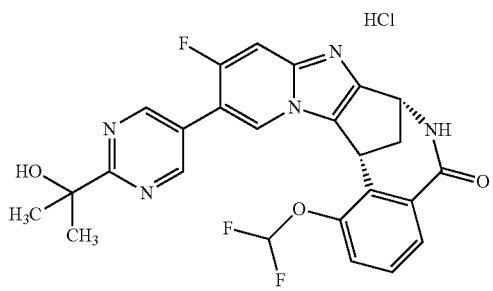 [SMILES: Cl ; CC(C)(O)c1ncc(-c2cn3c4c(nc3cc2F)[C@H]2C[C@@H]4c3c(OC(F)F)cccc3C(=O)N2)cn1]

(1R,11R)-18-(difluoromethoxy)-6-fluoro-5-[2-(2-hydroxypropan-2-yl)pyrimidin-5-yl]-3,9,12-triazapentacyclo[9.8.1.0$^{2,10}$.0$^{3,8}$.0$^{14,19}$]icosa-2(10),4,6,8,14(19),15,17-heptaen-13-one hydrochloride Intermediate 72 (260 mg, 0.52 mmol), Na$_2$CO$_3$ (274 mg, 2.59 mmol) and 2,2-dichloro-1,1,3,3-tetracyclohexyl-1λ$^5$,3λ$^5$-diphospha-2-palladacyclohexane (28 mg, 0.04 mmol) were suspended in degassed anhydrous dimethylacetamide (6 mL) in a 25 mL pressure vessel. The vessel was sealed and degassed thoroughly under vacuum then placed under an atmosphere of nitrogen. This process was repeated then the vessel was evacuated and charged with 3 bar CO gas. The mixture was heated to 140° C. overnight whereon the internal pressure reached 4.8 bar. On cooling to r.t, the mixture was diluted with DCM:MeOH (50 mL) and washed with water (30 mL). The aqueous layer was back extracted with DCM:MeOH (2×30 mL). The combined organic layer was filtered through Celite and concentrated under reduced pressure to afford a beige solid. Purification by column chromatography (KP-NH, Biotage isolera) eluting with 0-100% MeOH in DCM followed by purification using achiral SFC (20% MeOH: 80% CO$_2$ with Phenomenex Synergi 4µ Polar RP 25 cm column at 15 ml/min) gave the free base 65 mg (25%) as an off white solid. Suspension in 1:1 MeCN:water (3 mL) and treatment with 1N aqueous HCl (129.5 µL, 1 eq) followed by freeze drying gave the title compound (67.5 mg, 25%) as a fluffy colourless solid. Method 6 HPLC-MS: MH+ m/z 496, RT 2.27 min (100%), $^1$H NMR (500 MHz, DMSO-d$_6$) δ 8.98 (s, 2H), 8.88 (d, J=6.1 Hz, 1H), 8.27 (d, J=7.1 Hz, 1H), 8.22 (d, J=7.8 Hz, 1H), 7.78-7.68 (m, 1H), 7.67-7.38 (m, 1H), 7.46-7.32 (m, 2H), 5.19 (d, J=6.4 Hz, 1H), 4.73 (t, J=6.4 Hz, 1H), 3.77-3.15 (m, 2H), 2.43 (d, J=13.0 Hz, 1H), 1.54 (s, 6H).

Example 37

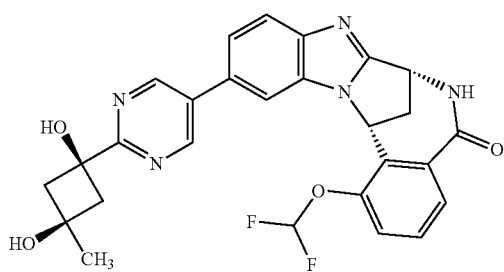 [SMILES: C[C@]1(O)C[C@](O)(c2ncc(-c3ccc4nc5n(c4c3)[C@@H]3C[C@H]5NC(=O)c4cccc(OC(F)F)c43)cn2)C1]

(7R,14R)-1-(difluoromethoxy)-11-[2-(cis-1,3-dihydroxy-3-methylcyclobutyl)pyrimidin-5-yl]-6,7-dihydro-7,14-methanobenzimidazo[1,2-b][2,5]benzodiazocin-5(14H)-one Intermediate 79 (500 mg, 1.34 mmol), bis(pinacolato)diboron (408.0 mg, 1.61 mmol), tricyclohexylphosphonium tetrafluoroborate (61.00 mg, 0.161 mmol), potassium carbonate (22 mg, 0.161 mmol), potassium acetate (398 mg, 4.02 mmol) were placed in a 8 mL vial filled with nitrogen. 1,4-dioxane (4.8 mL) was added and the solution homogenized for 5 minutes before addition of tris(dibenzylideneacetone)dipalladium(0) (63 mg, 0.067 mmol). The reaction mixture was heated at 100° C., using a preheated oil bath, for 1 hour. The reaction mixture was filtered giving a clear crude solution of boronic acid used without further treatment. LCMS basic RT 0.920 min. (ES+) 339.0 (M+H)$^+$ To Example 11 (127 mg, 0.338 mmol), tricyclohexylphosphonium tetrafluoroborate (15.4 mg, 0.04055 mmol), potassium phosphate (143 mg, 0.676 mmol) in a vial was added the above described crude solution of 3-[tert-butyl(dimethyl)silyl]oxy-1-methyl-3-[5-(4,4,5,5-tetramethyl-1,3,2-dioxaborolan-2-yl)pyrimidin-2-yl]cyclobutanol, and water (0.12 mL). The slurry was degassed before addition of tris(dibenzylideneacetone)dipalladium(0) (16 mg, 0.0169 mmol). The resulting solution was heated at 100° C. overnight. The reaction mixture was filtered through sodium sulfate and rinsed with EtOAc (10 mL). The filtrate was evaporated, and the residue was purified over silica gel (100% EtOAc) yielding a slightly yellow glass (192 mg). LCMS basic (ES+) RT 2.35 min, 635.0 (M+H)$^+$ The above intermediate (192 mg, 0.3029 mmol) was solubilised in THF (1.8 mL) and tetrabutylammonium fluoride (1 M in THF) (0.9 mL, 0.9 mmol) was added drop-wise. The reaction mixture was stirred at r.t for 2 hours. The volatiles were removed in vacuo and the residue was partitioned between dichloromethane (20 mL) and water (20 mL). The DCM layer was washed by 2×20 mL of water. The combined aqueous layers were extracted by 2×20 mL of DCM. The combined organic layers were washed by 4×20 mL of water and brine (1×10 mL), dried over sodium sulfate, filtered and concentrated in vacuo to give 109 mg of white solid. The white solid was recrystallized with 3 mL of isopropanol yielding 40 mg (26%) of the title compound as a white solid. LCMS basic Method 3 (ES+) RT 1.49 min, 520.4 (M+H)$^+$

Example 38

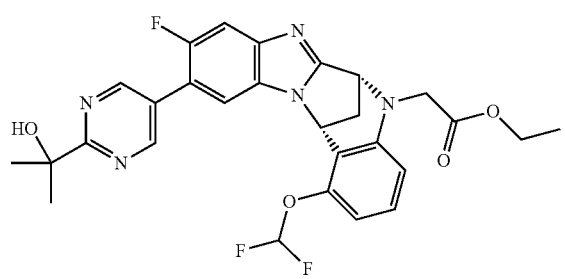 [SMILES: CCOC(=O)CN1c2cccc(OC(F)F)c2[C@H]2C[C@@H]1c1nc3cc(F)c(-c4cnc(C(C)(C)O)nc4)cc3n12]

Ethyl [(6R,12R)-11-(difluoromethoxy)-3-fluoro-2-[2-(2-hydroxypropan-2-yl)pyrimidin-5-yl]-6H-6,12-methanobenzimidazo[2,1-c][1,4]benzodiazepin-7(12H)-yl]acetate A solution of Intermediate 93 (250 mg, 0.39 mmol), (+/−)-2,2'-bis(diphenylphosphino)-1,1'-binaphthyl (36 mg, 0.058 mmol), cesium carbonate (261 mg, 0.80 mmol) and palladium acetate (12 mg, 0.053 mmol) in toluene (8 mL) was degassed and heated to 110° C. for 15 hours. The reaction mixture was cooled to ambient temperature, partitioned between EtOAc (30 mL) and water (30 mL) and the phases were separated. The aqueous layer was extracted with EtOAc (3×10 mL). The combined organic phases were washed with saturated brine (10 mL), dried with sodium sulphate, filtered and concentrated in vacuo to give an oil which was purified by flash chromatography in silica gel (0 to 100% EtOAc in hexanes) to afford the title compound (169 mg, 78% yield) as a brown solid.

LC/MS Method 3: RT 2.26 mins (pH 10), m/z 554.

$^1$H NMR: (CD$_3$OD, 300 MHz) δ:1.20 (t, J=7.1 Hz, 3H), 1.66 (s, 6H), 2.69 (d, J=11.7 Hz, 1H), 3.01 (dt, J=11.7, 4.5 Hz, 1H), 4.44-4.15 (m, 4H), 4.96 (d, J=3.4 Hz, 1H), 6.11 (d, J=4.5 Hz, 1H), 6.41 (d, J=8.4 Hz, 1H), 6.54 (d, J=8.3 Hz, 1H), 7.12 (t, J=8.4 Hz, 1H), 7.05 Hz (t, J=73.8, 1.5 Hz, 1H), 7.50 (d, J=11.2 Hz, 1H), 7.65 (d, J=6.7 Hz, 1H), 8.97 (d, J=1.6 Hz, 2H).

Example 39

(7R,14R)-1-(difluoromethoxy)-10-fluoro-11-[2-(2-hydroxypropan-2-yl)pyrimidin-5-yl]-6-methyl-6,7-dihydro-7,14-methanobenzimidazo[1,2-b][2,5]benzodiazocin-5(14H)-one

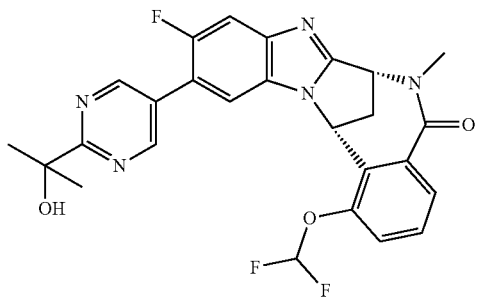 [SMILES: CN1C(=O)c2cccc(OC(F)F)c2[C@H]2C[C@@H]1c1nc3cc(F)c(-c4cnc(C(C)(C)O)nc4)cc3n12]

The title compound can be synthesised from Intermediate 158 and [2-(1-hydroxy-1-methyl-ethyl)pyrimidin-5-yl]boronic acid in accordance with the Method described for Example 20.

$^1$H NMR: (DMSO-d6, 300 MHz) δ 8.95 (d, J=1.7 Hz, 1H), 8.23 (dd, J=6.7, 2.8 Hz, 1H), 7.9-7.3 (m, 5H), 6.29 (d, J=7.1 Hz, 1H), 5.27 (d, J=7.1 Hz, 1H), 5.15 (s, 1H), 3.52 (m, 1H), 3.36 (s, 3H), 2.84 (d, J=13.9 Hz, 1H), 1.55 (s, 6H).

LC/MS: Method 3: MH$^+$ 510.3, RT 2.04 minutes.

Preparative Example 40

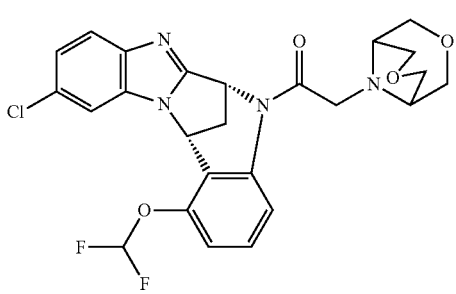 [SMILES: O=C(CN1C2COCC1COC2)N1c2cccc(OC(F)F)c2[C@H]2C[C@@H]1c1nc3ccc(Cl)cc3n12]

1-[(6R,12R)-2-chloro-11-(difluoromethoxy)-6H-6,12-methanobenzimidazo[2,1-c][1,4]benzodiazepin-7(12H)-yl]-2-(3,7-dioxa-9-azabicyclo[3.3.1]non-9-yl)ethanone To a solution of Example 19 (50 mg, 0.14 mmol) in dichloromethane (1 mL), was added triethylamine (24 µL, 0.17 mmol) followed by chloroacetyl chloride (12 µL, 0.015 mL). After stirring for 1 hour, a further 0.11 equiv of chloroacetyl chloride (1.2 µL, 0.014 mmol) was added and the reaction mixture was stirred for an additional 20 min. Triethylamine (24 µL, 0.17 mmol) was added to the reaction mixture followed by 3,7-dioxa-9-azabicyclo[3.3.1]nonane (11.5 mg, 0.168 mmol) and the reaction was stirred at room temperature for 18 h. The reaction mixture was directly purified by column chromatography over silica gel using hexane/ethyl acetate (0 to 100%) and then DCM/MeOH (from 0 to 20%) as eluent. A second purification by Prep-HPLC (basic conditions) afforded 20 mg (27%) of the title compound. LCMS Method 3 (ES+) RT 2.91 min. [M+H]$^+$=517/519. $^1$H NMR (400 MHz, DMSO-d6) δ 8.12 (d, J=8.7 Hz, 1H), 7.68-7.59 (m, 1H), 7.51-7.41 (m, 1H), 7.34-7.19 (m, 2H), 6.97 (d, J=8.3 Hz, 1H), 6.25 (s, 1H), 6.07 (d, J=4.3 Hz, 1H), 4.14 (s, 3H), 4.06 (s, 1H), 3.83 (s, 4H), 3.22 (d, J=12.1 Hz, 1H), 2.63 (d, J=12.1 Hz, 1H).

Example 41

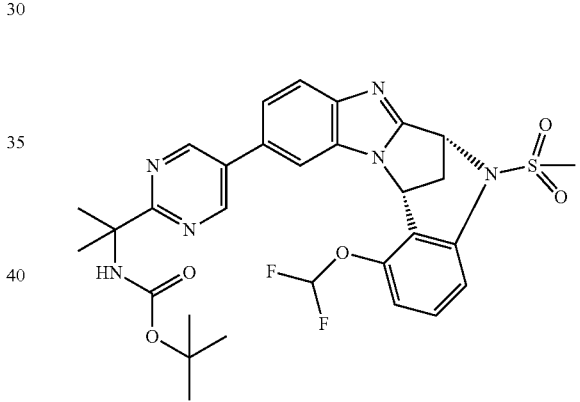

tert-butyl (2-{5-[(6R,12R)-11-(difluoromethoxy)-7-(methylsulfonyl)-7,12-dihydro-6H-6,12-methanobenzimidazo[2,1-c][1,4]benzodiazepin-2-yl]pyrimidin-2-yl}propan-2-yl)carbamate The title compound was prepared from tert-butyl N-[1-methyl-1-[5-(4,4,5,5-tetramethyl-1,3,2-dioxaborolan-2-yl)pyrimidin-2-yl]ethyl]carbamate, and Example 23 according to a method involving the same procedural steps as those described for Example 20, to give, following purification by Prep-HPLC the title compound as a white solid (100.5 mg, 48% yield). LC/MS Method 3: RT 2.46 mins, [M+H]$^+$=627. $^1$H NMR (300 MHz, DMSO-d6) δ 9.02 (s, 2H), 7.80 (d, J=8.5 Hz, 1H), 7.77-7.70 (m, 1H), 7.64-7.52 (m, 2H), 7.50 (t, J=73.5 Hz, 1H), 7.38 (d, J=73.0 Hz, 1H), 7.34 (t, J=8.5 Hz, 1H), 6.93 (d, J=8.2 Hz, 1H), 6.13 (d, J=4.3 Hz, 1H), 5.95 (d, J=4.0 Hz, 1H), 3.29-3.16 (m, 1H), 3.07 (s, 3H), 2.68 (d, J=12.1 Hz, 1H), 1.60 (s, 6H), 1.32 (bs, 9H).

Example 42

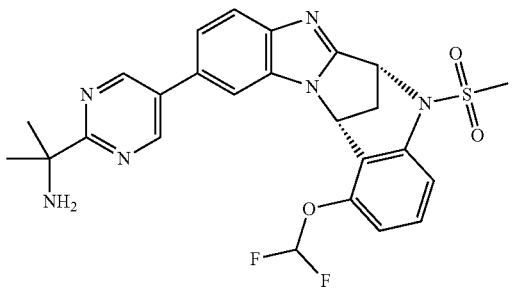 [SMILES: CC(C)(N)c1ncc(-c2ccc3nc4n(c3c2)[C@@H]2C[C@H]4N(S(C)(=O)=O)c3cccc(OC(F)F)c32)cn1]

2-{5-[(6R,12R)-11-(difluoromethoxy)-7-(methyl-sulfonyl)-7,12-dihydro-6H-6,12-methanobenzimi-dazo[2,1-c][1,4]benzodiazepin-2-yl]pyrimidin-2-yl}propan-2-amine To a solution of Example 41 (98 mg, 0.15 mmol) in 1,4-dioxane (2 mL) was added 4M HCl in dioxane (6 mL). The reaction was stirred for 1 hour at room temperature and then the solvent was evaporated and the crude was dissolved in dichloromethane (5 mL) and a saturated aqueous solution of $Na_2CO_3$ was added until pH=8-9. The two phases were separated and the aqueous layer was extracted with dichloromethane (2×5 mL) the combined organic layers were washed with brine, filtered through a phase separator and the solvent was evaporated. The solid obtained was triturated in ether and filtered to give the title compound as a white solid (49.2 mg, 60% yield). LC/MS Method 3: RT 1.65 mins (pH 10), [M+H]$^+$=527. $^1$H NMR (300 MHz, DMSO-d6) δ 9.04 (s, 2H), 7.85-7.71 (m, 2H), 7.64-7.46 (m, 2H), 7.50 (t, J=73.4 Hz, 1H), 7.34 (t, J=8.5 Hz, 1H), 6.93 (d, J=8.3 Hz, 1H), 6.13 (d, J=4.3 Hz, 1H), 5.95 (d, J=3.9 Hz, 1H), 3.23 (dt, J=12.2, 4.5 Hz, 1H), 3.07 (s, 3H), 2.68 (d, J=12.3 Hz, 1H), 2.31 (bs, 2H), 1.47 (s, 6H).

Example 43

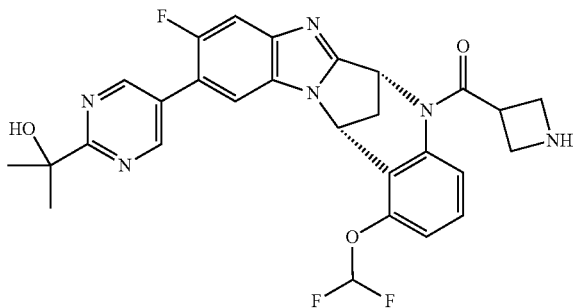 [SMILES: CC(C)(O)c1ncc(-c2cc3c(cc2F)nc2n3[C@@H]3C[C@H]2N(C(=O)C2CNC2)c2cccc(OC(F)F)c23)cn1]

Azetidin-3-yl[(6R,12R)-2-chloro-11-(difluoromethoxy)-6H-6,12-methanobenzimidazo[2,1-c][1,4]benzodiazepin-7(12H)-yl]methanone To Intermediate 95 (158 mg, 0.24 mmol) in 1,4-dioxane (2 mL) was added 4M HCl in 1,4-dioxane (2 mL) and the reaction was stirred for 10 minutes. Methanol (2 mL) was added to keep the mixture in solution. The reaction mixture was stirred for 3 hours before the solvent was evaporated. The crude material was purified by preparative HPLC, yielding 22 mg (15%) of the title compound as a white solid. LCMS Method 3. RT 1.57 min., [M+H]$^+$=551. $^1$H NMR (300 MHz, DMSO-d6) δ 8.97 (d, J=1.7 Hz, 2H), 8.22 (d, J=8.6 Hz, 1H), 7.70 (d, J=11.5 Hz, 1H), 7.61 (d, J=6.9 Hz, 1H), 7.43 (t, J=73.8 Hz, 1H), 7.29 (t, J=8.5 Hz, 1H), 6.92 (d, J=8.2 Hz, 1H), 6.07 (d, J=4.2 Hz, 1H), 5.61 (bs, 1H), 5.15 (bs, 1H), 4.38 (bs, 1H), 4.07 (bs, 1H), 3.84 (bs, 4H), 3.20-3.08 (m, 1H), 2.64 (d, J=12.1 Hz, 1H), 1.56 (s, 6H).

Example 44

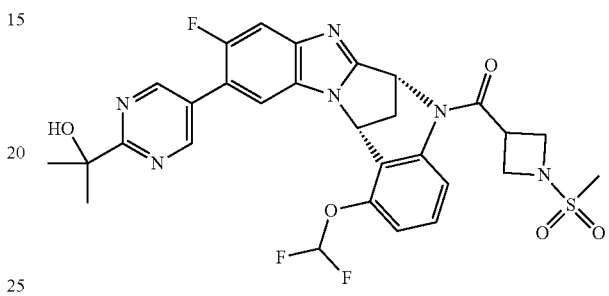

[(6R,12R)-11-(difluoromethoxy)-3-fluoro-2-[2-(2-hydroxypropan-2-yl)pyrimidin-5-yl]-6H-6,12-methanobenzimidazo[2,1-c][1,4]benzodiazepin-7(12H)-yl][1-(methylsulfonyl)azetidin-3-yl]methanone Methanesulfonyl chloride (3 μL, 0.038 mmol) was added to a solution of Example 43 (17 mg, 0.03 mmol), N,N-diisopropylethylamine (6 μL, 0.034 mmol) in DCM (0.3 mL) at 0° C. The reaction mixture was stirred at this temperature for 10 minutes and then at room temperature for 3 hours. The solvent was evaporated and the crude material was purified by preparative HPLC, yielding 1.5 mg (8%) of the title compound as a white solid. LCMS Method 3: RT 2.04 min., [M+H]$^+$=629. $^1$H NMR (300 MHz, Methanol-d4) δ 8.98 (d, J=1.6 Hz, 2H), 8.19 (s, 1H), 7.70 (d, J=6.6 Hz, 1H), 7.55 (d, J=11.1 Hz, 1H), 7.29 (t, J=8.5 Hz, 1H), 7.15 (t, J=73.5 Hz, 1H), 6.96 (d, J=8.3 Hz, 1H), 6.21 (d, J=4.4 Hz, 1H), 5.80 (s, 1H), 4.46 (dq, J=13.6, 6.2 Hz, 2H), 4.31 (td, J=13.6, 12.0, 5.9 Hz, 2H), 3.30-3.18 (m, 1H), 3.04 (s, 3H), 2.73 (d, J=12.1 Hz, 1H), 1.66 (s, 6H). OH signal is exchanged with water. One proton is missing due to overlapping with the solvent residual peak.

Example 45

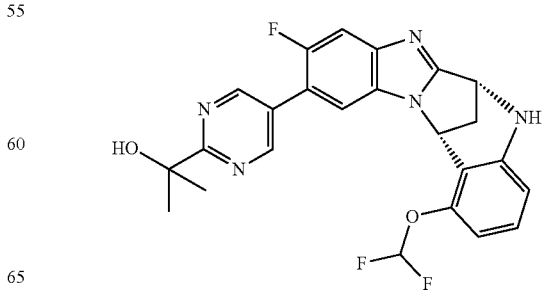

2-{5-[(6R,12R)-11-(difluoromethoxy)-3-fluoro-7,12-dihydro-6H-6,12-methanobenzimidazo[2,1-c][1,4]benzodiazepin-2-yl]pyrimidin-2-yl}propan-2-ol A mixture of Intermediate 92 (500 mg, 0.9117 mmol), cesium carbonate (594 mg, 1.82 mmol), (+/−)-2,2'-bis(diphenylphosphino)-1,1'-binapthyl (80 mg, 0.13 mmol) and palladium(II) acetate (25 mg, 0.11 mmol) in toluene (18 mL) was de-gassed and stirred at 110° C. under nitrogen for 15 hours. The reaction mixture was cooled to ambient temperature, filtered through a pad of celite and washed with ethyl acetate. The combined filtrate and washings were evaporated to dryness using an oil pump to give an oil which was purified by flash chromatography on silica gel (25 to 100% EtOAc in hexanes) to afford the title compound (165 mg, 0.35 mmol, 39% yield) as a brown solid. LC/MS Method 3: RT 1.99 mins, [M+H]$^+$=468. $^1$H NMR (300 MHz, DMSO-d6) δ 8.97 (d, J=1.7 Hz, 2H), 7.61 (d, J=11.7 Hz, 1H), 7.53 (d, J=6.9 Hz, 1H), 7.21-7.13 (m, 1H), 7.17 (t, J=74.2 Hz, 1H), 6.98 (t, J=8.2 Hz, 1H), 6.35 (t, J=8.6 Hz, 1H), 5.90 (d, J=4.3 Hz, 1H), 5.14 (s, 1H), 4.92 (t, J=3.7 Hz, 1H), 2.95 (dt, J=9.0, 4.3 Hz, 1H), 2.37 (d, J=11.4 Hz, 1H), 1.55 (s, 6H).

Example 46

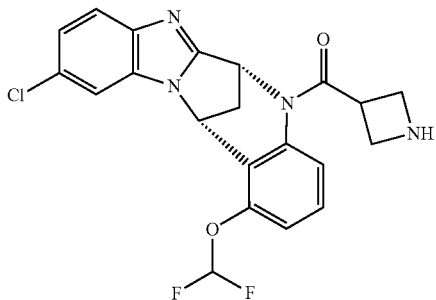 [SMILES: O=C(C1CNC1)N1c2cccc(OC(F)F)c2[C@H]2C[C@@H]1c1nc3ccc(Cl)cc3n12]

Azetidin-3-yl[(6R,12R)-2-chloro-11-(difluoromethoxy)-6H-6,12-methanobenzimidazo[2,1-c][1,4]benzodiazepin-7(12H)-yl]methanone HCl 4M in dioxane was added To Intermediate 97 (10 mg, 0.019 mmol) in 1,4-dioxane (2 mL) was added 4M HCl in 1,4-dioxan (2 mL) and the reaction stirred for 5 hours before the solvent was evaporated. The crude material was purified by preparative HPLC, yielding 3 mg (39%) of the title compound as a white solid.

LCMS Method 3: RT 2.12 min, [M+H]$^+$=431. $^1$H NMR (300 MHz, DMSO-d6) δ 8.21 (d, J=8.7 Hz, 1H), 7.64 (d, J=8.7 Hz, 1H), 7.46 (d, J=2.0 Hz, 1H), 7.42 (t, J=74.2 Hz, 1H), 7.27 (t, J=8.5 Hz, 1H), 7.20 (dd, J=8.7, 2.1 Hz, 1H), 6.92 (d, J=8.1 Hz, 1H), 6.03 (d, J=4.3 Hz, 1H), 5.56 (d, J=3.9 Hz, 1H), 4.41-4.30 (m, 1H), 4.10-3.65 (m, 4H), 3.09 (dt, J=12.1, 4.3 Hz, 1H), 2.60 (d, J=12.0 Hz, 1H).

Example 47

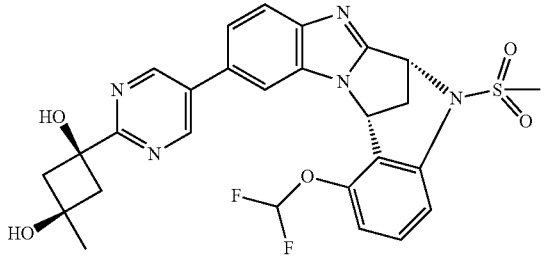 [SMILES: CS(=O)(=O)N1c2cccc(OC(F)F)c2[C@H]2C[C@@H]1c1nc3ccc(-c4cnc([C@]5(O)C[C@@](C)(O)C5)nc4)cc3n12]

cis-1-{5-[(6R,12R)-11-(difluoromethoxy)-7-(methylsulfonyl)-7,12-dihydro-6H-6,12-methanobenzimidazo[2,1-c][1,4]benzodiazepin-2-yl]pyrimidin-2-yl}-3-methylcyclobutane-1,3-diol A solution of tetrabutylammonium fluoride (1M in THF, 0.36 mL, 0.36 mmol) was added to a solution of Intermediate 98 (82 mg, 0.12 mmol) in tetrahydrofuran (0.72 mL) and the reaction was stirred at room temperature for 2 hours. The solvent was evaporated and the residue was partitioned between dichloromethane (20 mL) and brine (20 mL). The two layers were separated and the aqueous phase was extracted with dichloromethane (2×20 mL) and the combined organic layers were washed with brine, filtered through a phase separator and the solvent was removed in vacuo. The crude material was purified by column chromatography on silica gel with hexane/ethyl acetate (0 to 100%) as eluent, yielding 47 mg (68%) of the title compound as a brown solid. LCMS Method 3: RT 1.61 min. (pH 10), [M+H]$^+$=570. $^1$H NMR (300 MHz, DMSO-d6) δ 9.09 (s, 2H), 7.81 (dd, J=8.5, 0.7 Hz, 1H), 7.78-7.76 (m, 1H), 7.62 (dd, J=8.5, 1.8 Hz, 1H), 7.58 (d, J=8.6 Hz, 1H), 7.50 (t, J=73.7 Hz, 1H), 7.34 (t, J=8.5 Hz, 1H), 6.93 (d, J=8.1 Hz, 1H), 6.13 (d, J=4.4 Hz, 1H), 5.96 (d, J=3.8 Hz, 1H), 5.61 (s, 1H), 4.95 (s, 1H), 3.32-3.18 (m, 1H), 3.07 (s, 3H), 2.97-2.85 (m, 2H), 3.05 (s, 3H), 2.68 (d, J=12.1 Hz, 1H), 2.41 (d, 1.09 J=12.9 Hz, 2H).

Example 48

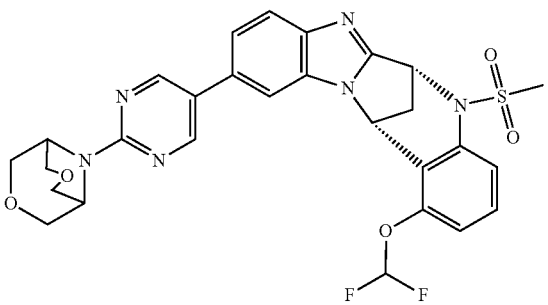 [SMILES: CS(=O)(=O)N1c2cccc(OC(F)F)c2[C@H]2C[C@@H]1c1nc3ccc(-c4cnc(N5C6COCC5COC6)nc4)cc3n12]

(6R,12R)-11-(difluoromethoxy)-2-{2-[(1s,5s)-3,7-dioxa-9-azabicyclo[3.3.1]non-9-yl]pyrimidin-5-yl}-7-(methylsulfonyl)-7,12-dihydro-6H-6,12-methanobenzimidazo[2,1-c][1,4]benzodiazepine The title compound was prepared from 9-[5-(4,4,5,5-tetramethyl-1,3,2-dioxaborolan-2-yl)pyrimidin-2-yl]-3,7- dioxa-9-azabicyclo[3.3.1]nonane and Example 23 according to a method involving the same procedural steps as those described for Example 20, to give, following purification by column chromatography over silica gel using hexane/ethyl acetate (0 to 100%) as eluent, the title compound as a white solid (114 mg, 58% yield). LC/MS Method 3: RT 1.88 mins (pH 10), [M+H]=597. ¹H NMR (300 MHz, DMSO-d6) δ 8.71 (s, 2H), 7.77-7.68 (m, 1H), 7.65-7.53 (m, 2H), 7.49 (t, J=1.6 Hz, 1H), 7.46 (t, J=73.5 Hz, 1H), 7.33 (t, J=8.5 Hz, 1H), 6.92 (d, J=8.3 Hz, 1H), 6.10 (d, J=4.3 Hz, 1H), 5.93 (d, J=3.9 Hz, 1H), 4.52 (s, 2H), 4.10-3.93 (m, 4H), 3.77 (dd, J=11.1, 2.7 Hz, 4H), 3.21 (dt, J=12.3, 4.4 Hz, 1H), 3.06 (s, 3H), 2.66 (d, J=12.1 Hz, 1H).

Example 49

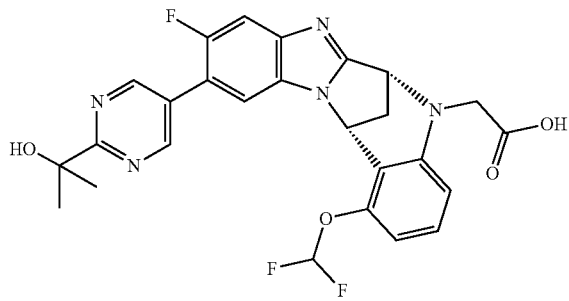 [SMILES: CC(C)(O)c1ncc(-c2cc3c(cc2F)nc2n3[C@@H]3C[C@H]2N(CC(=O)O)c2cccc(OC(F)F)c23)cn1]

[(6R,12R)-11-(difluoromethoxy)-3-fluoro-2-[2-(2-hydroxypropan-2-yl)pyrimidin-5-yl]-6H-6,12-methanobenzimidazo[2,1-c][1,4]benzodiazepin-7(12H)-yl]acetic acid A solution of 1M sodium hydroxide in water (30 µL, 0.03 mmol) was added to a solution of Example 38 (17 mg, 0.031 mmol) in ethanol (30 µL). The mixture was stirred for 3 hours and then purified directly by preparative HPLC affording the title compound as a white solid (9 mg, 54%). LC/MS Method 3: RT 1.68 minutes, [M+H]⁺=526. ¹H NMR (300 MHz, DMSO-d6) δ 8.96 (d, J=1.7 Hz, 2H), 7.66-7.58 (m, 1H), 7.54 (d, J=6.9 Hz, 1H), 7.35 (t, J=74.2 Hz, 1H), 7.04 (t, J=8.3 Hz, 1H), 6.37 (dd, J=8.3, 4.7 Hz, 2H), 5.95 (d, J=4.3 Hz, 1H), 5.15 (s, 1H), 4.95 (d, J=3.4 Hz, 1H), 3.86 (d, J=4.1 Hz, 2H), 2.95 (dt, J=11.3, 4.3 Hz, 1H), 1.55 (s, 6H). COOH signal interchange with the water of the DMSO and one proton is missing due to overlapping with the residual signal of DMSO.

Example 50

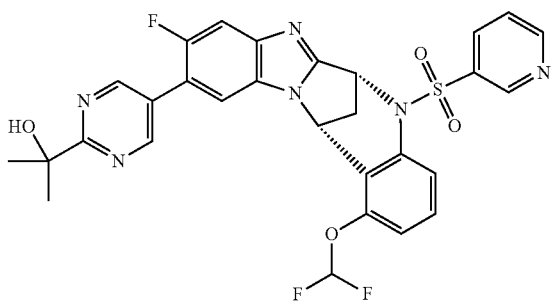 [SMILES: CC(C)(O)c1ncc(-c2cc3c(cc2F)nc2n3[C@@H]3C[C@H]2N(S(=O)(=O)c2cccnc2)c2cccc(OC(F)F)c23)cn1]

2-{5-[(6R,12R)-11-(difluoromethoxy)-3-fluoro-7-(pyridin-3-ylsulfonyl)-7,12-dihydro-6H-6,12-methanobenzimidazo[2,1-c][1,4]benzodiazepin-2-yl]pyrimidin-2-yl}propan-2-ol To Intermediate 99 (275 mg, 0.40 mmol), in a Schlenk tube were added cesium acetate (383 mg, 1.99 mmol), cuprous iodide (155 mg, 0.79 mmol) and dimethylsulfoxide (0.4 mL) and the mixture was sealed and purged 3 times with nitrogen. The reaction mixture was stirred at 100° C. for 18 hours before water and ethyl acetate was added to the reaction mixture and the two layers were separated. The aqueous layer was extracted with ethyl acetate (×2) and the combined organic layers were filtered through a phase separator and the solvent evaporated. The crude material was purified by column chromatography over silica gel using hexane/ethyl acetate (0 to 100%) as eluent, yielding 8 mg (3%) of the title compound as a white solid. LCMS Method 4: RT 2.15 min. (pH 3), [M+H]+=609.

¹H NMR (300 MHz, DMSO-d6) δ 9.24 (dd, J=2.5, 0.8 Hz, 1H), 8.95 (d, J=1.7 Hz, 2H), 8.81 (dd, J=4.8, 1.5 Hz, 1H), 8.58 (ddd, J=8.2, 2.5, 1.6 Hz, 1H), 7.75 (d, J=11.3 Hz, 1H), 7.64 (ddd, J=8.2, 4.8, 0.8 Hz, 1H), 7.56 (d, J=6.8 Hz, 1H), 7.42 (d, J=11.6 Hz, 1H), 7.41 (t, J=74.7 Hz, 1H), 7.27 (t, J=8.5 Hz, 1H), 6.88 (d, J=8.3 Hz, 1H), 6.36 (d, J=3.7 Hz, 1H), 6.08 (d, J=4.3 Hz, 1H), 5.15 (s, 1H), 3.28-3.18 (m, 1H), 2.61 (d, J=12.3 Hz, 1H).

Example 51

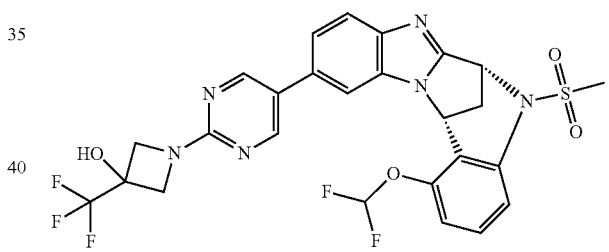

1-{5-[(6R,12R)-11-(difluoromethoxy)-7-(methylsulfonyl)-7,12-dihydro-6H-6,12-methanobenzimidazo[2,1-c][1,4]benzodiazepin-2-yl]pyrimidin-2-yl}-3-(trifluoromethyl)azetidin-3-ol The title compound was prepared from Example 23 (149 mg, 0.35 mmol), and Intermediate 100 (186 mg, 0.54 mmol), according to a method involving the same procedural steps as those described for Example 20. The crude material was purified by column chromatography (SiO₂, 40-100% EtOAc in hexane) and freeze dried from acetonitrile/water to give the title compound (119 mg, 56%) as a pale yellow solid. δ_H (300 MHz, DMSO-d₆) 8.70 (s, 2H), 7.71-7.75 (m, 1H), 7.61 (d, 1H, J 1.3 Hz), 7.57 (d, 1H, J 8.7 Hz), 7.49 (dd, 1H, J 73.9, 72.5 Hz), 7.46 (dd, 1H, J 8.5, 1.7 Hz), 7.42 (s, 1H), 7.33 (t, 1H, J 8.5 Hz), 6.92 (d, 1H, J 8.2 Hz), 6.10 (d, 1H, J 4.4 Hz), 5.93 (d, 1H, J 3.5 Hz), 4.34 (m, 2H), 4.12 (d, 2H, J 9.9 Hz), 3.17-3.25 (m, 1H), 3.06 (s, 3H), 2.63-2.70 (m, 1H). LCMS (ES+) Method 4: 609 (M+H)⁺, RT 2.21 minutes. LCMS (ES+) Method 5: 609 (M+H)⁺, RT 2.17 minutes.

Example 52

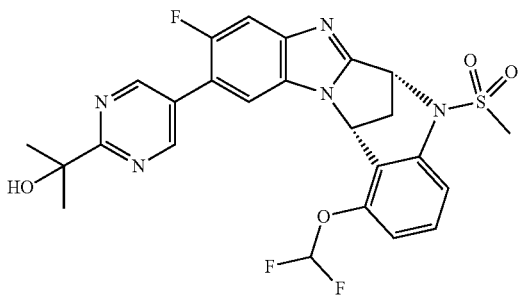 [SMILES: CC(C)(O)c1ncc(-c2cc3c(cc2F)nc2n3[C@@H]3C[C@H]2N(S(C)(=O)=O)c2cccc(OC(F)F)c23)cn1]

2-{5-[(6R,12R)-11-(difluoromethoxy)-3-fluoro-7-(methylsulfonyl)-7,12-dihydro-6H-6,12-methanobenzimidazo[2,1-c][1,4]benzodiazepin-2-yl]pyrimidin-2-yl}propan-2-ol The title compound was prepared from Intermediate 101 (192 mg, 0.31 mmol), potassium carbonate (107 mg, 0.77 mmol), (+/−)-2,2'-bis(diphenylphosphino)-1,1'-binaphthyl (92 mg, 0.15 mmol), palladium(II) acetate (24 mg, 0.11 mmol) and toluene (3 mL) in accordance with the Method described for Example 23. The crude material was purified by column chromatography (SiO$_2$, 20-100% EtOAc in hexane) and further purified by preparative HPLC to give the title compound (40 mg, 24%) as a white solid. $\delta_H$ (300 MHz, DMSO-d$_6$) 8.97 (d, 2H, J 1.7 Hz), 7.70-7.75 (m, 1H), 7.62 (d, 1H, J 6.8 Hz), 7.58 (d, 1H, J 8.6 Hz), 7.46 (dd, 1H, J 74.1, 72.6 Hz), 7.35 (t, 1H, J 8.5 Hz), 6.94 (d, 1H, J 8.1 Hz), 6.12 (d, 1H, J 4.3 Hz), 5.97 (d, 1H, J 3.6 Hz), 5.15 (s, 1H), 3.19-3.28 (m, 1H), 3.09 (s, 3H), 2.68 (d, 1H, J 12.1 Hz), 1.56 (s, 6H).

LCMS (ES+) Method 5: 546 (M+H)$^+$, RT 2.07 minutes.
LCMS (ES+) Method 4: 546 (M+H)$^+$, RT 2.13 minutes.

Example 53

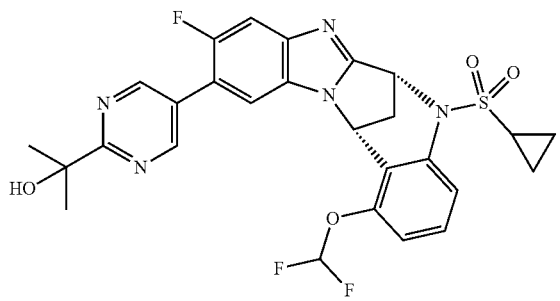 [SMILES: CC(C)(O)c1ncc(-c2cc3c(cc2F)nc2n3[C@@H]3C[C@H]2N(S(=O)(=O)C2CC2)c2cccc(OC(F)F)c23)cn1]

2-{5-[(6R,12R)-7-(cyclopropylsulfonyl)-11-(difluoromethoxy)-3-fluoro-7,12-dihydro-6H-6,12-methanobenzimidazo[2,1-c][1,4]benzodiazepin-2-yl]pyrimidin-2-yl}propan-2-ol The title compound was prepared from Intermediate 102 (110 mg, 0.17 mmol), potassium carbonate (60 mg, 0.43 mmol), (+/−)-2,2'-bis(diphenylphosphino)-1,1'-binaphthyl (44 mg, 0.07 mmol), palladium(II) acetate (10 mg, 0.045 mmol) and toluene (2 mL) in accordance with the synthetic Method of Example 23. The crude material was purified by column chromatography (SiO$_2$, 20-100% EtOAc in hexane) and further purified by preparative HPLC to give the title compound (6 mg, 6%) as an off-white solid. $\delta_H$ (300 MHz, DMSO-d$_6$) 8.98 (d, 2H, J 1.7 Hz), 7.71 (d, 1H, J 11.4 Hz), 7.63 (s, 1H), 7.60 (d, 1H, J 2.1 Hz), 7.47 (dd, 1H, J 74.3, 72.3 Hz), 7.33 (t, 1H, J 8.5 Hz), 6.92 (d, 1H, J 8.1 Hz), 6.11 (d, 1H, J 4.3 Hz), 5.98 (d, 1H, J 3.5 Hz), 5.15 (s, 1H), 3.16-3.25 (m, 1H), 2.85-2.95 (m, 1H), 2.63-2.70 (m, 1H), 1.56 (s, 6H), 1.21-1.31 (m, 2H), 0.94-1.05 (m, 2H).

LCMS (ES+) Method 5: 572 (M+H)$^+$, RT 2.71 minutes.
LCMS (ES+) Method 4: 572 (M+H)$^+$, RT 2.22 minutes.

Example 54

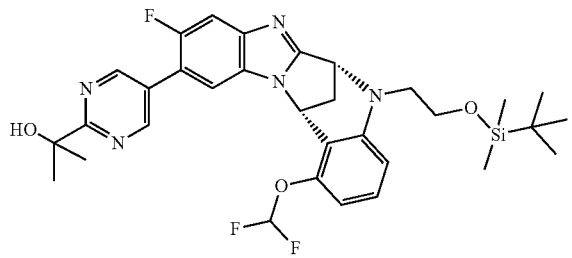 [SMILES: CC(C)(O)c1ncc(-c2cc3c(cc2F)nc2n3[C@@H]3C[C@H]2N(CCO[Si](C)(C)C(C)(C)C)c2cccc(OC(F)F)c23)cn1]

2-{5-[(6R,12R)-7-(2-{[tert-butyl(dimethyl)silyl]oxy}ethyl)-11-(difluoromethoxy)-3-fluoro-7,12-dihydro-6H-6,12-methanobenzimidazo[2,1-c][1,4]benzodiazepin-2-yl]pyrimidin-2-yl}propan-2-ol The title compound was prepared from Intermediate 103 (125 mg, 0.18 mmol), cesium carbonate (117 mg, 0.36 mmol), (+/−)-2,2'-bis(diphenylphosphino)-1,1'-binaphthyl (16 mg, 0.026 mmol) and palladium(II) acetate (6 mg, 0.027 mmol) and toluene (5 mL) by the method of Example 38. The crude material was purified by column chromatography (SiO$_2$, 20-50% EtOAc in hexane) and freeze dried from acetonitrile/water to give the title compound (84 mg, 76%) as an off-white solid.

$\delta_H$ (300 MHz, DMSO-d$_6$) 8.89 (d, 2H, J 1.7 Hz), 7.55 (d, 1H, J 11.4 Hz), 7.47 (d, 1H, J 6.9 Hz), 7.29 (dd, 1H J 74.3, 73.0 Hz), 7.01 (t, 1H, J 8.4 Hz), 6.54 (d, 1H, J 8.6 Hz), 6.36 (d, 1H, J 7.9 Hz), 5.88 (d, 1H, J 4.4 Hz), 5.07 (s, 1H), 4.93 (d, 1H, J 3.3 Hz), 3.70-3.92 (m, 2H), 3.33-3.52 (m, 2H), 2.90-2.98 (m, 1H), 2.31 (d, 1H, J 11.7 Hz), 1.48 (s, 6H), 0.81 (s, 9H), 0.00 (s, 6H).

LCMS (ES+) Method 5: 626 (M+H)$^+$, RT 3.37 minutes.
LCMS (ES+) Method 4: 626 (M+H)$^+$, RT 3.41 minutes.

Example 55

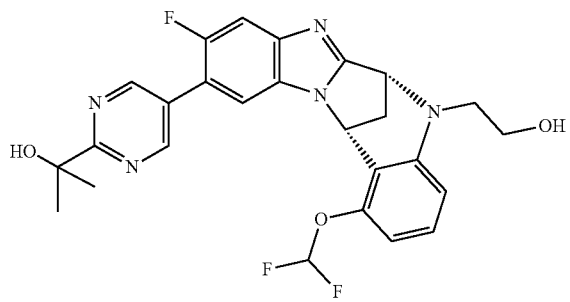 [SMILES: CC(C)(O)c1ncc(-c2cc3c(cc2F)nc2n3[C@@H]3C[C@H]2N(CCO)c2cccc(OC(F)F)c23)cn1]

2-{5-[(6R,12R)-11-(difluoromethoxy)-3-fluoro-7-(2-hydroxyethyl)-7,12-dihydro-6H-6,12-methanobenzimidazo[2,1-c][1,4]benzodiazepin-2-yl]pyrimidin-2-yl}propan-2-ol To a solution of Example 54 (78 mg) in THF (5 mL) was added tetrabutylammonium fluoride (1M in THF, 0.26 mL, 0.26 mmol) and the reaction stirred at room temperature for 1 hour. After which time the reaction mixture was concentrated in vacuo and the residue was partitioned between DCM (20 mL) and brine (20 mL), layers separated and organics washed with brine (2×20 mL), the combined aqueous extracted with DCM (2×20 mL). The combined organics were dried (phase separator) and the volatiles concentrated in vacuo. The crude material was purified by preparative HPLC to give the title compound (45 mg, 71%) as a white solid.

$\delta_H$ (300 MHz, DMSO-$d_6$) 8.96 (d, 2H, J 1.7 Hz), 7.64 (d, 1H, J 11.5 Hz), 7.55 (d, 1H, J 6.8 Hz), 7.36 (dd, 1H, J 74.5, 72.8 Hz), 7.08 (t, 1H, J 7.6 Hz), 6.59 (d, 1H, J 8.5 Hz), 6.42 (d, 1H, J 8.0 Hz), 5.95 (d, 1H, J 4.4 Hz), 5.05-5.22 (m, 1H), 5.01 (d, 1H, J 3.2 Hz), 3.69-3.79 (m, 1H), 3.54-3.65 (m, 1H), 3.36-3.53 (m, 2H), 3.12-3.21 (m, 1H), 2.94-3.03 (m, 1H), 2.44 (d, 1H, J 11.3 Hz), 1.55 (s, 6H).

LCMS (ES+) Method 5: 512 (M+H)+, RT 1.91 minutes.
LCMS (ES+) Method 4: 512 (M+H)+, RT 1.91 minutes.

Example 56

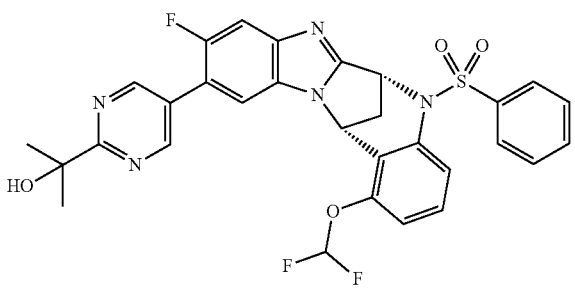 [SMILES: CC(C)(O)c1ncc(-c2cc3c(cc2F)nc2n3[C@@H]3C[C@H]2N(S(=O)(=O)c2ccccc2)c2cccc(OC(F)F)c23)cn1]

2-{5-[(6R,12R)-11-(difluoromethoxy)-3-fluoro-7-(phenylsulfonyl)-7,12-dihydro-6H-6,12-methanobenzimidazo[2,1-c][1,4]benzodiazepin-2-yl]pyrimidin-2-yl}propan-2-ol The title compound was prepared from Intermediate 104 (174 mg, 0.25 mmol), potassium carbonate (90 mg, 0.64 mmol), (+/−)-2,2′-bis(diphenylphosphino)-1,1′-binaphthyl (62 mg, 0.10 mmol), palladium(II) acetate (14 mg, 0.062 mmol) and toluene (3 mL) by the method of Example 23. The crude material was purified by column chromatography (SiO$_2$, 0-100% EtOAc in hexane) and further purified by preparative HPLC to give the title compound (6 mg, 4%) as a white solid.

$\delta_H$ (300 MHz, DMSO-$d_6$) 8.96 (d, 2H, J 1.6 Hz), 8.10-8.16 (m, 2H), 7.77 (d, 1H, J 11.3 Hz), 7.55-7.71 (m, 4H), 7.40 (dd, 1H, J 74.3, 72.1 Hz), 7.31-7.36 (m, 1H), 7.21 (t, 1H, J 8.4 Hz), 6.84 (d, 1H, J 8.1 Hz), 6.34 (d, 1H, J 3.6 Hz), 6.07 (d, 1H, J 4.1 Hz), 5.03-5.27 (m, 1H), 3.17-3.27 (m, 1H), 2.51-2.56 (m, 1H), 1.55 (s, 6H).

LCMS (ES+) Method 5: 608 (M+H)+, RT 2.45 minutes.
LCMS (ES+) Method 4: 608 (M+H)+, RT 2.48 minutes.

Example 57

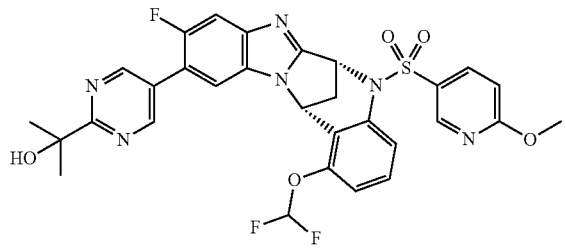 [SMILES: COc1ccc(S(=O)(=O)N2c3cccc(OC(F)F)c3[C@H]3C[C@@H]2c2nc4cc(F)c(-c5cnc(C(C)(C)O)nc5)cc4n23)cn1]

2-(5-{(6R,12R)-11-(difluoromethoxy)-3-fluoro-7-[(6-methoxypyridin-3-yl)sulfonyl]-7,12-dihydro-6H-6,12-methanobenzimidazo[2,1-c][1,4]benzodiazepin-2-yl}pyrimidin-2-yl)propan-2-ol To a microwave vial was added Intermediate 105 (146 mg, 0.20 mmol), potassium carbonate (71 mg, 0.51 mmol), (+/−)-2,2′-bis(diphenylphosphino)-1,1′-binaphthyl (51 mg, 0.08 mmol), palladium(II) acetate (11 mg, 0.05 mmol) and toluene (2.5 mL). The reaction mixture was sealed and degassed with nitrogen and heated to 120° C. in a microwave for 2 hours. After which time the reaction was cooled to room temperature, filtered through celite and washed with EtOAc and DCM. The filtrate was concentrated in vacuo and the crude material purified by column chromatography (SiO$_2$, 0-100% EtOAc in hexane) and further purified by preparative HPLC to give the title compound (6 mg, 5%) as an off-white solid.

$\delta_H$ (300 MHz, DMSO-$d_6$) 8.95 (d, J 1.7 Hz, 2H), 8.88 (dd, J 2.7, 0.7 Hz, 1H), 8.45 (dd, J 8.9, 2.7 Hz, 1H), 7.74 (d, J 11.3 Hz, 1H), 7.56 (d, J 6.8 Hz, 1H), 7.47 (d, J 8.6 Hz, 1H), 7.41 (dd, J 74.1, 72.2 Hz, 1H), 7.28 (t, J 8.5 Hz, 1H), 7.00 (dd, J 8.9, 0.7 Hz, 1H), 6.87 (d, J 8.2 Hz, 1H), 6.32 (d, J 3.8 Hz, 1H), 6.07 (d, J 4.3 Hz, 1H), 5.15 (s, 1H), 3.89 (s, 3H), 3.23 (dt, J 12.3, 4.4 Hz, 1H), 2.57 (d, J 12.3 Hz, 1H), 1.55 (s, 6H).

LCMS (ES+) Method 5 639 (M+H)+, RT 2.36 minutes.
LCMS (ES+) Method 4 639 (M+H)+, RT 2.48 minutes.

Example 58

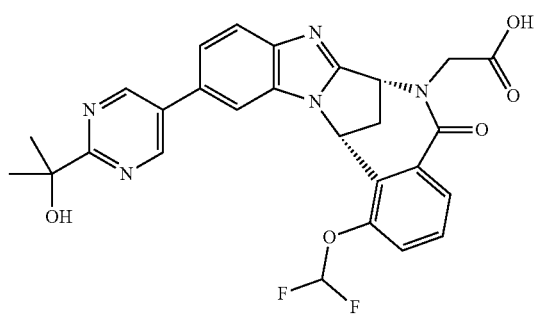 [SMILES: CC(C)(O)c1ncc(-c2ccc3nc4n(c3c2)[C@@H]2C[C@H]4N(CC(=O)O)C(=O)c3cccc(OC(F)F)c32)cn1]

[(7R,14R)-1-(difluoromethoxy)-11-[2-(2-hydroxy-propan-2-yl)pyrimidin-5-yl]-5-oxo-5,14-dihydro-7,14-methanobenzimidazo[1,2-b][2,5]benzodiazocin-6(7H)-yl]acetic acid To a solution of Intermediate 106 (20.0 mg, 0.03 mmol) in THF (1 mL) was added a solution of tetrabutylammonium fluoride (0.4 mL, 0.4 mmol, 1M in THF) at ambient temperature and the reaction stirred for 72 hours. The reaction mixture was partitioned between water (10 mL) and DCM (2×10 mL), and the organics were combined, dried with Na$_2$SO$_4$, filtered and concentrated in vacuo. Purification by preparative HPLC afforded the title compound (3.0 mg, 19%).

$^1$H NMR (300 MHz, DMSO-d$_6$) δ 9.06 (s, 2H), 8.27 (dd, J=6.3, 3.2 Hz, 1H), 7.84-7.56 (m, 3H), 7.55-7.40 (m, 2H), 6.82 (s, 1H), 6.31 (d, J=7.0 Hz, 1H), 5.22 (d, J=7.2 Hz, 1H), 5.12 (s, 1H), 4.56 (d, J=16.3 Hz, 1H), 3.86 (d, J=16.1 Hz, 1H), 3.56 (dt, J=14.0, 7.2 Hz, 1H), 2.89 (d, J=13.8 Hz, 1H), 1.55 (s, 6H). LC/MS Method 3: MH$^+$ 536, retention time 1.19 minutes.

Example 59

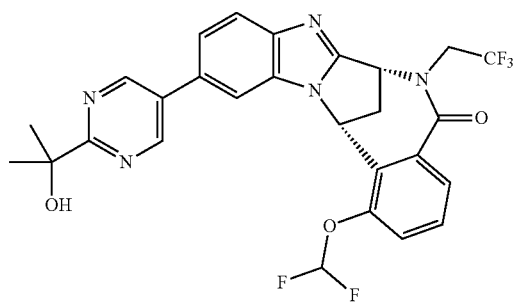 [SMILES: CC(C)(O)c1ncc(-c2ccc3nc4n(c3c2)[C@@H]2C[C@H]4N(CC(F)(F)F)C(=O)c3cccc(OC(F)F)c32)cn1]

(7R,14R)-1-(difluoromethoxy)-11-[2-(2-hydroxypropan-2-yl)pyrimidin-5-yl]-6-(2,2,2-trifluoroethyl)-6,7-dihydro-7,14-methanobenzimidazo[1,2-b][2,5]benzodiazocin-5(14H)-one To a solution of Intermediate 107 (100.0 mg, 0.148 mmol) in THF (10 mL) were added HCl (20 mL, 40 mmol, 2M in 1,4 dioxan), and the mixture was stirred at room temperature for 5 hours. The reaction mixture was neutralised with NaOH (10% aqueous solution) and extracted with DCM (2×10 mL), the organics were combined, dried with Na$_2$SO$_4$, filtered and concentrated in vacuo. Purification by preparative HPLC afforded the desired product (15.0 mg, 18%).

$^1$H NMR (300 MHz, DMSO-d$_6$) δ 9.06 (s, 2H), 8.26 (dd, J=7.0, 2.5 Hz, 1H), 8.03-7.37 (m, 6H), 6.38 (d, J=7.0 Hz, 1H), 5.45 (d, J=7.3 Hz, 1H), 5.12 (s, 1H), 4.94-4.70 (m, 1H), 4.59 (dt, J=15.3, 9.3 Hz, 1H), 3.60 (dt, J=14.3, 7.3 Hz, 1H), 2.90 (d, J=13.9 Hz, 1H), 1.55 (s, 6H). LC/MS Method 3: ESI MH$^+$ 560, retention time 2.19 minutes.

Example 60

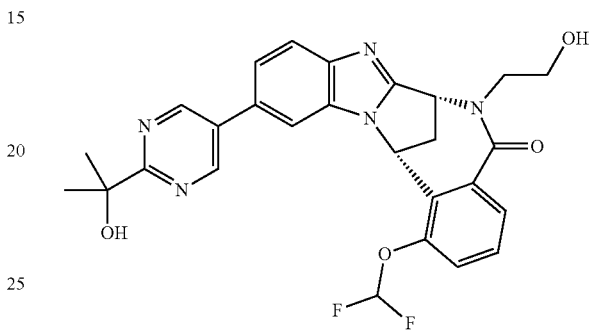

(7R,14R)-1-(difluoromethoxy)-6-(2-hydroxyethyl)-11-[2-(2-hydroxypropan-2-yl)pyrimidin-5-yl]-6,7-dihydro-7,14-methanobenzimidazo[1,2-b][2,5]benzodiazocin-5(14H)-one To a solution of Intermediate 109 (60.0 mg, 0.094 mmol) in THF (5.0 mL) were added aqueous HCl (10 mL, 20 mmol, 2M), and the mixture was stirred at room temperature for 18 hours before the completion of the reaction. The reaction mixture was neutralised with 10% aqueous NaOH solution and extracted with DCM (2×10 mL). The organics were combined, dried with Na$_2$SO$_4$, filtered and concentrated in vacuo. Purification by preparative HPLC (reverse phase) afforded the title compound (27.0 mg, 55%). $^1$H NMR (300 MHz, DMSO-d$_6$) δ 9.06 (s, 2H), 8.31 (dd, J=5.5, 4.1 Hz, 1H), 7.99-7.39 (m, 6H), 6.32 (d, J=7.0 Hz, 1H), 5.38 (d, J=7.2 Hz, 1H), 4.01-3.88 (m, 2H), 3.88-3.71 (m, 4H), 3.54 (dt, J=14.1, 7.2 Hz, 1H), 2.85 (d, J=13.8 Hz, 1H), 1.55 (s, 6H). LC/MS Method 3: ESI MH$^+$522, retention time 1.69 minutes.

Example 61

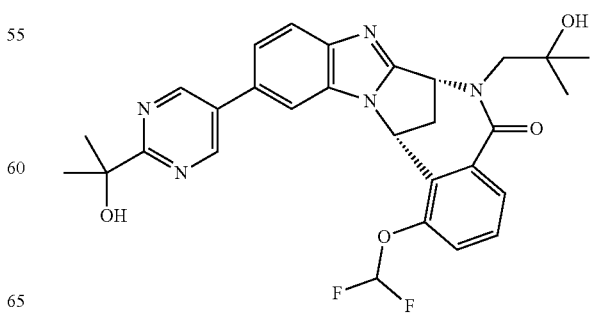

227

(7R,14R)-1-(difluoromethoxy)-6-(2-hydroxy-2-methylpropyl)-11-[2-(2-hydroxypropan-2-yl)pyrimidin-5-yl]-6,7-dihydro-7,14-methanobenzimidazo[1,2-b][2,5]benzodiazocin-5(14H)-one To a solution of Intermediate 23 (120 mg, 0.2 mmol) in DMF (4 mL) were added cesium carbonate (320 mg, 1.01 mmol) and 1-iodo-2-methylpropan-2-ol (50.0 μL, 0.41 mmol), and the mixture was heated in a microwave at 150° C. for 22 hours. The reaction mixture was partitioned between water and DCM (2×10 mL), and the organics were combined, dried with Na$_2$SO$_4$, filtered and concentrated in vacuo. Purification by preparative HPLC (reverse phase) afforded the title compound (12.0 mg, 11%). $^1$H NMR (300 MHz, DMSO-d$_6$) δ 9.06 (s, 2H), 8.32 (dd, J=5.5, 4.0 Hz, 1H), 7.99-7.37 (m, 6H), 6.34 (d, J=6.9 Hz, 1H), 5.65 (d, J=7.5 Hz, 1H), 4.05 (d, J=13.7 Hz, 1H), 3.72 (d, J=13.7 Hz, 1H), 3.58 (dd, J=14.0, 7.0 Hz, 1H), 2.86 (d, J=13.8 Hz, 1H), 1.55 (s, 6H), 1.21 (d, J=5.7 Hz, 6H). LC/MS Method 3: ESI MH$^+$ 550, retention time 1.57 minutes.

Example 62

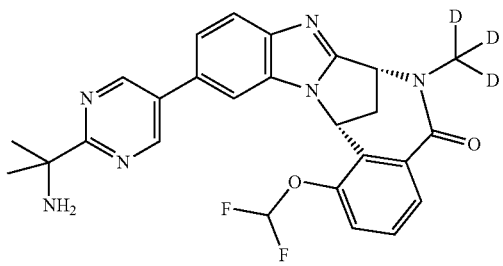 [SMILES: [2H]C([2H])([2H])N1C(=O)c2cccc(OC(F)F)c2[C@H]2C[C@@H]1c1nc3ccc(-c4cnc(C(C)(C)N)nc4)cc3n12]

(7R,14R)-11-[2-(2-aminopropan-2-yl)pyrimidin-5-yl]-1-(difluoromethoxy)-6-(trideutero)methyl-6,7-dihydro-7,14-methanobenzimidazo[1,2-b][2,5]benzodiazocin-5(14H)-one Intermediate 111 (36.0 mg, 0.06 mmol) was dissolved in a solution of HCl in dioxane (4 mL, 4 M) and stirred at room temperature for 1 hour. The reaction mixture was concentrated in vacuo and purified on silica eluting with 0-10% MeOH/DCM to give the title compound (10 mg, 34%). $^1$H NMR (400 MHz, D$_2$O) δ 8.97 (s, 2H), 8.21 (dd, J=7.4, 2.0 Hz, 1H), 7.94 (dd, J=1.7, 0.7 Hz, 1H), 7.74 (dd, J=8.7, 0.7 Hz, 1H), 7.59 (dd, J=8.7, 1.7 Hz, 1H), 7.50-7.36 (m, 1H), 7.15 (d, J=2.4 Hz, 2H), 6.64 (d, J=7.1 Hz, 1H), 5.51 (d, J=7.2 Hz, 1H), 3.59 (dt, J=14.4, 7.3 Hz, 1H), 3.03 (d, J=14.2 Hz, 1H), 1.75 (s, 6H). LC/MS Method 3: ESI MH$^+$ 494, retention time 1.45 minutes.

Example 63

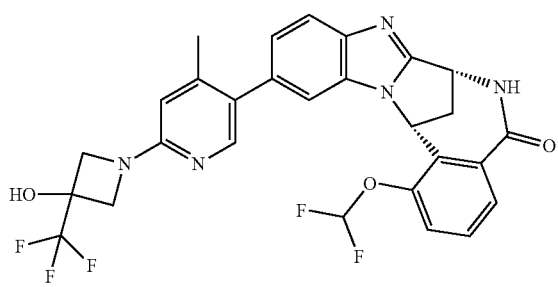 [SMILES: Cc1cc(N2CC(O)(C(F)(F)F)C2)ncc1-c1ccc2nc3n(c2c1)[C@@H]1C[C@H]3NC(=O)c2cccc(OC(F)F)c21]

228

(7R,14R)-1-(difluoromethoxy)-11-{6-[3-hydroxy-3-(trifluoromethyl)azetidin-1-yl]-4-methylpyridin-3-yl}-6,7-dihydro-7,14-methanobenzimidazo[1,2-b][2,5]benzodiazocin-5(14H)-one To a solution of Intermediate 138 (300 mg, 0.84 mmol) and Example 11 (350 mg, 0.93 mmol) in 1,4-dioxane (5 mL) and water (0.4 mL) were added K$_3$PO$_4$ (540 mg, 2.55 mmol), tricyclohexylphosphonium tetrafluoroborate (38 mg, 0.1 mmol) and tris(dibenzylideneacetone)-dipalladium(0) (40 mg, 0.042 mmol) were added. The mixture was degassed for 10 minutes before heating at 105° C. for 17 hours. The reaction mixture was quenched with water and extracted with EtOAc (3×10 mL), dried with Na$_2$SO$_4$, filtered and concentrated in vacuo. The crude product was purified by column chromatography on silica eluting with 0 to 10% MeOH in DCM to give the title compound, which was then treated with HCl (1.1 eq., 0.5M) to form the HCl salt (107 mg, 21%). $^1$H NMR (300 MHz, DMSO-d$_6$) δ 9.16 (d, J=6.8 Hz, 1H), 8.24 (dd, J=6.4, 3.1 Hz, 1H), 7.94 (s, 1H), 7.82-7.25 (m, 7H), 7.19 (dd, J=8.4, 1.7 Hz, 1H), 6.83 (s, 1H), 6.32 (d, J=7.1 Hz, 1H), 4.92 (t, J=6.7 Hz, 1H), 4.44 (d, J=10.2 Hz, 1H), 4.21 (d, J=10.1 Hz, 1H), 3.58-3.37 (m, 1H), 2.75 (d, J=13.2 Hz, 1H), 2.30-2.16 (s, 3H).

LC/MS Method 3: ESI MH$^+$ 572, retention time 1.86 minutes.

Example 64

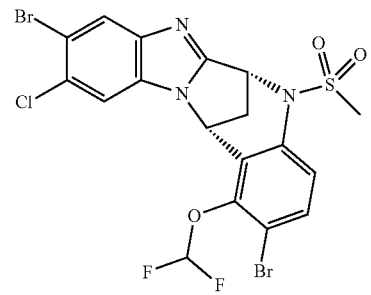 [SMILES: CS(=O)(=O)N1c2ccc(Br)c(OC(F)F)c2[C@H]2C[C@@H]1c1nc3cc(Br)c(Cl)cc3n12]

(6R,12R)-3,10-dibromo-2-chloro-11-(difluoromethoxy)-7-(methylsulfonyl)-7,12-dihydro-6H-6,12-methanobenzimidazo[2,1-c][1,4]benzodiazepine N-Bromosuccinimide (19 mg, 0.11 mmol) was added to a solution of Example 23 (35 mg, 0.08 mmol) in DMF (3 mL) at room temperature. The reaction was left to stir overnight. Further N-bromosuccinimide (19 mg, 0.11 mmol) was added and the reaction mixture heated at 80° C. for 2 hours. The reaction mixture was cooled and concentrated in vacuo to a yellow oil, azeotroping with heptane to remove excess DMF. The crude material was purified by chromatography on silica, eluting with 0-50% EtOAc in hexanes to afford a clear oil. The material was freeze-dried (MeCN/water) to afford the title compound as a white solid (20 mg, 42% yield). $^1$H NMR: (DMSO-d$^6$, 400 MHz) δ: 2.66 (d, J=12.4 Hz, 1H), 3.10 (s, 3H), 3.18 (dt, J=25.0, 8.3, 4.5 Hz, 1H), 5.93 (d, J=3.6 Hz, 1H), 6.10 (d, J=4.6 Hz, 1H), 7.31 (t, J=74.1 Hz, 1H), 7.62 (d, J=9.3 Hz, 1H), 7.65 (d, J=19.5 Hz, 1H), 7.70 (s, 1H), 8.11 (s, 1H). LC/MS Method 5 RT 2.87 mins, m/z 584 and 586.

Example 65

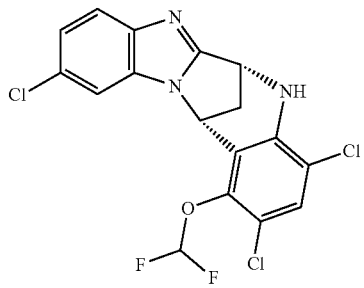 [SMILES: FC(F)Oc1c(Cl)cc(Cl)c2c1[C@H]1C[C@@H](N2)c2nc3ccc(Cl)cc3n21]

(6R,12R)-2,8,10-trichloro-11-(difluoromethoxy)-7,12-dihydro-6H-6,12-methanobenzimidazo[2,1-c][1,4]benzodiazepine N-Chlorosuccinimide (21 mg, 0.16 mmol) was added to a solution of Example 19 (43 mg, 0.12 mmol) in DMF (3 mL) at RT. The reaction was stirred at 60° C. for 6 hours. The reaction mixture was cooled and concentrated in vacuo to a yellow oil, azeotroping with heptane to remove the DMF. The crude material was subjected to chromatography on silica (0-50% EtOAc in hexanes) and evaporated to afford a clear oil. The material was freeze-dried (MeCN/water) to afford the title compound as an off white solid (9 mg, 17% yield). $^1$H NMR: (DMSO-d6, 400 MHz) δ: 2.35 (d, J=11.8 Hz, 1H), 3.00 (dt, J=16.0, 8.0, 4.0 Hz, 1H), 5.00 (d, J=3.7 Hz, 1H), 5.92 (d, J=4.4 Hz, 1H)), 7.20 (dd, J=8.6, 2.0 Hz, 1H), 7.26 (t, J=73.9 Hz, 1H), 7.29 (d, J=4.1 Hz, 1H), 7.42 (d, J=2.0 Hz, 1H), 7.50 (s, 1H), 7.60 (d, J=7.6 Hz, 1H). LC/MS Method 5 RT 2.60 mins (pH 10), m/z 417

Example 66

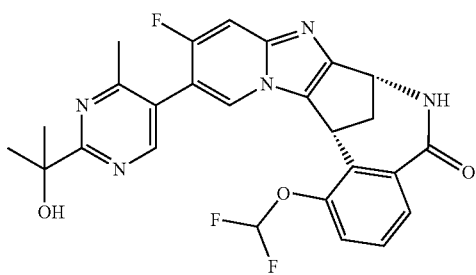 [SMILES: Cc1nc(C(C)(C)O)ncc1-c1cn2c3c(nc2cc1F)[C@H]1C[C@@H]3c2c(OC(F)F)cccc2C(=O)N1]

(7R,14R)-1-(difluoromethoxy)-10-fluoro-11-[2-(2-hydroxypropan-2-yl)-4-methylpyrimidin-5-yl]-7,14-dihydropyrido[1',2':1,2]imidazo[4,5-d][2]benzazocin-5(6H)-one Intermediate 112 (150 mg, 0.29 mmol), Na$_2$CO$_3$(s) (0.15 g, 1.45 mmol) and 2,2-dichloro-1,1,3,3-tetracyclohexyl-1λ$^5$,3λ$^5$-diphospha-2-palladacyclohexane (0.02 g, 0.02 mmol) were suspended in degassed anhydrous dimethylacetamide (3.0 mL) in a 25 mL pressure vessel. The vessel was sealed and degassed thoroughly under vacuum then placed under an atmosphere of nitrogen. This process was twice repeated then the vessel was evacuated and charged with 3 bar CO gas. The mixture was heated to 150° C. overnight whereon the internal pressure reached 5 bar. On cooling to room temperature, the mixture was thoroughly evacuated, diluted with EtOAc (20 mL) and filtered over a pad of celite, washing the filter cake with further EtOAc (2×50 mL). The filtrate was washed with water (25 mL) and the aqueous phase re-extracted with EtOAc (2×50 mL). The combined organic phase was washed with brine (50 mL), dried (MgSO$_4$), filtered and concentrated in vacuo to give the crude product (165 mg) as a brown glass. Column chromatography (C$_{18}$, biotage isolera, 30 g) eluting with 0 to 45% acetonitrile in water spiked with 0.1% formic acid afforded the racemic target (30 mg, 19%) as a tan solid.

Preparative chiral SFC employing a Chiralcel OD-H 25 cm eluting with 15% Methanol: 85% CO$_2$ eluting at 15 ml/min, gave the desired enantiomer eluting at 4.88 minutes. Freeze drying from 1:1 MeCN-water afforded the title compound (6.9 mg, 5%, 92% chiral purity) as a colourless solid. $^1$H NMR (500 MHz, DMSO-d$_6$) 1H NMR (500 MHz, DMSO-d6) δ 8.87 (d, J=6.4 Hz, 1H), 8.69 (s, 1H), 8.23 (dd, J=7.9, 1.4 Hz, 1H), 8.08 (d, J=7.2 Hz, 1H), 7.64 (d, J=11.1 Hz, 1H), 7.44 (t, J=75.0 Hz, 1H), 7.41 (d, J=7.6 Hz, 1H), 7.37 (t, J=8.0 Hz, 1H), 5.13 (d, J=6.3 Hz, 1H), 5.11 (s, 1H), 4.68 (t, J=6.4 Hz, 1H), 2.43-2.39 (m, 1H), 2.37 (s, 3H), 1.53 (s, 6H). LCMS Method 6: MH+ m/z 510, RT 2.37 min

Example 67

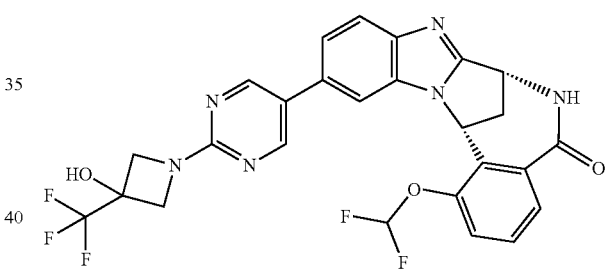

(7R,14R)-1-(difluoromethoxy)-11-{2-[3-hydroxy-3-(trifluoromethyl)azetidin-1-yl]pyrimidin-5-yl}-6,7-dihydro-7,14-methanobenzimidazo[1,2-b][2,5]benzodiazocin-5(14H)-one The title compound was prepared from Example 11 (350 mg, 0.933 mmol) and Intermediate 100 (642 mg, 1.86 mmol), according to a method involving the same procedural steps as those described for Example 20. The crude product was purified by flash chromatography (SiO$_2$, 0 to 100% EtOAc in DCM and then 1 to 12% MeOH in EtOAc) to give the title compound (305 mg, 59%). $^1$H NMR (300 MHz, DMSO-d$_6$) δ 9.13 (d, J=6.8 Hz, 1H), 8.68 (s, 2H), 8.22 (q, J=4.5 Hz, 1H), 7.73-7.64 (m, 1H), 7.60 (dd, J=1.9, 0.7 Hz, 1H), 7.57-7.38 (m, 4H), 6.34 (d, J=7.0 Hz, 1H), 4.88 (t, J=6.7 Hz, 1H), 4.39-4.29 (m, 2H), 4.17-3.96 (m, 2H), 3.60-3.39 (m, 1H), 2.73 (d, J=13.3 Hz, 1H). LCMS basic Method 5 (ES+) RT 1.87 min, 557 (M−H)$^-$

Example 68

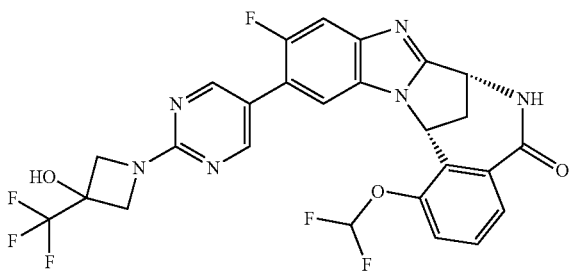 [SMILES: O=C1N[C@@H]2C[C@H](c3c(OC(F)F)cccc31)n1c2nc2cc(F)c(-c3cnc(N4CC(O)(C(F)(F)F)C4)nc3)cc21]

(7R,14R)-1-(difluoromethoxy)-10-fluoro-11-{2-[3-hydroxy-3-(trifluoromethyl)azetidin-1-yl]pyrimidin-5-yl}-6,7-dihydro-7,14-methanobenzimidazo[1,2-b][2,5]benzodiazocin-5(14H)-one The title compound was prepared from Example 10 (75 mg, 0.19 mmol) and Intermediate 100 (138 mg, 0.40 mmol), according to a method involving the same procedural steps as those described for Example 20. The crude product was purified by flash chromatography (SiO$_2$, 0 to 100% EtOAc in DCM and then 1 to 12% MeOH in EtOAc) to obtain the title compound (61 mg, 53%). $^1$H NMR (300 MHz, DMSO-d$_6$) δ 9.06 (d, J=6.8 Hz, 1H), 8.49 (d, J=1.7 Hz, 2H), 8.16 (dd, J=6.0, 3.4 Hz, 1H), 7.59-7.28 (m, 5H), 6.26 (d, J=7.0 Hz, 1H), 4.82 (t, J=6.8 Hz, 1H), 4.28 (d, J=10.3 Hz, 2H), 4.06 (d, J=10.1 Hz, 2H), 3.41 (dd, J=13.5, 6.8 Hz, 1H), 2.66 (d, J=13.4 Hz, 1H). LCMS Method 5: (ES+) RT 1.96 min, 575 (M−H)$^-$

Example 69

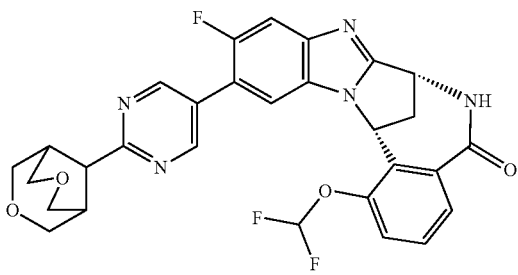 [SMILES: O=C1N[C@@H]2C[C@H](c3c(OC(F)F)cccc31)n1c2nc2cc(F)c(-c3cnc(C4C5COCC4COC5)nc3)cc21]

(7R,14R)-1-(difluoromethoxy)-11-{2-[(1s,5s)-3,7-dioxa-9-azabicyclo[3.3.1]non-9-yl]pyrimidin-5-yl}-10-fluoro-6,7-dihydro-7,14-methanobenzimidazo[1,2-b][2,5]benzodiazocin-5(141H)-one The title compound was prepared from Example 10 (75 mg, 0.19 mmol) and [5-(4,4,5,5-tetramethyl-1,3,2-dioxaborolan-2-yl)pyrimidin-2-yl]-3,7-dioxa-9-azabicyclo[3.3.1]nonane (126 mg, 0.38 mmol), by a palladium catalysed Suzuki coupling according to a method involving the same procedural steps as those described for Example 20. The crude compound was purified by preparative reverse phase HPLC to afford the title compound (5 mg, 5%). $^1$H NMR (400 MHz, DMSO-d$_6$) δ 9.14 (d, J=6.9 Hz, 1H), 8.57 (d, J=1.7 Hz, 2H), 8.24 (dd, J=5.6, 3.9 Hz, 1H), 7.65-7.56 (m, 1H), 7.54-7.42 (m, 4H), 6.33 (d, J=7.1 Hz, 1H), 4.90 (t, J=6.6 Hz, 1H), 4.53 (s, 2H), 4.03 (d, J=11.3 Hz, 4H), 3.82-3.74 (m, 4H), 3.48 (dt, J=13.5, 7.0 Hz, 1H), 2.74 (d, J=13.4 Hz, 1H). LCMS basic Method 5 (ES+) RT 1.79 min, 565 (M+H)$^+$

Example 70

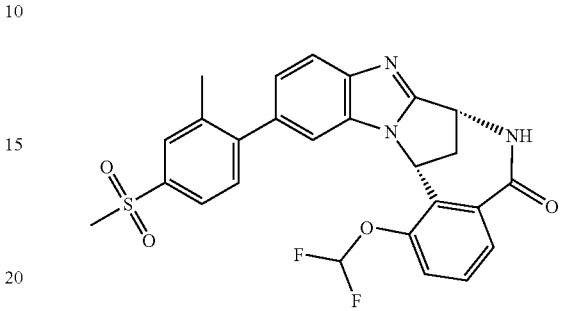

(7R,14R)-1-(difluoromethoxy)-11-[2-methyl-4-(methylsulfonyl)phenyl]-6,7-dihydro-7,14-methanobenzimidazo[1,2-b][2,5]benzodiazocin-5(14H)-one (1-bromo-4-methanesulfonyl-2-methylbenzene (483 mg, 1.86 mmol), bis(pinacolato)diboron (525 mg, 2.0 mmol), and potassium acetate (369 mg, 3.7 mmol) were dissolved in 1,4-dioxane (15 mL) and the mixture degassed thoroughly with nitrogen. 1,1'-bis(diphenylphosphino)ferrocene-palladium(II)dichloride dichloromethane complex (38 mg, 0.05 mmol) was then added and the mixture heated for 2.5 hours under nitrogen. The reaction mixture was separated between EtOAc (25 mL) and water (25 mL). The organic layer was passed through a phase separator and evaporated in vacuo.

The crude product was engaged in a Suzuki reaction with Example 11 (350 mg, 0.93 mmol), tricyclohexylphosphonium tetrafluoroborate (42 mg, 0.11 mmol), tris(dibenzylideneacetone)-dipalladium(0) (56 mg, 0.060 mmol), and K$_3$PO$_4$ (592 mg, 2.79 mmol) in dioxane (5 ml) plus 2 drops of water. The mixture was heated in microwave for 18 hours at 110 degrees. After this time the reaction mixture was separated between EtOAc (25 mL) and water (25 mL) and the organic layer was passed through a phase separator and evaporated in vacuo. The resultant residue was then purified by flash chromatography (SiO$_2$, 0 to 100% EtOAc in DCM and then 1 to 10% MeOH in EtOAc) to obtain mostly pure product (350 mg as brown solid 90% pure). Further purification by flash chromatography on silica gel 1-10% MeOH in DCM gave the title compound as off white powder (45 mg, 10%).

$^1$H NMR (300 MHz, DMSO-d$_6$) δ 9.15 (d, J=6.9 Hz, 1H), 8.31-8.18 (m, 1H), 7.89 (d, J=2.0 Hz, 1H), 7.87-7.65 (m, 2H), 7.59-7.38 (m, 4H), 7.45 (t, J=73 Hz, 1H), 7.36-7.15 (m, 1H), 6.31 (d, J=7.1 Hz, 1H), 4.89 (t, J=6.7 Hz, 1H), 3.49 (dt, J=13.6, 7.1 Hz, 1H), 3.26 (s, 3H), 2.74 (d, J=13.4 Hz, 1H), 2.30 (s, 3H). LCMS basic Method 5 (ES+) RT 1.83 min, 510 (M+H)$^+$.

Example 71

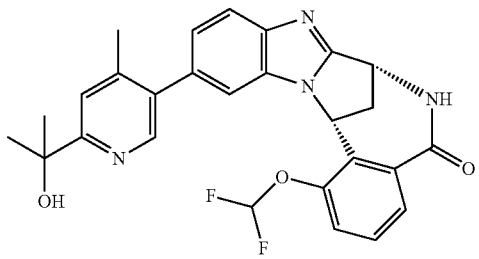 [SMILES: Cc1cc(C(C)(C)O)ncc1-c1ccc2nc3n(c2c1)[C@@H]1C[C@H]3NC(=O)c2cccc(OC(F)F)c21]

(7R,14R)-1-(difluoromethoxy)-11-[6-(2-hydroxypropan-2-yl)-4-methylpyridin-3-yl]-6,7-dihydro-7,14-methanobenzimidazo[1,2-b][2,5]benzodiazocin-5(14H)-one Intermediate 113 (650 mg, 0.97 mmol) was dissolved in tetrahydrofuran (6 mL) and treated with a solution of tetrabutylammonium fluoride (1M in THF, 2.90 mL, 2.90 mmol) dropwise and the reaction stirred at room temperature for 2 hours. The mixture was evaporated in vacuo and separated between water and DCM. The organic phase was evaporated in vacuo and treated with 2M HCl (aq) (20 mL) and THF (5 mL). The reaction was stirred overnight and a further 20 mL of 2M HCl (aq) added. After a further 18 hours the reaction mixture was diluted with water (75 mL) and then evaporated in vacuo to remove volatiles. The aqueous was washed with DCM (4×50 mL) to remove impurities and then the solution was then made basic with saturated sodium carbonate solution and extracted into DCM (2×75 mL). The combined organics were washed with water (50 mL) dried (sodium sulphate), filtered and evaporated in vacuo. The solid was then dissolved in 0.5N HCl (aq) and freeze dried to afford the title compound as the HCl salt. (332 mg, 70%).

$^1$H NMR (400 MHz, DMSO-d$_6$) δ 9.20 (d, J=6.9 Hz, 1H), 8.48 (s, 1H), 8.25 (dt, J=8.6, 4.3 Hz, 1H), 8.17 (s, 1H), 7.81 (d, J=8.4 Hz, 1H), 7.52 (m, 4H), 7.40-7.32 (m, 1H), 6.37 (d, J=7.1 Hz, 1H), 4.97 (t, J=6.8 Hz, 1H), 3.58-3.43 (m, 1H), 2.78 (d, J=13.4 Hz, 1H), 2.50 (s, 3H), 1.65 (s, 6H). LCMS basic Method 5 (ES+) RT 1.62 min, 491 (M+H)$^+$

Example 72

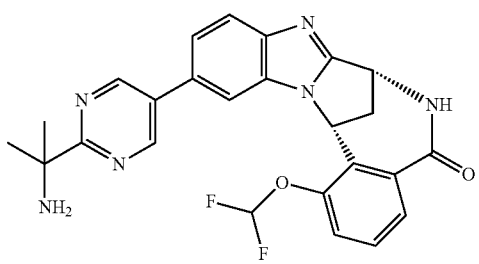 [SMILES: CC(C)(N)c1ncc(-c2ccc3nc4n(c3c2)[C@@H]2C[C@H]4NC(=O)c3cccc(OC(F)F)c32)cn1]

(7R,14R)-11-[2-(2-aminopropan-2-yl)pyrimidin-5-yl]-1-(difluoromethoxy)-6,7-dihydro-7,14-methanobenzimidazo[1,2-b][2,5]benzodiazocin-5(14H)-one Intermediate 115 (154 mg, 0.21 mmol) was dissolved in a solution of 4M HCl in dioxane (10 mL) and stirred for 3 hours at room temperature. After this time the mixture was evaporated in vacuo and separated between EtOAc (50 mL) and sodium carbonate (50 mL), the aqueous layer was extracted with EtOAc (50 mL) and the combined organics were dried (though a phase separator) and evaporated in vacuo. The crude compound was purified by preparative reverse phase HPLC to afford the title compound (27 mg, 27%).

$^1$H NMR (300 MHz, DMSO-d$_6$) δ 9.14 (d, J=6.8 Hz, 1H), 9.02 (s, 2H), 8.23 (dd, J=6.0, 3.4 Hz, 1H), 7.80-7.65 (m, 3H), 7.59 (dd, J=8.5, 1.8 Hz, 1H), 7.55-7.41 (m, 2H), 6.36 (d, J=7.1 Hz, 1H), 4.90 (t, J=6.8 Hz, 1H), 3.49 (dt, J=13.9, 7.1 Hz, 1H), 2.75 (d, J=13.4 Hz, 1H), 2.10 (s, 2H), 1.46 (s, 6H). LCMS basic Method 5 (ES+) RT 1.30 min, 477.2 (M+H)$^+$

Example 73

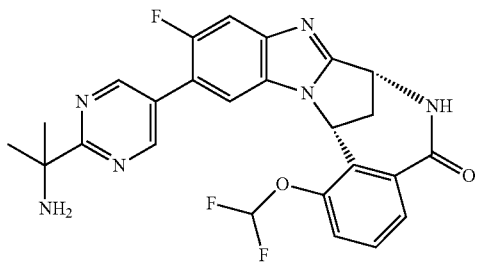 [SMILES: CC(C)(N)c1ncc(-c2cc3c(cc2F)nc2n3[C@@H]3C[C@H]2NC(=O)c2cccc(OC(F)F)c23)cn1]

(7R,14R)-11-[2-(2-aminopropan-2-yl)pyrimidin-5-yl]-1-(difluoromethoxy)-10-fluoro-6,7-dihydro-7,14-methanobenzimidazo[1,2-b][2,5]benzodiazocin-5(14H)-one Intermediate 116 was dissolved in a mixture of dioxane (5 mL) and 4M HCl in dioxane (5 mL). The mixture was stirred for 3 hours at room temperature before being evaporated in vacuo. The reaction mixture was then separated between EtOAc (25 mL) and 1M HCl (20 mL). The acid layer made basic with saturated sodium carbonate solution and extracted with DCM (3×25 mL). The combined organic layers were dried (phase separator) and evaporated in vacuo to afford the title compound as an off white solid (25 mg, 40% over two steps). $^1$H NMR (400 MHz, DMSO-d$_6$) δ 9.16 (d, J=6.9 Hz, 1H), 8.92 (d, J=1.7 Hz, 2H), 8.24 (p, J=4.2 Hz, 1H), 7.71-7.60 (m, 1H), 7.58-7.46 (m, 4H), 6.35 (d, J=7.0 Hz, 1H), 4.92 (t, J=6.8 Hz, 1H), 3.50 (dt, J=13.5, 7.0 Hz, 1H), 2.75 (d, J=13.4 Hz, 1H), 2.15 (s, 2H), 1.48 (s, 6H). LCMS basic Method 5 (ES+) RT 1.45 min, 495.2 (M+H)$^+$

Example 74

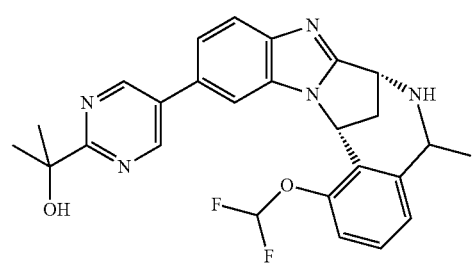 [SMILES: CC1N[C@@H]2C[C@H](c3c(OC(F)F)cccc31)n1c2nc2ccc(-c3cnc(C(C)(C)O)nc3)cc21]

2-{5-[(7R,14R)-1-(difluoromethoxy)-5-methyl-5,6,7,14-tetrahydro-7,14-methanobenzimidazo[1,2-b][2,5]benzodiazocin-11-yl]pyrimidin-2-yl}propan-2-ol Intermediate 119 (150 mg, 0.3991 mmol), 2-[5-(4,4,5,5-tetramethyl-1,3,2-dioxaborolan-2-yl)pyrimidin-2-yl]propan-2-ol (105 mg, 0.3976 mmol), cesium carbonate (0.260 g, 0.797 mmol), tris(dibenzylideneacetone)dipalladium(0) (18.3 mg., 0.020 mmol), and tricyclohexylphosphonium tetrafluoroborate (17.8 mg., 0.0479 mmol) were dissolved in a degassed mixture of 1,4-dioxane (2 mL) and water (0.5 mL). The reaction mixture was heated for 3 hours at 105° C. The mixture was cooled to room temperature and water was added. The mixture was extracted with ethyl acetate, the combined organic layers dried over magnesium sulfate, filtered and concentrated in vacuo. The crude product was purified by preparative HPLC-LCMS (basic conditions; Gr 5-70 $(NH_4)_2CO_3$) to afford 36 mg (19%) of the title compound as a white solid. LCMS Method 3 (ES+) RT 1.76 min., 478.2 (M+H)$^+$.

Example 75

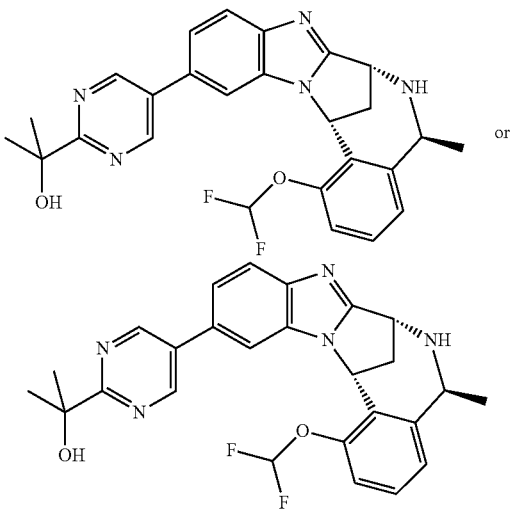

2-{5-[(5R or 5S,7R,14R)-1-(difluoromethoxy)-5-methyl-5,6,7,14-tetrahydro-7,14-methanobenzimidazo[1,2-b][2,5]benzodiazocin-11-yl]pyrimidin-2-yl}propan-2-ol The title compound was prepared from Intermediate 120 (40 mg, 0.106 mmol) and 2-[5-(4,4,5,5-tetramethyl-1,3,2-dioxaborolan-2-yl)pyrimidin-2-yl]propan-2-ol according to a method involving the same procedural steps as those described for Example 20, to afford the title compound 24 mg (47%).

$^1$H NMR (400 MHz, CDCl3) δ ppm 8.91 (s, 2H), 7.91 (d, 1H, J=9.2 Hz), 7.46 (m, 2H), 7.27 (t, 1H, J=8.3 Hz), 7.15 (m, 2H), 6.74 (t, 1H, J=73.8 Hz), 6.29 (d, 1H, J=7.5 Hz), 4.73 (d, 1H, J=5.8 Hz), 4.68 (s, 1H), 3.18 (m, 1H), 2.90 (q, 1H, J=6.3 Hz), 2.47 (d, 1H, J=12.4 Hz), 2.42 (s, 1H), 1.64 (s, 6H), 1.41 (d, 3H, J=6.4 Hz). LCMS Method 3 (ES+) RT 2.36 min., 478.2 (M+H)$^+$.

Example 76

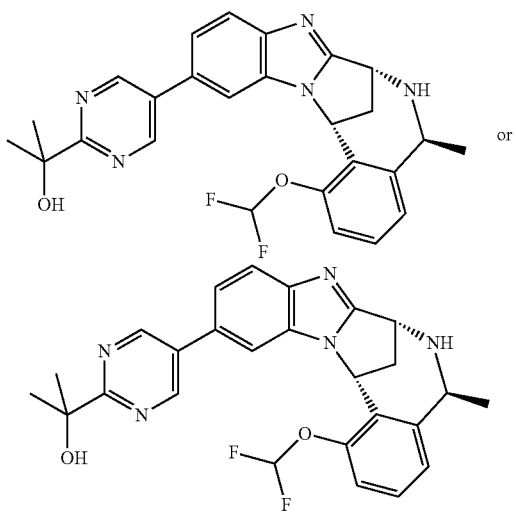

2-{5-[(5R or 5S,7R,14R)-1-(difluoromethoxy)-5-methyl-5,6,7,14-tetrahydro-7,14-methanobenzimidazo[1,2-b][2,5]benzodiazocin-11-yl]pyrimidin-2-yl}propan-2-ol The title compound was prepared from Intermediate 121 (40 mg, 0.106 mmol) and 2-[5-(4,4,5,5-tetramethyl-1,3,2-dioxaborolan-2-yl)pyrimidin-2-yl]propan-2-ol according to a method involving the same procedural steps as those described for Example 20, to afford the title compound 25 mg (49%).

$^1$H NMR (400 MHz, CDCl3) δ ppm 8.94 (s, 2H), 7.87 (d, 1H, J=8.4 Hz), 7.56 (d, 1H, J=1.4 Hz), 7.45 (dd, 1H, J=8.5, 1.7 Hz), 7.23 (t, 1H, J=8.1 Hz), 7.09 (d, 1H, J=8.1 Hz), 7.02 (d, 1H, J=7.6 Hz), 6.77 (t, 1H, J=73.5 Hz), 6.25 (d, 1H, J=7.6 Hz), 4.71 (m, 2H), 4.50 (q, 1H, J=7.5 Hz), 3.24 (ddd, 1H, J=13.0, 7.5, 6.0 Hz), 2.61 (d, 1H, J=12.6 Hz), 2.01 (s, 1H), 1.65 (s, 6H), 0.45 (d, 3H, J=7.4 Hz). LCMS Method 4 (ES+) RT 1.83 min., 478.2 (M+H)$^+$.

Example 77

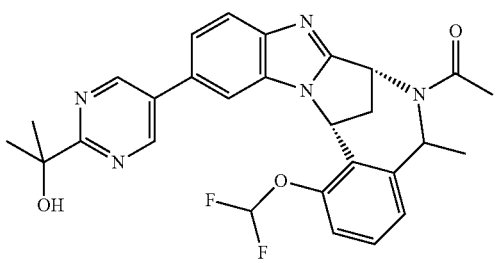 [SMILES: CC(=O)N1C(C)c2cccc(OC(F)F)c2[C@H]2C[C@@H]1c1nc3ccc(-c4cnc(C(C)(C)O)nc4)cc3n12]

1-[(7R,14R)-1-(difluoromethoxy)-11-[2-(2-hydroxypropan-2-yl)pyrimidin-5-yl]-5-methyl-5,14-dihydro-7,14-methanobenzimidazo[1,2-b][2,5]benzodiazocin-6(7H)-yl]ethanone To a solution of Example 74 (30 mg, 0.063 mmol) in dichloromethane (0.5 mL) was added pyridine (50 μL). The reaction mixture was cooled to 0° C. and acetic anhydride (0.5 mL) was added dropwise. The reaction mixture was stirred overnight at room temperature. Water and solid NaHCO$_3$ were added and the mixture was extracted with dichloromethane. The combined organic layers were dried over MgSO$_4$, filtered and concentrated in vacuo to afford 24 mg (74%) of the title compound as a mixture of diastereomers. LCMS Method 3 (ES+) RT 3.53 min and 3.70 min., 520.3 (M+H)$^+$.

Example 78

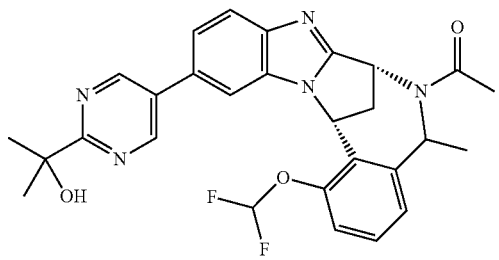 [SMILES: CC(=O)N1C(C)c2cccc(OC(F)F)c2[C@H]2C[C@@H]1c1nc3ccc(-c4cnc(C(C)(C)O)nc4)cc3n12]

1-[(7R,14R)-1-(difluoromethoxy)-11-[2-(2-hydroxypropan-2-yl)pyrimidin-5-yl]-5,14-dihydro-7,14-methanobenzimidazo[1,2-b][2,5]benzodiazocin-6(7H)-yl]ethanone To a solution of Intermediate 128 1 (300 mg, 0.48 mmol) in methanol (7 mL) was added p-toluenesulfonic acid monohydrate (460 mg, 2.42 mmol). The reaction mixture was stirred at room temperature for 4 hours. The methanol was evaporated at in vacuo. The residue was dissolved in DCM (2 mL). The organic layer was washed with a saturated solution of NaHCO$_3$ (3×1 mL), dried over Na$_2$SO$_4$, filtered and concentrated in vacuo. The crude material was purified by preparative basic reverse phase HPLC-MS to afford 150 mg (61%) of the title compound as a white powder.

LCMS Method 3 basic (ES+) RT 3.71 min., 506 (M+H)$^+$.
LCMS Method 4 acidic (ES+) RT 3.88 min., 506 (M+H)$^+$.

Example 79

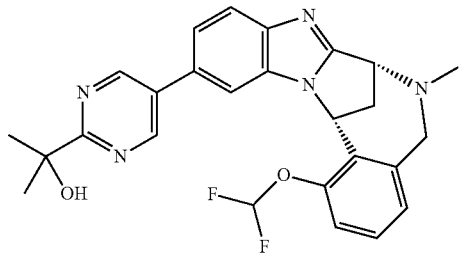 [SMILES: CN1Cc2cccc(OC(F)F)c2[C@H]2C[C@@H]1c1nc3ccc(-c4cnc(C(C)(C)O)nc4)cc3n12]

2-{5-[(7R,14R)-1-(difluoromethoxy)-6-methyl-5,6,7,14-tetrahydro-7,14-methanobenzimidazo[1,2-b][2,5]benzodiazocin-11-yl]pyrimidin-2-yl}propan-2-ol Intermediate 129 (80 mg, 0.135 mmol) was treated in accordance with the synthetic procedure described for Example 78. The crude material was purified by preparative basic reverse phase HPLC-MS affording 2.4 mg (4%) of the title compound as an off white solid.

LCMS Method 3 basic (ES+) RT 3.83 min., 478.1 (M+H)$^+$.

Example 80

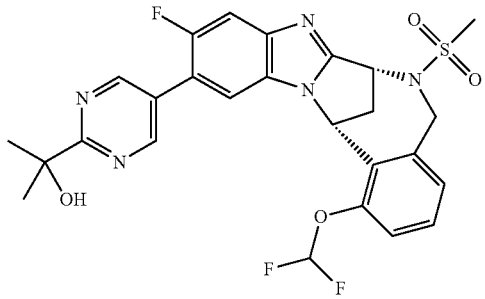 [SMILES: CC(C)(O)c1ncc(-c2cc3c(cc2F)nc2n3[C@@H]3C[C@H]2N(S(C)(=O)=O)Cc2cccc(OC(F)F)c23)cn1]

2-{5-[(7R,14R)-1-(difluoromethoxy)-10-fluoro-6-(methylsulfonyl)-5,6,7,14-tetrahydro-7,14-methanobenzimidazo[1,2-b][2,5]benzodiazocin-11-yl]pyrimidin-2-yl}propan-2-ol Example 16 (14.3 mg, 0.03 mmol) was dissolved in DCM (0.6 mL). The solution was cooled at −60° C. before successive addition of triethylamine (8.34 μL, 0.06 mmol) and a solution of methanesulfonyl chloride (2.31 μL, 0.03 mmol) in DCM (20 μL). The solution was slowly warmed to room temperature overnight. The reaction was quenched by addition of a saturated aqueous solution of NH$_4$Cl (1 mL) and diluted by DCM (2 mL). The organic layer was washed with successively a saturated solution of NH$_4$Cl (2×1 mL) and a saturated solution of NaHCO$_3$ (2×1 mL), dried over Na$_2$SO$_4$, filtered and concentrated in vacuo. The residue was purified by reverse phase basic preparative HPLC-MS yielding to 11 mg (66%) of the title compound as an off white solid.

LCMS Method 3 (ES+) RT 4.07 min., 560.13 (M+H)$^+$.
LCMS Method 4 (ES+) RT 4.24 min., 560.13 (M+H)$^+$.

Example 81

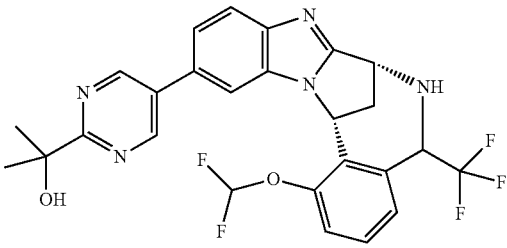 [SMILES: CC(C)(O)c1ncc(-c2ccc3nc4n(c3c2)[C@@H]2C[C@H]4NC(C(F)(F)F)c3cccc(OC(F)F)c32)cn1]

2-{5-[(7R,14R)-1-(difluoromethoxy)-5-(trifluoromethyl)-5,6,7,14-tetrahydro-7,14-methanobenzimidazo[1,2-b][2,5]benzodiazocin-11-yl]pyrimidin-2-yl}propan-2-ol To a solution of Intermediate 130 (7 mg, 0.011 mmol) in methanol (0.5 mL) was added p-toluenesulfonic acid monohydrate (10 mg, 0.053 mmol) and the resulting slurry was stirred overnight. The reaction mixture was then diluted with dichloromethane and aqueous saturated solution of NaHCO₃. The two phases were separated and the aqueous layer further extracted with dichloromethane. The combined organic extracts were dried over magnesium sulphate, filtered and concentrated under reduced pressure. The crude material was purified by basic reverse phase HPLC-MS, yielding to 2.8 mg (49%) of the title compound in a 83/17 ratio of diastereoisomers.

LCMS Method 3 (ES+) RT 4.1 min., 532.2 (M+H)$^+$.
LCMS Method 4 (ES+) RT 2.66 min., 532.2 (M+H)$^+$.

Example 82

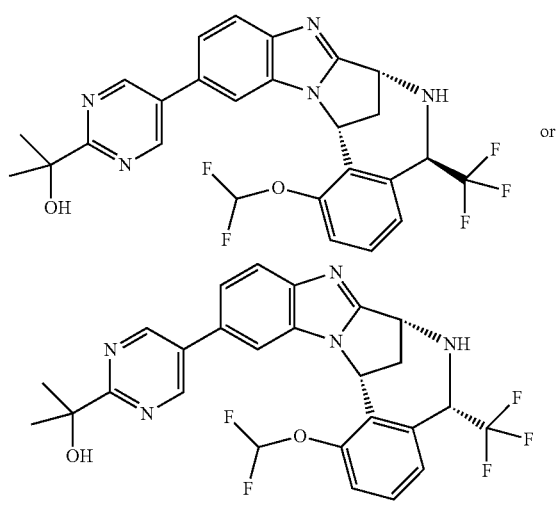

2-{5-[(5R,7R,14R)-1-(difluoromethoxy)-5-(trifluoromethyl)-5,6,7,14-tetrahydro-7,14-methanobenzimidazo[1,2-b][2,5]benzodiazocin-11-yl]pyrimidin-2-yl}propan-2-ol or 2-{5-[(5S,7R,14R)-1-(difluoromethoxy)-5-(trifluoromethyl)-5,6,7,14-tetrahydro-7,14-methanobenzimidazo[1,2-b][2,5]benzodiazocin-11-yl]pyrimidin-2-yl}propan-2-ol To a solution of Intermediate 131 (4.8 mg, 0.0074 mmol) in methanol (0.5 mL) was added p-toluenesulfonic acid monohydrate (7.1 mg, 0.037 mmol). The reaction mixture was stirred overnight. The methanol was evaporated at room temperature in vacuo. The crude material was purified by basic reverse phase HPLC-MS, yielding 3.9 mg (99%) of the title compound as a pale yellow oil. $^1$H NMR (400 MHz, CDCl₃) δ 8.72 (m, 2H), 7.17 (s, 1H), 7.03 (m, 4H), 6.86 (m, 2H), 6.38 (m, 1H), 5.32 (m, 1H), 4.61 (m, 1H), 4.51 (m, 1H), 3.48 (m, 1H), 2.83 (m, 1H), 2.41 (m, 1H), 1.62 (m, 6H). LCMS Method 3 (ES+) RT 2.33 min., 532.2 (M+H)$^+$. LCMS Method 4 (ES+) RT 2.35 min., 532.2 (M+H)$^+$.

Example 83

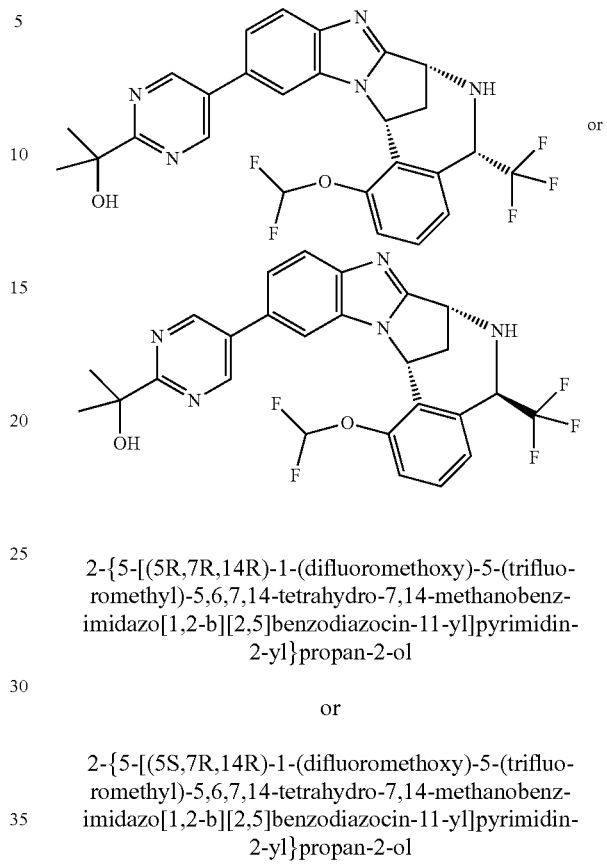

2-{5-[(5R,7R,14R)-1-(difluoromethoxy)-5-(trifluoromethyl)-5,6,7,14-tetrahydro-7,14-methanobenzimidazo[1,2-b][2,5]benzodiazocin-11-yl]pyrimidin-2-yl}propan-2-ol or 2-{5-[(5S,7R,14R)-1-(difluoromethoxy)-5-(trifluoromethyl)-5,6,7,14-tetrahydro-7,14-methanobenzimidazo[1,2-b][2,5]benzodiazocin-11-yl]pyrimidin-2-yl}propan-2-ol To a solution of Intermediate 132 (23 mg) in methanol (1 mL) was added p-toluenesulfonic acid monohydrate (34 mg). The reaction mixture was stirred overnight. The methanol was evaporated at room temperature in vacuo. The crude material was purified by basic reverse phase HPLC-MS, yielding 15 mg (80%) of the title compound as a pale yellow oil.

$^1$H NMR (400 MHz, CDCl₃) δ 8.93 (m, 2H), 7.97 (m, 1H), 7.51 (m, 2H), 7.33 (m, 2H), 7.23 (m, 1H), 6.77 (m, 1H), 6.32 (m, 1H), 4.91 (m, 1H), 4.68 (m, 1H), 3.39 (m, 1H), 3.21 (m, 1H), 2.67 (m, 1H), 2.54 (m, 1H), 1.63 (m, 6H). LCMS Method 4 (ES+) RT 2.33 min., 532.2 (M+H)$^+$. LCMS Method 3 (ES+) RT 2.59 min., 532.2 (M+H)$^+$.

Example 84

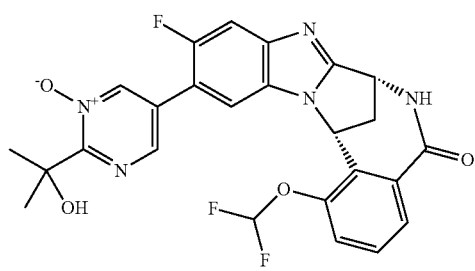

(7R,14R)-1-(difluoromethoxy)-10-fluoro-11-[2-(2-hydroxypropan-2-yl)-1-oxidopyrimidin-5-yl]-6,7-dihydro-7,14-methanobenzimidazo[1,2-b][2,5]benzodiazocin-5(14H)-one To a solution of Example 1 (10 mg, 0.02 mmol) in DCM (0.5 mL) were added m-chloroperbenzoic acid (57 mg, 0.33 mmol) and NaHCO₃ (14 mg; 0.16 mmol). The reaction mixture was stirred at ambient temperature for 24 hours. The mixture was diluted with DCM (1 mL) and washed with a saturated aqueous solution of NaHCO₃ (1 mL) and brine (1 mL), and concentrated in vacuo. The crude material was purified by LC-2D MS chromatography in acidic mode (formic acid) to give 0.5 mg (5%) of the title compound. LCMS Method 4 (ES+) RT 5.30 minutes, 512.2 (M+H)⁺.

Analytical method used for the separation:

semi preparative HPLC column: Sunfire prep C18 5 µm 10×150 mm column Gradient: 98% Solvent A (Water, acetonitrile, Formic acid (95/5/0.5, v/v/v)) to 90% Solvent B (Acetonitrile, Formic acid (99.3/0.7, v/v)) in 9 minutes with a hold at 90% B of 4 minutes.

Flow rate: 7 ml/min

Example 85

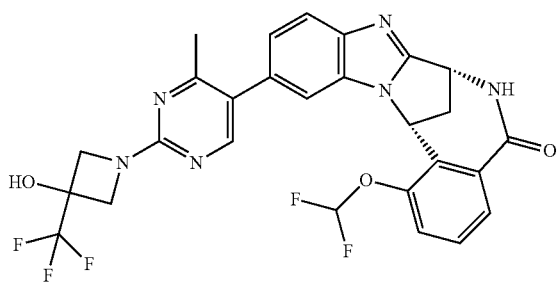 [SMILES: Cc1nc(N2CC(O)(C(F)(F)F)C2)ncc1-c1ccc2nc3n(c2c1)[C@@H]1C[C@H]3NC(=O)c2cccc(OC(F)F)c21]

(7R,14R)-1-(difluoromethoxy)-11-{2-[3-hydroxy-3-(trifluoromethyl)azetidin-1-yl]-4-methylpyrimidin-5-yl}-6,7-dihydro-7,14-methanobenzimidazo[1,2-b][2,5]benzodiazocin-5(14H)-one Example 11 (350 mg, 0.93 mmol) and crude Intermediate 133 (1.00 g, 2.8 mmol) were dissolved in dioxane (10 mL) and K₃PO₄ (592 mg, 2.79 mmol) in water (1 mL) was added, degassed and placed under nitrogen before adding tris(dibenzylideneacetone)dipalladium(0) (44 mg, 0.047 mmol) and tricyclohexylphosphonium tetrafluoroborate (42 mg, 0.11 mmol). The mixture was heated to 105° C. under nitrogen for 18 hours. The mixture was partitioned between EtOAc and water (50 mL each), separated and the organic phase dried (magnesium sulfate), filtered and concentrated in vacuo. The residue was purified by chromatography (silica 25 g, 0-15% gradient of methanol in dichloromethane) to give the title compound as an off-white solid (240 mg, 45% yield). LC/MS Method 3: RT 1.90 mins, m/z 573. ¹H NMR (300 MHz, DMSO-d₆) δ 9.13 (d, J=6.8 Hz, 1H), 8.31-8.13 (m, 2H), 7.89-7.24 (m, 6H), 7.18 (dd, J=8.4, 1.7 Hz, 1H), 6.30 (d, J=7.0 Hz, 1H), 4.88 (t, J=6.7 Hz, 1H), 4.31 (d, J=10.5 Hz, 2H), 4.08 (d, J=10.2 Hz, 2H), 3.48 (dt, J=13.6, 7.0 Hz, 1H), 2.73 (d, J=13.4 Hz, 1H), 2.29 (s, 3H).

Example 86

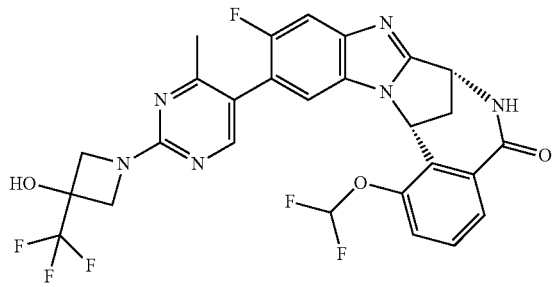 [SMILES: Cc1nc(N2CC(O)(C(F)(F)F)C2)ncc1-c1cc2c(cc1F)nc1n2[C@@H]2C[C@H]1NC(=O)c1cccc(OC(F)F)c12]

(7R,14R)-1-(difluoromethoxy)-10-fluoro-11-{2-[3-hydroxy-3-(trifluoromethyl)azetidin-1-yl]-4-methylpyrimidin-5-yl}-6,7-dihydro-7,14-methanobenzimidazo[1,2-b][2,5]benzodiazocin-5(14H)-one The title compound was prepared from Example 10 and Intermediate 133 in accordance with the synthetic procedure described for Example 85 to afford an off white solid. ¹H NMR (500 MHz, Chloroform-d) δ 8.44 (d, J=7.9 Hz, 1H), 8.09 (br s, 1H), 7.53-7.41 (m, 2H), 7.40-7.33 (m, 1H), 7.16 (br s, 1H), 6.77 (t, J=72.6 Hz, 1H), 6.32 (d, J=7.0 Hz, 1H), 4.97 (s, 1H), 4.52 (d, J=10.1 Hz, 2H), 4.24 (d, J=10.2 Hz, 2H), 3.57-3.40 (m, 1H), 2.87 (d, J=13.3 Hz, 1H), 2.26 (s, 3H). LCMS; Method 8, RT=2.78 min, m/z=591.0.

Example 87

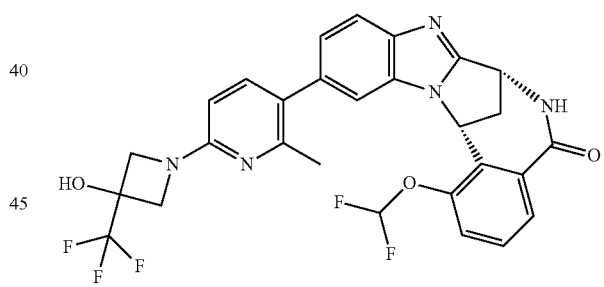

(7R,14R)-1-(difluoromethoxy)-11-{6-[3-hydroxy-3-(trifluoromethyl)azetidin-1-yl]-2-methylpyridin-3-yl}-6,7-dihydro-7,14-methanobenzimidazo[1,2-b][2,5]benzodiazocin-5(14H)-one Intermediate 135 (500 mg, 1.39 mmol) and Example 11 (300 mg, 0.80 mmol) were treated in accordance with the synthetic procedure described for Example 86. After purification by preparative HPLC, the title compound was obtained as a white solid (30 mg). ¹H NMR (400 MHz, DMSO-d₆) δ 9.14 (d, J=6.8 Hz, 1H), 8.24 (dd, J=5.9, 3.5 Hz, 1H), 7.76-7.24 (m, 7H), 7.13 (dd, J=8.4, 1.7 Hz, 1H), 6.44 (d, J=8.4 Hz, 1H), 6.29 (d, J=7.1 Hz, 1H), 4.88 (t, J=6.7 Hz, 1H), 4.24 (d, J=9.6 Hz, 2H), 3.98 (d, J=9.6 Hz, 2H), 3.48 (dt, J=13.5, 6.9 Hz, 1H), 2.73 (d, J=13.3 Hz, 1H), 2.28 (s, 3H). LC/MS Method 3: RT 2.02 minutes, m/z 572.

Example 88

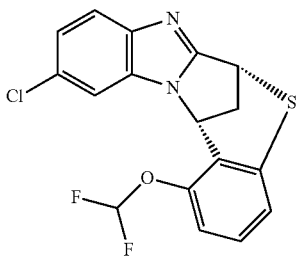 [SMILES: FC(F)Oc1cccc2c1[C@H]1C[C@@H](S2)c2nc3ccc(Cl)cc3n21]

(6R,12R)-2-chloro-11-(difluoromethoxy)-6H,12H-6,
12-methanobenzimidazo[2,1-c][1,4]benzothiazepine Intermediate 136, (1.90 g, 3.35 mmol) was dissolved in dry THF (20 mL), cooled to 0° C. under nitrogen and N,N-diisopropylethylamine (0.76 mL, 4.4 mmol) and then methanesulfonyl chloride (0.31 mL, 4.0 mmol) were added and the mixture stirred for 1 hour until TLC analysis shows conversion to the faster running mesylate. Sodium ethoxide 21% wt solution in ethanol (2.5 mL, 6.7 mmol) was added and the mixture allowed to warm to ambient temperature with stirring overnight. A further portion of the sodium ethoxide solution (2.5 mL) was added and stirred for another 48 hours. The mixture was concentrated in vacuo, then partitioned between dichloromethane and aqueous sodium bicarbonate solution (75 mL each). The organic phase was dried (sodium sulfate), filtered and concentrated in vacuo. Purification by chromatography (silica, isohexane/DCM 0-100% gradient, then 0-10% ethyl acetate in DCM) afforded the title compound as a pink solid (670 mg, 55% yield). $^1$H NMR (300 MHz, DMSO-$d_6$) δ 7.77-7.46 (m, 2H), 7.49 (t, 1H, $J_{H-F}$=73.4 Hz), 7.35 (d, J=2.1 Hz, 1H), 7.31-7.11 (m, 2H), 7.01-6.89 (m, 1H), 6.01 (d, J=5.3 Hz, 1H), 4.97 (d, J=5.0 Hz, 1H), 3.50-3.34 (m, 1H), 2.66 (d, J=12.2 Hz, 1H). LC/MS Method 3: RT 2.16 minutes, m/z 365/367.

Example 89

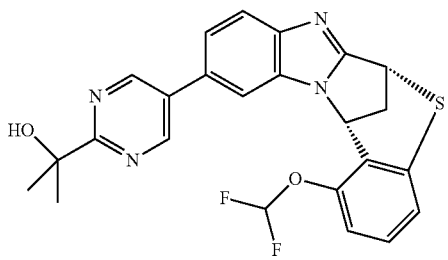 [SMILES: CC(C)(O)c1ncc(-c2ccc3nc4n(c3c2)[C@@H]2C[C@H]4Sc3cccc(OC(F)F)c32)cn1]

2-{5-[(6R,12R)-11-(difluoromethoxy)-6H,12H-6,12-
methanobenzimidazo[2,1-c][1,4]benzothiazepin-2-
yl]pyrimidin-2-yl}propan-2-ol Example 88 (100 mg, 0.25 mmol) and tris(dibenzylideneacetone)dipalladium(0) (13 mg, 0.014 mmol), tricyclohexylphosphonium tetrafluoroborate (13 mg, 0.033 mmol) and 2-(1-hydroxy-1-methylethyl)pyrimidine-5-boronic acid pinacol ester (116 mg, 0.44 mmol) were added to a microwave tube, dioxane (3 mL) added followed by $K_3PO_4$ (174 mg, 0.82 mmol) dissolved in water (300 μL) was added and the vessel placed under nitrogen. The mixture was heated to 140° C. under nitrogen in the microwave (3 bar pressure) until LCMS shows reaction to be complete (typically 1 hour). Purification by chromatography (silica, 0 to 10% methanol gradient in dichloromethane) followed by additional column chromatography (silica, EtOAc, 0 to 7% gradient of methanol) gave the title compound as an off white solid (105 mg, 82% yield). $^1$H NMR (400 MHz, DMSO-$d_6$) δ 9.07 (s, 2H), 7.82-7.35 (m, 4H), 7.26 (t, J=8.1 Hz, 1H), 6.96 (dd, J=8.1, 4.2 Hz, 2H), 6.08 (d, J=5.3 Hz, 1H), 5.13 (s, 1H), 5.06-4.97 (m, 1H), 3.47 (dt, J=12.2, 5.4 Hz, 1H), 2.71 (d, J=12.3 Hz, 1H), 1.55 (s, 6H). LC/MS Method 3: RT 2.02 minutes, m/z 467.0.

Example 90 and Example 91

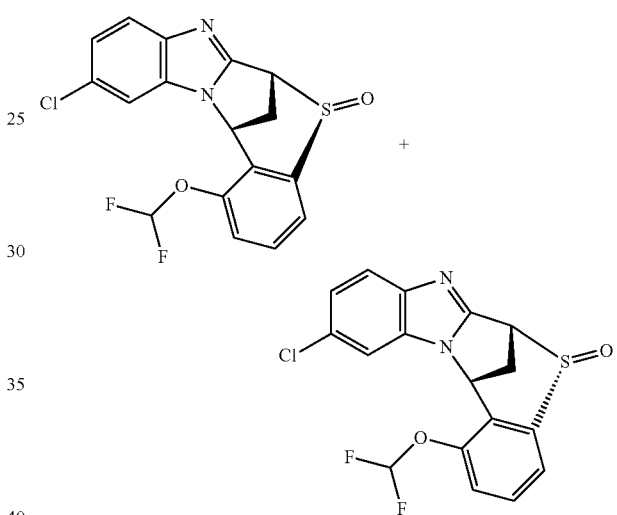

Example 90: (6R,7R,12S)-2-chloro-11-(difluoromethoxy)-6H,12H-6,12-methanobenzimidazo[2,1-c][1,4]benzothiazepine 7-oxide Example 91: (6R,7S,12S)-2-chloro-11-(difluoromethoxy)-6H,12H-6,12-methanobenzimidazo[2,1-c][1,4]benzothiazepine 7-oxide Example 88 (1.00 g, 2.741 mmol) was dissolved in dichloromethane (15 mL), saturated aqueous sodium bicarbonate solution (5 mL) was added and stirred vigorously, 3-meta-chloroperoxybenzoic acid (645 mg, 2.88 mmol, 77%) was added and the mixture stirred for 2 hours. The layers were separated and the organic phase dried (sodium sulfate), filtered and concentrated in vacuo. Purification by chromatography (silica, dichloromethane 0 to 5% methanol) gave the title compounds. The major diastereoisomer, Example 90, eluting first (771 mg, 74%) and then the minor diastereoisomer, Example 91 (44 mg, 4%).

Example 90, Major diastereoisomer: $^1$H NMR (300 MHz, Chloroform-d) δ 7.61 (d, J=8.7 Hz, 1H), 7.54-7.42 (m, 2H), 7.37 (d, J=2.0 Hz, 1H), 7.32-7.15 (m, 2H), 6.77 (dd, J=72.7, 71.8 Hz, 1H), 5.98 (d, J=5.4 Hz, 1H), 4.90 (d, J=5.3 Hz, 1H), 3.70 (d, J=13.0 Hz, 1H), 3.43 (dt, J=13.1, 5.4 Hz, 1H). LC/MS Method 3: RT 1.93 minutes, m/z 381.0/383.0.

Example 91, Minor diastereoisomer: ¹H NMR (300 MHz, Chloroform-d) δ 7.73-7.60 (m, 2H), 7.47 (t, J=8.1 Hz, 1H), 7.39 (d, J=2.0 Hz, 1H), 7.25-7.15 (m, 2H), 6.77 (dd, J=72.7, 71.8 Hz, 1H), 5.95 (d, J=5.6 Hz, 1H), 5.08 (d, J=6.3 Hz, 1H), 3.44 (dt, J=13.6, 6.0 Hz, 1H), 2.85 (d, J=13.5 Hz, 1H). LC/MS Method 3: RT 1.80 minutes, m/z 381.0/383.0.

Example 92

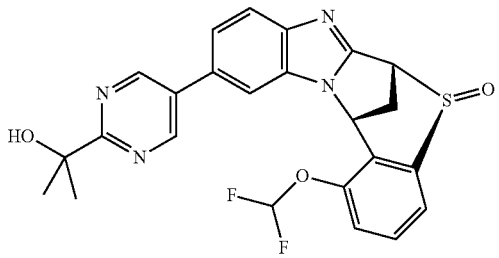 [SMILES: CC(C)(O)c1ncc(-c2ccc3nc4n(c3c2)[C@H]2C[C@H]4[S@@](=O)c3cccc(OC(F)F)c32)cn1]

2-{5-[(6R,7R,12S)-11-(difluoromethoxy)-7-oxido-6H,12H-6,12-methanobenzimidazo[2,1-c][1,4]benzothiazepin-2-yl]pyrimidin-2-yl}propan-2-ol Example 90 (56 mg, 0.147 mmol) and 2-(1-hydroxy-1-methylethyl)pyrimidine-5-boronic acid pinacol ester were treated in accordance with the synthetic procedure described for Example 89. Flash column chromatography (silica, 0 to 5% gradient of methanol in dichloromethane) afforded the title compound as a pale brown solid (12 mg, 17% yield).

¹H NMR (300 MHz, DMSO-d₆) δ 8.98 (s, 2H), 7.79-7.60 (m, 2H), 7.58-7.44 (m, 4H), 7.34 (q, J=4.3 Hz, 1H), 6.10 (d, J=4.7 Hz, 1H), 5.22 (d, J=4.5 Hz, 1H), 5.05 (s, 1H), 3.51-3.30 (m, 2H), 1.47 (s, 6H). LC/MS Method 3: RT 1.59 minutes, m/z 483.0

Example 93

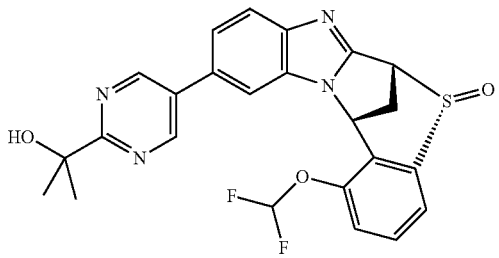 [SMILES: CC(C)(O)c1ncc(-c2ccc3nc4n(c3c2)[C@H]2C[C@H]4[S@](=O)c3cccc(OC(F)F)c32)cn1]

2-{5-[(6R,7S,12S)-11-(difluoromethoxy)-7-oxido-6H,12H-6,12-methanobenzimidazo[2,1-c][1,4]benzothiazepin-2-yl]pyrimidin-2-yl}propan-2-ol Example 91 (44 mg, 0.15 mmol) and 2-(1-hydroxy-1-methylethyl)pyrimidine-5-boronic acid pinacol ester were treated in accordance with the synthetic procedure described for Example 89. Flash column chromatography (silica, 0 to 5% gradient of methanol in dichloromethane) afforded the title compound as a pale brown solid (15 mg, 27% yield).

¹H NMR (300 MHz, DMSO-d₆) δ 9.08 (s, 2H), 7.89-7.49 (m, 6H), 7.40-7.23 (m, 1H), 6.08 (d, J=5.5 Hz, 1H), 5.46 (d, J=6.2 Hz, 1H), 5.12 (s, 1H), 3.44 (dt, J=13.6, 6.0 Hz, 1H), 2.93 (d, J=13.8 Hz, 1H), 1.55 (s, 6H). LC/MS Method 3: RT 1.56 minutes, m/z 483.0.

Example 94

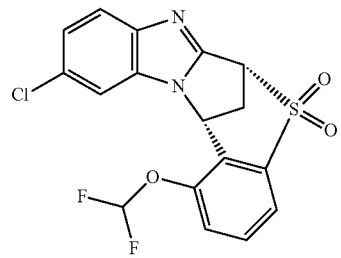 [SMILES: O=S1(=O)c2cccc(OC(F)F)c2[C@H]2C[C@@H]1c1nc3ccc(Cl)cc3n12]

(6R,12R)-2-chloro-11-(difluoromethoxy)-6H,12H-6,12-methanobenzimidazo[2,1-c][1,4]benzothiazepine 7,7-dioxide Example 88 (240 mg, 0.66 mmol) treated in accordance with the synthetic procedure described for Example 90/91 with 2 eq of mCPBA. The title compound was obtained after chromatography as a white solid (196 mg, 76% yield). ¹H NMR (300 MHz, DMSO-d₆) δ 7.75-7.60 (m, 3H), 7.56 (t, 1H, J$_{H-F}$=72.7 Hz), 7.53-7.45 (m, 1H), 7.41 (dd, J=2.1, 0.5 Hz, 1H), 7.26 (dd, J=8.7, 2.1 Hz, 1H), 6.12 (d, J=5.4 Hz, 1H), 5.61 (d, J=5.7 Hz, 1H), 3.75 (dt, J=13.6, 5.8 Hz, 1H), 3.52 (d, J=13.6 Hz, 1H). LC/MS Method 3: RT 1.86 minutes, m/z 397.0/399.0.

Example 95

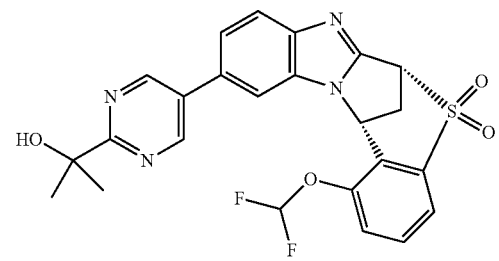 [SMILES: CC(C)(O)c1ncc(-c2ccc3nc4n(c3c2)[C@@H]2C[C@H]4S(=O)(=O)c3cccc(OC(F)F)c32)cn1]

2-{5-[(6R,12R)-11-(difluoromethoxy)-7,7-dioxido-6H,12H-6,12-methanobenzimidazo[2,1-c][1,4]benzothiazepin-2-yl]pyrimidin-2-yl}propan-2-ol Example 94 (198 mg, 0.50 mmol) and 2-(1-hydroxy-1-methylethyl)pyrimidine-5-boronic acid pinacol ester were treated in accordance with the synthetic procedure described for Example 89 to give the title compound after chromatography as an off-white solid (90 mg, 36% yield). ¹H NMR (300 MHz, DMSO-d₆) δ 9.08 (s, 2H), 7.91-7.79 (m, 1H), 7.74-7.58 (m, 5H), 7.54-7.41 (m, 1H), 6.17 (d, J=5.4 Hz, 1H), 5.63 (d, J=5.7 Hz, 1H), 5.13 (s, 1H), 3.87-3.70 (m, 1H), 3.56 (d, J=13.5 Hz, 1H), 1.55 (s, 6H). LC/MS Method 3: RT 1.72 minutes, m/z 499.0.

Example 96

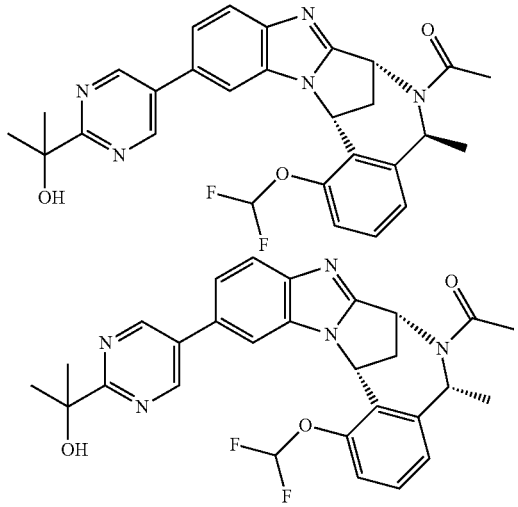

1-[(5R,7R,14R)-1-(difluoromethoxy)-11-[2-(2-hydroxypropan-2-yl)pyrimidin-5-yl]-5-methyl-5,14-dihydro-7,14-methanobenzimidazo[1,2-b][2,5]benzodiazocin-6(7H)-yl]ethanone or 1-[(5S,7R,14R)-1-(difluoromethoxy)-11-[2-(2-hydroxypropan-2-yl)pyrimidin-5-yl]-5-methyl-5,14-dihydro-7,14-methanobenzimidazo[1,2-b][2,5]benzodiazocin-6(7H)-yl]ethanone To a solution of Example 76 (22 mg, 0.046 mmol) and pyridine (5 µL, 0.06 mmol) in dichloromethane (0.5 mL), cooled at 0° C., was added acetic anhydride (460 µL; 4.6 mmol). The reaction was allowed to reach ambient temperature and stirred overnight. The crude reaction mixture was poured into ice water (2 mL), before neutralisation by solid NaHCO₃. The aqueous layer was extracted by ethyl acetate (2×2 mL). The combined organic layers were dried over Na₂SO₄, filtered and concentrated in vacuum. The residue was taken up in di-isopropyl ether and concentrated in vacuum. The resulting solid was dissolved in 1-4 dioxane/water (1:1 mixture, total volume 5 mL) before freeze drying to yield 21 mg (90%) of the title compound as a white solid. LCMS Method 3 (ES⁺): RT 2.18 min, [M+H]⁺=520.2

Example 97

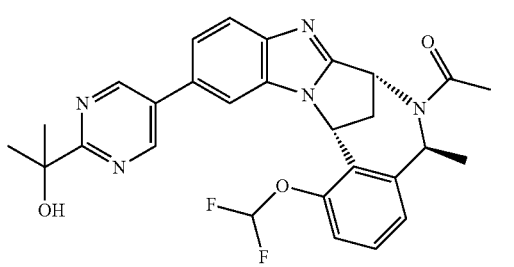

or

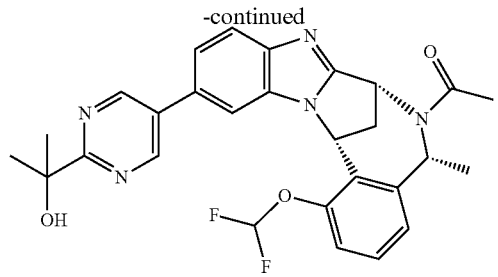

1-[(5R,7R,14R)-1-(difluoromethoxy)-11-[2-(2-hydroxypropan-2-yl)pyrimidin-5-yl]-5-methyl-5,14-dihydro-7,14-methanobenzimidazo[1,2-b][2,5]benzodiazocin-6(7H)-yl]ethanone Or 1-[(5S,7R,14R)-1-(difluoromethoxy)-11-[2-(2-hydroxypropan-2-yl)pyrimidin-5-yl]-5-methyl-5,14-dihydro-7,14-methanobenzimidazo[1,2-b][2,5]benzodiazocin-6(7H)-yl]ethanone The title compound was prepared from Example 75 (2.3 mg, 4.8 µmol) by the method of Example 96. The crude material was purified by basic reverse phase preparative HPLC-MS, yielding 2.1 mg (90%) of the title compound as a colorless oil. LCMS Method 3 (ES+): RT 2.20 min, [M+H]⁺=520.2.

Example 98

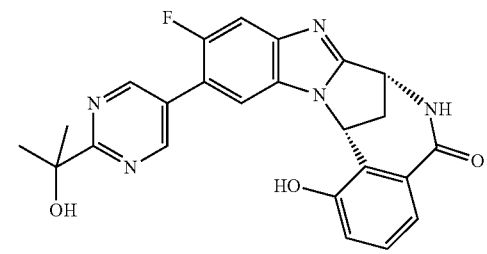 [SMILES: CC(C)(O)c1ncc(-c2cc3c(cc2F)nc2n3[C@@H]3C[C@H]2NC(=O)c2cccc(O)c23)cn1]

(7R,14R)-10-fluoro- 1-hydroxy-11-[2-(2-hydroxypropan-2-yl)pyrimidin-5-yl]-6,7-dihydro-7,14-methanobenzimidazo[1,2-b][2,5]benzodiazocin-5(14H)-one Example 1 (300 mg, 0.61 mmol) was dissolved in dry tetrahydrofuran (10 mL/mmol). The solution was cooled to 0° C. and sodiumbis(trimethylsilyl)amide (5 eq, 3.03 mmol) was added. The reaction mixture was stirred at 0° C. for 30 minutes and overnight at room temperature. The reaction mixture was cooled to 0° C. and quenched with water (5 mL). Tetrahydrofuran was evaporated; the aqueous layer was brought to pH 6-7 by addition of 0.1N HCl and extracted with ethyl acetate (3×10 mL). The organic layer was dried over MgSO₄, filtered and concentrated in vacuo. The residue was purified over silica gel (5-10% MeOH in DCM), yielding 85 mg (31%) of the title compound as a white solid. LCMS Method 3 (ES+): RT 1.64 min., [M+H]⁺ =446.2. ¹H NMR (400 MHz, DMSO-d₆) δ ppm 10.56 (s, 1H), 8.97 (d, J=1.5 Hz, 2H), 8.93 (d, J=7.0 Hz, 1H), 7.79 (dd, J1=8.0 Hz, J2=1.0 Hz, 1H), 7.71 (d, J=7.0 Hz, 1H), 7.63 (d, J=11.5 Hz, 1H), 7.20 (t, J=8.0 Hz, 1H), 7.10 (dd, J1=8.0 Hz, J2=1.2 Hz, 1H), 6.41 (d, J=7.0 Hz, 1H), 5.14 (s, 1H), 4.87 (t, J=6.9 Hz, 1H), 3.42 (m, 1H), 2.68 (d, J=13.2 Hz, 1H), 1.56 (s, 6H).

Example 99

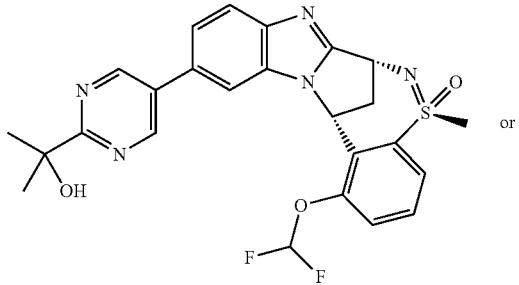

or

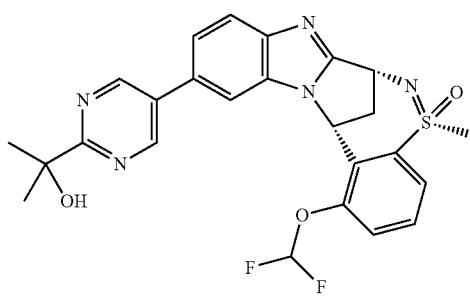

2-{5-[(7R,14R)-1-(difluoromethoxy)-5-methyl-5-oxido-7,14-dihydro-7,14-methano-5λ-4-benzimidazo[2,1-d][1,2,5]benzothiadiazocin-11-yl]pyrimidin-2-yl}propan-2-ol To a solution of Intermediate 142 (8 mg) in MeOH (5 mL) was added p-toluene sulfonic acid monohydrate (18.6 mg, 0.1 mmol). The reaction mixture was stirred at ambient temperature overnight. The methanol was evaporated and the residue was taken up in DCM (5 mL). The organic layer was washed with a mixture of saturated aqueous sodium bicarbonate solution and water ~50/50 (3 mL). The organic layer was dried over MgSO₄, filtered and concentrated in vacuo. The crude material was purified by reverse phase preparative LCMS yielding 3.7 mg (57%) of the title compound as a pale yellow solid.

LCMS Method 3 (ES+): RT 2.02 minutes, [M+H]+=512.1. ¹H NMR (300 MHz, MeOD-d₄) δ 9.04 (s, 2H), 7.99 (d, J=8.7 Hz, 1H), 7.94 (d, J=8.6 Hz, 1H), 7.84 (dd, J1=6.4 Hz, J2=2.4 Hz, 1H), 7.75 (s, 1H), 7.69 (d, J=6.4 Hz, 1H), 7.68 (s, 1H), 7.36 (t, J=72.6 Hz, 1H), 6.87 (d, J=7.9 Hz, 1H), 5.34 (d, J=5.1 Hz, 2H), 3.61 (m, 1H), 3.56 (s, 3H), 2.95 (d, J=13.2 Hz, 1H), 1.65 (s, 6H).

Example 100

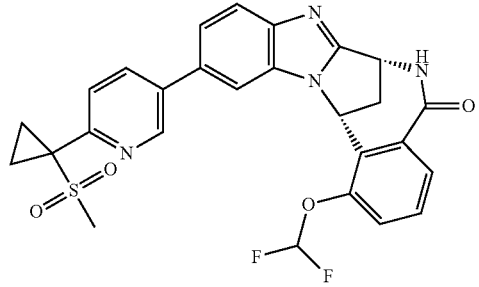 [SMILES: CS(=O)(=O)C1(c2ccc(-c3ccc4nc5n(c4c3)[C@@H]3C[C@H]5NC(=O)c4cccc(OC(F)F)c43)cn2)CC1]

(7R,14R)-1-(difluoromethoxy)-11-{6-[1-(methylsulfonyl)cyclopropyl]pyridin-3-yl}-6,7-dihydro-7,14-methanobenzimidazo[1,2-b][2,5]benzodiazocin-5(14H)-one Example 11 (30 mg, 0.08 mmol), bis(pinacolato)diboron (25 mg, 0.096 mmol), potassium acetate (24 mg, 0.24 mmol), tricyclohexylphosphonium tetrafluoroborate (7 mg, 0.019 mmol) and tris(dibenzenylideneacetone)dipaladium (0) (7 mg, 0.008 mmol) were mixed in degassed dioxane (1 mL). The reaction mixture was stirred at 80° C. for 24 hours. Intermediate 143 (29 mg, 0.08 mmol), [1,1'-bis(diphenylphosphino)ferrocene]dichloropalladium(II) (4 mg, 0.006 mmol), cesium carbonate (52 mg, 0.16 mmol) and water (0.11 mL) were added and the reaction mixture was stirred at 95° C. for 2 hours. The reaction mixture was concentrated in vacuum and the crude was purified by reverse phase basic preparative LCMS yielding 8 mg (19%) of the title compound as an white solid. LCMS Method 3 (ES+): RT 1.19 min, [M+H]+=537.1.

¹H NMR (300 MHz, MeOD-d₄) δ 8.90 (s, 1H), 8.36 (dd, J=7.0, 1.3 Hz, 1H), 8.23 (dd, J=8.2, 1.7 Hz, 1H), 8.02 (s, 1H), 7.88 (m, 3H), 7.55 (m, 2H), 7.35 (t, J=72.8 Hz, 1H). 6.74 (d, J=7.2 Hz, 1H), 5.27 (d, J=6.7 Hz, 1H), 3.67 (m, 1H), 3.04 (s, 3H), 3.01 (d, J=13.6 Hz, 1H), 1.87 (s, 2H), 1.58 (m, 2H).

Example 101

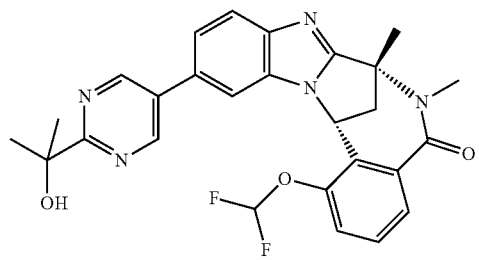 [SMILES: CN1C(=O)c2cccc(OC(F)F)c2[C@H]2C[C@]1(C)c1nc3ccc(-c4cnc(C(C)(C)O)nc4)cc3n12]

(7R,14R)-1-(difluoromethoxy)-11-[2-(2-hydroxypropan-2-yl)pyrimidin-5-yl]-6,7-dimethyl-6,7-dihydro-7,14-methanobenzimidazo[1,2-b][2,5]benzodiazocin-5(14H)-one Intermediate 149 (55 mg, 0.14 mmol), 2-(1-hydroxy-1-methylethyl)pyrimidine-5-boronic acid pinacol ester (75 mg, 0.27 mmol), tricyclohexylphosphonium tetrafluoroborate (12 mg, 0.033 mmol), tris(dibenzenylideneacetone)dipaladium(0) (12 mg, 0.014 mmol), potassium triphosphate (60 mg, 0.27 mmol) and water (0.22 mL) were mixed in degassed 1,4-dioxane (2.2 mL). The reaction mixture was stirred at 130° C. under nitrogen for 3 hours. The crude reaction mixture was partially concentrated and purified over silica gel (Heptane: EtOAc 75 to 100%), yielding 63 mg (93%) of the title compound as a white solid. LCMS Method 3 (ES+): RT 2.19 min, [M+H]$^+$=506.2. $^1$H NMR (300 MHz, CDCl$_3$) δ 8,96 (s, 2H), 8,55 (d, J=8.0 Hz, 1H), 7.93 (d, J=7.7 Hz, 1H), 7.82 (s, 1H), 7,54 (d, J=7.8 Hz, 1H), 7.49 (t, J=8.5 Hz, 1H), 7.35 (d, J=7.8 Hz, 1H), 6.90 (t, J=72.7 Hz, 1H), 6.23 (d, J=6.0 Hz, 1H), 4.70 (bs, 1H), 3.46 (m, 4H), 3.14 (d, J=13.5 Hz, 1H), 2.22 (s, 3H), 1.68 (s, 6H).

Example 102

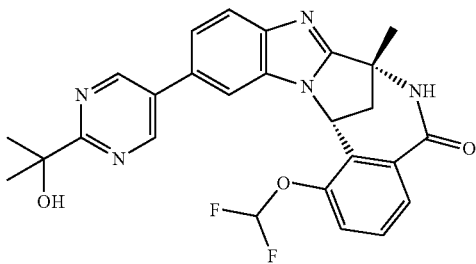 [SMILES: CC(C)(O)c1ncc(-c2ccc3nc4n(c3c2)[C@@H]2C[C@@]4(C)NC(=O)c3cccc(OC(F)F)c32)cn1]

(7R,14R)-1-(difluoromethoxy)-11-[2-(2-hydroxypropan-2-yl)pyrimidin-5-yl]-7-methyl-6,7-dihydro-7,14-methanobenzimidazo[1,2-b][2,5]benzodiazocin-5(14H)-one The title compound was prepared from Intermediate 148 (29 mg, 0.08 mmol) and 2-(1-hydroxy-1-methylethyl)pyrimidine-5-boronic acid pinacol ester (41 mg, 0.15 mmol) following the procedure used for Example 101. The crude material was purified by reverse phase basic preparative HPLC, yielding 6 mg (13%) of the title compound as a white solid. LCMS Method 3 (ES+): RT 2.05 minutes, [M+H]$^+$=492. $^1$H NMR (300 MHz, CDCl$_3$) δ 8,95 (s, 2H), 8,48 (d, J=8.0 Hz, 1H), 8,04 (d, J=8.2 Hz, 1H), 7.79 (s, 1H), 7.66 (d, J=8.3 Hz, 1H), 7.55 (t, J=8.3 Hz, 1H), 7.45 (d, J=7.7 Hz, 1H), 6.93 (t, J=72.8 Hz, 1H), 6.52 (d, J=4.3 Hz, 1H), 3.67 (s, 1H), 3.50 (m, 1H), 3.09 (d, J=13.3 Hz, 1H), 2.31 (s, 3H), 1.68 (s, 6H).

Example 103

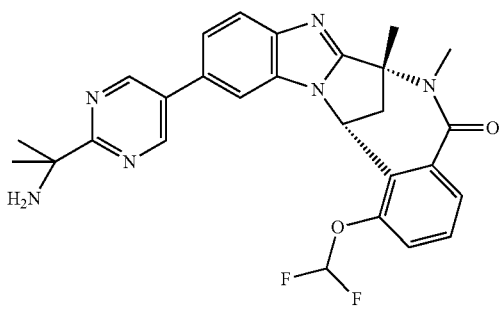 [SMILES: CN1C(=O)c2cccc(OC(F)F)c2[C@H]2C[C@]1(C)c1nc3ccc(-c4cnc(C(C)(C)N)nc4)cc3n12]

(7R,14R)-11-[2-(2-aminopropan-2-yl)pyrimidin-5-yl]-1-(difluoromethoxy)-6,7-dimethyl-6,7-dihydro-7,14-methanobenzimidazo[1,2-b][2,5]benzodiazocin-5(14H)-one To a solution of Intermediate 150 (13 mg, 0.022 mmol) in DMF (0.5 mL), at 0° C., was added sodium hydride (60% mineral oil) (0.88 mg, 0.022 mmol) at 0° C. and stirred at room temperature for 30 minutes. Iodomethane (3 mg, 0.022 mmol) was then added and the reaction mixture was stirred at room temperature overnight. The reaction mixture was purified by reverse phase basic preparative HPLC-MS to yield 7 mg (0.012 mmol, 53%) of a white solid. The intermediate was added to a solution of DCM/trifluoroacetic acid (1:1, 0.25 mL). The reaction mixture was stirred at ambient temperature for 1 hour before addition of a saturated aqueous solution of NaHCO$_3$ (1 mL). The aqueous layer was extracted by DCM (2×2 mL). The combined organic layers were dried over MgSO$_4$, filtered and concentrated in vacuo. The residue was purified by reverse phase basic preparative HPLC-MS, yielding 2.2 mg (38%) of the title compound as a beige solid.

LCMS Method 3 (ES+): RT 1.99 minutes, [M+H]$^+$=505.

Example 104

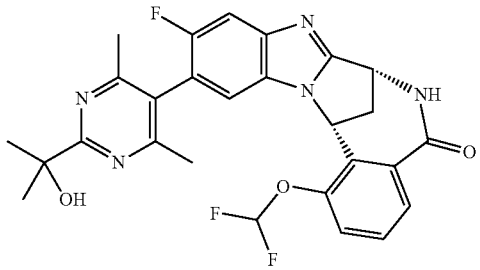 [SMILES: Cc1nc(C(C)(C)O)nc(C)c1-c1cc2c(cc1F)nc1n2[C@@H]2C[C@H]1NC(=O)c1cccc(OC(F)F)c12]

(7R,14R)-1-(difluoromethoxy)-10-fluoro-11-[2-(2-hydroxypropan-2-yl)-4,6-dimethylpyrimidin-5-yl]-6,7-dihydro-7,14-methanobenzimidazo[1,2-b][2,5]benzodiazocin-5(14H)-one Example 1 (25 mg, 0.052 mmol) was dissolved in a 1:1 mixture of TFA/MeCN (0.53 mL) in a 4 mL glass vial. [Ir{dF(CF$_3$)ppy}$_2$(dtbpy)]PF$_6$ (1.175 mg, 0.00105 mmol, Aldrich) and tert-butyl peroxyacetate (41.5 mg, 0.16 mmol, 50% solution in mineral spirits, 3.0 eq., Aldrich) were then added. The mixture was degassed with argon for 5 minutes then irradiated with blue light emitting diodes (460 nm visible light, OSRAM Oslon SSL 80 royal-blue on Star, 1000 mA, ~1 W) until UPLC-MS analysis indicates complete consumption of starting material (12 hours). The solvents were removed by evaporation to give an orange oil. Purification by reverse phase preparative chromatography (acidic mode, gradient from 30% MeCN in 0.1% TFA in water up to 95% MeCN) yielded the title compound as a colorless oil (5.8 mg, 21% yield). LCMS Method 4 (ES+): RT: 2.41 min, [M+H]+=524.2. LCMS Method 3 (ES+): RT: 2.21 min, [M+H]+=524.2. $^1$H NMR (400 MHz, MeOD-d$_4$) δ 8,26 (t, J=4.7 Hz, 1H), 7.52 (d, J=9.9 Hz, 1H), 7.42 (m, 3H), 7,05 (dd, J=73, 6, 72.1 Hz, 1H), 6.43 (d, J=7.1 Hz, 1H), 4.97 (d, J=6.7 Hz, 2H), 3.54 (s, 1H), 3.49 (m, 1H), 2.80 (d, J=13.6 Hz, 1H), 2.37 (s, 3H), 2.17 (s, 3H), 1.59 (s, 6H).

Example 105 and Example 106

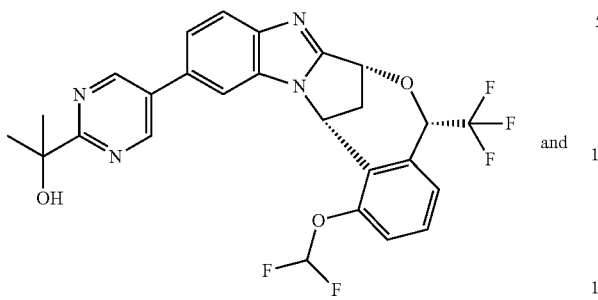

and

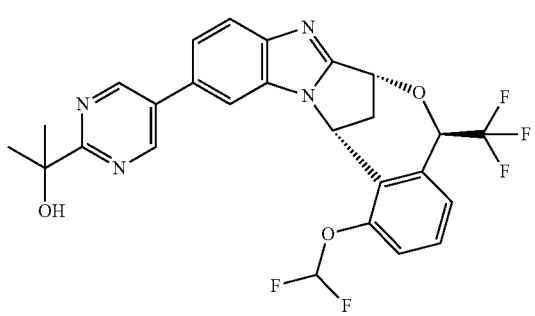

2-{5-[(5R,7R,14R)-1-(difluoromethoxy)-5-(trifluoromethyl)-5,14-dihydro-7H-7,14-methanobenzimidazo[2,1-d][2,5]benzoxazocin-11-yl]pyrimidin-2-yl}propan-2-ol and 2-{5-[(5S,7R,14R)-1-(difluoromethoxy)-5-(trifluoromethyl)-5,14-dihydro-7H-7,14-methanobenzimidazo[2,1-d][2,5]benzoxazocin-11-yl]pyrimidin-2-yl}propan-2-ol Intermediate 155 (50 mg, 0.091 mmol) was dissolved in toluene (1 mL), cyanomethylenetributylphosphorane (100 µL, 0.1 mmol) was added. The slurry was stirred overnight at 100° C. Additional cyanomethylenetributylphosphorane (100 µL, 0.1 mmol) was added and the reaction mixture stirred overnight at 100° C. to complete the reaction. The solvent was evaporated and the crude partitioned into EtOAc (2 mL) and water (1 mL). The aqueous layer was extracted with EtOAc (2×1 mL). The combined organic layers were dried over MgSO$_4$, filtered and concentrated under reduced pressure. The residue was purified by reverse phase basic HPLC-MS followed by reverse phase acid HPLC-MS purification. Each diastereoisomer was taken up in EtOAc (1 mL) and neutralized by a saturated solution of NaHCO$_3$ (1 mL). The aqueous layer was extracted with EtOAc (2×1 mL). The organic layers were dried over MgSO$_4$, filtered and concentrated under reduced pressure to give the following diastereoisomers. 3 mg (6%) of Diastereomer A was isolated as white solid. LCMS Method 3 (ES+): RT 2.39 min., 533 (M+H)+. LCMS Method 4 (ES+): RT 2.54 min., 533 (M+H)+. $^1$H NMR (400 MHz, CDCl$_3$) δ 8.95 (s, 2H), 7.91 (m, 1H), 7.67 (m, 1H), 7.48 (m, 1H), 7.38 (m, 1H), 7.28 (s, 1H), 7.23 (d, J=7.8 Hz, 1H), 6.85 (m, 1H), 6.23 (m, 1H), 5.60 (d, J=4.4 Hz, 1H), 5.49 (m, 1H), 4.70 (m, 1H), 3.20 (m, 1H), 3.00 (m, 1H), 1.66 (s, 6H). 9 mg (19%) of Diastereomer B was isolated as off white solid. LCMS Method 3 (ES+): RT 2.59 min., 533 (M+H)+. LCMS Method 4 (ES+): RT 2.76 min., 533 (M+H)+. $^1$H NMR (400 MHz, CDCl$_3$) δ 8.93 (m, 2H), 8.02 (m, 1H), 7.54 (m, 2H), 7.35 (d, J=5.3 Hz, 2H), 7.29 (m, 1H), 6.79 (m, 1H), 6.40 (m, 1H), 5.71 (m, 1H), 4.68 (m, 1H), 3.84 (m, 1H), 3.12 (m, 1H), 2.78 (m, 1H), 1.65 (s, 6H).

General Procedure for the Late Stage Trifluoromethylation

To a solution of Example 1 (600 mg, 1.211 mmol) in degassed acetonitrile (1 ml) and TFA (1 ml) was added trifluoromethanesulfonyl chloride (65 µL, 0.6045 mmol) followed by [Ir[DF(CF$_3$)PPY]$_2$(DTBPY)]PF$_6$ (4.5 mg, 0.0040 mmol) under argon. The slurry was stirred overnight under blue light emitting diodes (460 nm visible light, OSRAM Oslon SSL 80 royal-blue on Star, 1000 mA, ~1 W). The reaction was performed in 6 vials of 100 mg portions of Example 1. The six crude mixtures were gathered and diluted with EtOAc (10 mL) and washed by a saturated solution of NaHCO$_3$ (2×5 mL). The aqueous layer was back extracted by EtOAc (5 mL). The combined organic layers were dried over MgSO4, filtered and concentrated under reduced. The residue was purified by reverse phase basic LCMS to afford a mixture of the desired isomers as an yellow solid (218 mg, 33% yield).

Example 107

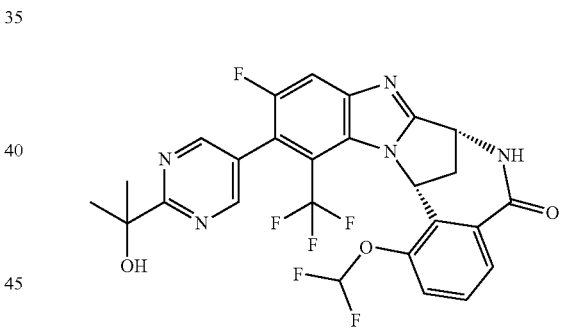

(7R,14R)-1-(difluoromethoxy)-10-fluoro-11-[2-(2-hydroxypropan-2-yl)pyrimidin-5-yl]-12-(trifluoromethyl)-6,7-dihydro-7,14-methanobenzimidazo[1,2-b][2,5]benzodiazocin-5(14H)-one 1.1 mg (0.5%) of the title compound as an off white solid was isolated from the above described mixture of diastereomers by LC-2D MS chromatography in acidic mode (formic acid) Method 14. LCMS Method 15 (ES+) RT 5.82 min., 564 (M+H)+. $^1$H NMR (400 MHz, DMSO-d$_6$) δ 8.99 (d, J=6.2 Hz, 1H), 8.86 (s, 1H), 8.75 (s, 1H), 8.10 (d, J=8.10, 1H) 8.06 (d, J=8.06 Hz, 1H), 7.51 (t, J=7.51 Hz, 1H), 7.44 (d, J=7.44 Hz, 1H), 7.14 (dd, J=73.9, 72.3 Hz, 1H), 6.46 (d, J=7.3 Hz, 1H), 5.14 (s, 1H), 4.92 (t, J=6.3 Hz, 1H), 3.51 (m, 1H), 2.67 (d, J=13.6 Hz, 1H), 1.54 (s, 6H).

Example 108

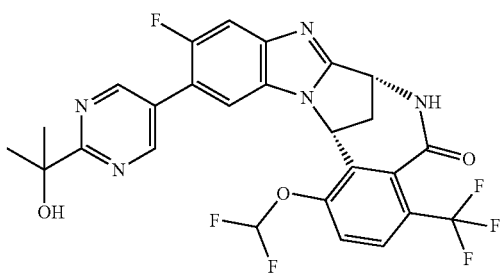 [SMILES: CC(C)(O)c1ncc(-c2cc3c(cc2F)nc2n3[C@@H]3C[C@H]2NC(=O)c2c(C(F)(F)F)ccc(OC(F)F)c23)cn1]

(7R,14R)-1-(difluoromethoxy)-10-fluoro-11-[2-(2-hydroxypropan-2-yl)pyrimidin-5-yl]-4-(trifluoromethyl)-6,7-dihydro-7,14-methanobenzimidazo[1,2-b][2,5]benzodiazocin-5(14H)-one 77.1 mg (35%) of the title compound as an off white solid was isolated from the above described mixture of diastereomers by LC-2D MS chromatography in acidic mode (formic acid) Method 14. LCMS Method 15 (ES+) RT 5.90 min., 564 (M+H)+. $^1$H NMR (400 MHz, DMSO-d$_6$) δ 8.97 (d, J=1.5 Hz, 2H), 8.85 (d, J=5.3 Hz, 1H), 7.90 (m, 1H), 7.71 (m, 2H), 7.54 (m, 2H), 6.29 (d, J=7.2 Hz, 1H), 5.16 (m, 1H), 4.90 (t, J=5.8 Hz, 1H), 3.49 (m, 1H), 2.77 (m, 1H), 1.56 (s, 6H).

Example 109

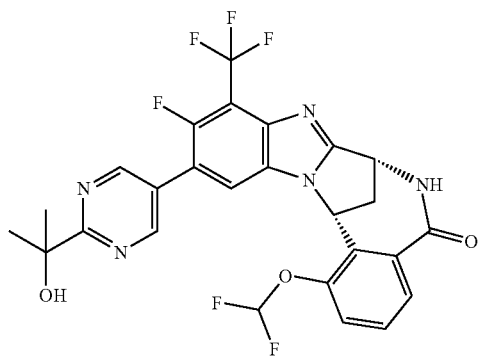 [SMILES: CC(C)(O)c1ncc(-c2cc3c(nc4n3[C@@H]3C[C@H]4NC(=O)c4cccc(OC(F)F)c43)c(C(F)(F)F)c2F)cn1]

(7R,14R)-1-(difluoromethoxy)-10-fluoro-11-[2-(2-hydroxypropan-2-yl)pyrimidin-5-yl]-9-(trifluoromethyl)-6,7-dihydro-7,14-methanobenzimidazo[1,2-b][2,5]benzodiazocin-5(14H)-one 16.6 mg (7.6%) of the title compound as an off white solid was isolated from the above described mixture of diastereomers by LC-2D MS chromatography in acidic mode (formic acid) Method 14. LCMS Method 15 (ES+) RT 5.95 min., 564 (M+H)+. $^1$H NMR (400 MHz, DMSO-d6) δ 9.20 (d, J=6.8 Hz, 1H), 8.99 (m, 2H), 8.25 (m, 1H), 7.81 (m, 1H), 7.52 (m, 3H), 6.42 (m, 1H), 5.23 (m, 1H), 4.99 (m, 1H), 3.53 (d, J=6.7 Hz, 1H), 2.80 (m, 1H), 1.56 (s, 6H).

Example 110

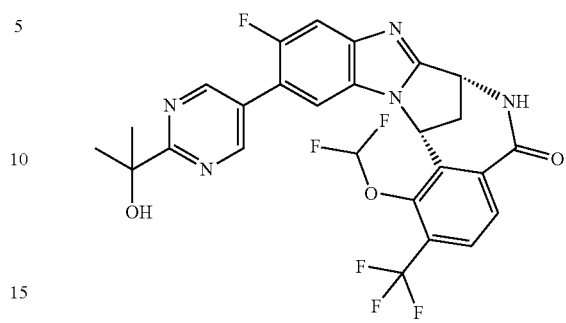

(7R,14R)-1-(difluoromethoxy)-10-fluoro-11-[2-(2-hydroxypropan-2-yl)pyrimidin-5-yl]-2-(trifluoromethyl)-6,7-dihydro-7,14-methanobenzimidazo[1,2-b][2,5]benzodiazocin-5(14H)-one 28.6 mg (13%) of the title compound as an off white solid was isolated from the above described mixture of diastereomers by LC-2D MS chromatography in acidic mode (formic acid) Method 14. LCMS Method 15 (ES+) RT 5.96 min., 564 (M+H)+. $^1$H NMR (400 MHz, DMSO-d6) δ 9.42 (m, 1H), 8.89 (m, 2H), 8.44 (m, 1H), 7.93 (m, 1H), 7.68 (m, 1H), 7.38 (m, 2H), 6.39 (m, 1H), 5.17 (m, 1H), 4.97 (m, 1H), 3.59 (m, 1H), 2.87 (m, 1H), 1.55 (s, 6H).

Example 111

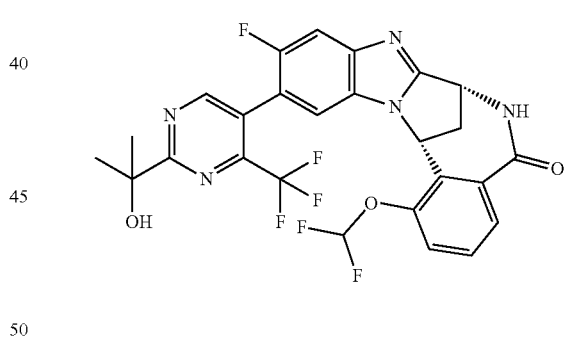

(7R,14R)-1-(difluoromethoxy)-10-fluoro-11-[2-(2-hydroxypropan-2-yl)-4-(trifluoromethyl)pyrimidin-5-yl]-6,7-dihydro-7,14-methanobenzimidazo[1,2-b][2,5]benzodiazocin-5(14H)-one 9.8 mg (5%) of the title compound as an off white solid was isolated from the above described mixture of diastereomers by LC-2D MS chromatography in acidic mode (formic acid) Method 14. LCMS Method 15 (ES+) RT 5.91 min., 564 (M+H)+. $^1$H NMR (400 MHz, DMSO-d6) δ 9.19 (m, 1H), 9.10 (m, 1H), 8.25 (m, 1H), 7.67 (m, 1H), 7.49 (m, 4H), 6.32 (s, 1H), 5.40 (m, 1H), 4.92 (m, 1H), 3.53 (m, 1H), 2.75 (m, 1H), 1.60 (s, 6H)

Example 112

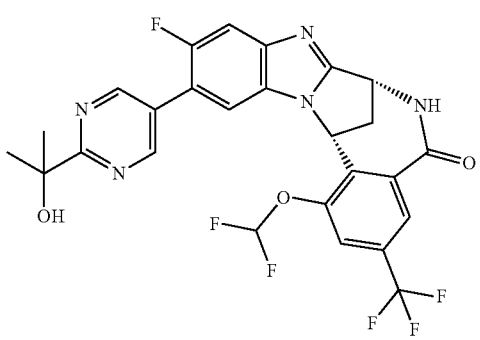 [SMILES: CC(C)(O)c1ncc(-c2cc3c(cc2F)nc2n3[C@@H]3C[C@H]2NC(=O)c2cc(C(F)(F)F)cc(OC(F)F)c23)cn1]

(7R,14R)-1-(difluoromethoxy)-10-fluoro-11-[2-(2-hydroxypropan-2-yl)pyrimidin-5-yl]-3-(trifluoromethyl)-6,7-dihydro-7,14-methanobenzimidazo[1,2-b][2,5]benzodiazocin-5(14H)-one 9.8 mg (5%) of the title compound as an off white solid was isolated from the above described mixture of diastereomers by LC-2D MS chromatography in acidic mode (formic acid) Method 14. LCMS Method 15 (ES+) RT 6.07 min., 564 (M+H)+. $^1$H NMR (400 MHz, DMSO-d6) δ 9.45 (d, J=6.8 Hz, 1H), 8.98 (m, 2H), 8.52 (m, 1H), 7.88 (m, 2H), 7.70 (m, 1H), 7.57 (d, J=6.8 Hz, 1H), 6.42 (m, 1H), 5.17 (m, 1H), 4.97 (m, 1H), 3.52 (m, 1H), 2.86 (m, 1H), 1.56 (s, 6H).

Example 113

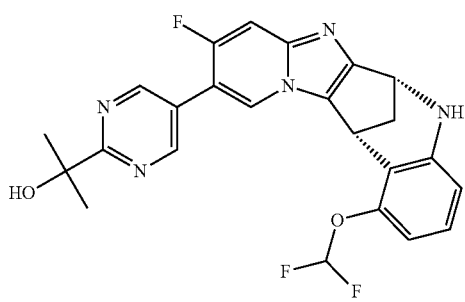 [SMILES: CC(C)(O)c1ncc(-c2cn3c4c(nc3cc2F)[C@H]2C[C@@H]4c3c(cccc3OC(F)F)N2)cn1]

2-{5-[(6R,12R)-11-(difluoromethoxy)-3-fluoro-7,12-dihydro-6H-6,12-methanopyrido[1',2':1,2]imidazo[4,5-c][1]benzazepin-2-yl]pyrimidin-2-yl}propan-2-ol To a solution of Intermediate 157 (69 mg, 0.12 mmol) in THF (3 mL) was added tetrabutylammonium fluoride (0.25 mL, 0.25 mmol) and reaction stirred at room temperature for 1.5 hours. The reaction mixture was concentrated in vacuo and the residue dissolved in EtOAc (30 mL) and the organic phase washed with water (2×30 mL), brine (30 mL), dried (MgSO₄), filtered and concentrated in vacuo. Crude material was purified by column chromatography (SiO₂, 0-20% MeOH in DCM) and further purified by preparative HPLC-MS to give the title compound as a yellow solid (2 mg, 3.6%).

$^1$H NMR (300 MHz, Methanol-d₄) δ 8.97 (s, 2H), 8.38 (d, J=7.1 Hz, 1H), 7.38 (d, J=11.0 Hz, 1H), 6.96 (t, J=74.3 Hz, 1H), 6.88 (t, J=8.2 Hz, 1H), 6.33 (dd, J=13.6, 8.3 Hz, 2H), 4.85-4.72 (m, 2H), 2.97-2.88 (m, 1H), 2.21 (d, J=10.3 Hz, 1H), 1.66 (s, 6H)

LCMS Method 3 (ES+) 468 (M+H)+, RT 1.94 minutes.
LCMS Method 4 (ES+) 468 (M+H)+, RT 1.76 minutes.

Example 114

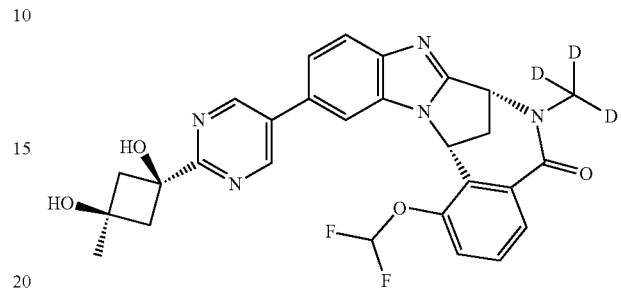

(7R,14R)-1-(difluoromethoxy)-11-[2-(cis-1,3-dihydroxy-3-methylcyclobutyl)pyrimidin-5-yl]-6-trideutero-methyl-6,7-dihydro-7,14-methanobenzimidazo[1,2-b][2,5]benzodiazocin-5(14H)-one To a solution of Intermediate 160 (220 mg, 0.34 mmol) in THF (3 mL) was added tetrabutylammonium fluoride (1 mL, 1.0M in THF) and the reaction stirred for 18 hours. Reaction mixture was diluted with DCM (25 mL) and washed with water (3×25 mL), the aqueous was extracted with DCM (3×25 mL), combined organics washed with brine and dried (by passage through a phase separator cartridge) and concentrated in vacuo. The crude material was purified by column chromatography (SiO₂, gradient elution with DCM/MeOH/0.88 aqueous NH₃: 97.5%:2.25%:0.25% to 87.5%:11.25%:1.25%), to give the title compound (134 mg, 74%) as an off-white solid.

$^1$H NMR (400 MHz, DMSO-d₆) δ 9.08 (s, 2H), 8.28 (dd, J=5.6, 3.8 Hz, 1H), 7.79 (d, J=8.5 Hz, 1H), 7.76 (d, J=1.3 Hz, 1H), 7.69 (t, J=73.6 Hz, 1H), 7.65 (dd, J=8.5, 1.7 Hz, 1H), 7.52-7.48 (m, 2H), 6.32 (d, J=7.1 Hz, 1H), 5.62 (s, 1H), 5.26 (d, J=7.2 Hz, 1H), 4.96 (s, 1H), 3.53 (dt, J=14.2, 7.3 Hz, 1H), 2.95-2.87 (m, 2H), 2.85 (d, J=13.8 Hz, 1H), 2.42 (d, J=13.2 Hz, 2H), 1.09 (s, 3H).

LCMS: Method 3 (ES+) 537 (M+H)+, RT 1.53 minutes.
LCMS: Method 4 (ES+) 537 (M+H)+, RT 1.54 minutes.

Example 115

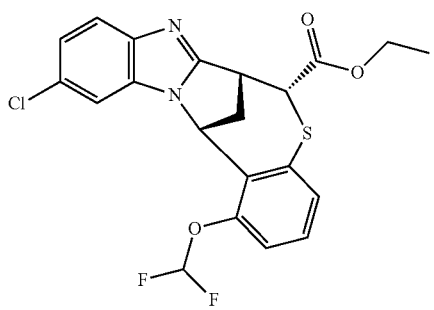 [SMILES: CCOC(=O)[C@@H]1Sc2cccc(OC(F)F)c2[C@H]2C[C@@H]1c1nc3ccc(Cl)cc3n12]

Ethyl (7R,14S)-11-chloro-1-(difluoromethoxy)-6,7-dihydro-14H-7,14-methanobenzimidazo[2,1-d][1,5]benzothiazocine-6-carboxylate To a solution of Intermediate 188 (1.57 g, 2.87 mmol) in THF (30 mL) at 0° C. was added potassium bis(trimethylsilyl)amide (4.4 mL, 4.4 mmol) and reaction stirred at 0° C. for 1 hour. The reaction was quenched with water (50 mL) and extracted with EtOAc (4×100 mL), the combined organics dried (MgSO$_4$), filtered and concentrated in vacuo to give an orange oil. Purification by column chromatography (SiO$_2$, 11-22% EtOAc in DCM) and freeze drying from acetonitrile/water gave the title compound (607 mg, 47%) as an orange solid.

LCMS: Method 3 (ES+) 451 (M+H)$^+$, RT 2.51 minutes.

LCMS: Method 4 (ES+) 451 (M+H)$^+$, RT 2.49 minutes.

Example 118

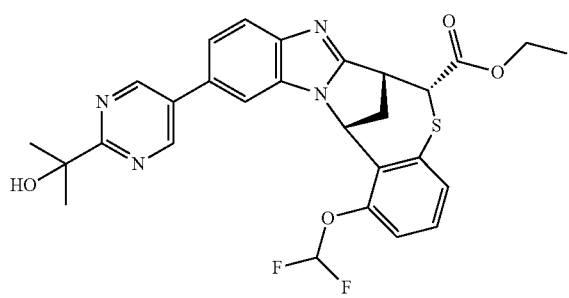 [SMILES: CCOC(=O)[C@@H]1Sc2cccc(OC(F)F)c2[C@H]2C[C@@H]1c1nc3ccc(-c4cnc(C(C)(C)O)nc4)cc3n12]

Ethyl (7R,14S)-1-(difluoromethoxy)-11-[2-(2-hydroxypropan-2-yl)pyrimidin-5-yl]-6,7-dihydro-14H-7,14-methanobenzimidazo[2,1-d][1,5]benzothiazocine-6-carboxylate The title compound was prepared in accordance with the Method described for Example 88 from. Example 115 (200 mg, 0.44 mmol), tris(dibenzylideneacetone)dipalladium(0) (21 mg, 0.022 mmol), tricyclohexylphosphonium tetrafluoroborate (21 mg, 0.055 mmol) and 2-(1-hydroxy-1-methylethyl)pyrimidine-5-boronic acid pinacol ester (190 mg, 0.72 mmol) and K$_3$PO$_4$ (282 mg, 1.33 mmol). The crude material was purified by column chromatography (SiO$_2$, 0-20% MeOH in DCM) and further purified by preparative HPLC to give Example 118 (3 mg, 1.2%) as a white solid.

Example 118—Ethyl (7R,14S)-1-(difluoromethoxy)-11-[2-(2-hydroxypropan-2-yl)pyrimidin-5-yl]-6,7-dihydro-14H-7,14-methanobenzimidazo[2,1-d][1,5]benzothiazocine-6-carboxylate LCMS: Method 3 (ES+) 553 (M+H)$^+$, RT 2.18 minutes LCMS: Method 4 (ES+) 553 (M+H)$^+$, RT 2.18 minutes

Example 119

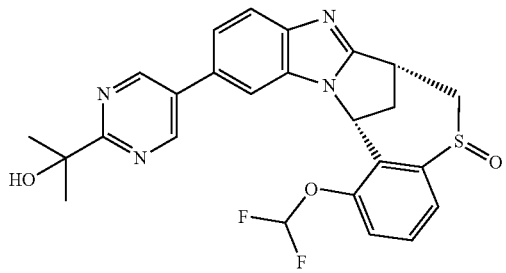 [SMILES: CC(C)(O)c1ncc(-c2ccc3nc4n(c3c2)[C@@H]2C[C@H]4CS(=O)c3cccc(OC(F)F)c32)cn1]

2-{5-[(5R,7R,14R)-1-(difluoromethoxy)-5-oxido-6,7-dihydro-14H-7,14-methanobenzimidazo[2,1-d][1,5]benzothiazocin-11-yl]pyrimidin-2-yl}propan-2-ol The title compound was prepared from Intermediate 163 (45 mg, 0.1 mmol), tris(dibenzylideneacetone)dipalladium (0) (6 mg, 0.0064 mmol), tricyclohexylphosphonium tetrafluoroborate (6 mg, 0.016 mmol) and 2-(1-hydroxy-1-methylethyl)pyrimidine-5-boronic acid pinacol ester (43 mg, 0.16 mmol), K$_3$PO$_4$ (64 mg, 0.30 mmol) dissolved in water (40 µL) and 1,4-dioxane (1 mL) by the method of Example 89. The reaction mixture was diluted with water (15 mL) and DCM (50 mL), acidified to pH 4 using acetic acid, layers separated and the aqueous phase extracted with DCM (4×15 mL). The combined organic phases were dried (phase separator) and concentrated in vacuo. The crude material was then dissolved in DMSO (450 µL) and water (50 µL) and lithium chloride (20 mg, 0.47 mmol) added and the reaction mixture heated at 130° C. in a sealed microwave vial for 1.5 hours. The material was purified by preparative HPLC to give the title compound (9 mg, 19%) as a white solid. $^1$H NMR (300 MHz, DMSO-d$_6$) δ 9.03 (s, 2H), 7.82 (d, J=8.5 Hz, 1H), 7.71-7.65 (m, 1H), 7.65-7.58 (m, 2H), 7.57-7.51 (m, 2H), 7.48 (t, J=73.2 Hz, 1H), 6.21 (d, J=8.3 Hz, 1H), 5.07 (s, 1H), 4.01 (t, J=6.7 Hz, 1H), 3.96-3.86 (m, 1H), 3.78 (d, J=12.3 Hz, 1H), 3.41-3.30 (m, 1H), 2.51 (d, J=1.8 Hz, 1H), 1.51 (s, 6H). LCMS: Method 3 (ES+) 497 (M+H)$^+$, RT 1.63 minutes.

LCMS: Method 4 (ES+) 497 (M+H)$^+$, RT 1.60 minutes

Example 120

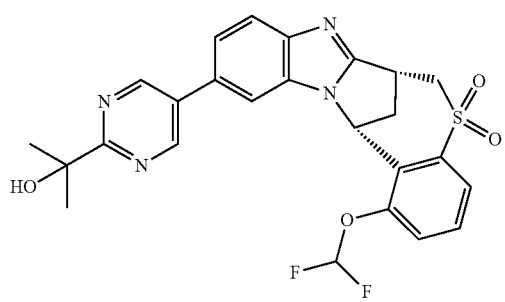 [SMILES: CC(C)(O)c1ncc(-c2ccc3nc4n(c3c2)[C@@H]2C[C@H]4CS(=O)(=O)c3cccc(OC(F)F)c32)cn1]

2-{5-[(7R,14R)-1-(difluoromethoxy)-5,5-dioxido-6,7-dihydro-14H-7,14-methanobenzimidazo[2,1-d][1,5]benzothiazocin-11-yl]pyrimidin-2-yl}propan-2-ol The title compound can be prepared from Intermediate 162, and 2-(1-hydroxy-1-methylethyl)pyrimidine-5-boronic acid pinacol ester by the Method of Example 89 to provide, after purification by column chromatography (SiO$_2$, 80-100% EtOAc in DCM, followed by 0-10% MeOH in EtOAc), the title compound as a white solid.

Note: The ester is observed to decarboxylate during the reaction conditions to provide the desired product. If decarboxylation is not complete it can be further enabled by hydrolysis of the ester to the carboxylic acid followed by acid catalysed decarboxylation. $^1$H NMR (300 MHz, DMSO-d$_6$) δ 9.05 (s, 2H), 7.94 (dd, J=6.6, 2.5 Hz, 1H), 7.72 (q, J=8.5 Hz, 2H), 7.63 (t, J=72 Hz, 1H), 7.59 (dd, J=8.4, 1.8 Hz, 1H), 7.51 (d, J=1.2 Hz, 2H), 6.34 (d, J=8.5 Hz, 1H), 5.09 (s, 1H), 4.37 (dd, J=14.6, 2.0 Hz, 1H), 4.18-3.95 (m, 2H), 3.56-3.43 (m, 1H), 2.77 (d, J=13.2 Hz, 1H), 1.53 (s, 6H). LCMS: Method 3 (ES+) 513 (M+H)$^+$, RT 1.65 minutes. LCMS: Method 4 (ES+) 513 (M+H)$^+$, RT 1.62 minutes Example 121

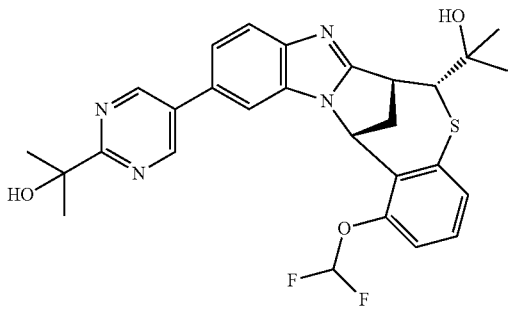 [SMILES: CC(C)(O)c1ncc(-c2ccc3nc4n(c3c2)[C@@H]2C[C@@H]4[C@H](C(C)(C)O)Sc3cccc(OC(F)F)c32)cn1]

2-{5-[(6R,7R,14S)-1-(difluoromethoxy)-6-(2-hydroxypropan-2-yl)-6,7-dihydro-14H-7,14-methanobenzimidazo[2,1-d][1,5]benzothiazocin-11-yl]pyrimidin-2-yl}propan-2-ol The title compound was prepared from Intermediate 164 (27 mg, 0.062 mmol), tris(dibenzylideneacetone)dipalladium(0) (3 mg, 0.0032 mmol), tricyclohexylphosphonium tetrafluoroborate (2.8 mg, 0.007 mmol) and 2-(1-hydroxy-1-methylethyl)pyrimidine-5-boronic acid pinacol ester (27 mg, 0.10 mmol), K$_3$PO$_4$ (40 mg, 0.19 mmol) suspended in a mixture of water (40 μL) and 1,4-dioxane (220 μL) in accordance with the method of Example 89. The reaction mixture was partitioned between DCM (10 mL) and saturated aqueous sodium bicarbonate solution (10 mL), layers separated and the aqueous phase extracted with DCM (3×10 mL). The combined organic phases were dried (phase separator) and concentrated in vacuo. The crude material was purified by preparative HPLC-MS to give the title compound (2 mg, 6%) as an off-white solid.

$^1$H NMR (300 MHz, Methanol-d$_4$) δ 8.96 (s, 2H), 7.80 (d, J=8.5 Hz, 1H), 7.56 (dd, J=8.4, 1.7 Hz, 1H), 7.37 (dd, J=8.9, 1.8 Hz, 2H), 7.32-7.22 (m, 2H), 7.15 (t, J=73.0 Hz, 1H), 6.40 (d, J=8.3 Hz, 1H), 4.36 (d, J=7.4 Hz, 1H), 3.60 (s, 1H), 3.51 (dt, J=12.4, 7.8 Hz, 1H), 3.32 (m, 1H), 2.32 (d, J=12.9 Hz, 1H), 1.62 (s, 6H), 1.52 (s, 3H), 1.50 (s, 3H).

LCMS: Method 3 (ES+) 539 (M+H)$^+$, RT 2.07 minutes.
LCMS: Method 4 (ES+) 539 (M+H)$^+$, RT 1.99 minutes.

Example 122

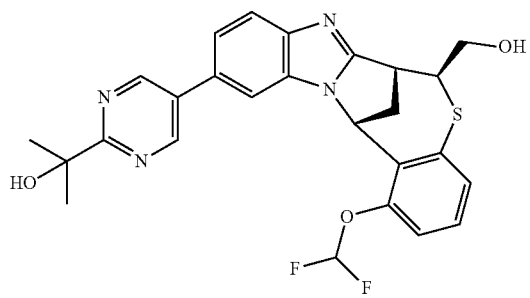 [SMILES: CC(C)(O)c1ncc(-c2ccc3nc4n(c3c2)[C@@H]2C[C@@H]4[C@@H](CO)Sc3cccc(OC(F)F)c32)cn1]

2-{5-[(6S,7R,14S)-1-(difluoromethoxy)-6-(hydroxymethyl)-6,7-dihydro-14H-7,14-methanobenzimidazo[2,1-d][1,5]benzothiazocin-11-yl]pyrimidin-2-yl}propan-2-ol Example 123

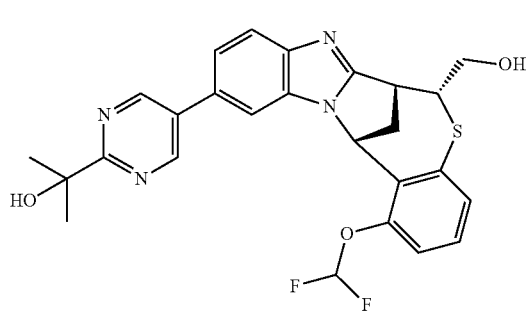 [SMILES: CC(C)(O)c1ncc(-c2ccc3nc4n(c3c2)[C@@H]2C[C@@H]4[C@H](CO)Sc3cccc(OC(F)F)c32)cn1]

2-{5-[(6R,7R,14S)-1-(difluoromethoxy)-6-(hydroxymethyl)-6,7-dihydro-14H-7,14-methanobenzimidazo[2,1-d][1,5]benzothiazocin-11-yl]pyrimidin-2-yl}propan-2-ol Intermediate 165 (30 mg, 0.07 mmol), 2-(1-hydroxy-1-methylethyl)pyrimidine-5-boronic acid pinacol ester (33 mg, 0.12 mmol), tris(dibenzylideneacetone)dipalladium(0) (4 mg, 0.01 mmol), tricyclohexylphosphonium tetrafluoroborate (4 mg, 0.01 mmol) and 1,4-dioxane (0.25 mL) were added to a microwave tube, degassed, then K$_3$PO$_4$ (50 mg, 0.23 mmol) dissolved in water (40 μL) was added the mixture deagassed and then heated at 130° C. under nitrogen in the microwave for 2 hours. The reaction mixture was partitioned between water (10 mL) and DCM (10 mL), the layers separated and the aqueous phase extracted with DCM (3×10 mL). The combined organics phases were dried (phase separator) and concentrated in vacuo. Purification by column chromatography (SiO$_2$, 50-100% EtOAc in hexane, followed by 0-20% MeOH in EtOAc) gave Example 122 (7 mg, 19%) as a white solid and Example 123 (3 mg, 8%) as a white solid.

Example 122: 2-{5-[(6S,7R,14S)-1-(difluoromethoxy)-6-(hydroxymethyl)-6,7-dihydro-14H-7,14-methanobenzimidazo[2,1-d][1,5]benzothiazocin-11-yl]pyrimidin-2-yl}propan-2-ol $^1$H NMR (300 MHz, DMSO-d$_6$) δ 9.00 (s, 2H), 7.77 (d, J=8.4 Hz, 1H), 7.58 (dd, J=8.4, 1.8 Hz, 1H), 7.50 (t, J=73.6

Hz, 1H), 7.40 (d, J=1.3 Hz, 1H), 7.27-7.19 (m, 3H), 6.23 (d, J=8.5 Hz, 1H), 5.29-5.22 (m, 1H), 5.07 (s, 1H), 4.01 (dd, J=7.6, 4.6 Hz, 1H), 3.81 (d, J=5.3 Hz, 1H), 3.66-3.54 (m, 1H), 3.45 (dt, J=9.7, 5.4 Hz, 1H), 3.26-3.13 (m, 1H), 2.53 (d, J=9.6 Hz, 1H), 1.52 (s, 6H).

LCMS: Method 3 (ES+) 511 (M+H)+, RT 1.81 minutes.

LCMS: Method 4 (ES+) 511 (M+H)+, RT 1.75 minutes.

Example 123. 2-{5-[(6R,7R,14S)-1-(difluoromethoxy)-6-(hydroxymethyl)-6,7-dihydro-14H-7,14-methanobenzimidazo[2,1-d][1,5]benzothiazocin-11-yl]pyrimidin-2-yl}propan-2-ol 1H NMR (300 MHz, DMSO-d6) δ 8.99 (s, 2H), 7.77 (d, J=8.4 Hz, 1H), 7.57 (dd, J=8.4, 1.8 Hz, 1H), 7.50 (t, J=73.5 Hz, 1H) 7.38 (s, 1H), 7.26 (d, J=4.2 Hz, 3H), 6.26 (d, J=8.5 Hz, 1H), 5.34 (s, 1H), 5.07 (s, 1H), 4.01 (d, J=6.5 Hz, 1H), 3.95-3.86 (m, 1H), 3.87-3.71 (m, 1H), 3.66-3.51 (m, 1H), 3.53-3.39 (m, 1H), 2.35 (d, J=13.2 Hz, 1H), 1.52 (s, 6H).

LCMS: Method 3 (ES+) 511 (M+H)+, RT 1.84 minutes.

LCMS: Method 4 (ES+) 511 (M+H)+, RT 1.77 minutes.

Example 124

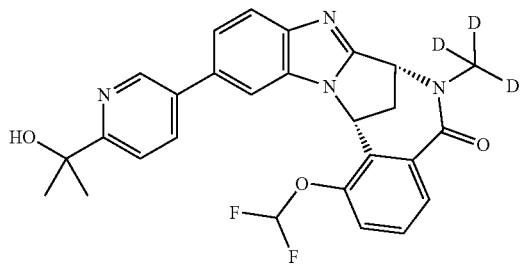 [SMILES: [2H]C([2H])([2H])N1C(=O)c2cccc(OC(F)F)c2[C@H]2C[C@@H]1c1nc3ccc(-c4ccc(C(C)(C)O)nc4)cc3n12]

(7R,14R)-1-(difluoromethoxy)-11-[6-(2-hydroxypropan-2-yl)pyridin-3-yl]-6-trideuteromethyl-6,7-dihydro-7,14-methanobenzimidazo[1,2-b][2,5]benzodiazocin-5(14H)-one Intermediate 166 (750 mg, 1.37 mmol) was dissolved in anhydrous tetrahydrofuran (20 mL) and cooled to −78° C. under nitrogen. Potassium bis(trimethylsilyl)amide (1.50 mL, 1.50 mmol, 1 mol/L) was added drop wise at −78° C. and stirred for 30 minutes before the addition of iodotrideuteromethane (0.13 mL, 2.1 mmol). The reaction mixture was stirred for 2 hours with warming to room temperature. 2M HCl (aq) (10 mL) was added and the mixture stirred for 2 hours to remove the trimethylsilyl protecting group. The mixture was treated with 2M NaOH (15 mL) and extracted with EtOAc (50 mL). The organic layer was dried (sodium sulfate), filtered and concentrated in vacuo. Purification by chromatography (silica, 0 to 10% MeOH in dichloromethane) gave the title compound as a white solid after drying under vacuum (500 mg, 74% yield). 1H NMR (300 MHz, DMSO-d6) δ 8.74 (dd, J=2.4, 0.8 Hz, 1H), 8.34-8.20 (m, 1H), 7.99 (dd, J=8.3, 2.4 Hz, 1H), 7.80-7.68 (m, 3H), 7.67 (t, 1H, J$_{H-F}$ 75 Hz), 7.60-7.46 (m, 3H), 6.29 (d, J=7.0 Hz, 1H), 5.24 (d, J=6.9 Hz, 2H), 3.52 (dt, J=14.1, 7.2 Hz, 1H), 2.83 (d, J=13.8 Hz, 1H), 1.48 (s, 6H). LC/MS Method 3: RT 1.77 minutes, m/z 494.

Example 125

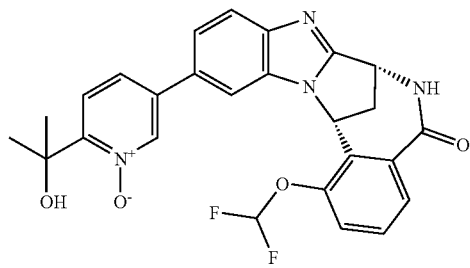 [SMILES: CC(C)(O)c1ccc(-c2ccc3nc4n(c3c2)[C@@H]2C[C@H]4NC(=O)c3cccc(OC(F)F)c32)c[n+]1[O-]]

(7R,14R)-1-(difluoromethoxy)-11-[6-(2-hydroxypropan-2-yl)-1-oxidopyridin-3-yl]-6,7-dihydro-7,14-methanobenzimidazo[1,2-b][2,5]benzodiazocin-5(14)-one Intermediate 166 (240 mg, 0.437 mmol) was dissolved in THF (20 mL) and 2 mL of 2M aqueous HCl added and the mixture was stirred at room temperature for 30 minutes. LCMS shows complete removal of TMS group. The mixture was partitioned between DCM and saturated aqueous sodium carbonate solution and concentrated in vacuo. The residue was redissolved in DCM (10 mL) and mCPBA (103 mg, 0.46 mmol) was added and the mixture stirred for 2 hours. The reaction was washed with 2M sodium hydroxide (10 mL) and the organic layer concentrated in vacuo. The residual solid was purified by chromatography (silica 10 g, 0 to 15% MeOH in DCM gradient) to give the title compound as an off-white solid, (100 mg, 46% yield). 1H NMR (300 MHz, DMSO-d6) δ 9.14 (d, J=6.8 Hz, 1H), 8.54 (t, J=1.1 Hz, 1H), 8.23 (dd, J=6.1, 3.3 Hz, 1H), 7.77-7.68 (m, 4H), 7.66 (t, 1H, J$_{H-F}$ 73.5 Hz) 7.56-7.45 (m, 2H), 7.00 (s, 1H), 6.36 (d, J=7.1 Hz, 1H), 4.89 (m, 1H) 3.49 (dt, J=13.7, 7.0 Hz, 1H), 2.75 (d, J=13.3 Hz, 1H), 1.61 (s, 6H). LC/MS Method 3: RT 1.57 minutes, m/z 493.

Example 126

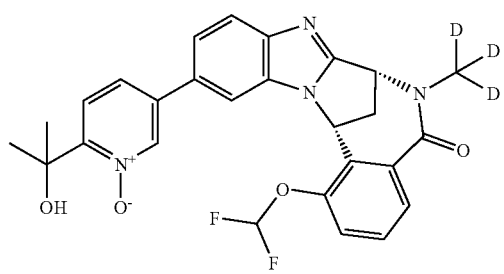 [SMILES: [2H]C([2H])([2H])N1C(=O)c2cccc(OC(F)F)c2[C@H]2C[C@@H]1c1nc3ccc(-c4ccc(C(C)(C)O)[n+]([O-])c4)cc3n12]

(7R,14R)-1-(difluoromethoxy)-11-[6-(2-hydroxypropan-2-yl)-1-oxidopyridin-3-yl]-6-trideuteromethyl-6,7-dihydro-7,14-methanobenzimidazo[1,2-b][2,5]benzodiazocin-5(14H)-one Example 124 (276 mg, 0.56 mmol) was dissolved in dichloromethane (15 mL) and 3-chloroperoxybenzoic acid (1.05 equiv., 0.59 mmol, 77%) was added and the mixture was stirred for 18 hours at room temperature. The mixture was then diluted with dichloromethane (50 mL), washed with saturated aqueous sodium bicarbonate solution (50 mL), and concentrated in vacuo. The residue was purified by chromatography (silica, 0 to 15% methanol gradient in dichloromethane). The product fractions were concentrated in vacuo and the residues freeze dried from acetonitrile/water to give the title compound as a white solid, (165 mg, 58% yield). $^1$H NMR (300 MHz, DMSO-d$_6$) δ 8.54 (t, J=1.1 Hz, 1H), 8.34-8.18 (m, 1H), 7.97-7.34 (m, 8H), 6.99 (s, 1H), 6.30 (d, J=7.1 Hz, 1H), 5.25 (d, J=7.1 Hz, 1H), 3.52 (dt, J=14.2, 7.3 Hz, 1H), 2.83 (d, J=13.8 Hz, 1H), 1.61 (s, 6H). LC/MS Method 3: RT 1.67 minutes, m/z 510.

Example 127

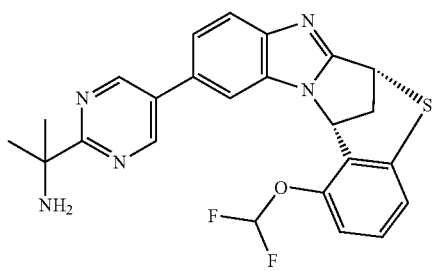 [SMILES: CC(C)(N)c1ncc(-c2ccc3nc4n(c3c2)[C@@H]2C[C@H]4Sc3cccc(OC(F)F)c32)cn1]

2-{5-[(6R,12R)-11-(difluoromethoxy)-6H,12H-6,12-methanobenzimidazo[2,1-c][1,4]benzothiazepin-2-yl]pyrimidin-2-yl}propan-2-amine, dihydrochloride salt Intermediate 114 (300 mg, 0.95 mmol), 1,1′-bis(diphenylphosphino)ferrocene-palladium(II)dichloride dichloromethane complex (0.05 equiv., 0.0474 mmol), potassium acetate (4 equiv., 3.80 mmol) and bis(pinacolato)diboron (292 mg, 1.14 mmol) were dissolved in dry dioxane (10 ml) and the mixture heated to reflux for 2 hours. The mixture was partitioned between dichloromethane and water and the organic layer was concentrated in vacuo to give the crude boronate. The intermediate was dissolved in 1,4-dioxane (2.5 ml) and added to a microwave tube containing Example 88 (300 mg, 0.822 mmol), tris(dibenzylideneacetone)-dipalladium(0) (39 mg, 0.041 mmol), tricyclohexylphosphonium tetrafluoroborate (38 mg, 0.1 mmol) and a solution of potassium phosphate (523 mg, 2.47 mmol) in water (0.5 ml). The mixture was degassed and refilled with nitrogen twice then heated to 140° C. in the microwave for 2 hours. After cooling the mixture was partitioned between dichloromethane (50 mL) and water (50 mL) and the organic layer dried (MgSO$_4$), filtered and concentrated in vacuo. The residue was purified by chromatography (silica, 0 to 100% EtOAc gradient in DCM) to give the BOC protected amine of the title compound as a pale brown solid. The solid was dissolved in 1,4-dioxane (2 mL) and 4.0M HCl in 1,4-dioxane (10 mL) added and the mixture stirred for 2 hours. The solvent was removed in vacuo and the residue partitioned between DCM and water. The aqueous layer was washed with DCM (5 mL) and the aqueous phase was freeze dried to give the title compound as an off-white solid, (330 mg, 75% yield). $^1$H NMR (300 MHz, DMSO-d$_6$) δ 9.20 (s, 2H), 8.89-8.54 (br m, 3H, R—NH$_3$+), 7.95-7.66 (m, 3H), 7.58 (dt, J$_{H-F}$=75 Hz, 1.8 Hz, 1H), 7.39-7.21 (m, 1H), 6.98 (dd, J=8.1, 2.6 Hz, 2H), 6.14 (d, J=5.2 Hz, 1H), 5.11 (d, J=5.0 Hz, 1H), 3.55-3.43 (m, 1H), 2.73 (d, J=12.3 Hz, 1H), 1.71 (s, 6H). LC/MS Method 3: RT 1.62 minutes, m/z 466.

Example 128

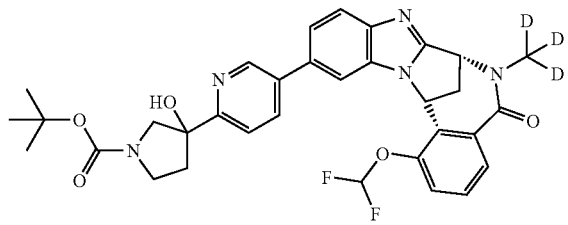

tert-Butyl 3-{5-[(7R,14R)-1-(difluoromethoxy)-6-trideuteromethyl-5-oxo-5,6,7,14-tetrahydro-7,14-methanobenzimidazo[1,2-b][2,5]benzodiazocin-11-yl]pyridin-2-yl}-3-hydroxypyrrolidine-1-carboxylate To a mixture of Intermediate 159 (200 mg, 0.41 mmol), tris(dibenzylideneacetone) dipalladium(0) (19 mg, 0.021 mmol), tricyclohexylphosphonium tetrafluoroborate (16 mg, 0.041 mmol) and Intermediate 167 (170 mg, 0.50 mmol) in 1,4-dioxane (1.5 mL) was added a solution of potassium phosphate tribasic (271 mg, 1.24 mmol) in water (0.15 mL). The reaction mixture was heated at 110° C. in the microwave for 3 hours. cooled, partitioned between EtOAc (100 mL) and water (100 mL) and the organic layer dried (sodium sulphate), filtered and concentrated in vacuo. The residue was purified by chromatography (silica, 100% EtOAc then to 7% MeOH in EtOAc gradient) to give the title compound as a white solid (128 mg, 50% yield). $^1$H NMR (300 MHz, DMSO-d$_6$) δ 8.79 (s, 1H), 8.27 (dd, J=5.8, 3.6 Hz, 1H), 8.05 (dd, J=8.2, 2.4 Hz, 1H), 7.85-7.68 (m, 3H), 7.67 (t, J$_{H-F}$=73.4 Hz, 1H), 7.60-7.45 (m, 3H), 6.30 (d, J=7.0 Hz, 1H), 5.71 (s, 1H), 5.24 (d, J=7.1 Hz, 1H), 3.72 (t, J=10.6 Hz, 1H), 3.64-3.38 (m, 2H), 2.83 (d, J=13.7 Hz, 1H), 1.76 (s, 2H), 1.40 (9H, s), 1.33-1.06 (m, 2H). LC/MS Method 3: RT 2.18 minutes, m/z 621.

Example 129

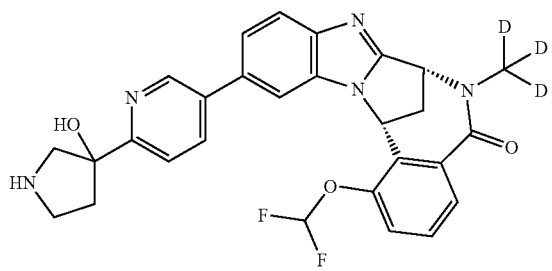 [SMILES: [2H]C([2H])([2H])N1C(=O)c2cccc(OC(F)F)c2[C@H]2C[C@@H]1c1nc3ccc(-c4ccc(C5(O)CCNC5)nc4)cc3n12]

(7R,14R)-1-(difluoromethoxy)-1-[6-(3-hydroxypyrrolidin-3-yl)pyridin-3-yl]-6-trideuteromethyl-6,7-dihydro-7,14-methanobenzimidazo[1,2-b][2,5]benzodiazocin-5(14H)-one, dihydrochloride salt Example 128 (120 mg, 0.193 mmol) was dissolved in 1,4-dioxane (5 mL) and 4M HCl in 1,4-dioxane (5 mL)

added and the mixture stirred at room temperature for 1 hour. After removing the solvent in vacuo the residue was treated with diethyl ether (5 mL) and isohexanes (5 mL). The resultant solid was filtered off, washed with diethyl ether (10 mL) and dried under high vacuum for 1 hour to give the title compound as an off-white solid (88 mg, 72%). $^1$H NMR (300 MHz, DMSO-d$_6$) δ 9.56 (s, 1H), 9.41 (s, 1H), 8.88-8.76 (m, 1H), 8.28 (dd, J=6.0, 3.4 Hz, 1H), 8.21-8.04 (m, 1H), 7.98-7.32 (m, 4H), 7.68 (t, J$_{H-F}$=73.5 Hz, 1H) 6.34 (d, J=7.0 Hz, 1H), 5.31 (d, J=7.1 Hz, 1H), 3.76-3.27 (m, 4H), 2.87 (d, J=13.8 Hz, 1H), 2.40 (t, J=11.1 Hz, 1H), 2.28-2.22 (m, 1H), 1.89-1.83 (m, 1H). LC/MS Method 3: RT 1.32 minutes, m/z 521.

Example 130

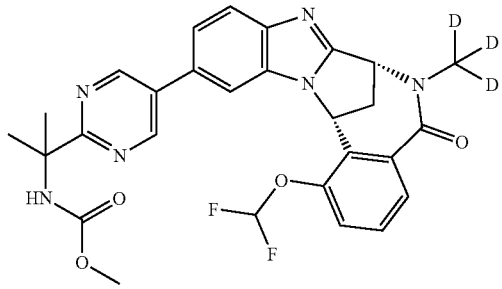 [SMILES: [2H]C([2H])([2H])N1C(=O)c2cccc(OC(F)F)c2[C@H]2C[C@@H]1c1nc3ccc(-c4cnc(C(C)(C)NC(=O)OC)nc4)cc3n12]

Methyl (2-{5-[(7R,14R)-1-(difluoromethoxy)-6-trideuteromethyl-5-oxo-5,6,7,14-tetrahydro-7,14-methanobenzimidazo[1,2-b][2,5]benzodiazocin-11-yl]pyrimidin-2-yl}propan-2-yl)carbamate Intermediate 168 (226 mg, 0.826 mmol) and Intermediate 159 (200 mg, 0.4130 mmol) were coupled in accordance with the method of Example 128. Purification by chromatography (silica, 0 to 10% MeOH in DCM) and freeze drying of the residue gave the title compound as a white solid (197 mg, 87% yield). $^1$H NMR (300 MHz, DMSO-d$_6$) δ 9.01 (s, 2H), 8.37-8.19 (m, 1H), 7.81-7.71 (m, 2H), 7.68 (dd, J$_{H-F}$=72.6, 73.8 Hz, 1H), 7.62 (dd, J=8.5, 1.8 Hz, 1H), 7.58 (s, 1H), 7.49 (d, J=4.9 Hz, 2H), 6.31 (d, J=7.1 Hz, 1H), 5.25 (d, J=7.1 Hz, 1H), 3.56-3.47 (m, 1H), 3.44 (s, 3H), 2.84 (d, J=13.8 Hz, 1H), 1.61 (s, 6H). LC/MS Method 3: RT 1.95 minutes, m/z 552.

Example 131

(7R,14R)-1-(difluoromethoxy)-11-[2-(2-hydroxypropan-2-yl)-4-methylpyrimidin-5-yl]-6-trideuteromethyl-6,7-dihydro-7,14-methanobenzimidazo[1,2-b][2,5]benzodiazocin-5(14H)-one The title compound was synthesised from Intermediate 110 (400 mg, 1.018 mmol) and Intermediate 62 (1.2 equivalents) in accordance with the Method described for Example 128. Purification by column chromatography (silica, DCM/EtOAc gradient) gave the desired product as a white solid.
$^1$H NMR (300 MHz, DMSO-d6) δ 8.59 (s, 1H), 8.28 (dt, J=8.3, 4.2 Hz, 1H), 7.86-7.24 (m, 6H), 6.27 (d, J=7.1 Hz, 1H), 5.25 (d, J=7.1 Hz, 1H), 5.06 (s, 1H), 3.61-3.40 (m, 1H), 2.83 (d, J=13.8 Hz, 1H), 2.45 (s, 3H), 1.53 (s, 6H). LC/MS: Method 3 ESI MH$^+$ 509, retention time 1.85 minutes.

Example 132

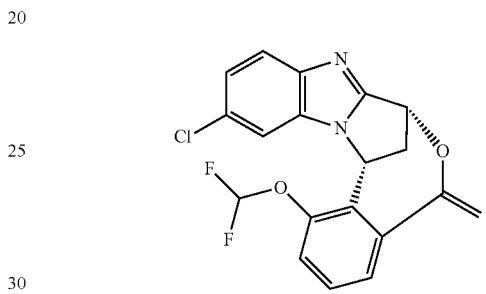

(7R,14R)-11-chloro-1-(difluoromethoxy)-5-methylidene-5,14-dihydro-7H-7,14-methanobenzimidazo[2,1-d][2,5]benzoxazocine Intermediate 169 (37.0 mg, 0.08 mmol) was dissolved in THF (2 mL), and sodium hydride (20.0 mg, 0.83 mmol) was added at 0° C. and the mixture was stirred for 1 hour. Water was added to quench the reaction and the mixture was partitioned between water and DCM (2×10 mL). The organics were combined, dried (MgSO$_4$), filtered and concentrated in vacuo. The crude product was purified by preparative HPLC-MS to give the O-alkylated product (3.5 mg, 12%).
$^1$H NMR (300 MHz, DMSO-d6) δ 7.78-7.65 (m, 2H), 7.53-7.14 (m, 5H), 6.19 (d, J=7.1 Hz, 1H), 5.68 (d, J=4.1 Hz, 1H), 4.73 (dd, J=13.8, 0.9 Hz, 2H), 3.27-3.13 (m, 1H), 2.79 (d, J=13.7 Hz, 1H). LC/MS: Method 3 ESI MH$^+$ 375, retention time 2.36 minutes.

Example 133

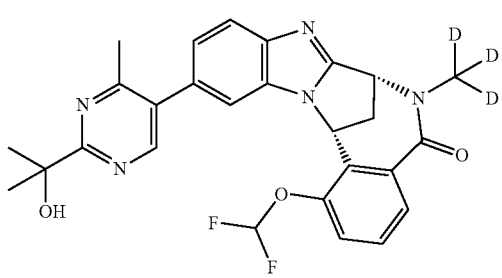 [SMILES: [2H]C([2H])([2H])N1C(=O)c2cccc(OC(F)F)c2[C@H]2C[C@@H]1c1nc3ccc(-c4cnc(C(C)(C)O)nc4C)cc3n12]

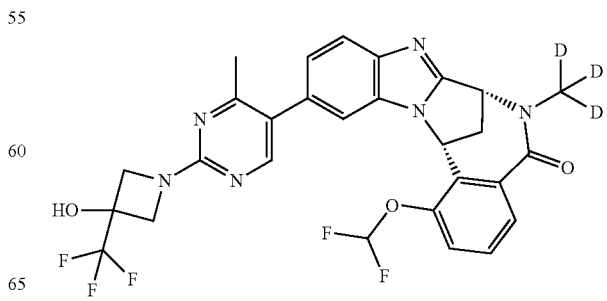

(7R,14R)-1-(difluoromethoxy)-11-{2-[3-hydroxy-3-(trifluoromethyl)azetidin-1-yl]-4-methyl pyrimidin-5-yl}-6-trideutero-methyl-6,7-dihydro-7,14-methanobenzimidazo[1,2-b][2,5]benzodiazocin-5(14H)-one A mixture of Intermediate 133 (600 mg, 0.84 mmol), Intermediate 110 (314 mg, 0.80 mmol), K₃PO₄ (594 mg, 2.80 mmol), tricyclohexylphosphonium tetrafluoroborate (37 mg, 0.1 mmol) and tris(dibenzylideneacetone)dipalladium(0) (90 mg, 0.1 mmol) were suspended in a mixture of 1,4-dioxane (5 mL) and water (0.4 mL). The mixture was degassed and purged with N₂ before heating in a microwave at 140° C. for 2 hours. The reaction mixture was quenched with water and extracted with EtOAc (3×10 mL). The combined organic phases were dried with Na₂SO₄, filtered and concentrated in vacuo. The crude product was purified by column chromatography (0-10% MeOH in DCM) to give the title compound (200 mg, 42%). ¹H NMR (400 MHz, DMSO-d6) δ 8.28 (dd, J=7.5, 2.0 Hz, 1H), 8.21 (s, 1H), 7.80-7.31 (m, 6H), 7.20 (dd, J=8.4, 1.7 Hz, 1H), 6.25 (d, J=7.1 Hz, 1H), 5.24 (d, J=7.1 Hz, 1H), 4.31 (d, J=10.1 Hz, 2H), 4.09 (d, J=10.1 Hz, 2H), 3.52 (dt, J=14.1, 7.3 Hz, 1H), 2.82 (d, J=13.7 Hz, 1H), 2.29 (s, 3H).

LC/MS: Method 3 ESI MH⁺ 590, retention time 1.97 minutes.

Example 134

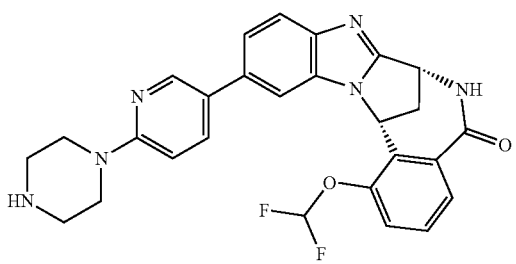 [SMILES: O=C1N[C@@H]2C[C@H](c3c(OC(F)F)cccc31)n1c2nc2ccc(-c3ccc(N4CCNCC4)nc3)cc21]

(7R,14R)-1-(difluoromethoxy)-11-[6-(piperazin-1-yl)pyridin-3-yl]-6,7-dihydro-7,14-methanobenzimidazo[1,2-b][2,5]benzodiazocin-5(14H)-one A mixture of 1-[5-(4,4,5,5-tetramethyl-1,3,2-dioxaborolan-2-yl)-2-pyridyl]piperazine (277 mg, 0.96 mmol), Example 11 (300 mg, 0.79 mmol), K₃PO₄ (600 mg, 2.83 mmol), tricyclohexylphosphonium tetrafluoroborate (37 mg, 0.1 mmol) were suspended in a mixture of 1,4-dioxane (3 mL) and water (0.3 mL). The mixture was degassed and purged with N₂ before the addition of tris(dibenzylideneacetone) dipalladium(0) (75 mg, 0.08 mmol). The mixture was degassed for 10 minutes before heating in a microwave at 105° C. for 1 hour. The reaction mixture was quenched with water and extracted with EtOAc (3×10 mL). The aqueous phase was basified with saturated aqueous NaHCO₃ solution and extracted with DCM (3×10 mL). The organics were combined, dried with Na₂SO₄, filtered and concentrated in vacuo. The crude product was purified by column chromatography (0-30% MeOH in DCM) to give the title compound (57 mg, 14%). The HCl salt was prepared by addition of 2 equivalents of HCl followed by freeze-drying. ¹H NMR (300 MHz, Deuterium Oxide) δ 8.13 (dd, J=7.2, 2.3 Hz, 1H), 8.06 (d, J=2.3 Hz, 1H), 7.85 (dd, J=9.2, 2.4 Hz, 1H), 7.60 (d, J=8.8 Hz, 2H), 7.48-7.27 (m, 3H), 7.00 (d, J=9.4 Hz, 2H), 6.54 (d, J=7.1 Hz, 1H), 5.17 (d, J=6.6 Hz, 1H), 3.82 (t, J=5.4 Hz, 4H), 3.56-3.34 (m, 5H), 2.90 (d, J=13.8 Hz, 1H).

LC/MS: Method 3 ESI MH⁺ 503, retention time 1.41 minutes.

Example 135

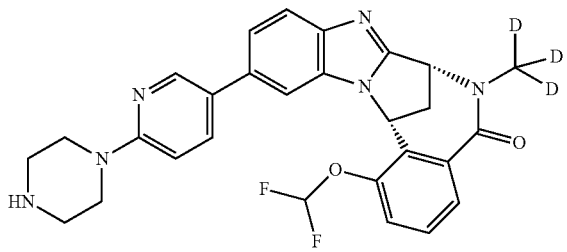 [SMILES: [2H]C([2H])([2H])N1C(=O)c2cccc(OC(F)F)c2[C@H]2C[C@@H]1c1nc3ccc(-c4ccc(N5CCNCC5)nc4)cc3n12]

(7R,14R)-1-(difluoromethoxy)-6-trideutero-methyl-11-[6-(piperazin-1-yl)pyridin-3-yl]-6,7-dihydro-7,14-methanobenzimidazo[1,2-b][2,5]benzodiazocin-5(14H)-one A mixture of 1-[5-(4,4,5,5-tetramethyl-1,3,2-dioxaborolan-2-yl)-2-pyridyl]piperazine (277 mg, 0.96 mmol), Intermediate 110 (300 mg, 0.80 mmol), K₃PO₄ (600 mg, 2.83 mmol), tricyclohexylphosphonium tetrafluoroborate (37.0 mg, 0.1 mmol) were suspended in a mixture of 1,4-dioxane (3 mL) and water (0.3 mL). The mixture was degassed and purged with N₂ before the addition of tris(dibenzylideneacetone) dipalladium(0) (75 mg, 0.08 mmol). The mixture was degassed for 10 min before heating in a microwave at 105° C. for 1 hour. The reaction mixture was quenched with saturated aqueous NaHCO₃ solution and extracted with EtOAc (3×10 mL). The combined organic phases were acidified with aqueous HCl (2N), extracted with water (3×10 mL), and the aqueous phase neutralised with NaOH solution (10%) and extracted with DCM (3×10 mL). The organics were combined, dried (MgSO₄), filtered and concentrated in vacuo to give the title compound (170 mg, 43%). ¹H NMR (300 MHz, DMSO-d6) δ 8.38 (d, J=2.6 Hz, 1H), 8.33-8.22 (m, 1H), 7.94-7.36 (m, 7H), 6.88 (d, J=8.7 Hz, 1H), 6.27 (d, J=7.0 Hz, 1H), 5.21 (d, J=7.1 Hz, 1H), 3.60-3.39 (m, 5H), 2.88-2.68 (m, 5H). LC/MS: Method 3 ESI MH⁺ 520, retention time 1.45 minutes.

Example 136

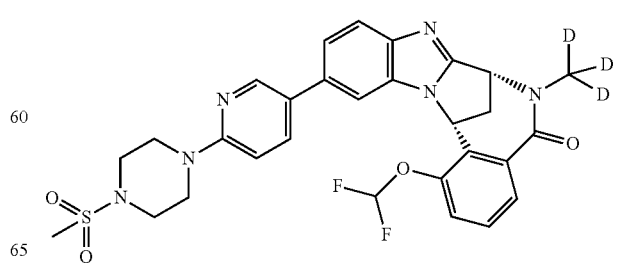

(7R,14R)-1-(difluoromethoxy)-6-trideutero-methyl-11-{6-[4-(methylsulfonyl)piperazin-1 yl]pyridine-3-yl}-6,7-dihydro-7,14-methanobenzimidazo[1,2-b][2,5]benzodiazocin-5(14H)-one Example 135 (80 mg, 0.15 mmol) was dissolved in DCM (5 mL) and N,N-diisopropylethylamine (55 µL, 0.31 mmol) was added to the mixture at 0° C. The mixture was stirred for 5 minutes before the addition of methanesulfonyl chloride (18 µL, 0.23 mmol). The mixture was stirred at 0° C. for 1 hour before the completion of the reaction. The mixture was quenched with saturated NH$_4$Cl solution and extracted with DCM (3×10 mL). The organic phases were combined, dried over Na$_2$SO$_4$, filtered and concentrated in vacuo. The crude product was purified by preparative HPLC-MS to give the title compound (30 mg, 32%). $^1$H NMR (300 MHz, DMSO-d6) δ 8.42 (d, J=2.5 Hz, 1H), 8.27 (dd, J=6.0, 3.5 Hz, 1H), 7.97-7.39 (m, 7H), 7.01 (d, J=8.9 Hz, 1H), 6.27 (d, J=7.0 Hz, 1H), 5.22 (d, J=7.1 Hz, 1H), 3.69 (t, J=5.1 Hz, 4H), 3.50 (dt, J=14.2, 7.3 Hz, 1H), 3.21 (t, J=5.1 Hz, 4H), 2.91 (s, 3H), 2.81 (d, J=13.8 Hz, 1H). LC/MS: Method 3 ESI MH$^+$ 598, retention time 1.95 minutes.

Example 137

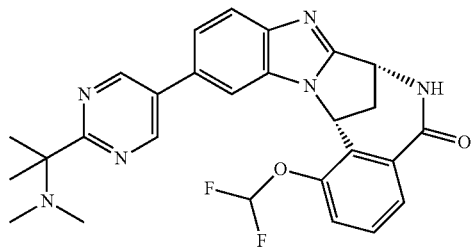 [SMILES: CN(C)C(C)(C)c1ncc(-c2ccc3nc4n(c3c2)[C@@H]2C[C@H]4NC(=O)c3cccc(OC(F)F)c32)cn1]

(7R,14R)-1-(difluoromethoxy)-11-{2-[2-(dimethylamino)propan-2-yl]pyrimidin-5-yl}-6,7-dihydro-7,14-methanobenzimidazo[1,2-b][2,5]benzodiazocin-5(14H)-one A solution of Intermediate 171 (175 mg, 0.37 mmol) in 1,4-dioxane (2 mL) was added to a mixture of Intermediate 170 (120 mg, 0.49 mmol), 1,1'-bis(diphenylphosphino)ferrocene-palladium (II) dichloromethane complex (16.0 mg, 0.0196 mmol), potassium phosphate tribasic (240 mg, 1.11 mmol) in 1,4-dioxane (2 mL) and water (0.3 mL). The mixture was degassed and purged with N$_2$ before heating at 110° C. for 2 hours. The reaction mixture was quenched with saturated aqueous NaHCO$_3$ solution and extracted with EtOAc (3×10 mL). The organics were combined, dried with Na$_2$SO$_4$, filtered and concentrated in vacuo. The crude product purified by column chromatography (0-40% MeOH in DCM (1% Et$_3$N)) to give the title compound (18 mg, 9%). $^1$H NMR (300 MHz, DMSO-d6) δ 9.16 (d, J=6.9 Hz, 1H), 9.05 (s, 2H), 8.23 (dd, J=6.3, 3.1 Hz, 1H), 8.03-7.37 (m, 6H), 6.37 (d, J=7.0 Hz, 1H), 4.90 (t, J=6.7 Hz, 1H), 3.59-3.39 (m, 1H), 2.75 (d, J=13.5 Hz, 1H), 2.13 (s, 6H), 1.51 (s, 6H). LC/MS: Method 3 ESI MH$^+$ 505, retention time 1.44 minutes.

Example 138

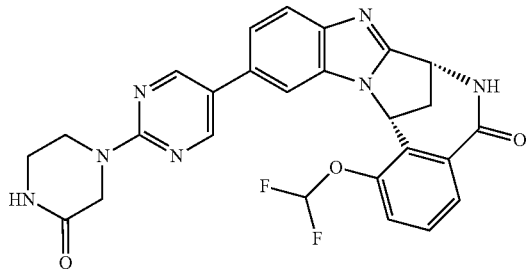 [SMILES: O=C1CN(c2ncc(-c3ccc4nc5n(c4c3)[C@@H]3C[C@H]5NC(=O)c4cccc(OC(F)F)c43)cn2)CCN1]

(7R,14R)-1-(difluoromethoxy)-11-[2-(3-oxopiperazin-1-yl)pyrimidin-5-yl]-6,7-dihydro-7,14-methanobenzimidazo[1,2-b][2,5]benzodiazocin-5(14H)-one A mixture of [2-(3-oxopiperazin-1-yl)pyrimidin-5-yl]boronic acid (310 mg, 1.40 mmol), Example 11 (350 mg, 0.93 mmol), K$_3$PO$_4$ (592 mg, 2.80 mmol), tricyclohexylphosphonium tetrafluoroborate (36 mg, 0.1 mmol) and tris(dibenzylideneacetone) dipalladium(0) (85 mg, 0.1 mmol) were suspended in a mixture of 1,4-dioxane (10 mL) and water (0.5 mL). The mixture was degassed and purged with N$_2$ before heating in an oil bath at 105° C. for 16 hours. The reaction mixture was quenched with water and extracted with EtOAc (3×10 mL), and the combined organics were dried (MgSO$_4$), filtered and concentrated in vacuo. Purification by column chromatography (0%-10% MeOH in DCM) afforded the title compound (130 mg, 27%). $^1$H NMR (300 MHz, DMSO-d$_6$) δ 9.12 (d, J=6.8 Hz, 1H), 8.69 (s, 2H), 8.29-8.16 (m, 1H), 8.11 (s, 1H), 7.74-7.63 (m, 2H), 7.60 (dd, J=1.8, 0.7 Hz, 1H), 7.55-7.39 (m, 3H), 6.33 (d, J=7.0 Hz, 1H), 4.87 (t, J=6.7 Hz, 2H), 4.23 (s, 2H), 3.96 (t, J=5.4 Hz, 2H), 3.47 (dt, J=13.5, 6.9 Hz, 2H), 2.73 (d, J=13.3 Hz, 1H). LC/MS: Method 3 ESI MH$^+$ 518, retention time 1.54 minutes.

Example 139

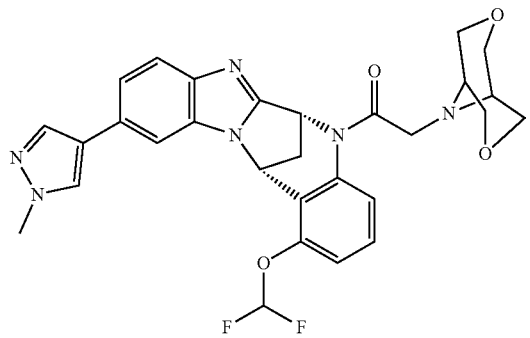 [SMILES: Cn1cc(-c2ccc3nc4n(c3c2)[C@@H]2C[C@H]4N(C(=O)CN3C4COCC3COC4)c3cccc(OC(F)F)c32)cn1]

1-[(6R,12R)-11-(difluoromethoxy)-2-(1-methyl-1H-pyrazol-4-yl)-6H-6,12-methanobenzimidazo[2,1-c][1,4]benzodiazepin-7(12H)-yl]-2-(3,7-dioxa-9-azabicyclo[3.3.1]non-9-yl)ethanone The title compound was prepared from 1-methyl-4-(4,4,5,5-tetramethyl-1,3,2-dioxaborolan-2-yl)-1H-pyrazole, and Preparative Example 40 in accordance with the Method described for Example 20 to give, following purification by preparative HPLC a white solid (2 mg, 4% yield). LC/MS: Method 3 RT 1.72 mins, [M+H]$^+$=563. $^1$H NMR (300 MHz, Methanol-d4) δ 8.19 (d, J=8.6 Hz, 1H), 7.93 (s, 1H), 7.81 (s, 1H), 7.70-7.55 (m, 2H), 7.49-7.42 (m, 1H), 7.25 (t, J=8.5 Hz, 1H), 7.13 (t, J=73.5 Hz, 1H), 6.94 (d, J=8.3 Hz, 1H), 6.35 (d, J=4.0 Hz, 1H), 6.14 (d, J=4.4 Hz, 1H), 4.37 (s, 2H), 4.24 (d, J=11.6 Hz, 2H), 4.11 (d, J=11.5 Hz, 2H), 3.95 (s, 3H), 3.86 (dd, J=11.5, 6.7 Hz, 4H), 3.29-3.20 (m, 1H), 2.76-2.62 (m, 3H).

Example 140

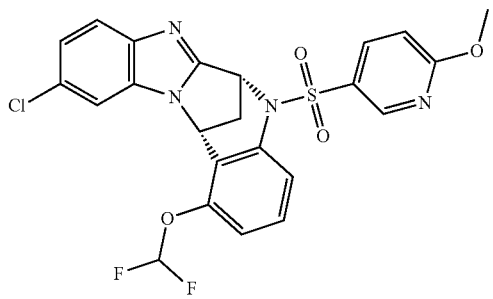 [SMILES: COc1ccc(S(=O)(=O)N2c3cccc(OC(F)F)c3[C@H]3C[C@@H]2c2nc4ccc(Cl)cc4n23)cn1]

(6R,12R)-2-chloro-11-(difluoromethoxy)-7-[(6-methoxypyridin-3-yl)sulfonyl]-7,12-dihydro-6H-6,12-methanobenzimidazo[2,1-c][1,4]benzodiazepine To Intermediate 172 (630 mg, 1.050 mmol) was added anhydrous cesium acetate (2000 mg, 10.41 mmol), cuprous iodide (510 mg, 2.62 mmol) and dimethyl sulfoxide (1.0 mL). The mixture was sealed and purged 3 times with nitrogen. The reaction mixture was stirred for 45 minutes at 160° C. The reaction mixture was cooled at room temperature the solid was filtered and the filtrate was evaporated under vacuum. The crude material was purified by column chromatography over silica gel using hexane/ethyl acetate (0 to 100%) as eluent, yielding 133 mg (25% yield) of the title compound as a brown solid.

LCMS Method 3: RT 2.07 min, [M+H]$^+$=519. δ $^1$H NMR (400 MHz, DMSO-d6) δ 8.86 (d, J=2.5 Hz, 1H), 8.39 (dd, J=8.9, 2.7 Hz, 1H), 7.69 (d, J=8.6 Hz, 1H), 7.49-7.41 (m, 2H), 7.40 (t, J=73.3 Hz, 1H). 7.27 (t, J=8.5 Hz, 1H), 7.21 (d, J=2.1 Hz, 1H). 6.99-6.92 (m, 1H), 6.89 (d, J=8.1 Hz, 1H), 6.28 (d, J=3.7 Hz, 1H), 6.04 (d, J=4.5 Hz, 1H), 3.89 (s, 3H), 3.23-3.13 (m, 1H), 2.54 (d, J=11.9 Hz, 1H).

Example 141

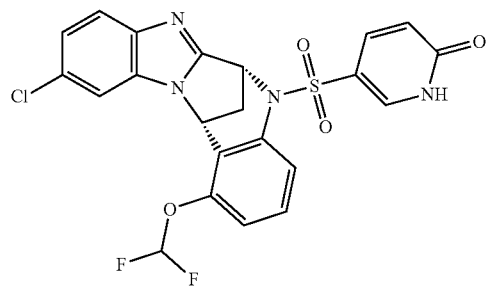 [SMILES: O=c1ccc(S(=O)(=O)N2c3cccc(OC(F)F)c3[C@H]3C[C@@H]2c2nc4ccc(Cl)cc4n23)c[nH]1]

5-{[(6R,12R)-2-chloro-11-(difluoromethoxy)-6H-6,12-methanobenzimidazo[2,1-c][1,4]benzodiazepin-7(12H)-yl]sulfonyl}pyridin-2(1H)-one To a solution of Example 140 (120 mg, 0.23 mmol) in acetonitrile (3.4 mL) was added chloromethyltrimethylsilane (0.15 mL, 1.2 mmol) in acetonitrile (3.4 mL) and potassium iodide (195 mg, 1.17 mmol) and the reaction mixture heated at 80° C. for 2 hours. The reaction mixture was concentrated under reduced pressure, the residue diluted with EtOAc, washed with water and Na$_2$S$_2$O$_{3-10}$% aq. solution. The combined organic layers were washed with brine and filtered through a phase separator and evaporated under vacuum. The crude material was purified by column chromatography over silica gel using hexane/ethyl acetate (0 to 100%) as eluent, yielding 106 mg (91% yield) of the title compound as a pale brown solid. LCMS Method 3: RT 2.06 min, [M–H]$^+$=503/505. $^1$H NMR (300 MHz, DMSO-d$_6$) δ 1H NMR (400 MHz, DMSO-d6) δ 1H NMR (300 MHz, DMSO-d6) δ 12.46 (s, 1H), 8.32 (s, 1H), 7.89 (s, 1H), 7.72-7.62 (m, 1H), 7.50-7.37 (m, 2H), 7.41 (t, J=73.3 Hz, 1H), 7.33-7.13 (m, 2H), 6.89 (d, J=8.0 Hz, 1H), 6.28 (d, J=9.7 Hz, 1H), 6.16 (d, J=3.7 Hz, 1H), 6.03 (d, J=4.3 Hz, 1H), 3.17 (d, J=12.4 Hz, 1H), 2.56 (d, J=12.4 Hz, 1H).

Example 142

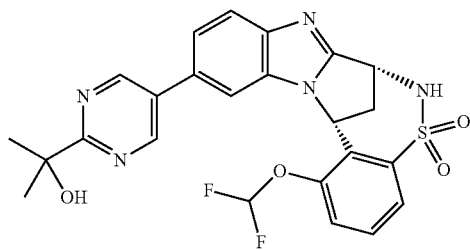 [SMILES: CC(C)(O)c1ncc(-c2ccc3nc4n(c3c2)[C@@H]2C[C@H]4NS(=O)(=O)c3cccc(OC(F)F)c32)cn1]

2-{5-[(7R,14R)-1-(difluoromethoxy)-5,5-dioxido-6,7-dihydro-14H-7,14-methanobenzimidazo[2,1-d][1,2,5]benzothiadiazocin-11-yl]pyrimidin-2-yl}propan-2-ol To a solution of Intermediate 175 (10 mg, 0.024 mmol) in 1,4-dioxane (0.1 mL), 2-[5-(4,4,5,5-tetramethyl-1,3,2-dioxaborolan-2-yl)pyrimidin-2-yl]propan-2-ol (9.6 mg, 0.036 mmol), potassium phosphate, (13 mg, 0.061 mmol), tris(dibenzylideneacetone)dipalladium (0) (1.2 mg, 0.0013 mmol), tricyclohexylphosphonium trifluoroborate (1.1 mg, 0.003 mmol) and water (10 μL) were added. The reaction mixture was de-gassed and stirred at 140° C. for 5 hours in the microwave. The reaction mixture was filtered through a pad of Celite and the residue washed successively with EtOAc, and 20% MeOH in DCM. The filtrate was evaporated under vacuum and the crude material was purified by preparative HPLC-MS (pH 10) yielding 1.2 mg (16% yield) of the title compound as a white solid. LCMS Method 3: RT 1.42 min, [M–H]$^+$=514. $^1$H NMR (400 MHz, Methanol-d4) δ 9.03 (s, 2H), 7.89 (dd, J=6.9, 2.2 Hz, 1H), 7.85 (d, J=8.5 Hz, 1H), 7.70 (d, J=1.7 Hz, 1H), 7.67-7.55 (m, 3H), 7.30 (t, J=72.8 Hz, 1H), 6.60 (d, J=7.8 Hz, 1H), 5.02 (d, J=4.9 Hz, 1H), 3.44 (ddd, J=13.2, 7.8, 5.0 Hz, 1H), 3.07 (d, J=13.6 Hz, 1H), 1.64 (s, 6H). (OH and NH signals are missing).

Example 143

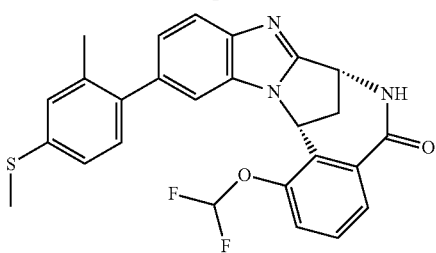 [SMILES: CSc1ccc(-c2ccc3nc4n(c3c2)[C@@H]2C[C@H]4NC(=O)c3cccc(OC(F)F)c32)c(C)c1]

(7R,14R)-1-(difluoromethoxy)-11-[2-methyl-4-(methylsulfanyl)phenyl]-6,7-dihydro-7,14-methanobenzimidazo[1,2-b][2,5]benzodiazocin-5(14H)-one To a solution of 4-bromo-3-methylthioanisole (500 mg, 2.23 mmol), in 1,4-dioxane (8 mL), bis(pinacolato)diboron (1.2 g, 4.46 mmol) potassium acetate (885 mg, 8.92 mmol), 1,1'-bis(diphenylphosphino)ferrocene-palladium(II)dichloridedichloromethanecomplex (92 mg, 0.11 mmol) were added and the solution was degassed and heated at 100° C., using a preheated oil bath, for 1 hour. The reaction was quenched by the addition of water and the mixture extracted with EtOAc (×3). The combined organic layers were filtered through a phase separator and the solvent was evaporated to give 590 mg (99%) of 4,4,5,5-tetramethyl-2-(2-methyl-4-methylsulfanyl-phenyl)-1,3,2-dioxaborolane which was used in the next step without further purification. LCMS (ES+) Method 3: 265 (M+H)+, RT 1.70 minutes.

To a solution of 4,4,5,5-tetramethyl-2-(2-methyl-4-methylsulfanyl-phenyl)-1,3,2-dioxaborolane (590 mg, 2.23 mmol) in 1,4-dioxane (3.8 mL) were added Example 11 (400 mg, 1.06 mmol), potassium phosphate (567 mg, 2.67 mmol), tricyclohexylphosphonium tetrafluoroborate (52 mg, 0.138 mmol) and tris(dibenzylideneacetone)dipalladium (0) (108 mg, 0.114 mmol). The reaction mixture was degassed for 10 mins before heating to 140° C. degree in a microwave for 2 hours. The reaction was quenched with water and extracted with EtOAc (×3). The combined organic layers were filtered through a phase separator and the solvent was evaporated to give a crude residue. Purification by column chromatography on silica eluting with EtOAc: MeOH (0 to 20%) gave the title compound (80 mg) as a white solid. LCMS (ES+) Method 3: 478 (M+H)+, RT 2.42 minutes. $^1$H NMR (300 MHz, DMSO-d6) δ 9.14 (d, J=6.8 Hz, 1H), 8.24 (dd, J=5.8, 3.6 Hz, 1H), 7.63 (dd, J=8.4, 0.7 Hz, 1H), 7.55-7.49 (m, 2H), 7.48 (t, J=83.2 Hz, 1H). 7.37 (dd, J=1.7, 0.7 Hz, 1H), 7.23-7.08 (m, 4H), 6.29 (d, J=7.0 Hz, 1H), 4.87 (t, J=6.7 Hz, 1H), 3.48 (dt, J=13.5, 7.0 Hz, 1H), 2.72 (d, J=13.3 Hz, 1H), 2.5 (s, 3H), 2.19 (d, J=0.6 Hz, 3H).

Example 144

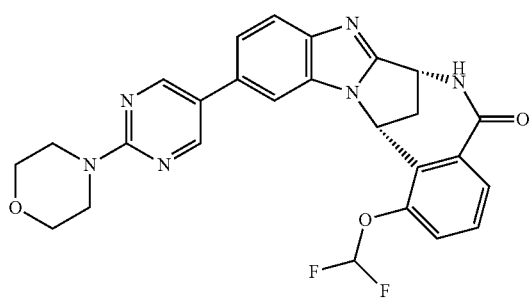 [SMILES: O=C1N[C@@H]2C[C@H](c3c(OC(F)F)cccc31)n1c2nc2ccc(-c3cnc(N4CCOCC4)nc3)cc21]

(7R,14R)-1-(difluoromethoxy)-11-[2-(morpholin-4-yl)pyrimidin-5-yl]-6,7-dihydro-7,14-methanobenzimidazo[1,2-b][2,5]benzodiazocin-5(14H)-one The title compound was prepared from Example 11 (450 mg, 1.20 mmol) and 2-morpholinopyrimidin-5-yl)boronic acid (380 mg, 1.82 mmol) in accordance with the Method described for Example 20 to give, following purification by column chromatography over silica gel using hexane/ethyl acetate (0 to 100%) then DCM:MeOH (0 to 20%) as eluent, the title compound (300 mg, 50% yield) as a pale yellow solid. LCMS (ES+) Method 3: 505 (M+H)+, RT 1.89 minutes. $^1$H NMR (300 MHz, DMSO-d6) δ 9.12 (d, J=6.7 Hz, 1H), 8.66 (s, 2H), 8.22 (t, J=4.7 Hz, 1H), 7.68 (d, J=2.7 Hz, 1H), 7.65 (t, J=79.0 Hz, 1H), 7.59 (d, J=1.6 Hz, 1H), 7.54-7.40 (m, 3H), 6.33 (d, J=7.1 Hz, 1H), 4.87 (t, J=6.7 Hz, 1H), 3.80-3.65 (m, 8H), 3.58-3.39 (m, 1H), 2.73 (d, J=13.3 Hz, 1H).

Example 145

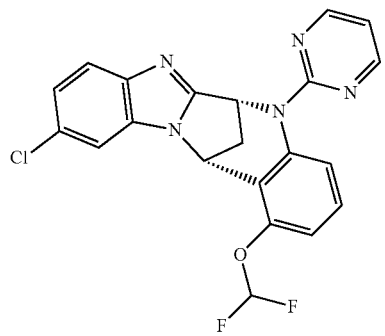 [SMILES: FC(F)Oc1cccc2c1[C@H]1C[C@H](c3nc4ccc(Cl)cc4n31)N2c1ncccn1]

(6R,12R)-2-chloro-11-(difluoromethoxy)-7-(pyrimidin-2-yl)-7,12-dihydro-6H-6,12-methanobenzimidazo[2,1-c][1,4]benzodiazepine To Intermediate 176 (200 mg, 0.39 mmol) was added cesium acetate anhydrous (600 mg, 3.12 mmol), cuprous iodide (192 mg, 1.0 mmol) and dimethyl sulfoxide (0.4 mL). The mixture was sealed and purged 3 times with nitrogen. The reaction mixture was stirred for 45 minutes at 160° C. The reaction mixture was cooled to room temperature the solid was filtered and the filtrate was evaporated under vacuum. The crude material was purified by column chromatography over silica gel using hexane/ethyl acetate (0 to 100%) as eluent, followed by a second purification by preparative HPLC, yielding 2 mg (1% yield) of the title compound as a white solid. LCMS Method 3: RT 2.37 min, [M+H]+=426. $^1$H NMR (300 MHz, DMSO-d6) δ 8.71 (d, J=4.8 Hz, 2H), 8.00 (d, J=8.7 Hz, 1H), 7.59-7.43 (m, 2H), 7.42 (t, J=73.7 Hz, 1H), 7.28-7.11 (m, 3H), 6.82 (d, J=8.3 Hz, 1H), 6.66 (s, 1H), 6.08 (d, J=4.3 Hz, 1H), 3.17 (d, J=11.9 Hz, 1H), 2.60 (d, J=12.0 Hz, 1H).

Example 146

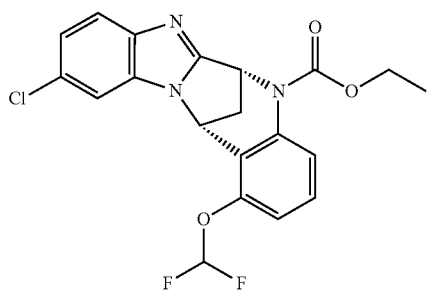 [SMILES: CCOC(=O)N1c2cccc(OC(F)F)c2[C@H]2C[C@@H]1c1nc3ccc(Cl)cc3n12]

Ethyl-(6R,12R)-2-chloro-11-(difluoromethoxy)-6H-6,12-methanobenzimidazo[2,1-c][1,4]benzodiazepine-7(12H)-carboxylate To Intermediate 177 (260 mg, 0.52 mmol) was added sodium acetate (167 mg, 2.04 mmol), cuprous iodide (101 mg, 0.52 mmol) and dimethyl sulfoxide (6.4 mL). The mixture was sealed and purged 3 times with nitrogen. The reaction mixture was stirred overnight at 100° C. Additional sodium acetate (167 mg, 2.03 mmol) and cuprous iodide (101 mg, 0.52 mmol) were added and the reaction was stirred at 160° C. for 1 hour. The reaction mixture was cooled to room temperature, the solid was filtered and the filtrate was evaporated under vacuum. The crude material was purified by column chromatography over silica gel using hexane/ethyl acetate (0 to 100%) as eluent, followed by a second purification by preparative HPLC, yielding 12 mg (6% yield) of the title compound as a white solid. LCMS Method 3: RT 2.47 min, [M+H]$^+$=420/422. $^1$H NMR (300 MHz, DMSO-d6) δ 8.02 (d, J=8.6 Hz, 1H), 7.63 (d, J=8.6 Hz, 1H), 7.45 (d, J=2.0 Hz, 1H), 7.42 (t, J=73.5 Hz, 1H), 7.29 (t, J=8.5 Hz, 1H), 7.19 (dd, J=8.7, 2.1 Hz, 1H), 6.90 (dd, J=8.4, 1.0 Hz, 1H), 6.04 (m, 2H), 4.38-4.23 (m, 2H), 3.10 (dt, J=12.1, 4.4 Hz, 1H), 2.56 (d, J=12.1 Hz, 1H), 1.38 (t, J=7.1 Hz, 3H).

Example 147

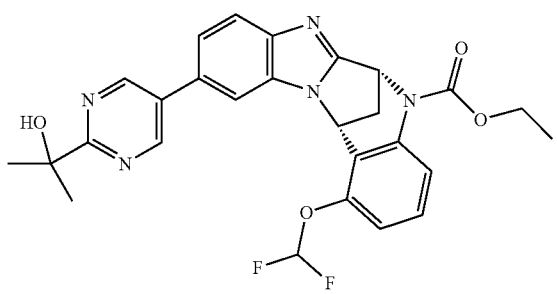 [SMILES: CCOC(=O)N1c2cccc(OC(F)F)c2[C@H]2C[C@@H]1c1nc3ccc(-c4cnc(C(C)(C)O)nc4)cc3n12]

Ethyl-(6R,12R)-11-(difluoromethoxy)-2-[2-(2-hydroxypropan-2-yl)pyrimidin-5-yl]-6H-6,12-methanobenzimidazo[2,1-c][1,4]benzodiazepine-7(12H)-carboxylate The title compound was prepared from 2-(1-hydroxy-1-methylethyl) pyrimidine-5-boronic acid pinacol ester, and Example 146 in accordance with the Method for Example 20 to give, following purification by preparative HPLC a white solid (1.2 mg, 8% yield).

LC/MS Method 3: RT 2.18 mins, [M+H]$^+$=522

$^1$H NMR (300 MHz, Methanol-d4) δ 9.05 (s, 2H), 8.17 (d, J=8.7 Hz, 1H), 7.87-7.73 (m, 2H), 7.58 (dd, J=8.5, 1.7 Hz, 1H), 7.25 (t, J=8.5 Hz, 1H), 7.14 (t, J=73.3 Hz, 1H), 6.93-6.84 (m, 1H), 6.20 (d, J=4.3 Hz, 2H), 4.43 (m, 2H), 3.20 (dt, J=12.1, 4.4 Hz, 1H), 2.65 (d, J=12.0 Hz, 1H), 1.65 (s, 6H), 1.49 (t, J=7.1 Hz, 3H).

Example 148

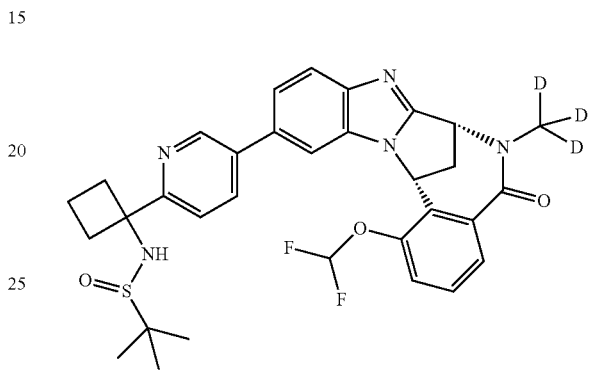

N-(1-{5-[(7R,14R)-1-(difluoromethoxy)-6-trideuteromethyl-5-oxo-5,6,7,14-tetrahydro-7,14-methanobenzimidazo[1,2-b][2,5]benzodiazocin-11-yl]pyridin-2-yl}cyclobutyl)-2-methylpropane-2-sulfinamide The title compound was prepared from Intermediate 178 (300 mg, 0.91 mmol) and Intermediate 159 (751 mg, 1.09 mmol) in accordance with the Method described for Example 20 to give, following purification by column chromatography in silica gel (Hexane: EtOAc (from 0 to 100%) then DCM:MeOH (from 0 to 15%) a yellow solid (600 mg, 98% yield). LC/MS Method 3: RT 2.03 minutes, [M+H]$^+$=609.

$^1$H NMR (400 MHz, DMSO-d6) δ 8.81 (s, 1H), 8.32-8.25 (m, 1H), 8.01 (d, J=6.3 Hz, 1H), 7.75 (d, J=8.3 Hz, 2H), 7.76 (t, J=73.6 Hz, 1H), 7.67 (d, J=8.2 Hz, 2H), 7.57 (d, J=8.2 Hz, 1H), 7.53-7.44 (m, 2H), 6.31 (d, J=6.9 Hz, 1H), 5.91 (s, 1H), 3.56-3.50 (m, 1H), 2.84 (d, J=13.9 Hz, 1H), 2.41-2.45 (m, 2H), 1.75-1.8 (m, 2H), 1.97-2.03 (m, 2H), 1.15 (s, 9H).

Example 149

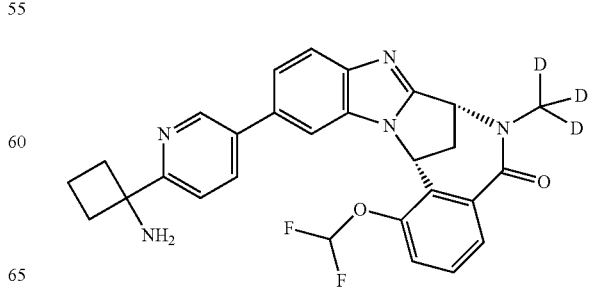

(7R,14R)-11-[6-(1-aminocyclobutyl)pyridin-3-yl]-1-(difluoromethoxy)-6-trideuteromethyl-6,7-dihydro-7,14-methanobenzimidazo[1,2-b][2,5]benzodiazocin-5(14H)-one Example 148 (600 mg, 0.89 mmol) was dissolved in methanol (4.5 mL) and HCl 4N in dioxane (0.50 mL, 2.0 mmol) was added at room temperature, the reaction was stirred for 5 hours. The solvent was evaporated and the crude mixture was dissolved in water and DCM. The aqueous layer was extracted with dichloromethane (×2) and then freeze dried to give the title compound as an HCl salt and a white solid (460 mg, 99% yield). LC/MS Method 3: RT 1.65 minutes, [M+H]$^+$=505. $^1$H NMR (300 MHz, DMSO-d$^6$) δ 8.91 (dd, J=2.4, 0.8 Hz, 1H), 8.89 (bs, 3H, NH$_3^+$), 8.34-8.15 (m, 2H), 7.96-7.76 (m, 3H), 7.73-7.63 (m, 1H), 7.69 (t, J=73.3 Hz, 1H), 7.53-7.49 (m, 2H), 6.36 (d, J=7.1 Hz, 1H), 5.34 (d, J=7.1 Hz, 1H), 3.56 (dt, J=14.2, 7.3 Hz, 1H), 2.88 (d, J=13.8 Hz, 1H), 2.63 (q, J=7.3 Hz, 2H), 2.35-2.12 (m, 2H), 2.11-1.93 (m, 2H).

Example 150

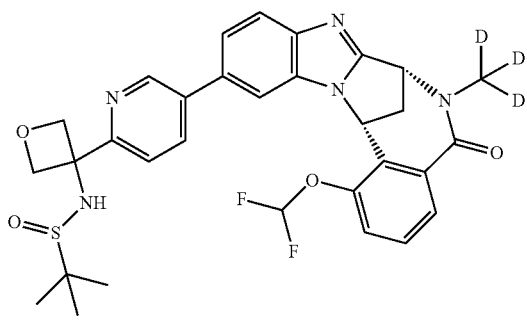 [SMILES: [2H]C([2H])([2H])N1C(=O)c2cccc(OC(F)F)c2[C@H]2C[C@@H]1c1nc3ccc(-c4ccc(C5(NS(=O)C(C)(C)C)COC5)nc4)cc3n12]

N-(3-{5-[(7R,14R)-1-(difluoromethoxy)-6-trideuteromethyl-5-oxo-5,6,7,14-tetrahydro-7,14-methanobenzimidazo[1,2-b][2,5]benzodiazocin-11-yl]pyridin-2-yl}oxetan-3-yl)-2-methylpropane-2-sulfinamide The title compound was prepared from Intermediate 159 (890 mg, 1.65 mmol), and Intermediate 179 (500 mg, 1.5 mmol) in accordance with the method described for Example 20 to give, following purification by column chromatography in silica gel (hexanes: EtOAc from 0 to 100% then DCM:MeOH from 0 to 15%), a yellow solid (750 mg, 82%). LC/MS Method 3: RT 1.82 minutes, [M+H]$^+$=611. $^1$H NMR (300 MHz, DMSO-d$^6$) δ 8.88 (d, J=2.3 Hz, 1H), 8.34-8.22 (m, 1H), 8.08 (dd, J=8.3, 2.4 Hz, 1H), 7.76 (dd, J=5.1, 3.3 Hz, 2H), 7.70-7.63 (m, 1H), 7.67 (t, J=73.3 Hz, 1H), 7.59 (dd, J=8.6, 1.7 Hz, 1H), 7.49 (d, J=5.0 Hz, 2H), 6.48 (s, 1H), 6.31 (d, J=7.1 Hz, 1H), 5.24 (d, J=7.1 Hz, 1H), 5.17 (d, J=6.1 Hz, 1H), 5.04-4.75 (m, 3H), 3.53 (dt, J=14.3, 7.4 Hz, 1H), 2.83 (d, J=13.8 Hz, 1H), 1.17 (d, J=1.2 Hz, 9H).

Example 151

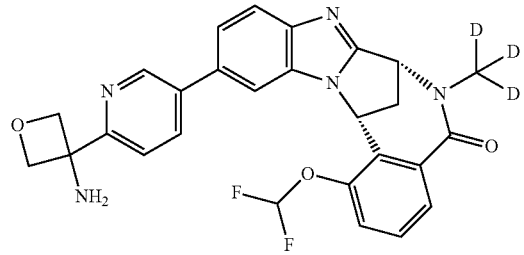 [SMILES: [2H]C([2H])([2H])N1C(=O)c2cccc(OC(F)F)c2[C@H]2C[C@@H]1c1nc3ccc(-c4ccc(C5(N)COC5)nc4)cc3n12]

(7R,14R)-11-[6-(3-aminooxetan-3-yl)pyridin-3-yl]-1-(difluoromethoxy)-6-trideuteromethyl-6,7-dihydro-7,14-methanobenzimidazo[1,2-b][2,5]benzodiazocin-5(14H)-one Example 150 (249 mg, 0.4077 mmol) was dissolved in methanol (8 mL) and HCl 4N in dioxane (0.2 mL, 0.8 mmol) was added at 0° C. and the reaction was kept in the fridge overnight. A saturated aqueous solution of NaHCO$_3$ was added at 0° C. and the reaction mixture was extracted with EtOAc. The combined organic layers were filtered through a phase separator and the solvent was evaporated to give the title compound (120 mg, 58%) as a pale brown solid. LC/MS Method 3: RT 1.49 mins, [M+H]$^+$=507. $^1$H 1H NMR (300 MHz, DMSO-d6) δ 8.85 (dd, J=2.4, 0.8 Hz, 1H), 8.34-8.21 (m, 1H), 8.05 (dd, J=8.3, 2.5 Hz, 1H), 7.80-7.71 (m, 3H), 7.67 (t, J=73.3 Hz, 1H), 7.61-7.44 (m, 3H), 6.30 (d, J=7.1 Hz, 1H), 5.24 (d, J=7.0 Hz, 1H), 4.93 (d, J=5.6 Hz, 2H), 4.59 (d, J=5.6 Hz, 2H), 3.60-3.44 (m, 1H), 2.83 (d, J=13.8 Hz, 1H).

Example 152

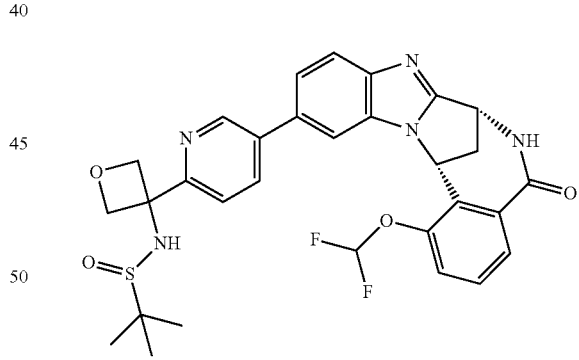

N-(3-{5-[(7R,14R)-1-(difluoromethoxy)-6-methyl-5-oxo-5,6,7,14-tetrahydro-7,14-methanobenzimidazo[1,2-b][2,5]benzodiazocin-11-yl]pyridin-2-yl}oxetan-3-yl)-2-methylpropane-2-sulfinamide The title compound was obtained as a by-product of the preparation of Example 150. LC/MS: RT 1.75 mins (pH 10), [M+H]$^+$=594.

$^1$H NMR 1H NMR (300 MHz, DMSO-d6) δ 9.14 (d, J=6.9 Hz, 1H), 8.88 (s, 1H), 8.22 (s, 1H), 8.08 (d, J=7.8 Hz, 1H), 7.78-7.63 (m, 2H), 7.69 (t, J=73.3 Hz, 1H), 7.62-7.40 (m, 2H), 6.47 (s, 1H), 6.37 (d, J=6.9 Hz, 1H), 5.17 (d, J=6.3

Hz, 1H), 4.93-4.81 (m, 4H), 3.28 (s, 2H), 3.56 (m, 1H), 2.75 (d, J=13.2 Hz, 1H), 1.17 (s, 9H).

Example 153

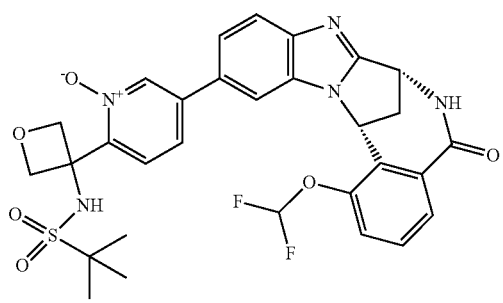

N-(3-{5-[(7R,14R)-1-(difluoromethoxy)-5-oxo-5,6,7,14-tetrahydro-7,14-methanobenzimidazo[1,2-b][2,5]benzo diazocin-11-yl]-1-oxidopyridin-2-yl}oxetan-3-yl)-2-methylpropane-2-sulfonamide To a solution of Example 152 (18 mg, 0.03 mmol) in dichloromethane (0.3 mL), 3-chloroperoxybenzoic acid (5.2 mg, 0.03 mmol) was added and the reaction was stirred overnight. More 3-chloroperoxybenzoic acid (10.4 mg, 0.060 mmol) was added and the reaction mixture was stirred for 48 hours. The reaction mixture was directly purified by column chromatography on silica gel (hexanes: EtOAc from 0 to 100% then DCM:MeOH from 0 to 15% to give the title compound as a white solid (12 mg, 63% yield).

LC/MS Method 3: RT 1.78 mins, [M+H]$^+$=626. $^1$H NMR (300 MHz, DMSO-d6) δ 9.16 (d, J=6.8 Hz, 1H), 8.57 (s, 1H), 8.27-8.18 (m, 1H), 7.89 (d, J=13.7 Hz, 1H), 7.77-7.64 (m, 3H), 7.67 (t, J=73.3 Hz, 1H), 7.63-7.46 (m, 2H), 6.36 (d, J=7.0 Hz, 1H), 5.02-4.88 (m, 2H), 4.87 (d, J=7.8 Hz, 3H), 3.56 (m, 1H), 2.77 (s, 1H), 1.14 (s, 9H).

Example 154

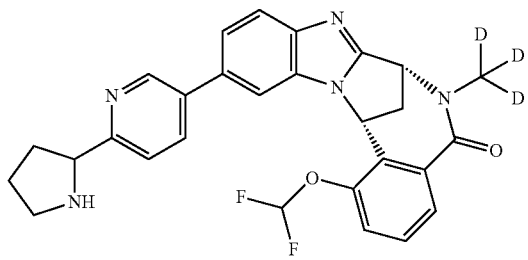 [SMILES: [2H]C([2H])([2H])N1C(=O)c2cccc(OC(F)F)c2[C@H]2C[C@@H]1c1nc3ccc(-c4ccc(C5CCCN5)nc4)cc3n12]

(7R,14R)-1-(difluoromethoxy)-11-[4-(2,4-dimethyl-1H-imidazol-5-yl)phenyl]-6-trideuteromethyl-6,7-dihydro-7,14-methanobenzimidazo[1,2-b][2,5]benzodiazocin-5(14H)-one The title compound was prepared from Intermediate 159 (600 mg, 1.24 mmol), and 5-bromo-2-pyrrolidin-2-yl-pyridine (352 mg, 1.55 mmol) in accordance with the Method described for Example 20 to give, following purification by column chromatography in silica gel (Hex: EtOAc from 0 to 100% then DCM:MeOH with 2% of NH$_3$ from 0 to 20%) and subsequent SCF purification, a white solid (20 mg, 3.2% yield). LC/MS Method 3: RT 1.62 minutes, [M+H]$^+$=505. $^1$H NMR (300 MHz, DMSO-d6) δ 8.74 (d, J=2.4 Hz, 1H), 8.27 (dd, J=5.9, 3.6 Hz, 1H), 8.01-7.93 (m, 1H), 7.78-7.58 (m, 2H), 7.67 (t, J=73.3 Hz, 1H), 7.58-7.44 (m, 4H), 6.29 (d, J=7.2 Hz, 1H), 5.24 (d, J=7.2 Hz, 1H), 4.24 (d, J=7.9 Hz, 1H), 3.52 (dt, J=14.0, 7.3 Hz, 1H), 3.11-2.87 (m, 2H), 2.83 (d, J=13.7 Hz, 1H), 2.18 (m, 2H), 1.74 (m, 2H).

Example 155

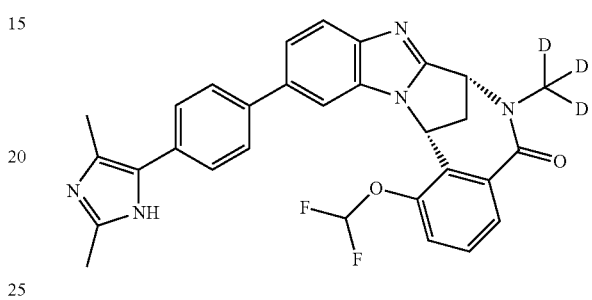

(7R,14R)-1-(difluoromethoxy)-11-[4-(2,4-dimethyl-1H-imidazol-5-yl)phenyl]-6-trideuteromethyl-6,7-dihydro-7,14-methanobenzimidazo[1,2-b][2,5]benzodiazocin-5(14H)-one The title compound was prepared from Intermediate 159 (466 mg, 0.9622 mmol), and Intermediate 180 (200 mg, 0.789 mmol) in accordance with the Method described for Example 20. The reaction mixture was filtered and the solid was washed with dichloromethane and water to give the title compound (110 mg, 27% yield) as a white solid. LC/MS Method 3: RT 1.72 mins, [M+H]$^+$=529. Free base: $^1$H NMR (300 MHz, DMSO-d6) δ 8.32-8.23 (m, 1H), 7.75-7.64 (m, 2H), 7.68 (t, J=73.3 Hz, 1H), 7.63 (s, 4H), 7.57-7.46 (m, 3H), 6.29 (d, J=7.1 Hz, 1H), 5.23 (d, J=7.1 Hz, 1H), 3.58-3.46 (m, 1H), 2.82 (d, J=13.8 Hz, 1H), 2.36 (s, 3H), 2.27 (s, 3H).

Example 156

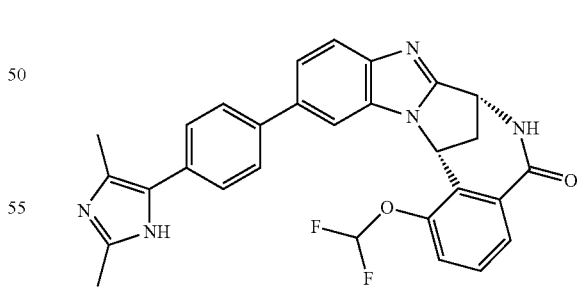

(7R,14R)-1-(difluoromethoxy)-11-[4-(2,4-dimethyl-1H-imidazol-5-yl)phenyl]-6,7-dihydro-7,14-methanobenzimidazo[1,2-b][2,5]benzodiazocin-5(14H)-one The title compound was prepared from Intermediate 171 (114 mg, 0.2196 mmol), and Intermediate 180 (50 mg, 0.2 mmol) in accordance with the Method described for Example 20. The reaction mixture was diluted in dicholoromethane:MeOH (10%) and extracted with water. The aqueous layer was extracted with dichloromethane:MeOH (10%) five times and the combined organic layer was filtered through a phase separator and the solvent was evaporated in vacuo. The solid obtained was triturated in dichloromethane and water to give the title compound (75 mg, 73% yield) as a yellow solid. HCl in methanol was added and the solid was freeze dried to give the HCl salt of the title compound. LC/MS Method 3: RT 1.65 mins, [M+H]$^+$=512.

$^1$H NMR (300 MHz, DMSO-d$^6$) 1H NMR (300 MHz, DMSO-d6) δ 14.24 (s, 1H), 14.13 (s, 1H), 9.15 (d, J=6.8 Hz, 1H), 8.24 (t, J=4.7 Hz, 1H), 7.85-7.64 (m, 5H), 7.68 (t, J=73.3 Hz, 1H), 7.62-7.47 (m, 3H), 6.37 (d, J=6.9 Hz, 1H), 4.91 (t, J=6.6 Hz, 1H), 3.50-3.45 (m, 1H), 2.78 (m, 1H), 2.61 (s, 3H), 2.46 (s, 3H).

Example 157

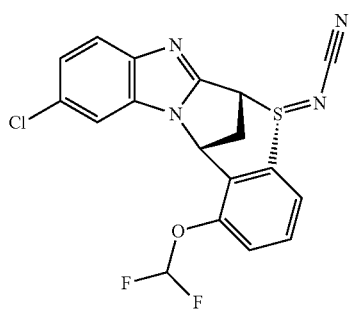 [SMILES: N#C/N=[S@@]1/c2cccc(OC(F)F)c2[C@H]2C[C@@H]1c1nc3ccc(Cl)cc3n12]

[(6R,7E,12R)-2-chloro-11-(difluoromethoxy)-6H-6,12-methano-7λ-4-benzimidazo[2,1-c][1,4]benzothiazepin-7(12H)-ylidene]cyanamide To a solution of Example 88 (200 mg, 0.55 mmol) and cyanamide (34 mg, 0.81 mmol) in acetonitrile (5 mL) at 0° C., was added iodobenzene diacetate (388 mg, 1.21 mmol). The reaction was stirred for 3 hours at 0° C. The solvent was evaporated and the crude mixture was purified by column chromatography on silica gel, hexane:EtOAc (0 to 100%) to give the title compound (145 mg) as a yellow solid. LC/MS Method 3: RT 1.98 mins, [M+H]$^+$=405. $^1$H NMR (300 MHz, DMSO-d$^6$) δ 7.75-7.62 (m, 3H), 7.57 (t, J=73.1 Hz, 1H), 7.68-7.50 (m, 1H), 7.43 (d, J=2.1 Hz, 1H), 7.27 (dd, J=8.7, 2.1 Hz, 1H), 6.24 (t, J=2.9 Hz, 1H), 5.85 (dd, J=3.2, 2.1 Hz, 1H), 3.60 (t, J=3.5 Hz, 2H).

Example 158

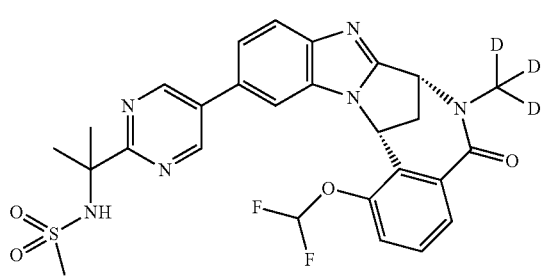 [SMILES: [2H]C([2H])([2H])N1C(=O)c2cccc(OC(F)F)c2[C@H]2C[C@@H]1c1nc3ccc(-c4cnc(C(C)(C)NS(C)(=O)=O)nc4)cc3n12]

N-(2-{5-[(7R,14R)-1-(difluoromethoxy)-6-methyl-5-oxo-5,6,7,14-tetrahydro-7,14-methanobenzimidazo[1,2-b][2,5]benzodiazocin-11-yl]pyrimidin-2-yl}propan-2-yl)methanesulfonamide To a solution of Example 62 (350 mg, 0.66 mmol) cooled to 0° C. in DCM (5 mL) was added sequentially, 4-dimethylaminopyridine (0.1 equiv., 0.066 mmol), di-isopropylethylamine (2.2 equiv., 1.45 mmol) followed by drop wise addition of methane sulphonyl chloride (1.1 equiv., 0.73 mmol) and the mixture allowed to stir at ambient temperature for 2 hours. The reaction mixture was quenched by addition of water (20 mL), the organic phase separated, dried over sodium sulphate, filtered and the solvents removed in vacuo. The crude residue was purified by preparative HPLC to afford the title compound as an off white solid (200 mg).

$^1$H NMR (300 MHz, DMSO-d$^6$) δ 9.08 (s, 2H), 8.27 (t, J=4.7 Hz, 1H), 8.01-7.72 (m, 2H), 7.71-7.59 (m, 1H), 7.57-7.35 (m, 3H), 6.31 (d, J=7.1 Hz, 1H), 5.25 (d, J=7.1 Hz, 1H), 3.53 (dt, J=14.1, 7.3 Hz, 1H), 2.86 (m, 4H), 1.70 (s, 6H). LCMS Method 3 RT=1.85 minutes (M+H)$^+$ 572, LCMS Method 4 RT=1.79 minutes (M+H)$^+$ 572.

Example 159

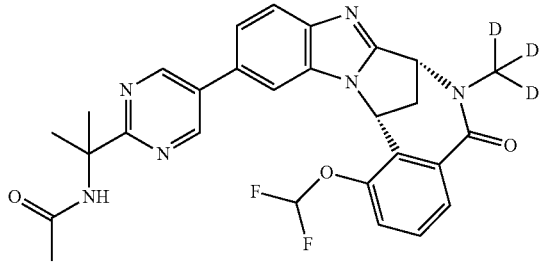 [SMILES: [2H]C([2H])([2H])N1C(=O)c2cccc(OC(F)F)c2[C@H]2C[C@@H]1c1nc3ccc(-c4cnc(C(C)(C)NC(C)=O)nc4)cc3n12]

N-(2-{5-[(7R,14R)-1-(difluoromethoxy)-6-methyl-5-oxo-5,6,7,14-tetrahydro-7,14-methanobenzimidazo[1,2-b][2,5]benzodiazocin-11-yl]pyrimidin-2-yl}propan-2-yl)acetamide The title compound was synthesised from Example 62 (350 mg, 0.66 mmol) and acetyl chloride (1.1 eq, 0.73 mmol) in accordance with the Method described for Example 158. Purification by preparative HPLC gave an off white solid (50 mg). $^1$H NMR (300 MHz, DMSO-d$^6$) δ 8.99 (s, 2H), 8.39-8.13 (m, 2H), 8.01-7.66 (m, 3H), 7.61 (dd, J=8.5, 1.8 Hz, 1H), 7.53-7.41 (m, 2H), 6.30 (d, J=7.1 Hz, 1H), 5.25 (d, J=7.1 Hz, 1H), 3.53 (dt, J=14.1, 7.3 Hz, 1H), 2.84 (d, J=13.8 Hz, 1H), 1.80 (s, 3H), 1.60 (s, 6H). LCMS Method 4 RT=1.62 minutes 536 (M+H)$^+$. LCMS Method 3 RT=1.68 minutes 536 (M+H)$^+$

Example 160

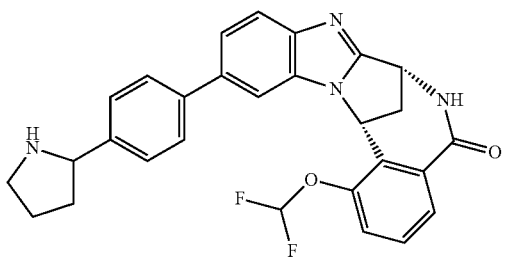 [SMILES: O=C1N[C@@H]2C[C@H](c3c(OC(F)F)cccc31)n1c2nc2ccc(-c3ccc(C4CCCN4)cc3)cc21]

(7R,14R)-1-(difluoromethoxy)-11-[4-(pyrrolidin-2-yl)phenyl]-6,7-dihydro-7,14-methanobenzimidazo[1,2-b][2,5]benzodiazocin-5(14H)-one Intermediate 182 (275 mg, 0.42 mmol) was dissolved in HCl/dioxane (4M) (10 mL) and stirred for 3 hrs at room temperature. After this time the solution was evaporated in vacuo. The mixture was separated between DCM (20 mL) and aqueous HCl (0.5M) (20 mL) and the DCM layer was discarded. The aqueous layer was then made basic with sodium carbonate solution and then extracted into DCM (2×50 mL) and the combined organics were dried (phase separator) and evaporated in vacuo. to provide the title compound as the HCl salt (90 mg, 44%). $^1$H NMR (300 MHz, DMSO-$d_6$) δ 9.13 (d, J=6.8 Hz, 1H), 8.23 (dd, J=5.9, 3.6 Hz, 1H), 7.70-7.61 (m, 2H), 7.60-7.37 (m, 7H), 6.33 (d, J=7.0 Hz, 1H), 4.87 (t, J=6.7 Hz, 1H), 4.06 (t, J=7.6 Hz, 1H), 3.48 (dt, J=13.5, 7.2 Hz, 1H), 3.11-2.82 (m, 1H), 2.73 (d, J=13.4 Hz, 1H), 2.14 (dtd, J=12.1, 7.5, 4.8 Hz, 1H), 1.77 (dq, J=13.2, 7.8, 7.4 Hz, 1H), 1.60-1.41 (m, 1H), 0.91-0.76 (m, 1H).
LC/MS Method 3: RT 1.76 minutes, m/z 487.2

Example 161

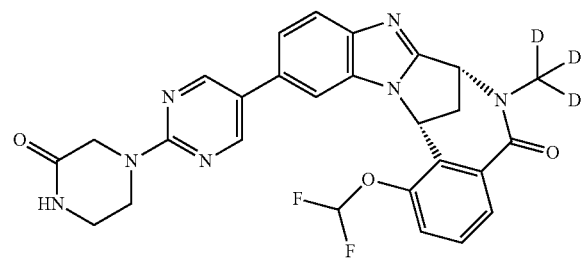 [SMILES: [2H]C([2H])([2H])N1C(=O)c2cccc(OC(F)F)c2[C@H]2C[C@@H]1c1nc3ccc(-c4cnc(N5CCNC(=O)C5)nc4)cc3n12]

(7R,14R)-1-(difluoromethoxy)-6-trideutero-methyl-11-[2-(3-oxopiperazin-1-yl)pyrimidin-5-yl]-6,7-dihydro-7,14-methanobenzimidazo[1,2-b][2,5]benzodiazocin-5(14H)-one The title compound was prepared from Intermediate 110 (350 mg, 0.89 mmol) and [2-(3-oxopiperazin-1-yl)pyrimidin-5-yl]boronic acid (296 mg, 1.33 mmol) in accordance with the Method described for Example 20. The product was purified by crystallisation from EtOAc to afford the title compound (245 mg, 51%). $^1$H NMR (300 MHz, DMSO-$d_6$) δ 8.69 (s, 2H), 8.26 (dd, J=6.2, 3.2 Hz, 1H), 8.14 (s, 1H), 7.70 (d, J=8.5 Hz, 2H), 7.60 (d, J=1.7 Hz, 1H), 7.56-7.41 (m, 3H), 6.28 (d, J=7.1 Hz, 1H), 5.23 (d, J=7.1 Hz, 1H), 4.22 (s, 2H), 3.96 (t, J=5.4 Hz, 2H), 3.60-3.42 (m, 2H), 3.30 (s, 1H), 2.82 (d, J=13.7 Hz, 1H). LC/MS Method 3: RT 1.50 minutes, m/z 535.2

Example 162

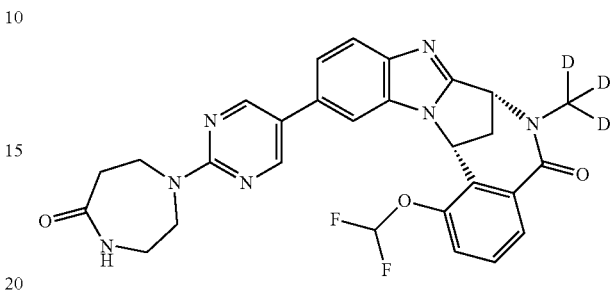

(7R,14R)-1-(difluoromethoxy)-6-methyl-11-[2-(5-oxo-1,4-diazepan-1-yl)pyrimidin-5-yl]-6,7-dihydro-7,14-methanobenzimidazo[1,2-b][2,5]benzodiazocin-5(14H)-one The title compound was prepared from Intermediate 110 (350 mg, 0.89 mmol) and [2-(5-oxo-1,4-diazepan-1-yl)pyrimidin-5-yl]boronic acid (315 mg, 1.33 mmol) in accordance with the Method described for Example 20. Purification by flash chromatography on silica gel (0 to 10% gradient of MeOH in DCM) and then crystallisation from EtOAc afforded the title compound (245 mg, 51%). $^1$H NMR (300 MHz, DMSO-$d_6$) δ 8.67 (s, 2H), 8.27 (dd, J=5.9, 3.5 Hz, 1H), 7.76-7.65 (m, 2H), 7.60 (d, J=1.7 Hz, 1H), 7.56-7.40 (m, 3H), 6.27 (d, J=7.1 Hz, 1H), 5.22 (d, J=7.1 Hz, 1H), 3.97 (q, J=4.3, 3.8 Hz, 4H), 3.50 (dt, J=14.1, 7.2 Hz, 1H), 3.24 (d, J=6.9 Hz, 2H), 2.82 (d, J=13.8 Hz, 1H), 2.54 (s, 2H). LC/MS Method 3: RT 1.63 minutes, m/z 549.2

Example 163

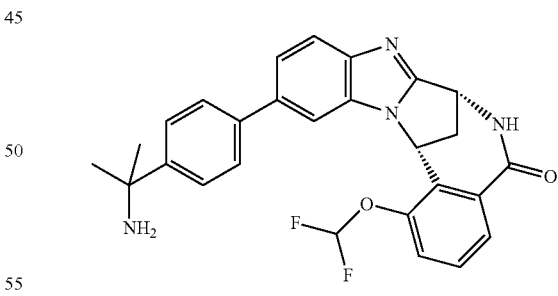

(7R,14R)-11-[4-(2-aminopropan-2-yl)phenyl]-1-(difluoromethoxy)-6,7-dihydro-7,14-methanobenzimidazo[1,2-b][2,5]benzodiazocin-5(14H)-one Intermediate 182(a) (0.10 g, 0.13 mmol) (75% pure) was dissolved in HCl dioxane (4M, 10 mL) and stirred for 18 hrs at r.t. and before being evaporated in vacuo. The mixture was separated between DCM (20 mL) and sodium carbonate (20 mL) and the organic layer was then dried (phase separator) and evaporated in vacuo. Purification by flash chromatography on silica gel (0 to 10% gradient of MeOH in DCM) and freeze drying from HCl (0.5M) to obtain the HCl salt of the title compound as a white powder. (36 mg, 58%). $^1$H NMR (300 MHz, DMSO-$d_6$) δ 9.13 (d, J=6.8 Hz, 1H), 8.23 (dd, J=6.0, 3.5 Hz, 1H), 7.72-7.54 (m, 5H), 7.59-7.32 (m, 7H), 6.34 (d, J=7.1 Hz, 1H), 4.87 (t, J=6.7 Hz, 1H), 3.60-3.43 (m, 1H), 2.73 (d, J=13.2 Hz, 1H), 1.44 (s, 6H), 1.24 (s, 1H).

LC/MS Method 3: RT 1.80 minutes, m/z 475.2

Example 164

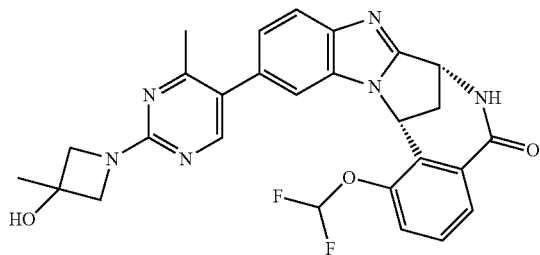 [SMILES: Cc1nc(N2CC(C)(O)C2)ncc1-c1ccc2nc3n(c2c1)[C@@H]1C[C@H]3NC(=O)c2cccc(OC(F)F)c21]

(7R,14R)-1-(difluoromethoxy)-11-[2-(3-hydroxy-3-methylazetidin-1-yl)-4-methylpyrimidin-5-yl]-6,7-dihydro-7,14-methanobenzimidazo[1,2-b][2,5]benzodiazocin-5(14H)-one The title compound can be prepared from Intermediate 171 (0.35 g, 0.93 mmol, 1 eq) and 1-(5-bromo-4-methyl-pyrimidin-2-yl)-3-methyl-azetidin-3-ol (1 eq) in accordance with the Method described for Example 137. The product was purified by column chromatography on silica gel (EtOAc in DCM (0 to 100% gradient) and then MeOH in EtOAc (0 to 15% gradient)) to afford the free base of the title compound as a brown solid. The solid could be further purified by dissolving into aqueous 0.5M HCl (20 mL) and then washing the aqueous solution with DCM (2×25 mL). Sodium carbonate solution was then added until precipitation was observed and the mixture extracted into DCM (3×50 mL). The organics were dried (phase separator) and evaporated in vacuo before being again dissolved into aqueous 0.5M HCl and freeze dried to afford the HCl salt of the title compound (215 mg, 42%). $^1$H NMR (300 MHz, DMSO-$d_6$) δ 9.14 (d, J=6.9 Hz, 1H), 8.23 (dd, J=5.8, 3.6 Hz, 1H), 8.15 (s, 1H), 7.71-7.45 (m, 4H), 7.41-7.27 (m, 1H), 7.17 (dd, J=8.4, 1.7 Hz, 1H), 6.31 (d, J=7.1 Hz, 1H), 4.90 (t, J=6.7 Hz, 1H), 3.93 (d, J=1.9 Hz, 4H), 3.60-3.32 (m, 1H), 2.74 (d, J=13.3 Hz, 1H), 2.26 (s, 3H), 1.45 (s, 3H).

LC/MS Method 3: RT 1.58 minutes, m/z 519.2.

Example 165

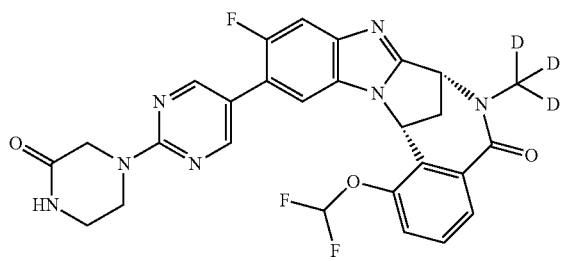 [SMILES: [2H]C([2H])([2H])N1C(=O)c2cccc(OC(F)F)c2[C@H]2C[C@@H]1c1nc3cc(F)c(-c4cnc(N5CCNC(=O)C5)nc4)cc3n12]

(7R,14R)-1-(difluoromethoxy)-10-fluoro-6-trideutero-methyl-11-[2-(3-oxopiperazin-1-yl)pyrimidin-5-yl]-6,7-dihydro-7,14-methanobenzimidazo[1,2-b][2,5]benzodiazocin-5(14H)-one Intermediate 187 (120 mg, 0.18 mmol) was suspended in 2-propanol (20 mL) and treated with hydrochloric acid (5 ml, 20 mmol, 4M in 1,4-dioxane) and stirred for 3 hours at ambient temperature. The solvent was removed in vacuo and the residual solid used without further purification.

The residue was suspended in acetonitrile (10 ml), cooled to 0° C. and 4-methylmorpholine (0.1 mL, 0.9 mmol) added followed by COMU (87 mg, 0.197 mmol) and the mixture allowed to stir and reach ambient temperature. After 1 hour the mixture was diluted with water (25 mL) and extracted into EtOAc (3×20 mL). Combined organics were washed with water (20 mL) and dried (Na$_2$SO$_4$), filtered and concentrated in vacuo to give a crude beige solid. Purification by column chromatography eluting with 0 to 100% DCM/EtOAc and then a gradient of DCM/MeOH 1 to 10% before freeze drying afforded the title compound as a white solid (46 mg, 47%). $^1$H NMR (300 MHz, DMSO-$d_6$) δ 8.56 (t, J=1.7 Hz, 2H), 8.27 (dd, J=7.0, 2.5 Hz, 1H), 8.15 (s, 1H), 7.66-7.56 (m, 2H), 7.56-7.35 (m, 3H), 6.27 (d, J=7.0 Hz, 1H), 5.24 (d, J=7.1 Hz, 1H), 4.23 (s, 2H), 3.96 (t, J=5.4 Hz, 2H), 3.50 (d, J=7.2 Hz, 1H), 3.31 (s, 2H), 2.82 (d, J=13.8 Hz, 1H). LC/MS Method 3: RT 1.52 minutes, m/z 553.2

General Method A: Suzuki Coupling Between Intermediate 171 and Aryl Bromides

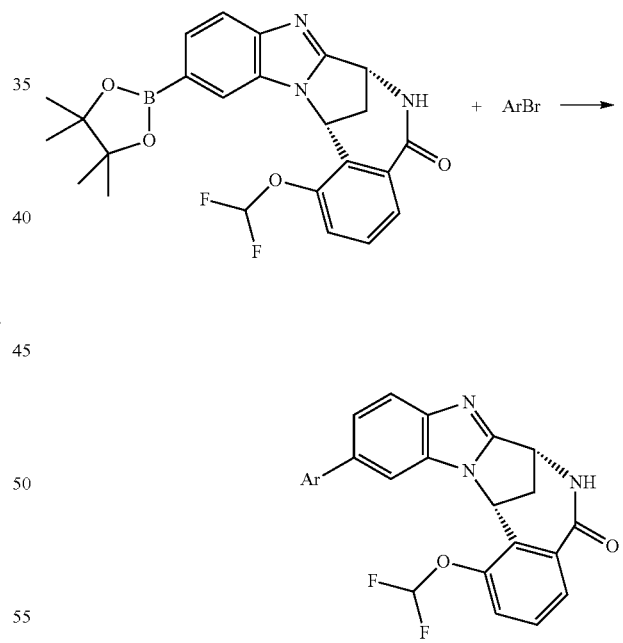

To a degassed suspension of Intermediate 171 (0.08 mmol), Pd$_2$dba$_3$ (5% mol), tricyclohexylphosphonium tetrafluoroborate (12% mol) and K$_3$PO$_4$ (2.5 eq) in 1,4-dioxane/water (2 ml/0.1 mL) was added the appropriate aryl bromide (1.5 eq). The resultant mixture was stirred in an Anton Paar microwave at 110° C. for 2 hours and then concentrated in vacuo. The residue was dissolved into EtOAc, washed with water, concentrated in vacuo and subsequently purified by preparative HPLC in basic mode to afford the title compounds described in Table 1.

TABLE 1

EXAMPLES 166 to 173

| Example | Structure | IUPAC_NAME | LCMS Method 4 Mass | RT (mins) |
|---|---|---|---|---|
| 166 | 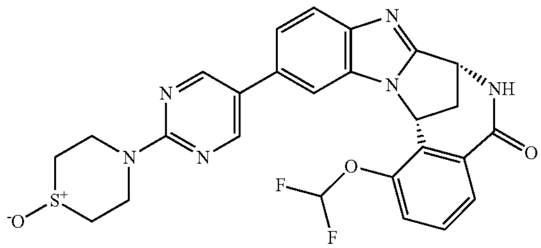 | (7R,14R)-1-(difluoromethoxy)-11-[2-(1-oxidothiomorpholin-4-yl)pyrimidin-5-yl]-6,7-dihydro-7,14-methanobenzimidazo[1,2-b][2,5]benzodiazocin-5(14H)-one | 537.1 | 3.6 |
| 167 | 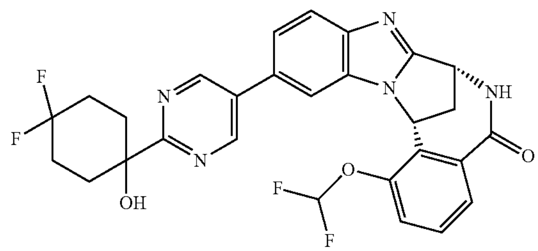 [SMILES: O=C1N[C@@H]2C[C@H](c3c(OC(F)F)cccc31)n1c2nc2ccc(-c3cnc(C4(O)CCC(F)(F)CC4)nc3)cc21] | (7R,14R)-11-[2-(4,4-difluoro-1-hydroxycyclohexyl)pyrimidin-5-yl]-1-(difluoromethoxy)-6,7-dihydro-7,14-methanobenzimidazo[1,2-b][2,5]benzodiazocin-5(14H)-one | 554.1 | 4.67 |
| 168 | 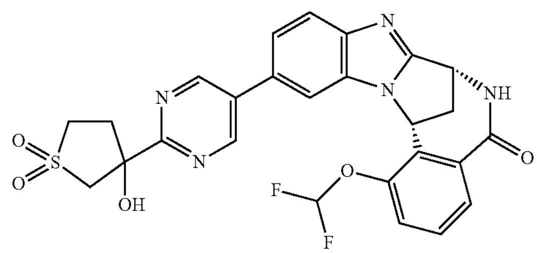 [SMILES: O=C1N[C@@H]2C[C@H](c3c(OC(F)F)cccc31)n1c2nc2ccc(-c3cnc(C4(O)CCS(=O)(=O)C4)nc3)cc21] | (7R,14R)-1-(difluoromethoxy)-11-[2-(3-hydroxy-1,1-dioxidotetrahydrothiophen-3-yl)pyrimidin-5-yl]-6,7-dihydro-7,14-methanobenzimidazo[1,2-b][2,5]benzodiazocin-5(14H)-one | 554.1 | 3.66 |
| 169 | 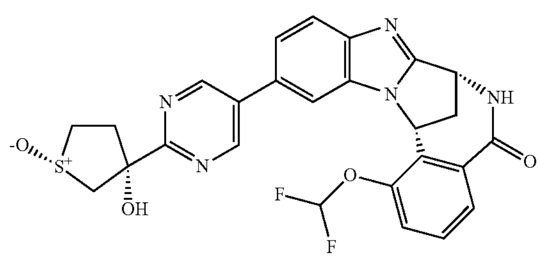 | (3R)-3-{5-[(7R,14R)-1-(difluoromethoxy)-5-oxo-5,6,7,14-tetrahydro-7,14-methanobenzimidazo[1,2-b][2,5]benzodiazocin-11-yl]pyrimidin-2-yl}-3-hydroxytetrahydrothiophenium-1-olate | 538.1 | 3.35 |
| 170 | 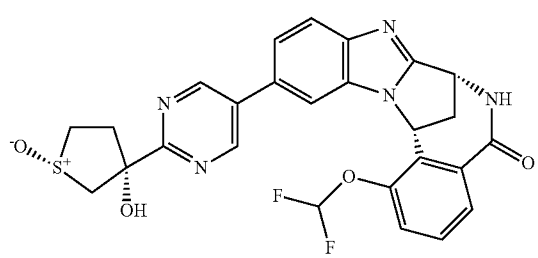 | (3S)-3-{5-[(7R,14R)-1-(difluoromethoxy)-5-oxo-5,6,7,14-tetrahydro-7,14-methanobenzimidazo[1,2-b][2,5]benzodiazocin-11-yl]pyrimidin-2-yl}-3-hydroxytetrahydrothiophenium-1-olate | 538.1 | 3.33 |

TABLE 1-continued

EXAMPLES 166 to 173

| Example | Structure | IUPAC_NAME | LCMS Method 4 Mass | RT (mins) |
|---|---|---|---|---|
| 171 | 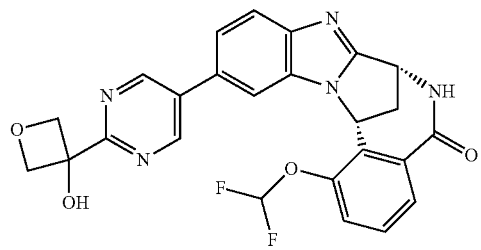 [SMILES: O=C1N[C@@H]2C[C@H](c3c(OC(F)F)cccc31)n1c2nc2ccc(-c3cnc(C4(O)COC4)nc3)cc21] | (7R,14R)-1-(difluoromethoxy)-11-[2-(3-hydroxyoxetan-3-yl)pyrimidin-5-yl]-6,7-dihydro-7,14-methanobenzimidazo[1,2-b][2,5]benzodiazocin-5(14H)-one | 492.1 | 3.58 |
| 172 | 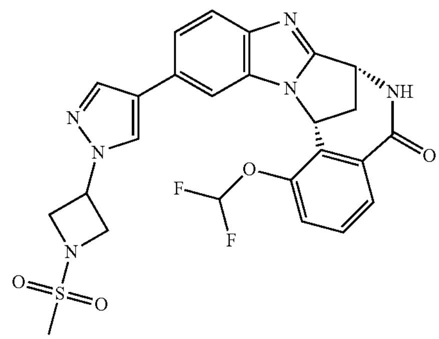 [SMILES: CS(=O)(=O)N1CC(n2cc(-c3ccc4nc5n(c4c3)[C@@H]3C[C@H]5NC(=O)c4cccc(OC(F)F)c43)cn2)C1] | (7R,14R)-1-(difluoromethoxy)-11-{1-[1-(methylsulfonyl)azetidin-3-yl]-1H-pyrazol-4-yl}-6,7-dihydro-7,14-methanobenzimidazo[1,2-b][2,5]benzodiazocin-5(14H)-one | 541.1 | 3.8 |
| 173 | 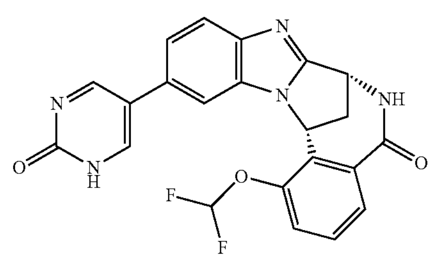 [SMILES: O=C1N[C@@H]2C[C@H](c3c(OC(F)F)cccc31)n1c2nc2ccc(-c3cnc(=O)[nH]c3)cc21] | (7R,14R)-1-(difluoromethoxy)-11-(2-hydroxypyrimidin-5-yl)-6,7-dihydro-7,14-methanobenzimidazo[1,2-b][2,5]benzodiazocin-5(14H)-one | 436.1 | 3.06 |

General Method B: Suzuki Coupling Between Example 11 and Aryl Boronic Acids

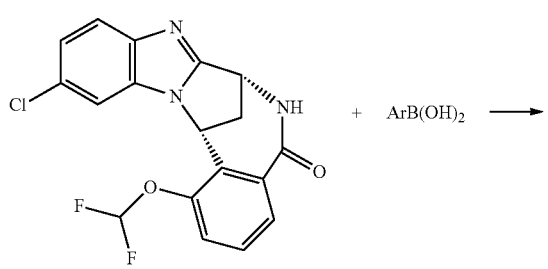

+ ArB(OH)$_2$ ⟶

-continued

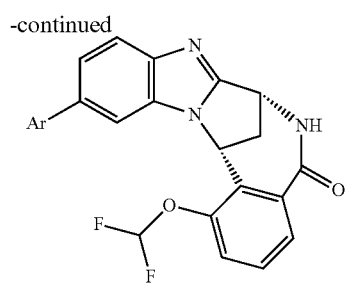

To a degassed suspension of Example 11 (0.1 mmol), Pd$_2$dba$_3$ (5% mol), tricyclohexylphosphonium tetrafluoroborate (12% mol) and K$_3$PO$_4$ (2.5 eq) in 1,4-dioxane/water (2 ml/0.1 mL) was added the appropriate aryl boronic acid or pinacolato ester (1.5 eq). The resultant mixture was stirred in an Anton Paar microwave at 110° C. for 2 hours and then concentrated in vacuo. The residue was dissolved into EtOAc, washed with water, concentrated in vacuo and subsequently purified by preparative HPLC in basic mode to afford the title compounds described in Table 2.

TABLE 2

EXAMPLES 174 to 185

| Example | Structure | IUPAC_NAME | LCMS Method 4 Mass | RT (mins) |
|---|---|---|---|---|
| 174 | 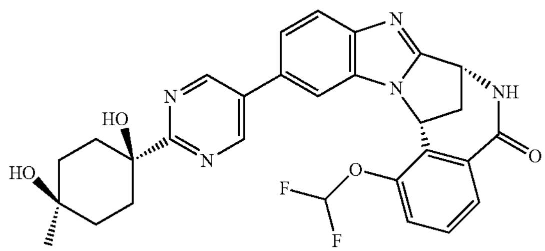 [SMILES: C[C@]1(O)CC[C@](O)(c2ncc(-c3ccc4nc5n(c4c3)[C@@H]3C[C@H]5NC(=O)c4cccc(OC(F)F)c43)cn2)CC1] | (7R,14R)-1-(difluoro-methoxy)-11-[2-(1,4-dihydroxy-4-methyl-cyclohexyl)pyrimidin-5-yl]-6,7-dihydro-7,14-methanobenzimidazo[1,2-b][2,5]benzo-diazocin-5(14H)-one | 548.2 | 3.88 |
| 175 | 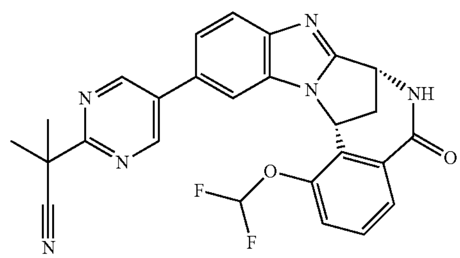 [SMILES: CC(C)(C#N)c1ncc(-c2ccc3nc4n(c3c2)[C@@H]2C[C@H]4NC(=O)c3cccc(OC(F)F)c32)cn1] | 2-{5-[(7R,14R)-1-(difluoromethoxy)-5-oxo-5,6,7,14-tetrahydro-7,14-methanobenz-imidazo[1,2-b][2,5]benzodiazocin-11-yl]pyrimidin-2-yl}-2-methylpropanenitrile | 487.2 | 4.49 |
| 176 | 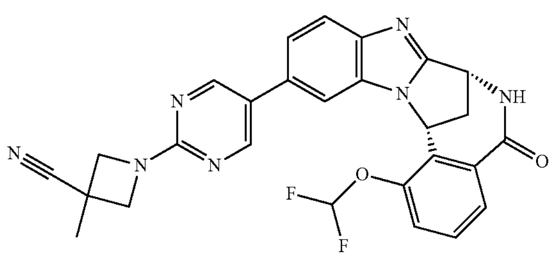 [SMILES: CC1(C#N)CN(c2ncc(-c3ccc4nc5n(c4c3)[C@@H]3C[C@H]5NC(=O)c4cccc(OC(F)F)c43)cn2)C1] | 1-{5-[(7R,14R)-1-(difluoromethoxy)-5-oxo-5,6,7,14-tetrahydro-7,14-methanobenz-imidazo[1,2-b][2,5]benzodiazocin-11-yl]pyrimidin-2-yl}-3-methylazetidine-3-carbonitrile | 514.2 | 4.18 |
| 177 | 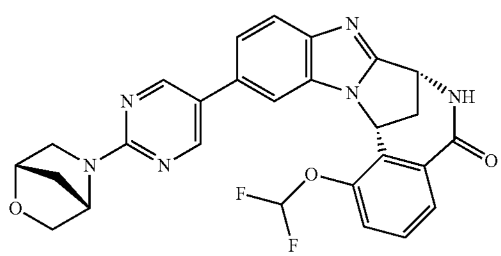 [SMILES: O=C1N[C@@H]2C[C@H](c3c(OC(F)F)cccc31)n1c2nc2ccc(-c3cnc(N4C[C@@H]5C[C@H]4CO5)nc3)cc21] | (7R,14R)-1-(difluoro-methoxy)-11-{2-[(1S,4S)-2-oxa-5-azabicyclo[2.2.1]hept-5-yl]pyrimidin-5-yl}-6,7-dihydro-7,14-methanobenzimidazo[1,2-b][2,5]benzo-diazocin-5(14H)-one | 517.1 | 3.94 |
| 178 | 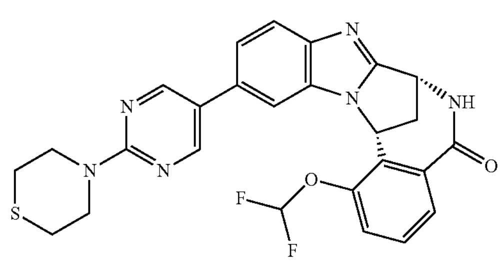 [SMILES: O=C1N[C@@H]2C[C@H](c3c(OC(F)F)cccc31)n1c2nc2ccc(-c3cnc(N4CCSCC4)nc3)cc21] | (7R,14R)-1-(difluoro-methoxy)-11-[2-(thiomorpholin-4-yl)pyrimidin-5-yl]-6,7-dihydro-7,14-methanobenzimidazo[1,2-b][2,5]benzo-diazocin-5(14H)-one | 521.1 | 4.86 |

TABLE 2-continued

EXAMPLES 174 to 185

| | | | LCMS Method 4 | |
|---|---|---|---|---|
| Example | Structure | IUPAC_NAME | Mass | RT (mins) |
| 179 | | (7R,14R)-1-(difluoromethoxy)-11-{2-[3-(2-hydroxypropan-2-yl)azetidin-1-yl]pyrimidin-5-yl}-6,7-dihydro-7,14-methanobenzimidazo[1,2-b][2,5]benzodiazocin-5(14H)-one | 533.2 | 3.86 |
| 180 | | (7R,14R)-11-[2-(3,3-difluoroazetidin-1-yl)pyrimidin-5-yl]-1-(difluoromethoxy)-6,7-dihydro-7,14-methanobenzimidazo[1,2-b][2,5]benzodiazocin-5(14H)-one | 511.1 | 4.47 |
| 181 | | (7R,14R)-1-(difluoromethoxy)-11-[2-(3-oxa-8-azabicyclo[3.2.1]oct-8-yl)pyrimidin-5-yl]-6,7-dihydro-7,14-methanobenzimidazo[1,2-b][2,5]benzodiazocin-5(14H)-one | 531.2 | 4.39 |
| 182 | | (7R,14R)-1-(difluoromethoxy)-11-[2-(7-oxo-3,6-diazabicyclo[3.2.2]non-3-yl)pyrimidin-5-yl]-6,7-dihydro-7,14-methanobenzimidazo[1,2-b][2,5]benzodiazocin-5(14H)-one | 558.2 | 3.73 |
| 183 | | (7R,14R)-1-(difluoromethoxy)-11-[2-(1,1-dioxidothiomorpholin-4-yl)pyrimidin-5-yl]-6,7-dihydro-7,14-methanobenzimidazo[1,2-b][2,5]benzodiazocin-5(14H)-one | 553.1 | 4.02 |

TABLE 2-continued

EXAMPLES 174 to 185

| Example | Structure | IUPAC_NAME | LCMS Method 4 Mass | RT (mins) |
|---|---|---|---|---|
| 184 | 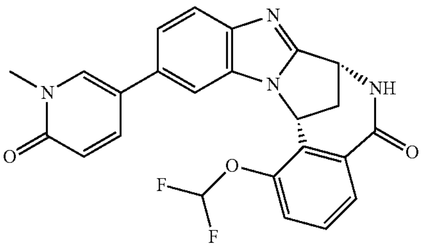 [SMILES: Cn1cc(-c2ccc3nc4n(c3c2)[C@@H]2C[C@H]4NC(=O)c3cccc(OC(F)F)c32)ccc1=O] | (7R,14R)-1-(difluoro-methoxy)-11-(1-methyl-6-oxo-1,6-dihydropyridin-3-yl)-6,7-dihydro-7,14-methanobenzimidazo[1,2-b][2,5]benzo-diazocin-5(14H)-one | 449.1 | 3.48 |
| 185 | 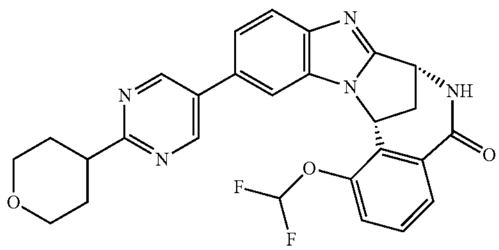 | (7R,14R)-1-(difluoro-methoxy)-11-[2-(tetrahydro-2H-pyran-4-yl)pyrimidin-5-yl]-6,7-dihydro-7,14-methanobenzimidazo[1,2-b][2,5]benzo-diazocin-5(14H)-one | 504.1 | 4.05 |

Example 186

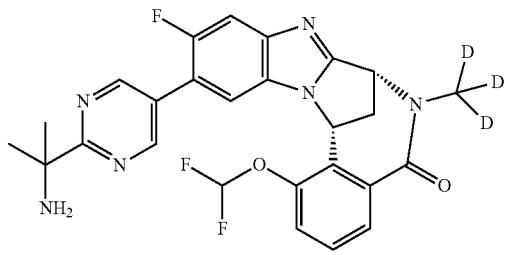 [SMILES: [2H]C([2H])([2H])N1C(=O)c2cccc(OC(F)F)c2[C@H]2C[C@@H]1c1nc3cc(F)c(-c4cnc(C(C)(C)N)nc4)cc3n12]

(7R,14R)-11-[2-(2-aminopropan-2-yl)pyrimidin-5-yl]-1-(difluoromethoxy)-10-fluoro-6-trideutero methyl-6,7-dihydro-7,14-methanobenzimidazo[1,2-b][2,5]benzodiazocin-5(14H)-one Intermediate 191 (420 mg, 0.70 mmol) was dissolved in HCl (4M in 1,4-dioxane) 10 mL and stirred for 3 hours at room temperature. After 3 hours the solution was concentrated in vacuo.

The mixture was separated between DCM and aqueous HCl (0.5M) and the DCM layer was discarded. The aqueous layer was then made basic with sodium carbonate solution and then extracted with DCM (3×50 mL) and the combined organics were dried (MgSO$_4$), filtered and evaporated in vacuo. The product was purified by column chromatography on silica eluting with 0 to 15% MeOH in DCM to afford an off-white solid. The compound was freeze dried with an equivalent of hydrochloric acid to afford the title compound as an HCl salt (275 mg, 72%).

$^1$H NMR (400 MHz, DMSO-d$_6$) δ 9.10 (d, J=1.6 Hz, 2H), 8.61 (bs, 3H, NH$_3^+$), 8.29 (dd, J=7.5, 1.9 Hz, 1H), 7.82-7.70 (m, 1H), 7.60 (d, J=6.7 Hz, 2H), 7.57-7.45 (m, 2H), 6.29 (d, J=7.1 Hz, 1H), 5.29 (d, J=7.2 Hz, 1H), 3.54 (dt, J=14.0, 7.5 Hz, 1H), 2.86 (d, J=13.8 Hz, 1H), 1.70 (s, 6H). LC/MS Method 3: RT 1.67 minutes, m/z 512.2

Example 187

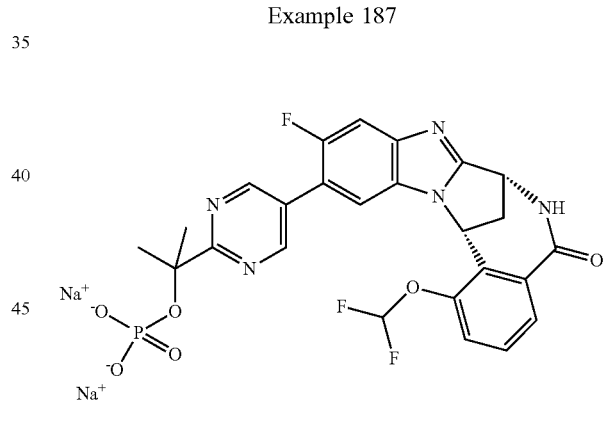

2-{5-[(7R,14R)-1-(difluoromethoxy)-10-fluoro-5-oxo-5,6,7,14-tetrahydro-7,14-methanobenzimidazo[1,2-b][2,5]benzodiazocin-11-yl]pyrimidin-2-yl}propan-2-yl phosphate, disodium salt To a solution of Intermediate 192 (31.0 g, 41.0 mmol) in a mixture of ethanol (450 mL) and sodium hydroxide (410 mL, 82.0 mmol, 0.200 mol/L) was added 10% Pd/C (3.10 g). The reaction mixture was degassed under vacuum and placed under a hydrogen atmosphere using a balloon. The reaction mixture was stirred vigorously until LCMS analysis showed the reaction was complete. It was necessary to add a further portion of Pd/C catalyst (775 mg, 2.5% w/w) after 1 hour and the mixture stirred under hydrogen for a further 30 minutes. The reaction mixture was degassed with nitrogen, filtered through a pad of celite which was washed with EtOH/H$_2$O (1/1, 1000 mL), collecting the colourless eluent. The ethanol was removed in vacuo and the aqueous reduced to ~400 mL volume in vacuo. The aqueous was washed with dichloromethane (3×250 mL) which was discarded, before further concentrating the aqueous solution in vacuo to a 200 mL volume. The aqueous layer was stirred with phosphonics MTU resin (15 g) for 2.5 hours to remove palladium residues. After filtration to remove the resin, the aqueous was concentrated down to ~100 mL in vacuo and then freeze dried to give the title compound as a white solid (23.15 g, 91%). $^1$H NMR: (D$_2$O, 300 MHz) 1.76 (s, 6H), 2.61 (d, 1H, J=13.6 Hz), 3.16 (m, 1H), 4.83 (d, 1H, J=6.5 Hz), 6.19 (d, 1H, J=7.0 Hz), 6.84 (m, 1H), 7.05 (t, 1H, J=73.3 Hz) 7.12 (m, 1H), 7.30 (m, 2H), 7.93 (dd, 1H, J=8.2, 0.9 Hz), 8.56 (d, 2H, J=1.2 Hz). LC/MS Method 3: RT 1.00 minutes, m/z 576.

Example 188

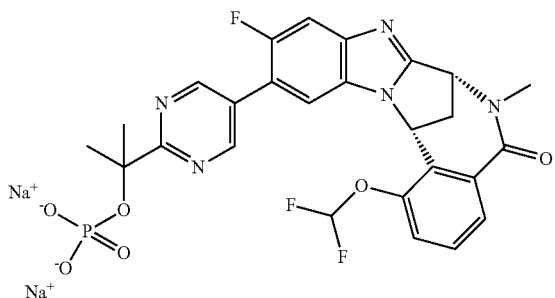

2-{5-[(7R,14R)-1-(difluoromethoxy)-10-fluoro-6-methyl-5-oxo-5,6,7,14-tetrahydro-7,14-methanobenzimidazo[1,2-b][2,5]benzodiazocin-11-yl]pyrimidin-2-yl}propan-2-yl phosphate, disodium salt To a solution of Intermediate 193 (3.2 g, 4.2 mmol) in a mixture of ethanol (60 mL) and sodium hydroxide solution (330 mg in 42 mL of water) was added 10% Pd/C (480 mg). The reaction was degassed and placed under a hydrogen atmosphere, and stirred vigorously for 40 minutes before the reaction completed. The reaction mixture was filtered through a pad of celite, washed with EtOH/H$_2$O (1:1, 200 mL), and most of the EtOH was removed in vacuo. The aqueous was washed with DCM (5×50 mL) before being further concentrated in vacuo, and treated with MTU resin (1.5 g) to remove palladium impurities and stirred for 1.5 hours before filtration through a pad of celite. The water was removed in vacuo and further dried on freezer-drier to give the desired product as the disodium salt (2.43 g, 92%). $^1$H NMR (D$_2$O, 400 MHz) δ 8.65 (s, 2H), 8.01 (d, J=8.1 Hz, 1H), 7.43 (d, J=6.7 Hz, 1H), 7.3-6.9 (m, 4H), 6.16 (d, J=7.1 Hz, 1H), 5.04 (d, J=7.2 Hz, 1H), 3.34 (s, 3H), 3.27 (m, 1H), 2.67 (d, J=14.0 Hz, 1H), 1.76 (s, 6H). LC/MS Method 3: ES$^+$ (M+H)$^+$ 590, retention time 0.91 minutes.

Example 189

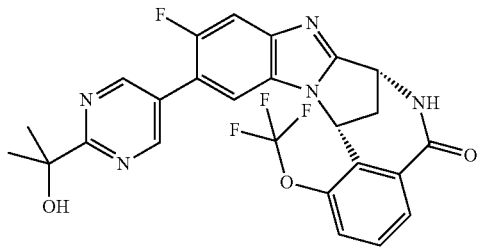 [SMILES: CC(C)(O)c1ncc(-c2cc3c(cc2F)nc2n3[C@@H]3C[C@H]2NC(=O)c2cccc(OC(F)(F)F)c23)cn1]

(7R,14R) 10-fluoro-11-[2-(2-hydroxypropan-2-yl)pyrimidin-5-yl]-1-(trifluoromethoxy)-6,7-dihydro-7,14-methanobenzimidazo[1,2-b][2,5]benzodiazocin-5(14H)-one A 0.6M solution of phenol in anhydrous DMSO (1.15 ml, 0.69 mmol) was added to a solution of Intermediate 206 (0.300 g, 0.57 mmol) in anhydrous DMSO (5 ml). Potassium carbonate (0.120 g, 0.86 mmol), dried 4 Å molecular sieves (0.360 g), dichloro-[bis(dicyclohexylphosphino)propane]palladium(II) (0.035 g, 0.057 mmol) were added and the reaction mixture was heated to 100° C. under 3 bars of carbon monoxide for 48 hours.

Water (50 ml) was added and the resulting mixture was extracted with EtOAc (1x 150 ml). The organic phase was then washed with brine (2×300 ml), dried over sodium sulfate, filtered and concentrated under reduced pressure. The resulting crude residue was purified by SiO$_2$ flash chromatography with DCM/MeOH (100/0 to 95/5) as eluent to give a brown solid. The solid was treated with iPr$_2$O (10 ml), filtered, and dried under reduced pressure at 45° C. to give the title compound (0.110 g, 37% yield).

LCMS (Method 20, ES+) RT 1.02 min., 514 [M+H]$^+$. $^1$H NMR (400 MHz, DMSO-d6) 1.55 (s, 6H), 2.82 (d, J=13.5 Hz, 1H), 3.51 (m, 1H), 4.95 (t, J=6.9 Hz, 1H), 5.15 (s, 1H), 6.32 (d, J=7.2 Hz, 1H), 7.42 (d, J=6.8 Hz, 1H), 7.58 (t, J=8.3 Hz, 1H), 7.69 (d, J=11.5 Hz, 1H), 7.72 (m, 1H), 8.38 (dd, J=1.3 and 8.3 Hz, 1H), 8.92 (d, J=1.8 Hz, 2H), 9.21 (d, J=6.9 Hz, 1H).

Example 190

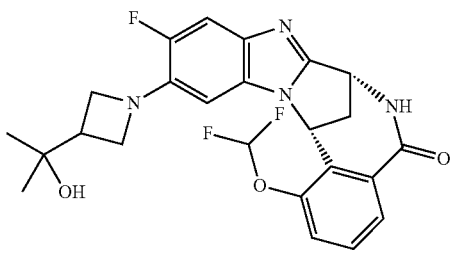 [SMILES: CC(C)(O)C1CN(c2cc3c(cc2F)nc2n3[C@@H]3C[C@H]2NC(=O)c2cccc(OC(F)F)c23)C1]

(7R,14R)-1-(difluoromethoxy)-10-fluoro-11-(3-(2-hydroxypropan-2-yl)azetidin-1-yl)-6,7-dihydro-7,14-methanobenzimidazo[1,2-b][2,5]benzodiazocin-5(14H)-one The title compound was prepared from Intermediate 208 (0.265 g, 0.55 mmol) in accordance with the synthetic procedure described for Example 191. Purification by SiO$_2$ flash chromatography with DCM/MeOH (100/0 to 95/5) as eluent to give a pink solid. This solid was treated with iPr$_2$O (10 ml) and the resulting suspension was filtered, and before being dried under reduced pressure at 45° C., the isolated solid was washed with iPr$_2$O (2×10 ml) and with pentane (3×10 ml) to give the title compound (0.082 g, 36% yield).

LCMS (Method 20, ES+) RT 0.88 min., 473 [M+H]$^+$. $^1$H NMR (400 MHz, DMSO-d6) 1.05 (s, 6H), 2.66 (d, J=13.5 Hz, 1H), 2.69 (m, 1H), 3.40 (m, 1H), 3.71-3.85 (m, 4H), 4.38 (s, 1H), 4.77 (t, J=6.9 Hz, 1H), 6.18 (d, J=7.2 Hz, 1H), 6.49 (d, J=8.3 Hz, 1H), 7.27 (d, J=13.2 Hz, 1H), 7.49 (m, 2H), 7.63 (t, J=74.3 Hz, 1H), 8.21 (m, 1H), 9.05 (d, J=6.9 Hz, 1H).

Example 191

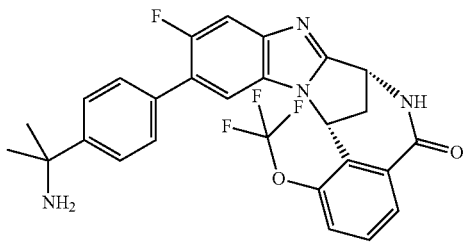 [SMILES: CC(C)(N)c1ccc(-c2cc3c(cc2F)nc2n3[C@@H]3C[C@H]2NC(=O)c2cccc(OC(F)(F)F)c23)cc1]

(7R,14R)-11-((2-aminopropan-2-yl)phenyl)-10-fluoro-1-(trifluoromethoxy)-6,7-dihydro-7,14-methanobenzimidazo[1,2-b][2,5]benzodiazocin-5(14H)-one The title compound was prepared from Intermediate 210 (0.195 g, 0.38 mmol) in accordance with the synthetic procedure described for Example 189 to give after purification by SiO$_2$ flash chromatography with DCM/MeOH/NH$_4$OH (100/0/0 to 94.5/5/0.5) as eluent followed flash chromatography on amino modified silica eluting with DCM/MeOH (100/0 to 98/8) as eluent and subsequent trituration with iPr$_2$O to give (0.055 g, 26% yield).

LCMS (Method 20, ES+) RT 0.65 min., 511 [M+H]$^+$. $^1$H NMR (400 MHz, DMSO-d6) 1.42 (s, 6H), 2.25 (broad m, 2H), 2.81 (d, J=13.5 Hz, 1H), 3.50 (m, 1H), 4.91 (t, J=6.9 Hz, 1H), 6.30 (d, J=7.2 Hz, 1H), 7.32 (d, J=7.0 Hz, 1H), 7.40 (broad d, J=8.5 Hz, 2H), 7.54 (d, J=12.0 Hz, 1H), 7.57 (t, J=8.3 Hz, 1H), 7.63 (d, J=8.5 Hz, 2H), 7.70 (broad d, J=8.3 Hz, 1H), 8.49 (dd, J=1.2 and 8.3 Hz, 1H), 9.20 (d, J=6.9 Hz, 1H).

Example 192

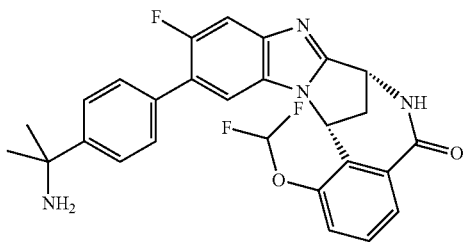 [SMILES: CC(C)(N)c1ccc(-c2cc3c(cc2F)nc2n3[C@@H]3C[C@H]2NC(=O)c2cccc(OC(F)F)c23)cc1]

(7R,14R)-11-((2-aminopropan-2-yl)phenyl)-1-(difluoromethoxy)-10-fluoro-6,7-dihydro-7,14-methanobenzimidazo[1,2-b][2,5]benzodiazocin-5(14H)-one The title compound was prepared from Intermediate 212 (0.240 g, 0.48 mmol) in accordance with the synthetic procedure described for Example 191. Purification by SiO$_2$ flash chromatography with DCM/MeOH/NH$_4$OH (100/0/0 to 94.5/5/0.5) as eluent gave a pink solid. This solid was purified with preparative HPLC using C18 Nucleodur gravity 250×4.6 mm Macherey-Nagel column and a gradient of acetonitrile (B) in water (A) containing 0.1% TFA (B/A 5/95 to 1/1 in 23 min, 1 ml/min) to afford the title compound (0.041 g, 17% yield).

LCMS (Method 20, ES+) RT 0.60 min., 493 [M+H]$^+$. $^1$H NMR (400 MHz, DMSO-d$_6$) 1.68 (s, 6H), 2.74 (d, J=13.5 Hz, 1H), 3.48 (m, 1H), 4.90 (t, J=6.9 Hz, 1H), 6.31 (d, J=7.2 Hz, 1H), 7.47-7.54 (m, 3H), 7.58 (t, J=73.4 Hz, 1H), 7.59 (m, 3H), 7.65 (d, J=8.5 Hz, 2H), 8,24 (m, 1H), 9.15 (d, J=6.9 Hz, 1H).

Example 193

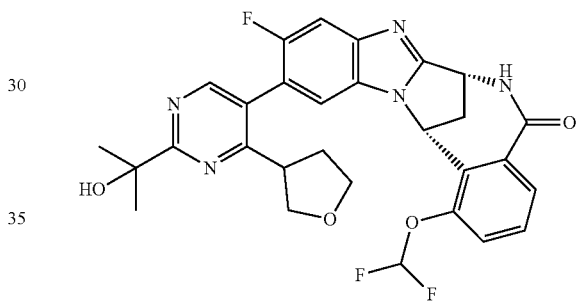

(7R,14R)-1-(difluoromethoxy)-10-fluoro-11-[2-(2-hydroxypropan-2-yl)-4-(tetrahydrofuran-3-yl)pyrimidin-5-yl]-6,7-dihydro-7,14-methanobenzimidazo[1,2-b][2,5]benzodiazocin-5(14H)-one The title compound was prepared from Example 1 (100 mg, 0,202 mmol), tetrahydrofuran-3-sulfonyl chloride (106 mg, 0,6026 mmol) and [Ir[DF(CF$_3$)PPY]$_2$(DTBPY)]PF$_6$ (4.5 mg, 0,0040 mmol) in acetonitrile/TFA (1/1) (2 mL), following the General procedure for the late stage trifluoromethylation described for Example 107. The crude reaction was purified by LC-2D MS chromatography in acidic mode (formic acid) Method 14 yielding to 6.6 mg (6%) of the title compound as a white solid. LCMS Method 15 (ES+) RT 5.23 min., 566 (M+H)+. $^1$H NMR (400 MHz, DMSO-d6) δ 9.05 (d, J=6.8 Hz, 1H), 8.62 (s, 1H), 8.26 (dd, J=6.3, 3.1 Hz, 1H), 7.62 (d, J=10.6 Hz, 1H), 7.53-7.47 (m, 2H), 7.46 (t, J=73.6 Hz, 1H), 7.36 (t, J=5.9 Hz, 1H), 6.34 (d, J=7.1 Hz, 1H), 5.04-4.77 (m, 2H), 4.02-3.80 (m, 2H), 3.80-3.60 (m, 2H), 3.52 (dd, J=13.8, 6.9 Hz, 1H), 3.42-3.27 (m, 1H), 2.75 (d, J=13.5 Hz, 1H), 2.28-2.08 (m, 1H), 2.07-1.90 (m, 1H), 1.57 (s, 6H).

Example 194

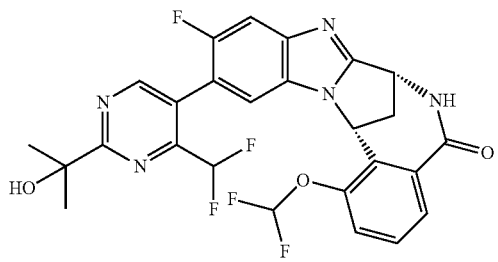 [SMILES: CC(C)(O)c1ncc(-c2cc3c(cc2F)nc2n3[C@@H]3C[C@H]2NC(=O)c2cccc(OC(F)F)c23)c(C(F)F)n1]

(7R,14R)-1-(difluoromethoxy)-11-[4-(difluoromethyl)-2-(2-hydroxypropan-2-yl)pyrimidin-5-yl]-10-fluoro-6,7-dihydro-7,14-methanobenzimidazo[1,2-b][2,5]benzodiazocin-5(14H)-one The title compound was prepared from Example 1 (100 mg, 0,202 mmol), difluoromethanesulfonyl chloride (54 μL, 0.61 mmol) and [IR[DF(CF$_3$)PPY]$_2$(DTBPY)]PF$_6$ (4.5 mg, 0,0040 mmol) in acetonitrile/TFA (1/1) (2 mL), following the General procedure for the late stage trifluoromethylation described for Example 107. The crude reaction was taken up in methanol (4 mL) before addition of potassium carbonate (170 mg, 1,218 mmol) and stirred at room temperature for 1 hour. The reaction mixture was filtered and concentrated under vacuum. The residue was purified by LC-2D MS chromatography Method 14 yielding to 13.7 mg (13%) of the title compound as a white solid. LCMS Method 15 (ES+) RT 5.40 min., 546 (M+H)$^+$. $^1$H NMR (400 MHz, DMSO-d6) δ 9.17 (d, J=6.8 Hz, 1H), 8.98 (s, 1H), 8.25 (dd, J=6.6, 2.1 Hz, 1H), 7.67 (d, J=10.3 Hz, 1H), 7.55-7.49 (m, 2H), 7.48 (t, J=73.1 Hz, 1H), 7.44 (d, J=6.5 Hz, 1H), 6.83 (t, J=53.0 Hz, 1H), 6.33 (d, J=7.0 Hz, 1H), 5.28 (s, 1H), 4.93 (t, J=6.6 Hz, 1H), 3.51 (dd, J=13.6, 7.0 Hz, 1H), 2.76 (d, J=13.4 Hz, 1H), 1.60 (s, 6H).

Example 195

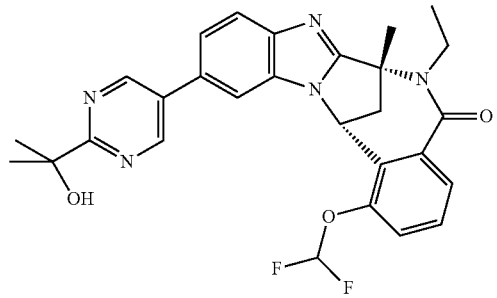 [SMILES: CCN1C(=O)c2cccc(OC(F)F)c2[C@H]2C[C@]1(C)c1nc3ccc(-c4cnc(C(C)(C)O)nc4)cc3n12]

(7R,14R)-1-(difluoromethoxy)-6-ethyl-11-[2-(2-hydroxypropan-2-yl)pyrimidin-5-yl]-7-methyl-6,7-dihydro-7,14-methanobenzimidazo[1,2-b][2,5]benzodiazocin-5(14H)-one The title compound was prepared from Intermediate 194 (5 mg, 0,012 mmol) and 2-(1-hydroxy-1-methylethyl)pyrimidine-5-boronic acid pinacol ester (6.58 mg, 0,024 mmol), following the synthetic protocol described for Example 101. Purification over silica gel (heptane/ethyl acetate 25/75 to 0/100) to afforded 3 mg (48%) of the title compound as an off-white solid. LCMS Method 3 (ES+): RT 2.32 min, [M+H]$^+$=520.2.

Example 196

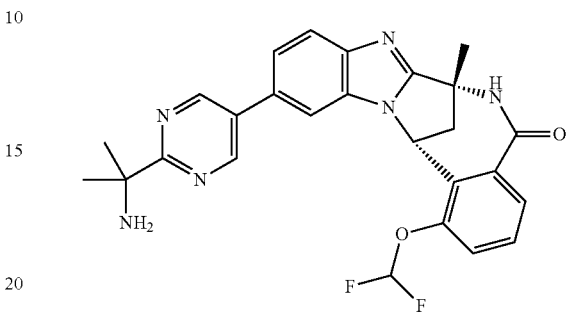

(7R,14R)-11-[2-(2-aminopropan-2-yl)pyrimidin-5-yl]-1-(difluoromethoxy)-7-methyl-6,7-dihydro-7,14-methanobenzimidazo[1,2-b][2,5]benzodiazocin-5(14H)-one Intermediate 150 (7 mg, 0.012 mmol) was added to a solution of DCM/trifluoroacetic acid (1:1, 0.17 mL). The reaction mixture was stirred at ambient temperature for 1 hour before addition of a saturated aqueous solution of NaHCO$_3$ (1 mL). The aqueous layer was extracted with DCM (2×2 mL). The combined organic layers were dried over MgSO$_4$, filtered and concentrated in vacuo, yielding 6 mg (100%) of the title compound as a white solid. LCMS Method 3 (ES+): RT 3.04 minutes, [M+H]+=491.

Example 197

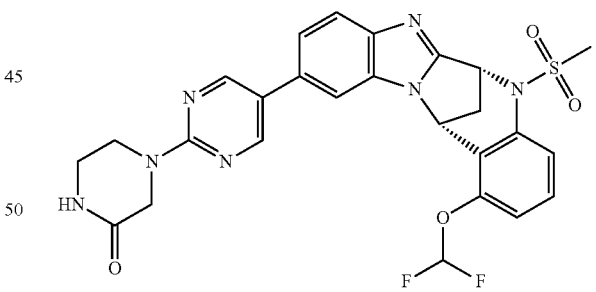

(7R,14R)-1-(difluoromethoxy)-11-(2-{2-[di(prop-2-en-1-yl)amino]propan-2-yl}pyrimidin-5-yl)-6,7-dihydro-7,14-methanobenzimidazo[1,2-b][2,5]benzodiazocin-5(14H)-one The title compound was prepared from [2-(3-oxopiperazin-1-yl)pyrimidin-5-yl]boronic acid pinacol ester, and Example 23 in accordance with General Method B to give, following purification by preparative HPLC, a white solid (30 mg, 15% yield). LC/MS Method 3: RT 1.84 mins (pH 10), [M+H]+=568. $^1$H NMR (300 MHz, DMSO-d6) δ 8.71 (s, 2H), 8.12 (s, 1H), 7.72 (d, J=8.6 Hz, 1H), 7.65-7.25 (m, 4H), 7.33 (t, J=8.5 Hz, 1H), 6.92 (d, J=8.2 Hz, 1H), 6.10 (d, J=4.3 Hz, 1H), 5.93 (d, J=3.9 Hz, 1H), 4.23 (s, 2H), 3.96 (t, J=5.4 Hz, 2H), 3.35-3.28 (m, 2H), 3.32-3.15 (m, 1H), 3.06 (s, 3H), 2.66 (d, J=12.2 Hz, 1H).

Example 198

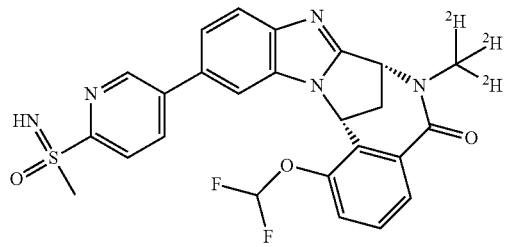 [SMILES: [2H]C([2H])([2H])N1C(=O)c2cccc(OC(F)F)c2[C@H]2C[C@@H]1c1nc3ccc(-c4ccc(S(C)(=N)=O)nc4)cc3n12]

(7R,14R)-1-(difluoromethoxy)-6-trideuteromethyl-11-[6-(S-methylsulfonimidoyl)pyridin-3-yl]-6,7-dihydro-7,14-methanobenzimidazo[1,2-b][2,5]benzodiazocin-5(14H)-one The title compound was prepared from Intermediate 159 (0.5 g, 1.03 mmol) in 1,4-dioxane (10 mL, 116 mmol) and N-[(5-bromopyridin-2-yl)(methyl)oxido-λ6-sulfanylidene]-2,2,2-trifluoroacetamide (0.42 g, 1.29 mmol) in accordance with General Method A. Purification by flash chromatography on silica in ethyl acetate/DCM (gradient from 0 to 100%) and then methanol in ethyl acetate (0 to 15%) gave the title compound as a white solid (50 mg, 9%). $^1$H NMR (400 MHz, DMSO-d6) δ 8.96 (d, J=2.2 Hz, 1H), 8.30 (m, 2H), 8.15 (d, J=8.2 Hz, 1H), 7.79 (m, 2H), 7.71-7.59 (m, 2H), 7.59-7.46 (m, 2H), 6.32 (d, J=7.1 Hz, 1H), 5.26 (d, J=7.2 Hz, 1H), 4.47 (s, 1H), 3.54 (dt, J=14.1, 7.2 Hz, 1H), 3.22 (d, J=1.1 Hz, 3H), 2.85 (d, J=13.8 Hz, 1H). LC/MS Method 3: RT 1.45 mins (pH 10), [M+H]+=513.2

Example 199

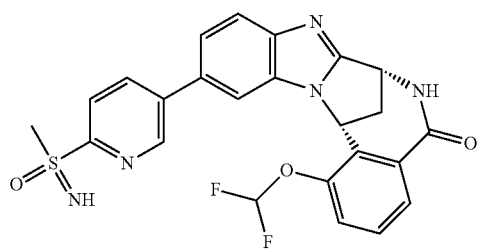 [SMILES: CS(=N)(=O)c1ccc(-c2ccc3nc4n(c3c2)[C@@H]2C[C@H]4NC(=O)c3cccc(OC(F)F)c32)cn1]

(7R,14R)-1-(difluoromethoxy)-11-[6-(S-methylsulfonimidoyl)pyridin-3-yl]-6,7-dihydro-7,14-methanobenzimidazo[1,2-b][2,5]benzodiazocin-5(14H)-one The title compound was prepared from Intermediate 171 (250 mg, 0.43 mmol) and, N-[(5-bromopyridin-2-yl)(methyl)oxido-λ6-sulfanylidene]-2,2,2-trifluoroacetamide (216 mg, 0.652 mmol), in accordance with General Method A. Purification by preparative HPLC gave the title compound (66 mg, 31%) as a white solid. LC/MS Method 3: ESI MH+496, retention time 0.76 minutes (pH 10). $^1$H NMR (300 MHz, DMSO-d$^6$) δ 9.15 (d, J=6.8 Hz, 1H), 8.96 (dd, J=2.3, 0.8 Hz, 1H), 8.31 (dd, J=8.3, 2.3 Hz, 1H), 8.23 (dd, J=5.8, 3.6 Hz, 1H), 8.14 (dd, J=8.3, 0.8 Hz, 1H), 7.95-7.66 (m, 3H), 7.61 (dd, J=8.6, 1.7 Hz, 1H), 7.55-7.47 (m, 2H), 6.38 (d, J=7.0 Hz, 1H), 4.91 (t, J=6.8 Hz, 1H), 4.47 (s, 1H), 3.50 (dt, J=13.6, 7.0 Hz, 1H), 3.21 (d, J=1.1 Hz, 3H), 2.76 (d, J=13.4 Hz, 1H).

Example 200

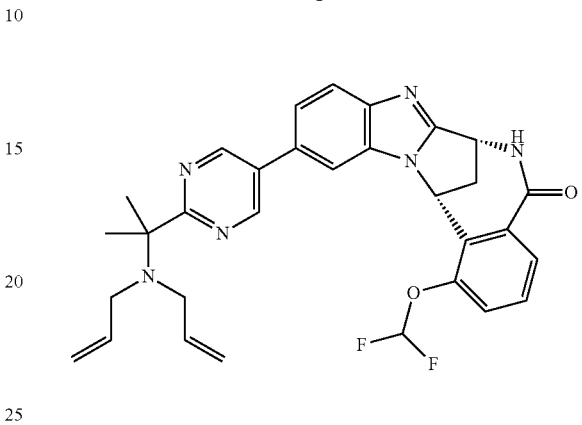

(7R,14R)-1-(difluoromethoxy)-11-(2-{2-[di(prop-2-en-1-yl)amino]propan-2-yl}pyrimidin-5-yl)-6,7-dihydro-7,14-methanobenzimidazo[1,2-b][2,5]benzodiazocin-5(14H)-one Intermediate 171 (400 mg, 0.86 mmol), Intermediate 213 (254 mg, 0.86 mmol), tris(dibenzylideneacetone)-dipalladium(0) (39.2 mg, 0.043 mmol) and tricyclohexylphosphonium tetrafluoroborate (32.5 mg, 0.086 mmol) were added to a microwave tube and dioxane (2.5 ml) was added, followed by potassium phosphate tribasic (562 mg, 2.57 mmol) dissolved in water (0.5 ml). The mixture was degassed and refilled with nitrogen then heated to 105° C. for 2 hours. The mixture was partitioned between ethyl acetate and water (50 ml) each. The organic layer was dried (sodium sulfate), filtered and concentrated in vacuo. Purification by flash chromatography (silica, 0 to 10% methanol in dichloromethane) afforded the title compound as an off-white solid (200 mg, 42% yield). LCMS Method 3 (ES+) RT 2.62 minutes, 557.2 (M+H)$^+$. $^1$H NMR (300 MHz, DMSO-d$^6$) δ 9.14 (d, J=6.8 Hz, 1H), 9.03 (s, 2H), 8.23 (dd, J=6.4, 3.1 Hz, 1H), 7.83-7.70 (m, 2H), 7.68 (t, J$_{H-F}$=73.4 Hz, 1H), 7.60 (dd, J=8.5, 1.8 Hz, 1H), 7.55-7.45 (m, 2H), 6.37 (d, J=7.1 Hz, 1H), 5.87-5.60 (m, 2H), 5.05 (dt, J=17.1, 1.8 Hz, 2H), 4.95-4.82 (m, 3H), 3.61-3.41 (m, 1H), 3.22 (dt, J=6.0, 1.6 Hz, 4H), 2.75 (d, J=13.4 Hz, 1H), 1.57 (s, 6H).

Example 201

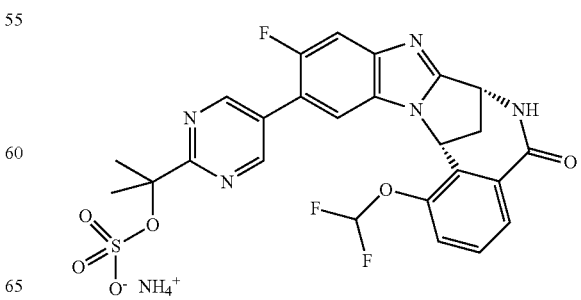

Ammonium 2-(5-((7R,14R)-1-(difluoromethoxy)-10-fluoro-5-oxo-5,6,7,14-tetrahydro-7,14-methano-benzo[f]benzo[4,5]imidazo[1,2-a][1,4]diazocin-11-yl)pyrimidin-2-yl)propan-2-yl sulfate A 4 mL reaction vial was charged with Example 1 (100 mg, 0.202 mmol), sulfur trioxide trimethylamine complex (56.2 mg, 0.404 mmol) and pyridine (1 mL). The vial was closed and heated at 130° C. for 20 hours. After cooling to room temperature, the mixture was concentrated under reduced pressure and the residue was purified by reverse phase HPLC (Reveleris Prep; Detection: UV (220 nm), Column: XSelect™ CSH C18, 145×25 mm, Flow: 40 mL/min, Gradient: to =5% B, $t_{1min}$=5% B, $t_{2min}$=20% B, $t_{17min}$=60% B, $t_{18min}$=100% B, Post time: 5 min 100% B, Eluent A: 10 mM ammoniumbicarbonate in water (pH=9.0), Eluent B: 99% acetonitrile+1% 10 mM ammoniumbicarbonate in water in acetonitrile) to afford the title compound (71 mg, 61%) as a white solid after lyophilisation of the product fractions.

LCMS (Method 9): RT=1.69 minutes; $[M-NH_4^+]^-$=574.
$^1$H NMR (400 MHz, DMSO-$d_6$) δ 9.15 (d, J=6.9 Hz, 1H), 8.88 (d, J=1.5 Hz, 2H), 8.23 (dd, J=7.7, 1.5 Hz, 1H), 7.66 (d, J=11.5 Hz, 1H), 7.63 (dd, J=72.2, J=1.6 Hz, 1H), 7.57-7.46 (m, 3H), 7.07 (bs, 4H), 6.36 (d, J=7.1 Hz, 1H), 4.91 (t, J=6.8 Hz, 1H), 3.54-3.44 (m, 1H), 2.75 (d, J=13.4 Hz, 1H), 1.75 (s, 6H).

Example 202

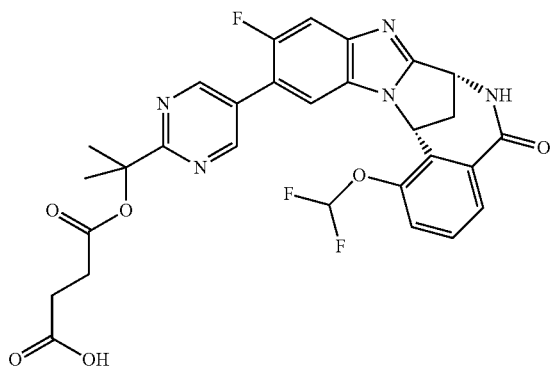 [SMILES: CC(C)(OC(=O)CCC(=O)O)c1ncc(-c2cc3c(cc2F)nc2n3[C@@H]3C[C@H]2NC(=O)c2cccc(OC(F)F)c23)cn1]

4-((2-(5-((7R,14R)-1-(difluoromethoxy)-10-fluoro-5-oxo-5,6,7,14-tetrahydro-7,14-methanobenzo[f]benzo[4,5]imidazo[1,2-a][1,4]diazocin-11-yl)pyrimidin-2-yl)propan-2-yl)oxy)-4-oxobutanoic acid A mixture of Example 1(1.5 g, 3.03 mmol), succinic anhydride (1.82 g, 18.2 mmol) and 4-dimethylaminopyridine (555 mg, 4.54 mmol) in acetonitrile (20 mL) was heated to reflux temperature for 6 days. After cooling to room temperature, the mixture was concentrated under reduced pressure. The residue was partitioned between aqueous HCl solution (1M) and EtOAc and the aqueous layer was extracted with EtOAc. The combined organic layers were washed with aqueous HCl solution (1M) and brine, dried over $Na_2SO_4$, filtered and concentrated under reduced pressure to afford a brown residue. The material was purified by flash column chromatography (silica (80 g); 5-10% MeOH in DCM) to afford the title compound (515 mg, 28%) as a white solid after trituration with $Et_2O$.

LCMS (Method 10): RT=3.09 minutes; $[M+H]^+$=596.
$^1$H NMR (400 MHz, DMSO-d6) δ 12.20 (bs, 1H), 9.16 (d, J=6.8 Hz, 1H), 8.92 (d, J=1.6 Hz, 2H), 8.23 (dd, J=6.8, 2.6 Hz, 1H), 7.67 (d, J=11.5 Hz, 1H), 7.62 (t, J=72.5 Hz, 1H), 7.57-7.47 (m, 3H), 6.35 (d, J=7.1 Hz, 1H), 4.91 (t, J=6.8 Hz, 1H), 3.54-3.44 (m, 1H), 2.75 (d, J=13.4 Hz, 1H), 2.58-2.47 (m, 2H, coincides with DMSO), 2.42 (t, J=6.7 Hz, 2H), 1.74 (s, 6H).

Example 203 and Example 204

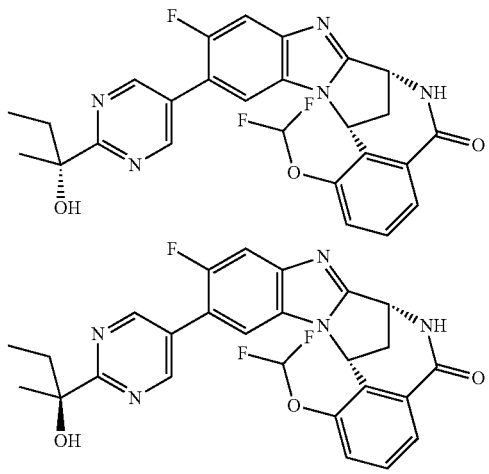

(7R,14R)-1-(difluoromethoxy)-10-fluoro-11-(2-((2R*)-hydroxybutan-2-yl)pyrimidin-5-yl)-6,7-dihydro-7,14-methanobenzo[f]benzo[4,5]imidazo[1,2-a][1,4]diazocin-5(14H)-one (7R,14R)-1-(difluoromethoxy)-10-fluoro-11-(2-((2S*)-hydroxybutan-2-yl)pyrimidin-5-yl)-6,7-dihydro-7,14-methanobenzo[f]benzo[4,5]imidazo[1,2-a][1,4]diazocin-5(14H)-one 1M Tetrabutylammonium fluoride (8.46 ml, 8.46 mmol) was added to a solution of Intermediate 216 (0.176 g, 0.28 mmol). The reaction mixture was stirred at room temperature over 15 days.

Water (50 ml) was added and the resulting mixture was extracted with EtOAc (3×50 ml). The organic phase was washed with brine (50 ml), dried over magnesium sulfate, filtered and concentrated under reduced pressure. The resulting crude residue was purified by $SiO_2$ flash chromatography with DCM/MeOH (98/2) as eluent to afford the expected product as a mixture of diastereoisomers.

The mixture was purified by preparative chiral HPLC using Chiralcel OD 10 μm 250×30 mm with EtOH/MeOH/Triethylamine (50/50/0.1) as eluent and with 45 ml/min flow in 18 min to afford each pure diastereoisomer.

Diastereomer A Example 203

12.8 mg: Analytical Chiral HPLC Chiralcel OD 10 μm 250×4.6 mm with EtOH/MeOH/Triethylamine (50/50/0.1) as eluant and with 1 ml/min flow over 15 minutes with RT=7.7 min.
LCMS (Method 20, ES+) RT 1.04 min., 510 $[M+H]^+$.

¹H NMR (400 MHz, DMSO-d6) 0.75 (t, J=7 Hz, 3H), 1.50 (s, 3H), 1.80-2.00 (m, 2H), 2.75 (d, J=13 Hz, 1H), 3.49 (m, 1H), 4.90 (t, J=7 Hz, 1H), 5.00 (s, 1H), 6.35 (d, J=7 Hz, 1H), 7.50 (m, 2H), 7.56 (d, J=6 Hz, 1H), 7.62 (t, J=73 Hz, 1H), 7.68 (d, J=9 Hz, 1H), 8.23 (m, 1H), 8.97 (d, J=2 Hz, 1H), 9.15 (d, J=6 Hz, 1H).

Diastereomer B Example 204

10.7 mg: Analytical Chiral HPLC Chiralcel OD 10 μm 250×4.6 mm with EtOH/MeOH/Triethylamine (50/50/0.1) as eluent and with a 1 ml/min flow rate over 15 minutes with RT=12.9 minutes.

LCMS (Method 20, ES+) RT 1.04 min., 510 [M+H]⁺.

¹H NMR (400 MHz, DMSO-d6) 0.75 (t, J=7 Hz, 3H); 1.50 (s, 3H); 1.80 t 2.00 (m, 2H); 2.75 (d, J=13 Hz, 1H); 3.49 (m, 1H); 4.90 (t, J=7 Hz, 1H); 5.00 (s, 1H); 6.35 (d, J=7 Hz, 1H); 7.50 (m, 2H); 7.56 (d, J=6 Hz, 1H); 7.62 (t, J=73 Hz, 1H); 7.68 (d, J=9 Hz, 1H); 8.23 (m, 1H); 8.97 (d, J=2 Hz, 1H); 9.15 (d, J=6 Hz, 1H).

The invention claimed is:

1. A method for the treatment of an inflammatory or autoimmune disorder, a neurological or neuro-degenerative disorder, pain or a nociceptive disorder, a cardiovascular disorder, a metabolic disorder, an ocular disorder, or an oncological disorder, which method comprises administering to a patient in need of such therapy an effective amount of a compound represented by formula (IB), or an N-oxide thereof, or a pharmaceutically acceptable salt thereof,

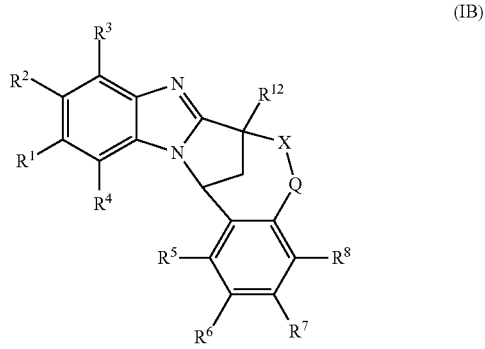

(IB)

wherein

—X—Q— represents —O—, —O—C(O)—, —O—C(CH—CN)—, —S—, —SO—, —SO₂—; or —N(R$^g$)—, —N(R$^f$)—CO—, —N(R$^f$)—SO₂—, —O—CH₂—, —CH₂—S—, —CH₂—SO—, —CH₂—SO₂—, —N(R$^g$)—CH₂—, —N(R$^f$)—C(S)—, —N=S(O)(CH₃)—, —O—C(=CH₂)— or —S(=N—CN);

R¹ represents chloro or cyano; or phenyl, pyridinyl, pyrimidinyl, cyclopropyl-pyridinyl-, cyclobutyl-pyrimidinyl, cyclobutyl-pyridinyl-, cyclohexyl-pyrimidinyl-, (3,7-dioxa-9-azabicyclo[3.3.1]non-9-yl)-primidinyl-, azetidinyl-pyrimidinyl-, azetidinyl-pyridinyl, pyrrolidinyl-pyridinyl-, pyrrolidinyl-phenyl-, piperazinyl-pyridinyl-, piperazinyl-pyrimidinyl-, pyrazolyl-, morpholinyl-pyrimidinyl-, thiomorpholinyl-pyrimidinyl-, (dioxo)thiomorpholinyl-pyrimidinyl-, (oxo)thiomorpholinyl-pyrimidinyl-, oxetanyl-pyridinyl-, oxetanyl-pyrimidinyl-, imidazolyl-phenyl, diazepanyl-pyrimidinyl-, (oxo)tetrahydrothiophenyl-pyrimidinyl-, (dioxo)tetrahydrothiophenyl-pyrimidinyl-, tetrahydrothiophenyl-pyrimidinyl-, azetidinyl-pyrazolyl-, (2-oxa-5-azabicyclo[2.2.1]heptanyl)-pyrimidinyl-, (3-oxa-8-azabicyclo[3.2.1]oct-8-yl)-pyrimidinyl-, (3,6-diazabicyclo[3.2.2]nonanyl)-pyrimidinyl-, tetrahydropyranyl-pyrimidinyl, azetidinyl, 1,2-dihydropyridinyl, or 1,2-dihydropyrimidinyl, any of which groups is optionally substituted by one or more substituents selected from cyano, methyl, difluoromethyl, trifluoromethyl, hydroxy, hydroxyisopropyl, methoxy, methoxyisopropyl, phosphate-isopropyl, (tert-butoxycarbonyl)amino-isopropyl, aminoisopropyl, dimethylaminoisopropyl, methyl-sulphonyl, methylsulphoximinyl, oxo, tert-butoxycarbonyl, (methoxycarbonyl)amino-isopropyl, methylthio, (tert-butyl)sulphinyl-amino, amino, (tert-butyl)sulphonyl-amino, methylsulphonylamino-isopropyl, methylcarbonylamino-isopropyl, fluoro, cyanoisopropyl, di(propenyl)aminoisopropyl, sulphate-isopropyl, carboxyethyl-carbonyloxy-isopropyl, (hydroxy)isobutyl, and tetrahydrofuranyl;

R² represents hydrogen or fluoro or chloro;

R³ and R⁴ independently represent hydrogen, chloro or fluoro, trifluoromethyl or C$_{1-6}$ alkyl;

R⁵ represents fluoro or chloro, —OR$^a$, difluoromethoxy or trifluoromethoxy;

R⁶ represents hydrogen, fluoro or chloro, or trifluoromethyl;

R⁷ represents hydrogen or trifluoromethyl;

R⁸ represents hydrogen, fluoro or chloro or trifluoromethyl;

R¹² represents hydrogen or C$_{1-6}$ alkyl;

R$^a$ represents C$_{1-6}$ alkyl;

R$^f$ represents hydrogen; or C$_{1-6}$ alkyl, which group is optionally substituted by one or more substituents selected from fluoro or chloro or C$_{1-6}$ alkyl; and R$^g$ represents hydrogen; or C$_{1-6}$ alkyl, —CO—(C$_{1-6}$) alkyl, —SO₂—(C$_{1-6}$)alkyl, —CO—(C$_{3-7}$)heterocycloalkyl, —SO₂—(C$_{3-7}$)cycloalkyl, —SO₂-aryl, —SO₂-heteroaryl, heteroaryl or (C$_{2-6}$)alkoxycarbonyl, any of which groups is optionally substituted by one or more substituents selected from fluoro, chloro and C$_{1-6}$ alkyl.

2. A method as claimed in claim 1 wherein —X-Q-represents —O—, —O—CO—, —O—C(CH—CN)—, —S—, —SO—, —SO₂—, —NH—, —N(CO—CH₃)—, —N(SO₂—CH₃)—, —N(CH₂—CO—O—CH₂—CH₃)—, —N[(CO—CH₂-(3,7-dioxa-9-azabicyclo[3.3.1]non-9-yl)]-, —N[CO-(azetidin-3-yl)]-, —N[CO-(methylsulphonyl)azetidin-3-yl)]-, —N(CH₂—COOH)—, —N[(tert-butyl)(dimethyl)silyloxyethyl]-, —N(SO₂-pyridine-3-yl)-, —N—(SO₂-cyclopropyl)-, —N(CH₃)—CH₂—, —N(CH₂—CH₂—OH)—, —N(SO₂-phenyl)-, —N[SO₂-(6-methoxypyridin-3-yl)]-, —NH—CO—, —N(CH₃)—CO—, —N(CH₂CH₃)—CO—, —N(CH(CH₃)₂)—CO—, —N(CH₂—COOH)—CO—, —N(CH₂—CF₃)—CO—, —N(CH₂—CH₂—OH)—CO—, —N(CH₂—C(OH)(CH₃)₂)—CO—, —N(CD₃)-CO—, —NH—CH₂—, —N(CH₂—COOH)—CH₂—, —NH—CH(CF₃)—, —NH—CH(CH₃)—, —NH—C(S)—, —N(CO—CH₃)—CH(CH₃)—, —N(SO₂—CH₃)—CH₂—, —N(CO—CH₃)—CH(CH₃)—, —N=S(O)(CH₃)—, —O—CH(CF₃)—, —CH(COOC₂H₅)—S—, —CH₂—S(O)—, —CH₂—S(O)₂—, —CH(C(OH)(CH₃)₂)—S—, —CH(CH₂OH)—S—, —O—C(=CH₂)—, —N[S(O)₂-(pyridin-1H-2-one)]-, —NH—

S(O)₂—, —N(pyrimidinyl)-, —N(COOC₂H₅)—, —S(=N—CN)—, —N(SO₂—CH₃)— or —N(C₂H₅)—CO—.

3. A method as claimed in claim 1, wherein —X-Q- represents —N(R$^f$)—C(O)—.

4. A method as claimed in claim 1 wherein the compound of formula (IB) is a compound of formula (IIB) or an N-oxide thereof, or a pharmaceutically acceptable salt thereof,

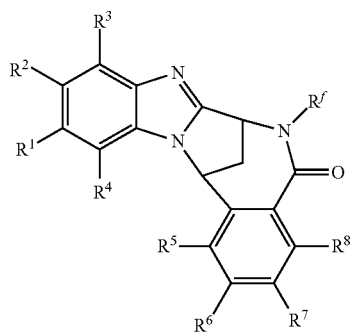
(IIB)

Wherein
R$^1$ is defined as in claim 1;
R$^2$ represents hydrogen or fluoro or chloro,
R$^3$ and R$^4$ independently represent hydrogen, fluoro or chloro, trifluoromethyl or C$_{1-6}$ alkyl;
R$^5$ represents fluoro or chloro, —OR$^a$, difluoromethoxy or trifluoromethoxy;
R$^6$ represents hydrogen, fluoro or chloro or trifluoromethyl;
R$^7$ represents hydrogen or trifluoromethyl;
R$^8$ represents hydrogen, fluoro or chloro or trifluoromethyl;
R$^a$ represents C$_{1-6}$ alkyl;
R$^f$ represents hydrogen; or C$_{1-6}$ alkyl, which group is optionally substituted by one or more substituents selected from fluoro, chloro and C$_{1-6}$ alkyl; and
R$^g$ represents hydrogen; or C$_{1-6}$ alkyl, —CO—(C$_{1-6}$) alkyl, —SO$_2$—(C$_{1-6}$)alkyl, —CO—(C$_3$-)heterocycloalkyl, —SO$_2$—(C$_{3-7}$)cycloalkyl, —SO$_2$-aryl, —SO$_2$-heteroaryl, heteroaryl or (C$_{2-6}$)alkoxycarbonyl, any of which groups is optionally substituted by one or more substituents selected from fluoro, chloro and C$_{1-6}$ alkyl.

5. A method as claimed in claim 1 wherein the compound of formula (IB) is a compound represented by formula (IIB-A), or an N-oxide thereof, or a pharmaceutically acceptable salt thereof,

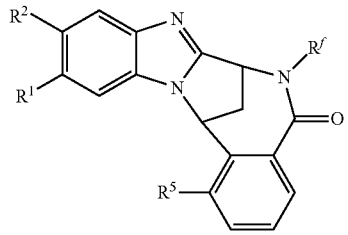
(IIB-A)

wherein
R$^1$, R$^2$, R$^5$, and R$^f$ are as defined in claim 1.

6. A method as claimed in claim 5 where the compound of formula (IIB-A) is a compound represented by formula (IIB-AB-A), an N-oxide thereof, or pharmaceutically acceptable salt thereof,

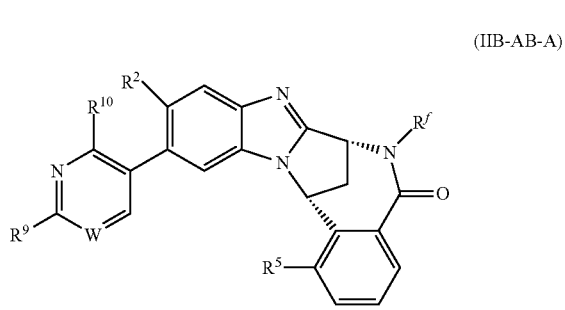
(IIB-AB-A)

wherein
R$^9$ represents hydroxyisopropyl, methoxyisopropyl, or aminoisopropyl;
R$^{10}$ represents hydrogen or methyl;
R$^2$, R$^5$, R$^a$, and R$^f$ are as defined in claim 5;
and
W represents N or C—H.

7. A method as claimed in claim 6 wherein W represents N.

8. A method as claimed in claim 6 wherein R$^{10}$ represents hydrogen.

9. A method as claimed in claim 6 wherein R$^9$ represents 2-hydroxy-prop-2-yl.

10. A method as claimed in claim 4 wherein
R$^2$ represents fluoro; and/or
R$^5$ represents difluoromethoxy; and/or
R$^f$ represents hydrogen.

* * * * *